US010807977B2

(12) United States Patent
Zheng et al.

(10) Patent No.: US 10,807,977 B2
(45) Date of Patent: Oct. 20, 2020

(54) COMPOUNDS THAT INDUCE DEGRADATION OF ANTI-APOPTOTIC BCL-2 FAMILY PROTEINS AND THE USES THEREOF

(71) Applicant: BioVentures, LLC, Little Rock, AR (US)

(72) Inventors: Guangrong Zheng, Gainesville, FL (US); Daohong Zhou, Gainesville, FL (US); Xuan Zhang, Gainesville, FL (US); Yingying Wang, Chengdo (CN); Jianhui Chang, Chengdo (CN)

(73) Assignee: BioVentures, LLC, Little Rock, TX (US)

( * ) Notice: Subject to any disclaimer, the term of this patent is extended or adjusted under 35 U.S.C. 154(b) by 0 days.

(21) Appl. No.: 16/095,260

(22) PCT Filed: Apr. 21, 2017

(86) PCT No.: PCT/US2017/028875
§ 371 (c)(1),
(2) Date: Oct. 19, 2018

(87) PCT Pub. No.: WO2017/184995
PCT Pub. Date: Oct. 26, 2017

(65) Prior Publication Data
US 2019/0135801 A1    May 9, 2019

Related U.S. Application Data

(60) Provisional application No. 62/325,856, filed on Apr. 21, 2016.

(51) Int. Cl.
*C07D 417/14* (2006.01)
*C07D 401/14* (2006.01)
*C07D 471/04* (2006.01)
*A61K 45/06* (2006.01)
*A61K 35/00* (2006.01)
*C07D 405/14* (2006.01)

(52) U.S. Cl.
CPC ............ *C07D 417/14* (2013.01); *A61K 35/00* (2013.01); *A61K 45/06* (2013.01); *C07D 401/14* (2013.01); *C07D 405/14* (2013.01); *C07D 471/04* (2013.01)

(58) Field of Classification Search
CPC ............................ C07D 417/14; C07D 471/04
See application file for complete search history.

(56) References Cited

U.S. PATENT DOCUMENTS

| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,223,409 A | 6/1993 | Ladner et al. |
| 5,264,618 A | 11/1993 | Feigner et al. |
| 5,403,484 A | 4/1995 | Ladner et al. |
| 5,491,069 A | 2/1996 | Dirmi et al. |
| 5,571,698 A | 11/1996 | Ladner et al. |
| 5,888,764 A | 3/1999 | Mountz et al. |
| 6,492,389 B1 | 12/2002 | Huang et al. |
| 6,566,495 B1 | 5/2003 | Fodor et al. |
| 7,390,799 B2 | 6/2008 | Bruncko et al. |
| 7,939,313 B2 | 5/2011 | Heyduk et al. |
| 8,232,273 B2 | 7/2012 | Baell et al. |
| 8,691,184 B2 * | 4/2014 | Wang .................. C07D 403/12 424/1.11 |
| 9,403,856 B2 * | 8/2016 | Wang .................. C07F 9/65583 |
| 10,071,087 B2 | 9/2018 | Zheng et al. |
| 2005/0084876 A1 | 4/2005 | Tschopp et al. |
| 2005/0208151 A1 | 9/2005 | Hurez et al. |
| 2006/0140959 A1 | 6/2006 | Fisher et al. |
| 2007/0072860 A1 | 3/2007 | Bruncko et al. |
| 2009/0312373 A1 | 12/2009 | Lee et al. |
| 2010/0086941 A1 | 4/2010 | Adami et al. |
| 2010/0093613 A1 | 4/2010 | Kunkel |
| 2010/0310504 A1 | 12/2010 | Lowe et al. |
| 2011/0028387 A1 | 2/2011 | Garcia et al. |
| 2011/0053938 A1 | 3/2011 | Foley et al. |
| 2011/0086860 A1 | 4/2011 | Kimura et al. |
| 2012/0059004 A1 | 3/2012 | Elliott et al. |
| 2012/0156134 A1 | 6/2012 | Squires |
| 2012/0157455 A1 | 6/2012 | Foley et al. |
| 2013/0195884 A1 | 8/2013 | Boutros et al. |
| 2013/0237539 A1 | 9/2013 | Foley et al. |
| 2014/0005190 A1 | 1/2014 | Baell et al. |
| 2014/0024639 A1 | 1/2014 | Adams et al. |
| 2014/0199234 A1 | 7/2014 | Wang et al. |
| 2014/0356322 A1 * | 12/2014 | Crews ..................... C12N 9/93 424/85.2 |
| 2015/0291562 A1 | 10/2015 | Crew et al. |

(Continued)

FOREIGN PATENT DOCUMENTS

| CN | 101774875 A | 7/2010 |
| CN | 102125552 A | 7/2011 |

(Continued)

OTHER PUBLICATIONS

M. Zengerle et al., ACS Chemical Biology, 1770-1777 (2015) (Year: 2015).*

(Continued)

*Primary Examiner* — Paul V Ward
(74) *Attorney, Agent, or Firm* — Hubbard Johnston, PLLC

(57) ABSTRACT

The present disclosure provides compositions and methods for selectively killing senescent cells, wherein the composition comprises a compound of Formula (I) or a compound of Formula (II). The selective killing of senescent cells may delay aging and/or treat age-related disorders.

19 Claims, 5 Drawing Sheets

(56) References Cited

U.S. PATENT DOCUMENTS

| | | | |
|---|---|---|---|
| 2016/0176916 | A1 | 6/2016 | Bradner et al. |
| 2016/0272639 | A1* | 9/2016 | Crew .................. C07D 471/04 |
| 2016/0339019 | A1 | 11/2016 | Laberge et al. |
| 2017/0056421 | A1 | 3/2017 | Zhou et al. |
| 2017/0065719 | A1* | 3/2017 | Qian ...................... A61K 47/55 |
| 2017/0246155 | A1 | 8/2017 | Zheng et al. |
| 2017/0348307 | A1 | 12/2017 | Laberge et al. |
| 2018/0002431 | A1 | 1/2018 | Zhou et al. |
| 2018/0021323 | A1 | 1/2018 | Zhou et al. |
| 2018/0110787 | A1* | 4/2018 | Laberge .................. A61K 9/12 |
| 2018/0369223 | A1 | 12/2018 | Zheng et al. |
| 2019/0054097 | A1 | 2/2019 | Zhou et al. |

FOREIGN PATENT DOCUMENTS

| | | | |
|---|---|---|---|
| CN | 102146054 | A | 8/2011 |
| CN | 103601670 | A | 2/2014 |
| CN | 105085620 | A | 11/2015 |
| EP | 0532767 | A1 | 3/1993 |
| EP | 2985285 | A1 | 2/2016 |
| JP | 11349568 | A | 12/1999 |
| WO | 2002026940 | A1 | 4/2002 |
| WO | 2002097053 | A2 | 12/2002 |
| WO | 2004106328 | A1 | 12/2004 |
| WO | 2006023778 | A2 | 3/2006 |
| WO | 2008119741 | A2 | 10/2008 |
| WO | 2009114126 | A1 | 9/2009 |
| WO | 2009155386 | A1 | 12/2009 |
| WO | 2010080503 | A1 | 7/2010 |
| WO | 2010120943 | A1 | 10/2010 |
| WO | 2010138588 | A2 | 12/2010 |
| WO | 2011009861 | A1 | 1/2011 |
| WO | 2011130395 | A1 | 10/2011 |
| WO | 2012030408 | A1 | 3/2012 |
| WO | 2012071374 | A1 | 5/2012 |
| WO | 2013083098 | A2 | 6/2013 |
| WO | 2013106643 | A2 | 7/2013 |
| WO | 2013178821 | A1 | 12/2013 |
| WO | 2014089124 | A1 | 6/2014 |
| WO | 2014108452 | A1 | 7/2014 |
| WO | 2014174511 | A1 | 10/2014 |
| WO | 2015116740 | A1 | 8/2015 |
| WO | 2015171591 | A1 | 11/2015 |
| WO | 2016014625 | A1 | 1/2016 |
| WO | 2016118855 | A1 | 7/2016 |
| WO | 2016118859 | A1 | 7/2016 |
| WO | 2017012774 | A1 | 1/2017 |
| WO | 2017101851 | A1 | 6/2017 |
| WO | 2017184995 | A1 | 10/2017 |
| WO | WO-2019144117 | A1 * | 7/2019 .............. A61P 35/04 |

OTHER PUBLICATIONS

Carra et al., 130 Blood (Dec. 7, 2017) (Year: 2017).*
A. Ruefli-Brasse, 474 Biochemical Journal, 3643-3657 (2017) (Year: 2017).*
M.H. Kang et al., 15 Clinical Cancer Research, 1126-1132 (2009) (Year: 2009).*
J. Liu et al., 5 Nature Communications (2014) (Year: 2014).*
Duh, C. et al., "Cytotoxic Pyridone Alkaloids From the Leaves of Piper Aborescens," J. Nat. Prod., Nov.-Dec. 1990, pp. 1575-1577, vol. 53, No. 6.
Dykstra, B. et al., "Clonal analysis reveals multiple functional defects of aged murine hematopoietic stem cells," J. Exp. Med., 2011, pp. 2691-2703, vol. 208.
Erb, E. et al., "Recursive deconvolution of combinatorial chemical libraries," PNAS, Nov. 1994, pp. 11422-11426, vol. 91.
Extended European Search Report dated Oct. 5, 2017 from related European Patent Application No. 15789264.7; 7 pgs.
Extended European Search Report dated Jan. 2, 2018 from related European Patent Application No. 15824181.0; 9 pgs.
Felici, F., "Selection of Antibody Ligands from a Large Library of Oligopeptides Expressed on a Multivalent Exposition Vector," J. Mol. Biol., 1991, pp. 301-310, vol. 222.
Fleenor, C. et al., "Ionizing radiation and hematopoietic malignancies: altering the adaptive landscape," Cell Cycle, 2010, pp. 3005-3011, vol. 9.
Fodor, S. et al., "Multiplexed biochemical assays with biological chips," Nature, 1993, pp. 555-556, vol. 364, No. 6437.
Fontenele, J. et al., "Antiplatelet effects of piplartine, an alkamide isolated from Piper tuberculatum: possible involvement of cyclooxygenase blockade and antioxidant activity," J. Pharm. Pharmacol., 2009, pp. 511-515, vol. 61, No. 4.
Galatin, P. et al., "A Nonpeptidic Sulfonamide Inhibits the p53-mdm2 Interaction and Activates p53-Dependent Transcription in mdm2-Overexpressing Cells," J. Med. Chem., 2004, pp. 4163-4165, vol. 47, No. 17.
Gallop, M. et al., "Applications of Combinatorial Technologies to Drug Discovery. 1. Background and Peptide Combinatorial Libraries," J. Med. Chem., Apr. 1994, pp. 1233-1251, vol. 37, No. 9.
Geiger, H. et al., "Regulation of hematopoietic stem cell aging in vivo by a distinct genetic element," PNAS, 2005, pp. 5102-5107, vol. 102.
Geiger, H. et al., "The ageing haematopoietic stem cell compartment," Nat. Rev. Immunol., 2013, pp. 376-389, vol. 13.
Gobom, J. et al., "Detection and Quantification of Neurotensin in Human Brain Tissue by Matrix-Asserted Laser Desorption/Ionization Time-of-Flight Mass Spectrometry," Anal. Chem., 2000, pp. 3320-3326, vol. 72.
Gustafson, J. et al., "Small-Molecule-Mediated Degradation of the Androgen Receptor through Hydrophobic Tagging," Angew. Chem. Int. Ed., Aug. 10, 2015, pp. 9659-9662, vol. 54, No. 33.
Harfouche, G. et al., "Response of normal stem cells to ionizing radiation: a balance between homeostasis and genomic stability," Mutat. Res., 2010, pp. 167-174, vol. 704.
Houghten, R. et al., "The Use of Synthetic Peptide Combinatorial Libraries for the Identification of Bioactive Peptides," Biotechniques, 1991, pp. 412-421, vol. 13, No. 3.
International Search Report and Written Opinion dated Sep. 18, 2015 from related International Patent Application No. PCT/US2015/029208; 13 pgs.
International Search Report and Written Opinion dated Oct. 23, 2015 from related International Patent Application No. PCT/US2015/041470; 9 pgs.
International Search Report and Written Opinion dated Apr. 1, 2016 from related International Patent Application No. PCT/US2016/014518; 9 pgs.
International Search Report and Written Opinion dated Apr. 1, 2016 from related International Patent Application No. PCT/US2016/014510; 12 pgs.
International Search Report and Written Opinion dated Jul. 11, 2017 from related International Patent Application No. PCT/US2017/028875; 9 pgs.
International Search Report and Written Opinion dated Jun. 29, 2015 from related International Patent Application No. PCT/US2015/013387; 34 pgs.
International Search Report and Written Opinion dated Aug. 7, 2018 from related International Patent Application No. PCT/US2018/033479; 9 pgs.
Janzen, V. et al., "Stem-cell ageing modified by the cyclin-dependent kinase inhibitor p16INK4a," Nature, 2006, pp. 421-426, vol. 443.
Joshi, B. et al., "On the Structure of Piplartine and a Synthesis of Dihydropiplartine," Tetrahedron Lett., 1968, pp. 2395-2400, vol. 9, No. 20, Pergamon Press, Great Britain.
Jozefczuk, J. et al., "Preparation of Mouse Embryonic Fibroblast Cells Suitable for Culturing Human Embryonic and Induced Pluripotent Stem Cells," J. Vis. Exp., Jun. 2012, pp. 1-5, vol. 64, Issue e3854.
Kubo, M. et al., "Evaluation of Constituents of Piper retrofractum Fruits on Neurotrophic Activity," J. Nat. Prod., 2013, pp. 769-773, vol. 76, No. 4, The American Chemical Society and American Society of Pharmacognosy.

(56) References Cited

OTHER PUBLICATIONS

Kumar, J. et al., "Synthesis, anticancer, and antibacterial activities of piplartine derivatives on cell cycle regulation and growth inhibition," Journal of Asian Natural Products Research, Jun. 1, 2013, pp. 658-669, vol. 15, No. 6, Taylor & Francis Group.

Laberge, R. et al., "Mitochondrial DNA damage induces apoptosis in senescent cells," Cell Death Dis., 2013, p. e727, vol. 4.

Lam, K. "Mini-review. Application of combinatorial library methods in cancer research and drug Discovery," Anti-Cancer Drug Des., 1997, pp. 145-167, vol. 12, No. 3.

Lam, K. et al., "A new type of synthetic peptide library for identifying ligand-binding activity," Nature, Nov. 7, 1991, pp. 82-84, vol. 354.

Le, O. et al., "Ionizing radiation-induced long-term expression of senescence markers in mice is independent of p53 and immune status," Aging Cell, 2010, pp. 398-409, vol. 9.

Le Couteur, D. et al., "Aging biology and novel targets for drug Discovery," J. Gerontol. A Biol. Sci. Med. Sci., 2012, pp. 168-174, vol. 67.

Lee, S-J. et al., "Berberine sensitizes Trail-induced apoptosis through proteasome-mediated downregulation of c-FLIP and Mcl-1 proteins," Int. J. Oncol., 2011, pp. 485-492, vol. 38.

Lessene, G., et al., "BCL-2 family antagonists for cancer therapy," Nat. Rev. Drug Discov., Dec. 2008, pp. 989-1000, vol. 7.

Lessene, G. et aL, "Structure-guided design of a selective BCL-X(L) inhibitor," Nat. Chem. Biol., 2013, pp. 390-397, vol. 9.

Lin, C. et al., "Endostatin and transglutaminase 2 are involved in fibrosis of the aging kidney," HHS Public Access Author Manuscript, Jun. 1, 2017, pp. 1-20, published in final edited form as: Kidney Int., Jun. 2016, pp. 1281-1292, vol. 89, No. 6.

Liu, J. et al., "Droxinostat, a Histone Deacetylase Inhibitor, Induces Apoptosis in Hepatocellular Carcinoma Cell Lines via Activation of the Mitochondrial Pathway and Downregulation of FLIP," Translational Oncology, Feb. 2016, pp. 70-78, vol. 9, No. 1, Elsevier Inc. on behalf of Neoplasia Press, Inc.

Loo, D. et al., "Measurement of Cell Death," Methods Cell Biol., 1998, pp. 251-264, vol. 57, Chapter 14, Academic Press.

Lu, Y. et al., "Discovery of a Nanomolar Inhibitor of the Human Murine Double Minute 2 (MDM2)-p53 Interaction through an Integrated, Virtual Database Screening Strategy," J. Med. Chem., 2006, pp. 3759-3762, vol. 49, No. 13.

Lu, J., et al., "Hijacking the E3 Ubiquitin Ligase Cereblon to Efficiently Target BRD4," Chem. Biol., Jun. 18, 2015, pp. 155-763, vol. 22.

Marcotte, R. et al., "Replicative senescence revisited," J. Gerontol. A Biol. Sci. Med. Sci., 2002, pp. B257-B269, vol. 57.

Matthews, C. et al., "Vascular Smooth Muscle Cells Undergo Telomere-Based Senescence in Human Atherosclerosis. Effects of Telomerase and Oxidative Stress," Cir. Res., Jul. 21, 2006, pp. 156-164, vol. 99.

Mawji, I. et al., "A Chemical Screen Identifies Anisomycin as an Anoikis Sensitizer That Functions by Decreasing FLIP Protein Synthesis," Cancer Res., Sep. 1, 2007, pp. 8307-8315, vol. 67, No. 17.

Meng, A. et al,. "Sphingomyelin synthase as a potential target for D609-induced apoptosis in U937 human monocytic leukemia cells," Exp. Cell Res., 2004, pp. 385-392, vol. 292.

Mirgorodskaya, E. et al., "Characterization of Protein Glycosylation by MALDI-TOFMS," Meth. Mol. Biol., 2000, pp. 273-292, vol. 146, Humana Press Inc.

Munoz-Espin, D. et al., "Cellular senescence: from physiology to pathology," Nat. Rev. Mol. Cell Biol., 2014, pp. 482-496, vol. 15.

Nopora, A. et al., "Bcl-2 Controls Dendritic Cell Longevity In Vivo," J. Immunol., Sep. 2002, pp. 3006-3014, vol. 169 Vo. 6.

Notice of Allowance dated May 8, 2018 from related U.S. Appl. No. 15/328,368; 5 pgs.

Adams, D. et al., "Synthesis, cellular evaluation, and mechanism of action of piperlongumine analogs," PNAS, Sep. 18, 2012, pp. 15115-15120, vol. 109, No. 38.

Aguilar, A., et al., "A Potent and Highly Efficacious Bcl-2/Bcl-xL Inhibitor," J. Med. Chem., 2013, pp. 3048-3067, vol. 56.

Baar, M. et al., "Targeted Apoptosis of Senescent Cells Restores Tissue Homeostasis in Response to Chemotoxicity end Aging," HHS Public Access Author Manuscript, Mar. 23, 2018, pp. 1-37, published in final edited form as: Cell, Mar. 23, 2017, pp. 132-147, vol. 169, No. 1.

Bai, L., et al., "BM-1197: A Novel and Specific Bcl-2/Bcl-xL Inhibitor Inducing Complete and Long-Lasting Tumor Regression In Vivo," PLOS One, Jun. 2014, pp. 1-13, vol. 9, No. 6, e99404.

Bajwa, N., et al., "Inhibitors of the anti-apoptotic Bcl-2 proteins: a patent review," NIH Public Access Author Manuscript, Jan. 17, 2013, pp. 1-25, published in final edited form as: Expert Opin. Ther. Pat., Jan. 2012, pp. 37-55, vol. 22, No. 1.

Baker, D et al., "Clearance of p16Ink4a-positive senescent cells delays ageing-associated disorders," Nature, Nov. 10, 2011, pp. 232-236, vol. 479, No. 7372, Macmillian Publishers Limited.

Baker, D. et al., "Naturally occurring p16Ink4a-positive cells shorten healthy lifespan," HHS Public Access Author Manuscript, Aug. 3, 2016, pp. 1-30, published in final edited form as: Nature, Feb. 11, 2016, pp. 184-189, vol. 530, No. 7589.

Banerjee, T. et al., "The crystal and molecular structure of N-(3,4,5-trimethoxycinnamoyl)-A3-piperidine-2-one, an amide alkaloid (piperlongumine), $C_{17}H_{19}NO_5$," Can. J. Chem., 1986, pp. 876-880, vol. 64.

Baritaki, S. et al., "Chemotherapeutic drugs sensitize cancer cells to TRAIL-mediated apoptosis: up-regulation of DR5 and inhibition of Yin Yang 1," Mol. Cancer Ther., Apr. 2007, pp. 1387-1399, vol. 6, No. 4.

Barton, K. et al., "Selective HDAC Inhibition for the Disruption of Latent HIV-1 Infection," PLOS ONE, Aug. 2014, pp. 1-11, vol. 9, No. 8, e102684.

Beerman, I. et al., "Stem cells and the aging hematopoietic system," Cuff. Opin. Immunol., 2010, pp. 500-506, vol. 22.

Bensoussan, C. et al., "Iron-catalyzed cross-coupling between C-bromo mannopyranoside derivatives and a vinyl Grignard reagent: toward the synthesis of the C31-052 fragment of amphidinol 3," Tetrahedron, 2013, pp. 7759-7770, vol. 69, No. 36, Elsevier Ltd.

Bezerra, D. et al., "Overview of the therapeutic potential of piplartine (piperlongumine)," Eur. J. Pharma. Sci., 2013, pp. 453-463, vol. 48, No. 3, Elsevier B.V., Amsterdam.

Blagosklonny, M., "Selective anti-cancer agents as anti-aging drugs," Cancer Biol. Ther., Dec. 2013, pp. 1092-1097, vol. 14, No. 12, Landes Bioscience.

Bokesch, H. et al., "A New Hypoxia Inducible Factor-2 Inhibitory Pyrrolinone Alkaloid from Roots and Stems of Piper sarmentosum," Chem. Pharm. Bull., 2011, pp. 1178-1179, vol. 59, No. 9, Pharmaceutical Society of Japan.

Braun, H. et al., "Cellular Senescence Limits Regenerative Capacity and Allograft Survival," J. Am. Soc. Nephrol., Sep. 2012, pp. 1467-1473, vol. 23, No. 9.

Brenkman, A. et al., "Mdm2 Induces Mono-Ubiquitination of FOXO4," PLOS One, Jul. 2008, pp. 1-7, vol. 3, No. 7, e2819.

Bruncko, M., et al., "Studies Leading to Potent, Dual Inhibitors of Bcl-2 and Bcl-xL," J. Med. Chem., 2007, pp. 641-662, vol. 50, No. 4.

Bruncko, M., et al., "Structure-Guided Design of a Series of MCL-1 Inhibitors with High Affinity and Selectivity," J. Med. Chem., 2015, pp. 2180-2194, vol. 58, No. 5.

Bucknall, M. et al., "Practical Quantitative Biomedical Applications of MALDI-TOF Mass Spectrometry," J. Am. Soc. Mass. Spectrom., 2002, pp. 1015-1027, vol. 13, Elsevier Science Inc.

Burd, C. et al., "Monitoring tumorigenesis and senescence in vivo with a p16(INK4a)-luciferase model," Cell, 2013, pp. 340-351, vol. 152.

Campisi, J., "Aging, cellular senescence, and cancer," Annu. Rev. Physiol., 2013, pp. 685-705, vol. 75.

Campisi, J. et al., "Senescent Cells, Tumor Suppression, and Organismal Aging: Good Citizens, Bad Neighbors," Cell, Feb. 25, 2005, pp. 513-522, vol. 120, Elsevier Inc.

(56) References Cited

OTHER PUBLICATIONS

Campisi, J., "Cellular senescence: putting the paradoxes in perspective," Curr. Opin. Genet. Dev., 2011, pp. 107-112, vol. 21, Elsevier.
Carell, T. et al., "A Solution-Phase Screening Procedure for the Isolation of Active Compounds from a Library of Molecules," Angew. Chem. Int. Ed. Engl., 1994, pp. 2059-2061, vol. 33, No. 20.
Caserta, T. et al., "Q-VD-OPh, a broad spectrum caspase inhibitor with potent antiapoptotic properties," Apoptosis, 2003, pp. 345-352, vol. 8.
Chang, J. et al., "Clearance of senescent cells by ABT263 rejuvenates aged hematopoietic stem cells in mice," Nat. Med., Jan. 2016, pp. 78-83, vol. 22, No. 1.
Chatterjee, A. et al., "Alkaloids of Piper Longum Linn-I: Structure and Synthesis of Piperlongumine and Piperlonguminine," Tetrahedron, 1967, pp. 1769-1781, vol. 23, No. 4, Pergamon Press, Northern Ireland.
Chen, Q. et al., "Apo2L/TRAIL and Bcl-2-related proteins regulate type I interferon-induced apoptosis in multiple myeloma," Blood, Oct. 1, 2001, pp. 2183-2192, vol. 98, No. 7.
Chen, L. et al., "p53 alpha-Helix mimetics antagonize p53/MDM2 interaction and activate p53," Mol. Cancer Ther., Jun. 2005, pp. 1019-1025, vol. 4, No. 6.
Chen, S. et al., "Celecoxib Promotes c-FLIP Degradation through Akt-Independent Inhibition of GSK3," Cancer Res., 2011, pp. 6270-6281, vol. 71, No. 19.
Chen, J. et al., "The Bcl-2/Bcl-XL/Bcl-w Inhibitor, Navitoclax, Enchances the Activity of Chemotherapeutic Agents In Vitro and In Vivo," Mol. Cancer Ther., 2011, pp. 2340-2349, vol. 10, No. 12.
Chen, J. et al., "Structure-Based Discovery of BM-957 as a Potent Small-Molecule Inhibitor of Bcl-2 and Bcl-xL Capable of Achieving Complete Tumor Regression," NIH Public Access Author Manuscript, Oct. 11, 2013, pp. 1-33, published in final edited form as: J. Med. Chem., Oct. 11, 2012, pp. 8502-8514, vol. 55, No. 19.
Childs, B. et al., "Senescence and apoptosis: dueling or complementary cell fates?," EMBO Rep., 2014, pp. 1139-1153, vol. 15.
Childs, B. et al., "Senescent cells: an emerging target for diseases of ageing," HHS Public Access Author Manuscript, May 9, 2018, pp. 1-41, published in final edited form as: Nat. Rev. Drug Discov., Oct. 2017, pp. 718-735, vol. 16, No. 10.
Cho, C. et al., "An Unnatural Biopolymer," Sci., Sep. 3, 1993, pp. 1303-1305, vol. 261.
Citrin, D. et al., "Role of type II pneumocyte senescence in radiation-induced lung fibrosis," J. Natl. Can. Inst., 2013, pp. 1474-1484, vol. 105.
Coppe, J. et al., "The senescence-associated secretory phenotype: the dark side of tumor suppression," Annu. Rev. Pathol., 2010, pp. 99-118, vol. 5.
Cory, S. et al., "The Bcl2 family: regulators of the cellular life-or-death switch," Nat. Rev. Can., 2002, pp. 647-656, vol. 2.
Cull, M. et al., "Screening for receptor ligands using large libraries of peptides linked to the C terminus of the lac repressor," PNAS, Mar. 1992, pp. 1865-1869, vol. 89.
Cwirla, S. et al., "Peptides on phage: A vast library of peptides for identifying ligands," PNAS, Aug. 1990, pp. 6378-6382, vol. 87.
Czabotar, P. et al., "Control of apoptosis by the BCL-2 protein family: implications for physiology and therapy," Nat. Rev. Mol. Cell Biol., 2014, pp. 49-63, vol. 15.
Debacq-Chainiaux, F. et al., "Protocols to detect senescence-associated beta-galactosidase (SA-betagal) activity, a biomarker of senescent cells in culture and in vivo," Nat. Protoc., 2009, pp. 1798-1806, vol. 4.
Demaria, M. et al., "An Essential Role for Senescent Cells in Optimal Wound Healing through Secretion of PDGF-AA," Dev. Cell, 2014, pp. 722-733, vol. 31.
Delbridge, A. et al., "Thirty years of BCL-2: translating cell death discoveries into novel cancer therapies," Nat. Rev. Cancer, Feb. 2016, pp. 99-109—vol. 16.
Devlin, J. et al., "Random Peptide Libraries: A Source of Specific Protein Binding Molecules," Sci., Jul. 27, 1990, pp. 404-406, vol. 249, No. 4967, American Association for Advancement of Science.
Dewitt, S. et al., "'Diversomers': An approach to nonpeptide, nonoligomeric chemical diversity," PNAS, Aug. 1993, pp. 6909-6913, vol. 90.
Di Pietro, R. et al., "Ionnizing radition sensitizes erythroleukemic cells but not normal erythroblasts to tumor necrosis factor-related apoptosis-inducing ligand (TRAIL)-mediated cytotoxicity by selective up-regulation of TRAIL-R1," Blood, May 1, 2001, pp. 2596-2603, vol. 97, No. 9.
Dodson, C. et al., "Cenocladamide, a dihydropyridone alkaloid from Piper cenocladum," Phytochemistry, 2000, pp. 51-54, vol. 53, Elsevier Science Ltd.
Office Action dated May 29, 2019 from related U.S. Appl. No. 15/308,552 17 pgs.
Office Action dated Jun. 11, 2019 from related European Patent Application No. 157892641; 4 pgs.
Office Action dated Jun. 26, 2019 from related U.S.Appl. No. 16/057,021; 10 pgs.
Wu, Y. et al., "Design, synthesis and biological activity of piperlongumine derivatives as selective anticancer agents," Eur. J. Med. Chem., 2014, pp. 545-551, vol. 82, Elsevier Masson SAS.
Yao, L. et al., "Piperlongumine alleviates lupus nephritis in MRL-Fas(lpr) mice by regulating the frequency of Th17 and regulatory T cells," Immunol. Lett., Sep. 2014, pp. 76-80, vol. 161, No. 1, Abstract Only.
Yin, H. et al., "Terphenyl-Based Helical Mimetics That Disurpt the p53/HDM2 Interaction," Angew. Chem. Int. Ed., Apr. 2005, pp. 2704-2707, vol. 44, No. 18, Wiley-VCH Verlag GmbH & Co. KGaA, Weinheim.
Zengerle, M. et al., "Selective Small Molecule Induced Degradation of the BET Bromodomain Protein BRD4," ACS Chem. Biol., 2015, pp. 1770-1777, vol. 10, American Chemical Society.
Zhou, H. et al., "Design of Bcl-2 and Bcl-xL Inhibitors with Subnanomolar Binding Affinities Based Upon a New Scaffold," NIH Public Access Author Manuscript, May 24, 2013, pp. 1-42, published in final edited form as: J. Med. Chem., May 24, 2012, pp. 4664-4682, vol. 55, No. 10.
Zhou, H. et al., "Structure-based Design of Potent Bcl-2/Bcl-xL Inhibitors with Strong in vivo Antitumor Activity," NIH Public Access Author Manuscript, Jul. 12, 2013, pp. 1-31, published in final edited form as: J. Med. Chem., Jul. 12, 2012, pp. 6149-6161, vol. 55, No. 13.
Zhu, Y. et al., "The Achilles' heel of senescent cells: from transcriptome to senolytic drugs," Aging Cell, Aug. 2015, pp. 644-658, vol. 14, No. 4.
Zhu, Y. et al., Identification of a novel senolytic agent, navitoclax, targeting the Bcl-2 family of anti-apoptotic factors, Aging Cell, Jun. 2016, pp. 428-435, vol. 15, No. 3.
Zuckermann, R. et al., "Discovery of Nanomolar Ligands for 7-Transmembrane G-Protein-Coupled Receptors from a Diverse N-(Substituted)glycine Peptoid Library," J. Med. Chem., 1994, pp. 2678-2685, vol. 37.
Office Action dated Oct. 23, 2017 from related U.S. Appl. No. 15/328,368; 8 pgs.
Office Action dated Feb. 27, 2018 from related U.S. Appl. No. 15/328,368; 6 pgs.
Office Action dated Oct. 4, 2018 from related U.S. Appl. No. 15/545,480; 4 pgs.
Office Action dated Oct. 4, 2018 from related U.S. Appl. No. 15/308,552; 16 pgs.
Park, C-M. et al., "Discovery of an Orally Bioavailable Small Molecule Inhibitor of Prosurvival B-Cell Lymphoma 2 Proteins," J. Med. Chem., 2008, pp. 6902-6915, vol. 51, No. 21.
Pelz, N. et al., "Discovery of 2-Indole-acylsulfonamide Myeloid Cell Leukemia 1 (Mcl-1) Inhibitors Using Fragment-Based Methods," J. Med. Chem., 2016, pp. 2054-2066, vol. 59.
Raj, L. et al., "Selective killing of cancer cells by a small molecule targeting the stress response to ROS," Nature, Jul. 14, 2011, pp. 231-234, vol. 475, Macmillan Publishers Limited.
Raja, S. et al., "The natural product honokiol preferentially inhibits cellular FLICE-inhibitory protein and augments leath receptor-induced apoptosis," Mol. Cancer Ther., 2008, pp. 2212-2223, vol. 7, No. 7.

(56) References Cited

OTHER PUBLICATIONS

Rao, V. et al., "Synthesis and biological evaluation of new piplartine analogues as potent aldose reductase inhibitors (ARIs)," Eur. J. Med. Chem., 2012, pp. 344-361, vol. 57, Elsevier Masson SAS.
Ricci, M. et al., "Chemotherapeutic Approaches for Targeting Cell Death Pathways," The Oncologist, 2006, pp. 342-357, vol. 11.
Richardson, R., "Ionizing radiation and aging: rejuvenating an old idea," Aging, 2009, pp. 887-902, vol. 1.
Rockett, J. et al., "DNA arrays: technology, options and toxicological applications," Xenobiotica, 2000, pp. 155-177, vol. 30, No. 2.
Rodier, F. et al., "Four faces of cellular senescence," J. Cell Biol., Feb. 14, 2011, pp. 547-556, vol. 192, The Rockefeller University Press.
Rudin, C. et al., "Phase II Study of Single-Agent Navitoclax (ABT-263) and Biomarker Correlates in Patients with Relapsed Small Cell Lung Cancer," Clin. Cancer Res., Jun. 2012, pp. 3163-3169, vol. 18, No. 11.
Safa, A. et al., "Targeting the Anti-Apoptotic Protein c-Flip for Cancer Therapy," Cancers, 2011, pp. 1639-1671, vol. 3.
Sanders, Y. et al., "Histone Modifications in Senescence-Associated Resistance to Apoptosis by Oxidative Stress," Redox Biol., 2013, pp. 8-16, vol. 1, Elsevier B.V.
Schafer, M. et al., "Targeting Senescent Cells in Fibrosis: Pathology, Paradox, and Practical Considerations," Curr. Rheumatol. Rep., Jan. 26, 2018, Article 3, vol. 20, Issue 1, SpringerLink, Abstract Only.
Schimmer, A. et al., "Identification of Small Molecules that Sensitize Resistant Tumor Cells to Tumor Necrosis Factor-Family Death Receptors," Cancer Res., 2006, pp. 2367-2375, vol. 66, No. 4.
Scott, J. et al., "Searching for Peptide Ligands with an Epitope Library," Sci., Jul. 27, 1990, pp. 386-390, vol. 249, No. 4967.
Seo, Y. et al., "Synthesis and biological evaluation of piperlongumine derivatives as potent anti-inflammatory agents," Bioorg. Med. Chem. Lett., Dec. 15, 2014, pp. 5727-5730, vol. 24, No. 24, Elsevier Ltd.
Serrano, M. et al., "Oncogenic ras provokes premature cell senescence associated with accumulation of p53 and p16INK4a," Cell, 1997, pp. 593-602, vol. 88.
Serrano, M. et al., "Putting the stress on senescence," Curr. Opin. Cell Biol., 2001, pp. 748-753, vol. 13.
Shao, L. et al., "Total body irradiation causes long-term mouse BM injury via induction of HSC premature senescence in an Ink4a- and Arf-independent manner," Blood, 2014, pp. 3105-3115, vol. 123.
Shao, L. et al., "Hematopoietic stem cell injury induced by ionizing radiation," Antioxid. Redox Signal., 2014, pp. 1447-1462, vol. 20.
Shirley, S. et al., "Targeting c-FLIP in cancer," Cancer Lett., 2013, pp. 141-150, vol. 332, No. 2, Elsevier Ireland Ltd.
Siegelin, M. et al., "Genistein enhances proteasomal degradation of the short isoform of FLIP in malignant glioma cells and thereby augments TRAIL-mediated apoptosis," Neurosci. Lett., Apr. 3, 2009, pp. 92-97, vol. 453, No. 2, Elsevier Ireland Ltd.
Sleebs, B. et al., "Quinazoline Sulfonamides as Dual Binders of the Proteins B-Cell Lymphoma 2 and B-Cell Lymphoma Extra Long with Potent Proapoptotic Cell-Based Activity," J. Med. Chem., 2011, pp. 1914-1926, vol. 54, No. 6.
Sleebs, B. et al., "Discovery of Potent and Selective Benzothiazole Hydrazone Inhibitors of Bcl-XL," J. Med. Chem., 2013, pp. 5514-5540, vol. 56, No. 13.
Son, D. et al., Piperlongumine inhibits atherosclerotic plaque formation and vascular smooth muscle cell proliferation by suppressing PDGF receptor signaling, Biochem. Biophys. Res. Commun., 2012, pp. 349-354, vol. 427.
Sorrentino, J. et al., "p16INK4a reporter mice reveal age-promoting effects of environmental toxicants," J. Clin. Invest., 2014, pp. 169-173, vol. 124.
Souers, A. et al., "ABT-199, a potent and selective BCL-2 inhibitor, achieves antitumor activity while sparing platelets," Nat. Med., 2013, pp. 202-208, vol. 19.
Stoll, R. et al., "Chalcone Derivatives Antagonize Interactions between the Human Oncoprotein MDM2 and p53," Biochem., 2001, pp. 336-344, vol. 40.
Tanaka, Y. et al., "Discovery of Potent Mcl-1/Bcl-xL Dual Inhibitors by Using a Hybridization Strategy Based on Structural Analysis of Target Proteins," J. Med. Chem., 2013, pp. 9635-9645, vol. 56, No. 23.
Tao, Z-F. et al., "Discovery of a Potent and Selective BCL-XL Inhibitor with in Vivo Activity," ACS Med. Chem. Lett., 2014, pp. 1088-1093, vol. 5.
Tchkonia, T. et al., "Cellular senescence and the senescent secretory phenotype: therapeutic opportunities," J. Clin. Invest., 2013, pp. 966-972, vol. 123.
Tse, C. et al., "ABT-263: a potent and orally bioavailable Bcl-2 family inhibitor," Can. Res., 2008, pp. 3421-3428, vol. 68.
Valentijn, F. et al., "Cellular senescence in the aging and diseased kidney," J. Cell Commun. Signal., 2018, pp. 69-82, vol. 12, Springer.
Van Deursen, J., "The role of senescent cells in ageing," Nature, 2014, pp. 439-446, vol. 509.
Van Willigenburg, H. et al., "Cellular senescence as a therapeutic target to improve renal transplantation outcome," Pharmacol. Res., Apr. 2018, pp. 322-330, vol. 130.
Vogler, M. et al., "Bcl-2 inhibitors: small molecules with a big impact on cancer therapy," Cell Death Differ., 2009, pp. 360-367, vol. 16.
Vogler, M., Targeting BCL2-Proteins for the Treatment of Solid Tumours, Adv. Med., 2014, pp. 1-14, Article ID 943648, Hindawi Publishing Corporation.
Wang, Y. et al., "Inhibition of phosphatidylinostol 3-kinase uncouples H2O2-induced senescent phenotype and cell aycle arrest in normal human diploid fibroblasts," Exp. Cell Res., 2004, pp. 188-196, vol. 298, Elsvier Inc.
Wang, Y. et al., "Total body irradiation selectively induces murine hematopoietic stem cell senescence," Blood, Jan. 1, 2006, pp. 358-366, vol. 107, No. 1.
Wang, Y. et al., "Microrna Regulation of Ionizing Radiation-Induced Premature Senescence," Int. J. Radiation Oncology Biol. Phys., 2011, pp. 839-848, vol. 81, No. 3, Elsevier Inc.
Wang, B. et al., "The Bcl-2/xL inhibitor Abt-263 increases the stability of Mcl-1 mRNA and protein in hepatocellular carcinoma cells," Molecular Cancer, 2014, pp. 1-11, vol. 13, No. 98.
Wang, E., "Senescent Human Fibroblasts Resist Programmed Cell Death, and Failure to Suppress bcl2 Is Involved," Cancer Res., Jun. 1, 1995, pp. 2284-2292, vol. 55.
Wang, Y. et al., "Total body irradiation causes residual bone marrow injury by induction of persistent oxidative stress in murine hematopoietic stem cells," Free Rad. Biol. Med., 2010, pp. 348-356, vol. 48, Elsevier Inc.
Waring, P. et al., "Cell death induced by the Fas/Fas ligand pathway and its role in pathology," Immunology and Cell Biology, 1999, pp. 312-317, vol. 77.
Warner, H. et al., "What Does Cell Death Have to Do With Aging?," JAGS, 1997, pp. 1140-1146, vol. 45, No. 9.
Wood, T. et al., "Selective Inhibition of Histone Deacetylases Sensitizes Malignant Cells to Death Receptor Ligands," Mol. Cancer Ther., Jan. 2010, pp. 246-256, vol. 9, No. 1.
Kirkland, J. et al., "Clinical strategies and animal models for developing senolytic agents," Exp. Gastroenterol., 2015, pp. 19-25, vol. 68, Elsevier Inc.
Office Action dated Apr. 17, 2019 from related U.S. Appl. No. 15/545,480; 15 pgs.
Tampe, D. et al., "Potential approaches to reverse or repair renal fibrosis," Nat. Rev. Nephrol., Apr. 2014, pp. 226-237, vol. 10.
International Search Report and Written Opinion dated Apr. 26, 2019 from related International Patent Application No. PCT/US2019/014545; 10 pgs.
Extended European Search Report dated Sep. 30, 2019 from European Patent Application No. 17786729.8.
Kirkland, et al., Am Geriatr Soc. Oct. 2017; 65(10); 2297-2301 (Year : 2017).
Varnes, Jeffrey G., et al., "Towards the next generation of dual Bcl-2/Bcl-xLinhibitors, Bioorganic & Medicinal Chemistry Letters, vol. 24, No. 14, May 20, 2014, pp. 3026-3033."

(56) References Cited

OTHER PUBLICATIONS

Wang, Xin, et al., New Strategy for Renal Fibrosis: Targeting Smad3 Proteins for Ubiquitination and Degradation, Biochemical Pharmacology, vol. 115, Sep. 15, 2016, pp. 200-209.

* cited by examiner

COMPOUNDS THAT INDUCE DEGRADATION OF ANTI-APOPTOTIC BCL-2 FAMILY PROTEINS AND THE USES THEREOF

CROSS REFERENCE TO RELATED APPLICATIONS

This application claims the benefit of International Application No. PCT/US17/28875, filed Apr. 21, 2017, and U.S. Provisional Application No. 62/325,856, filed Apr. 21, 2016, the disclosures of which are hereby incorporated by reference in their entirety.

FIELD OF THE INVENTION

The present invention relates to compositions that induce the degradation of anti-apoptotic Bcl-2 family proteins and their method of use in the treatment of various cancers and treatment and prevention of diseases and pathologies related to accumulation of senescent cells during aging, such as aging, cancer, chronic obstructive pulmonary disease (COPD), osteoarthritis, atherosclerosis, neurodegenerative diseases, diabetes, and many others. The present invention also relates to pharmaceutical compositions containing these compounds as well as various uses thereof.

BACKGROUND OF THE INVENTION

Aging is the major risk factor for most functional deficits and many diseases in human, such as cancers, osteoarthritis, osteoporosis, atherosclerosis, neurodegenerative diseases, and diabetes. An increasing body of evidence demonstrates that aging is associated with an accumulation of senescent cells (Campisi, *Cell* 120:513-522, 2005; Campisi, *Curr. Opin. Genet. Dev.* 21:107-112, 2011; Rodier and Campisi, *J. Cell Biol.* 192:547-556, 2011). Senescent cell accumulation in tissues and organs is believed to cause tissue degradation and loss of function due to the increased levels of free radicals and various inflammatory mediators produced by senescent cells. Therefore, selective depletion of senescent cells may be a novel anti-aging strategy that may prevent cancer and various human diseases associated with aging and rejuvenate the body to live a healthier lifespan. This hypothesis is supported by recent findings that selective elimination of p16$^{Ink4a}$ (p16)-positive senescent cells in BubR1 hypomorphic progeroid mouse model via a genetic approach extended the animals' healthy lifespan by delaying the onset of several age-related pathologies, such as cataracts, sarcopenia, and lordokyphosis (Baker et al., *Nature* 479:232-236, 2011; Baker et al., *Nature* 530.184-189, 2016). These studies validated the great therapeutic potential of targeting senescent cells.

The Bcl-2 (B-cell lymphoma-2) family of proteins is a group of regulator proteins that plays a central role in regulating cell death by either inducing (pro-apoptotic) or inhibiting (anti-apoptotic) apoptosis. Anti-apoptotic Bcl-2 family of proteins, such as Bcl-2, Bcl-xL, Bcl-W, and Mcl-1, has been proven to be an attractive target for the development of novel anti-cancer agents (Lessene et al., *Nat. Rev. Drug Discov.* 7:989-1000, 2008; Vogler et al., *Cell Death Differ.* 2009; 16:360-367; Delbridge et al., *Nat. Rev. Cancer* 16:99-109, 2016). Numerous Bcl-2 small molecule inhibitors have been reported (Bajwa et al., *Expert Opin. Ther. Patents* 22:37-55, 2012; Vogler, *Adv. Med.* 1-14, 2014). The following are some of the Bcl-2 small molecule inhibitors that have been investigated at various stages of drug development: ABT-737 (US20070072860), navitoclax (ABT-263, WO2009155386), venetoclax (ABT-199, WO2010138588), obatoclax (GX 15-070, WO2004106328), (−)-gossypol (AT-101, WO2002097053), sabutoclax (BI-97C1, WO2010120943), TW-37 (WO2006023778), BM-1252 (APG-1252), and A-1155463 (WO2010080503). Venetoclax, a selective Bcl-2 inhibitor, was approved by the FDA in April 2016 for the treatment of chronic lymphocytic leukemia with 17-p deletion.

The Bcl-2 family of proteins has also been found to be a potential target for the development of "senolytic" drugs, drugs that targeting senescent cells for the delay of aging or treatment of aging-associated disease. For example, navitoclax (ABT-263), an inhibitor of Bcl-2, Bcl-xL, and Bcl-W, has been shown to selectively kill senescent cells in culture and deplete senescent cells in aged mice (WO2015171591; Chang et al., *Nat. Med.* 22:78-83, 2016; Zhu et al., *Aging Cell* 2016).

Thus, there is a need in the art to develop compounds capable of selectively targeting senescent cells and degrading the Bcl-2 family of proteins.

SUMMARY OF THE INVENTION

One aspect of the present invention encompasses a compound comprising Formula (II):

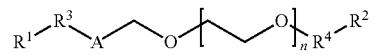

wherein
R$^1$ is selected from the group consisting of:

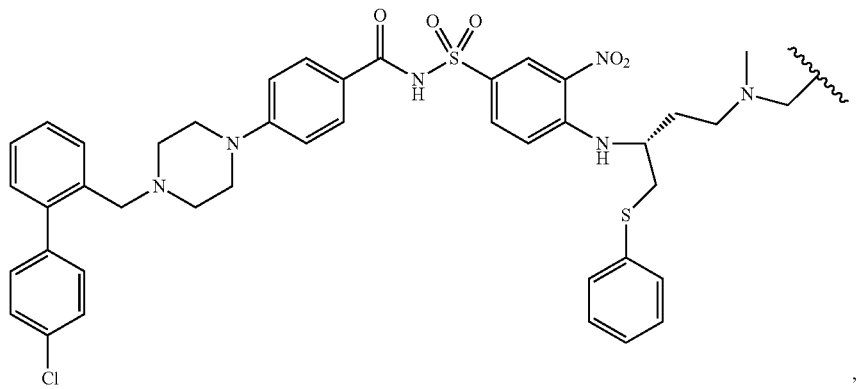

-continued
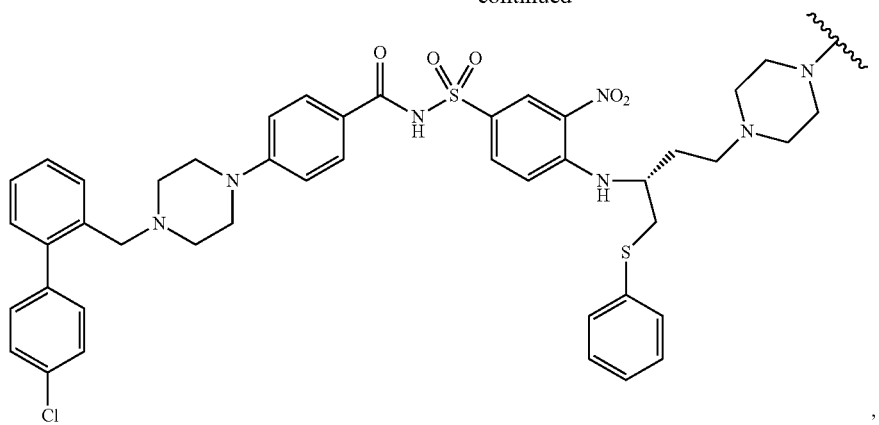
,
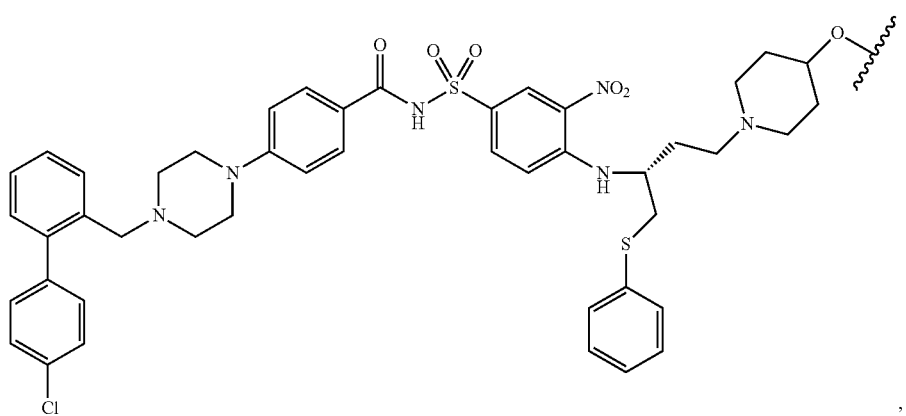
,
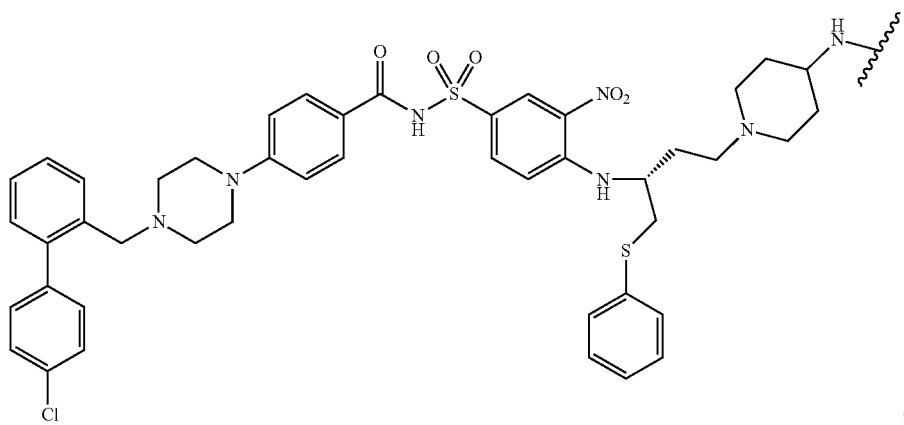
,
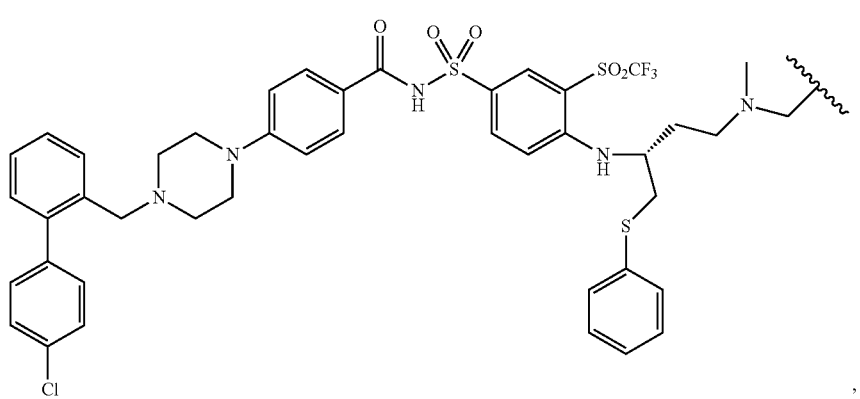
,

-continued
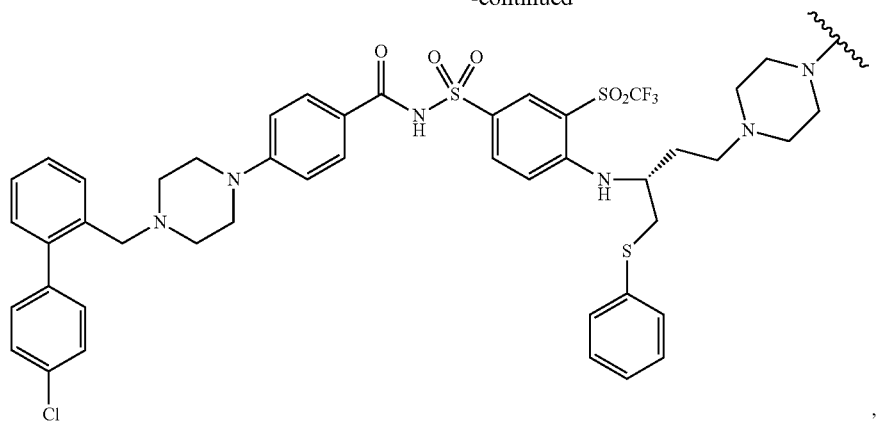
,
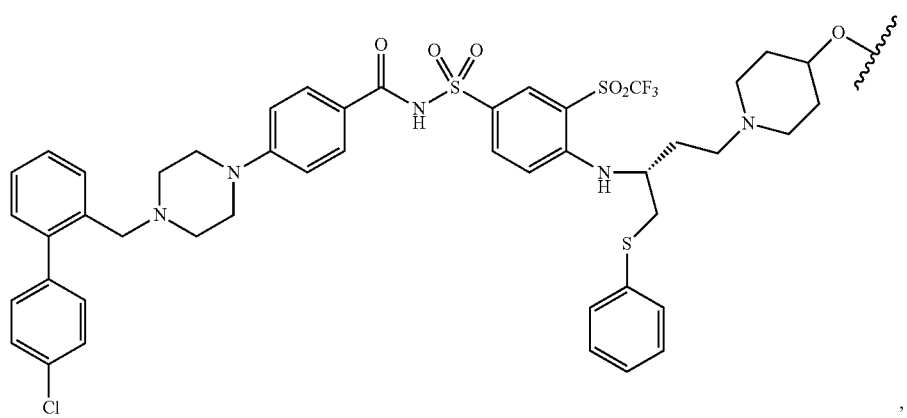
,
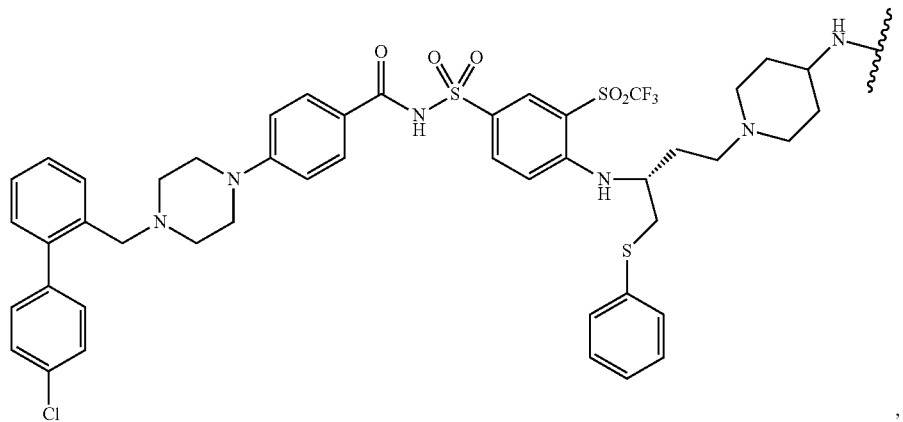
,
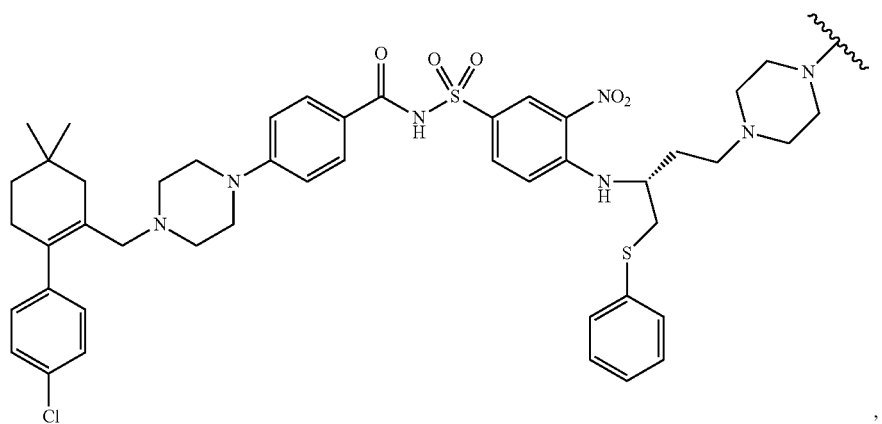
,

-continued
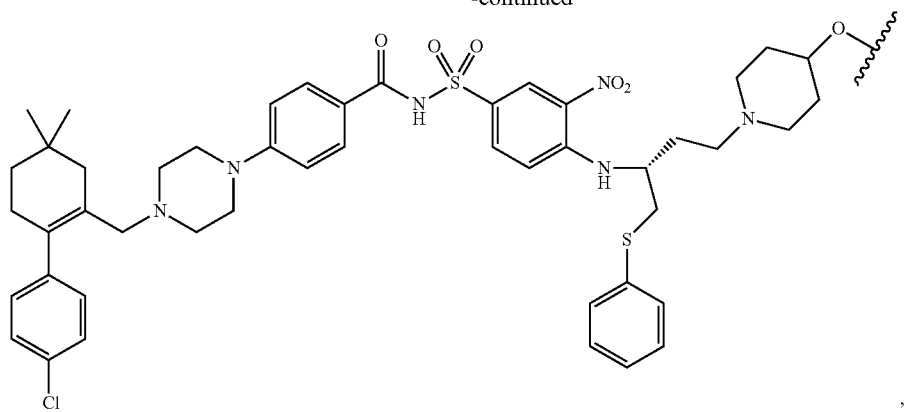
,
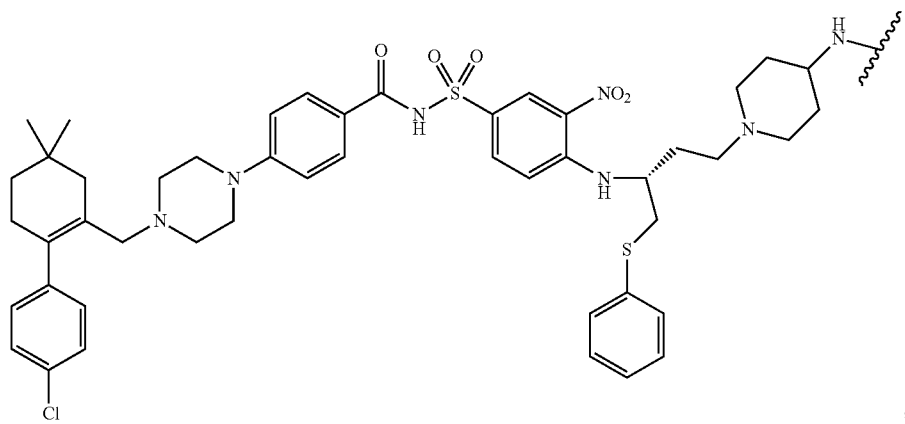
,
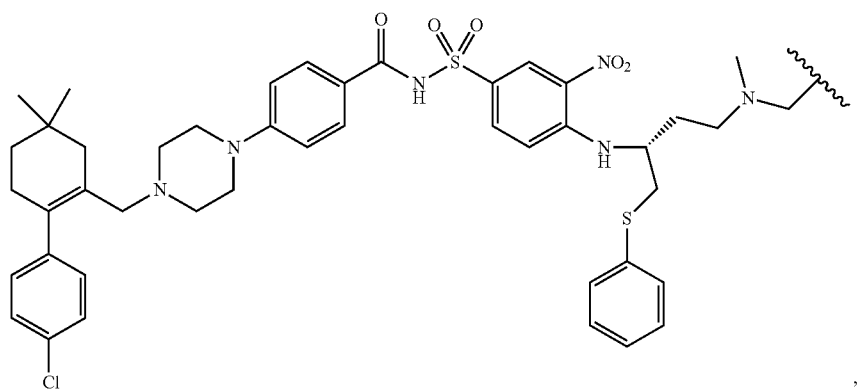
,
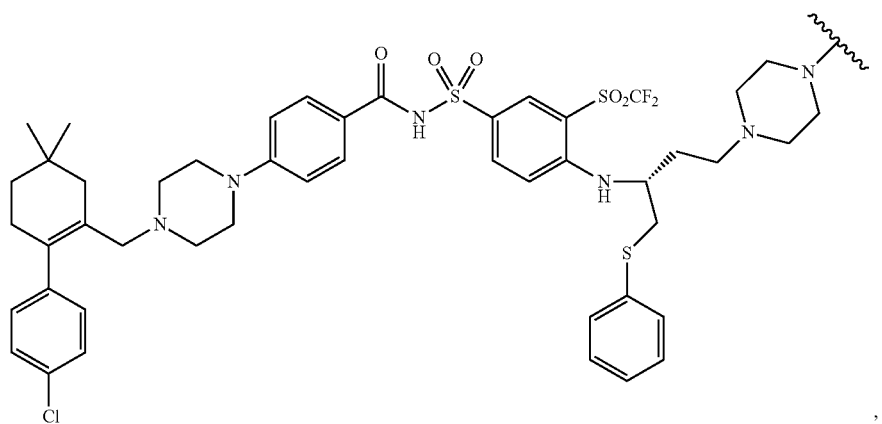
,

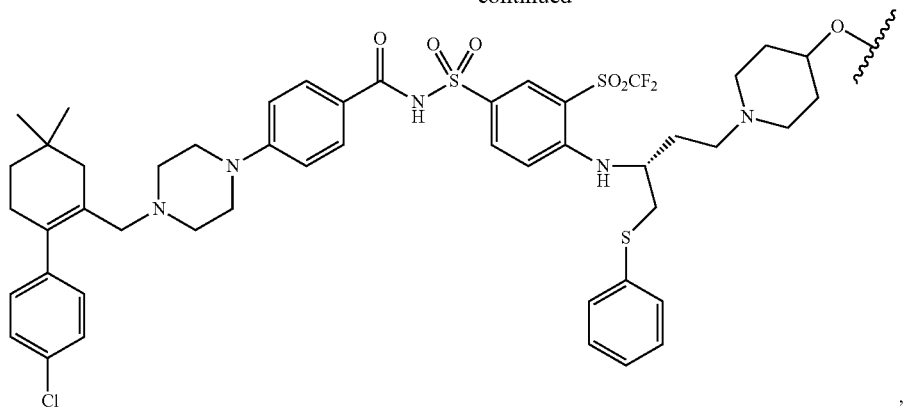
,
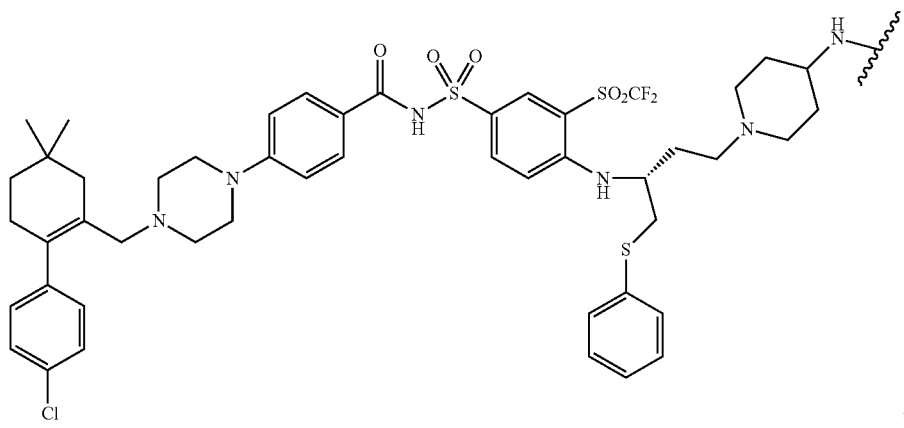
,
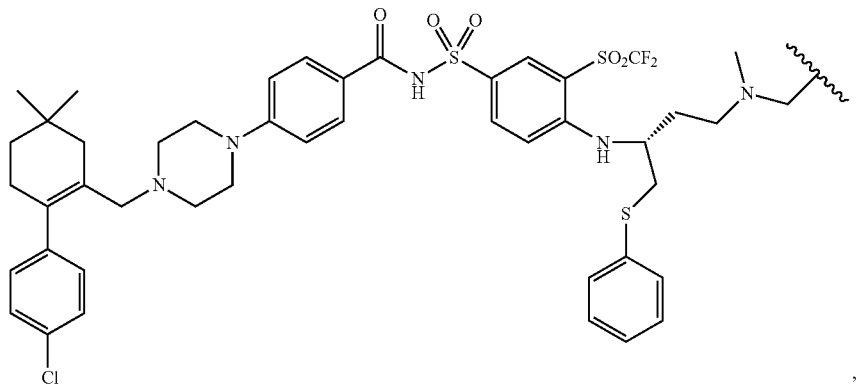
,
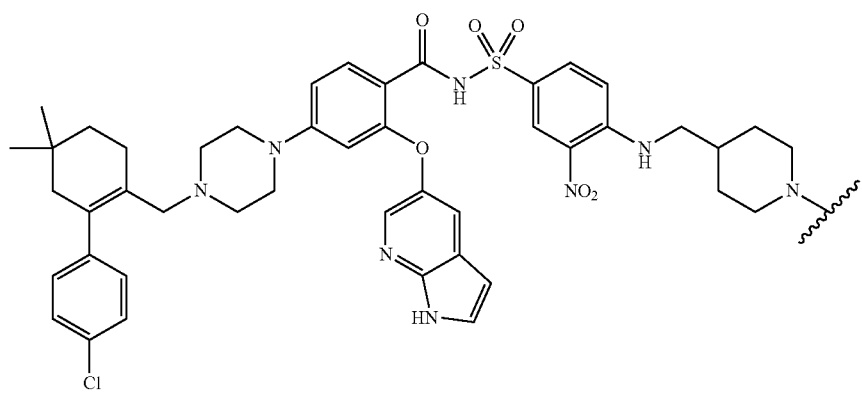
,

-continued
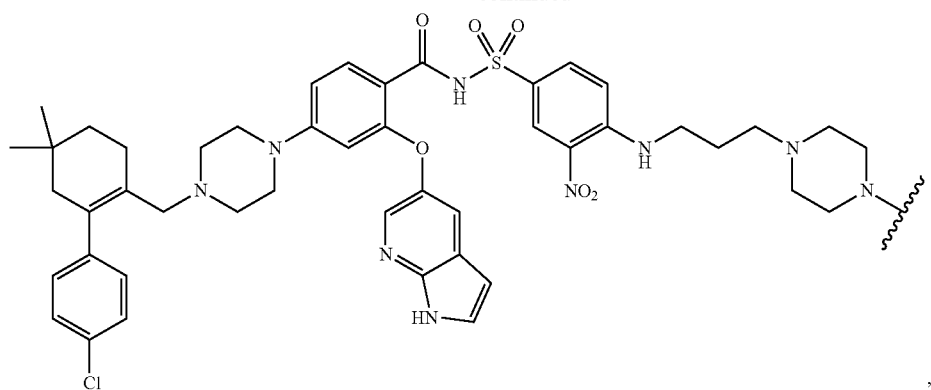
,
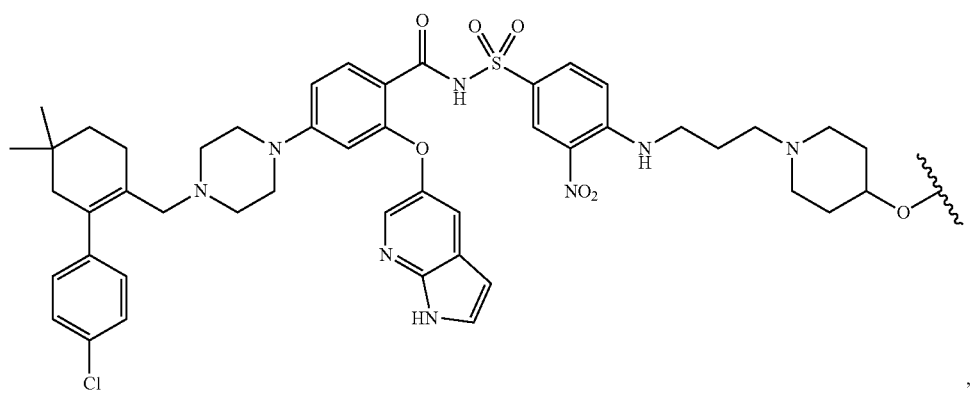
,
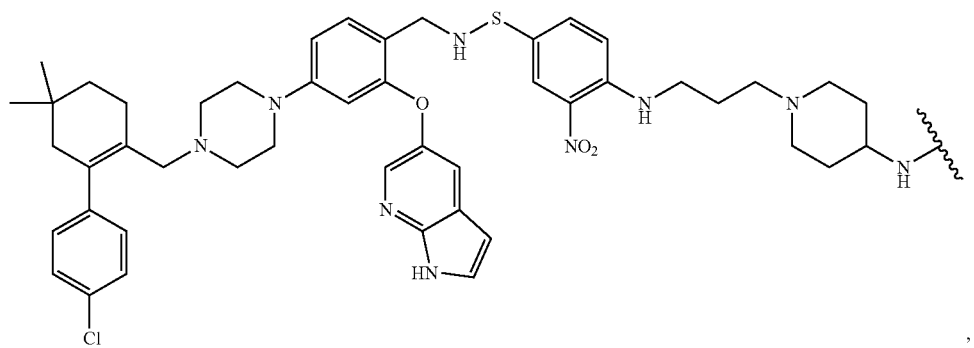
,
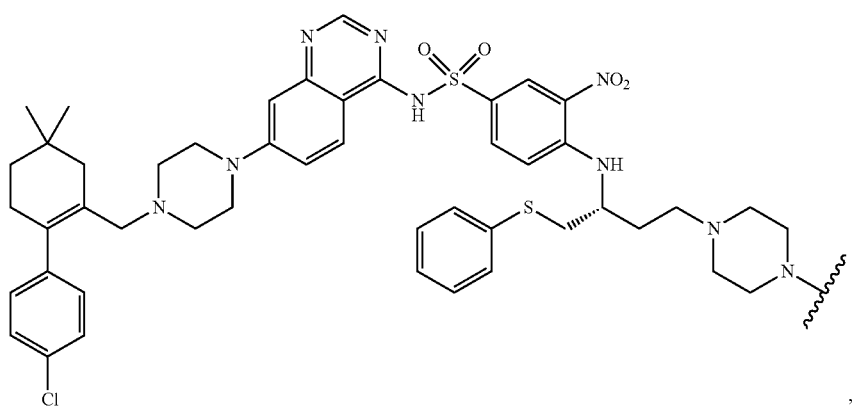
,

-continued
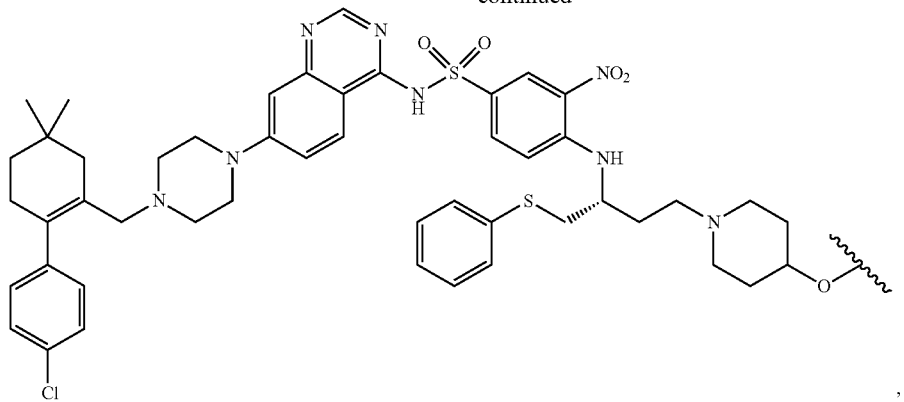
,
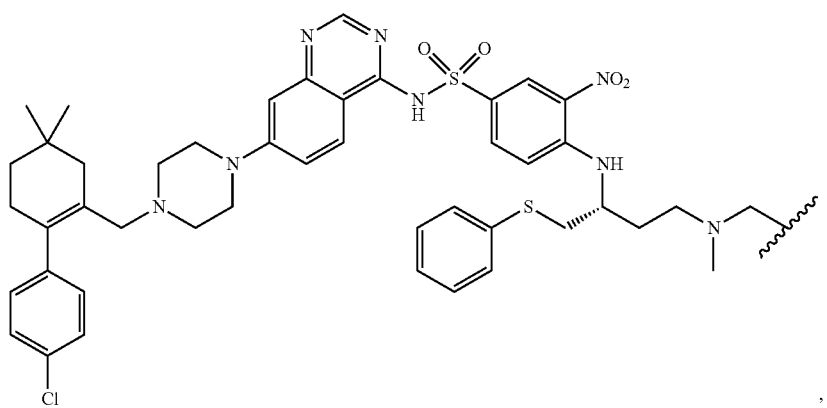
,
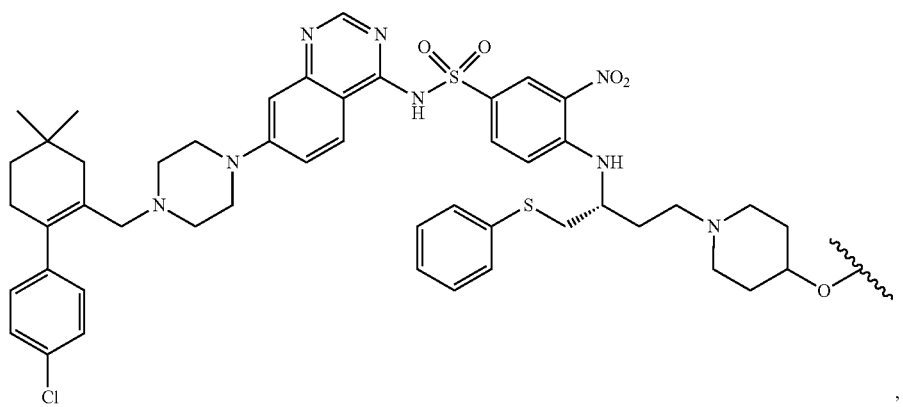
,
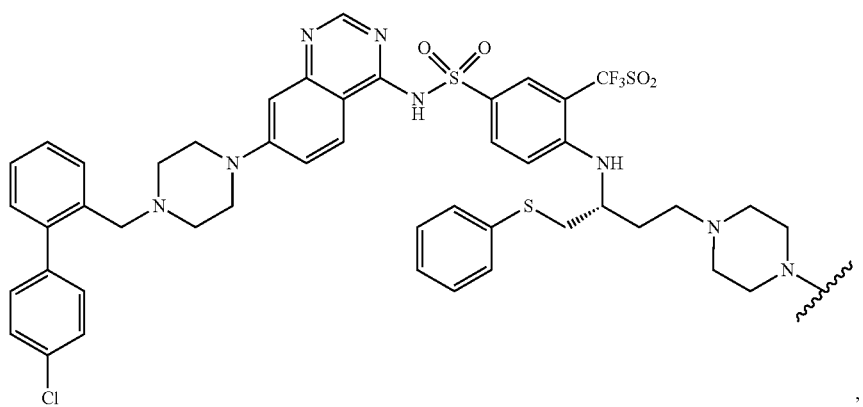
,

-continued
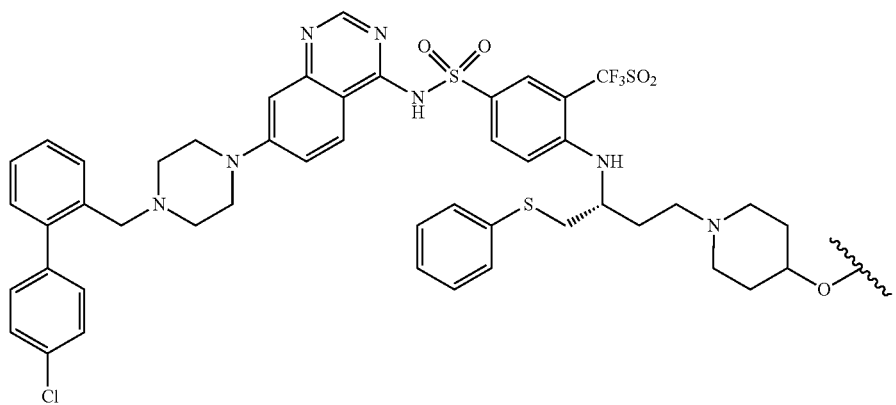
,
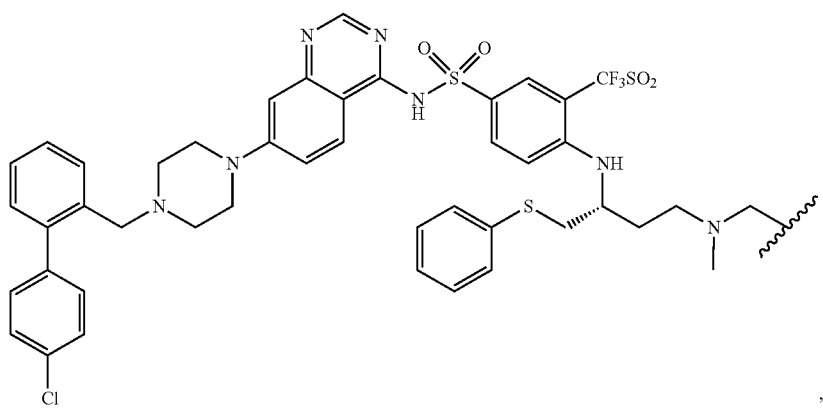
,
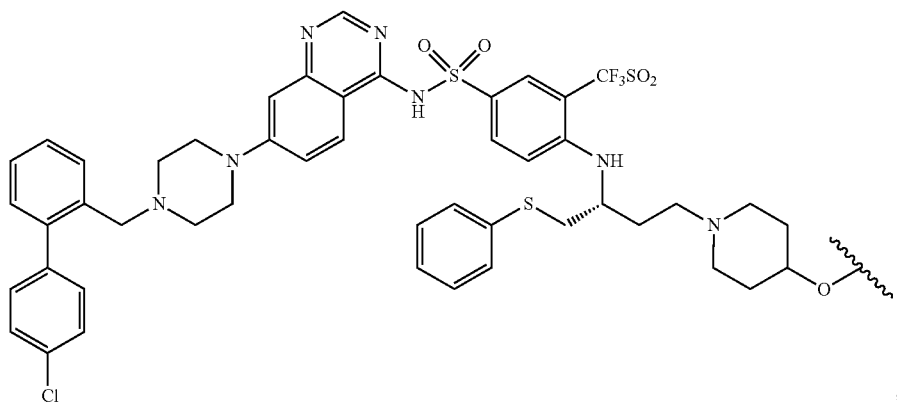
,
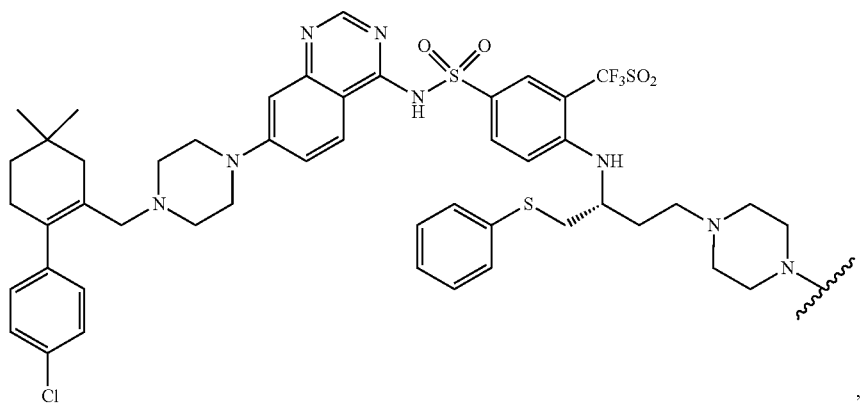
,

-continued
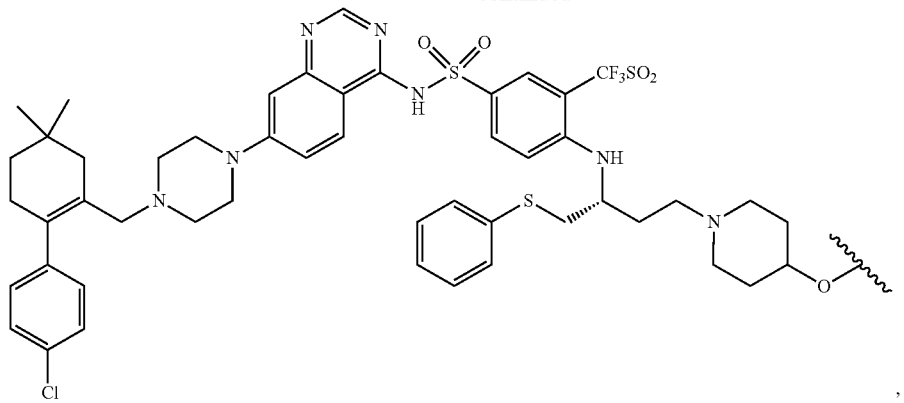
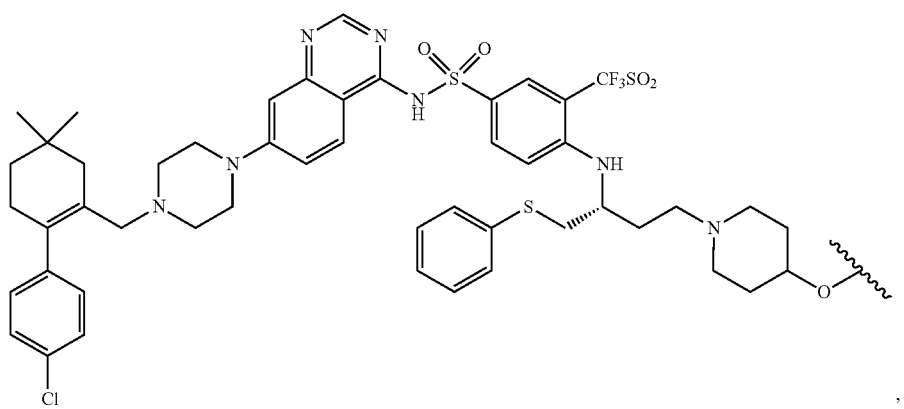
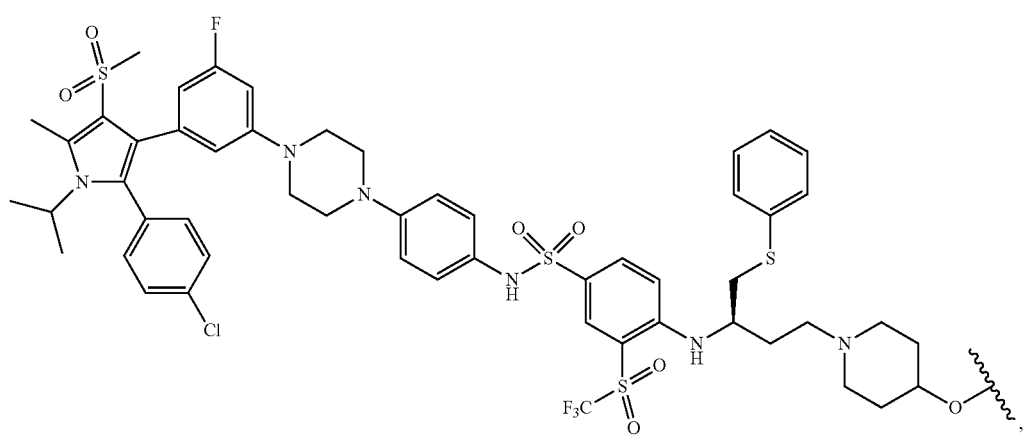

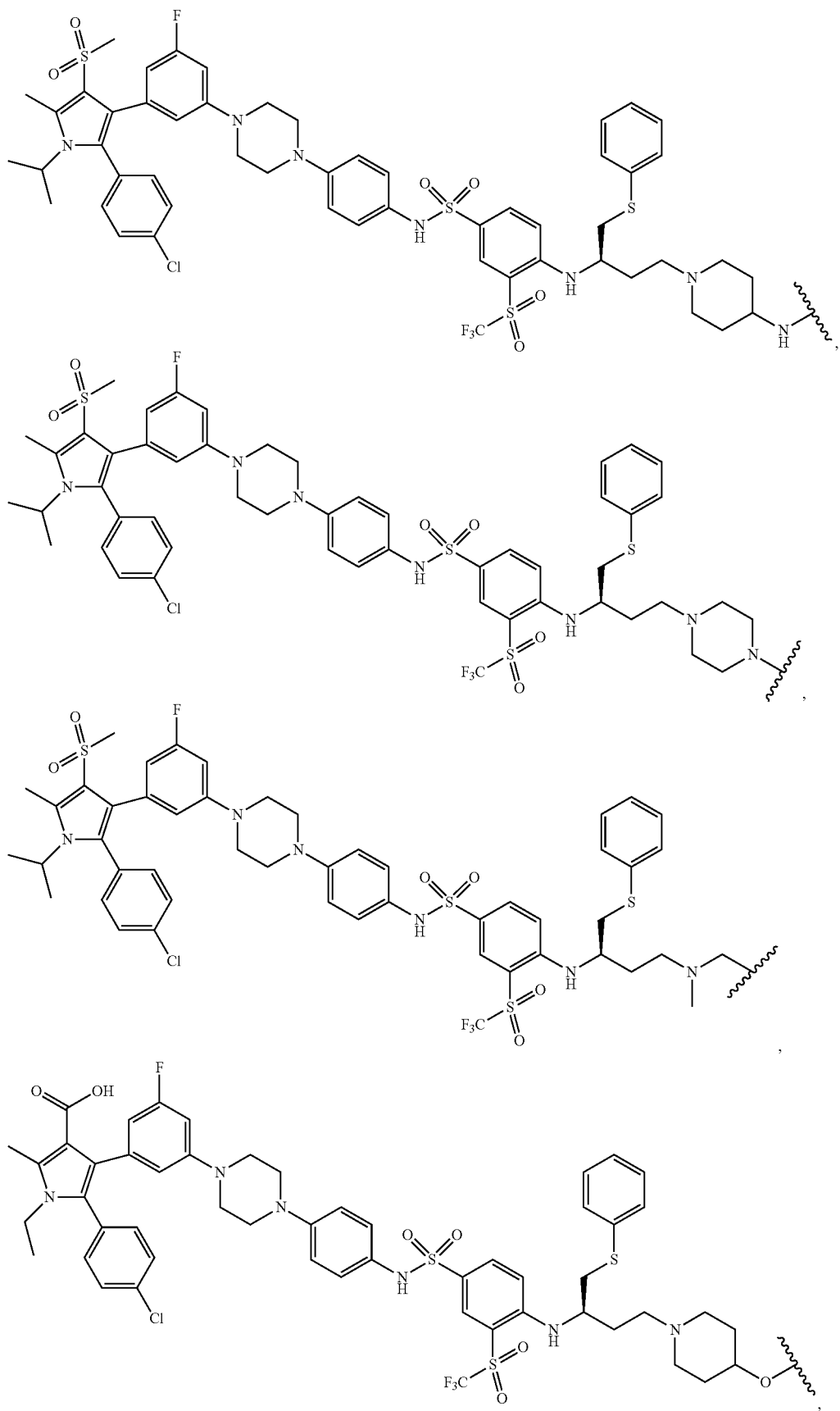

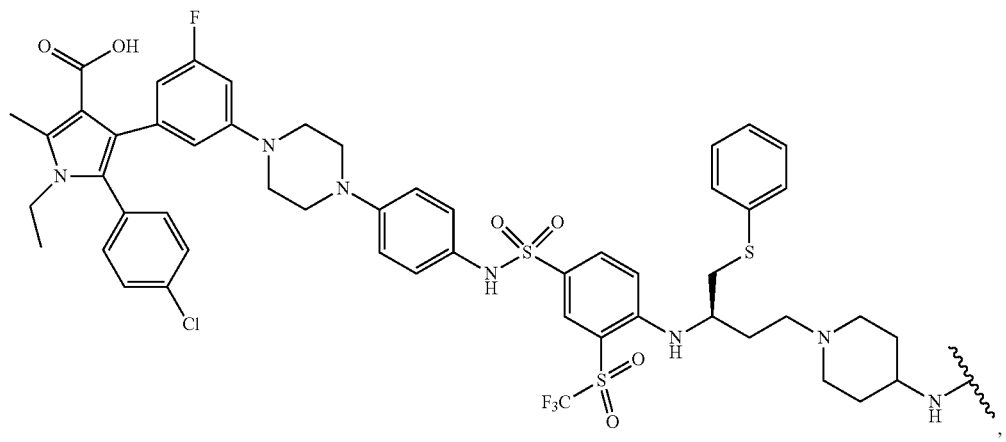
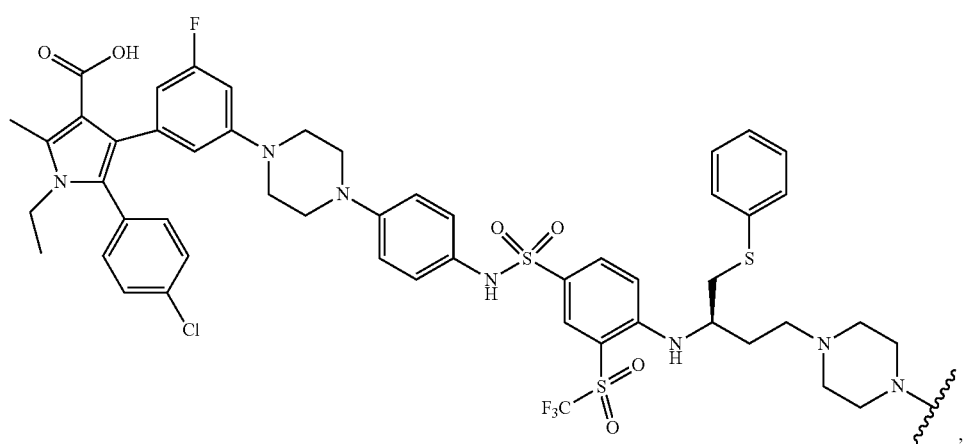
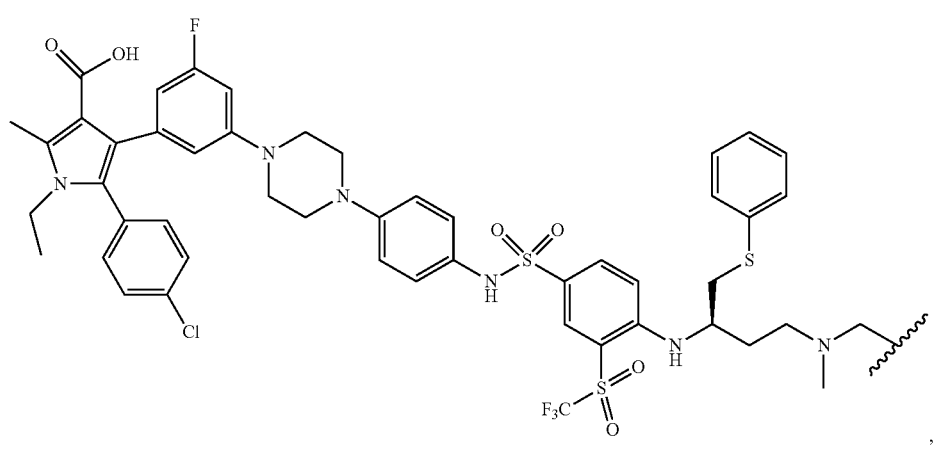
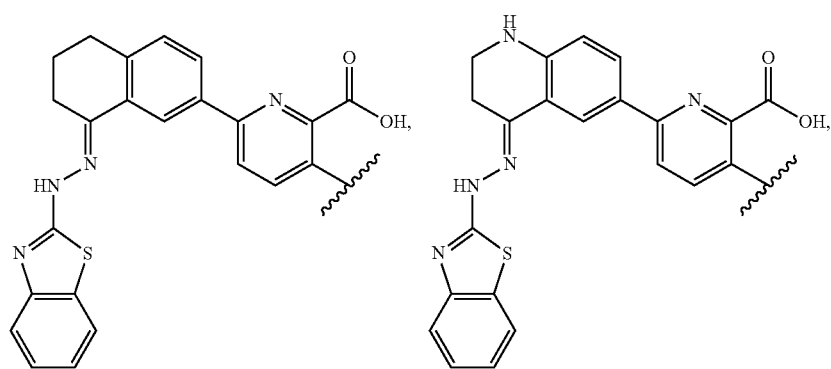

-continued
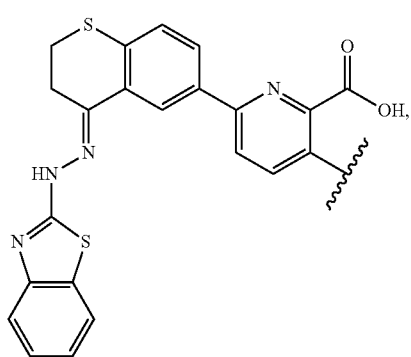
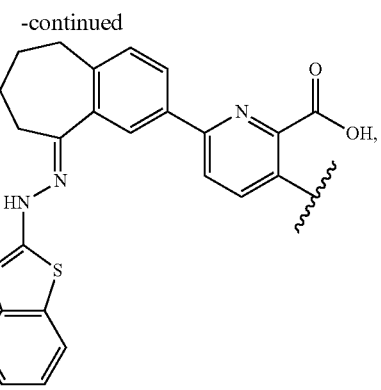
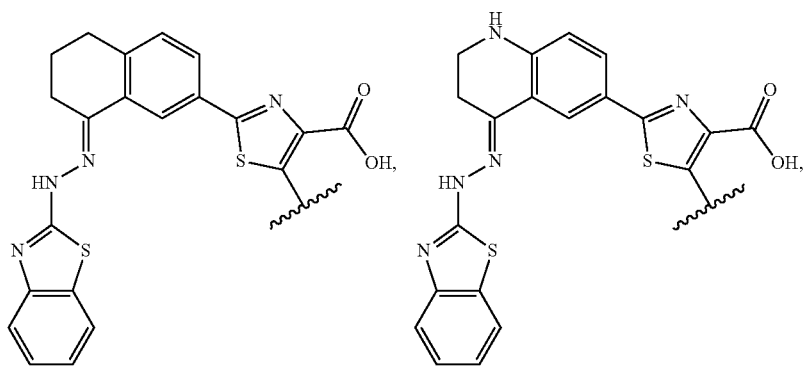
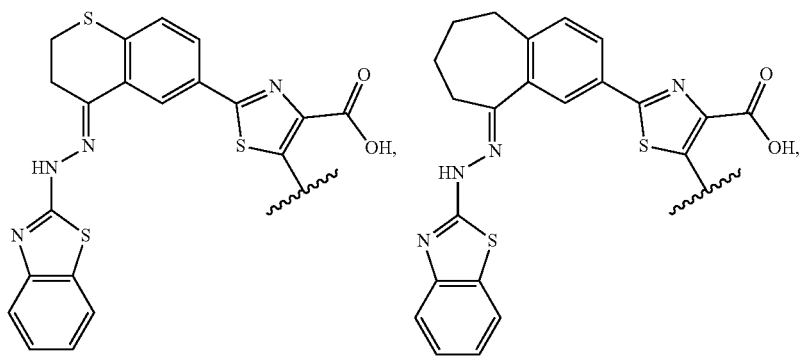
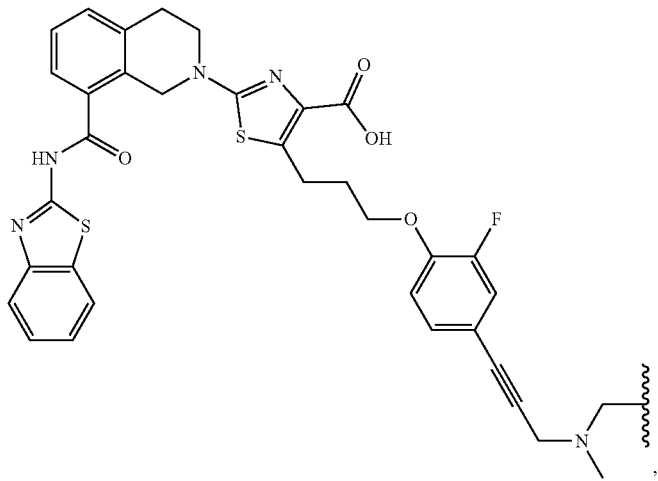

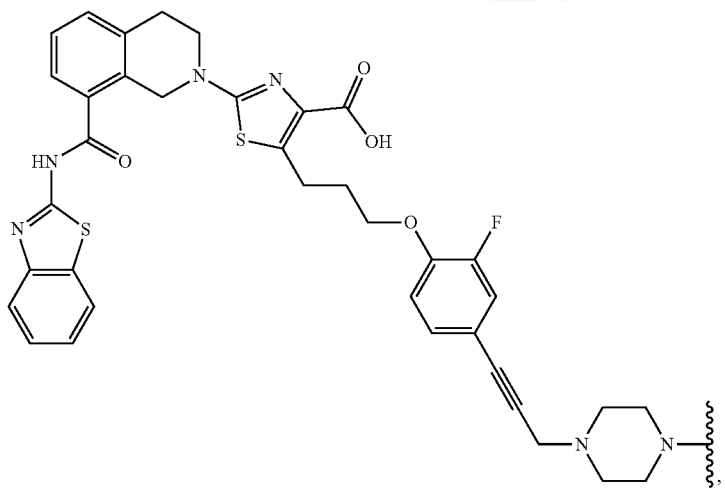
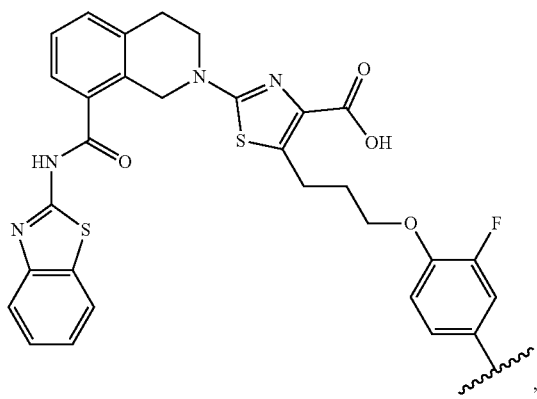
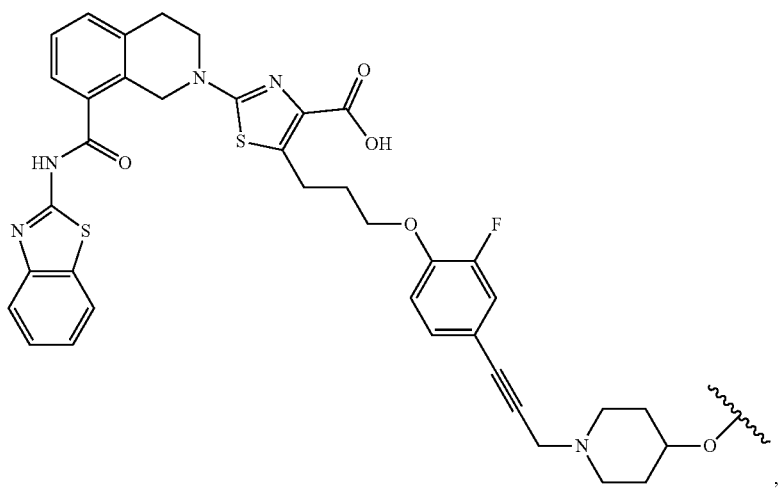

-continued
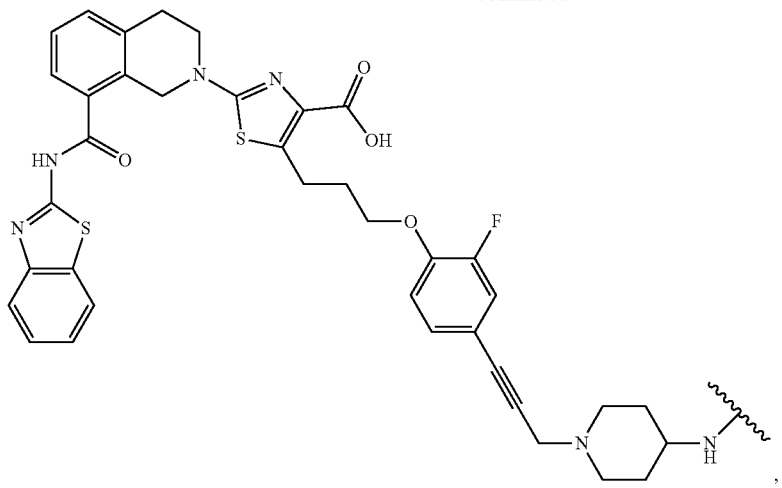
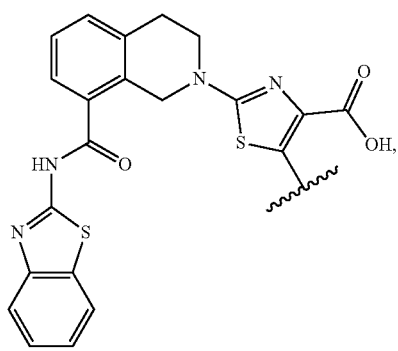
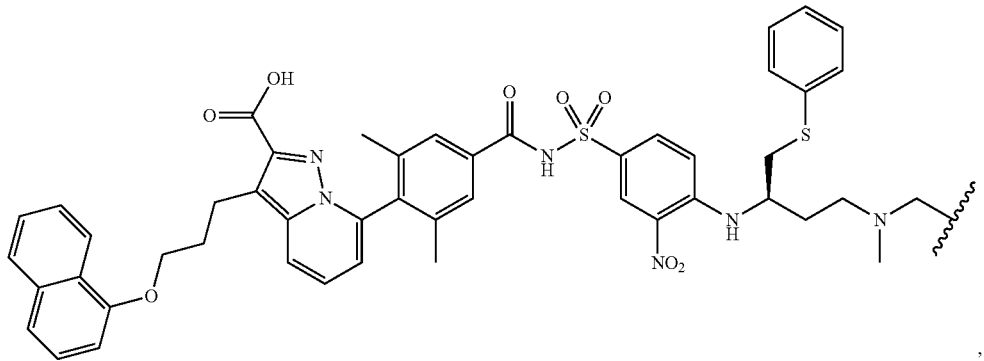
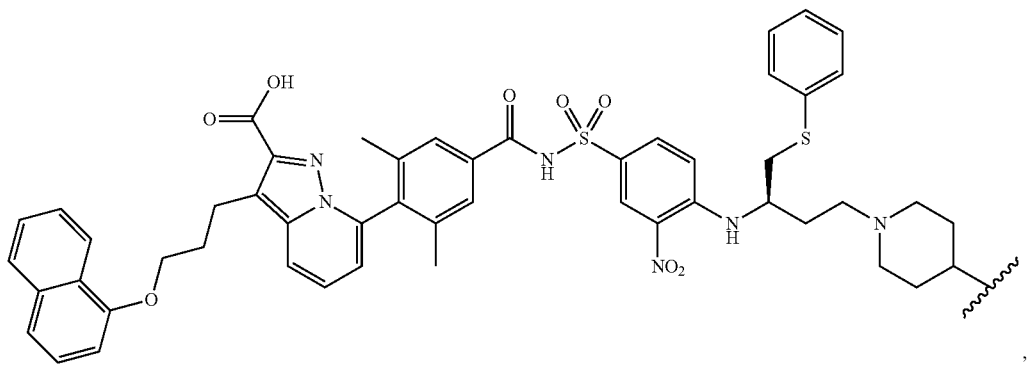

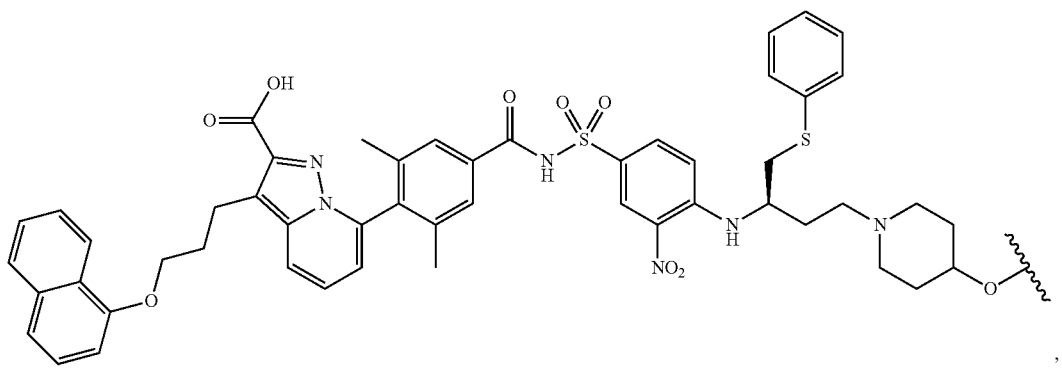
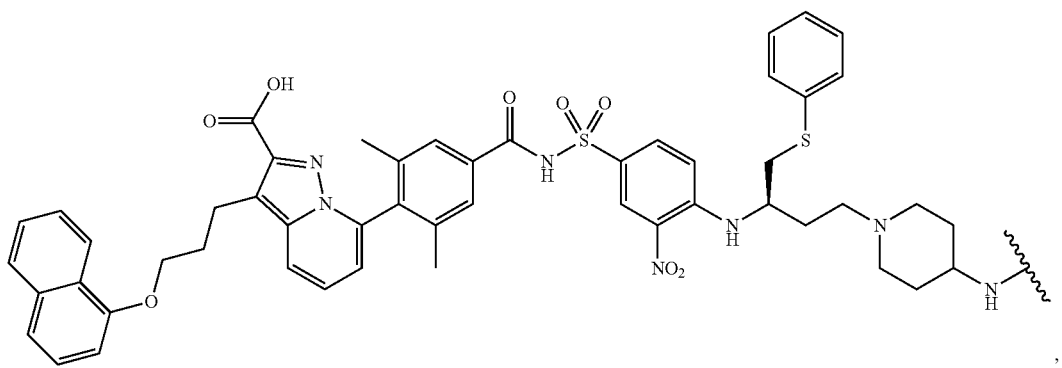
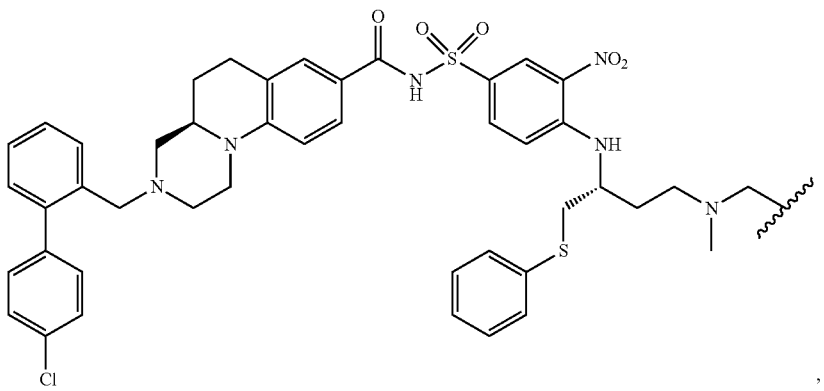
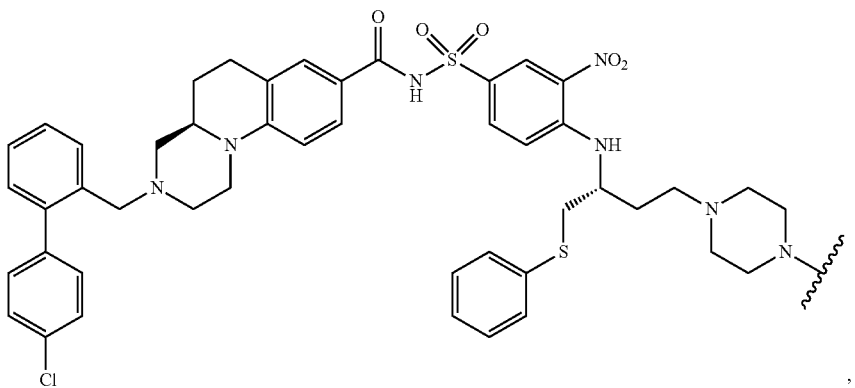

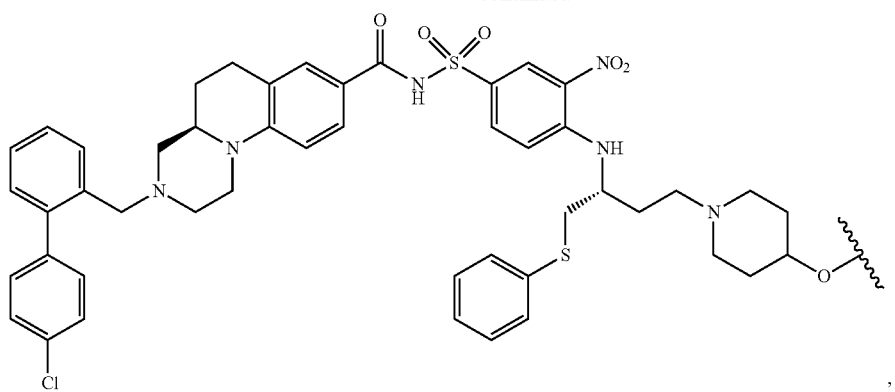
,
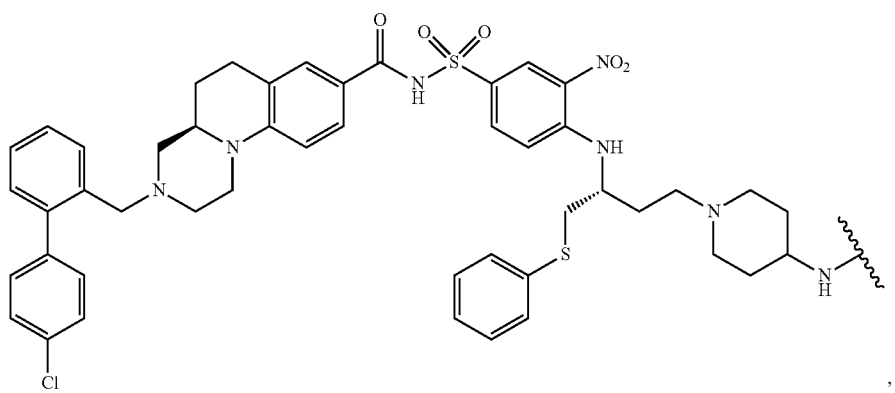
,
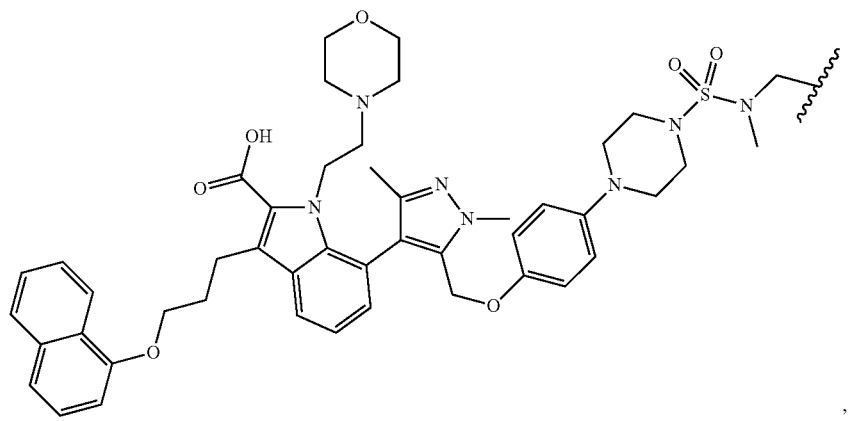
,
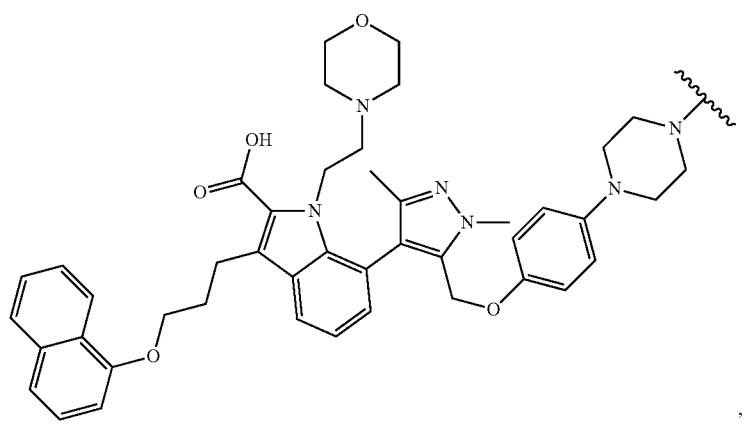
,

-continued
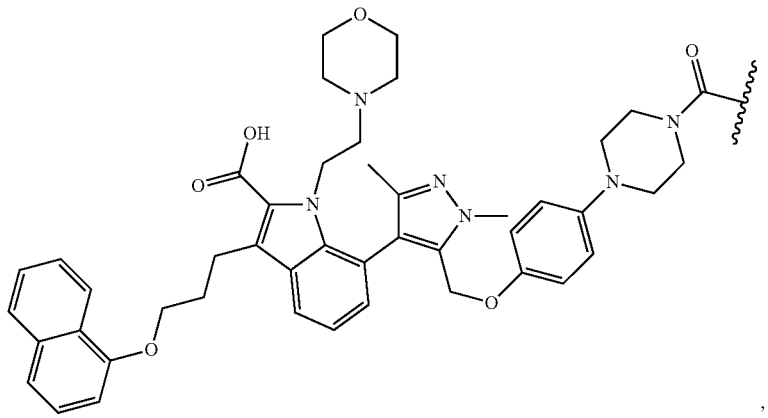
,
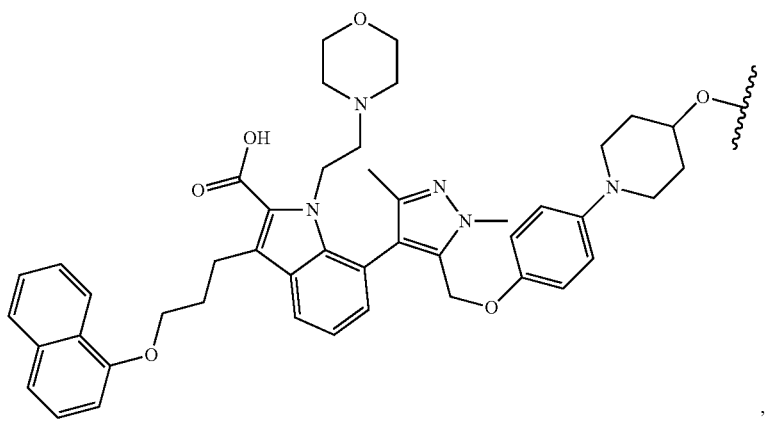
,
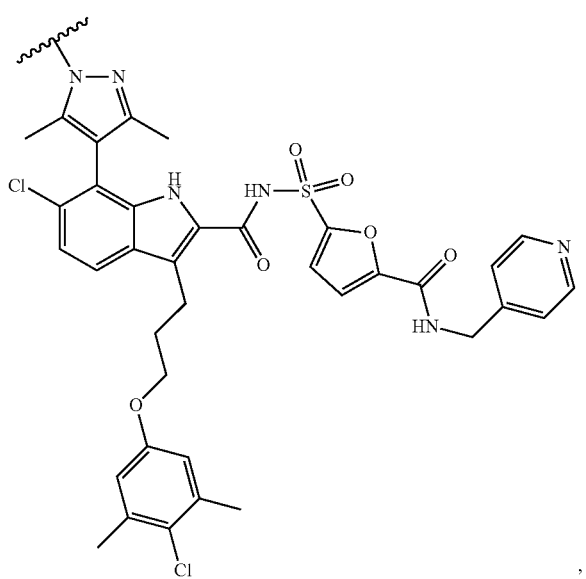
,

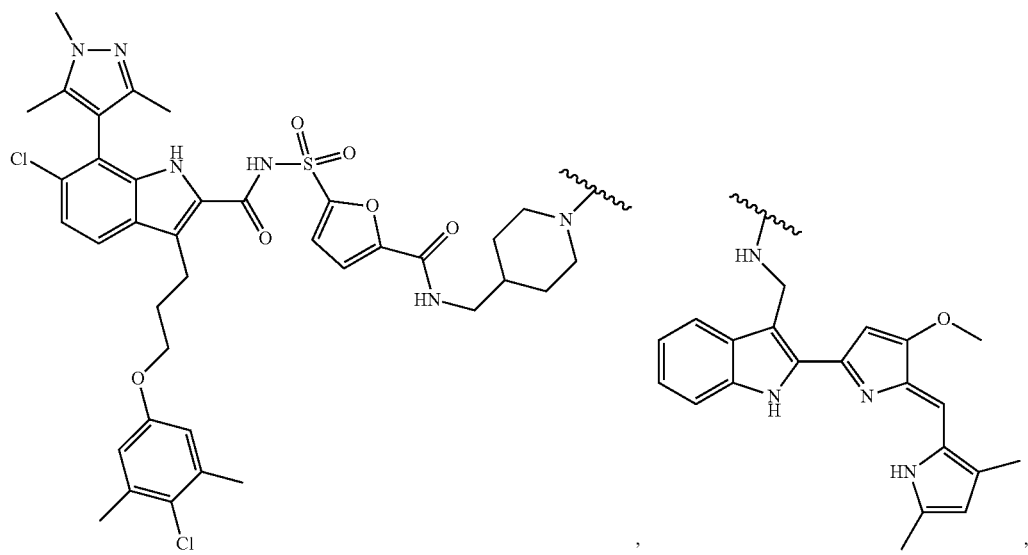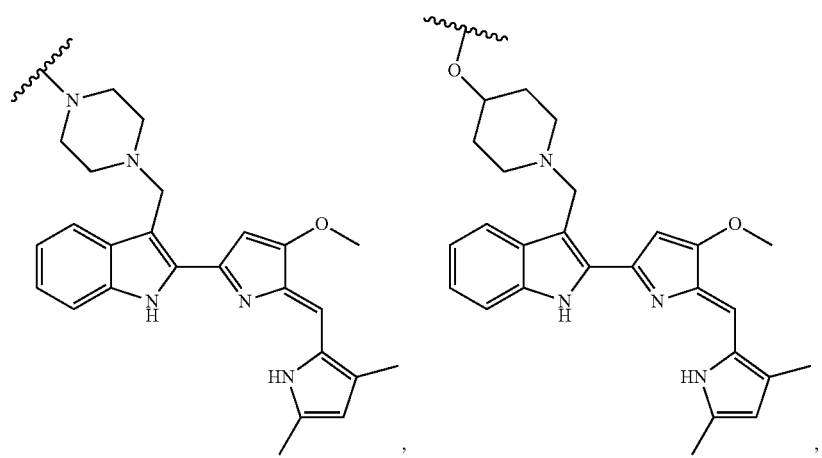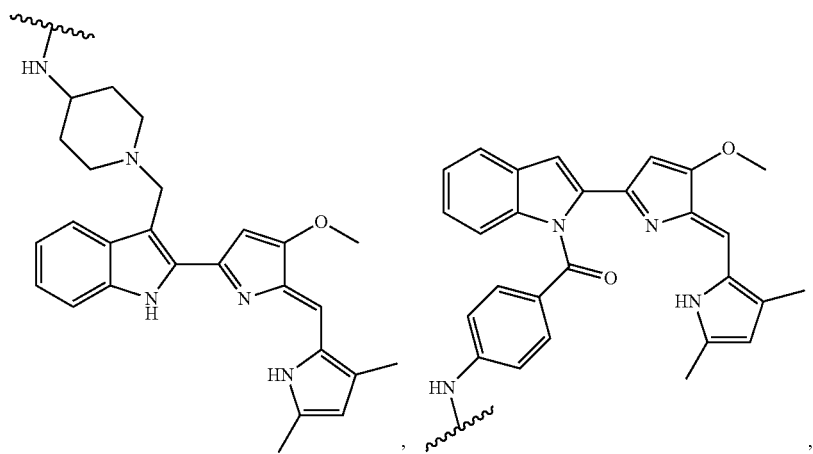

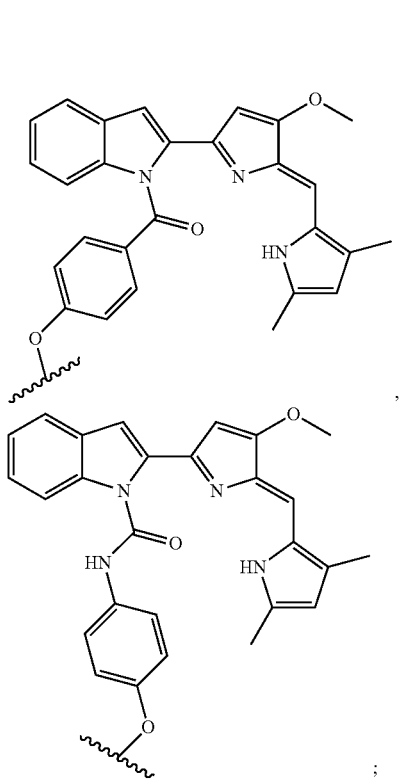
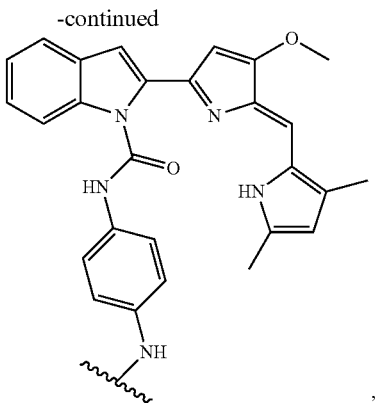
, and
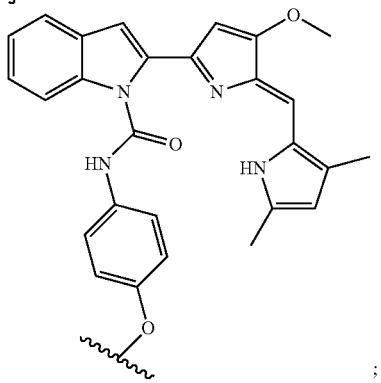
;
R³ is absent, a bond, or a substituted or unsubstituted C₁-C₁₀ alkyl;
A is absent, a bond, a substituted or unsubstituted C₁-C₆ aryl, a substituted or unsubstituted C₁-C₆ cycloalkyl, or a substituted or unsubstituted C₁-C₆ heterocyclic group;
R⁴ is a bond or a substituted or unsubstituted C₁-C₁₀ alkyl;
n is an integer from 0 to 5;
R² is selected from the group consisting of
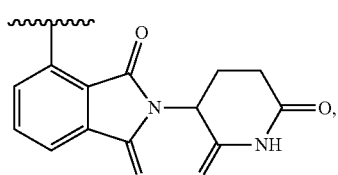
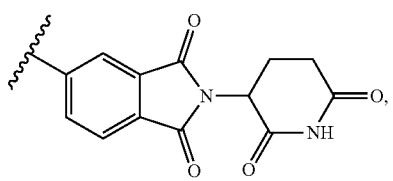
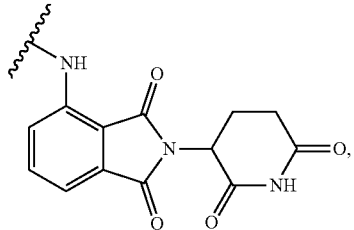
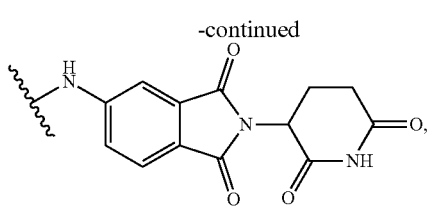
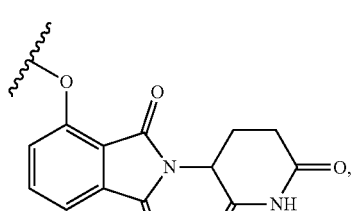
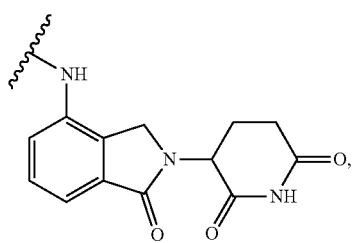

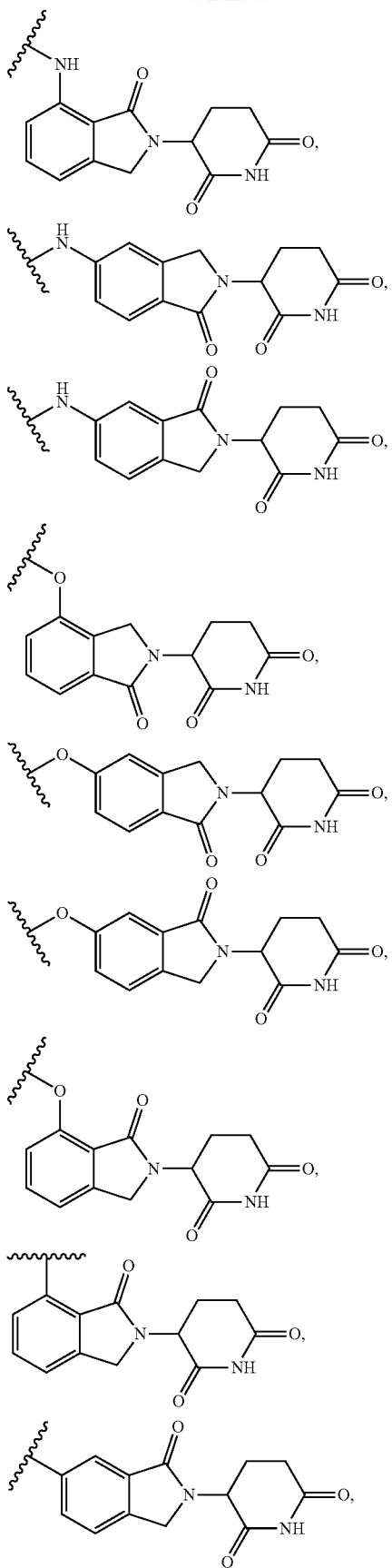
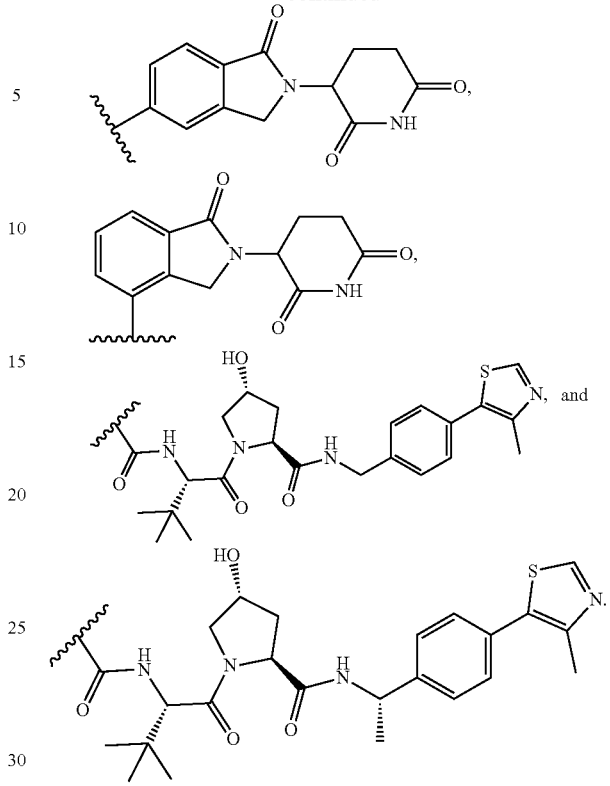

The invention also encompasses a method of killing one or more senescent cells in a subject. The method comprises administering a therapeutically effective amount of a compound of the invention to a subject in need thereof.

In another aspect, the invention encompasses a method for delaying at least one feature of aging in a subject. The method comprises administering a therapeutically effective amount of a compound of the invention to a subject in need thereof.

In yet another aspect, the invention encompasses a method of treating an age-related disease or condition. The method comprises administering a therapeutically effective amount of a compound of the invention to a subject in need thereof.

In still yet another aspect, the invention encompasses a method of killing therapy-induced senescent cells. The method comprises administering a therapeutically effective amount of a compound of the invention to a subject in need thereof who has received DNA-damaging therapy and killing therapy induced-senescent cells in normal and tumor tissues following DNA-damaging therapy.

DETAILED DESCRIPTION OF THE INVENTION

Figure 1A:
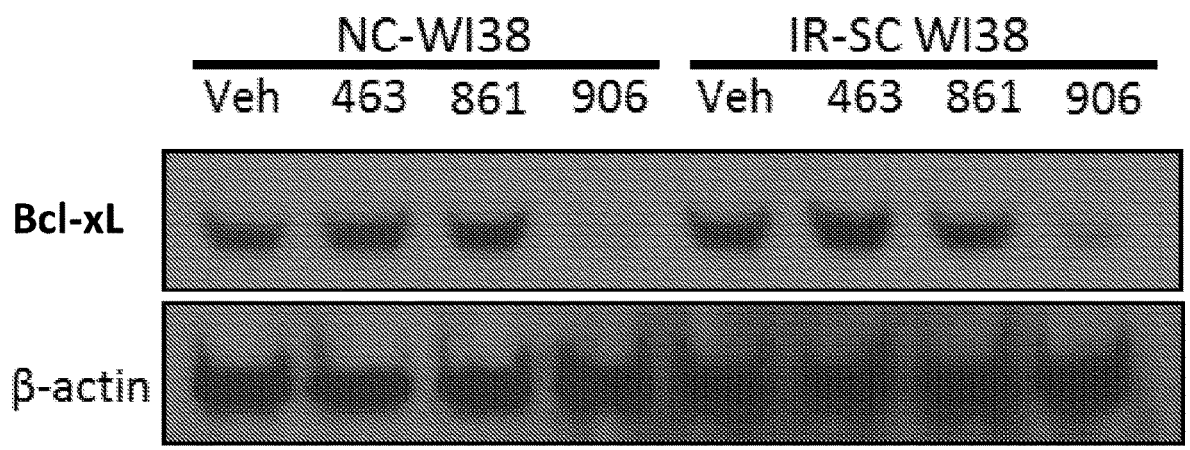
FIG. 1A and FIG. 1B depicts graphs that show XZ-13906 (2 µM) depletes Bcl-xL in normal WI38 (NC-WI38) and ionizing radiation induced senescent WI38 (IR-SC WI38 cells).
Figure 1B:
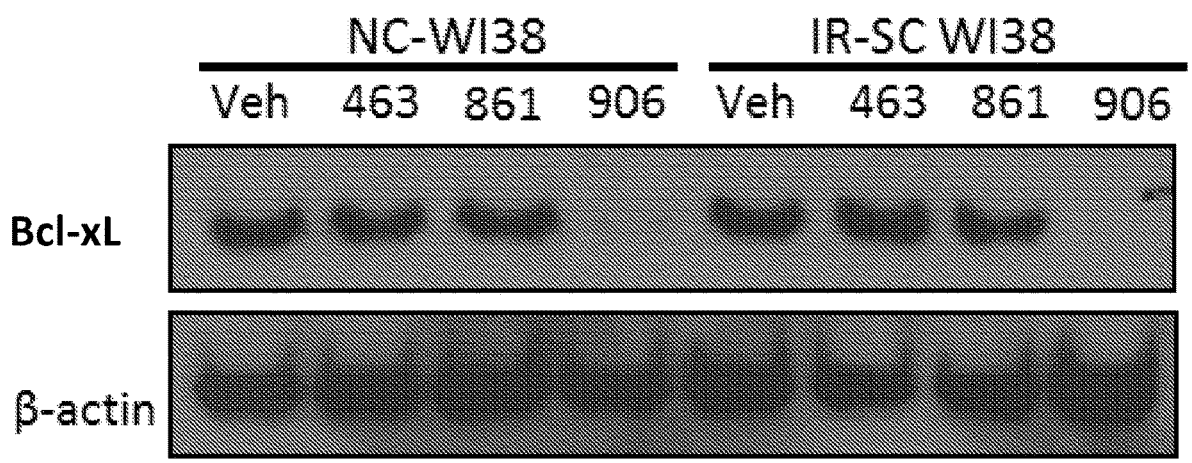

The present invention relates to compounds which are capable of degrading the Bcl-2 family of proteins. The bivalent compounds connect a Bcl-2 small molecule inhibitor or ligand to an E3 ligase binding moiety, such as cereblon (CRBN) E3 ligase binding moiety (thalidomide derivatives such as pomalidomide) or von Hippel-Landau (VHL) E3 ligase binding moiety (such as HIF-1α-derived (R)-hydroxyproline containing VHL E3 ligase ligands). CRBN is part of the cullin-4 (CUL4) containing E3 ubiquitin ligase complex CUL4-RBX1-DDB1-CRBN (known as CRL4CRBN. Thalidomide and its derivatives, such as lenalidomide and pomalidomide, interact specifically with this CRBN complex and inducing degradation of essential IKAROS transcription factors. VHL is part of the cullin-2 (CUL2) containing E3 ubiquitin ligase complex elongin BC-CUL2-VHL (known as CRL2VHL) responsible for degradation of the transcription factor HIF-1α. (R)-Hydroxyproline containing VHL E3 ligase ligands derived from HIF-1α have been identified with high affinity. The bivalent compounds can actively recruit the Bcl-2 family of proteins to an E3 ubiquitin ligase, such as CRBN or VHL E3 ligase, resulting in their degradation by ubiquitin proteasome system.

Applicants have discovered that compounds comprising a moiety that selectively binds to an E3 ubiquitin ligase and a moiety that selectively binds a target protein, results in ubiquitination and subsequent degradation of the target protein through the ubiquitin proteasome system. Accordingly, the present disclosure provides compositions and methods for selectively degrading the Bcl-2 family of proteins. Additional aspects of the invention are described below.

I. Compositions

In an aspect, a composition of the invention comprises a compound of Formula (I) or a compound of Formula (II). Derivatives of Formula (I) or Formula (II) may be made to improve potency, bioavailability, solubility, stability, handling properties, or a combination thereof, as compared to an unmodified version.

A composition of the invention may optionally comprise one or more additional drugs or therapeutically active agents in addition to a compound of Formula (I) or a compound of Formula (II). A composition of the invention may further comprise a pharmaceutically acceptable excipient, carrier or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants.

(a) Compounds of Formula (I)

Provide herein are compounds comprising Formula (I):

$$R_1\text{-}L\text{-}R_2 \quad (I)$$

wherein $R_1$ is a protein targeting unit which binds to one or more anti-apoptotic Bcl-2 family of proteins;

L is a linker unit which covalently links $R_1$ and $R_2$ through an alkyl, branched alkyl, ether, thioether, ester, amine, amide, carbamate, carbamide, sulfone, aryl, heteroaryl, cycloalkyl, or heterocyclic group, both end can be same or different; the linker unit could contain a combination of two or more groups among alkyl, branched alkyl, ether, thioether, ester, amine, amide, carbamate, carbamide, sulfone, aryl, heteroaryl, cycloalkyl, and heterocyclic groups; the linker unit comprises a length of 1-30 atoms in shortest length; and $R_2$ is an E3 ubiquitin ligase binding unit which binds to the CRBN or VHL E3 ubiquitin ligase.

(b) Compounds of Formula (II)

The compounds described by Formula (II) are a subset of the compounds described by Formula (I). Thus, $R_1$ and $R_2$ in Formula (I) are equivalent to $R_1$ and $R_2$ in Formula (II), respectively. The L in Formula (I) is defined as the following in Formula (II):

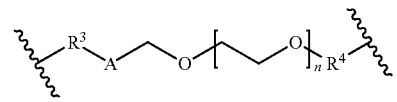

Also provided herein are compounds comprising Formula (II) or an isomer thereof:

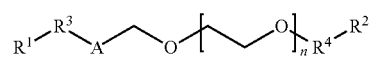

wherein $R^1$ is selected from the group consisting of:

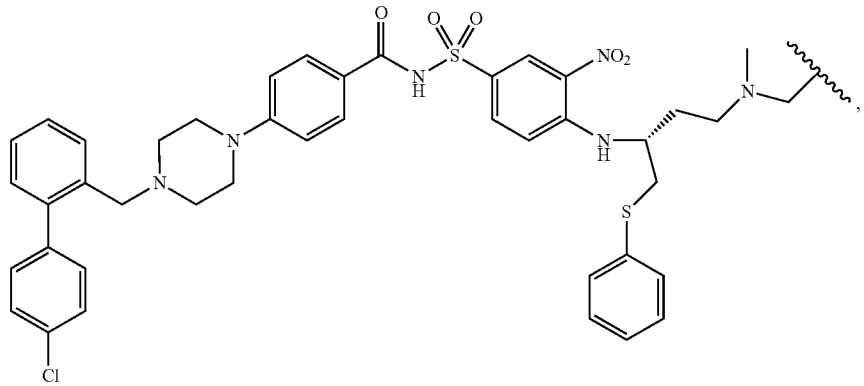

-continued
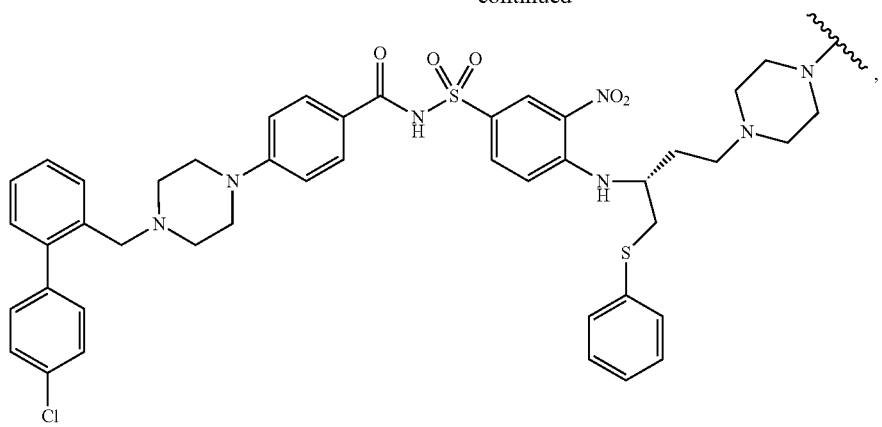
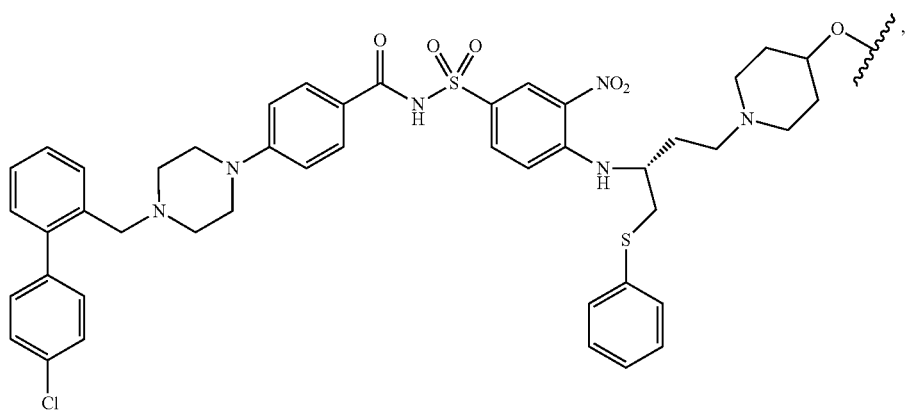
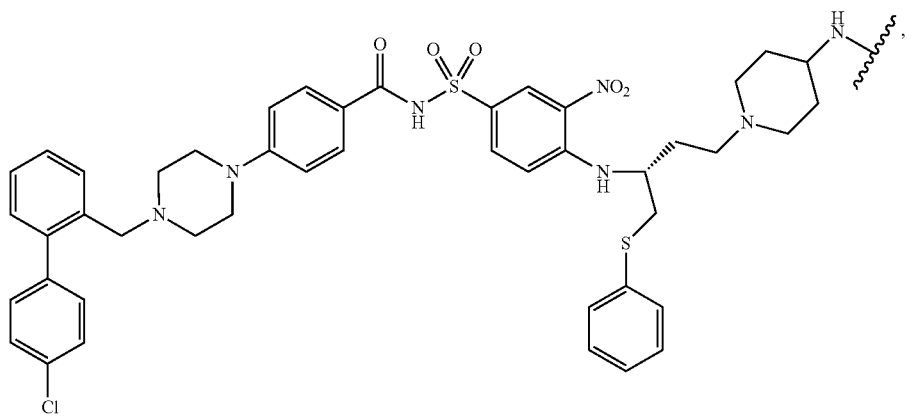
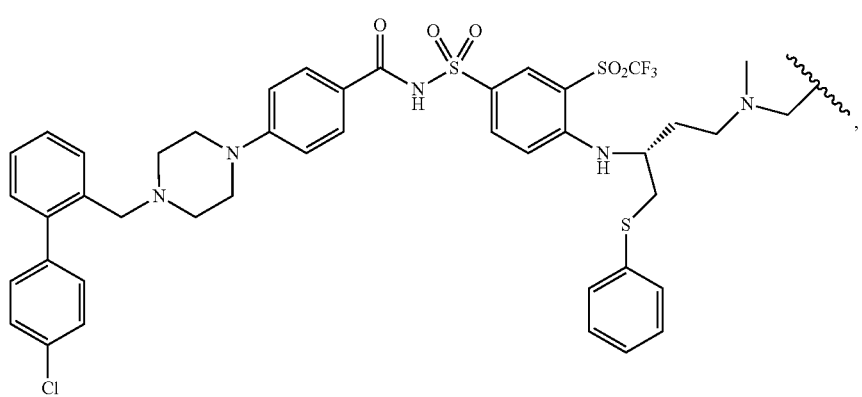

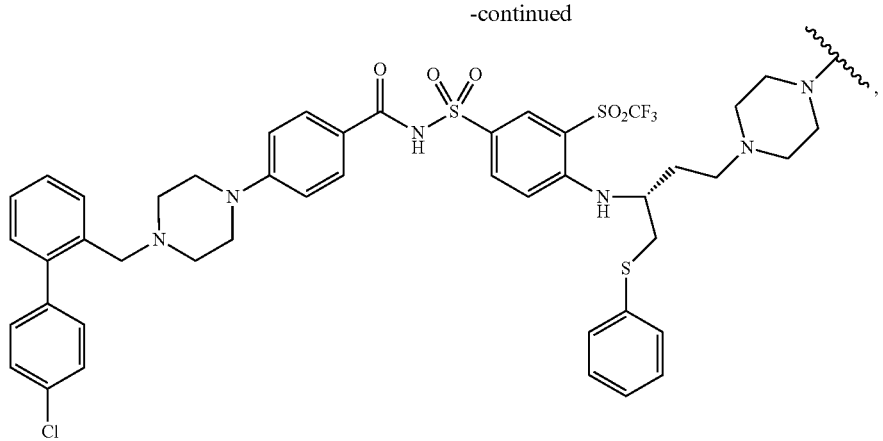
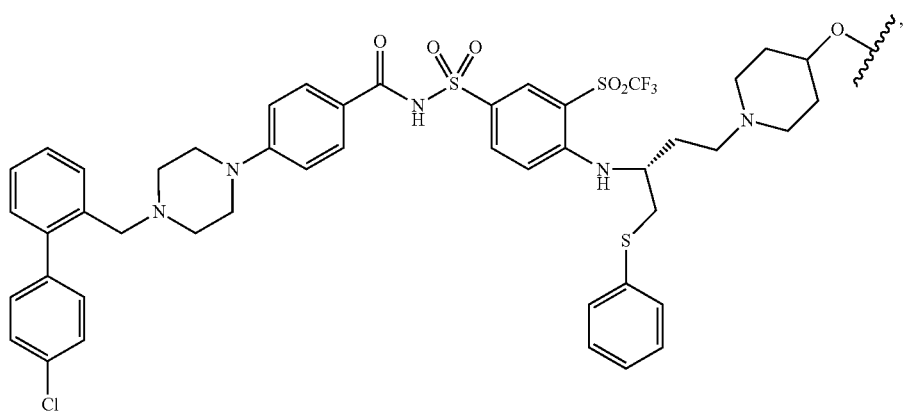
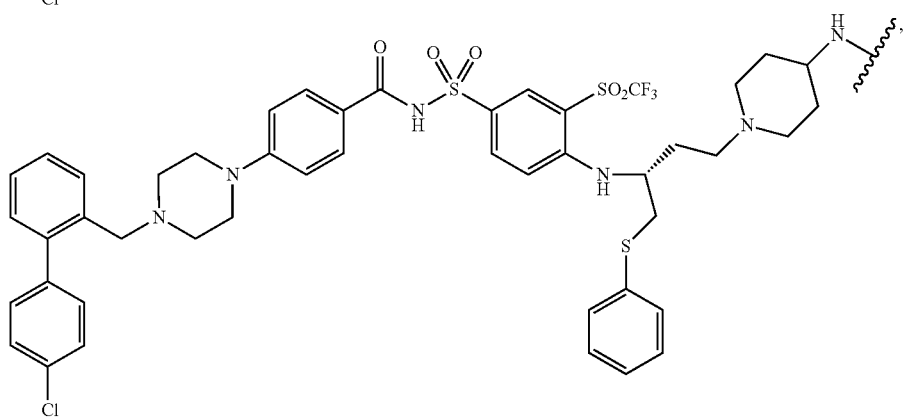
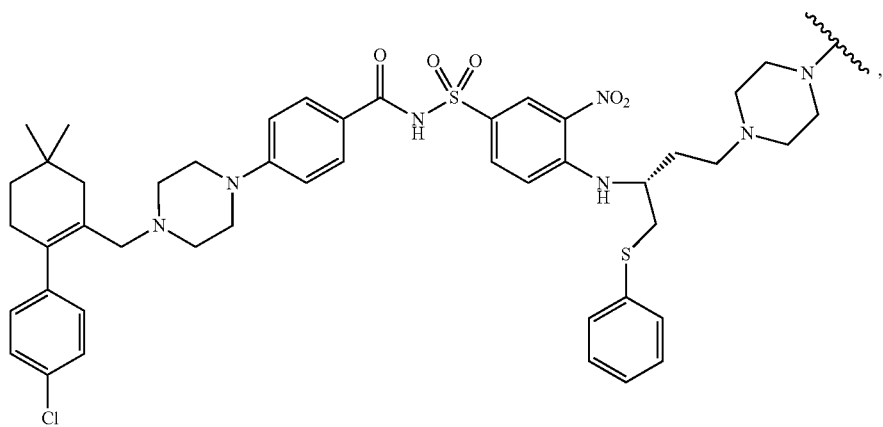

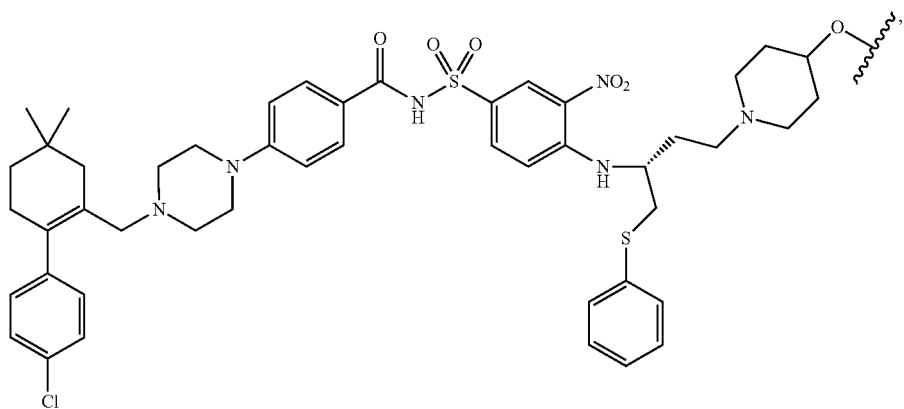
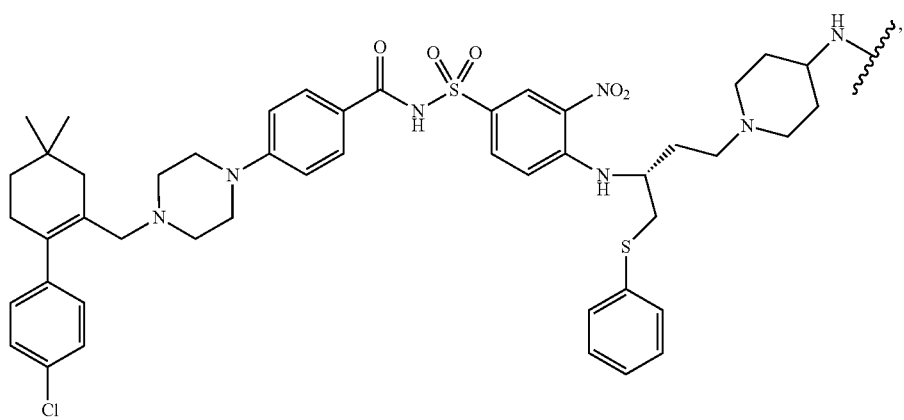
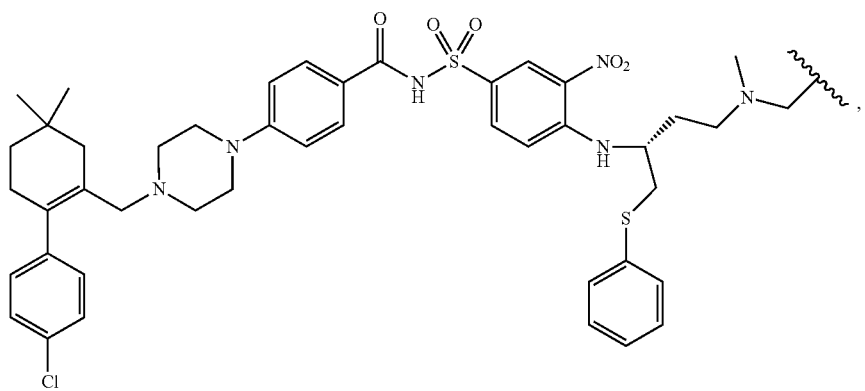
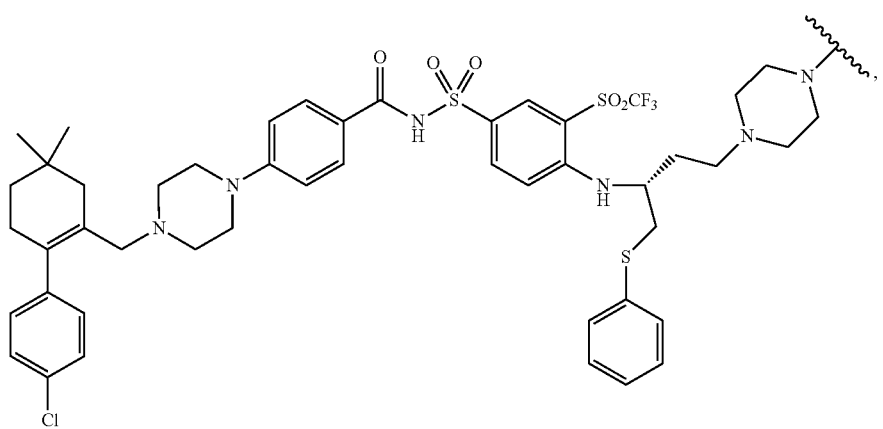

-continued
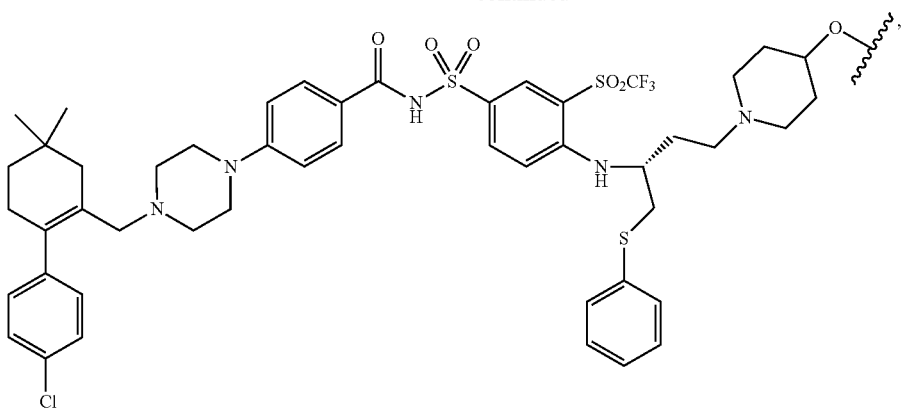
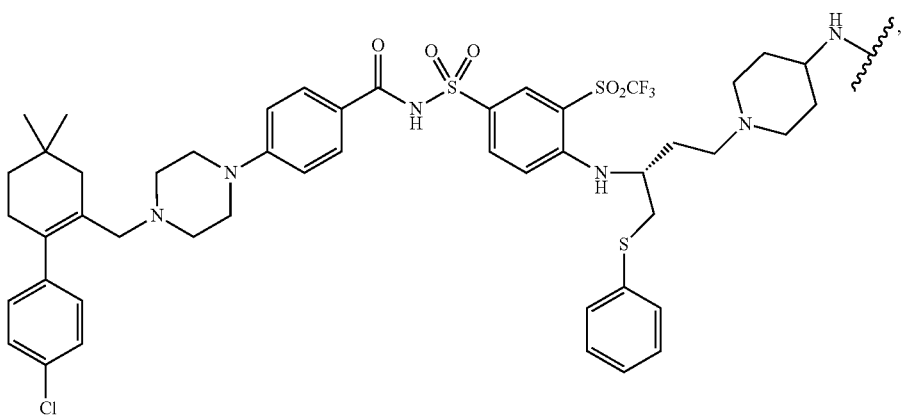
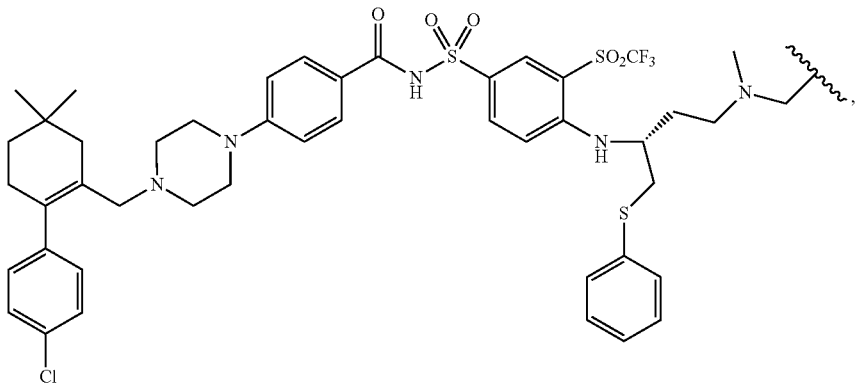
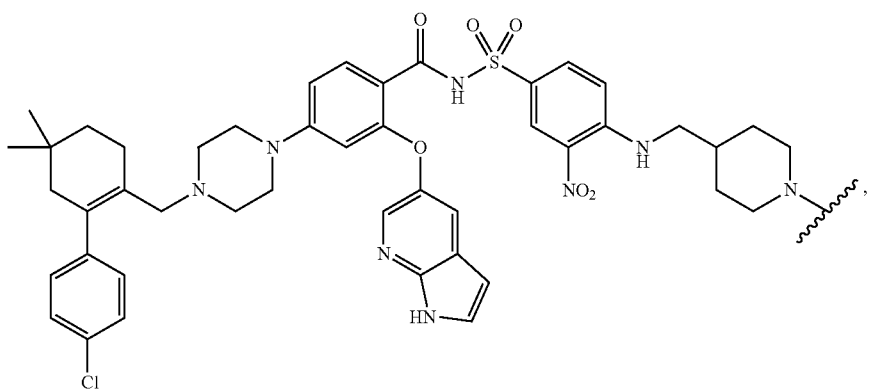

-continued
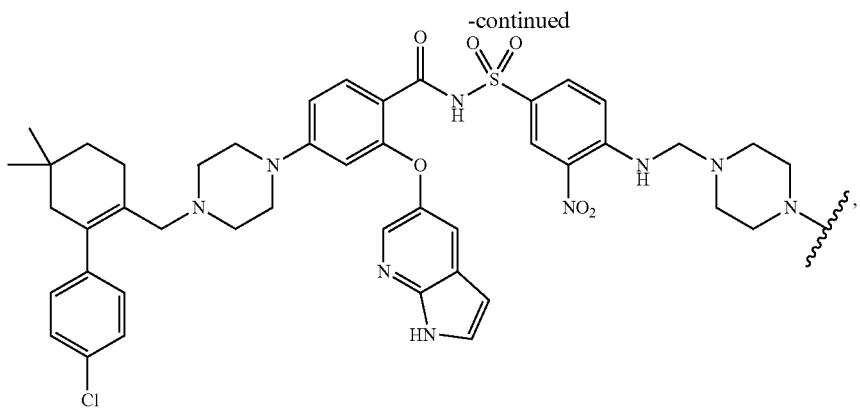
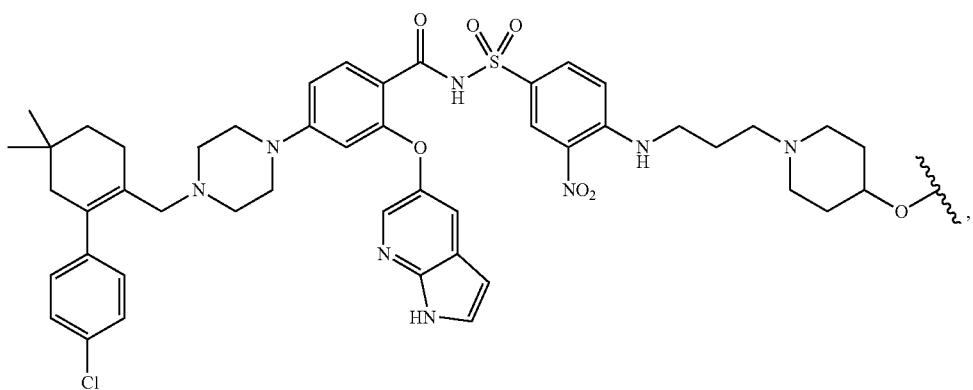
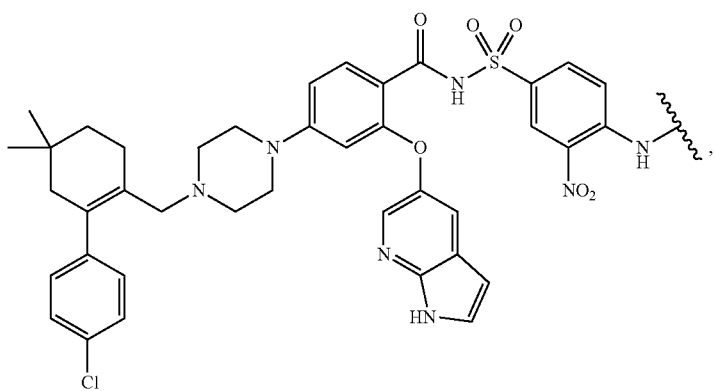
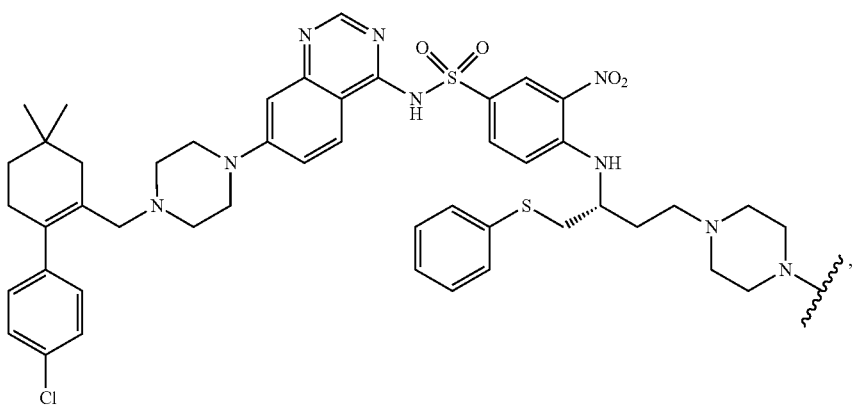

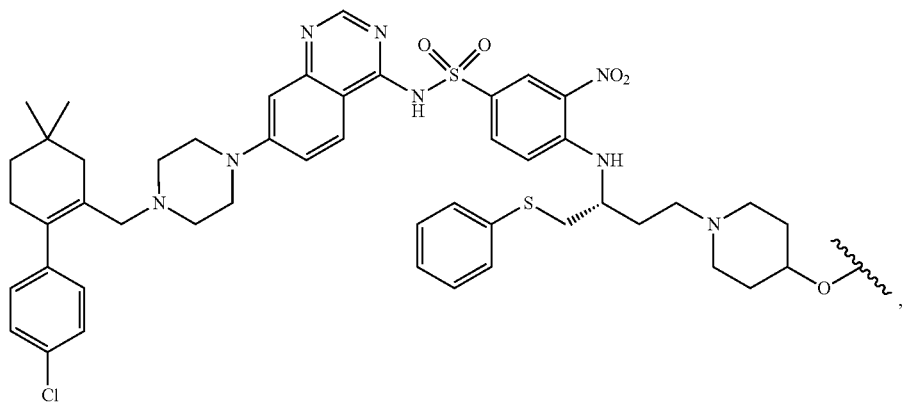
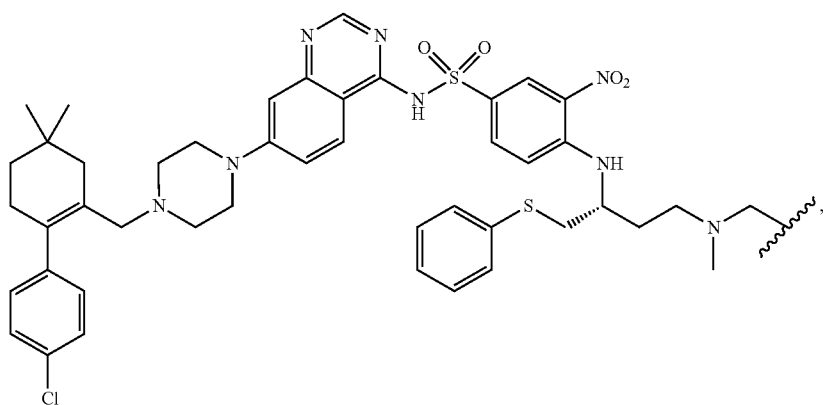
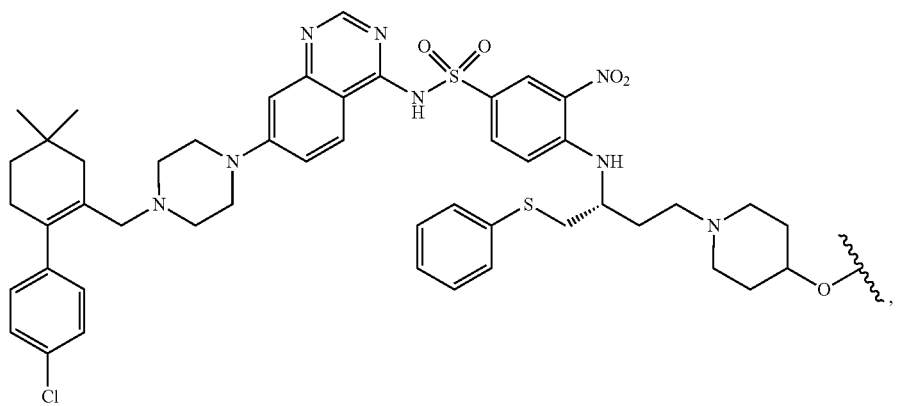
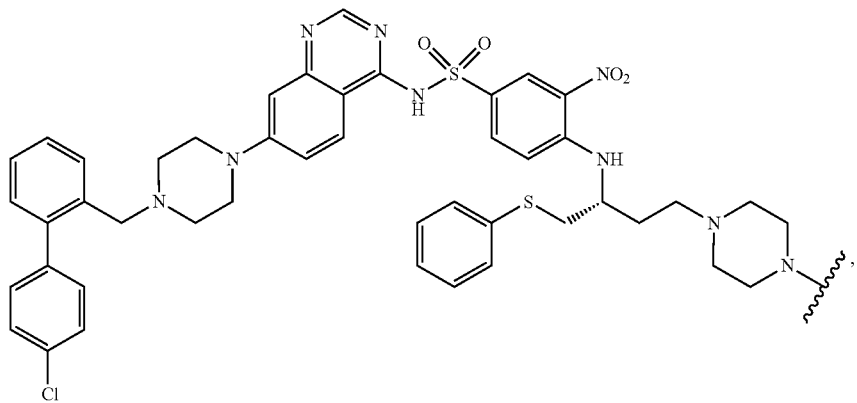

-continued
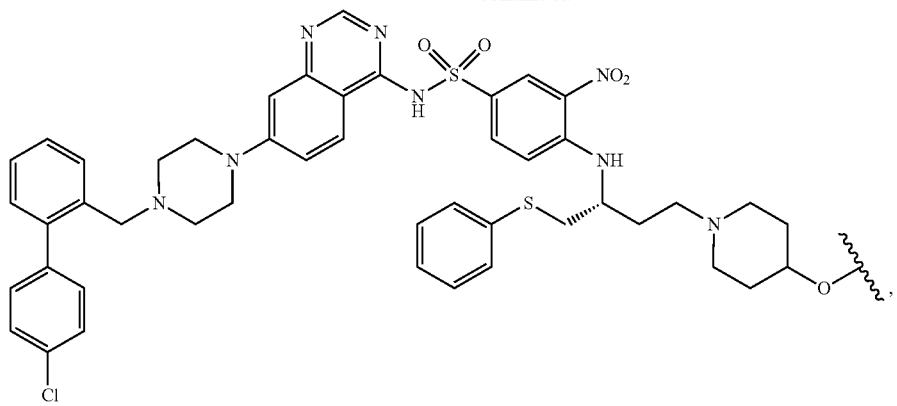
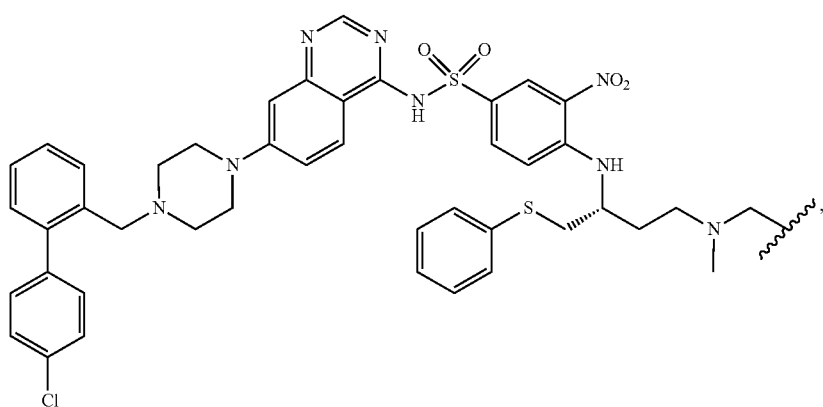
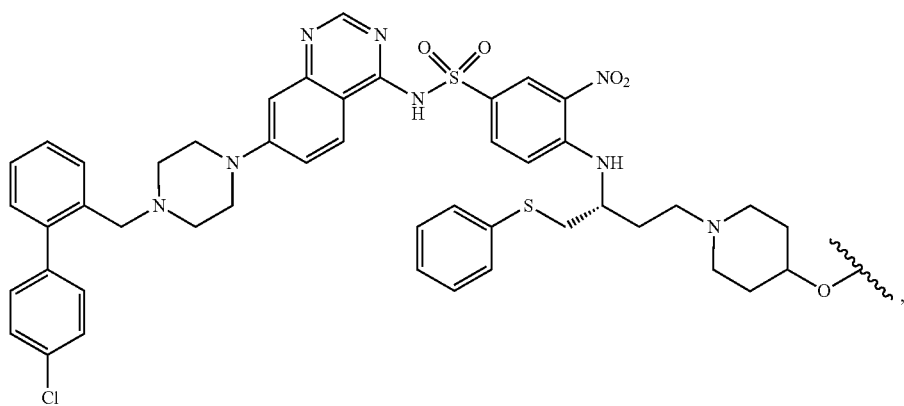
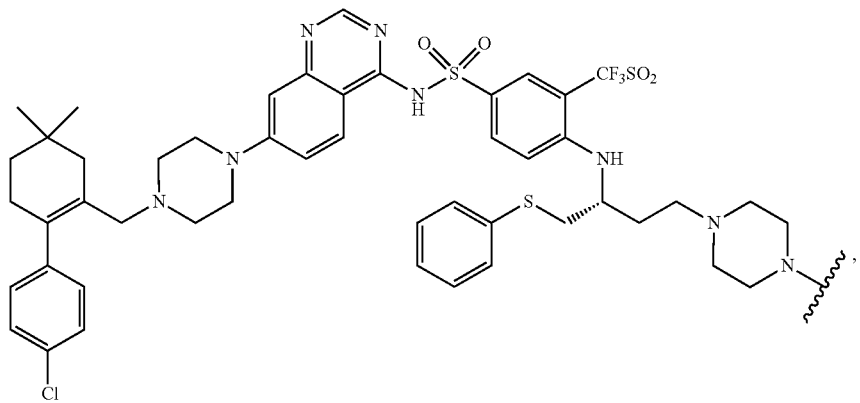

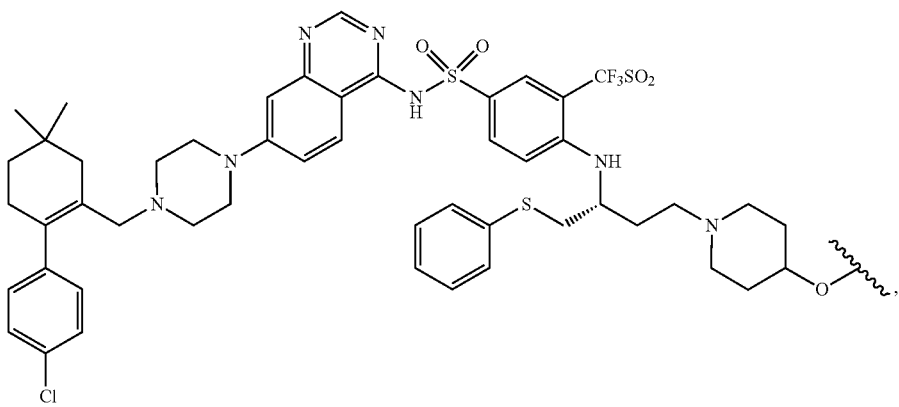
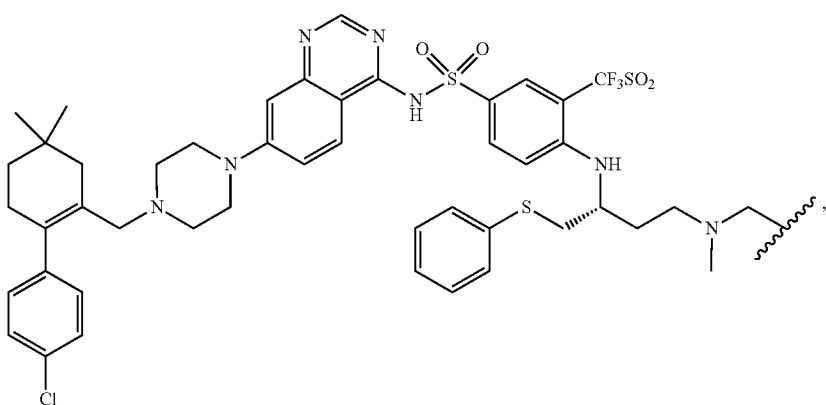
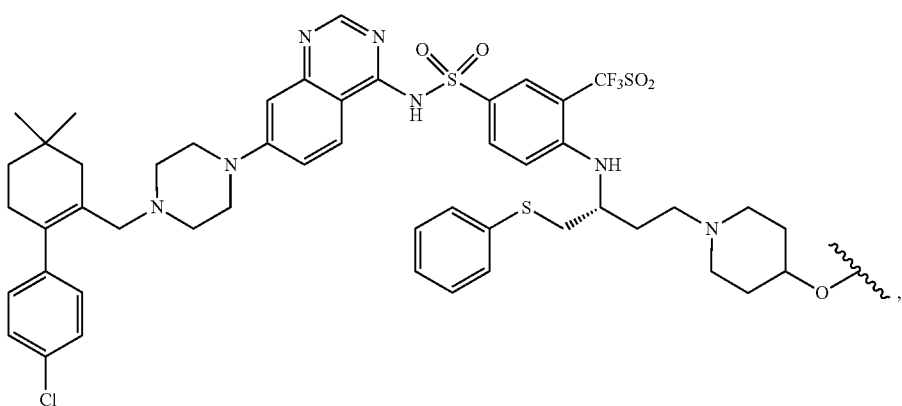
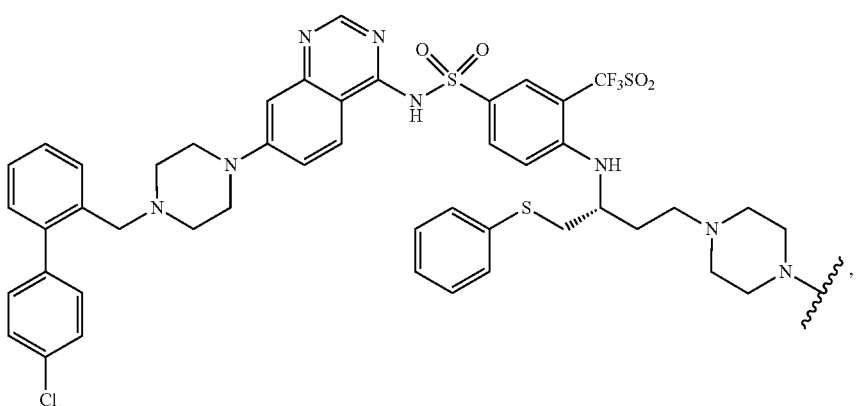

-continued
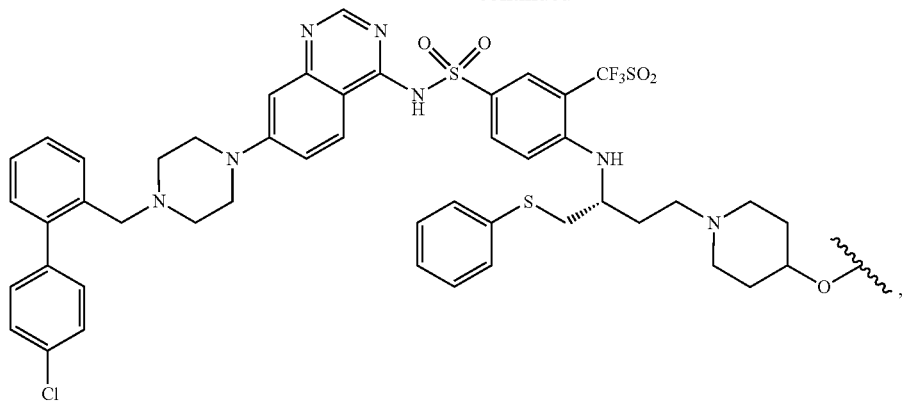
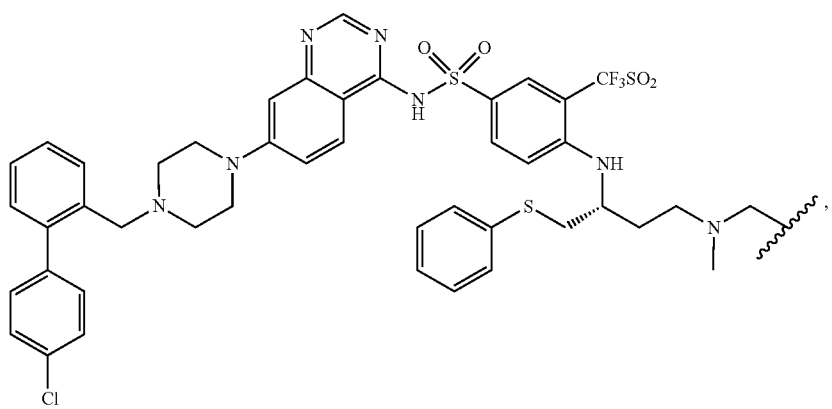
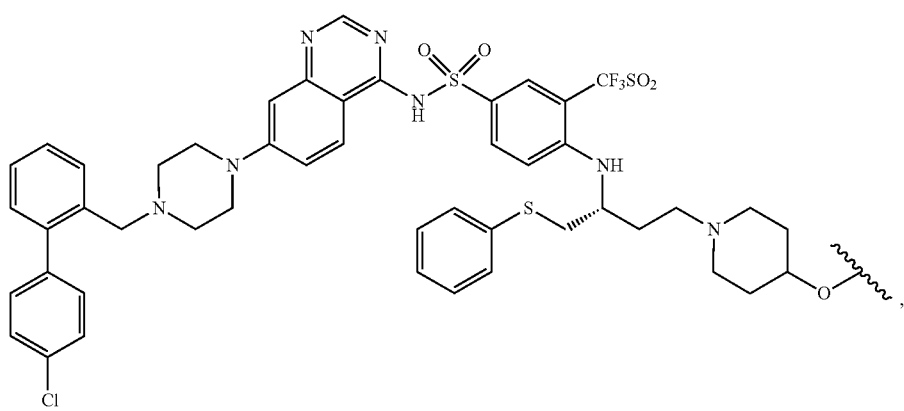
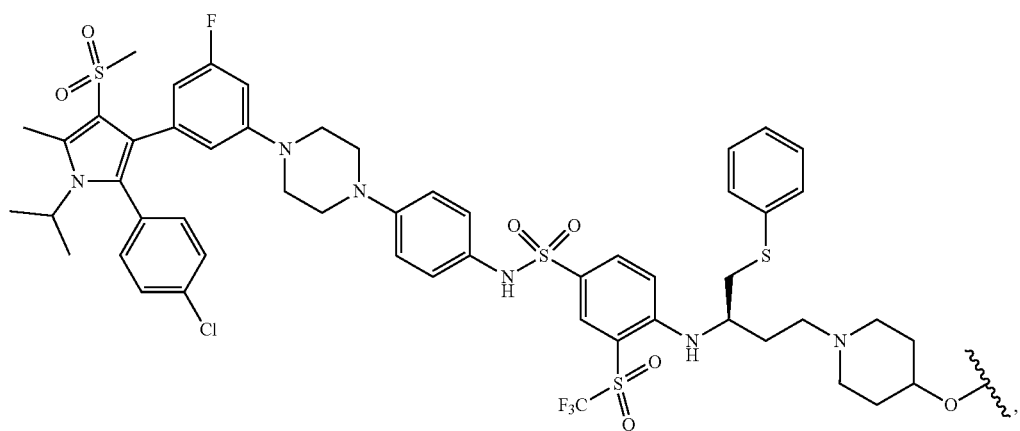

-continued
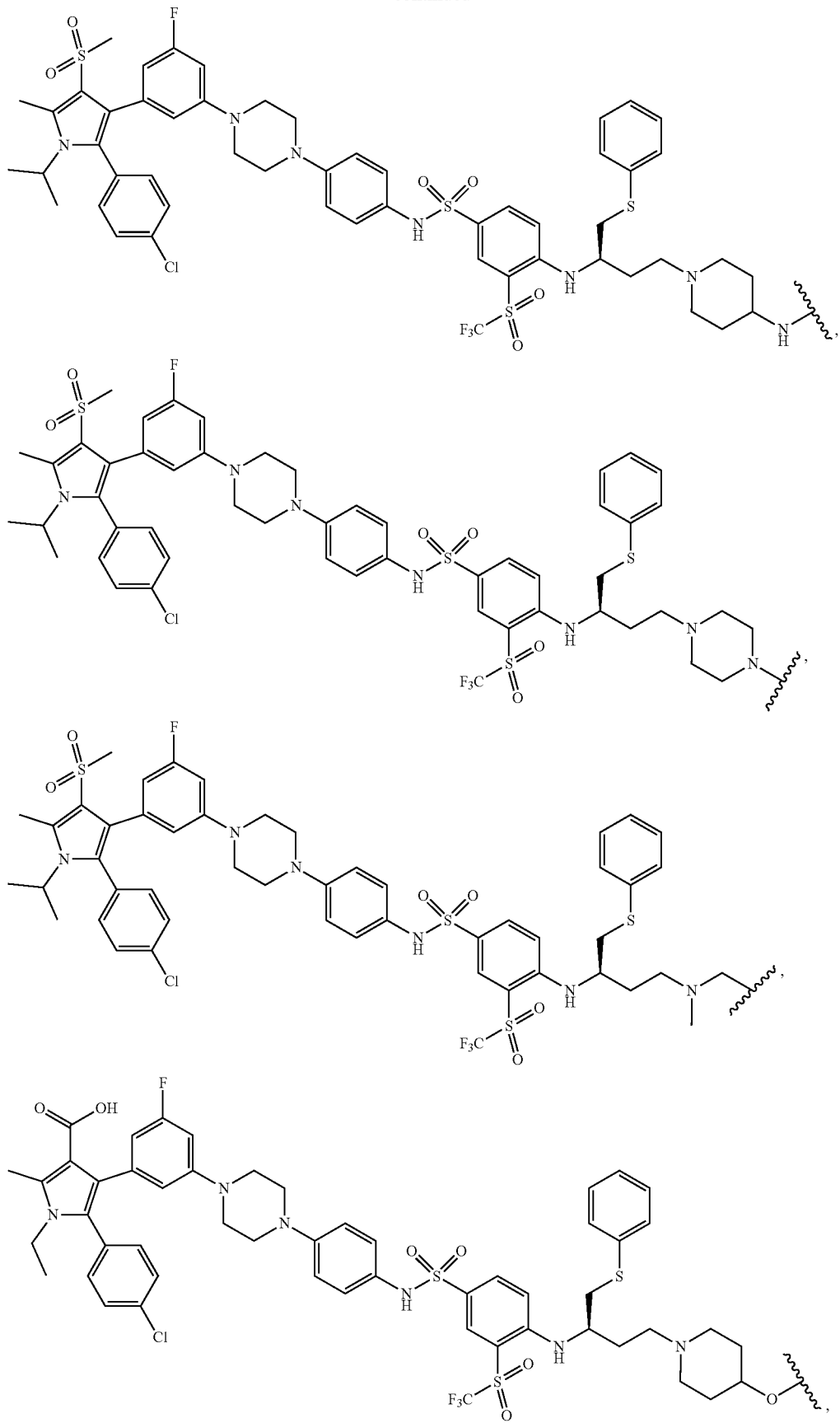

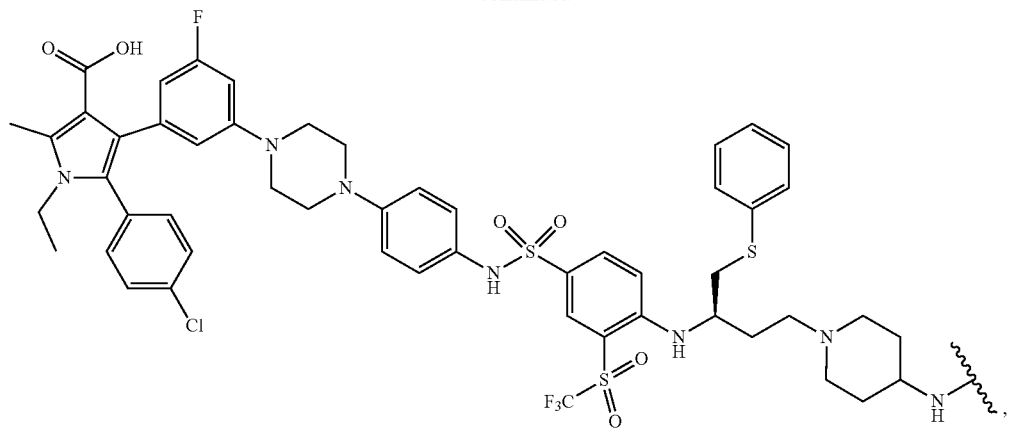
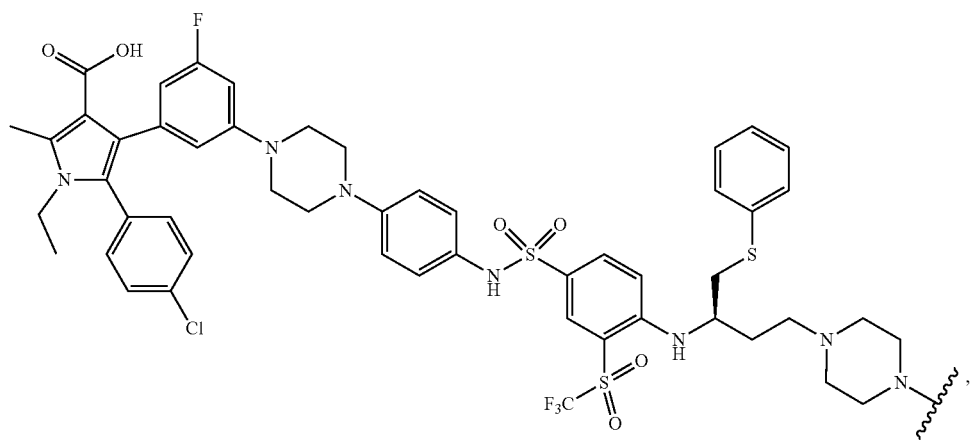
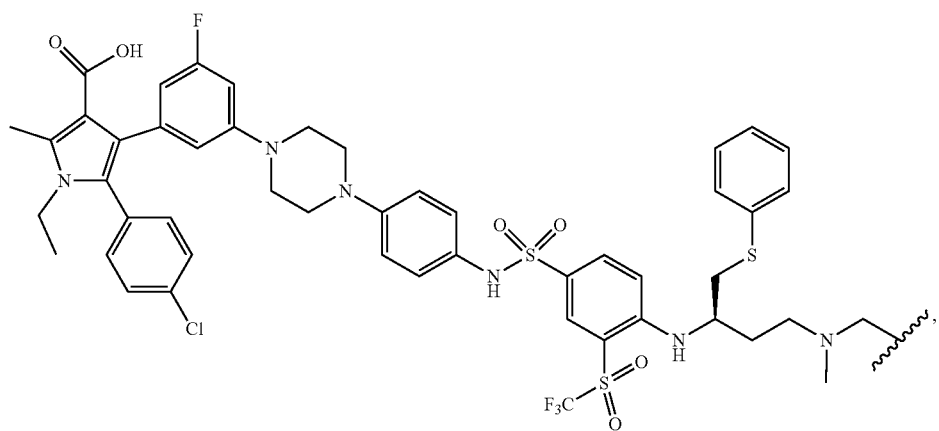
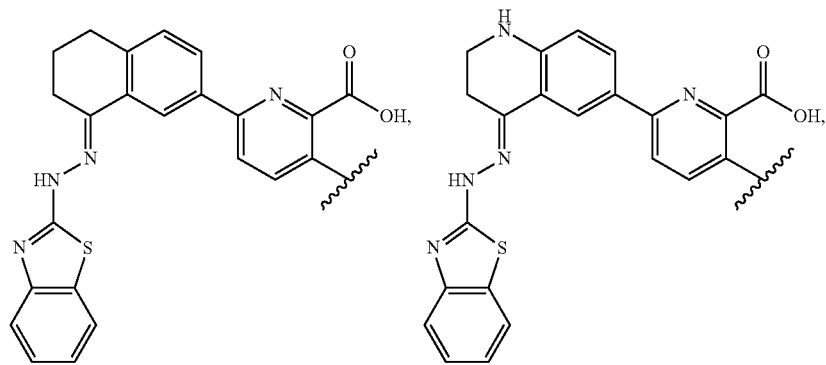

-continued
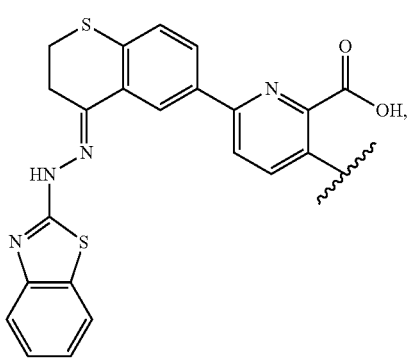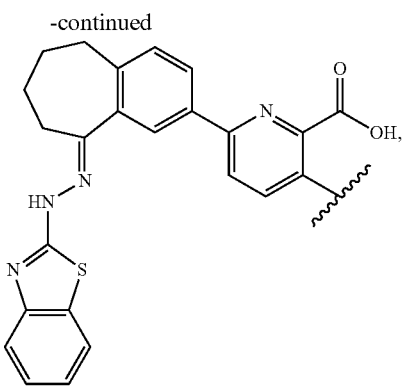
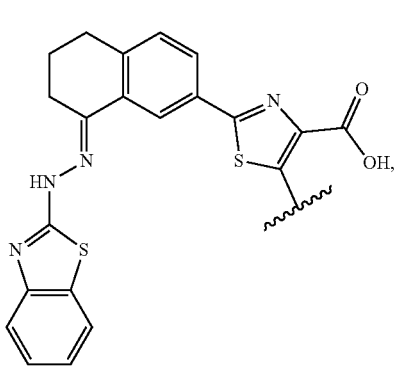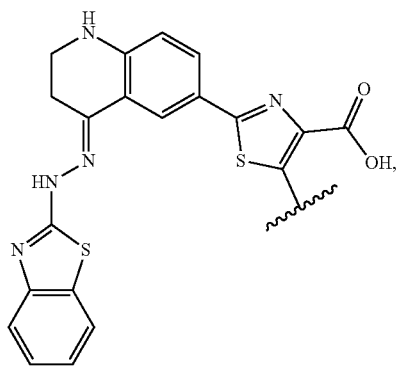
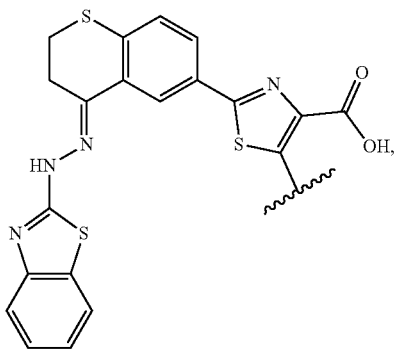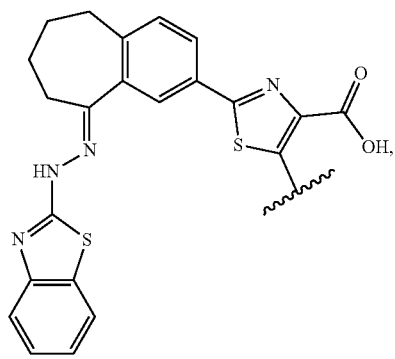
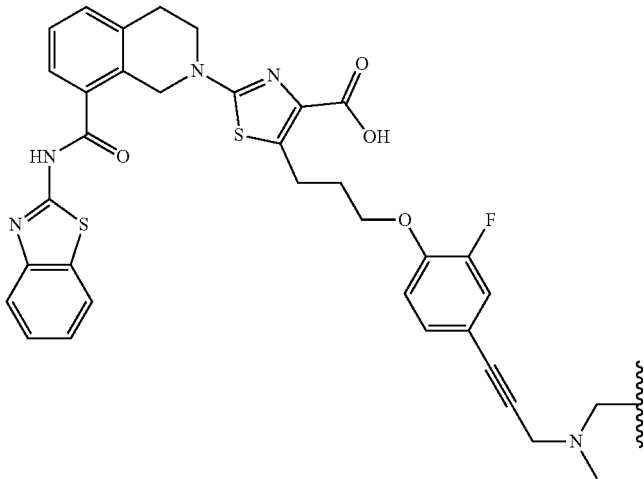

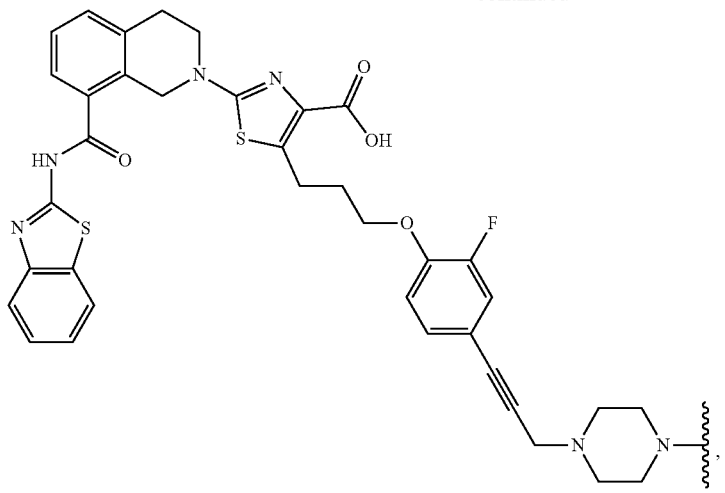
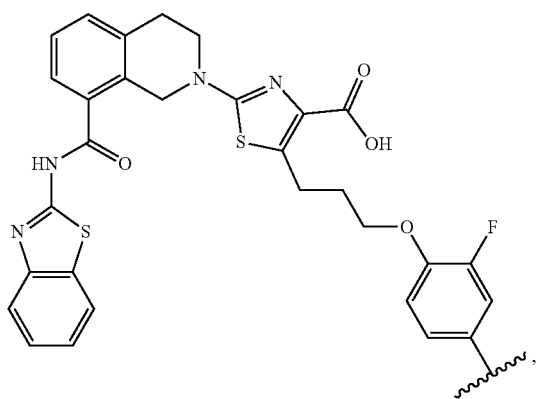
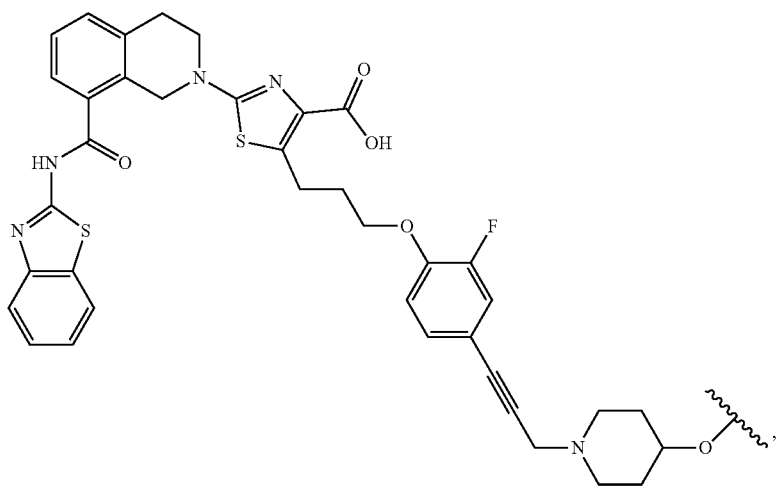

-continued
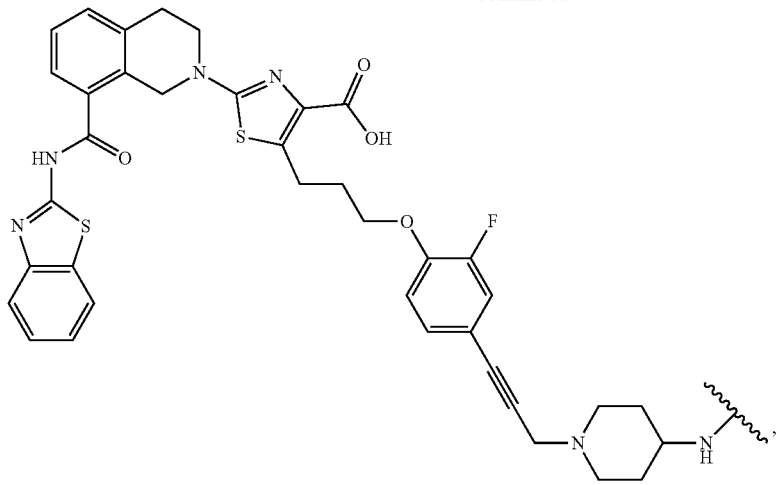
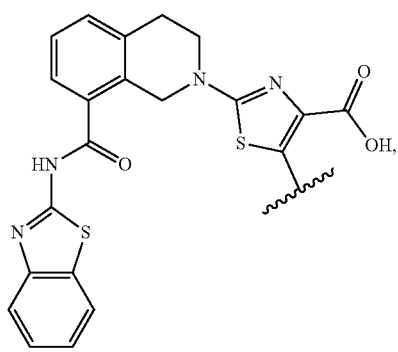
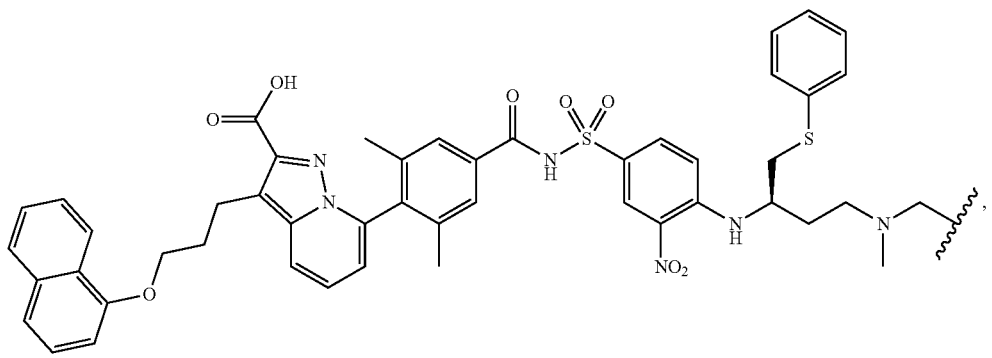
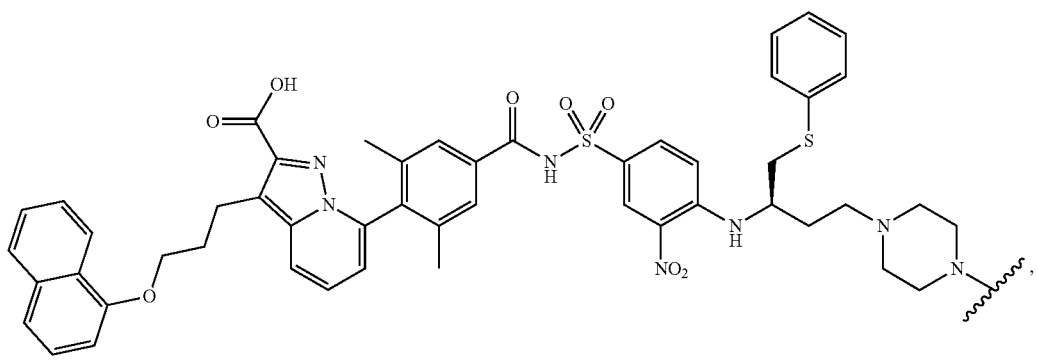

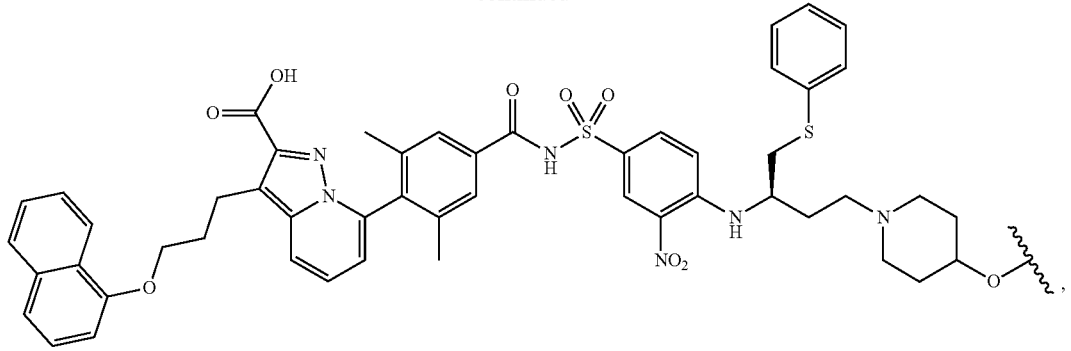
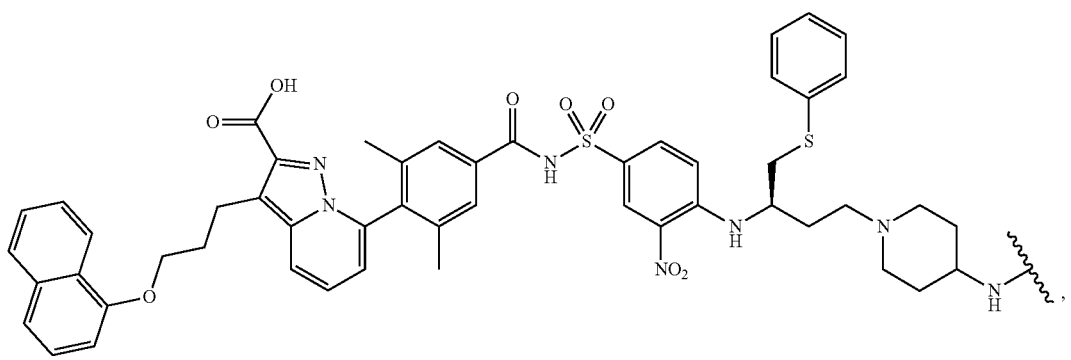
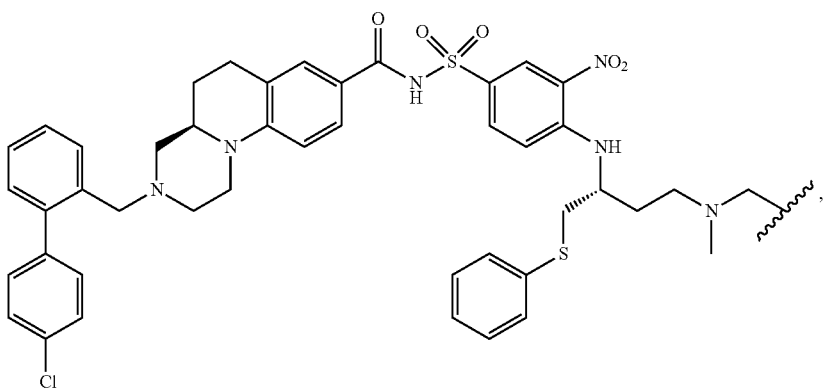
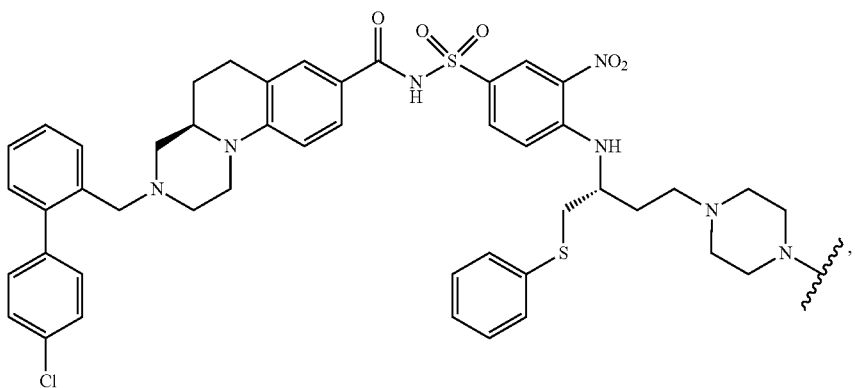

-continued
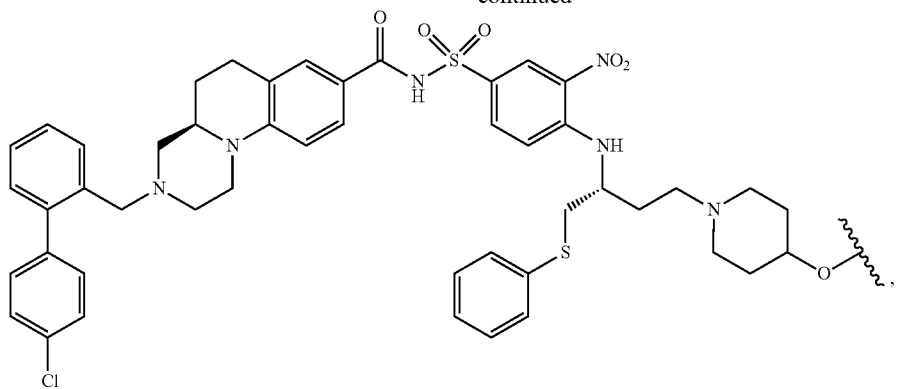
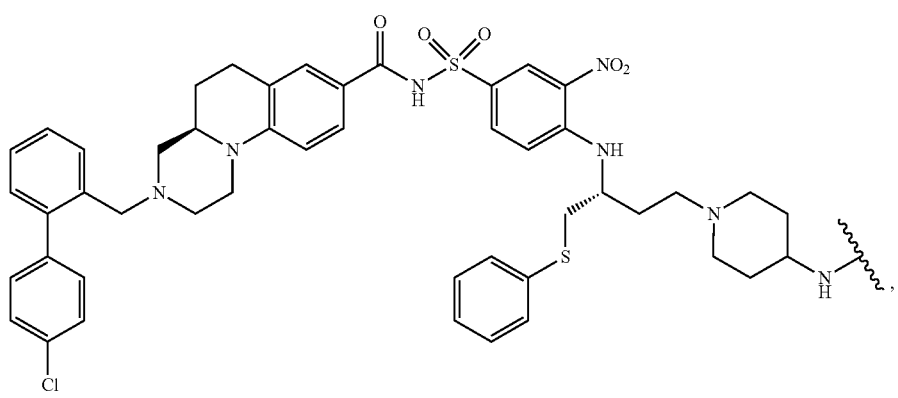
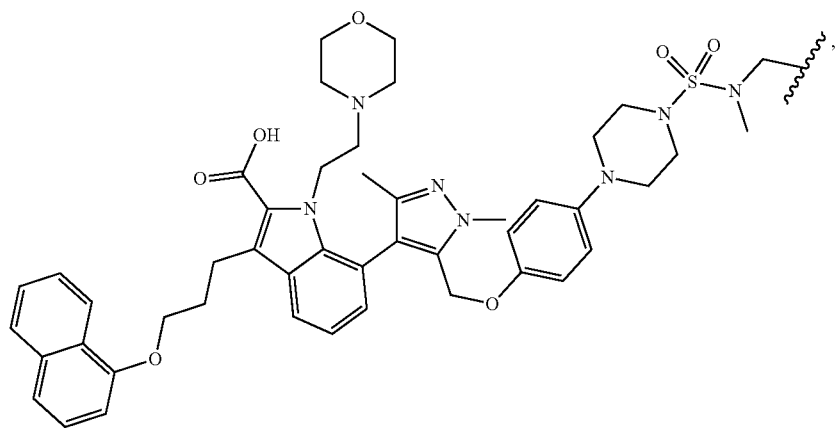
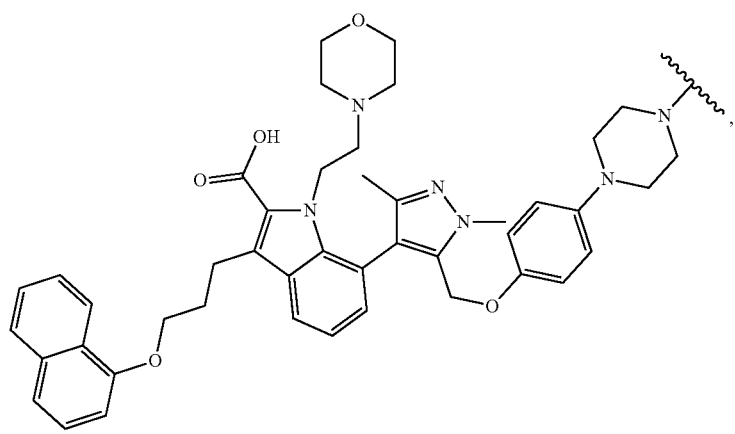

-continued
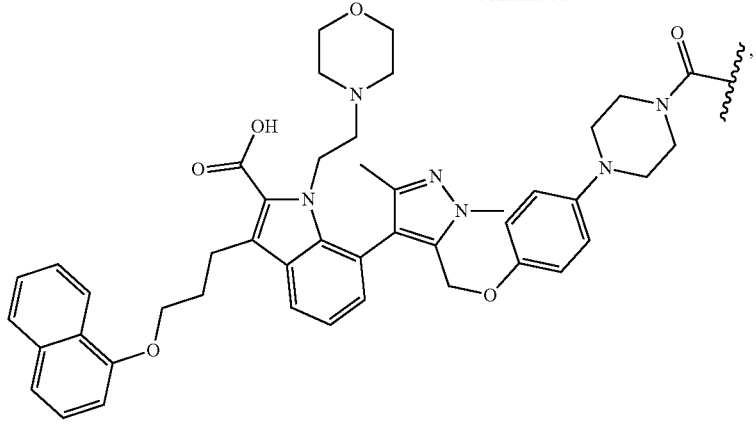
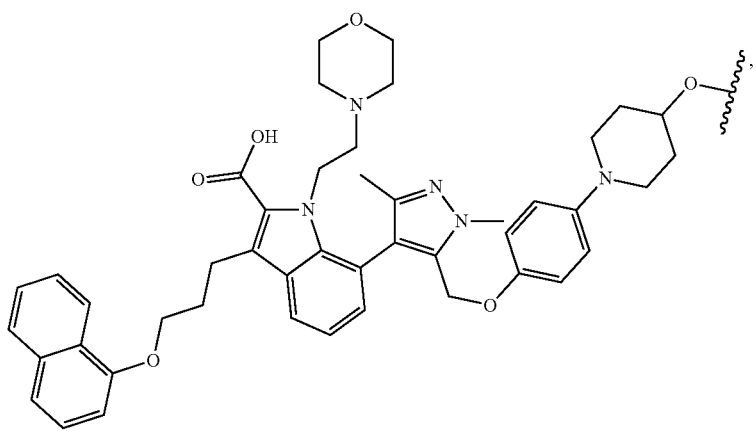
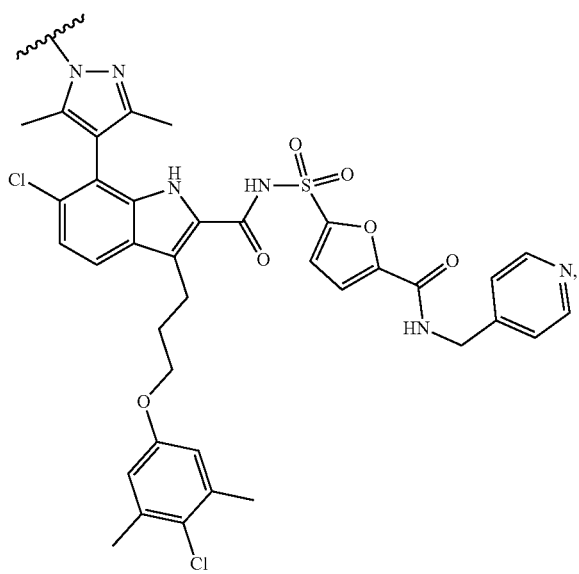

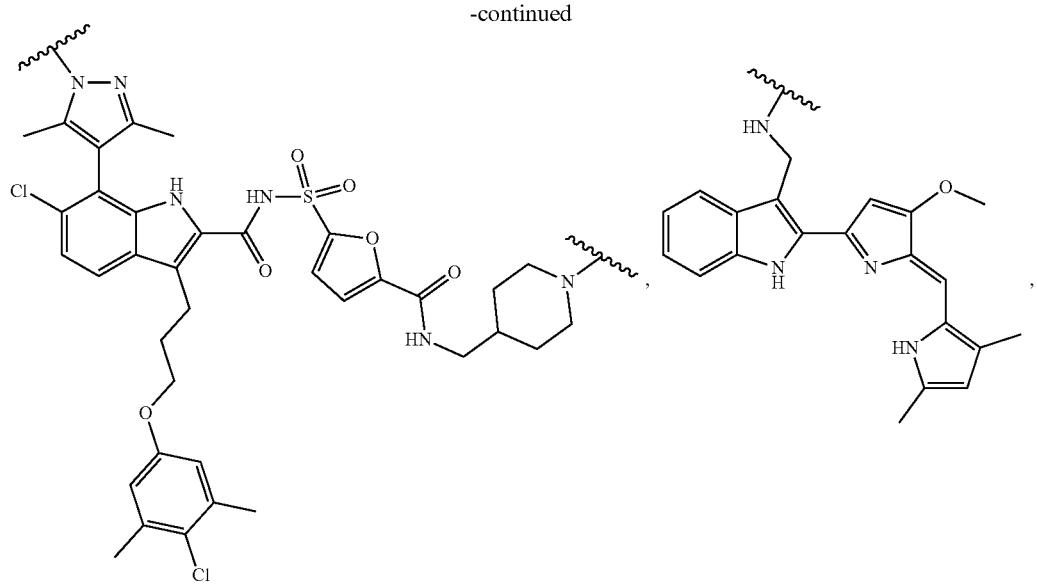
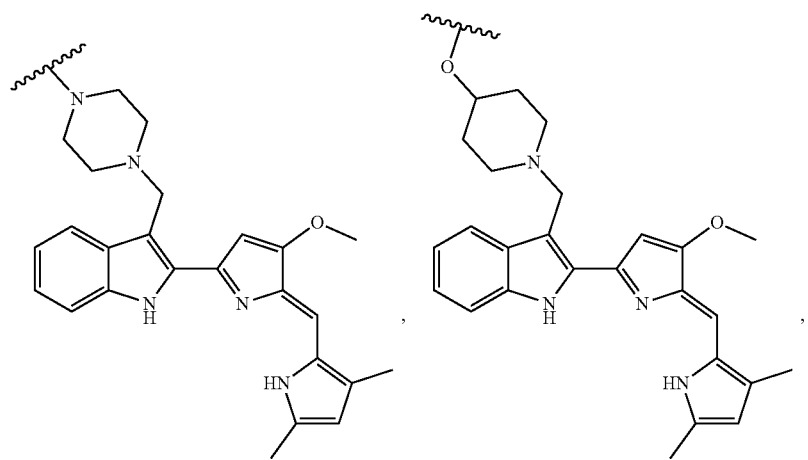
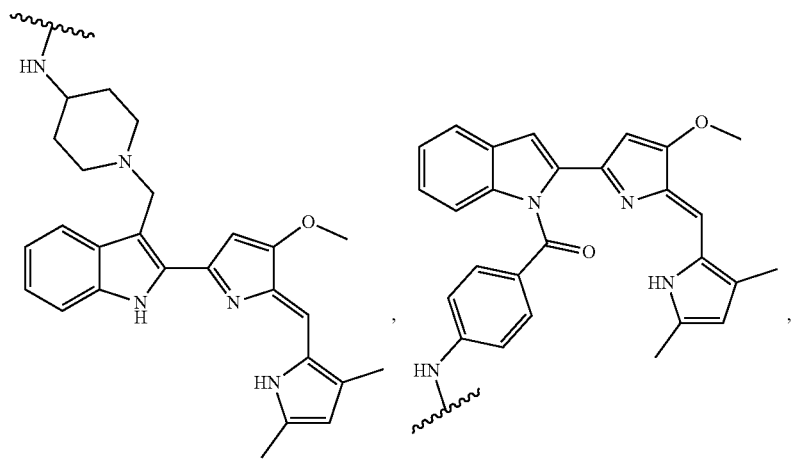

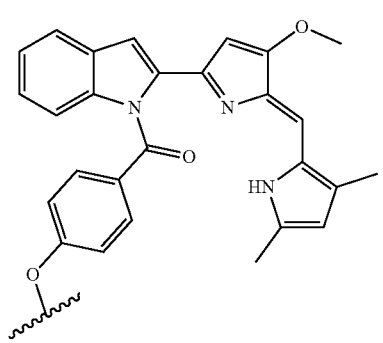 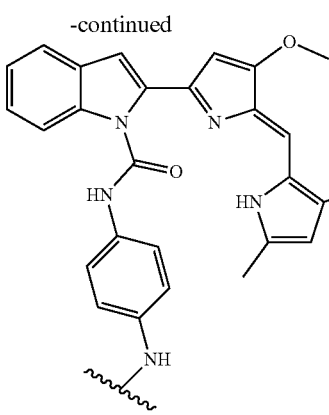
, and
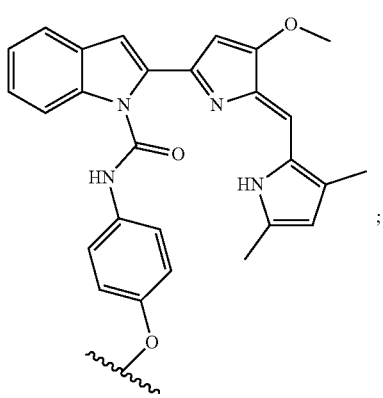
;
R³ is absent, a bond, or a substituted or unsubstituted C₁-C₁₀ alkyl;
A is absent, a bond, a substituted or unsubstituted C₁-C₆ aryl, a substituted or unsubstituted C₁-C₆ cycloalkyl, a substituted or unsubstituted C₁-C₆ heterocyclic group;
R⁴ is a bond or a substituted or unsubstituted C₁-C₁₀ alkyl;
n is an integer from 0 to 5;
R² is selected from the group consisting of
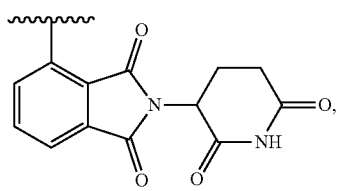
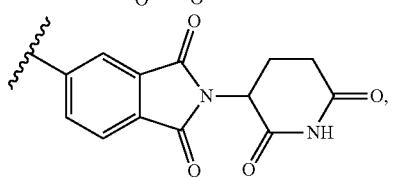
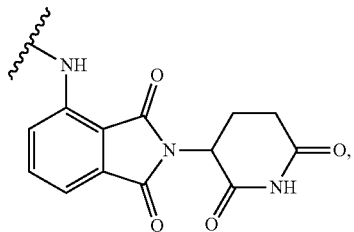
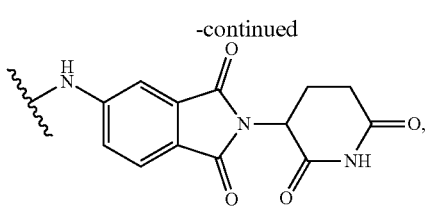
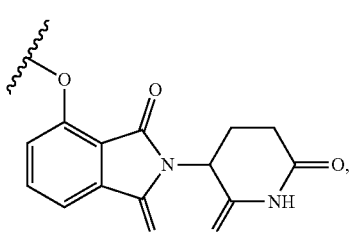
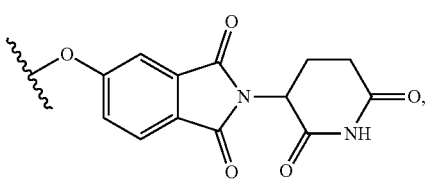
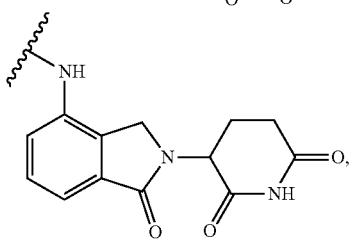

-continued
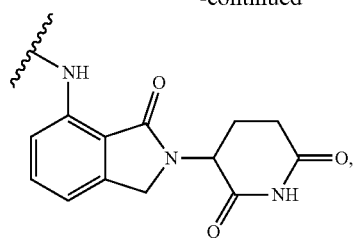
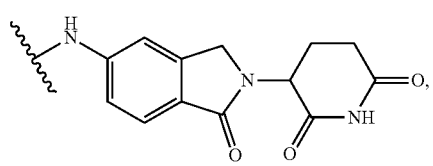
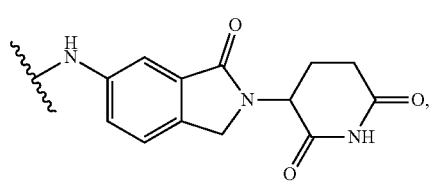
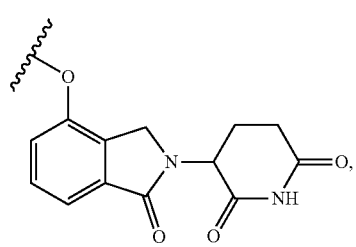
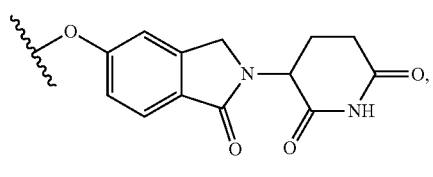
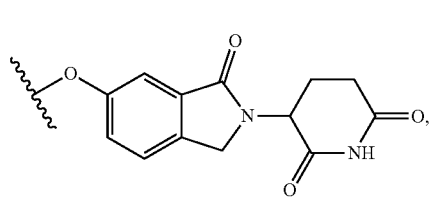
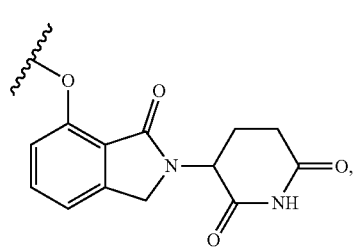
-continued
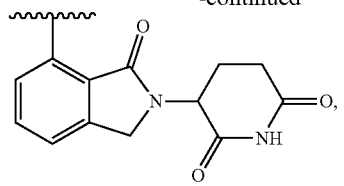
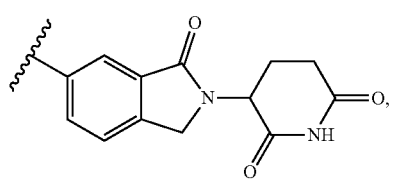
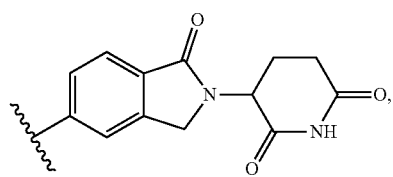
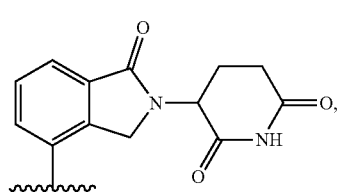
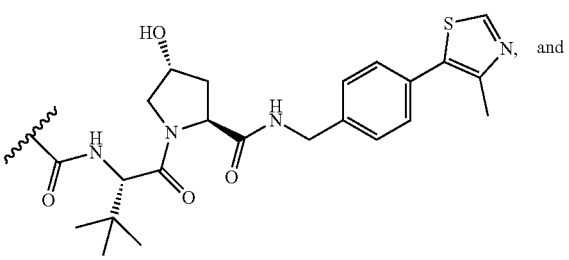
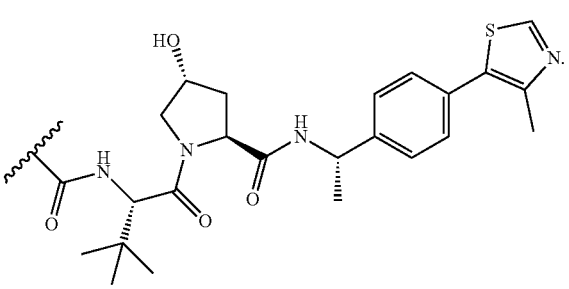

In an embodiment, a compound of Formula (II) comprises any of the preceding compounds of Formula (II), wherein $R^1$ may be
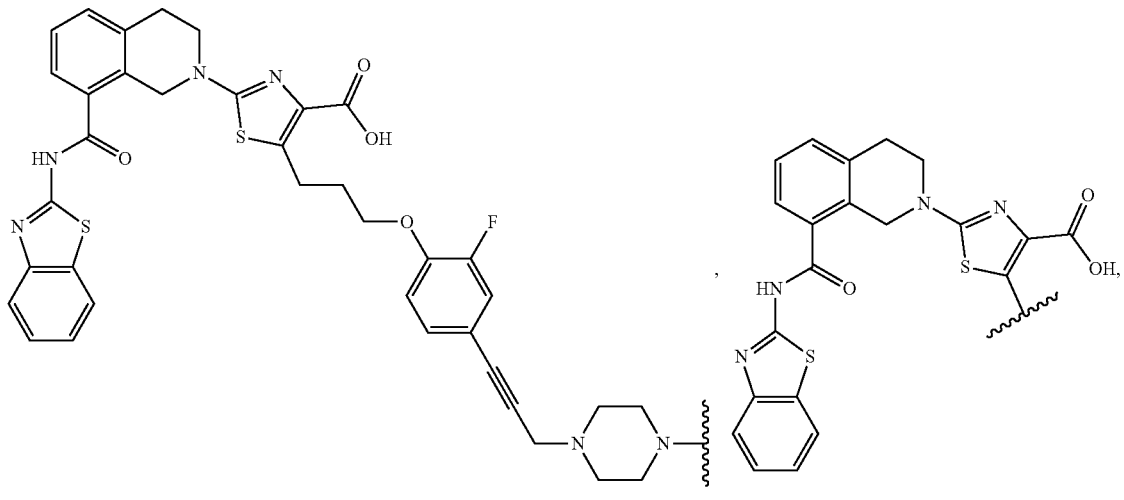
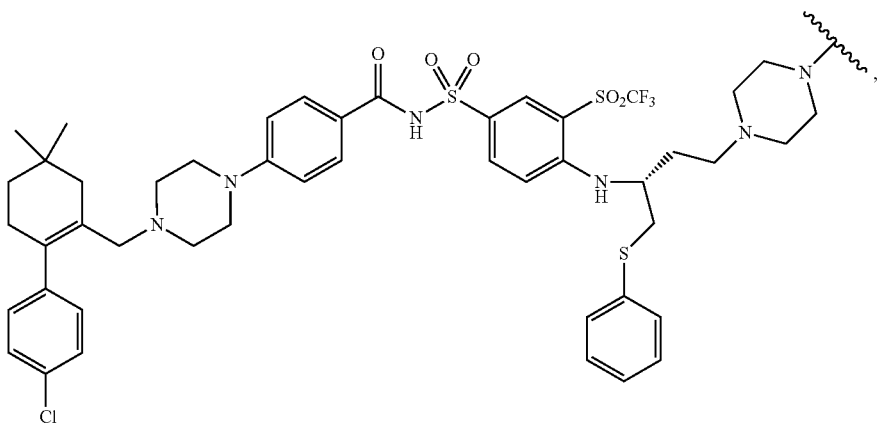
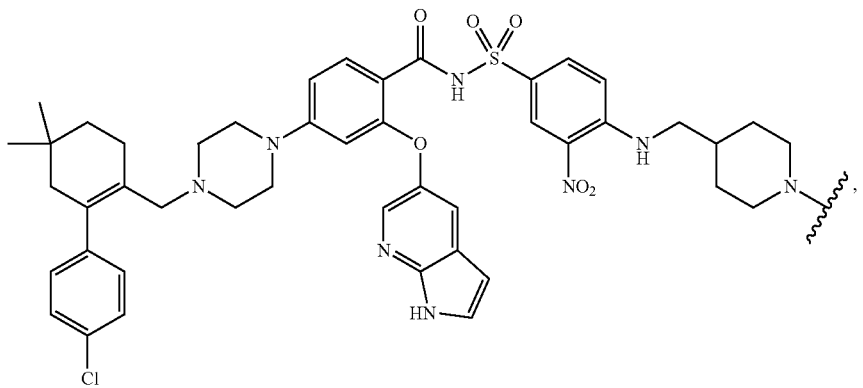

-continued
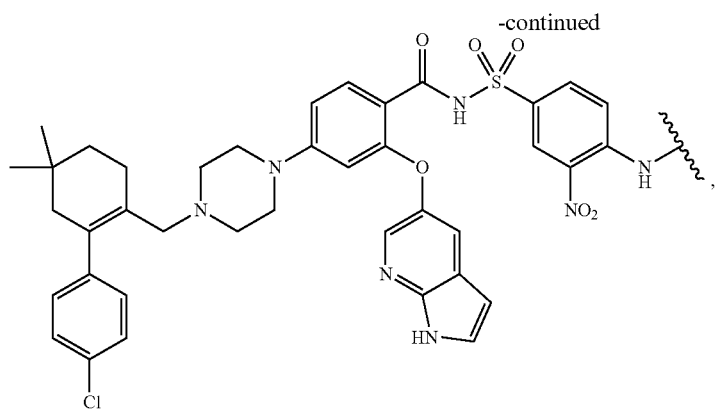
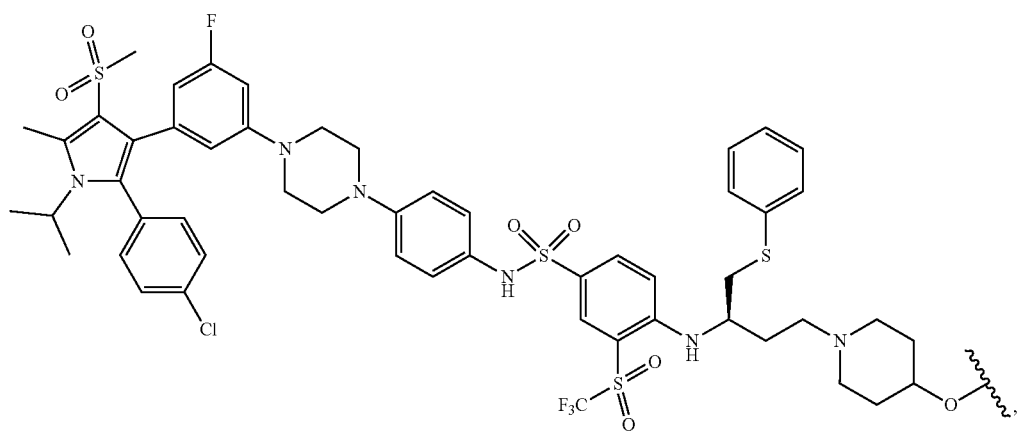
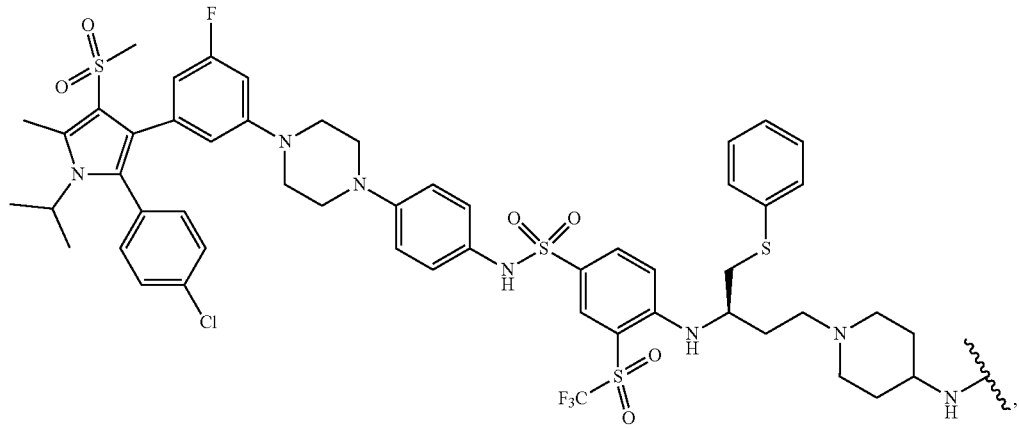
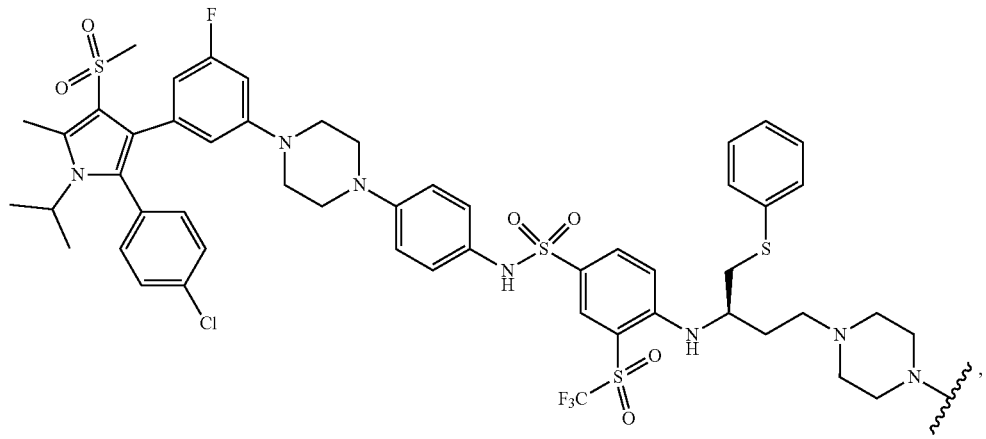

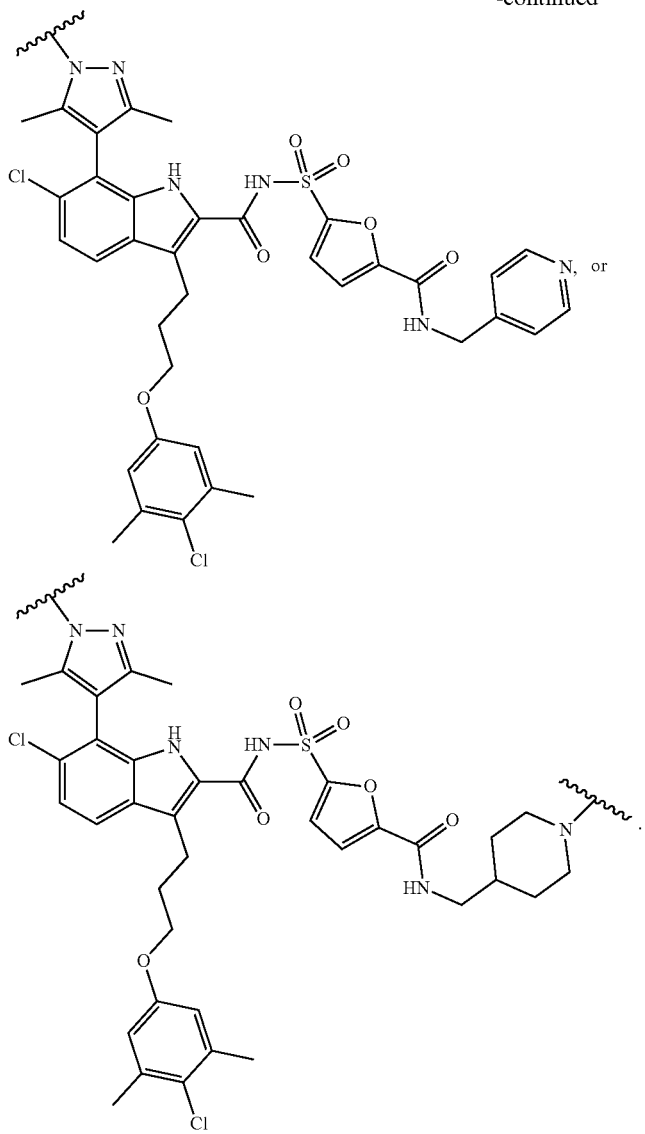

In an embodiment, a compound of Formula (II) comprises any of the preceding compounds of Formula (II), wherein $R^3$ may be absent, an unsubstituted $C_1$-$C_6$ alkyl, or a substituted or unsubstituted $C_3$-$C_6$ ketone.

In a preferred embodiment, a compound of Formula (II) comprises any of the preceding compounds of Formula (II), wherein $R^3$ may be absent, a bond, an unsubstituted $C_1$-$C_3$ alkyl, or an unsubstituted $C_3$-$C_6$ ketone.

In still a preferred embodiment, a compound of Formula (II) comprises any of the preceding compounds of Formula (II), wherein $R^3$ may be absent, a bond, 2-pentanone, or an unsubstituted $C_2$-$C_3$ alkyl.

In another embodiment, a compound of Formula (II) comprises any of the preceding compounds of Formula (II), wherein A may be absent, a bond, or a substituted or unsubstituted $C_1$-$C_6$ heterocyclic group.

In a preferred embodiment, a compound of Formula (II) comprises any of the preceding compounds of Formula (II), wherein A may be absent, a bond, or an unsubstituted $C_5$ heterocyclic group.

In still a preferred embodiment, a compound of Formula (II) comprises any of the preceding compounds of Formula (II), wherein A may be absent, a bond, or a triazole.

In another embodiment, a compound of Formula (II) comprises any of the preceding compounds of Formula (II), wherein n may be 0 to 3.

In a preferred embodiment, a compound of Formula (II) comprises any of the preceding compounds of Formula (II), wherein n may be 0 to 2.

In still a preferred embodiment, a compound of Formula (II) comprises any of the preceding compounds of Formula (II), wherein n may be 1 to 2.

In another embodiment, a compound of Formula (II) comprises any of the preceding compounds of Formula (II), wherein $R^4$ may be a bond or a substituted or unsubstituted $C_1$-$C_{10}$ alkyl.

In a preferred embodiment, a compound of Formula (II) comprises any of the preceding compounds of Formula (II), wherein $R^4$ may be a bond or a substituted $C_1$-$C_{10}$ alkyl.

In another embodiment, a compound of Formula (II) comprises any of the preceding compounds of Formula (II), wherein $R^2$ is

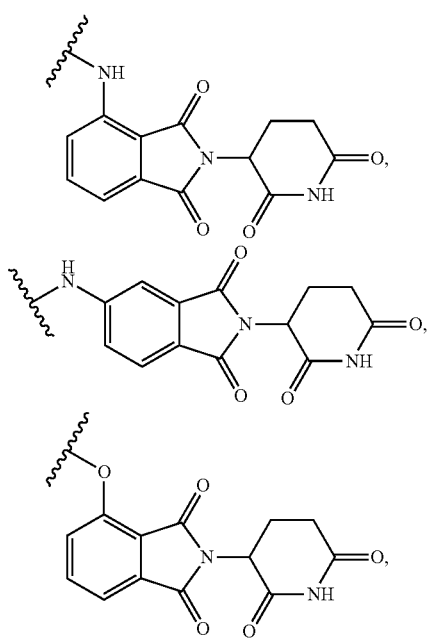
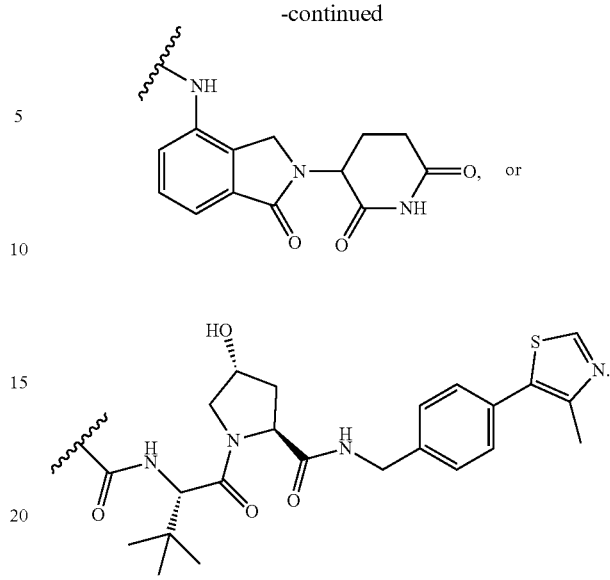
In one embodiment, a compound of the disclosure comprises Formula (II), wherein $R^1$ may be
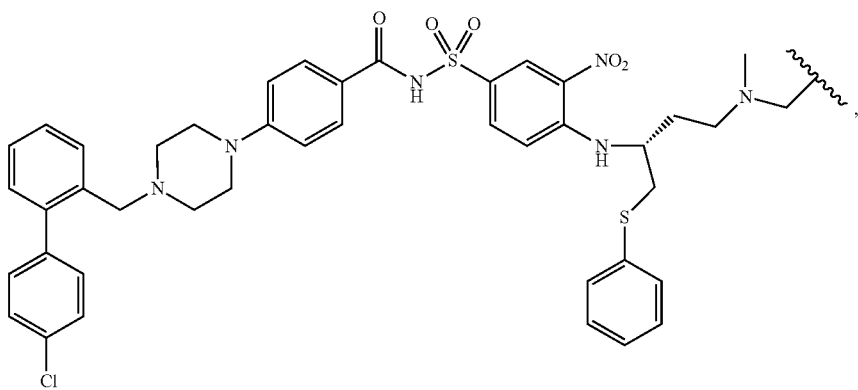
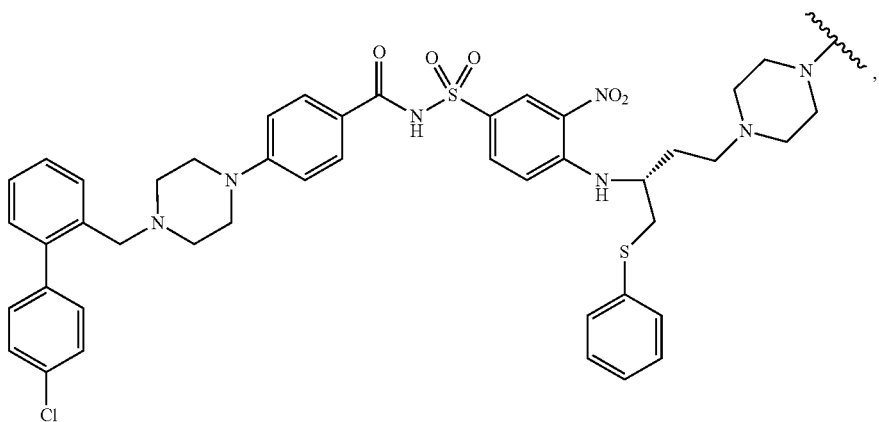

-continued
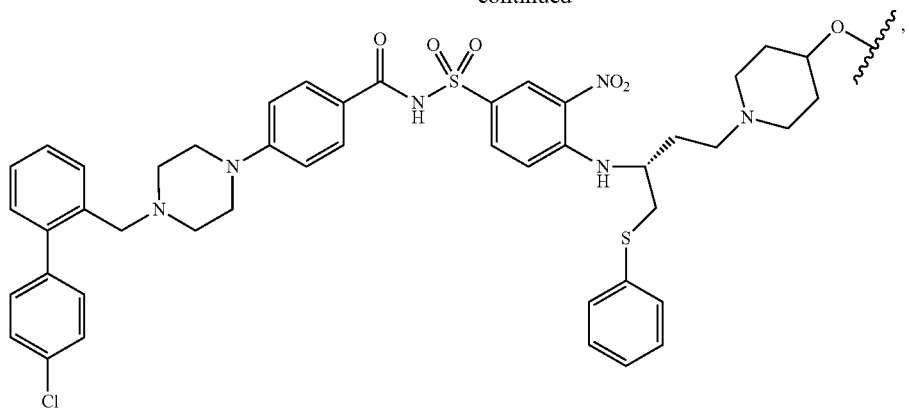
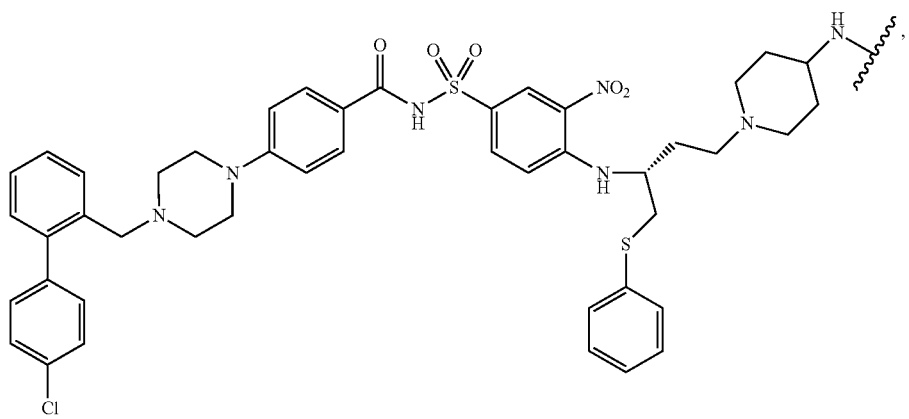
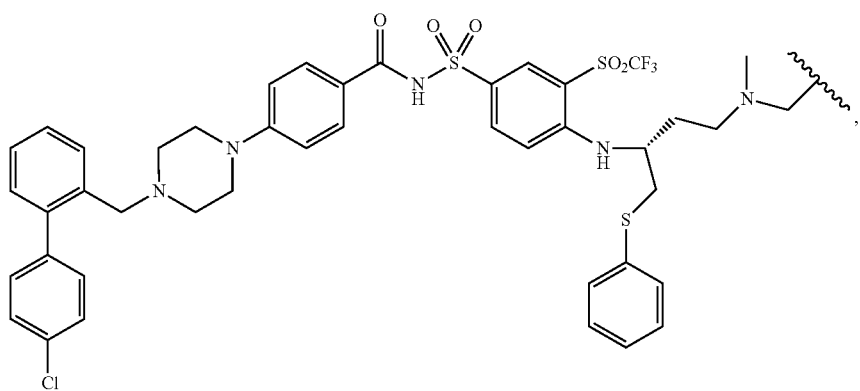
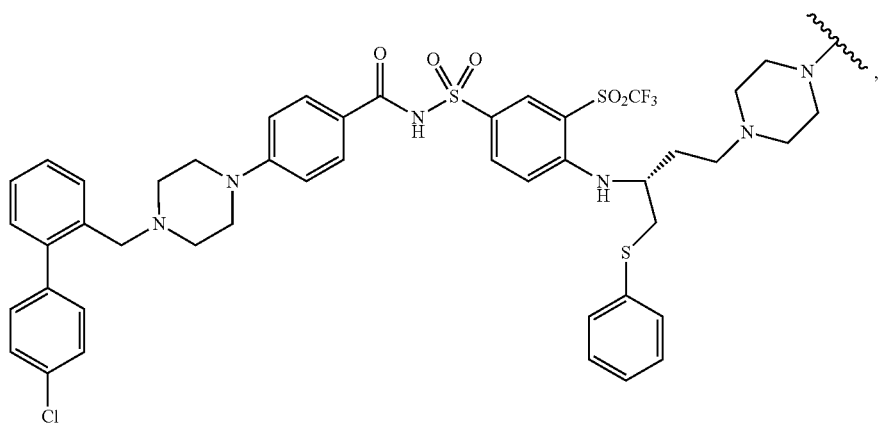

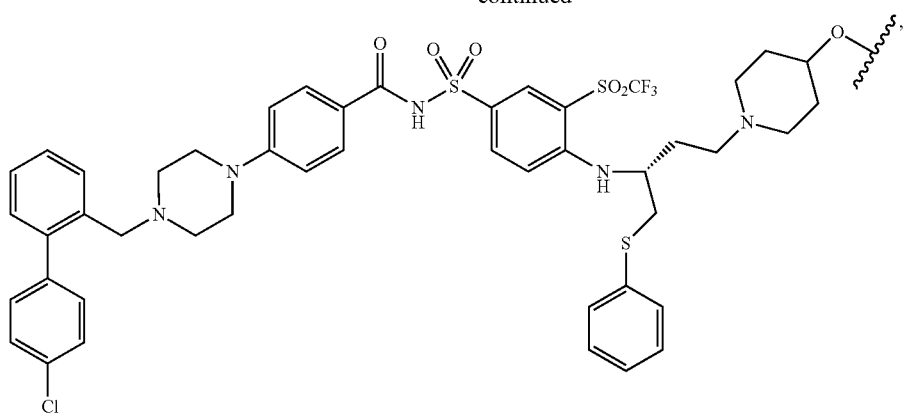
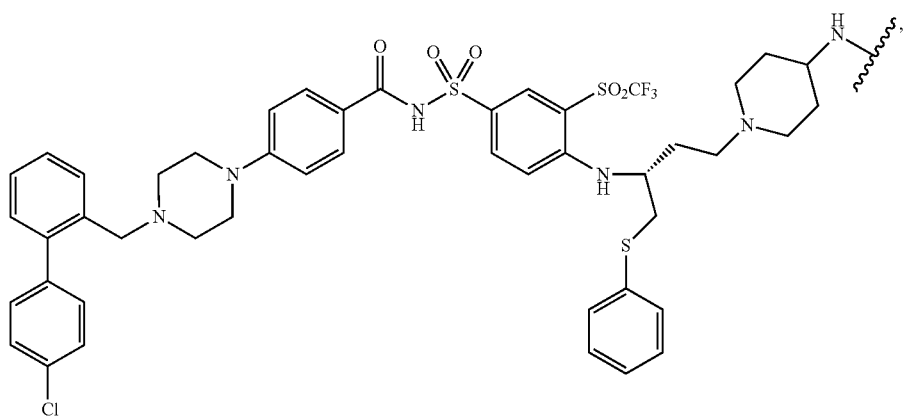
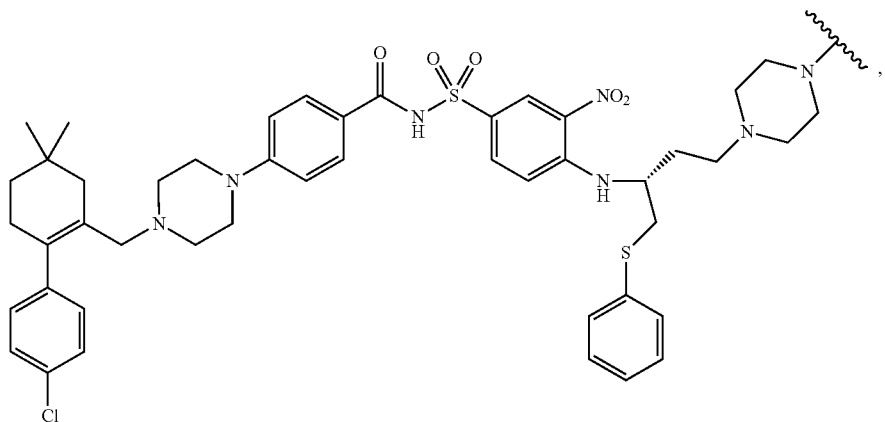
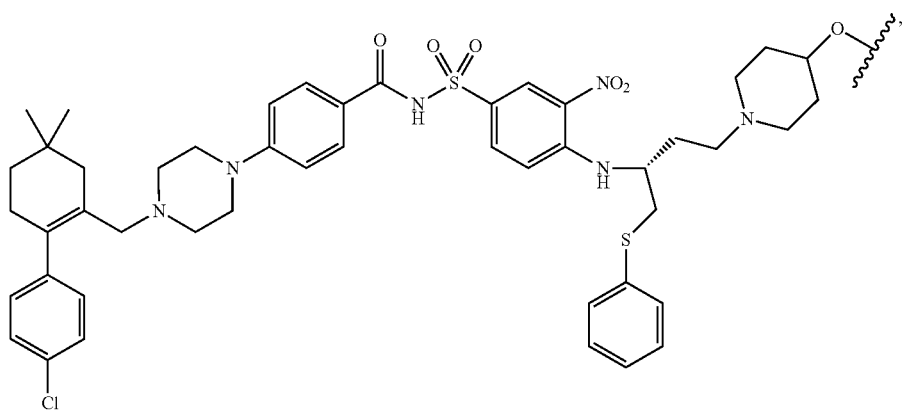

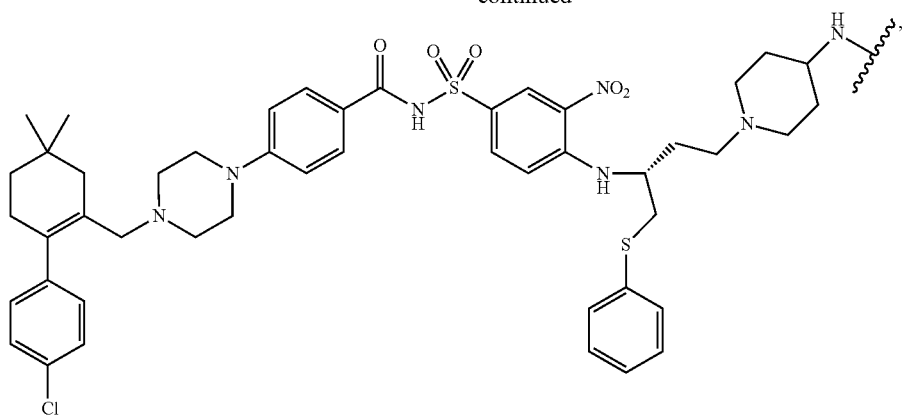
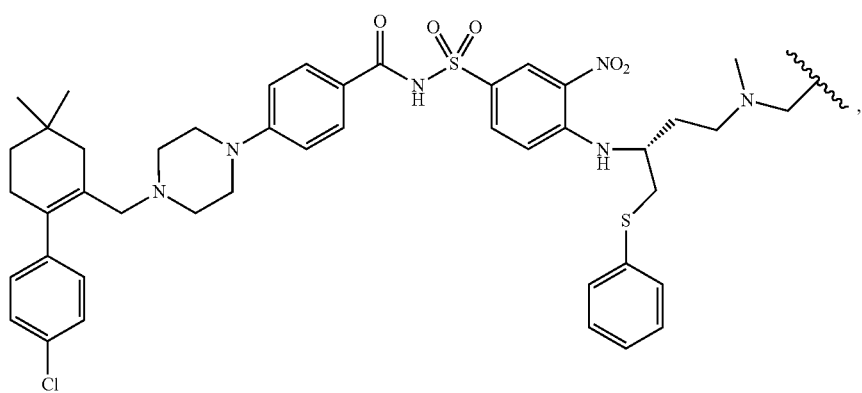
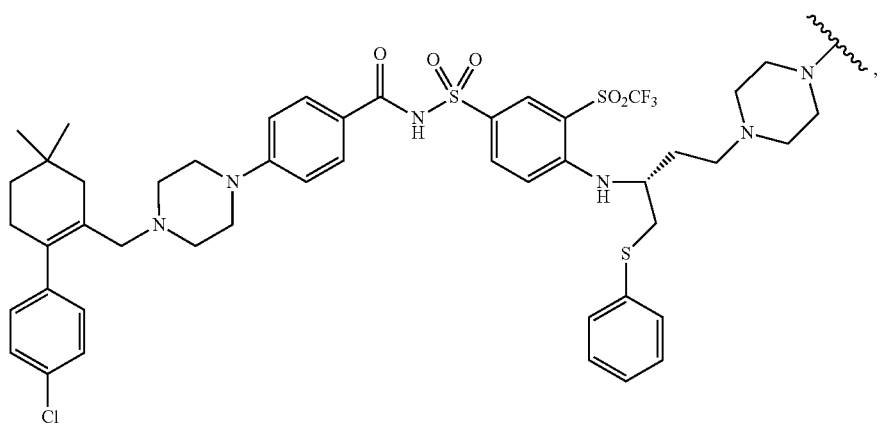
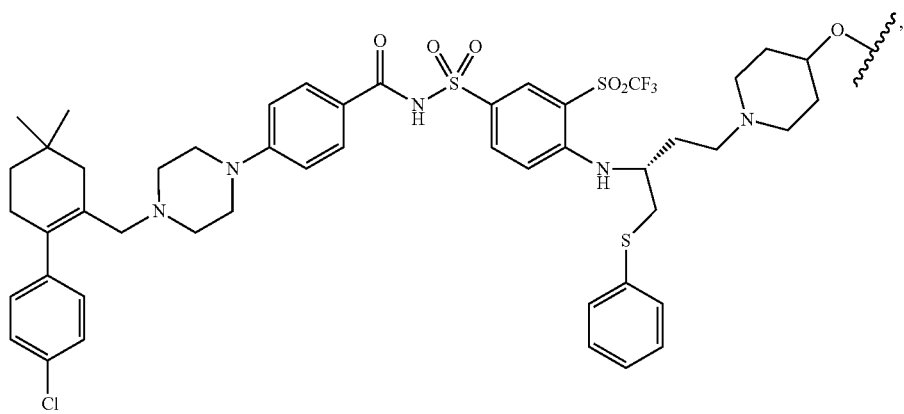

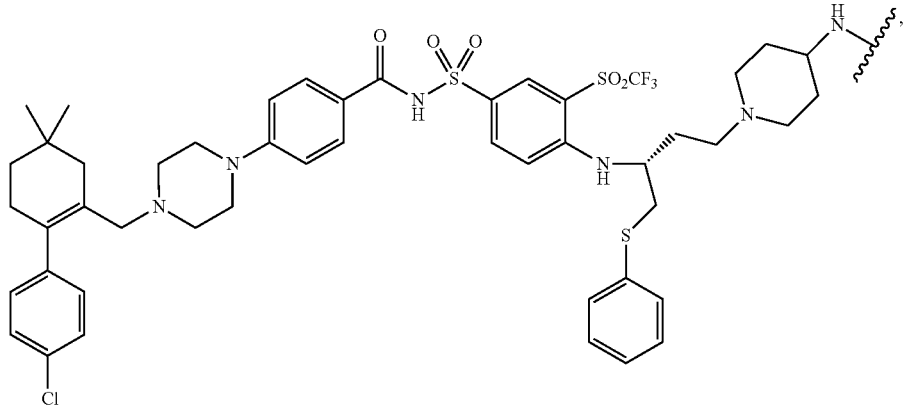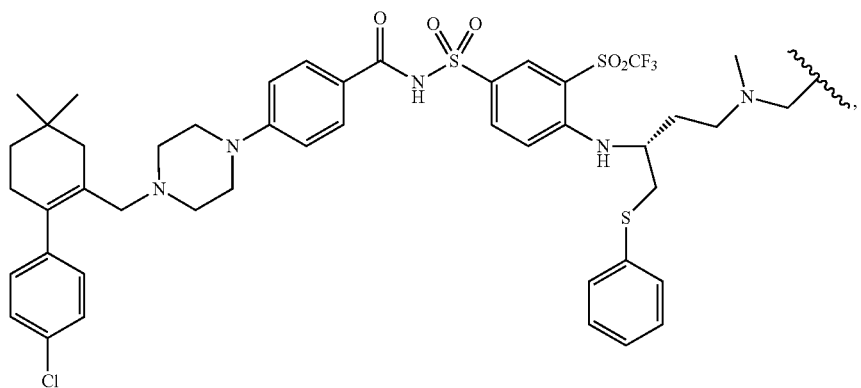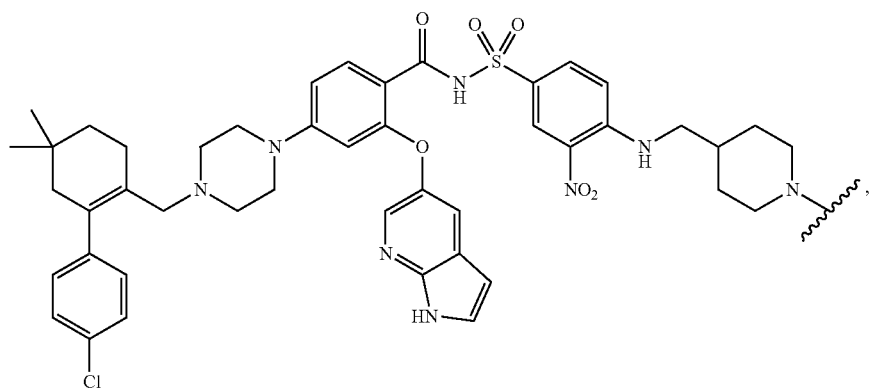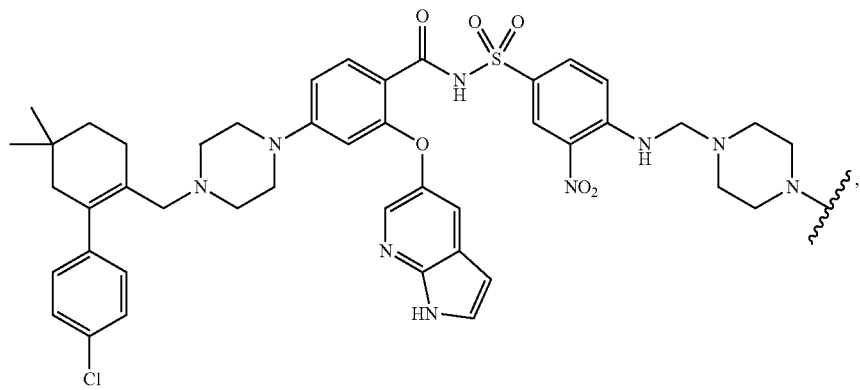

-continued
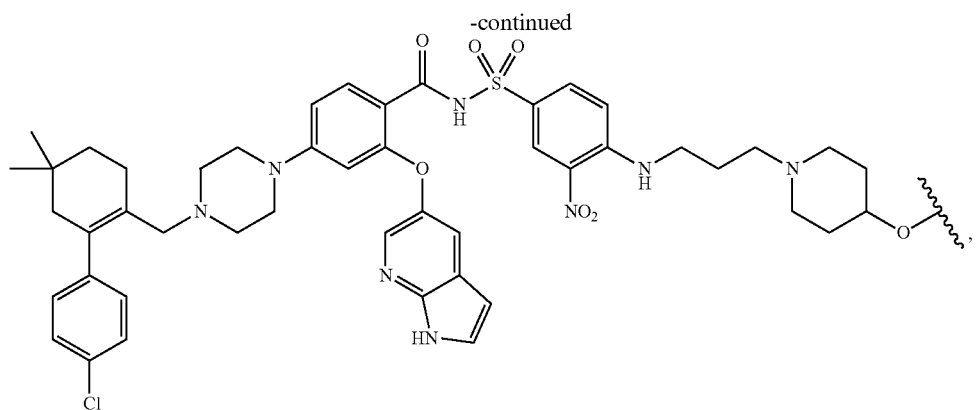
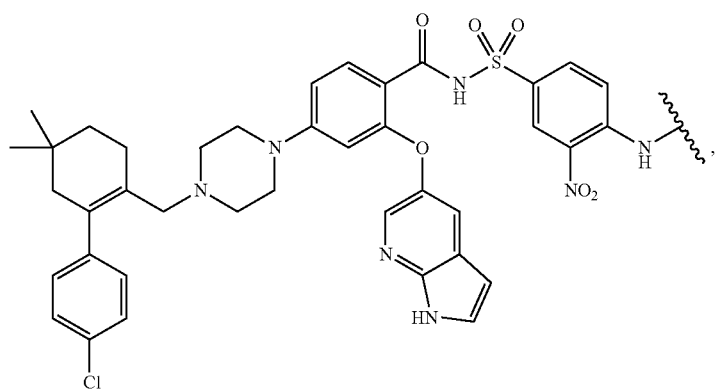
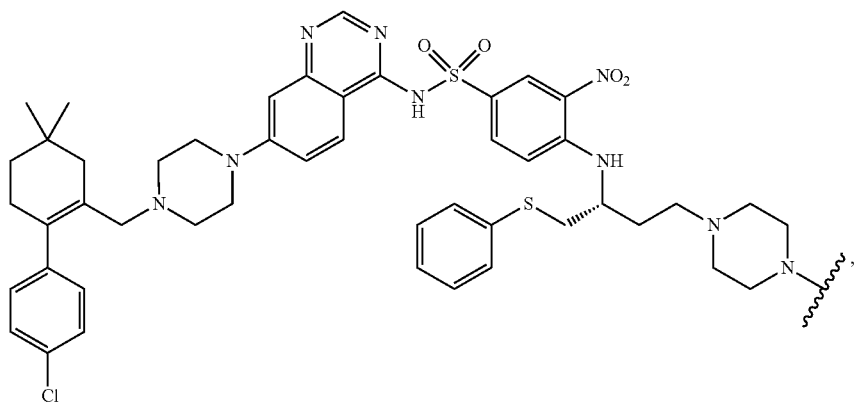
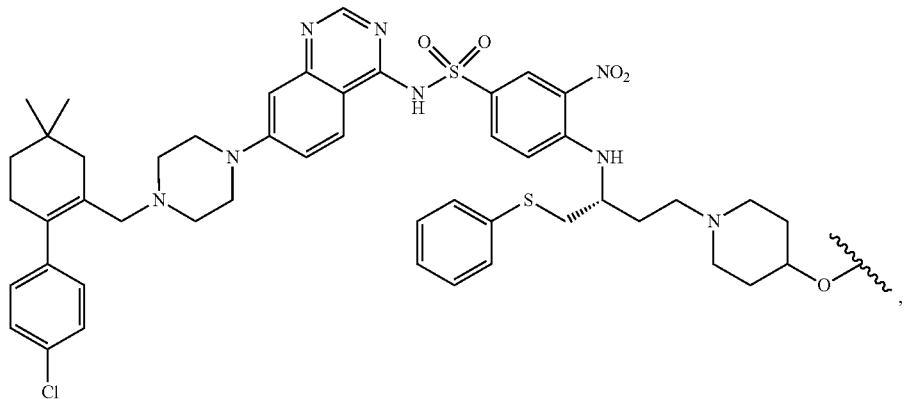

-continued
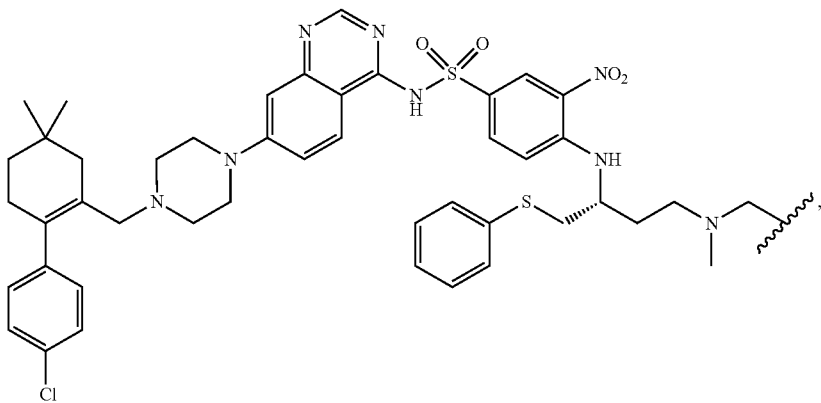
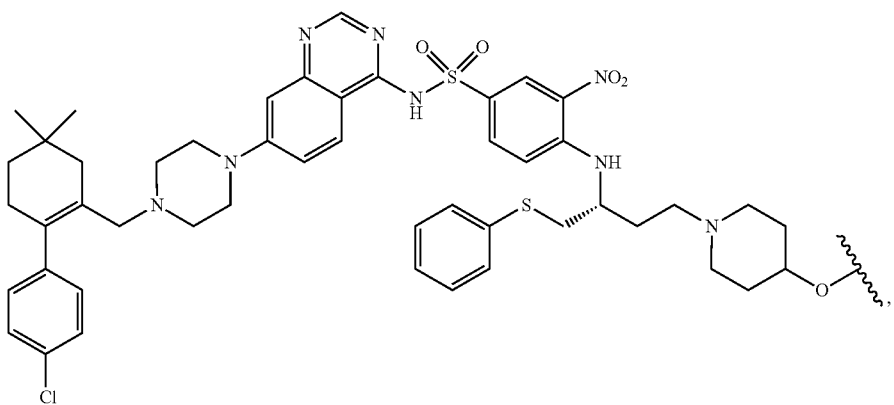
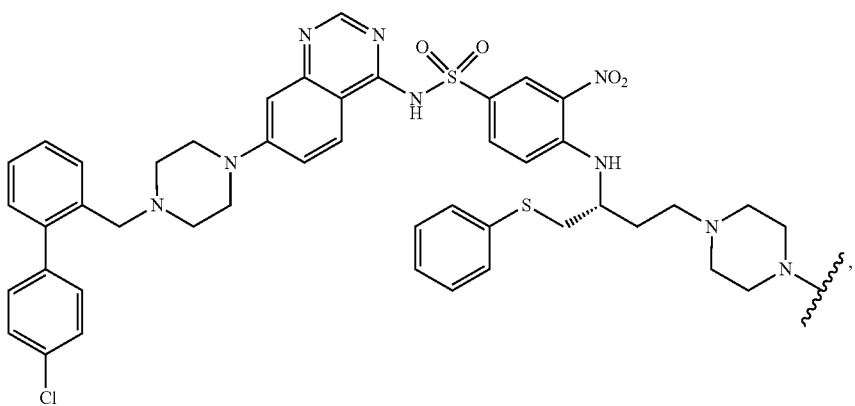
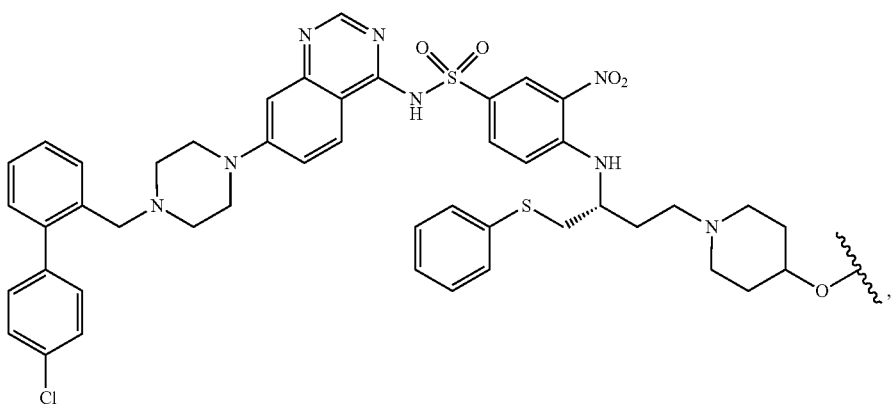

-continued
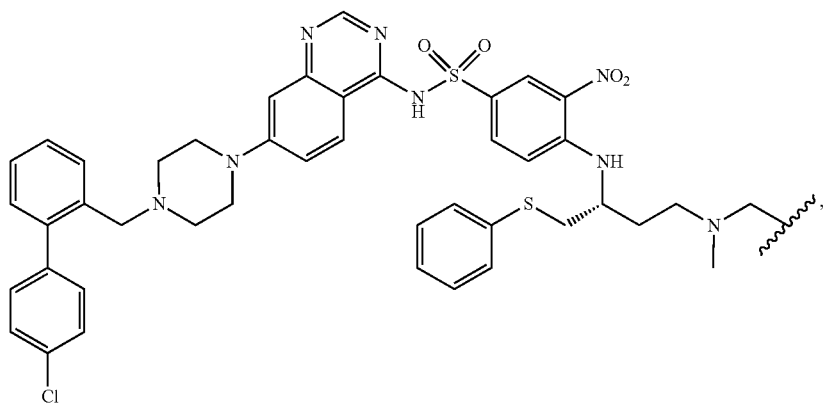
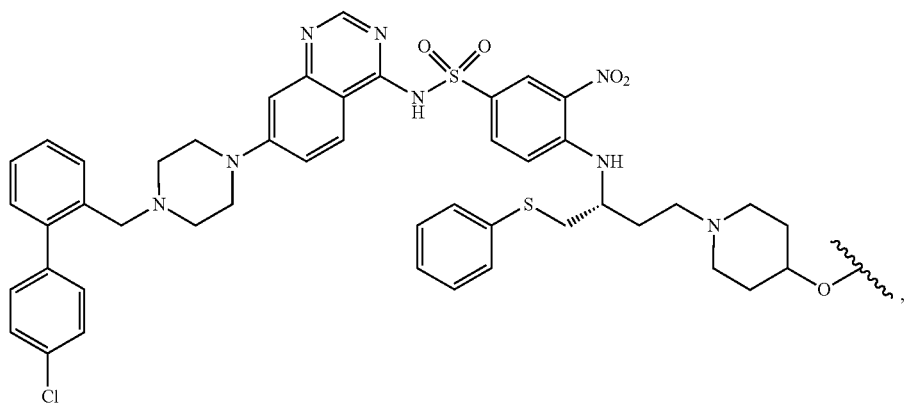
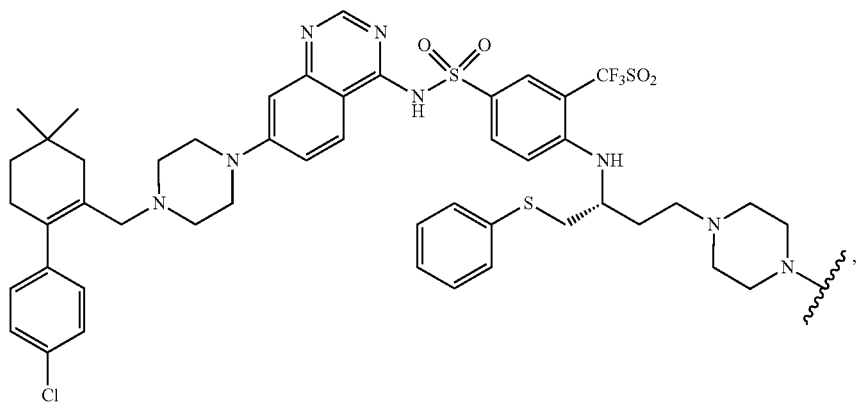
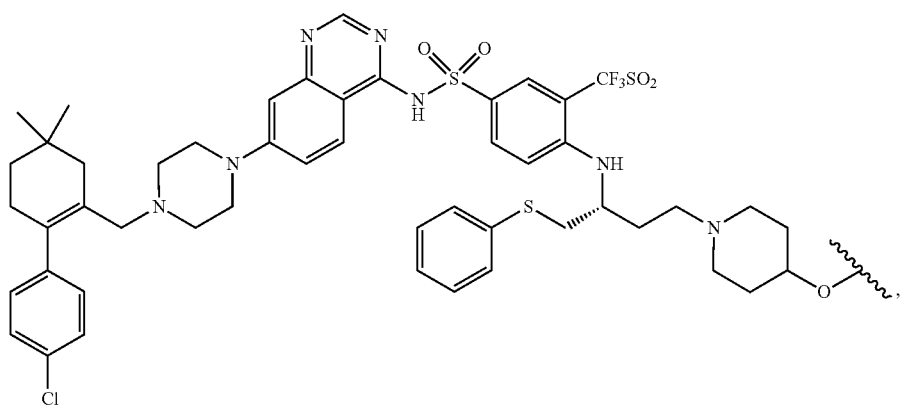

-continued
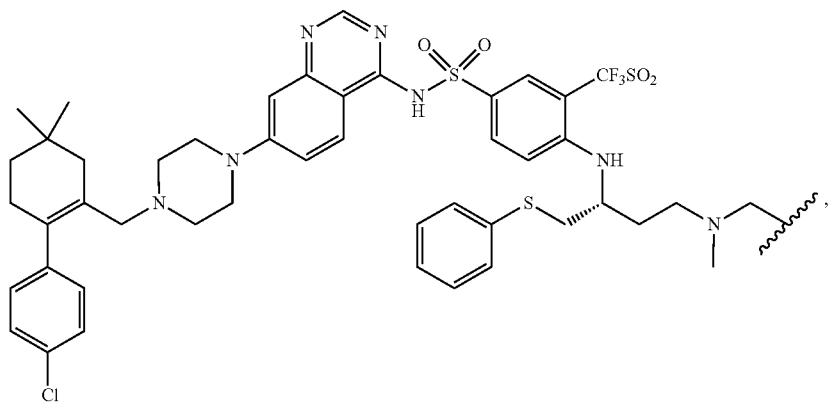
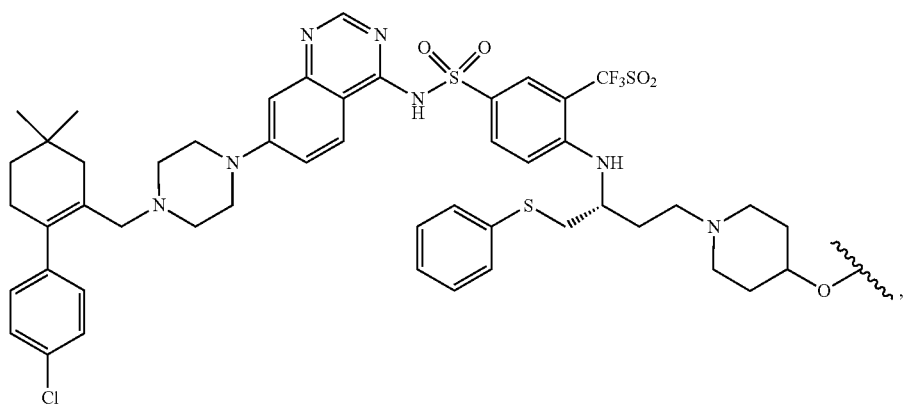
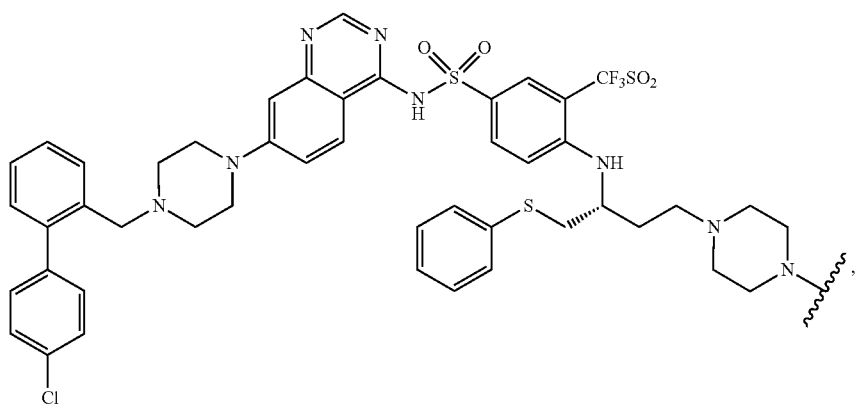
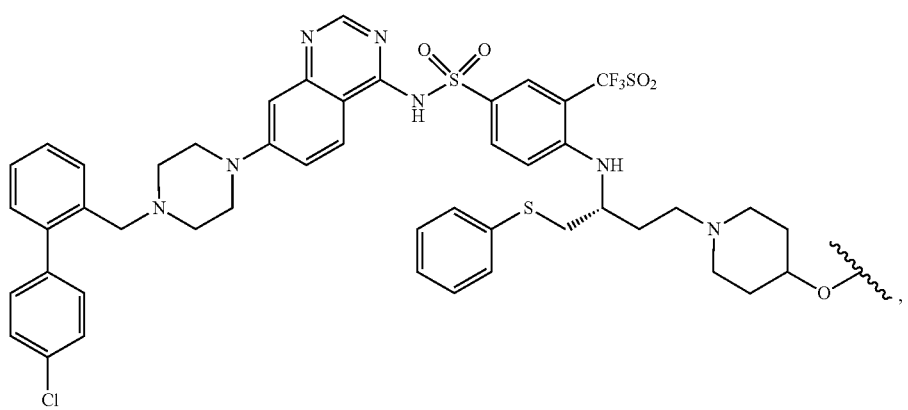

-continued
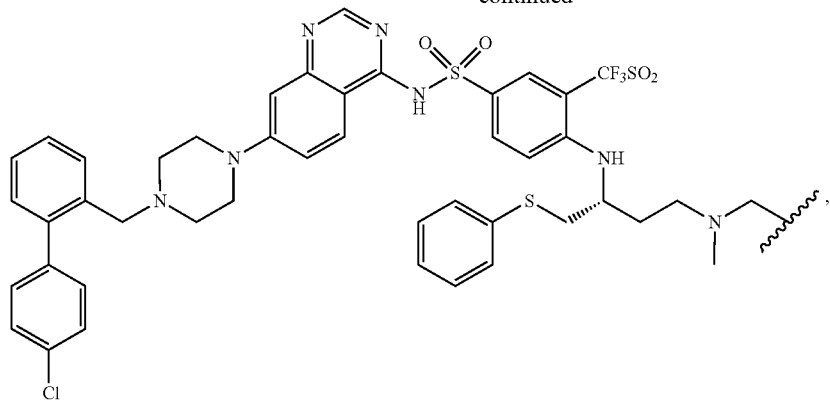
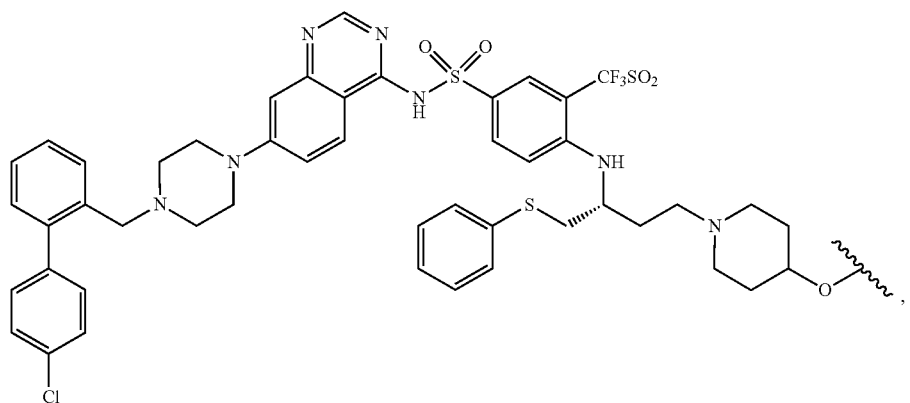
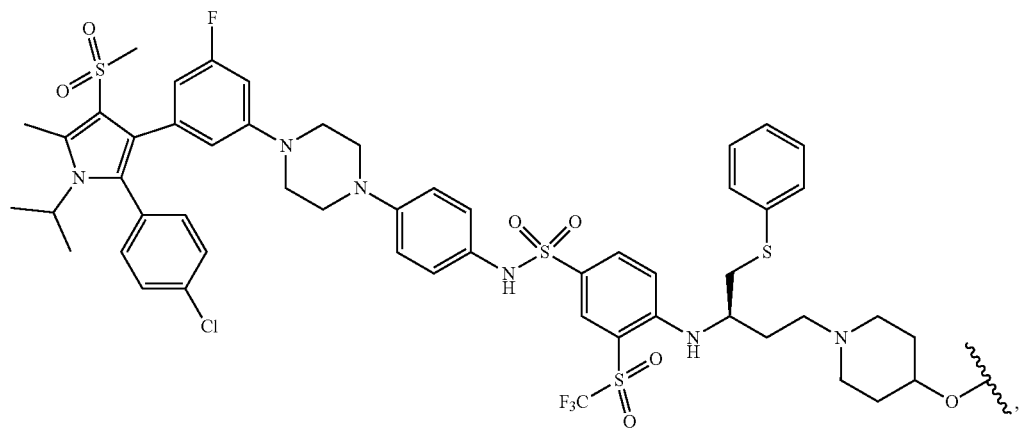
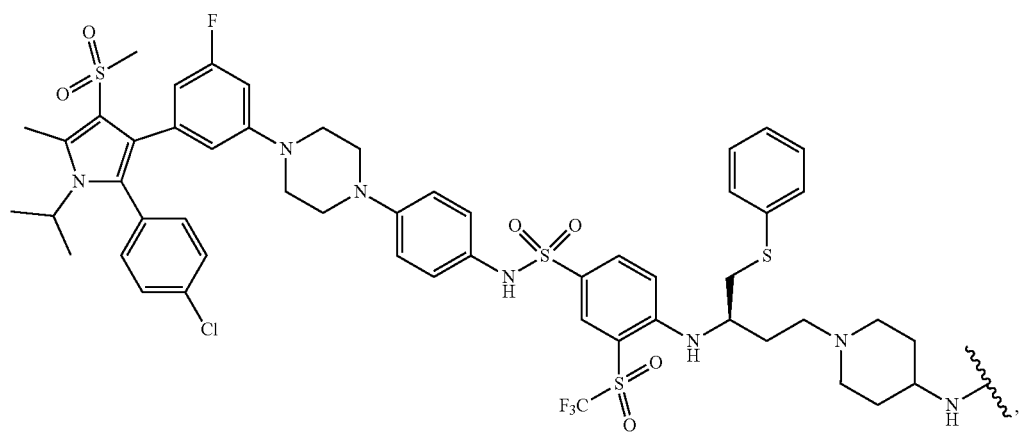

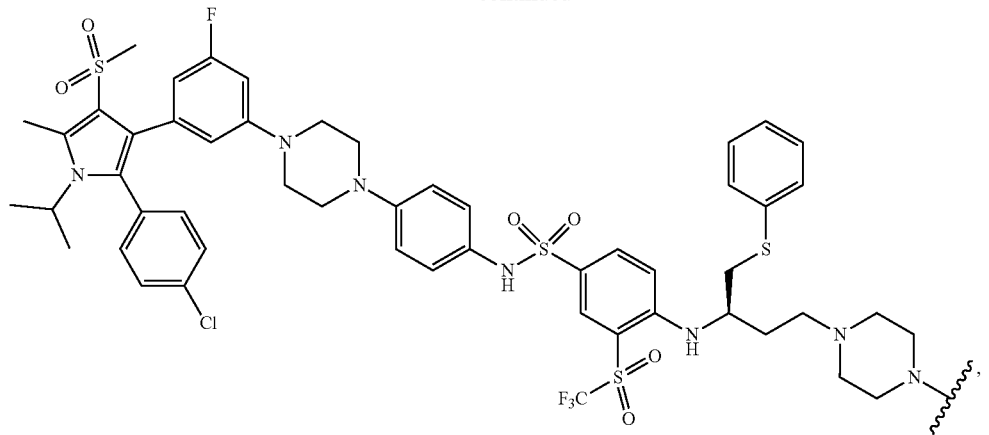
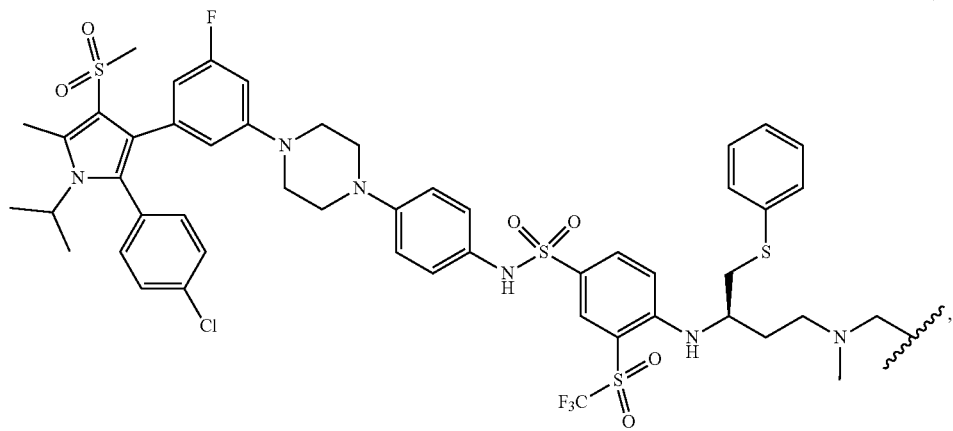
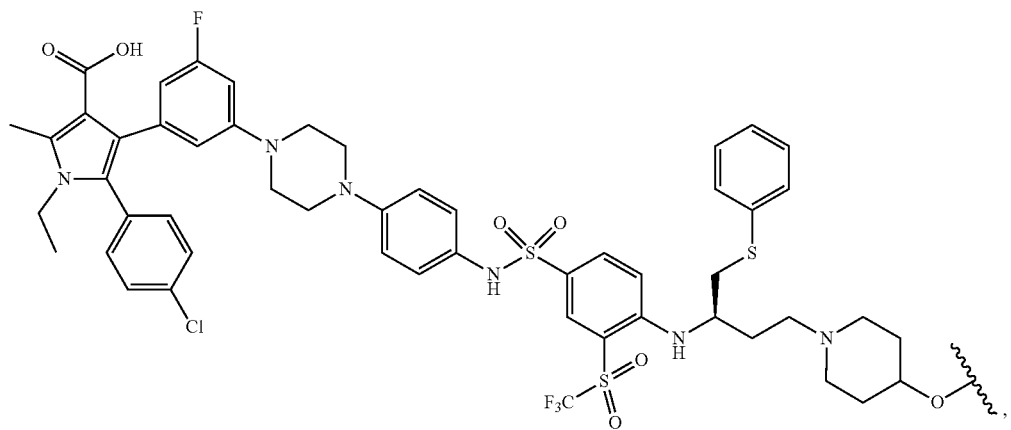
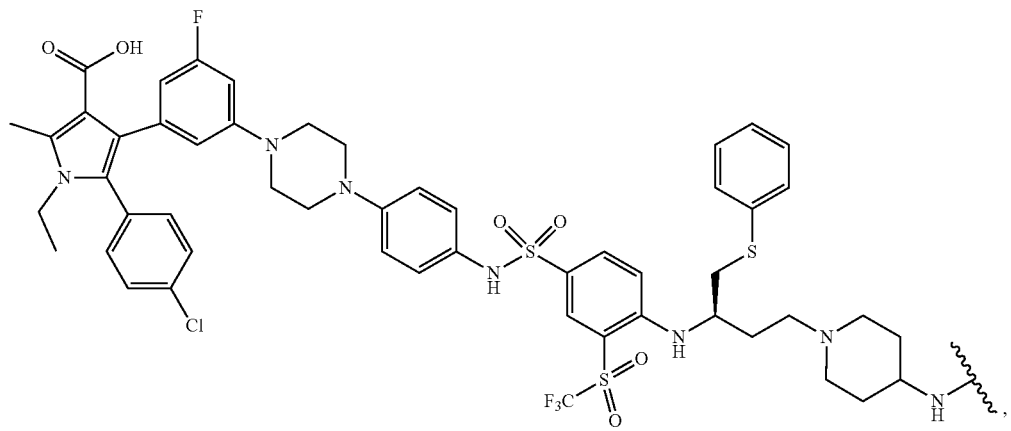

-continued
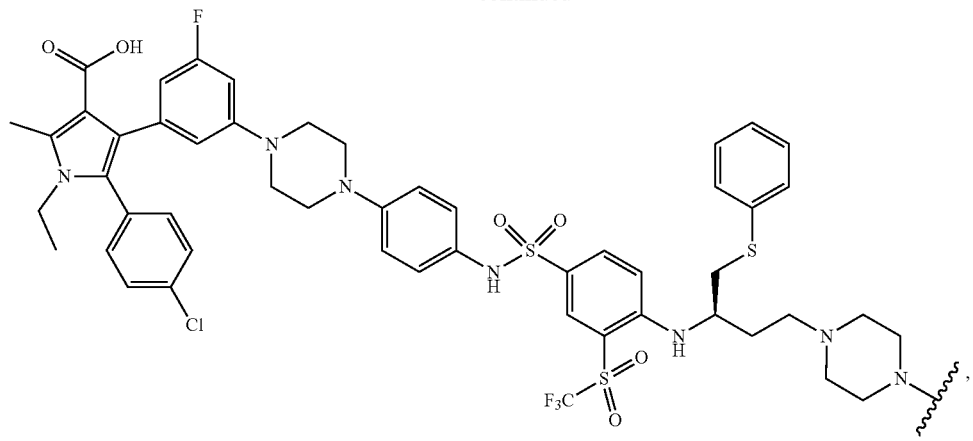
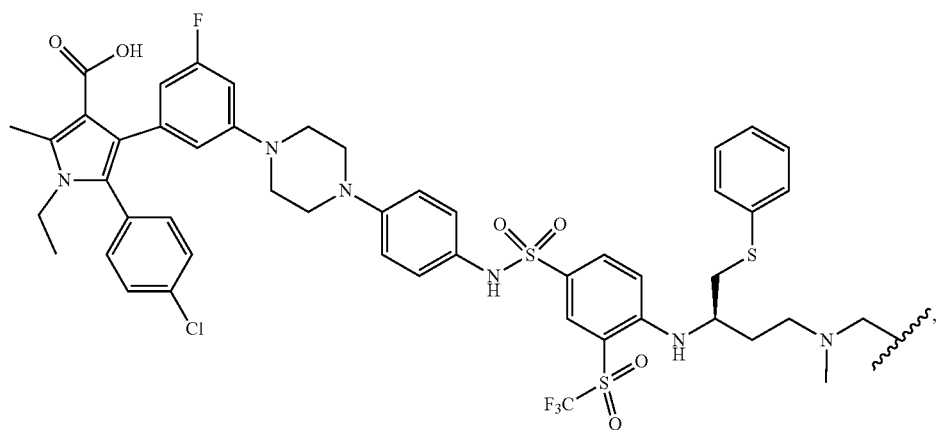
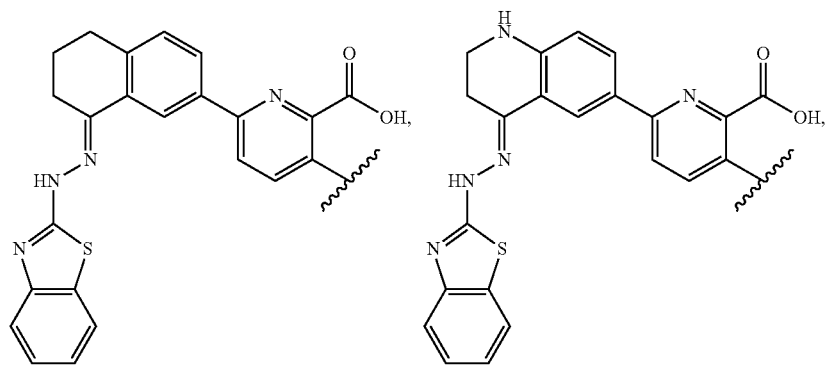
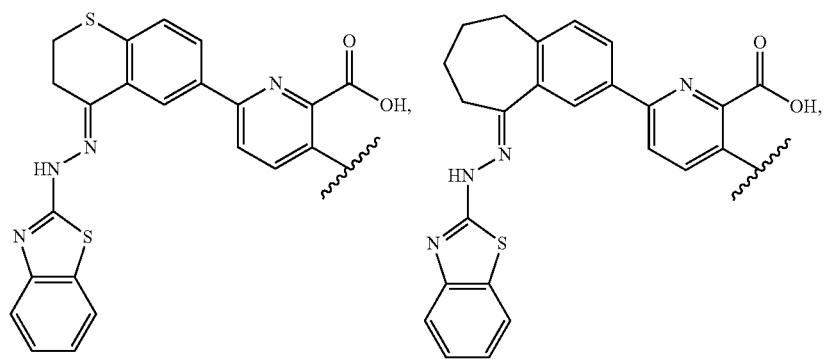

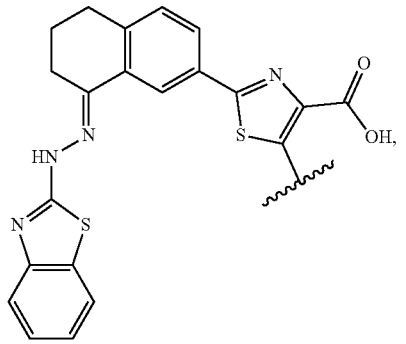
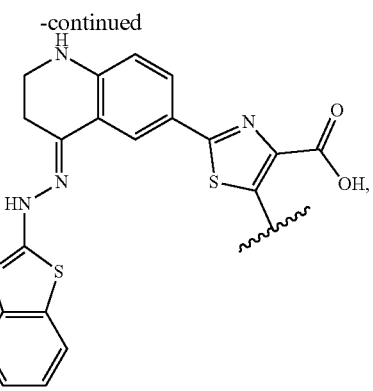
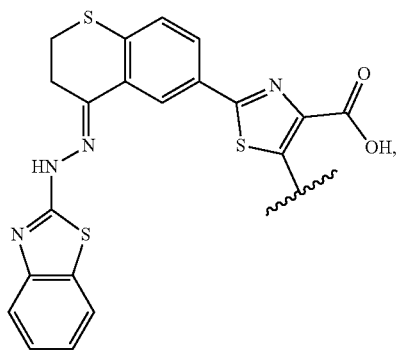
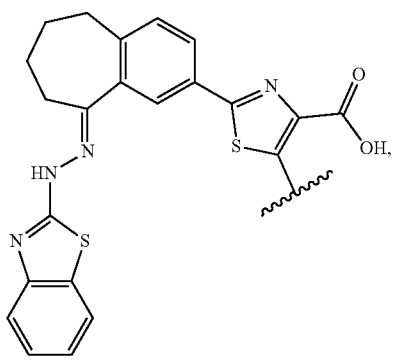
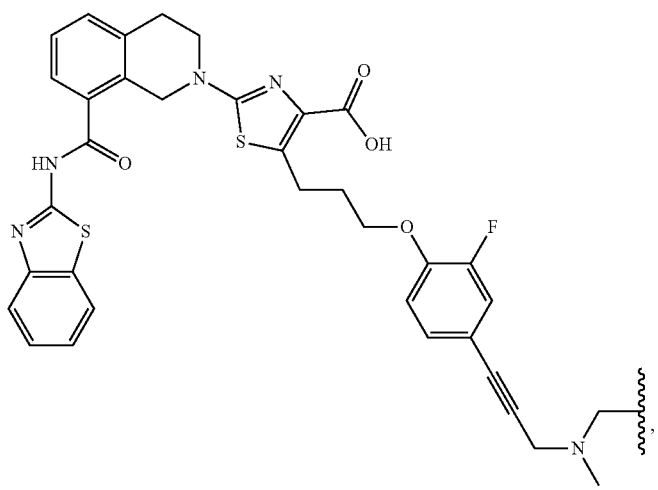
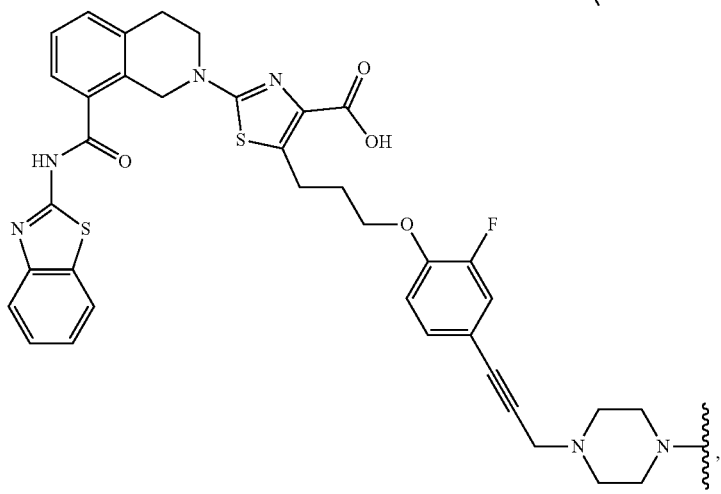

-continued
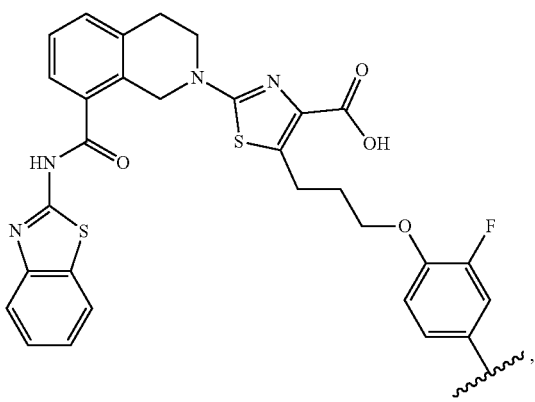
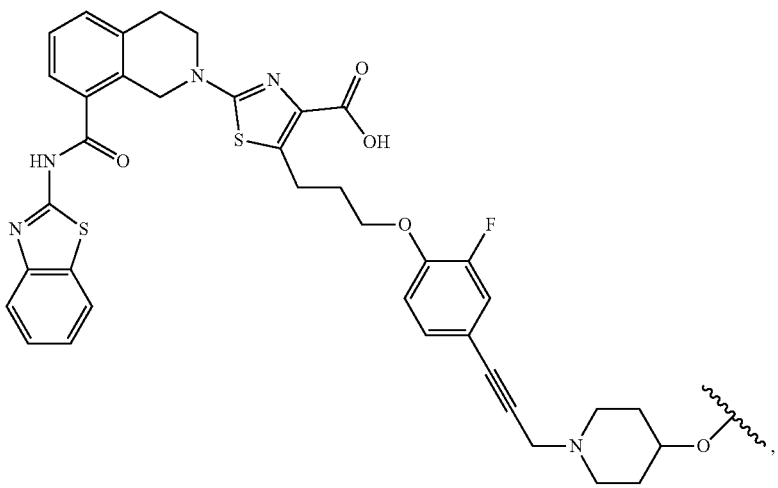
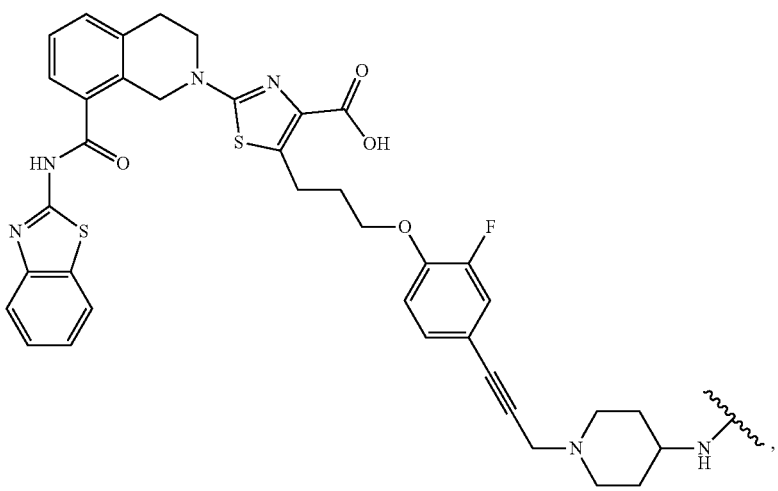
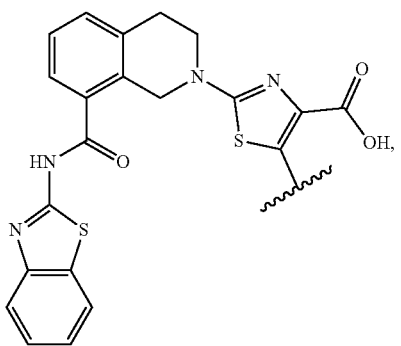

-continued
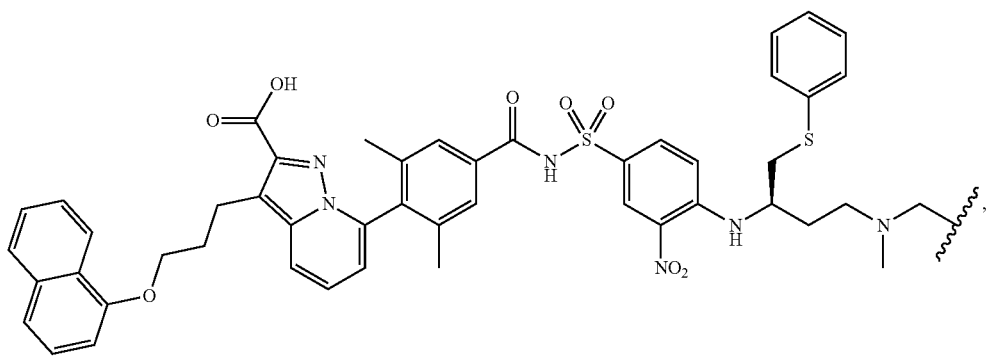
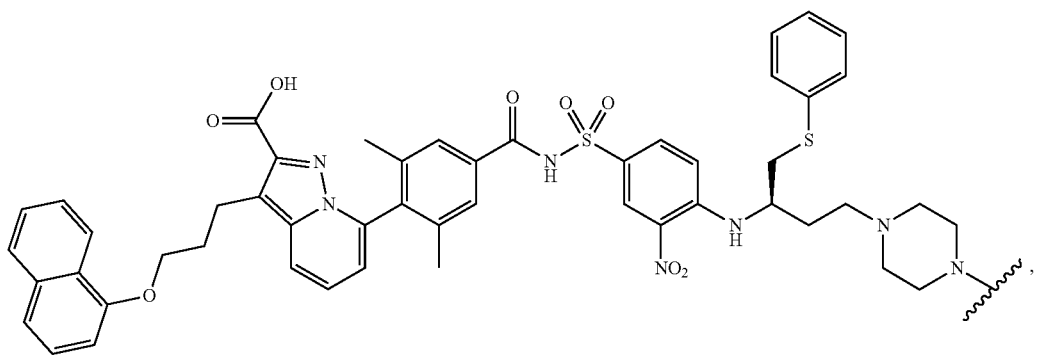
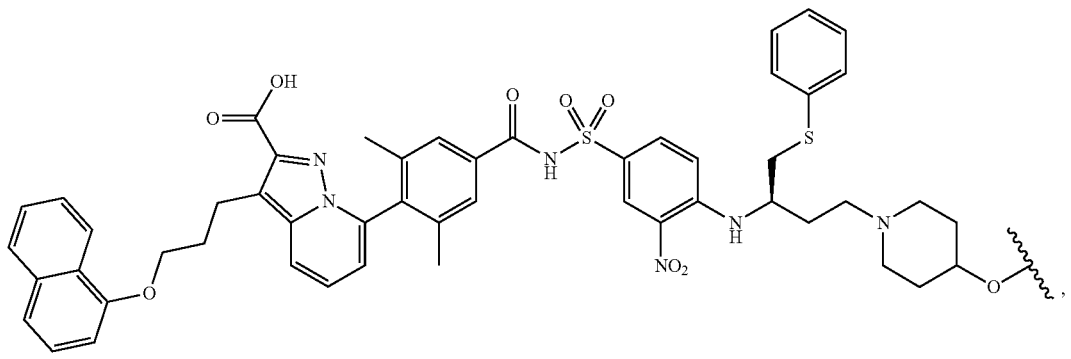
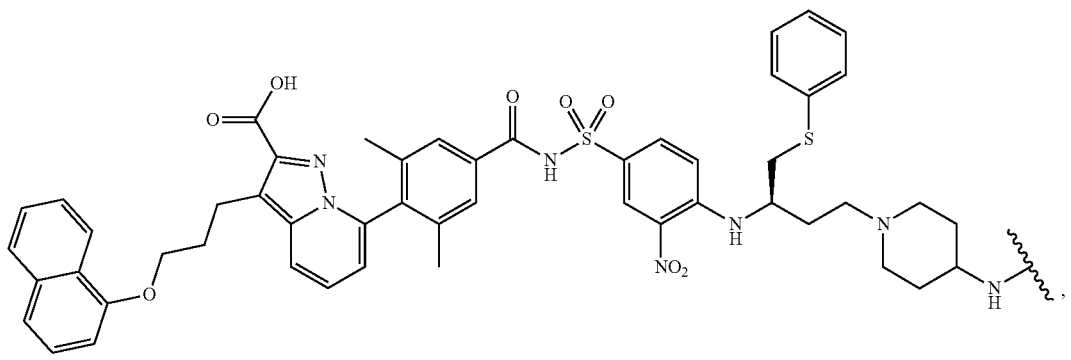

-continued
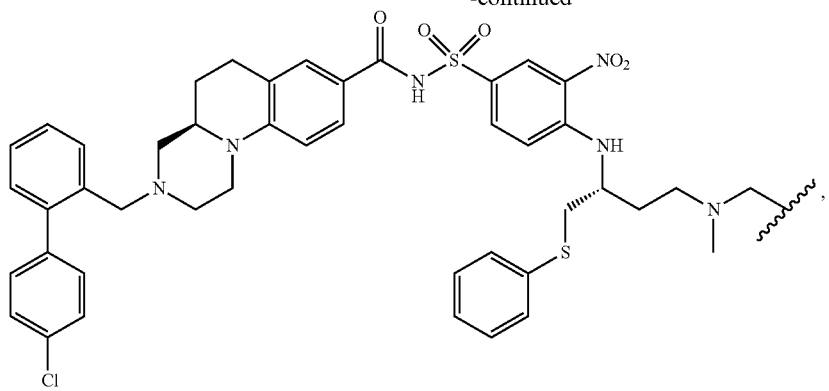
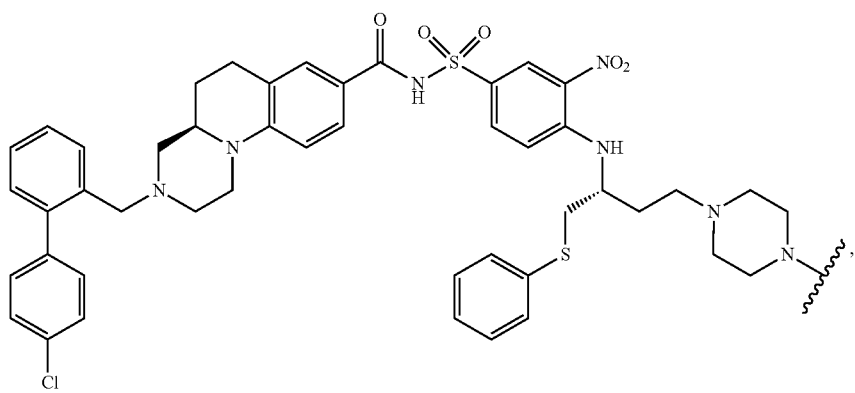
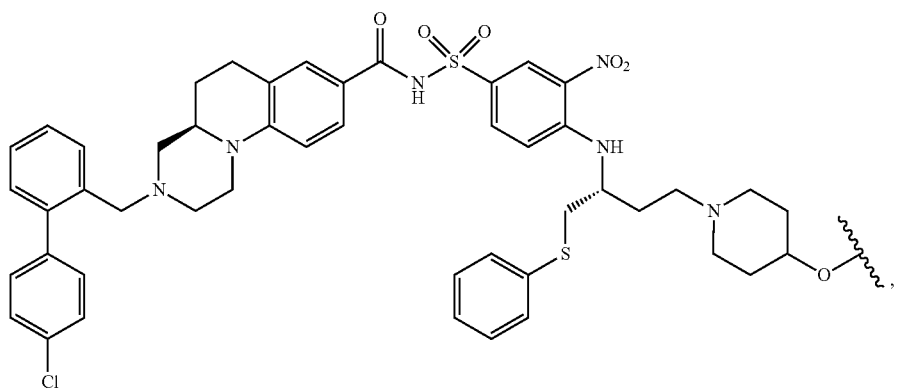
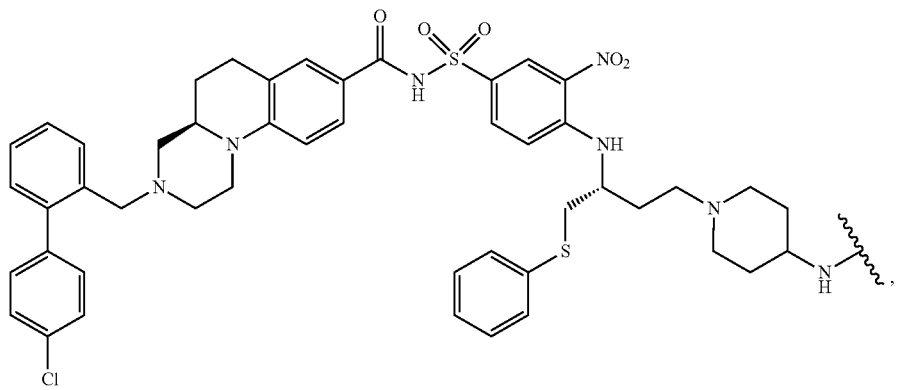

-continued
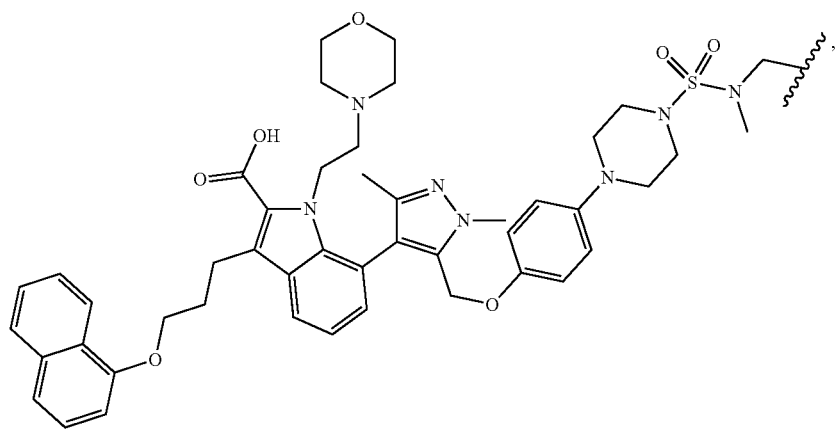
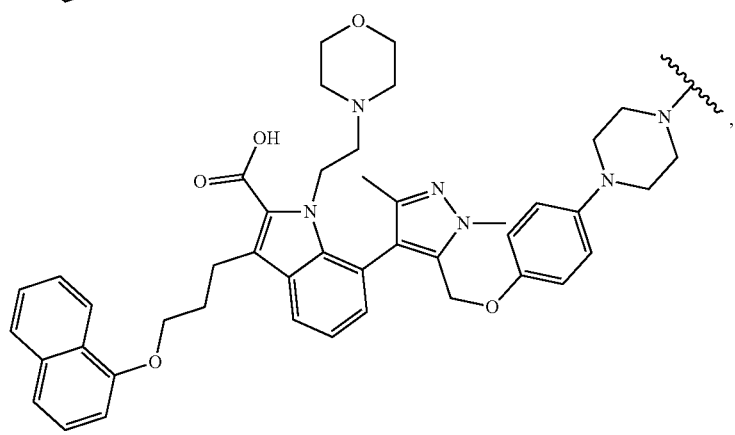
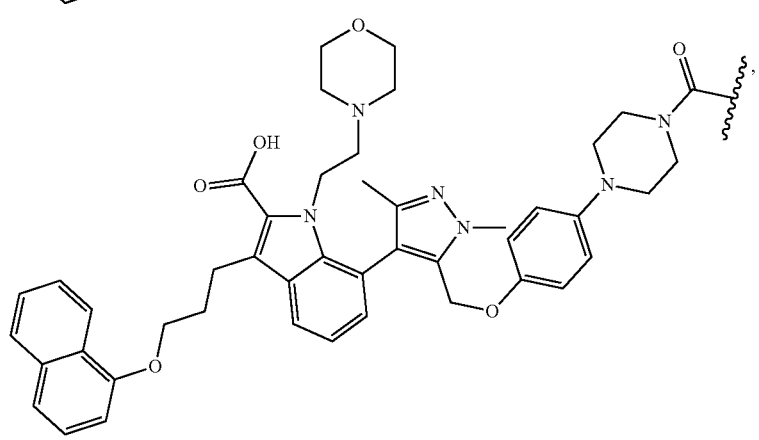
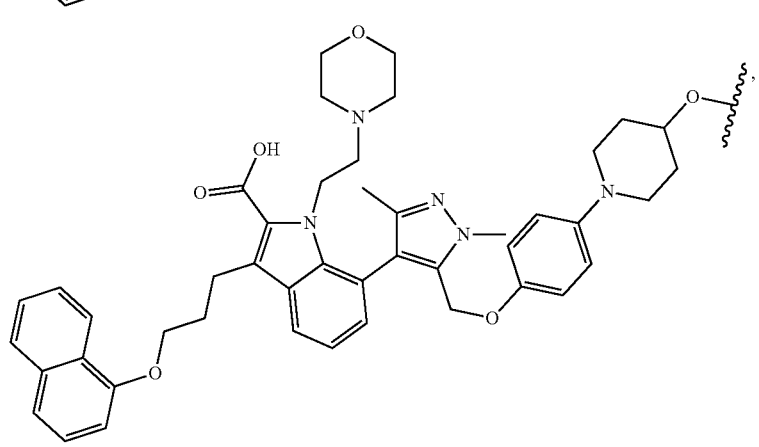

-continued
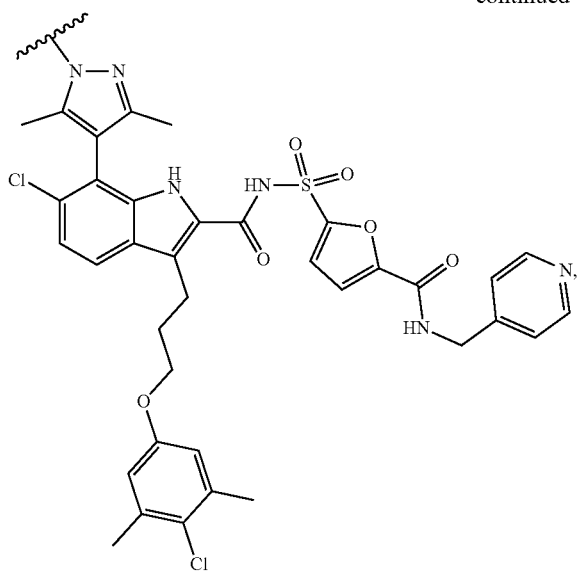
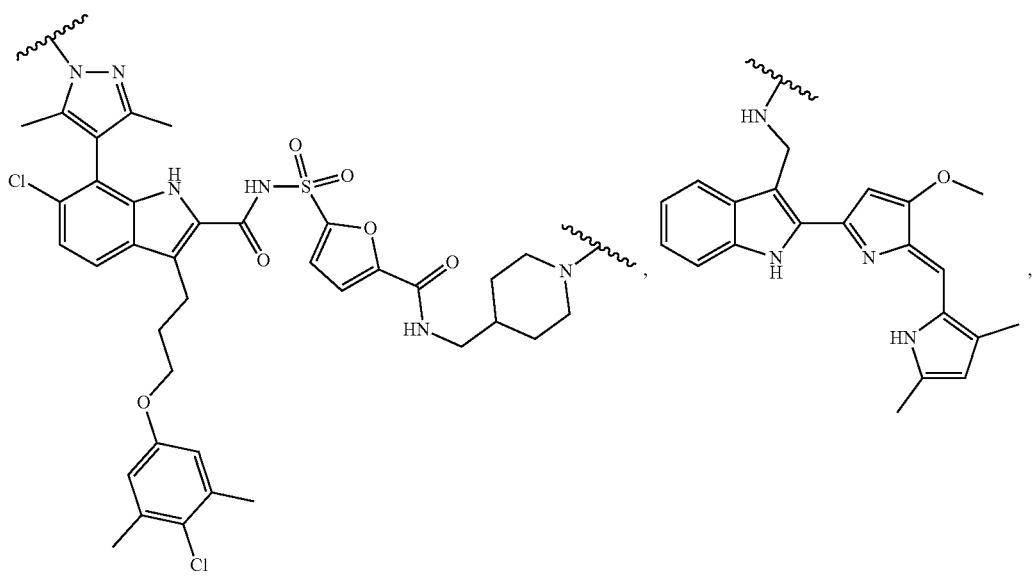
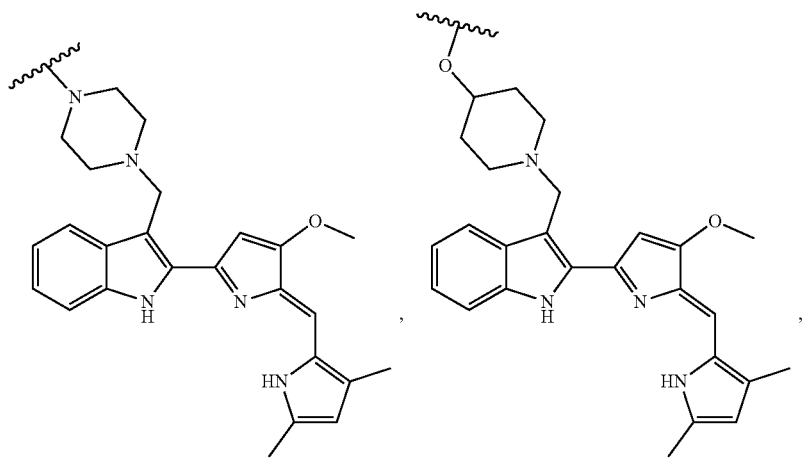

-continued
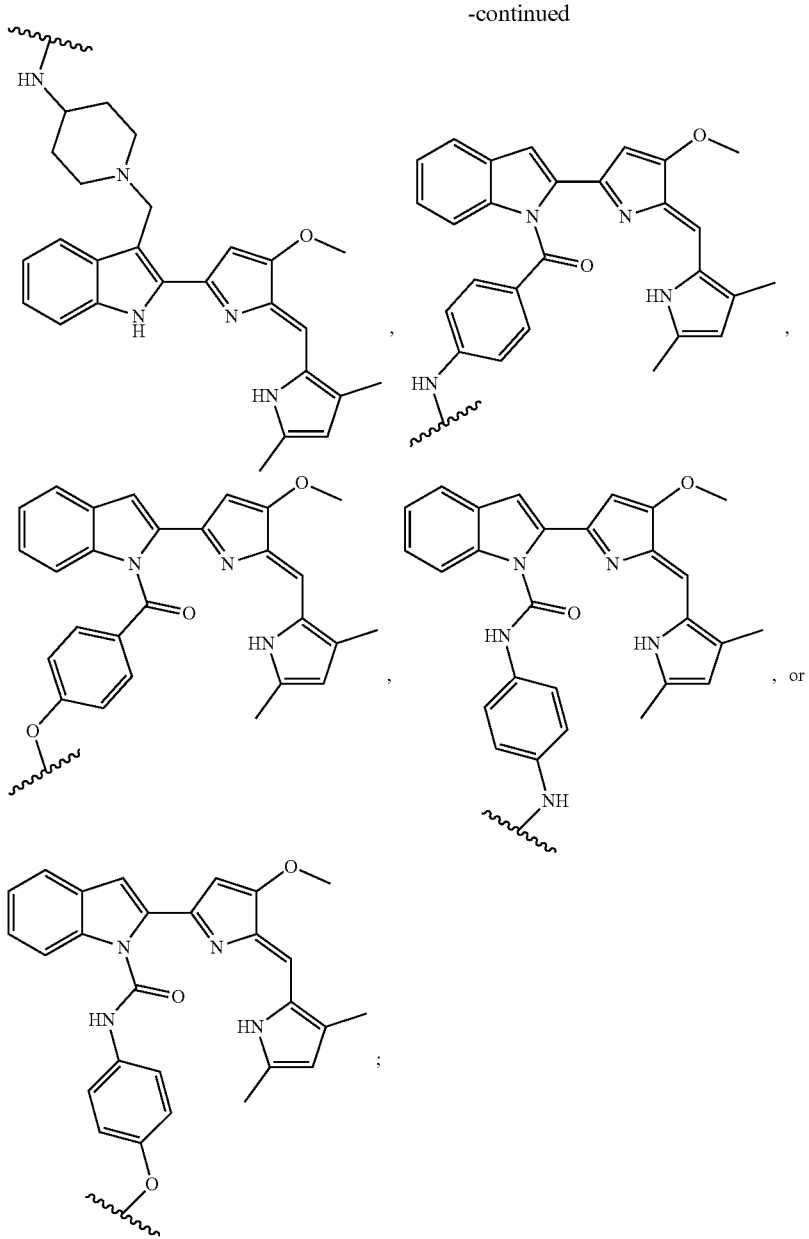
R³ may be absent, an unsubstituted C₁-C₆ alkyl, or a substituted or unsubstituted C₃-C₆ ketone; A may be absent, a bond, or a substituted or unsubstituted C₁-C₆ heterocyclic group; n may be 0 to 3; R⁴ may be a bond or a substituted or unsubstituted C₁-C₁₀ alkyl; and R² may be
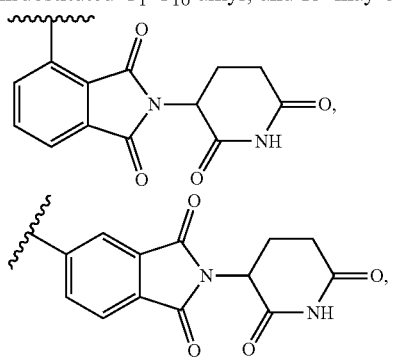
-continued
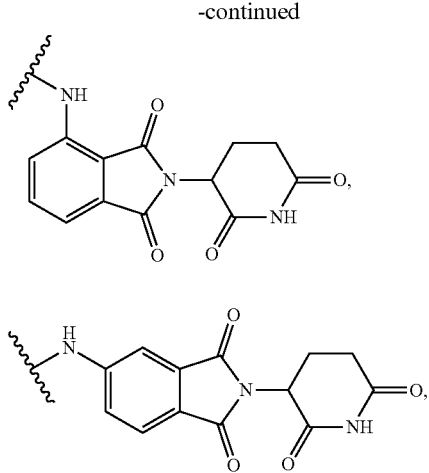

127
-continued
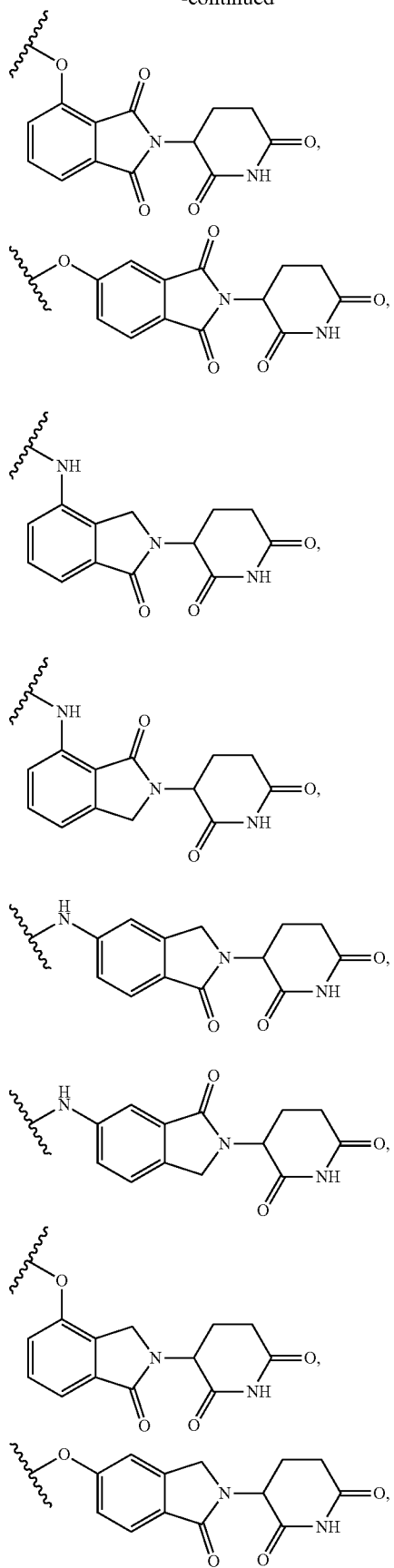
128
-continued
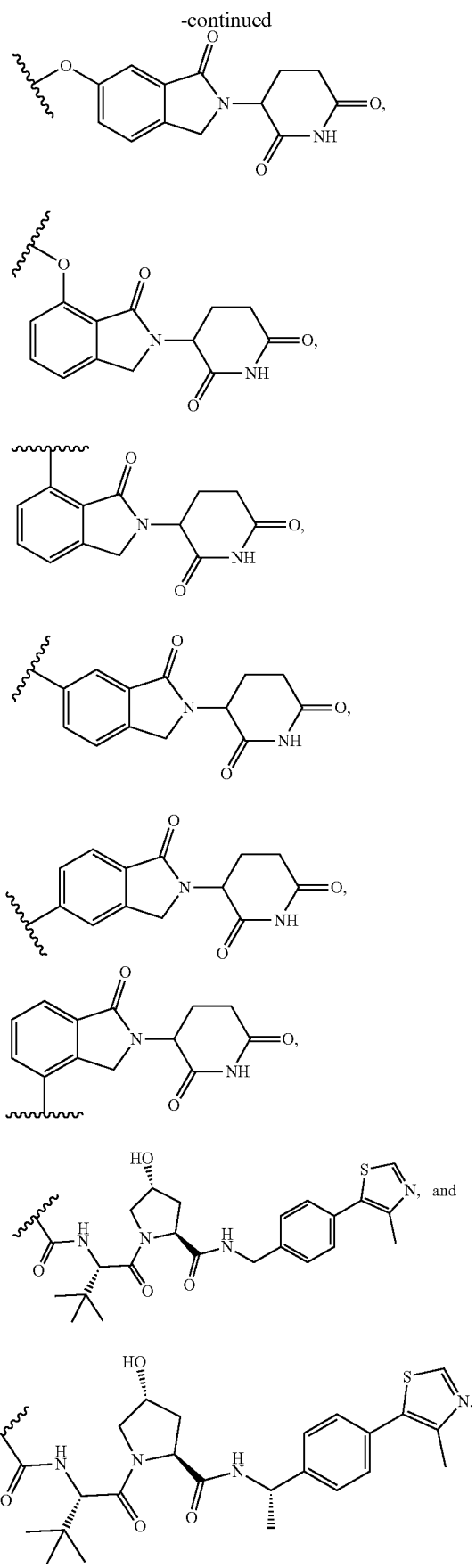

In another embodiment, a compound of the disclosure comprises Formula (II), wherein R¹ may be
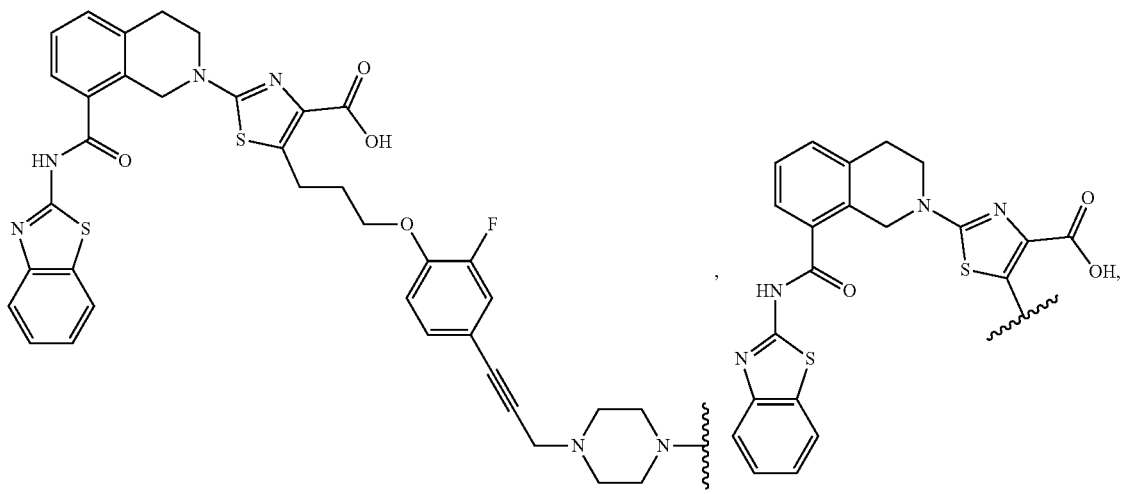
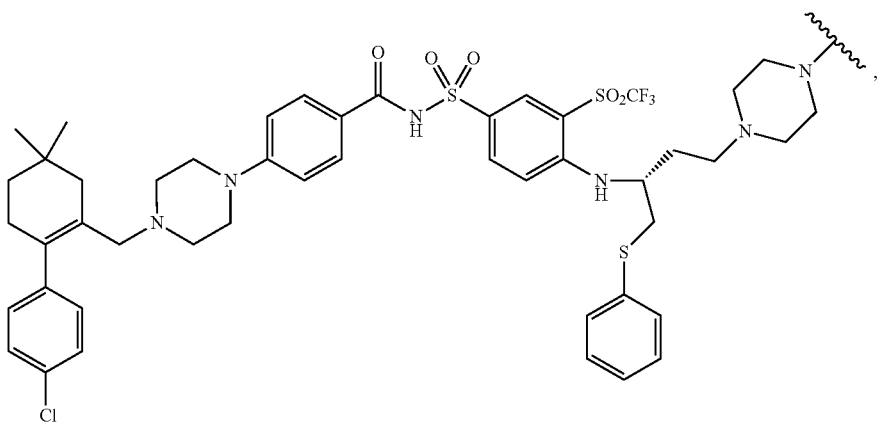
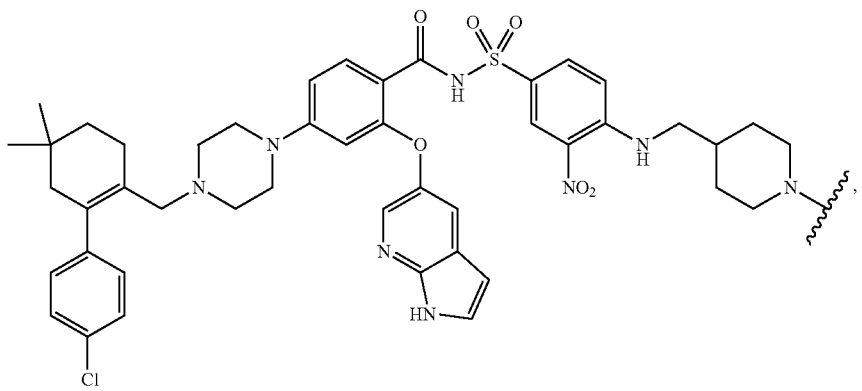

-continued
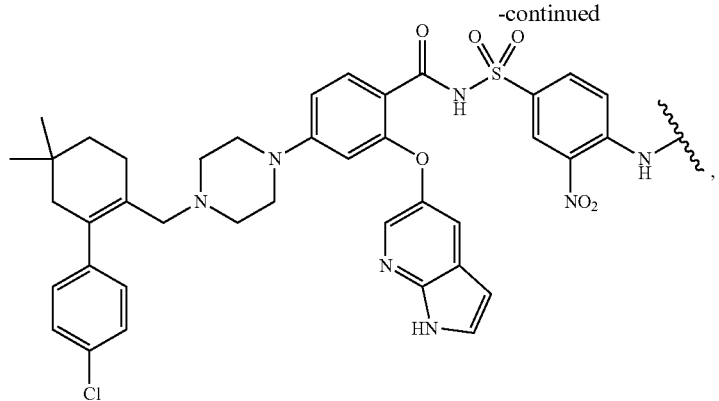
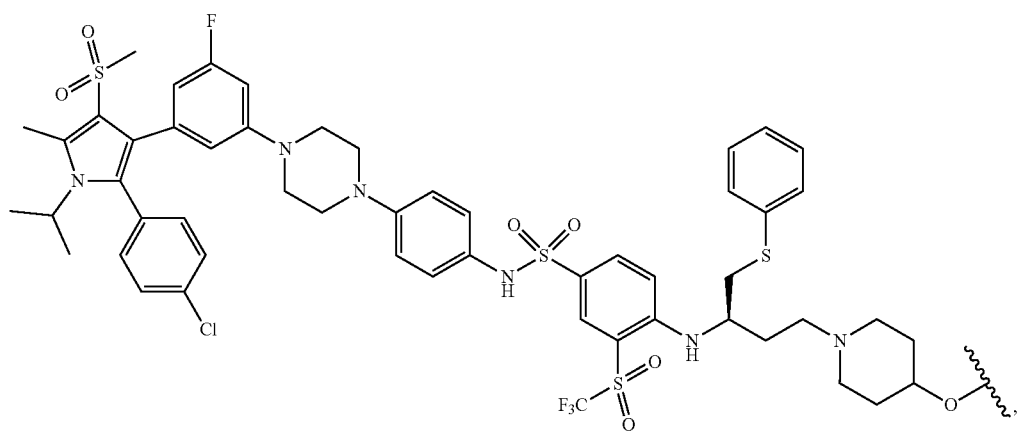
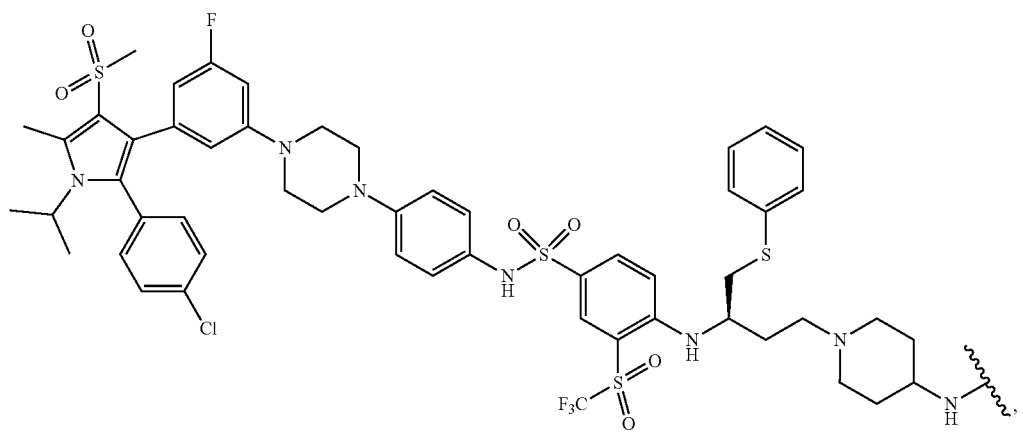
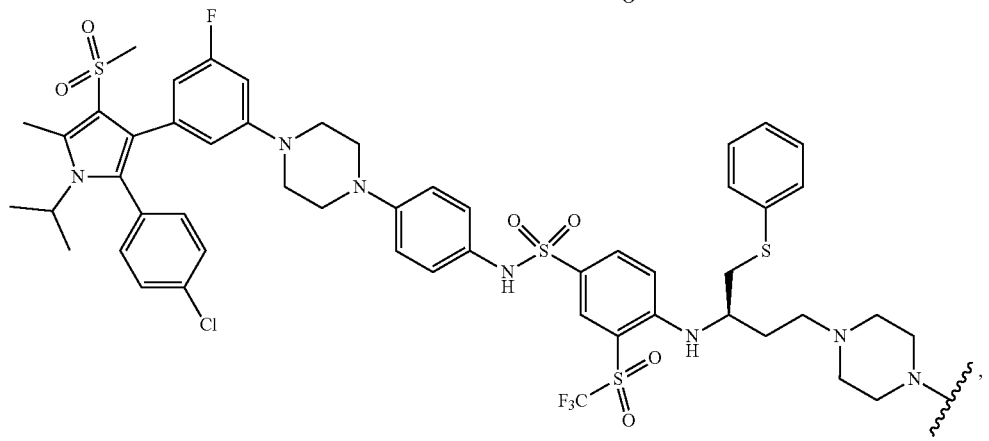

-continued
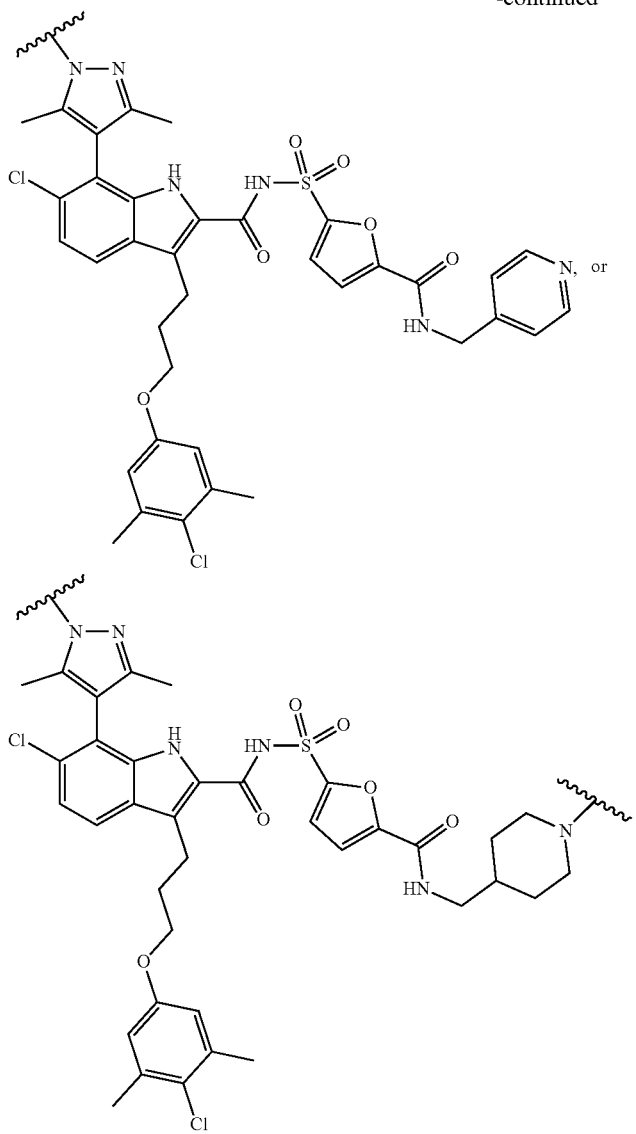
R³ may be absent, an unsubstituted C₁-C₆ alkyl, or a substituted or unsubstituted C₃-C₆ ketone; A may be absent, a bond, or a substituted or unsubstituted C₁-C₆ heterocyclic group; n may be 0 to 3, R⁴ may be a bond or a substituted or unsubstituted C₁-C₁₀ alkyl; and R² may be
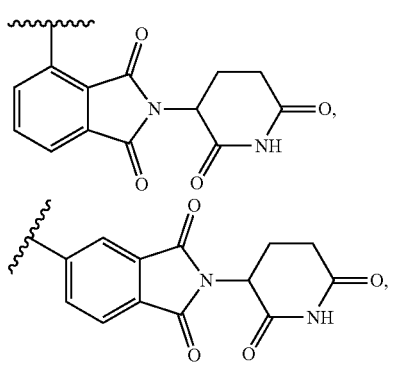
-continued
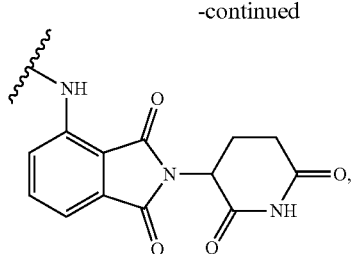
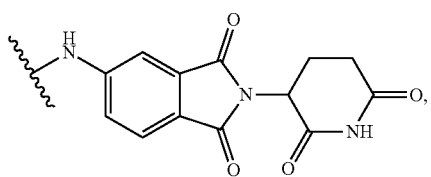

-continued
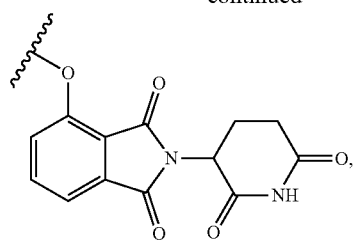
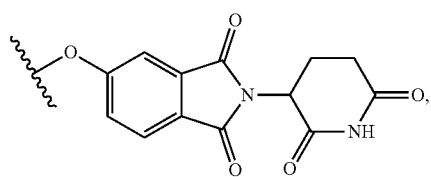
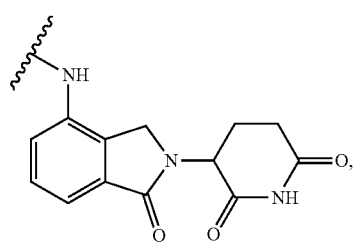
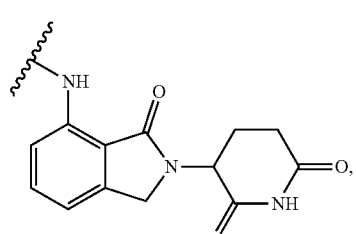
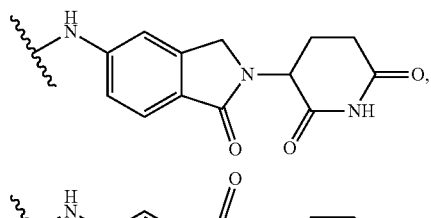
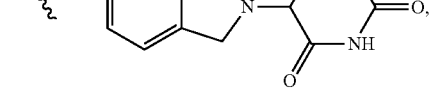
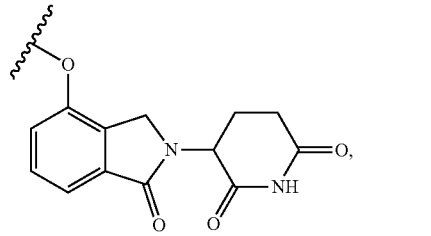
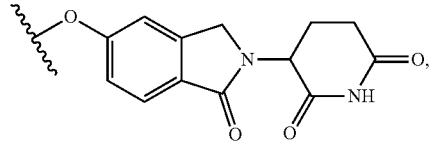
-continued
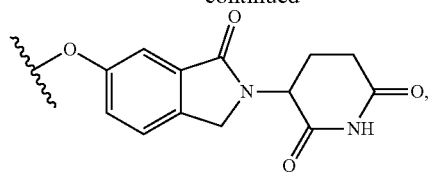
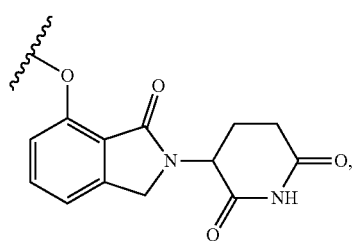
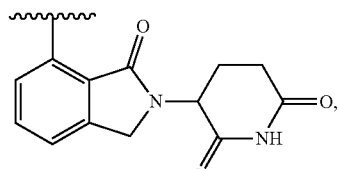
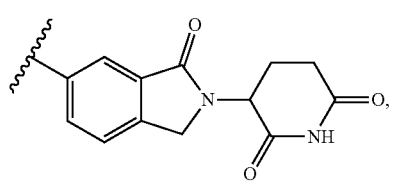
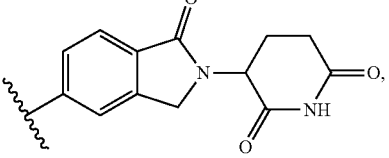
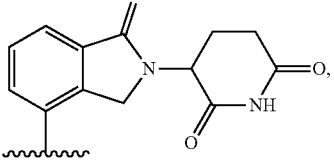
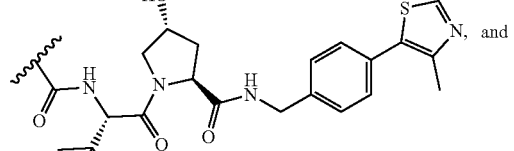
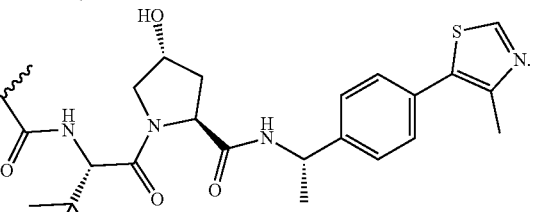
In still another embodiment, a compound of the disclosure comprises Formula (II), wherein $R^1$ may be

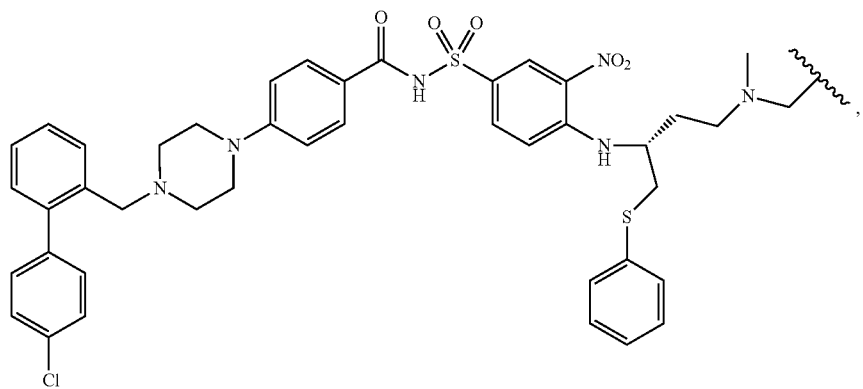
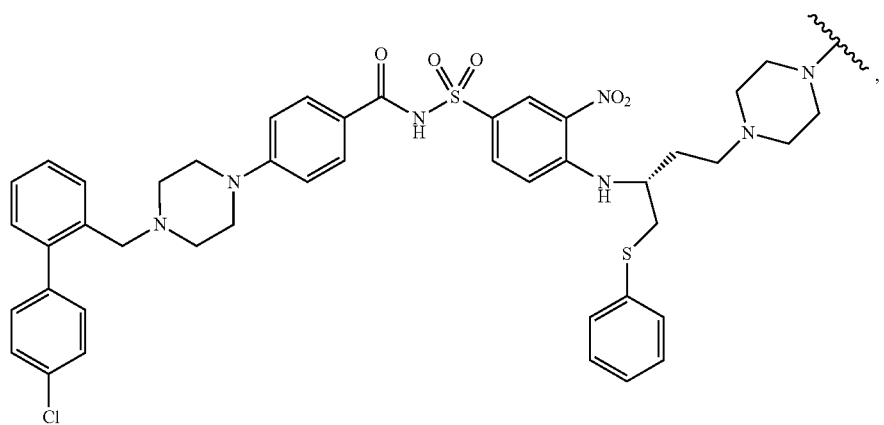
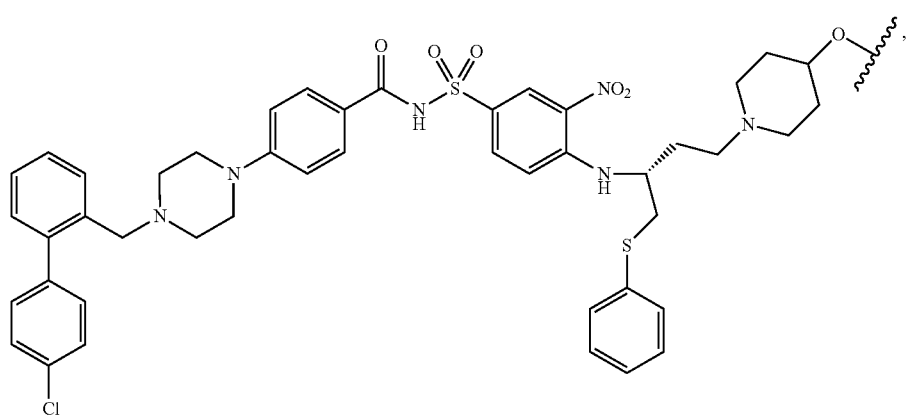
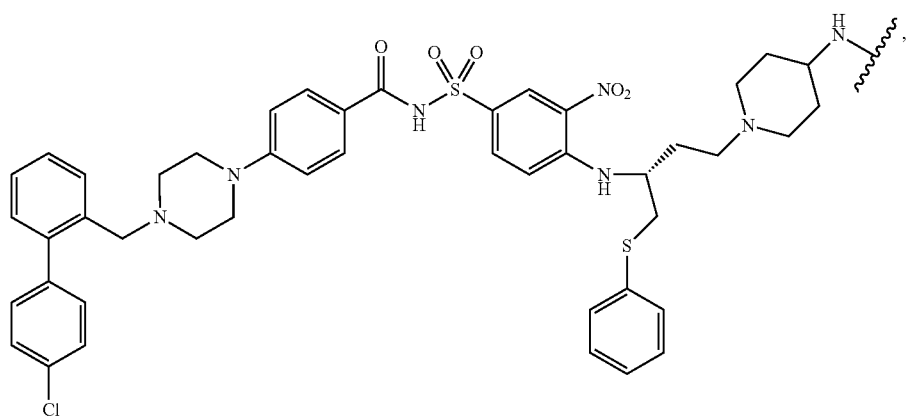

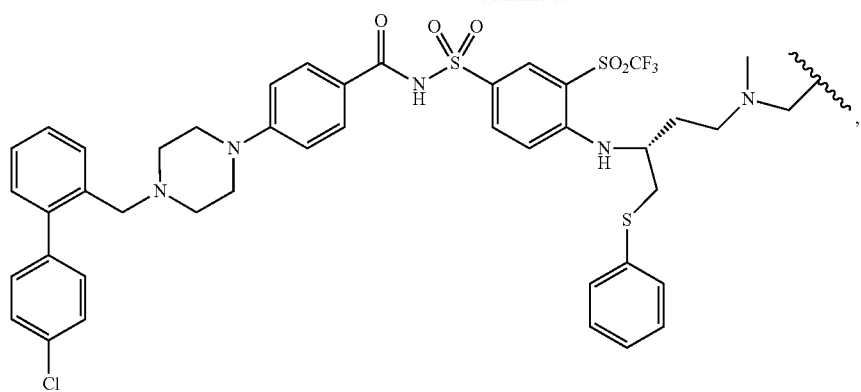
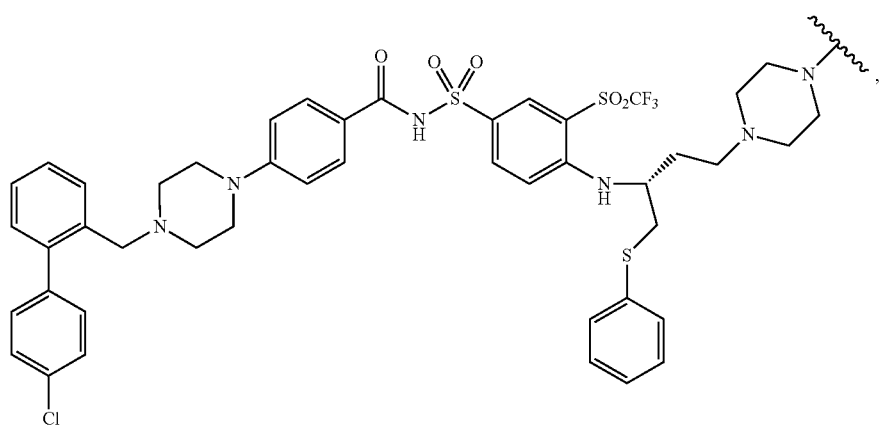
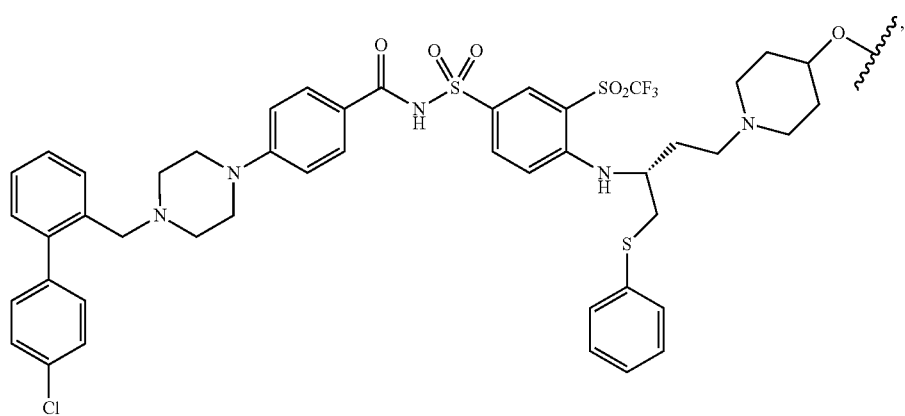
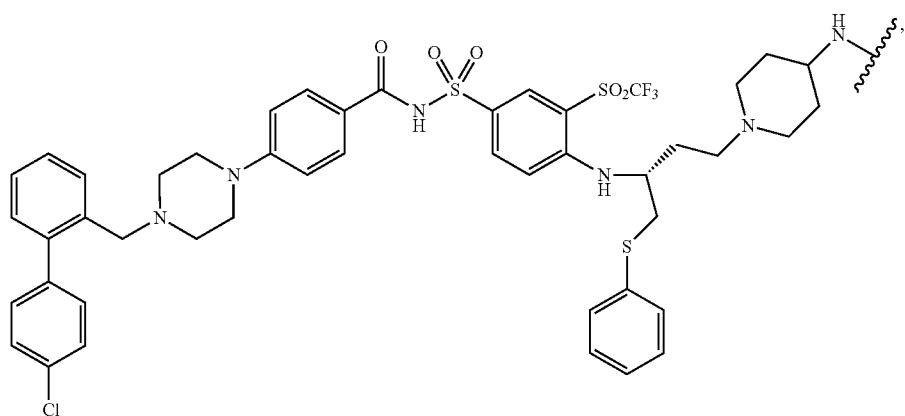

-continued
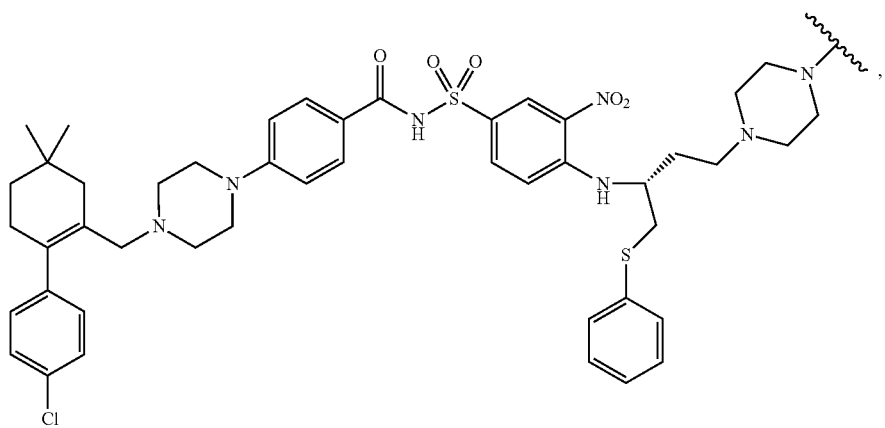
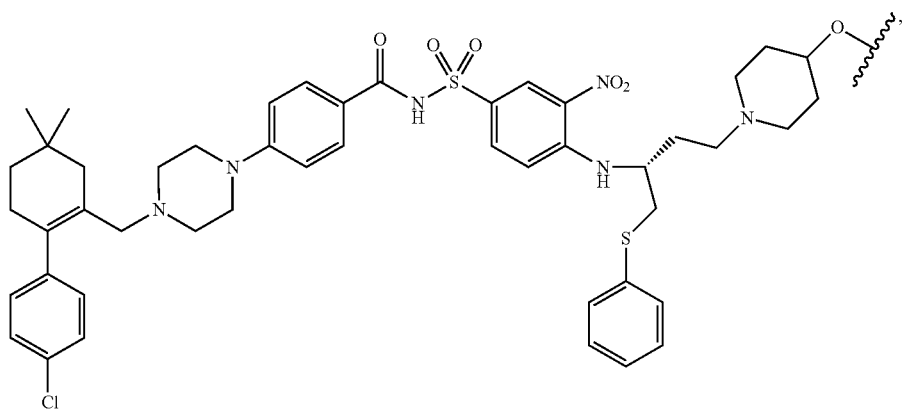
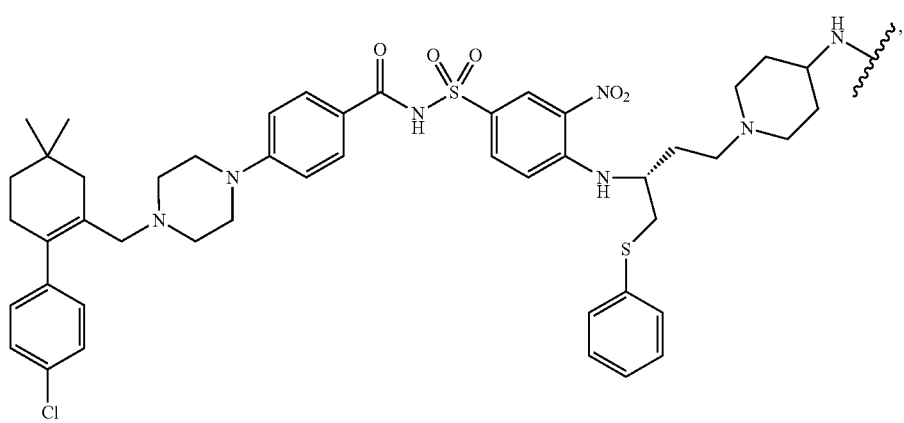
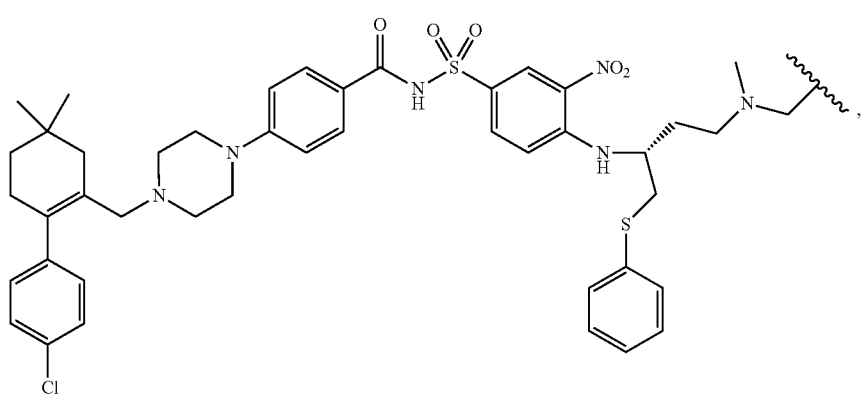

-continued
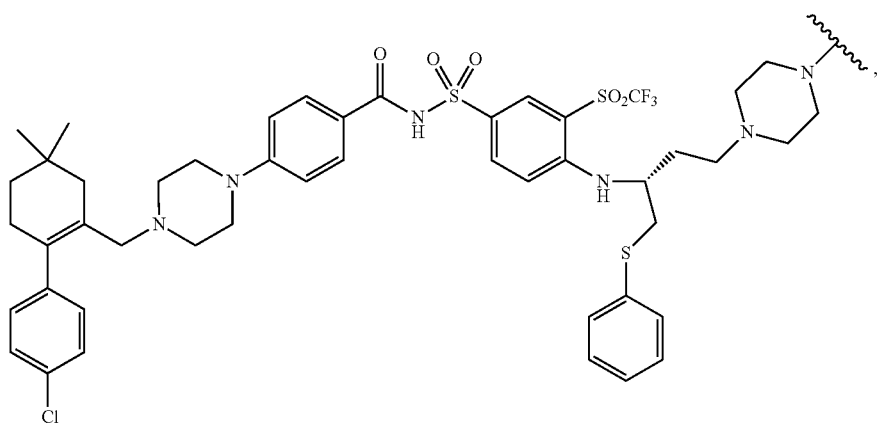
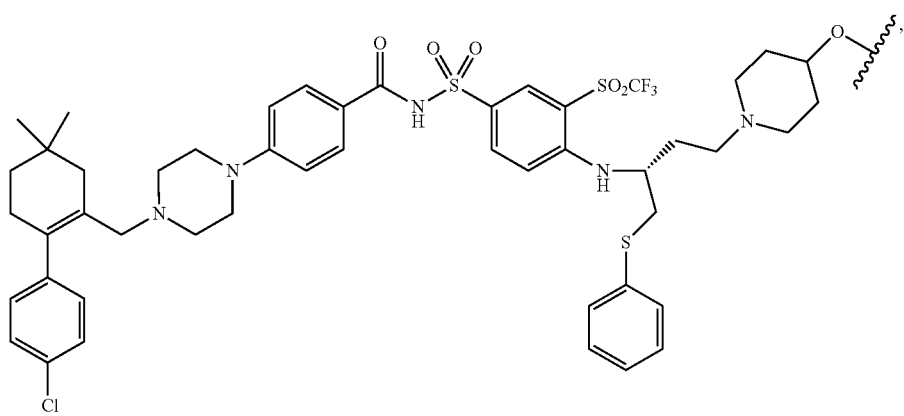
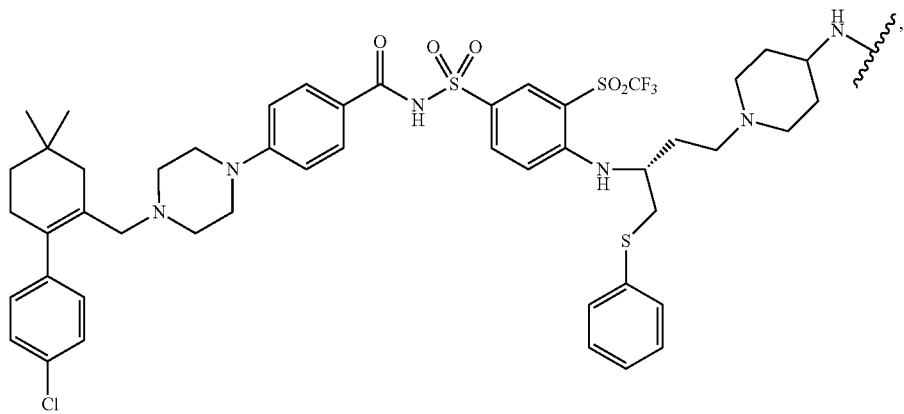
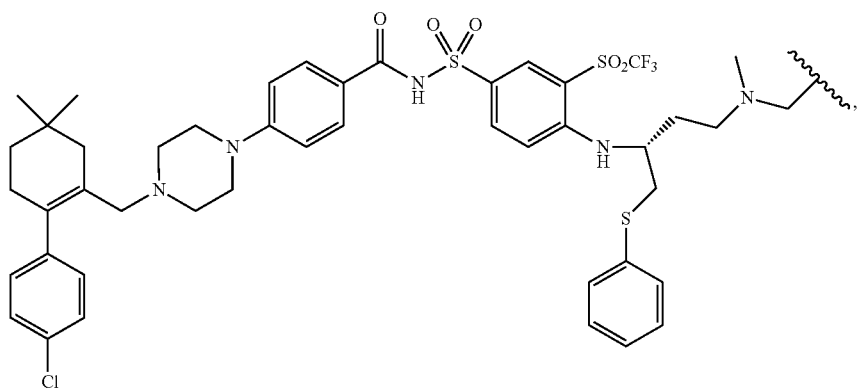

-continued
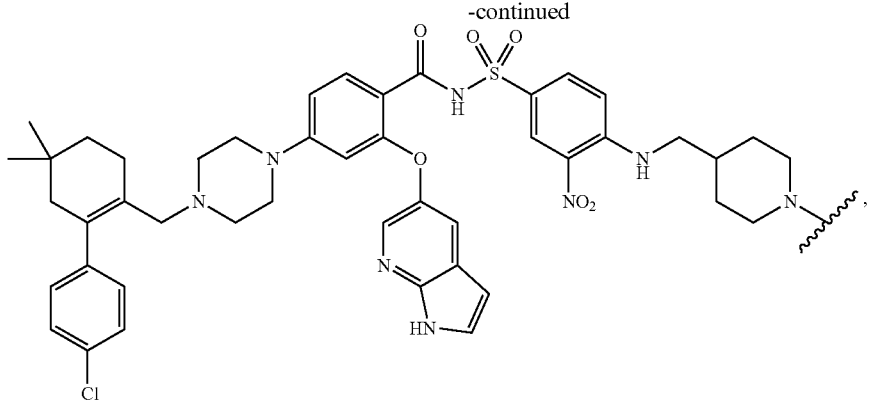
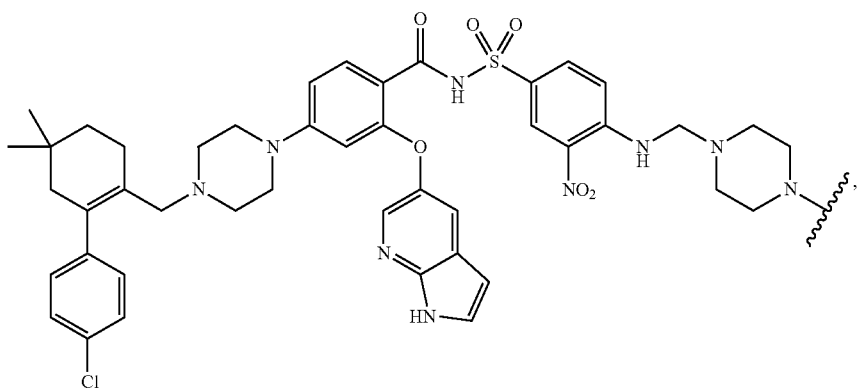
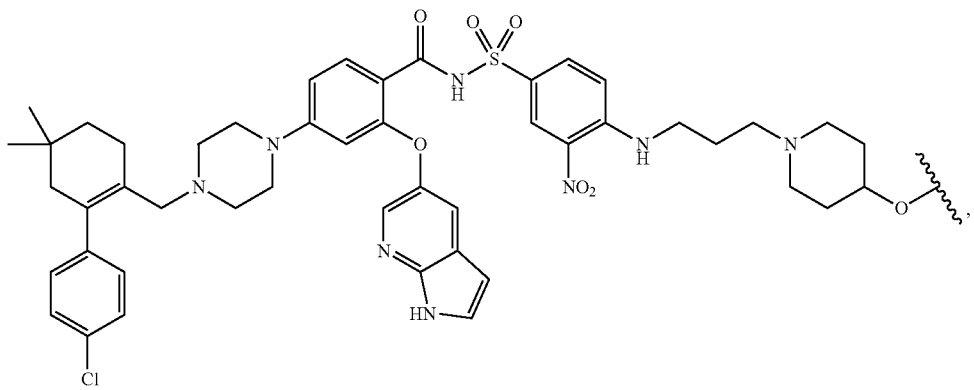
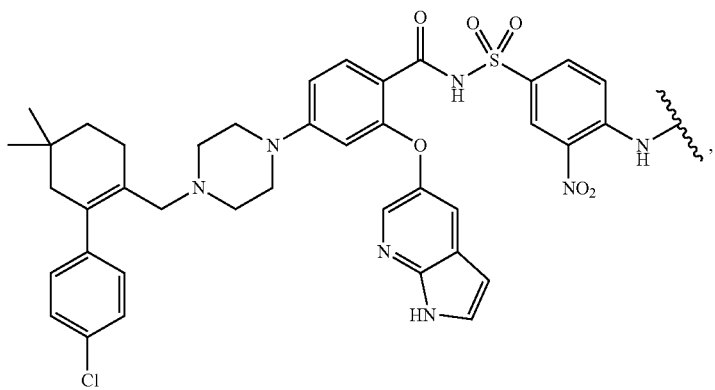

-continued
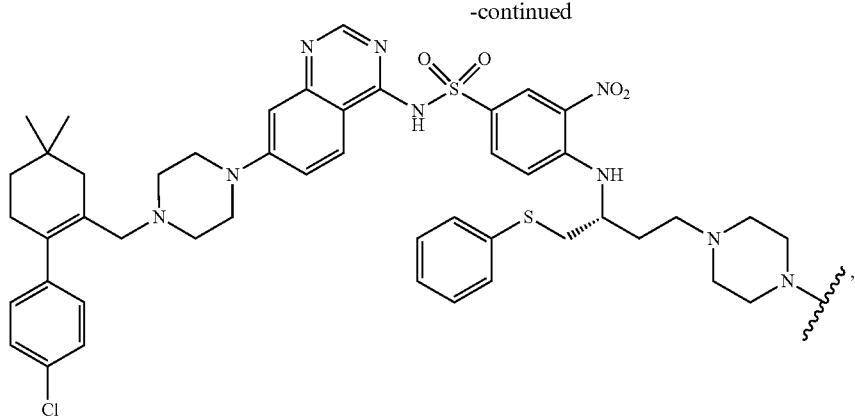
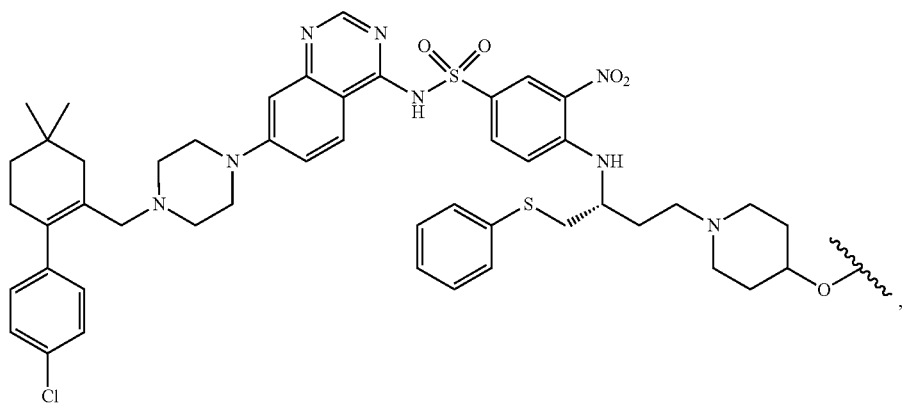
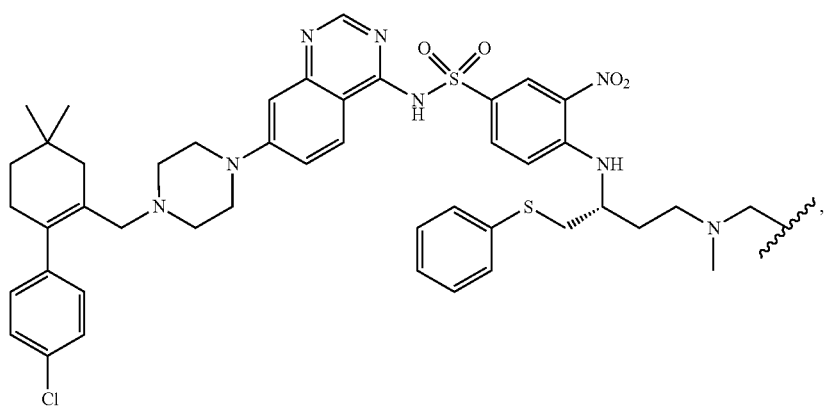
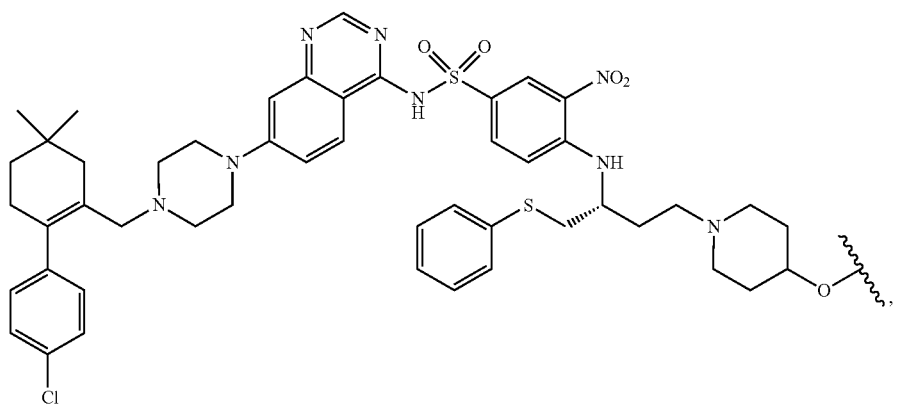

-continued
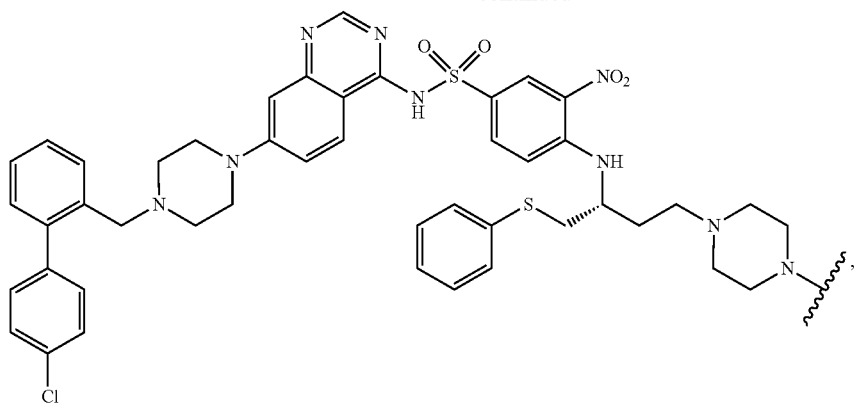
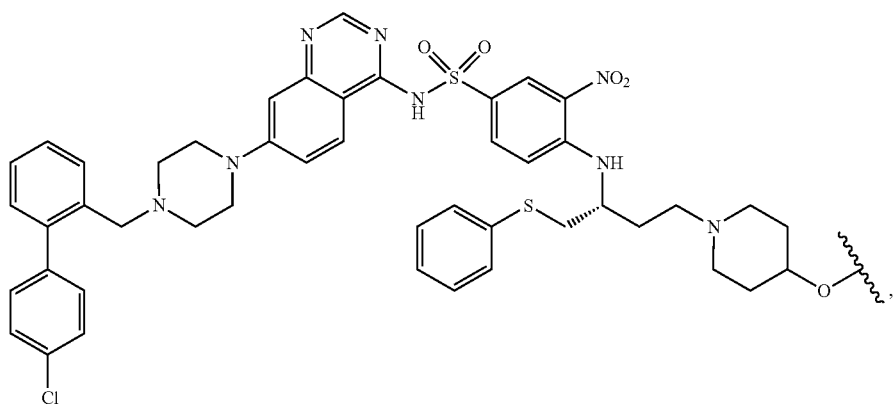
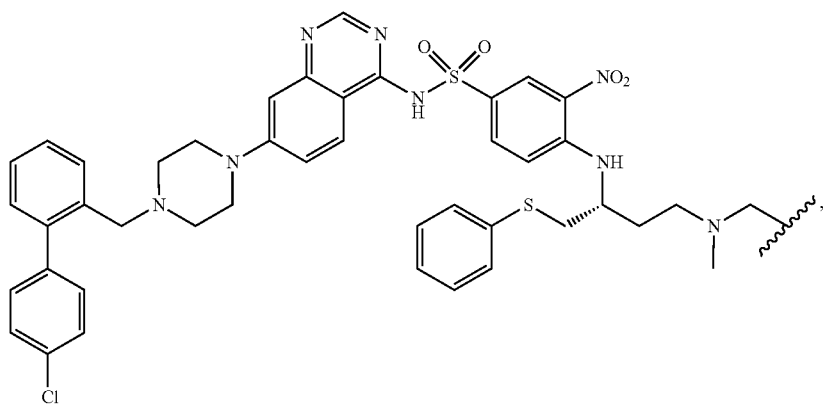
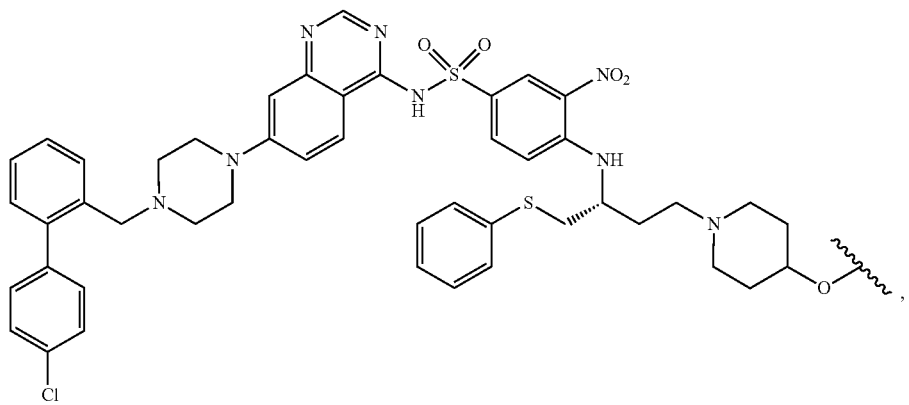

-continued
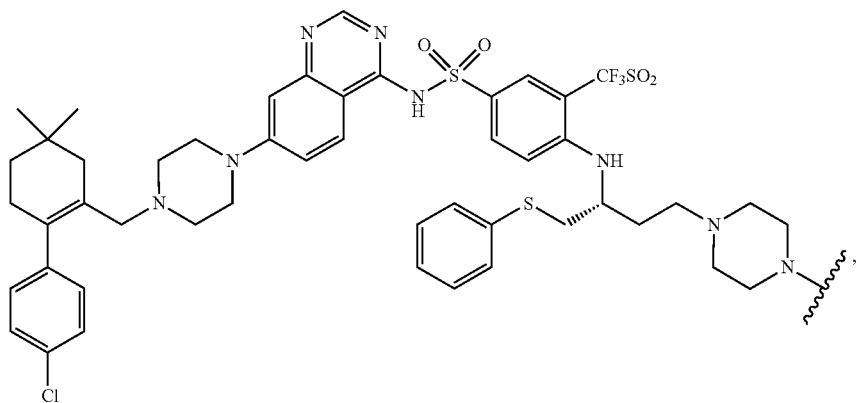
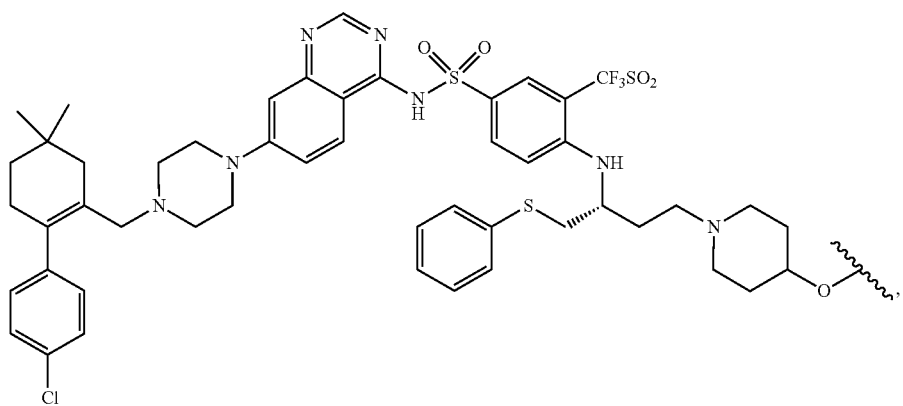
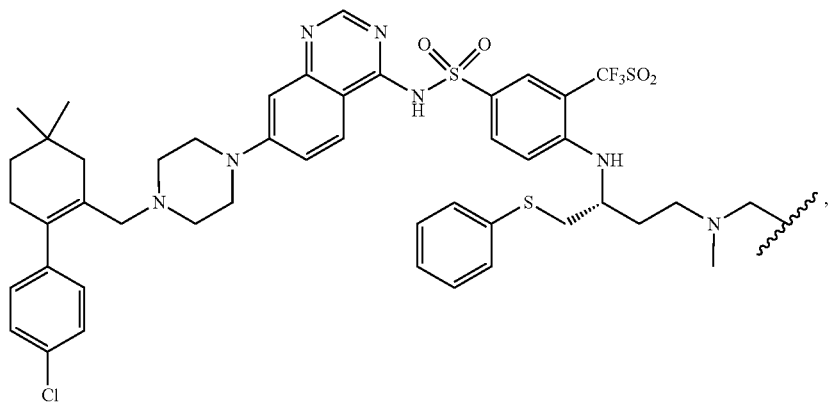
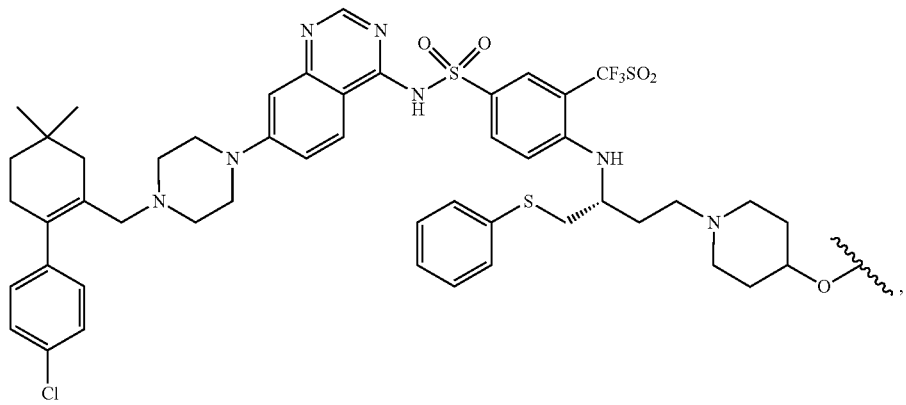

-continued
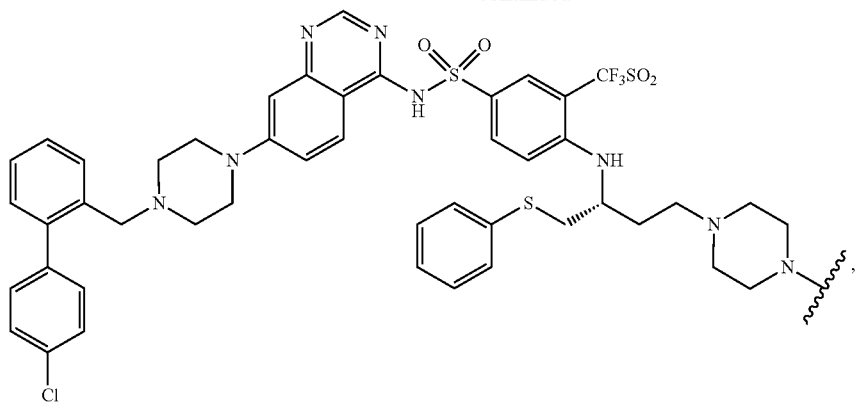
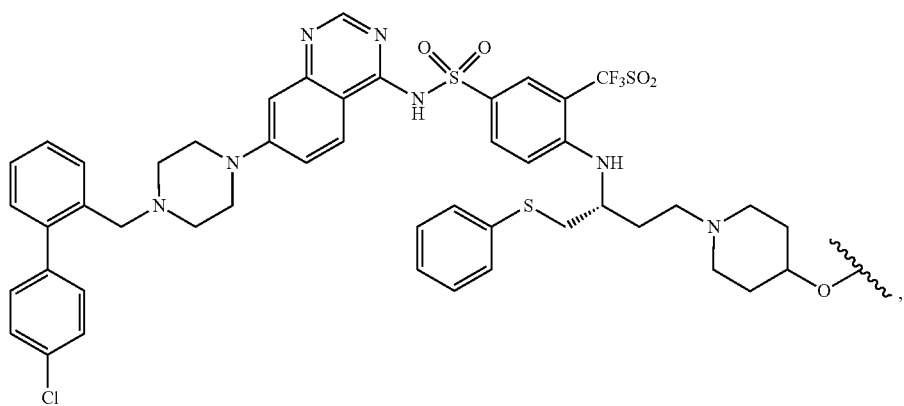
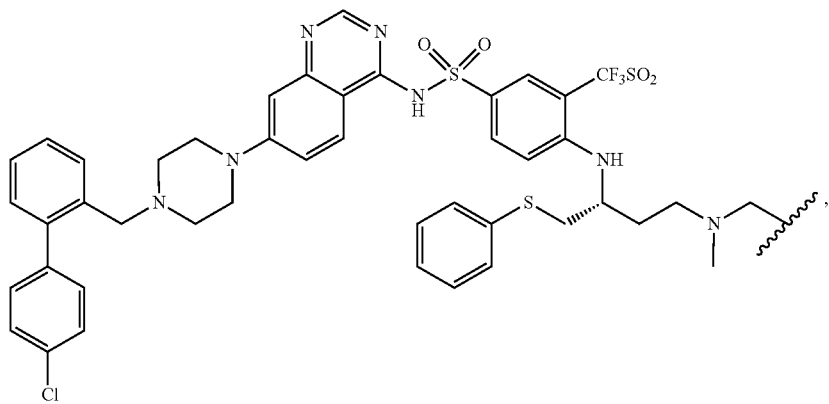
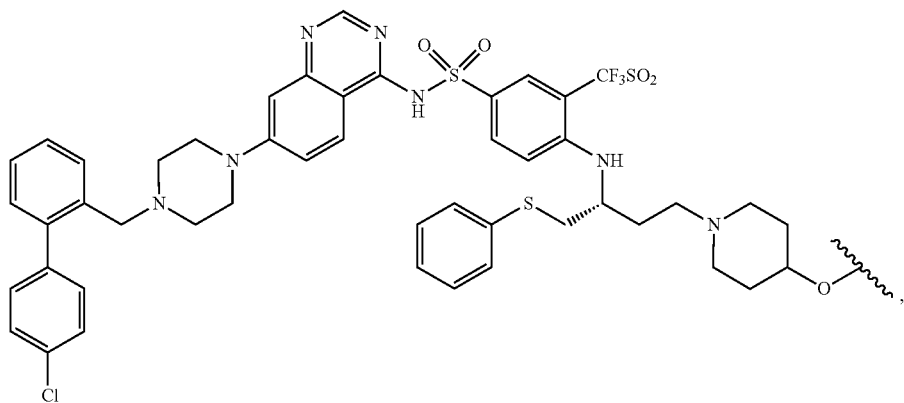

-continued
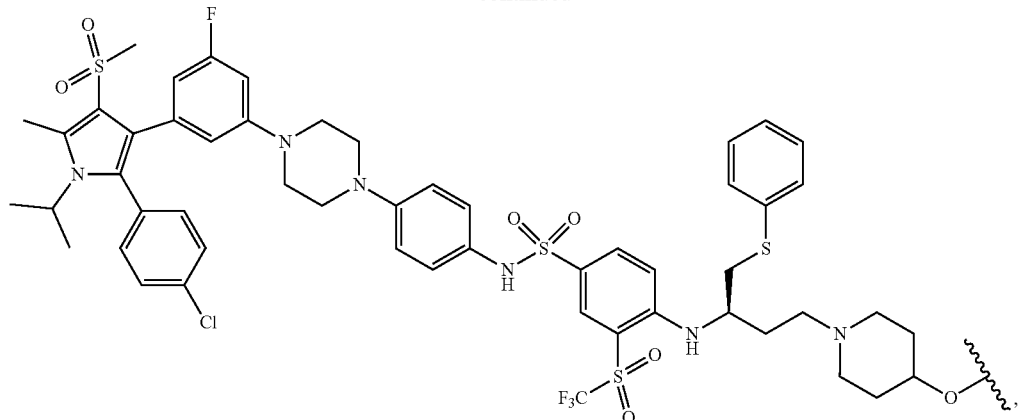
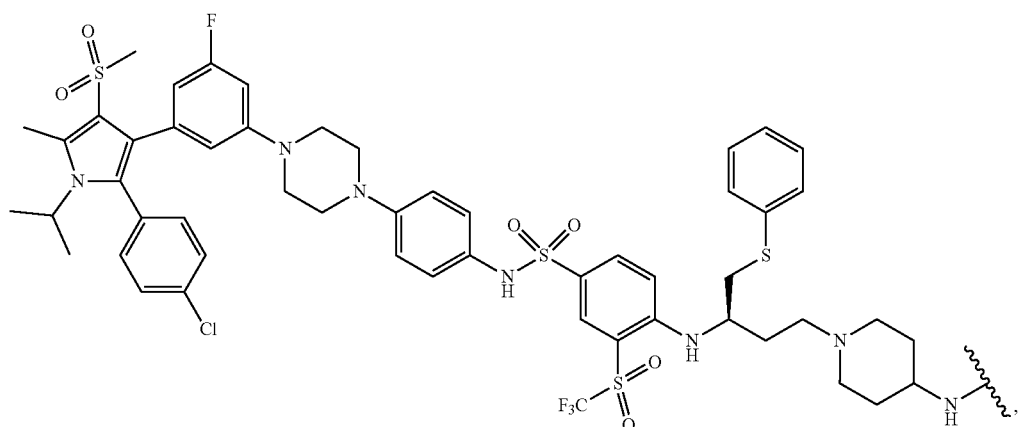
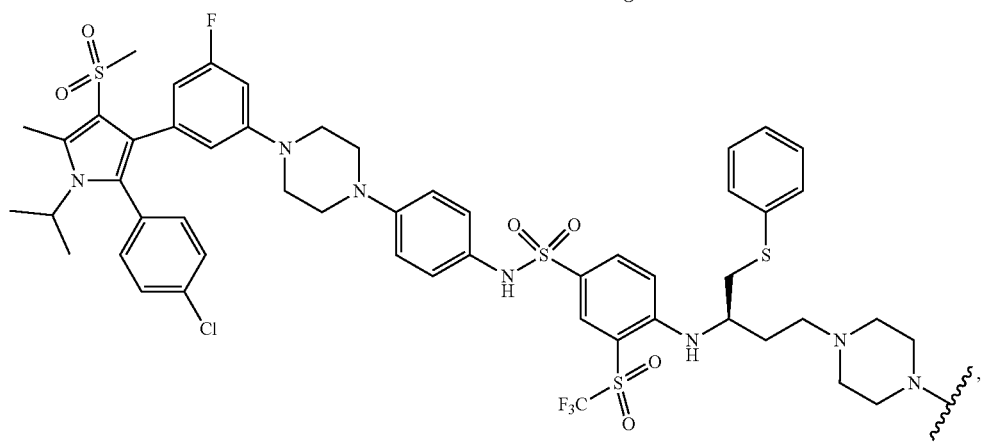
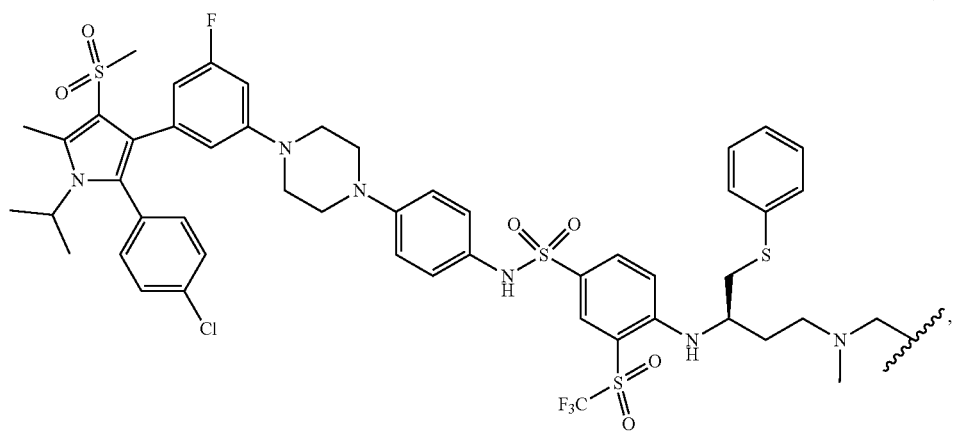

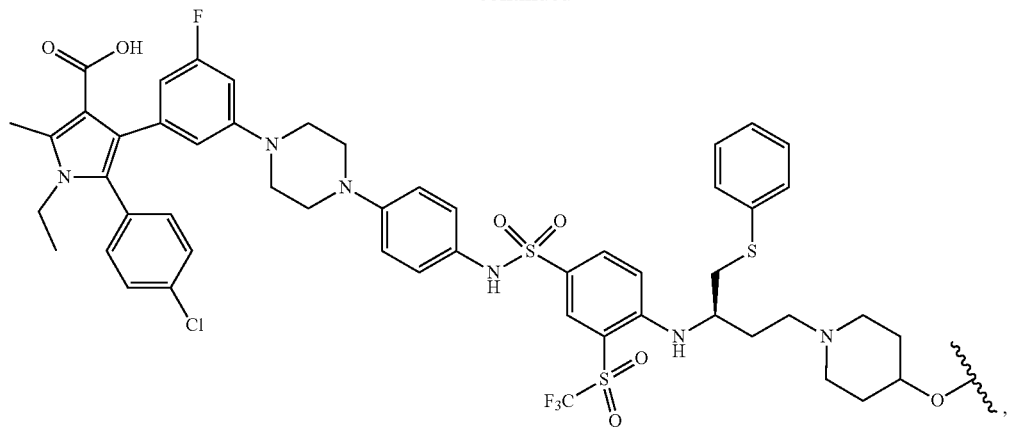
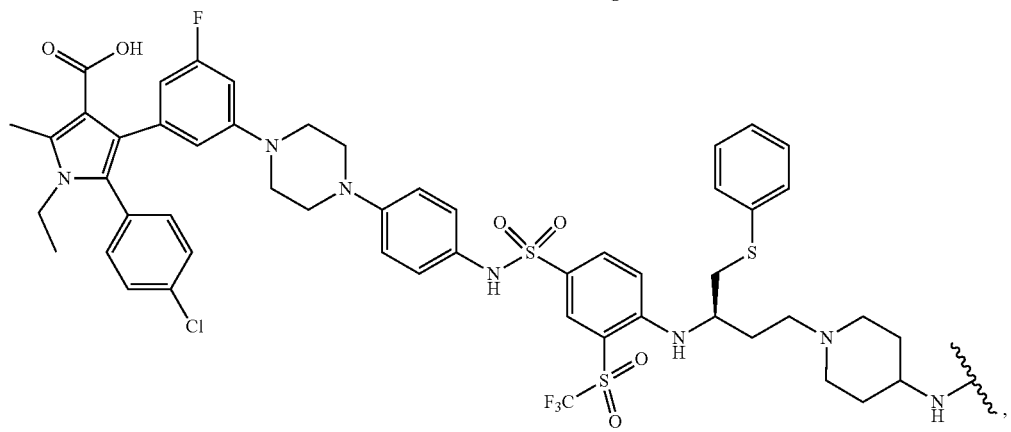
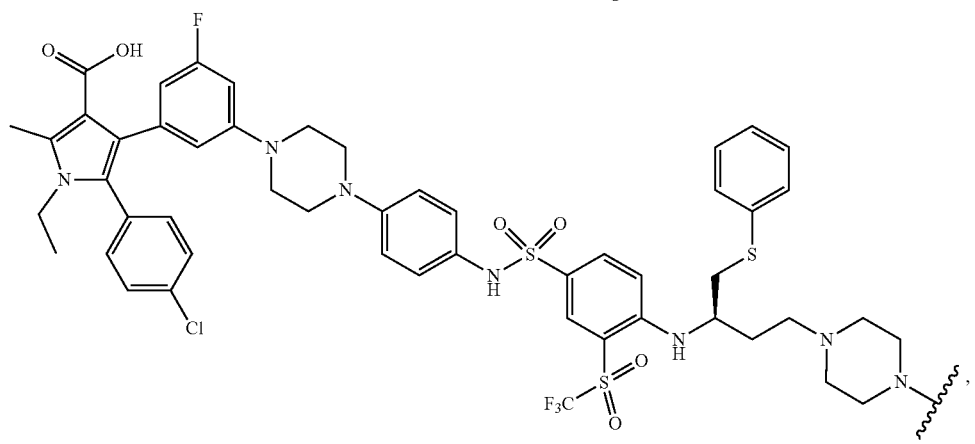
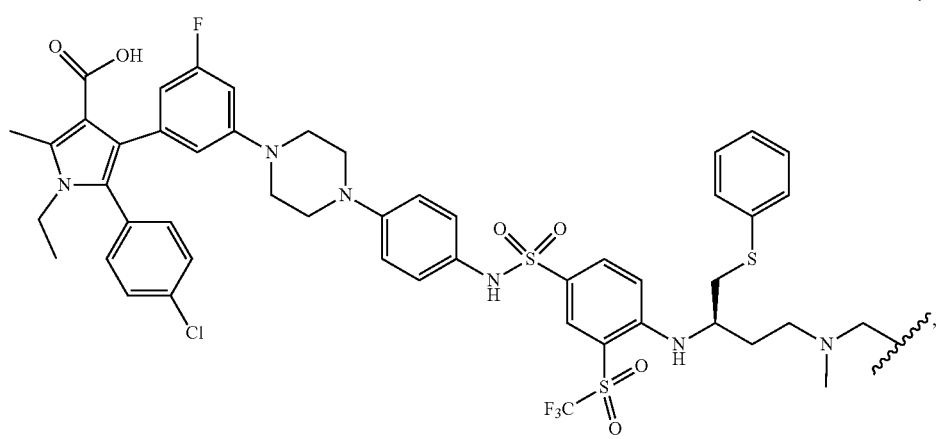

-continued
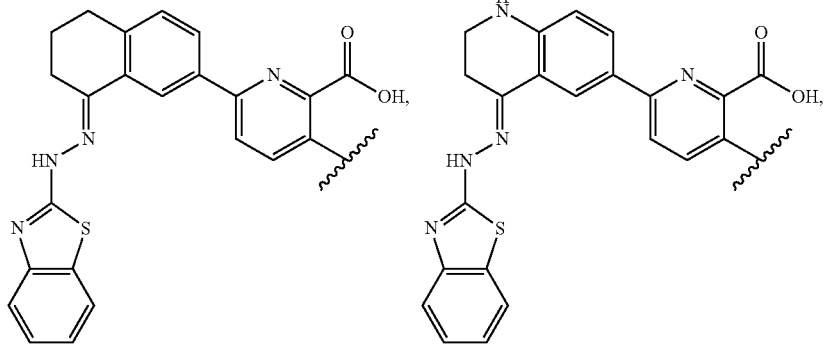
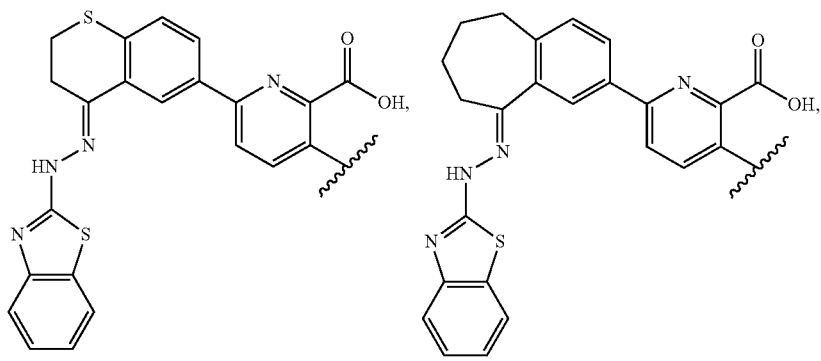
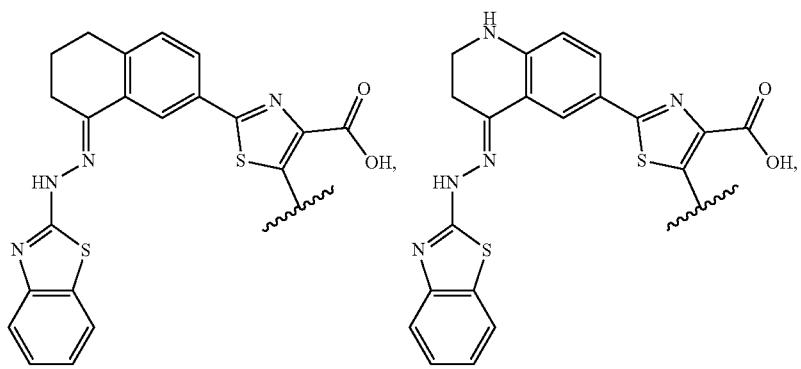
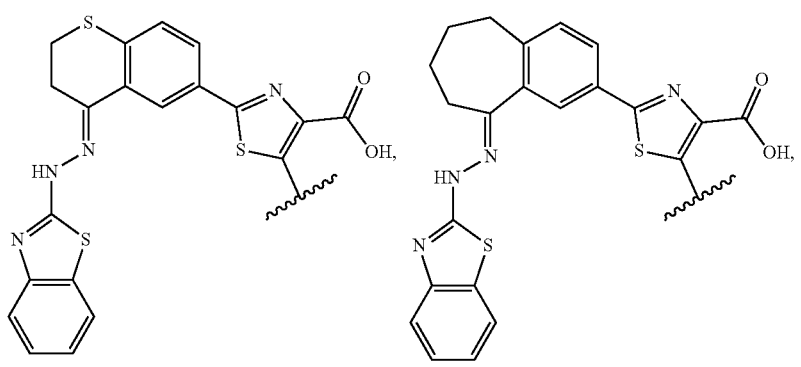

-continued
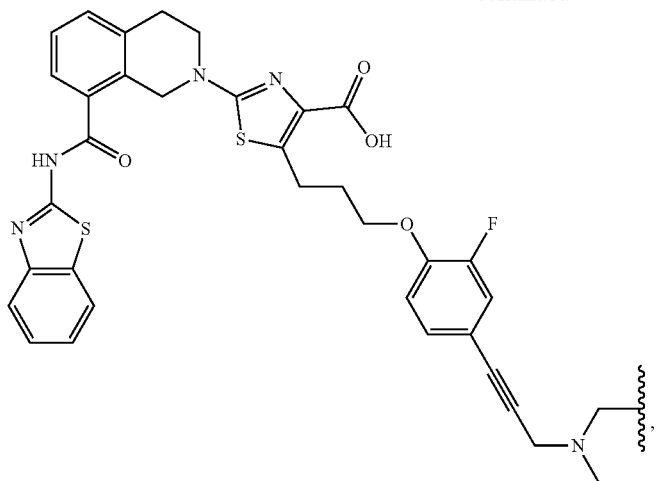
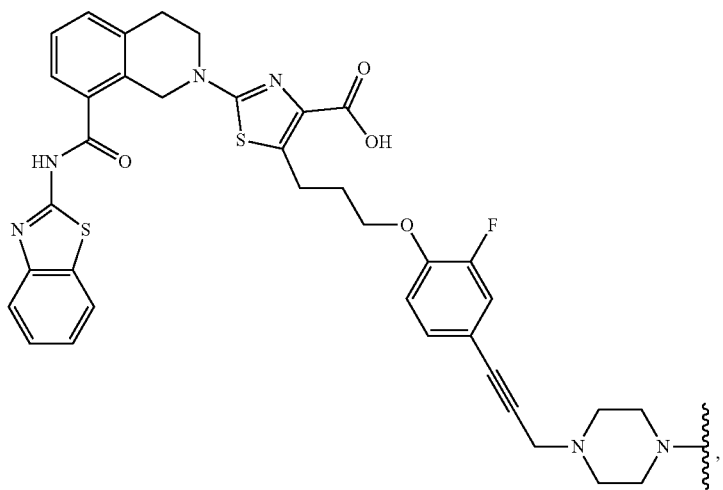
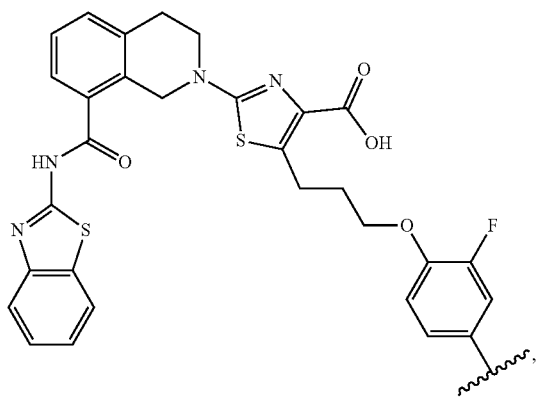

-continued
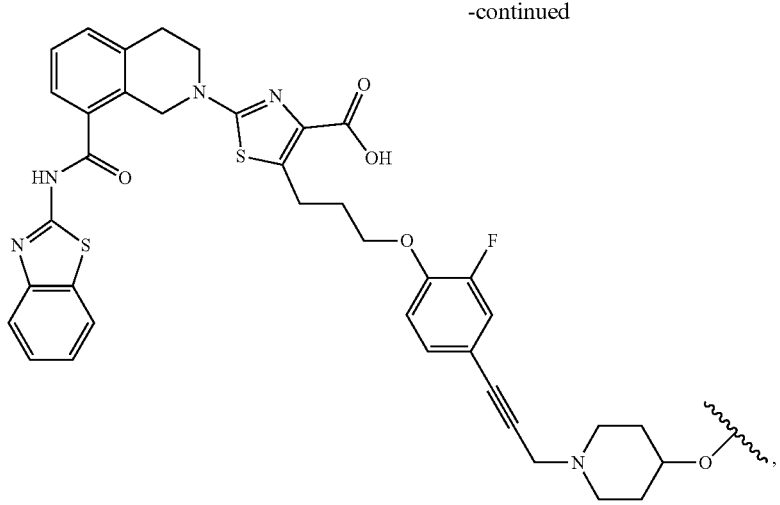
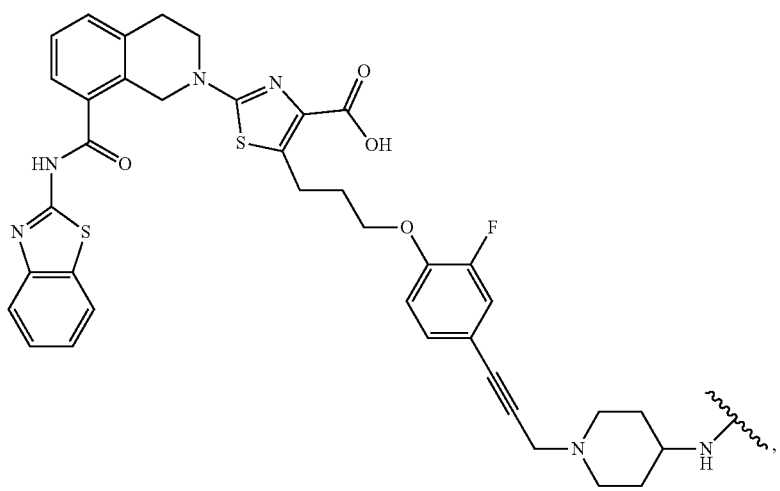
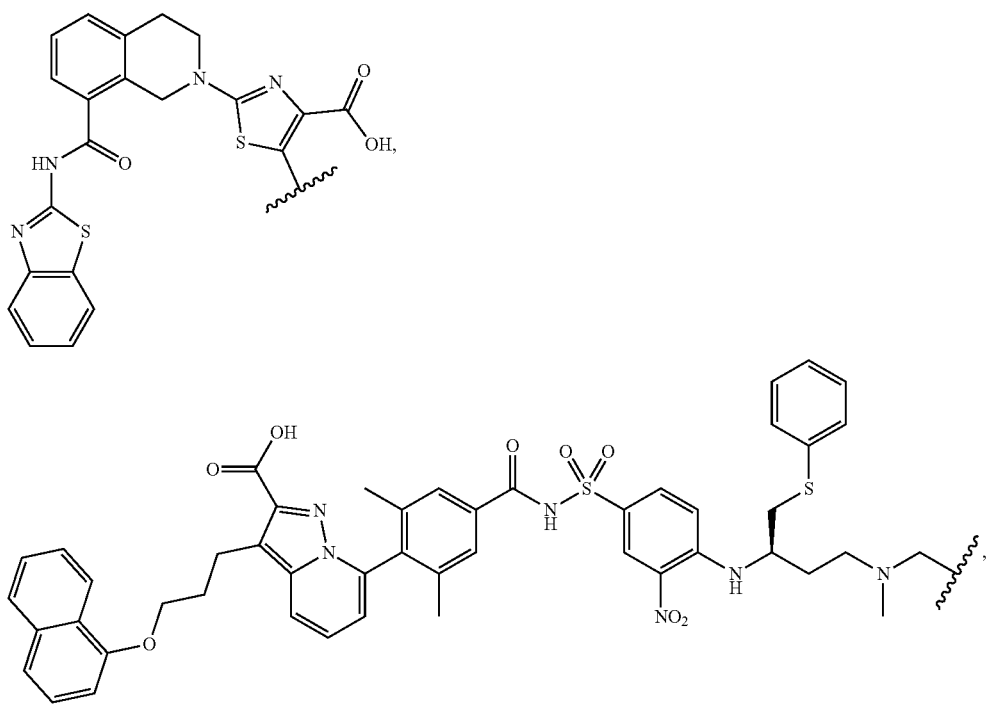

-continued
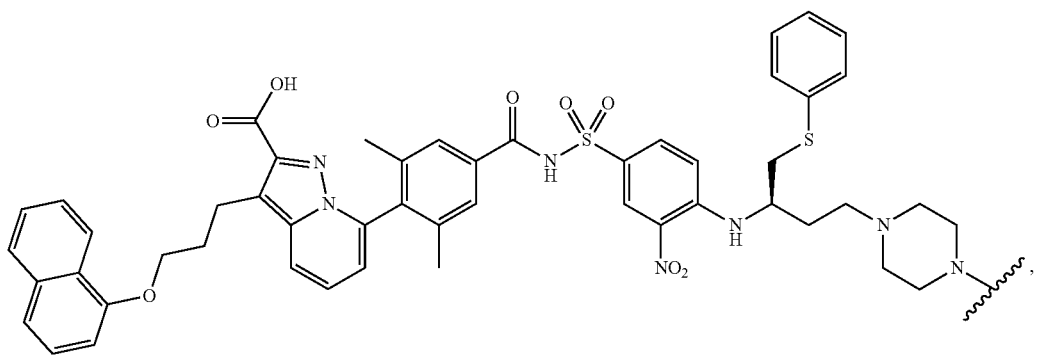
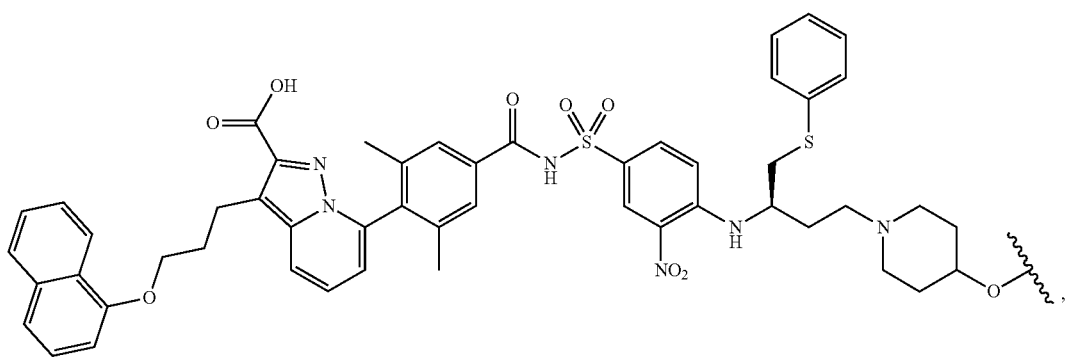
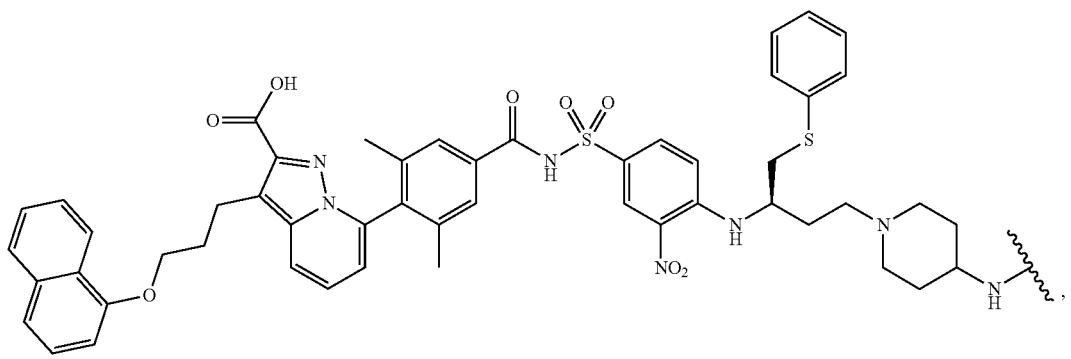
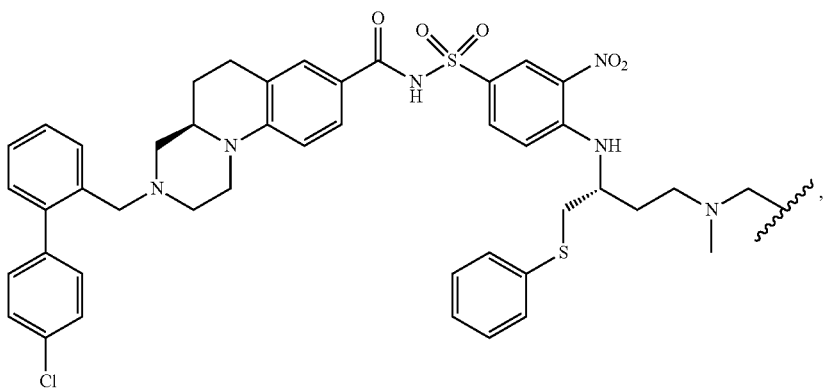

-continued
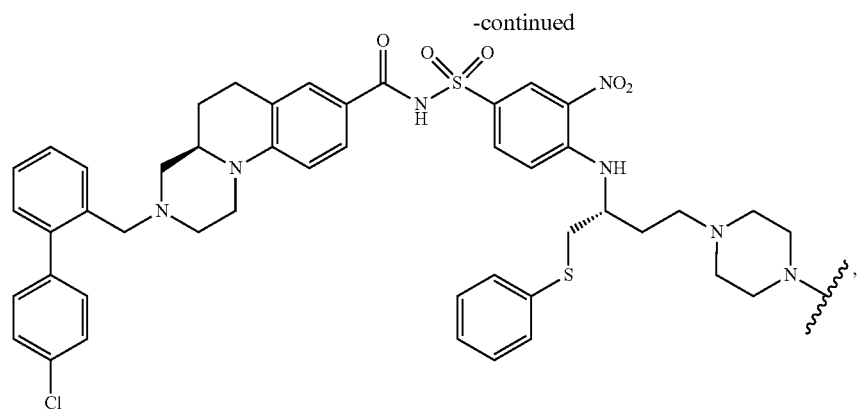
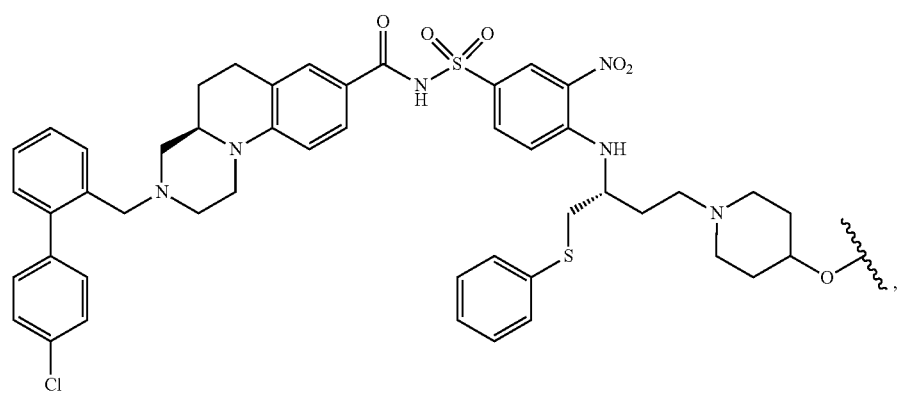
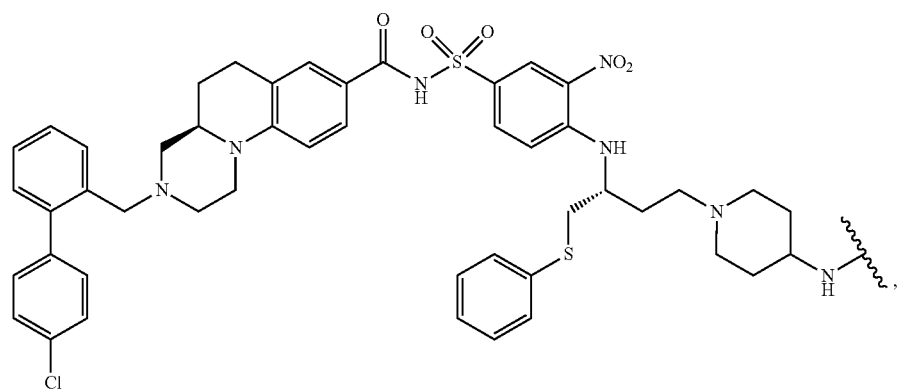
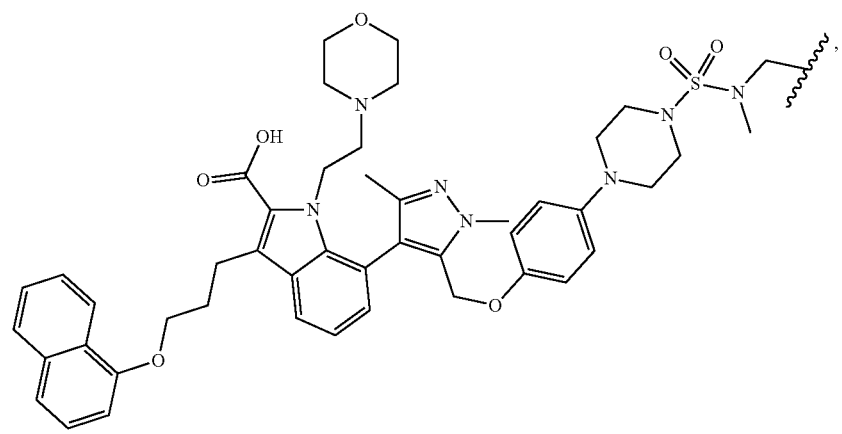

-continued
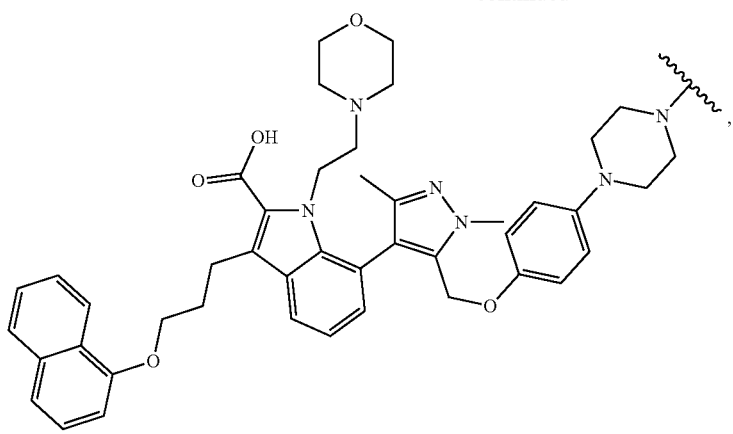
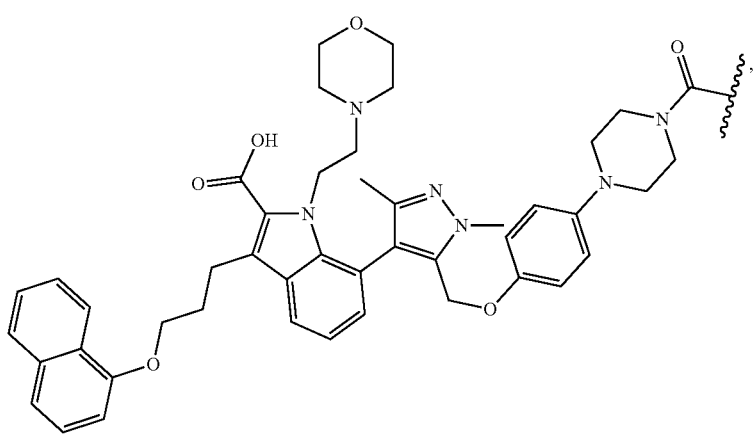
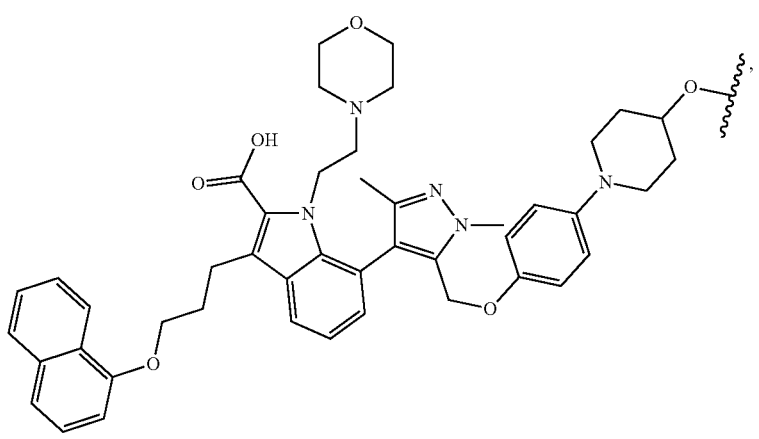

-continued
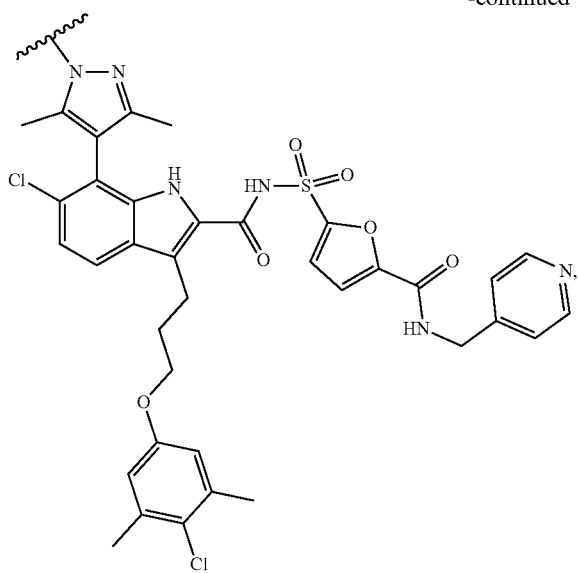
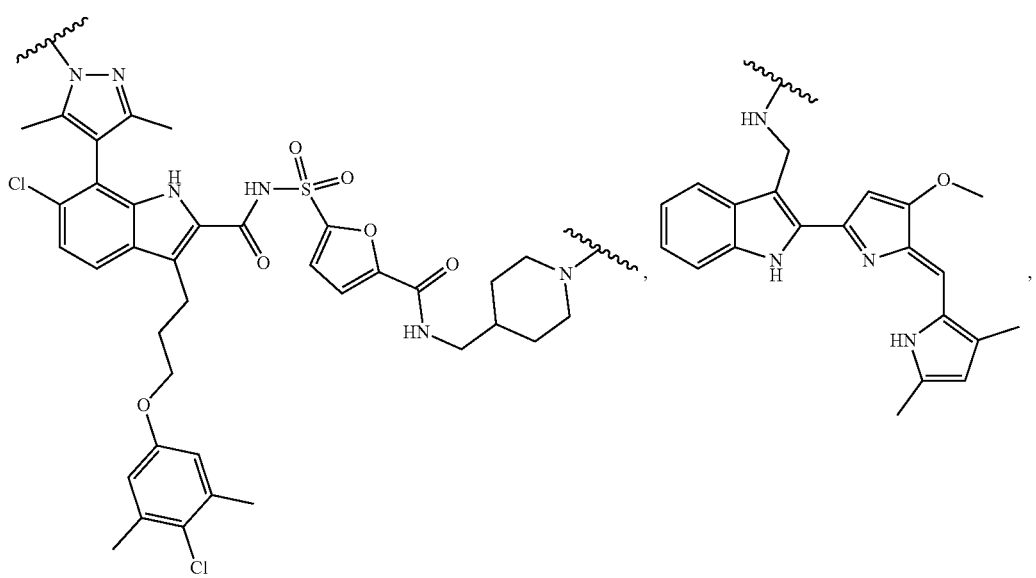
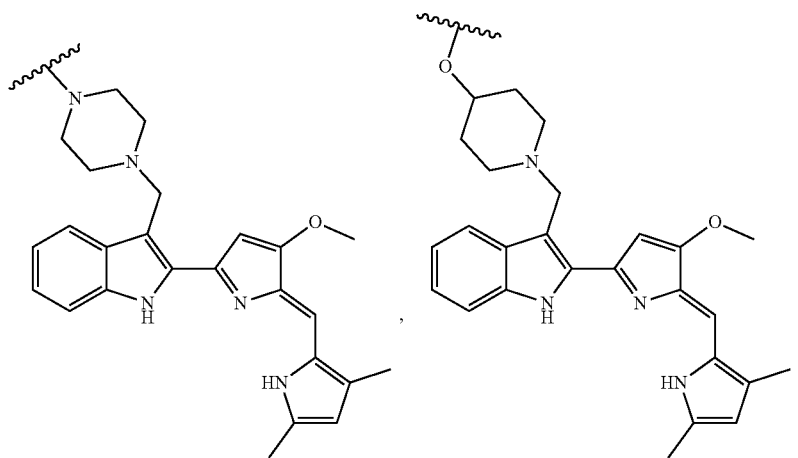

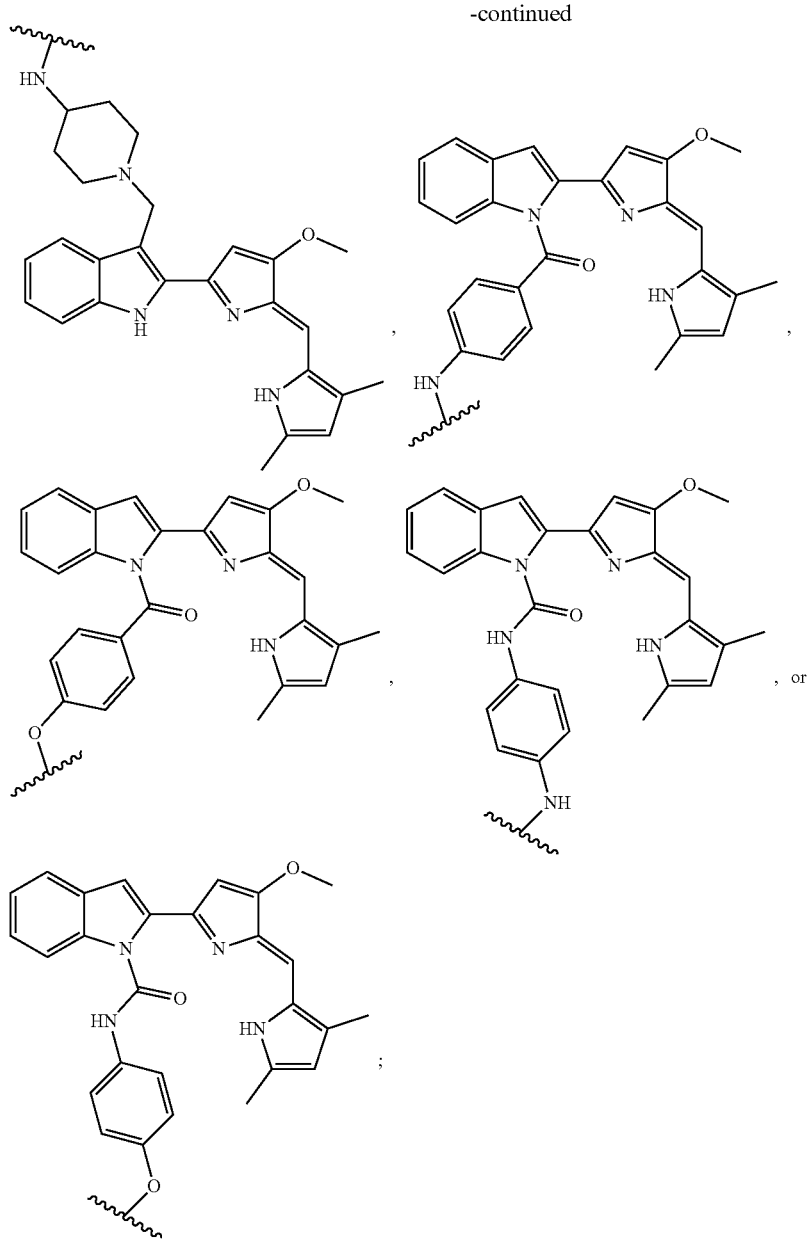
R³ may be absent, a bond, 2-pentanone, or an unsubstituted C₂-C₃ alkyl; B may be absent, a bond, or a substituted or unsubstituted C₁-C₆ heterocyclic group; n may be 0 to 3; R⁴ may be a bond or a substituted or unsubstituted C₁-C₁₀ alkyl; and R² may be
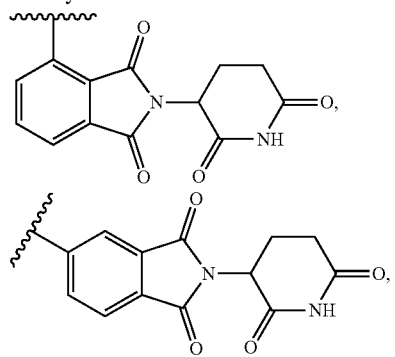
-continued
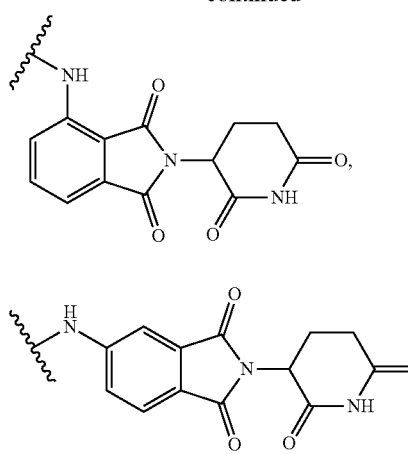

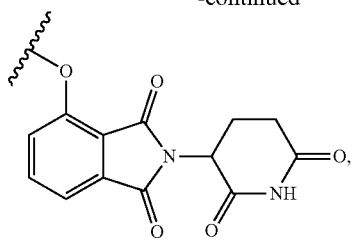
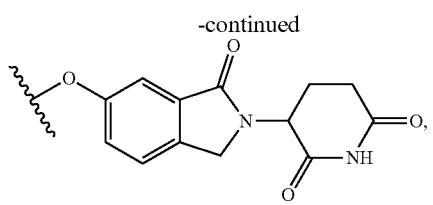
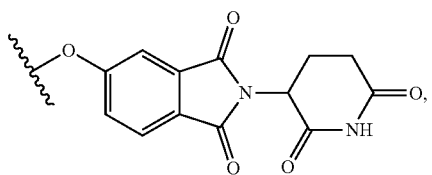
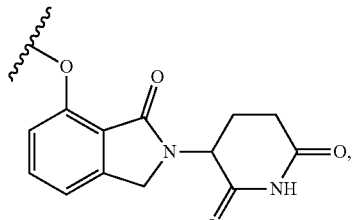
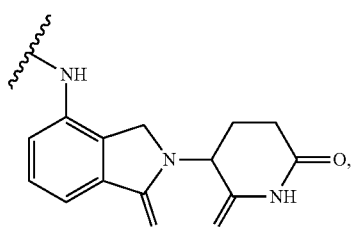
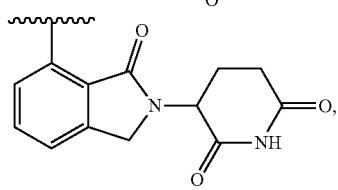
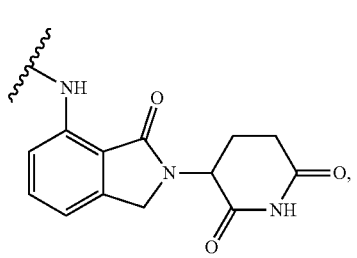
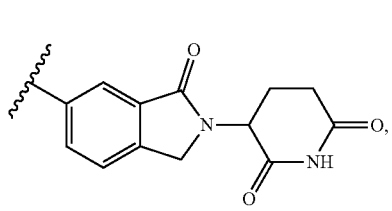
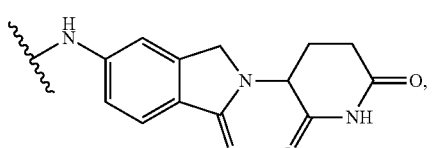
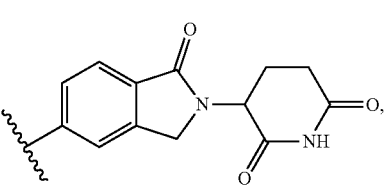
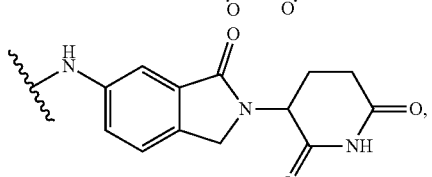
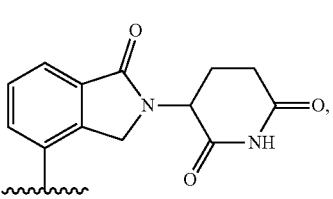
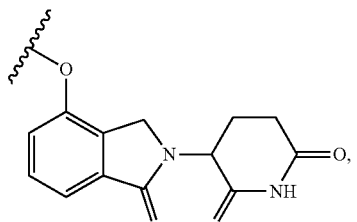
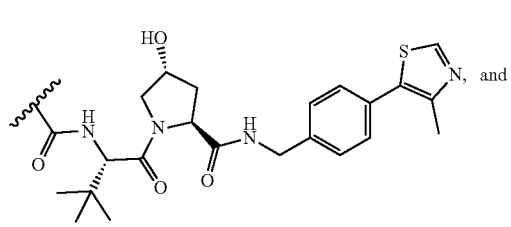
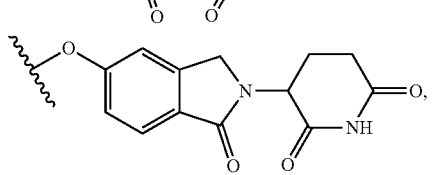
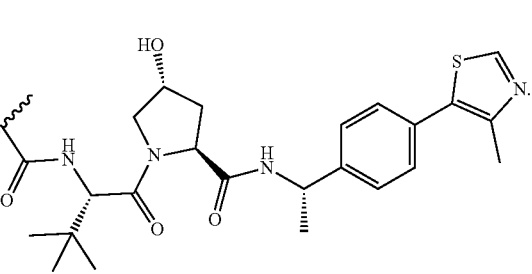

In still another embodiment, a compound of the disclosure comprises Formula (II), wherein R¹ may be
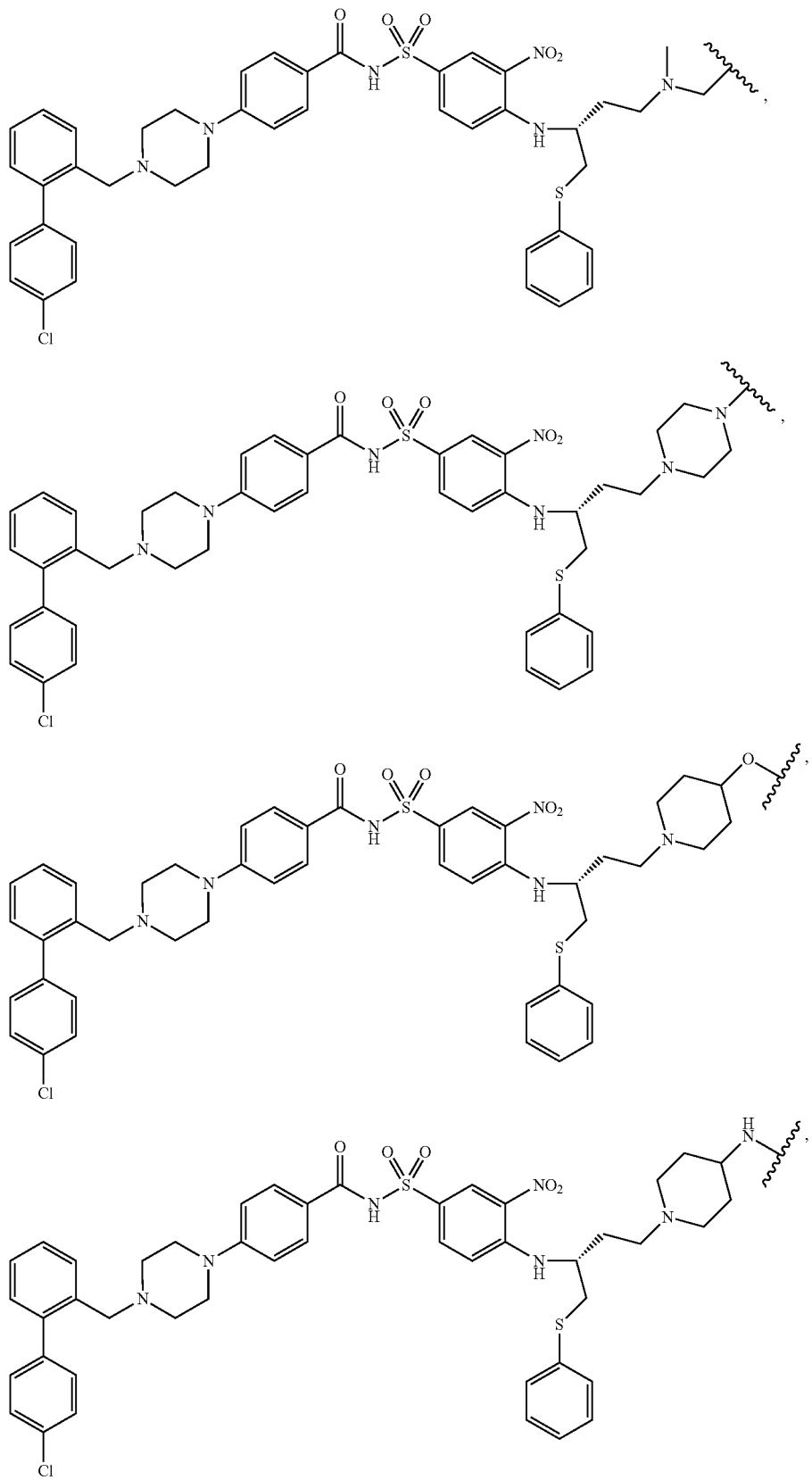

-continued
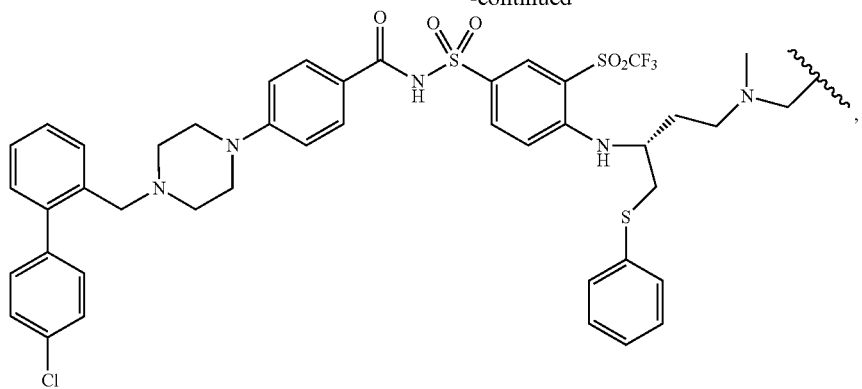
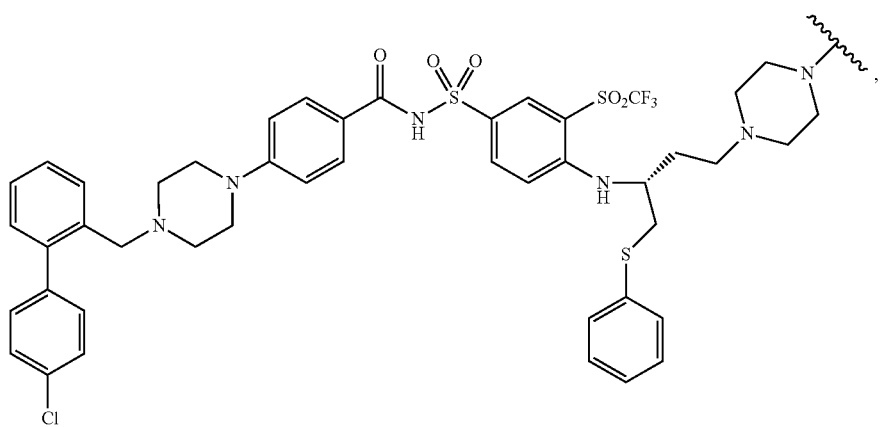
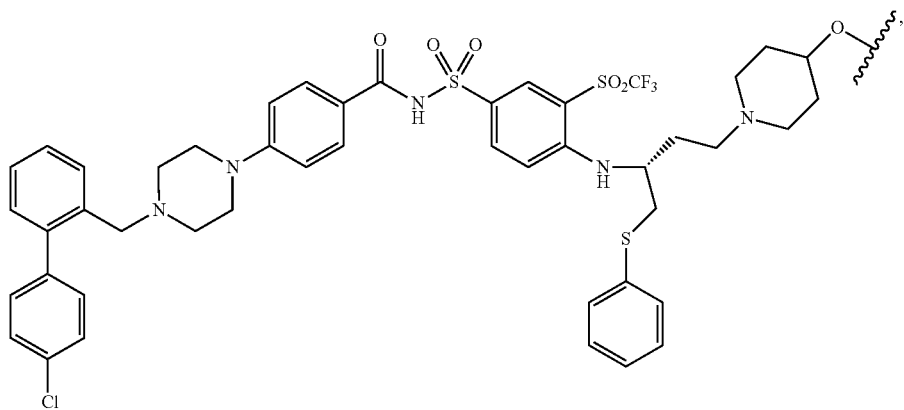
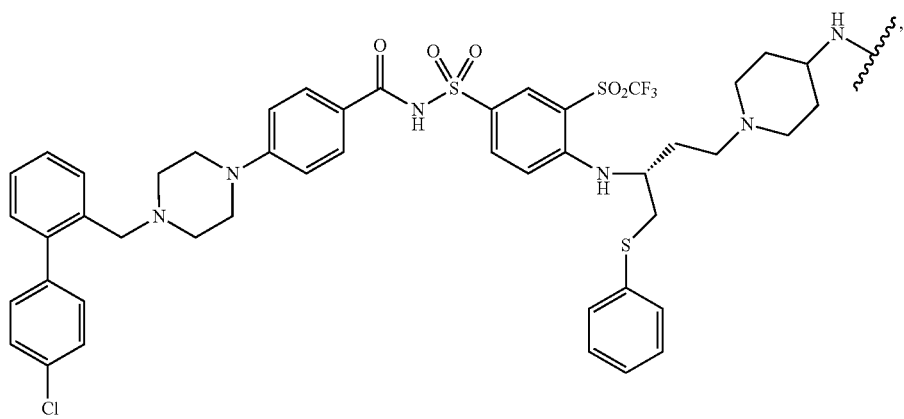

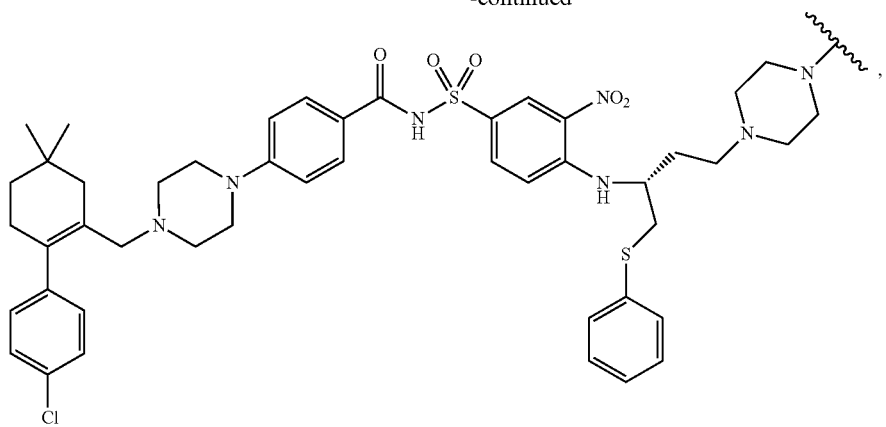
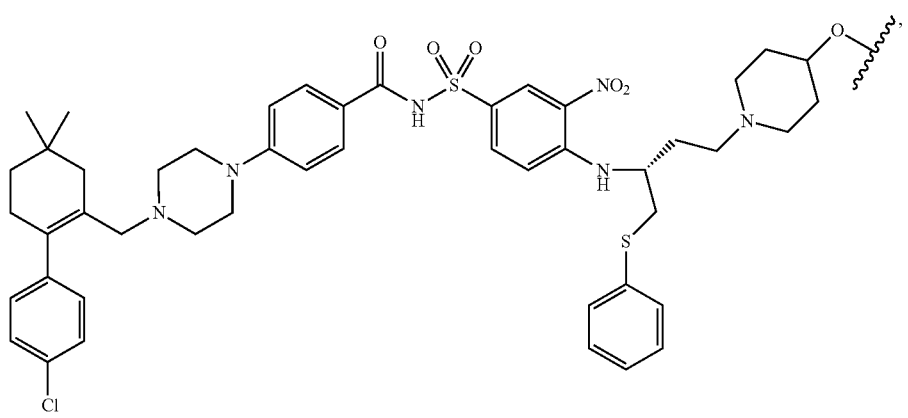
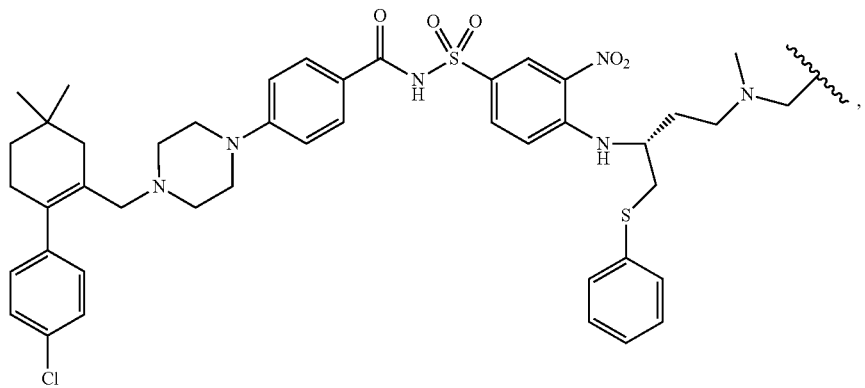

-continued
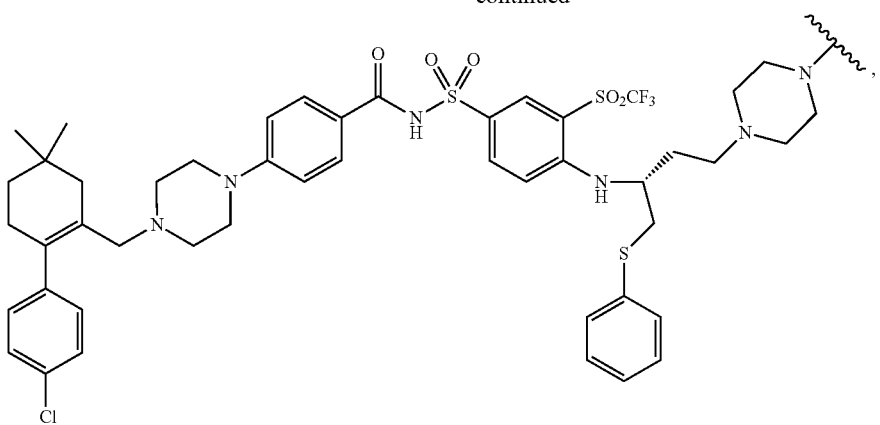
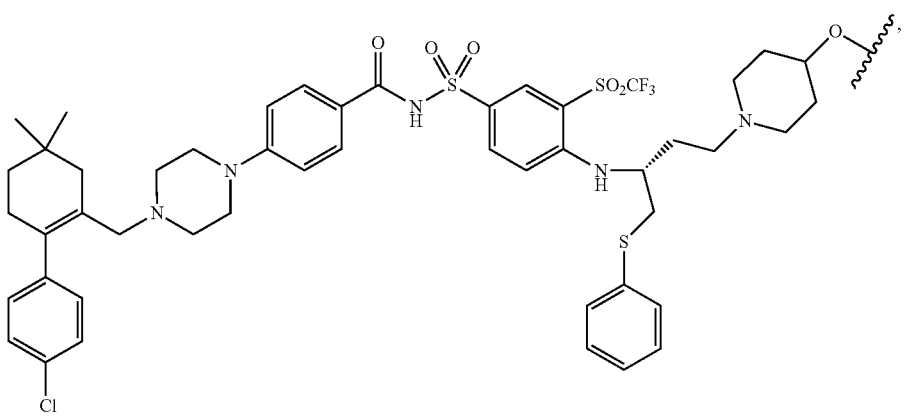
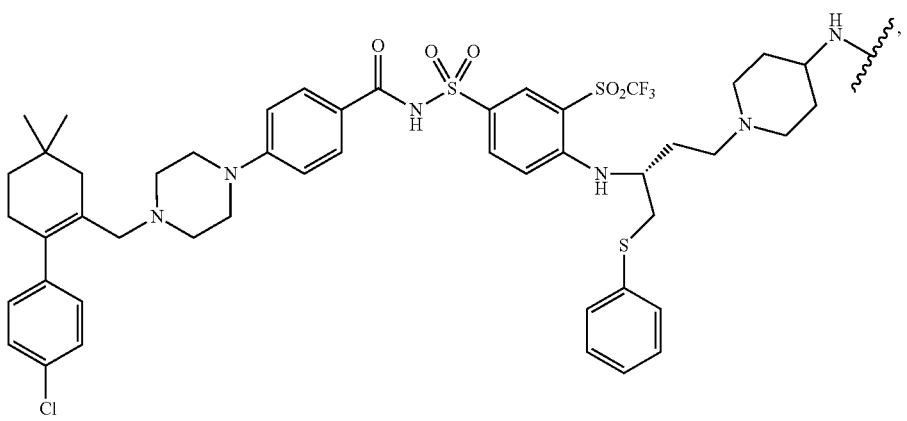
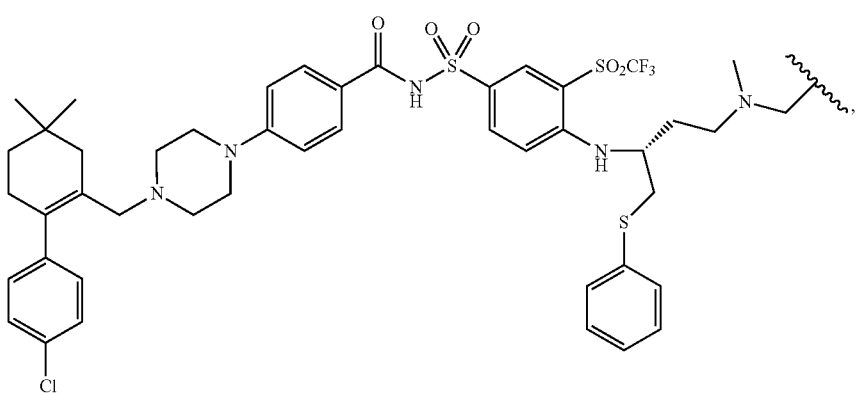

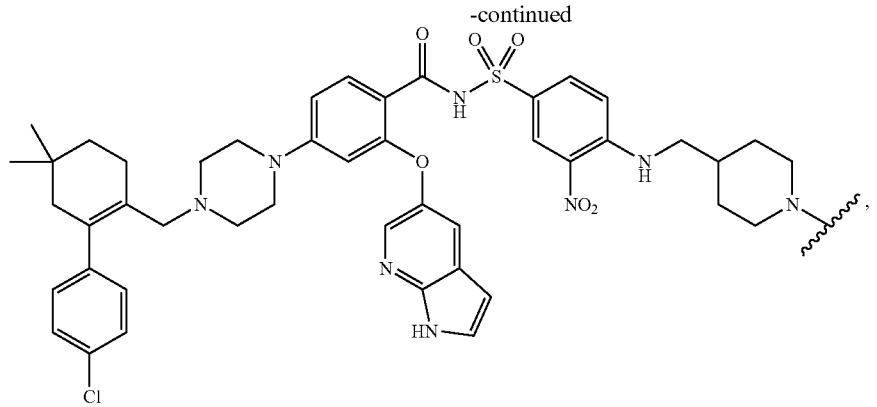
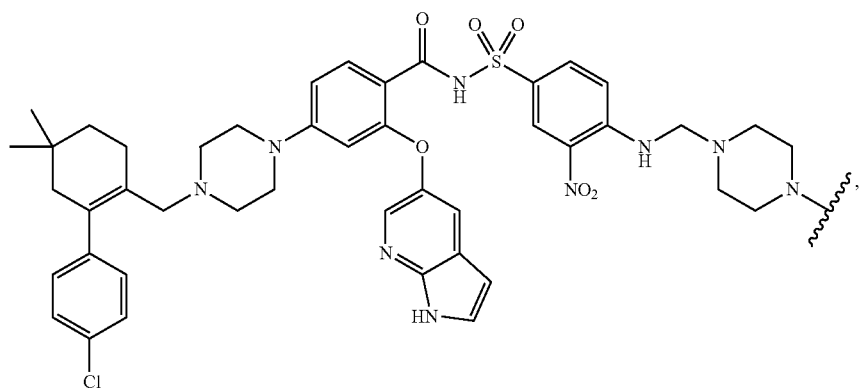
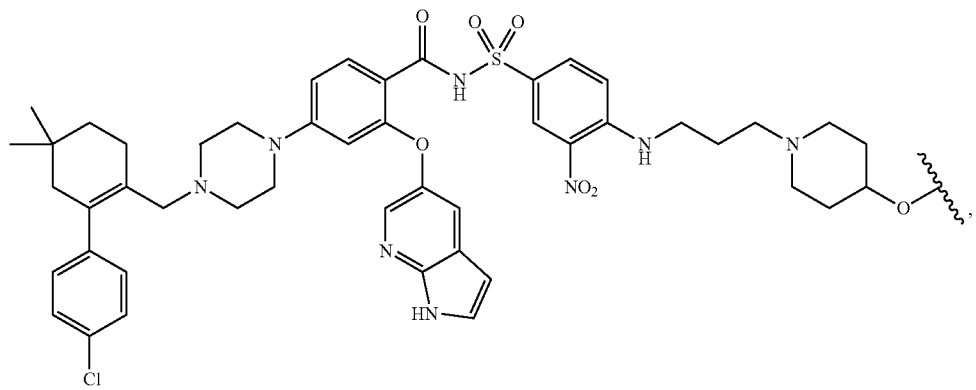
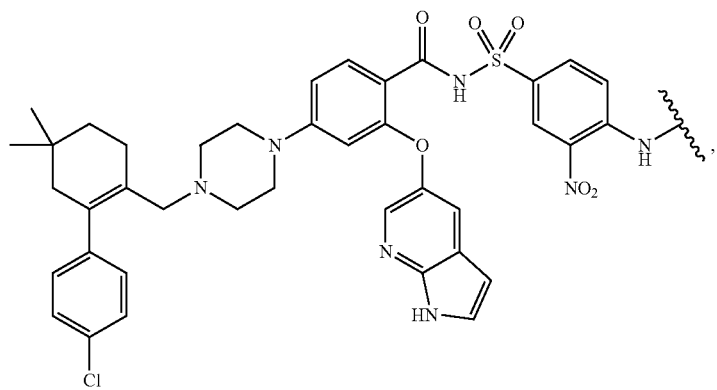

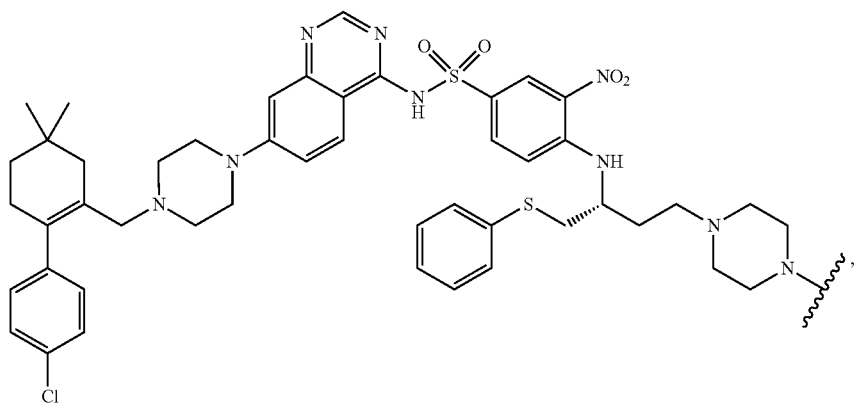
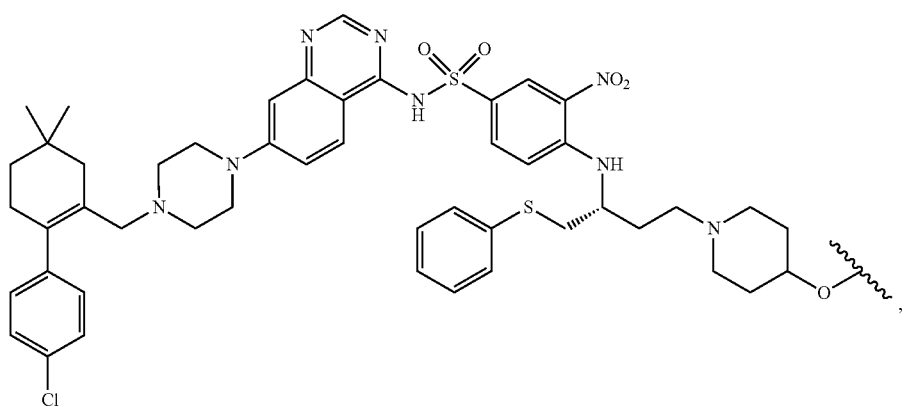
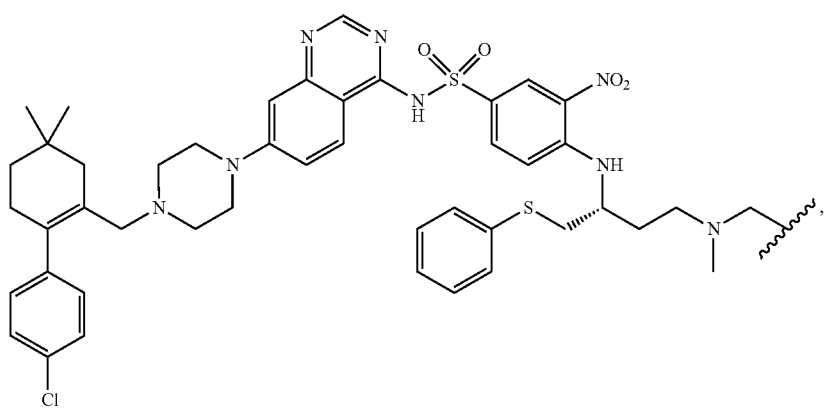
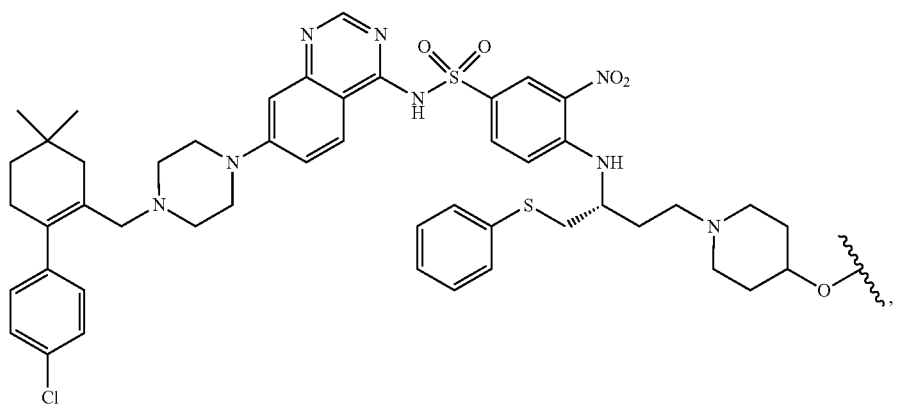

-continued
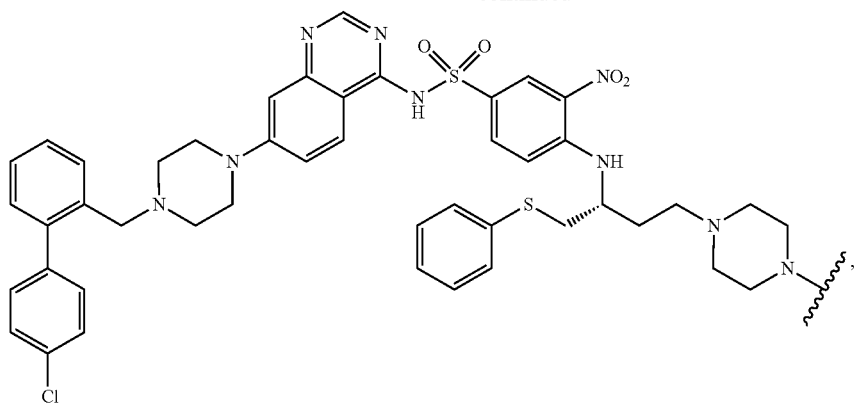
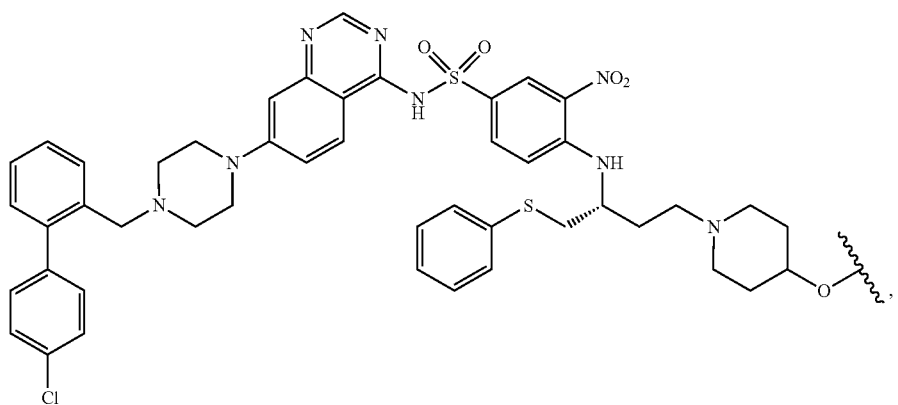
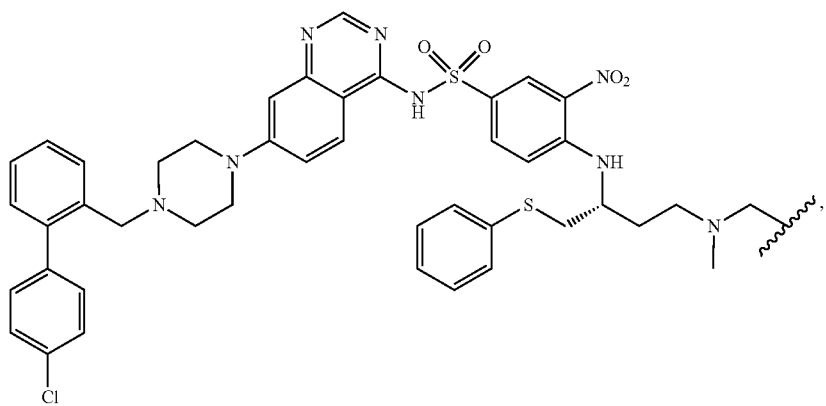
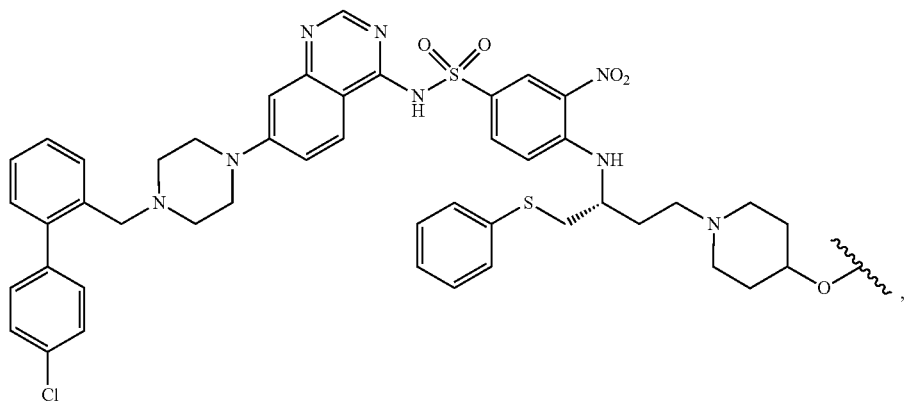

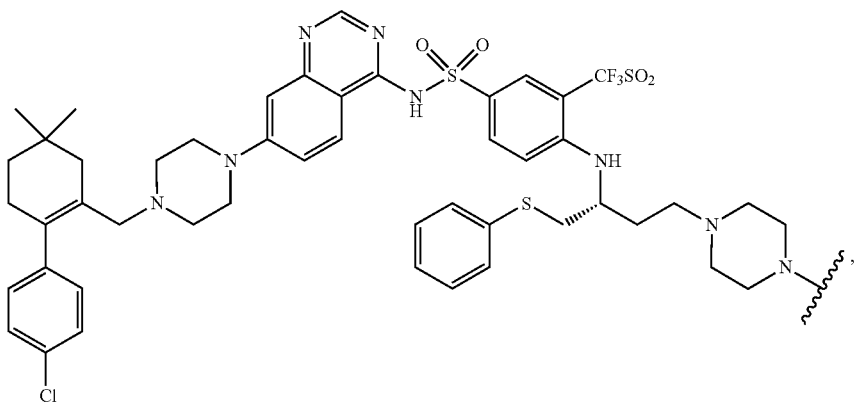
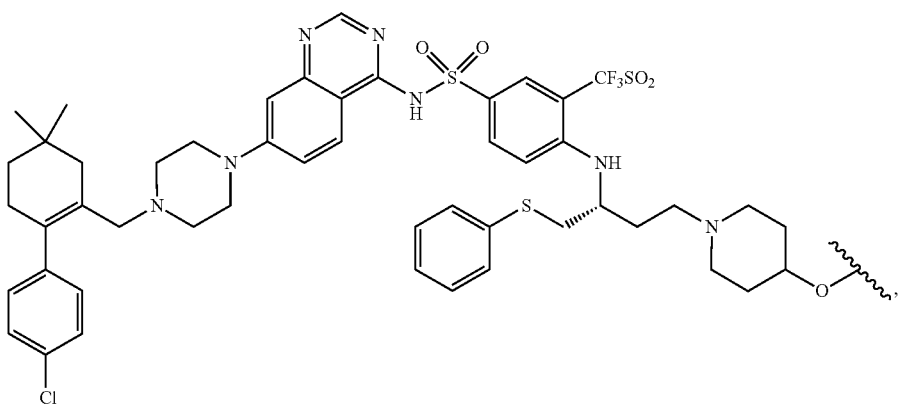
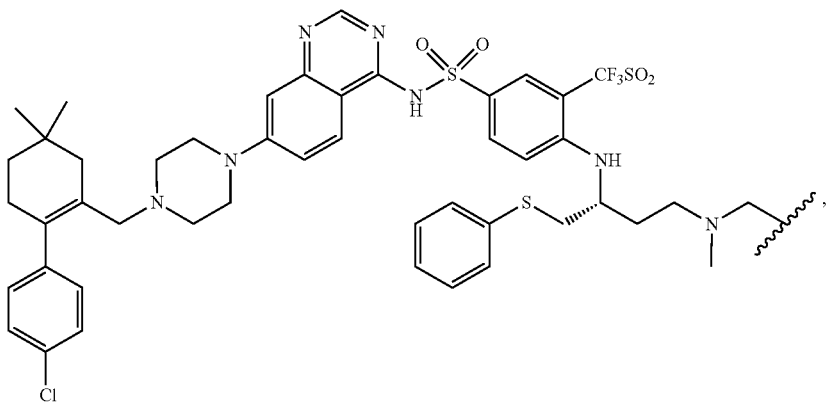
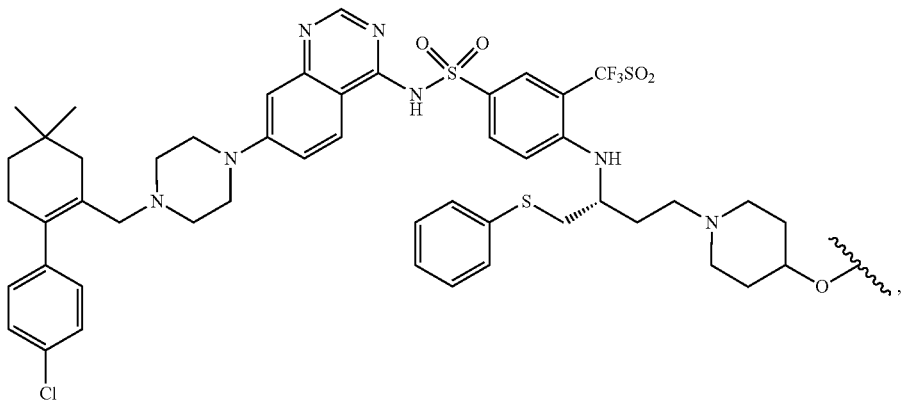

-continued
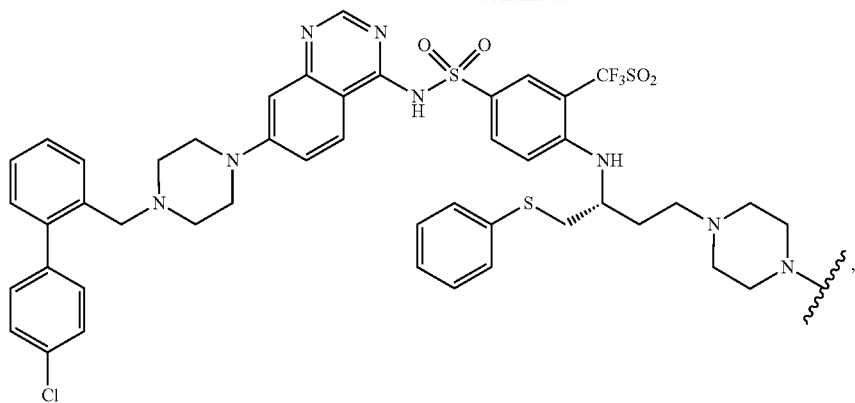
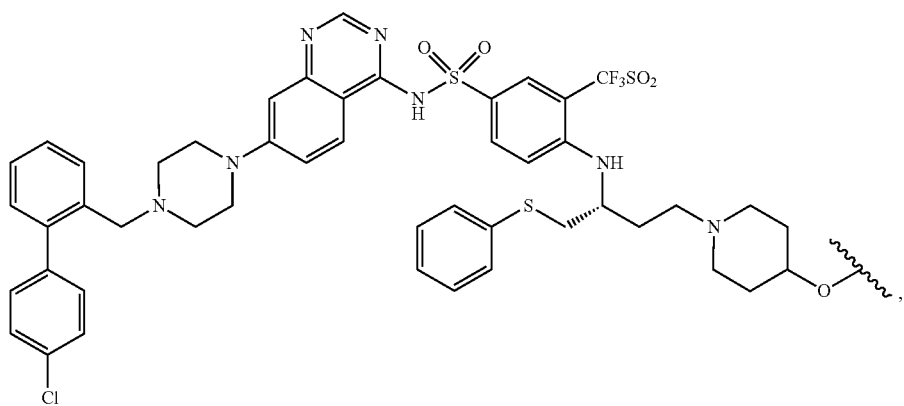
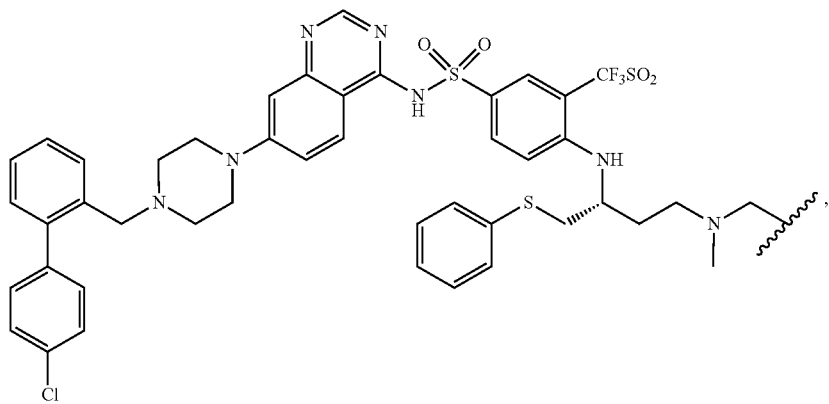
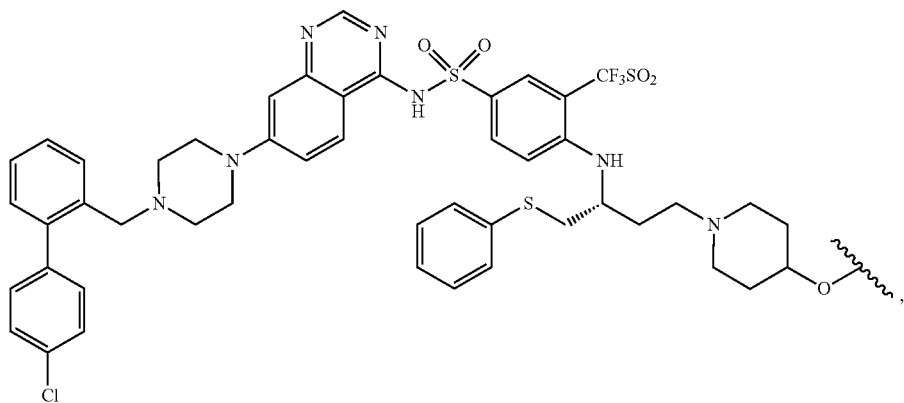

-continued
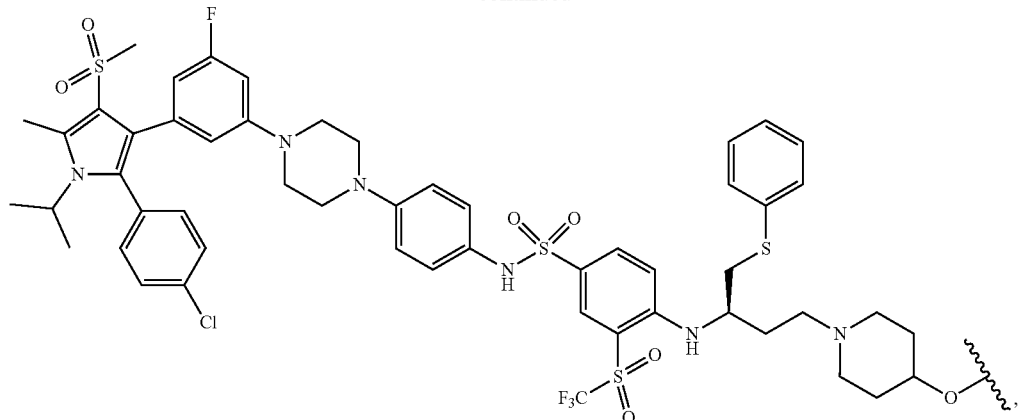
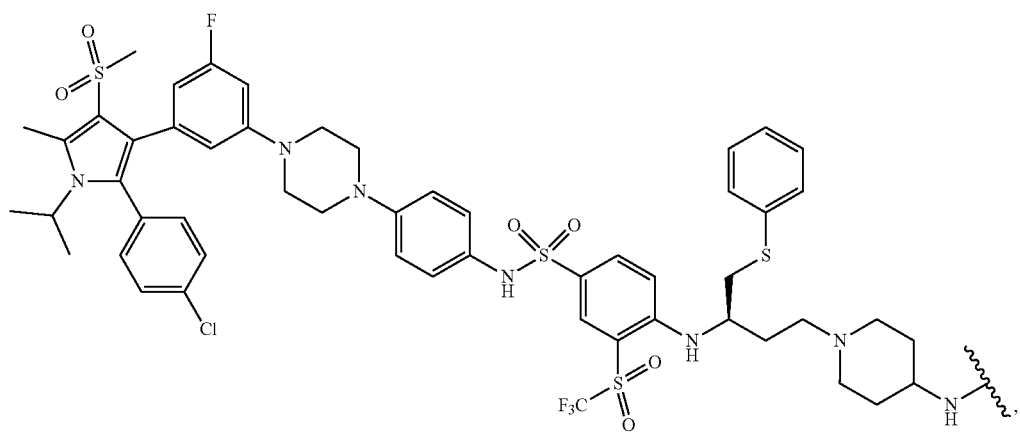
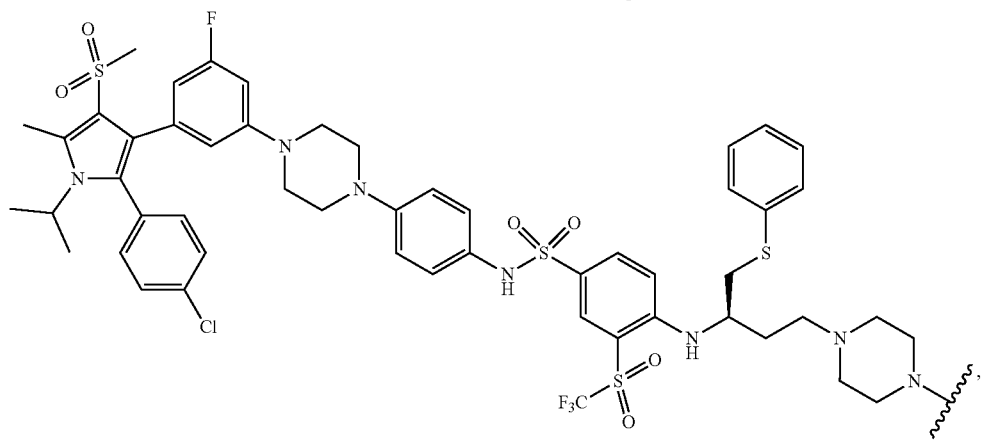
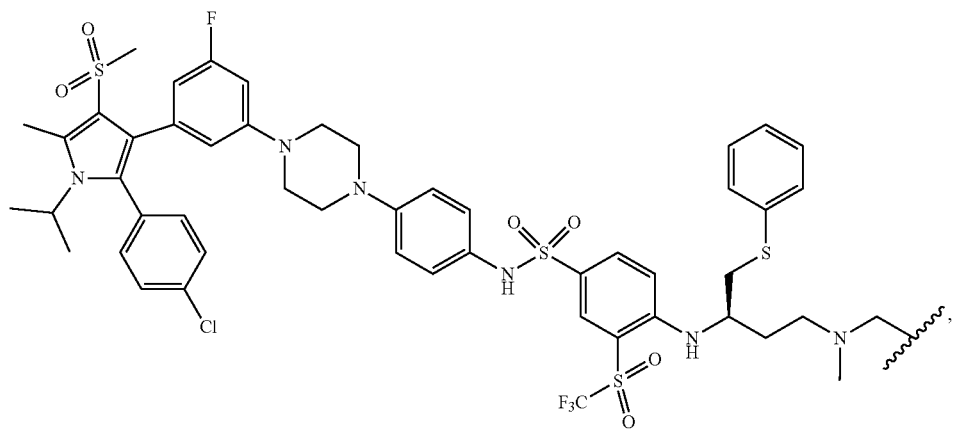

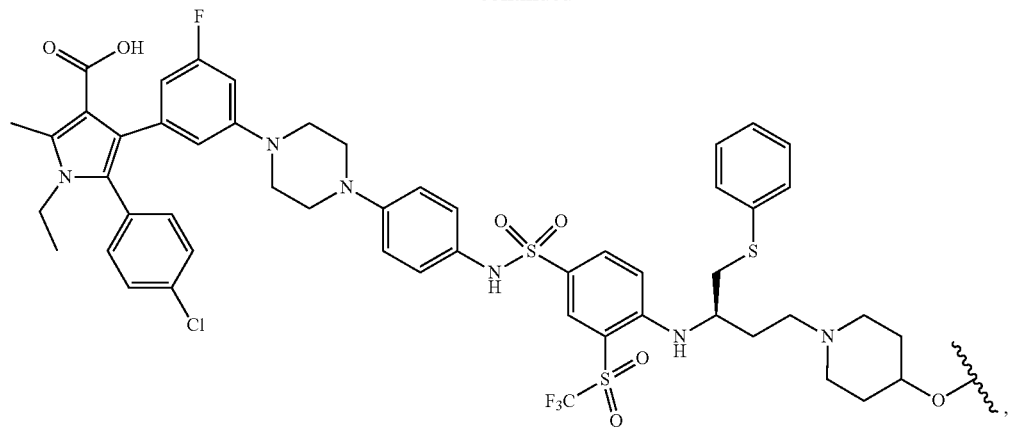
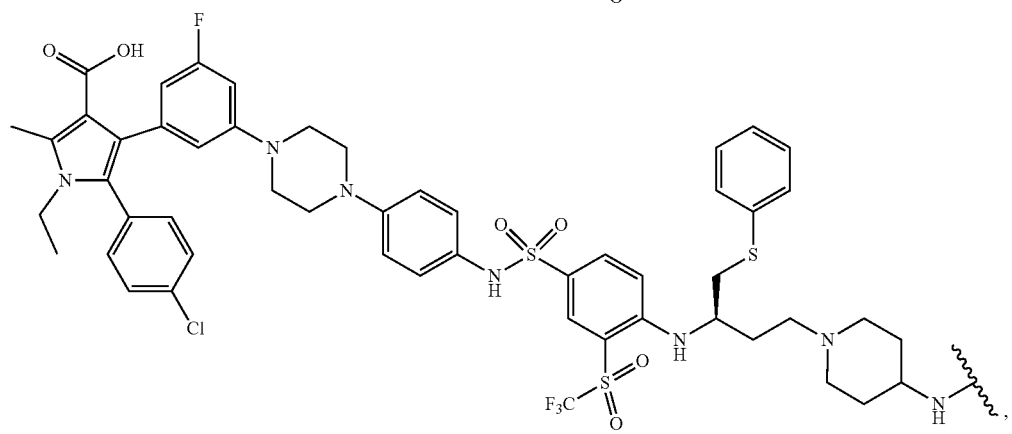
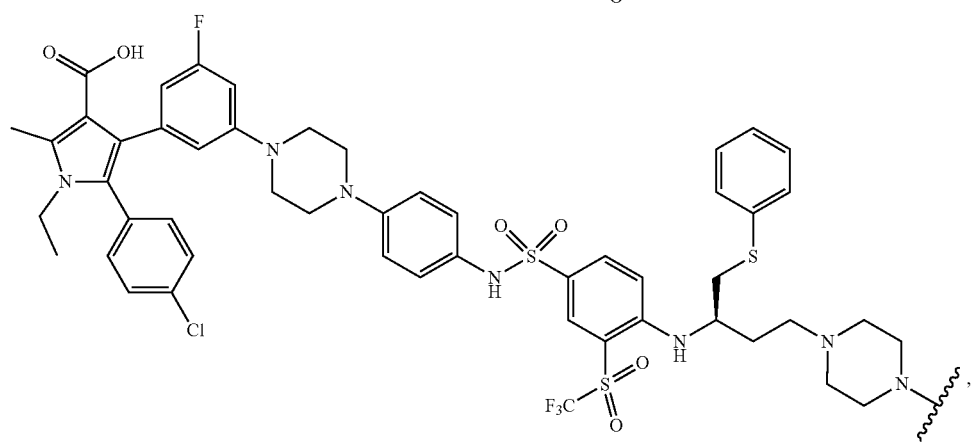
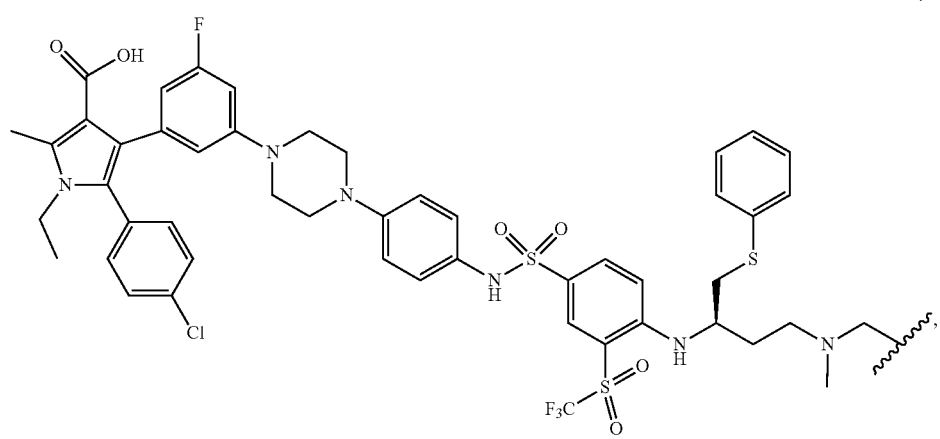

-continued
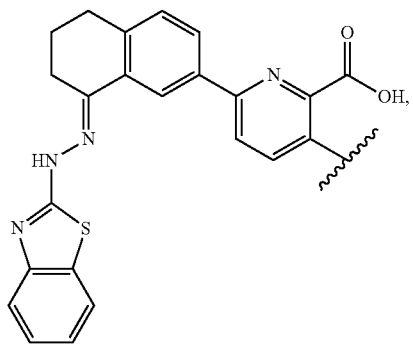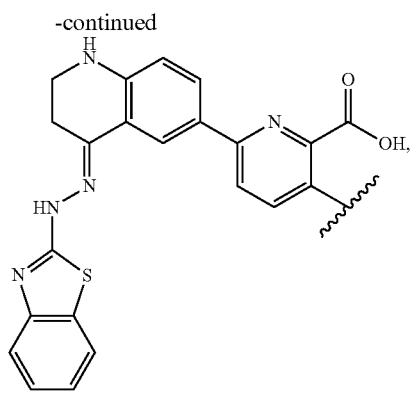
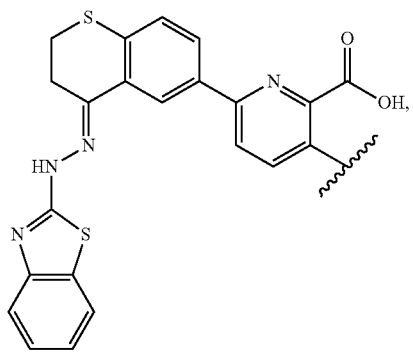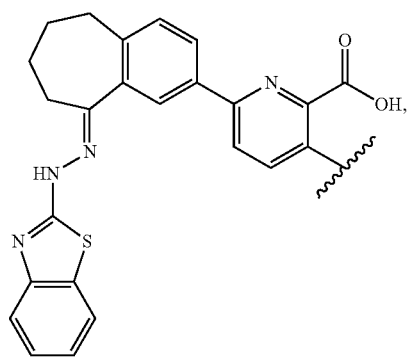
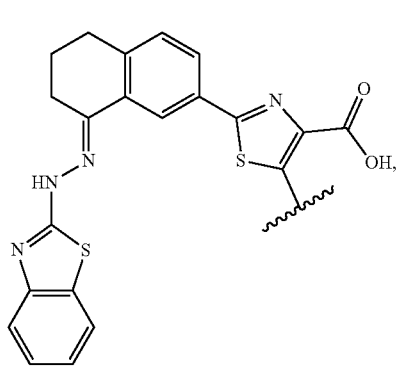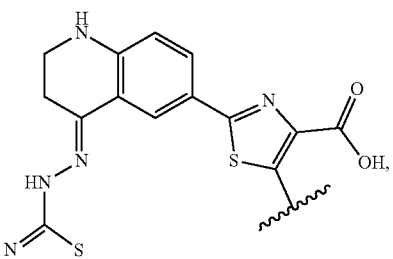
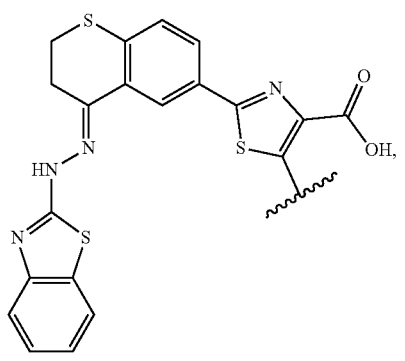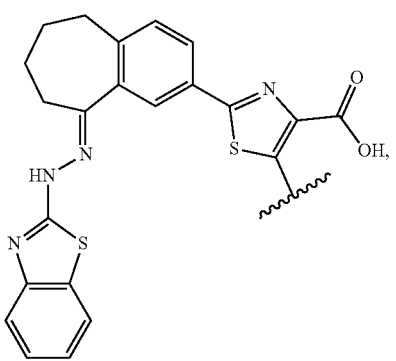

-continued
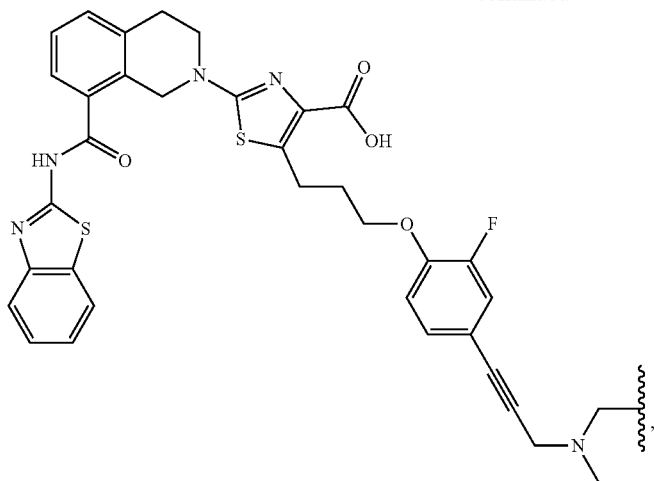
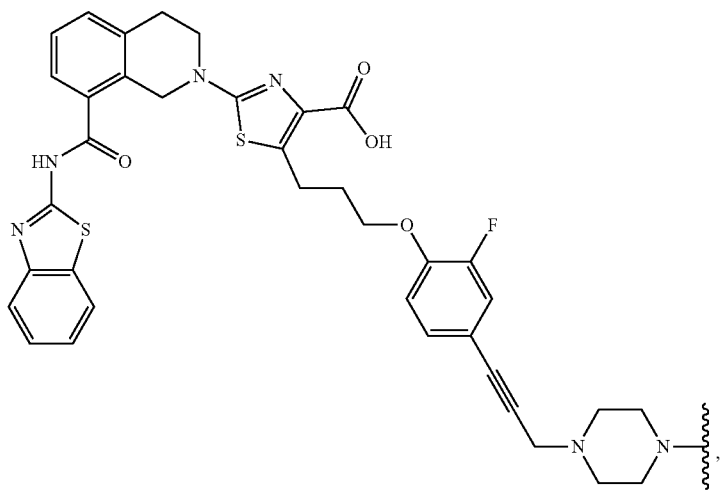
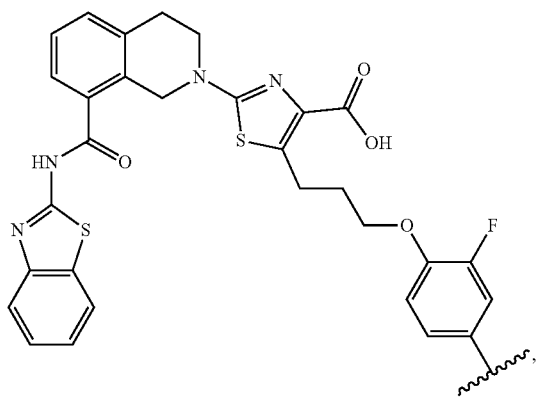

-continued
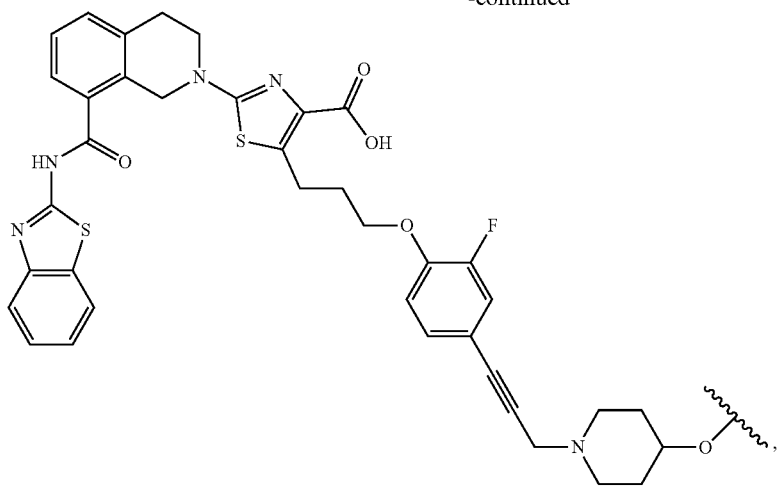
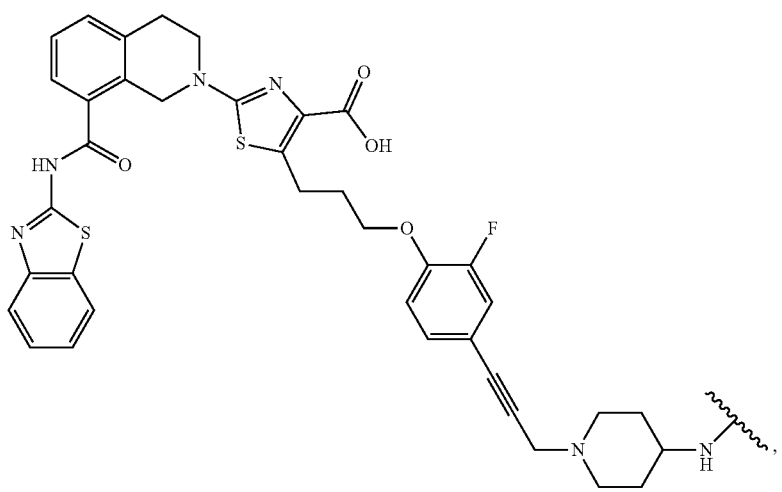
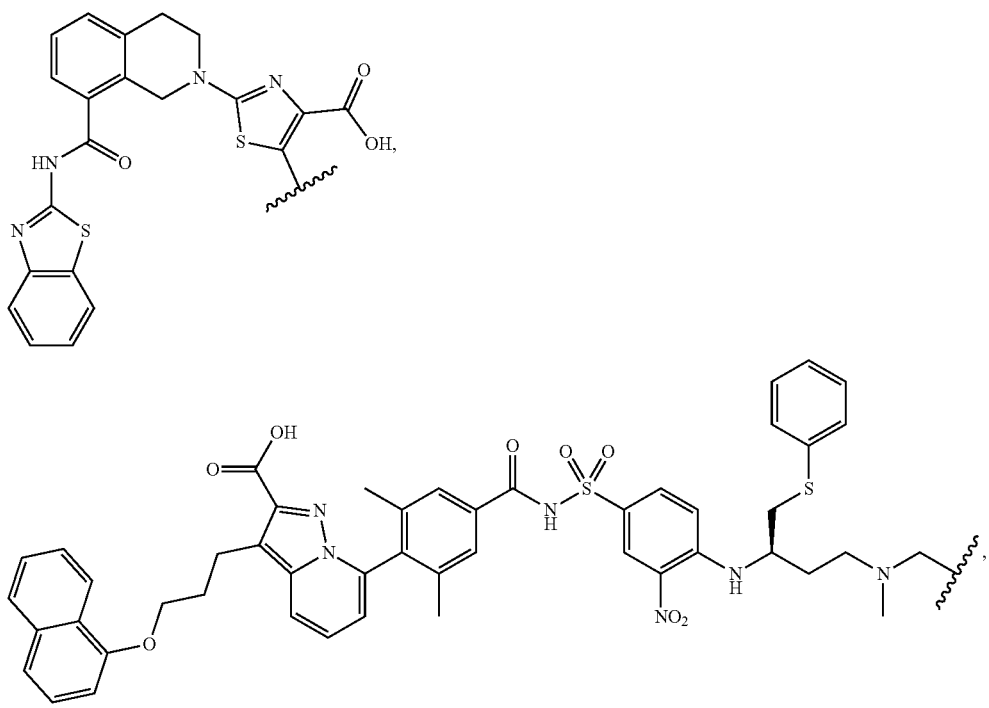

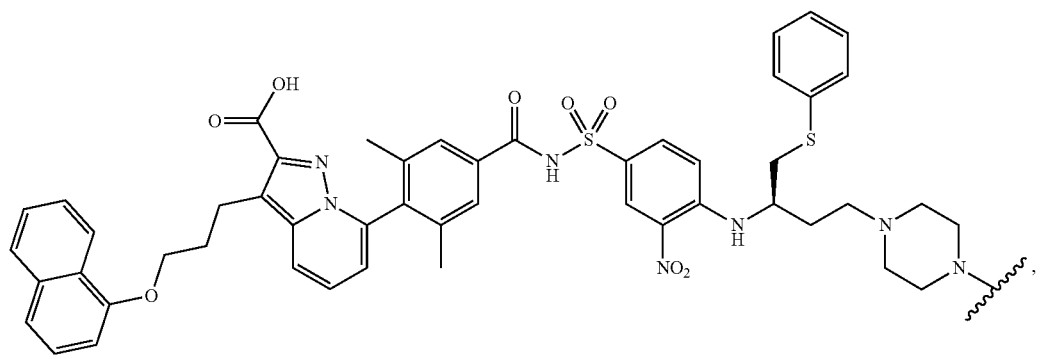
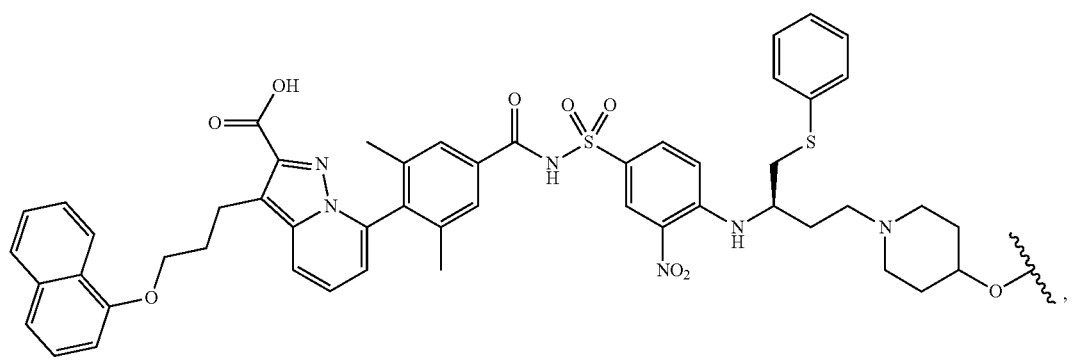
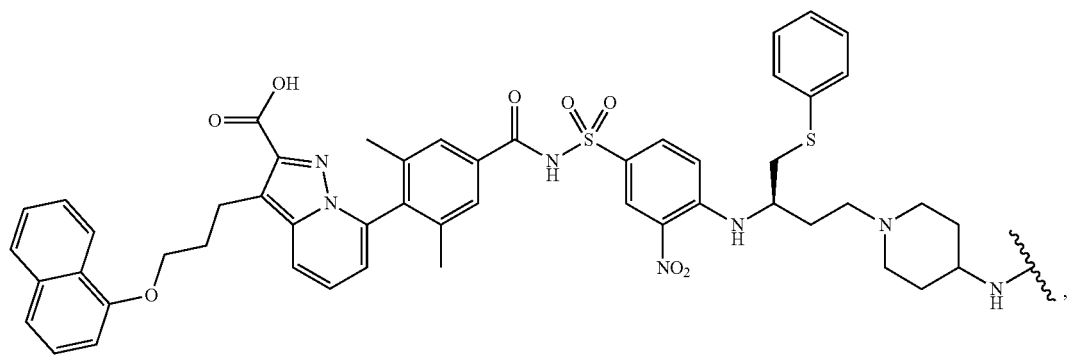
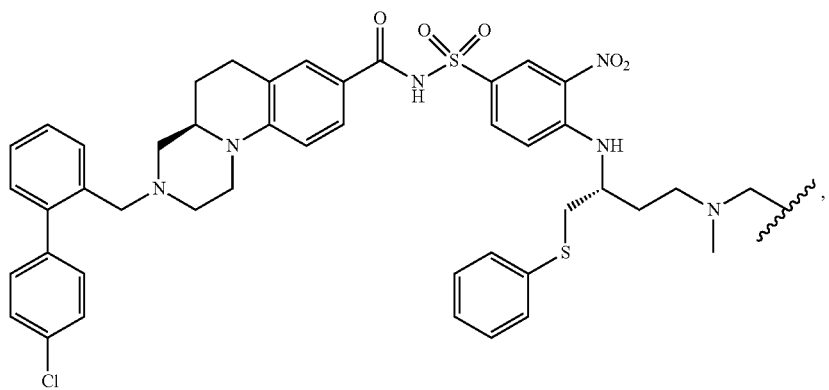

-continued
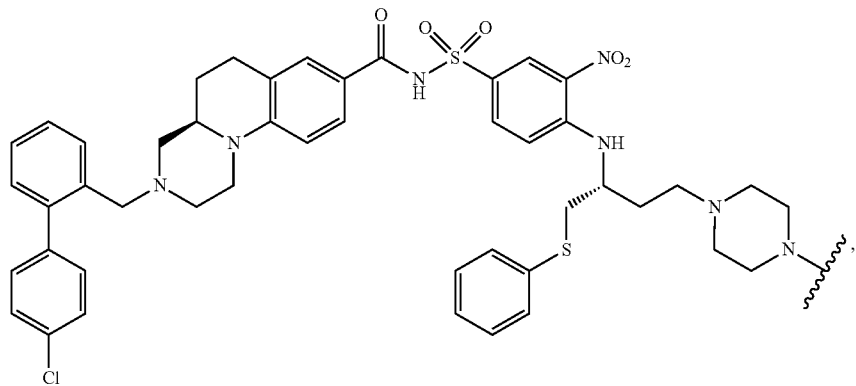
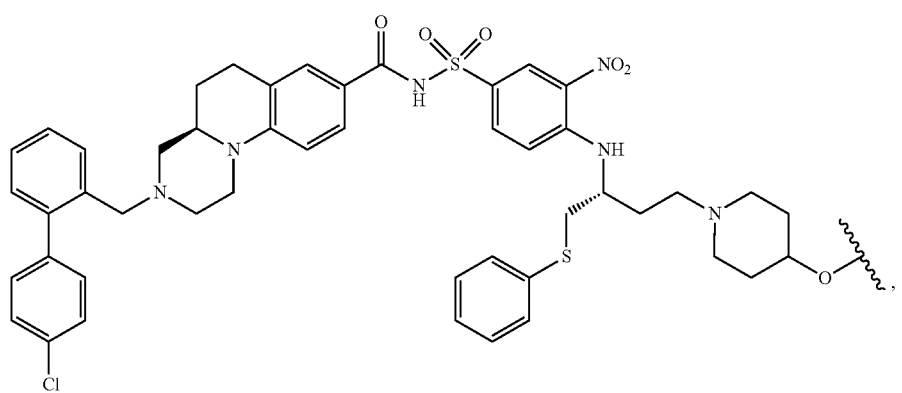
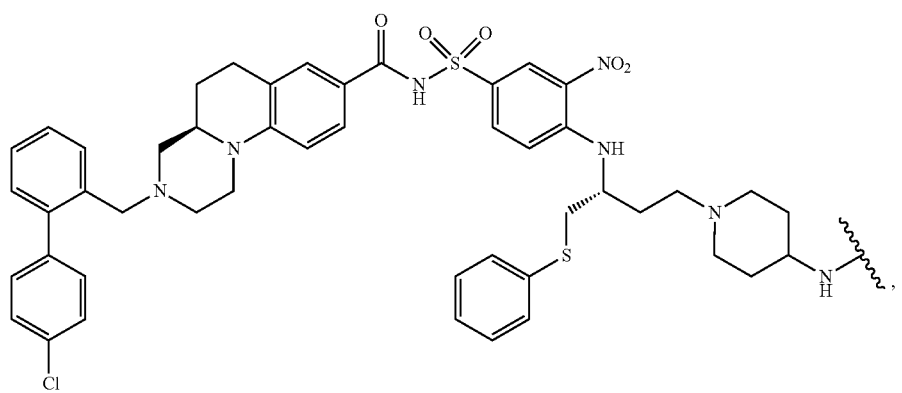
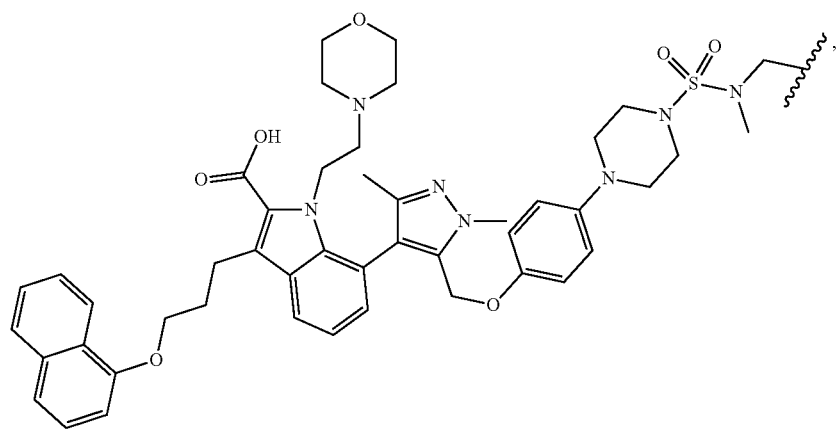

-continued
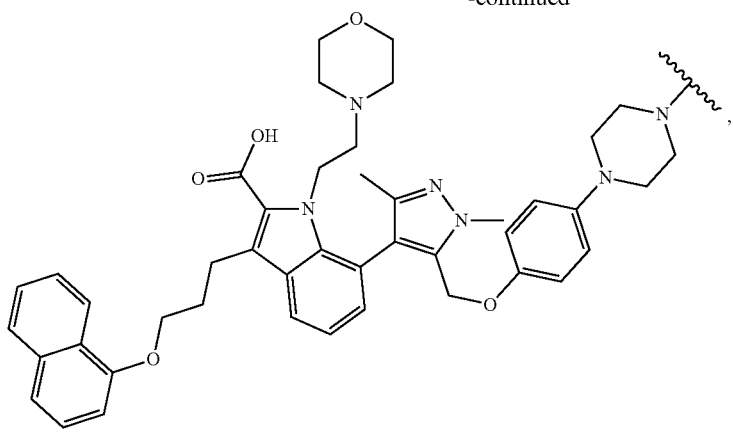
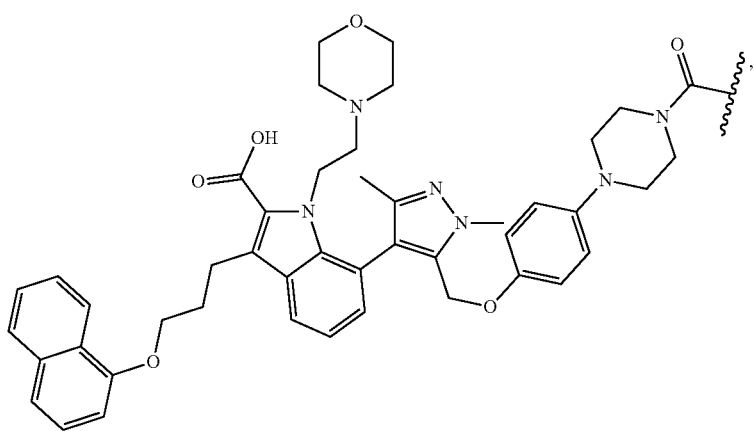
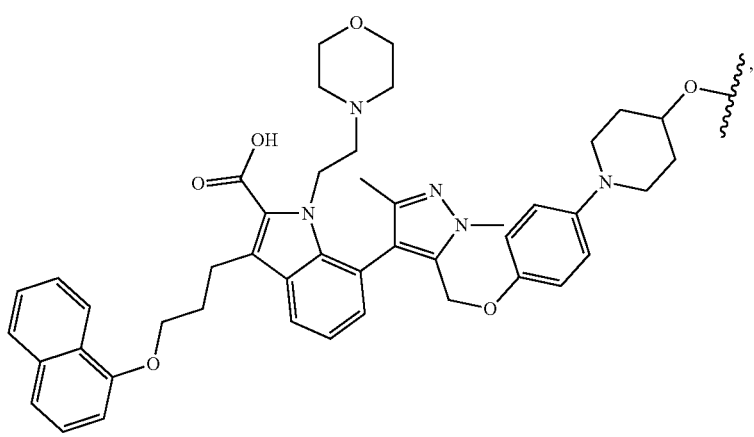

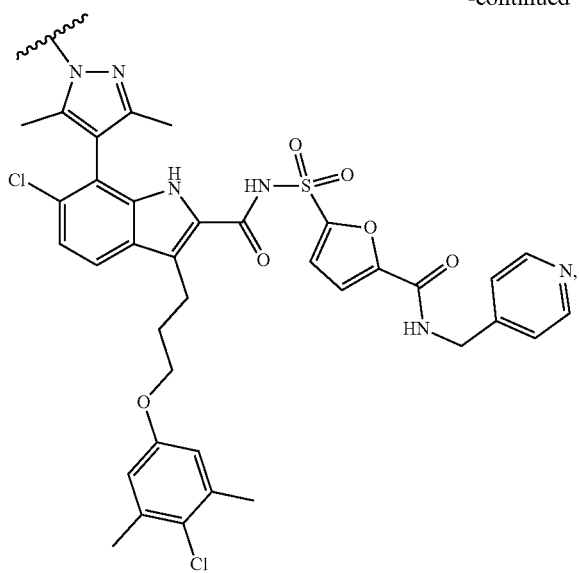
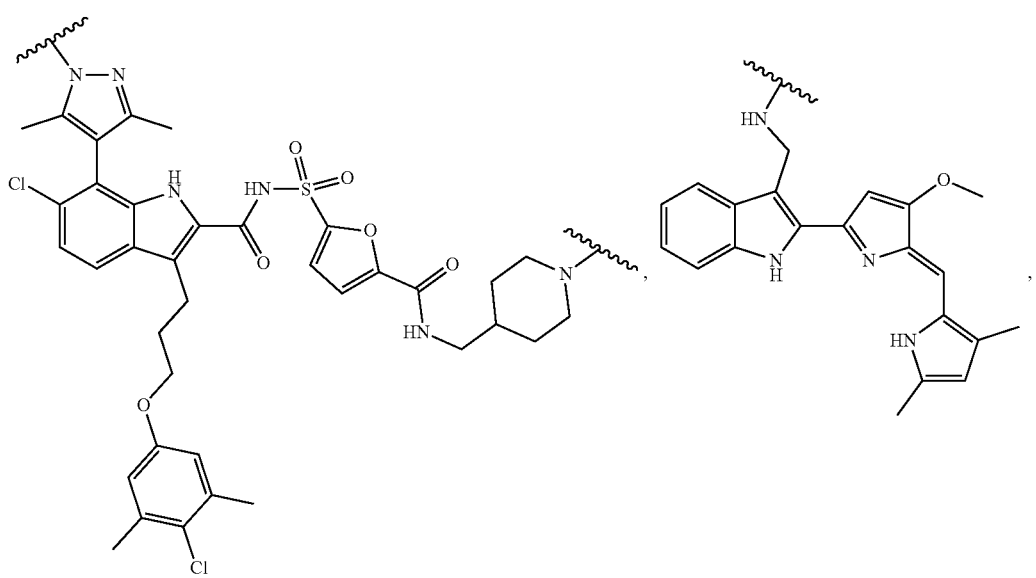
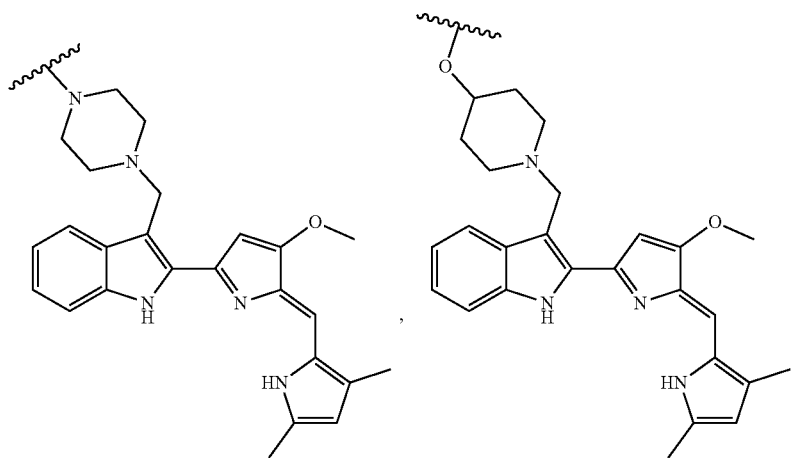

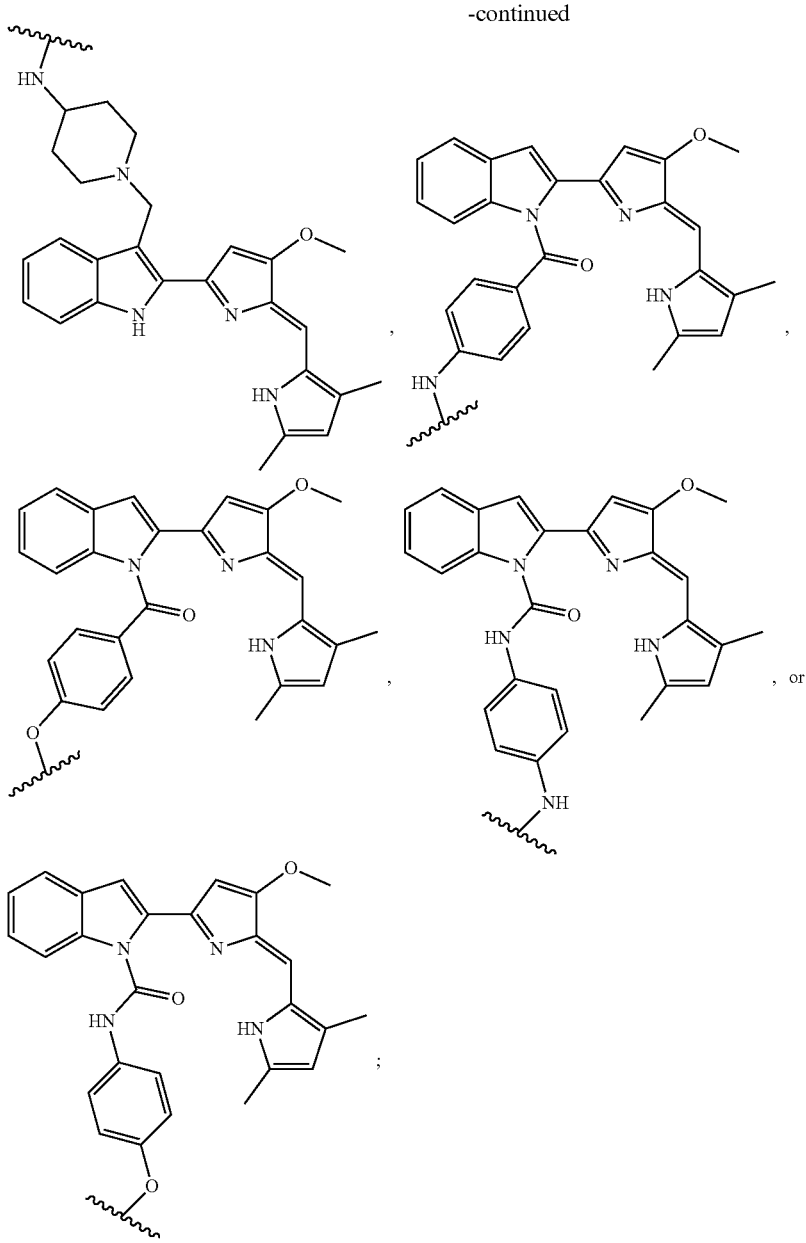
R³ may be absent, an unsubstituted $C_1$-$C_6$ alkyl, or a substituted or unsubstituted $C_3$-$C_6$ ketone; A may be absent, a bond, or a triazole; n may be 0 to 3; R⁴ may be a bond or a substituted or unsubstituted $C_1$-$C_{10}$ alkyl; and wherein R² may be
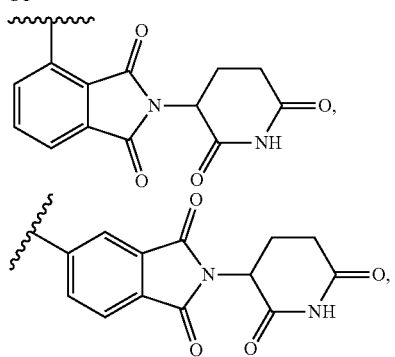
-continued
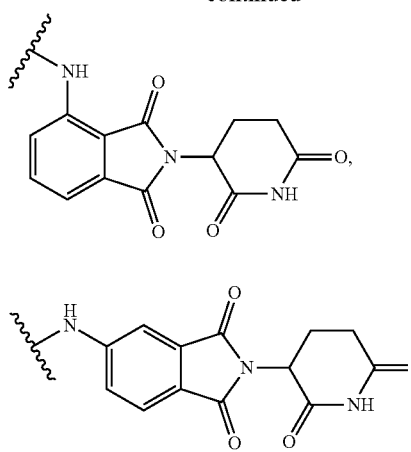

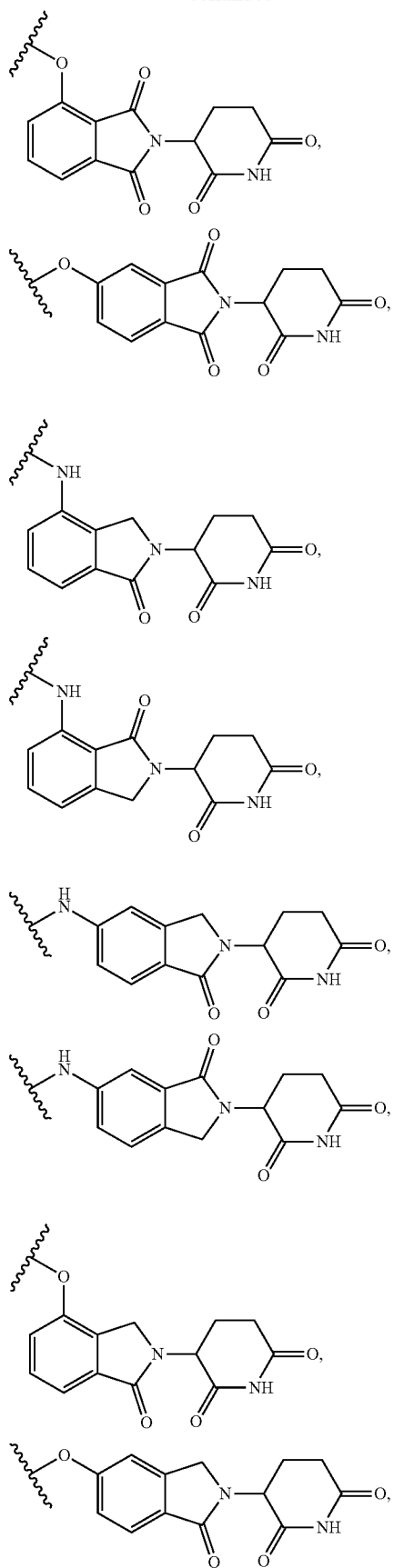
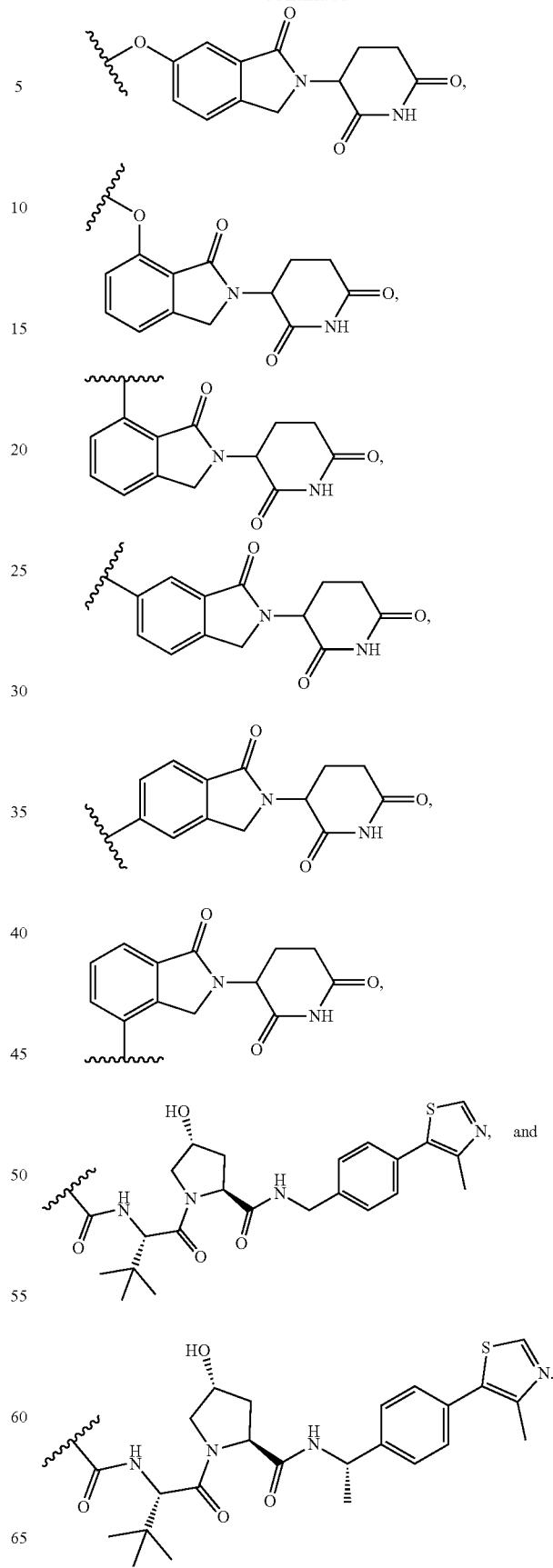

In still another embodiment, a compound of the disclosure comprises Formula (II), wherein R¹ may be
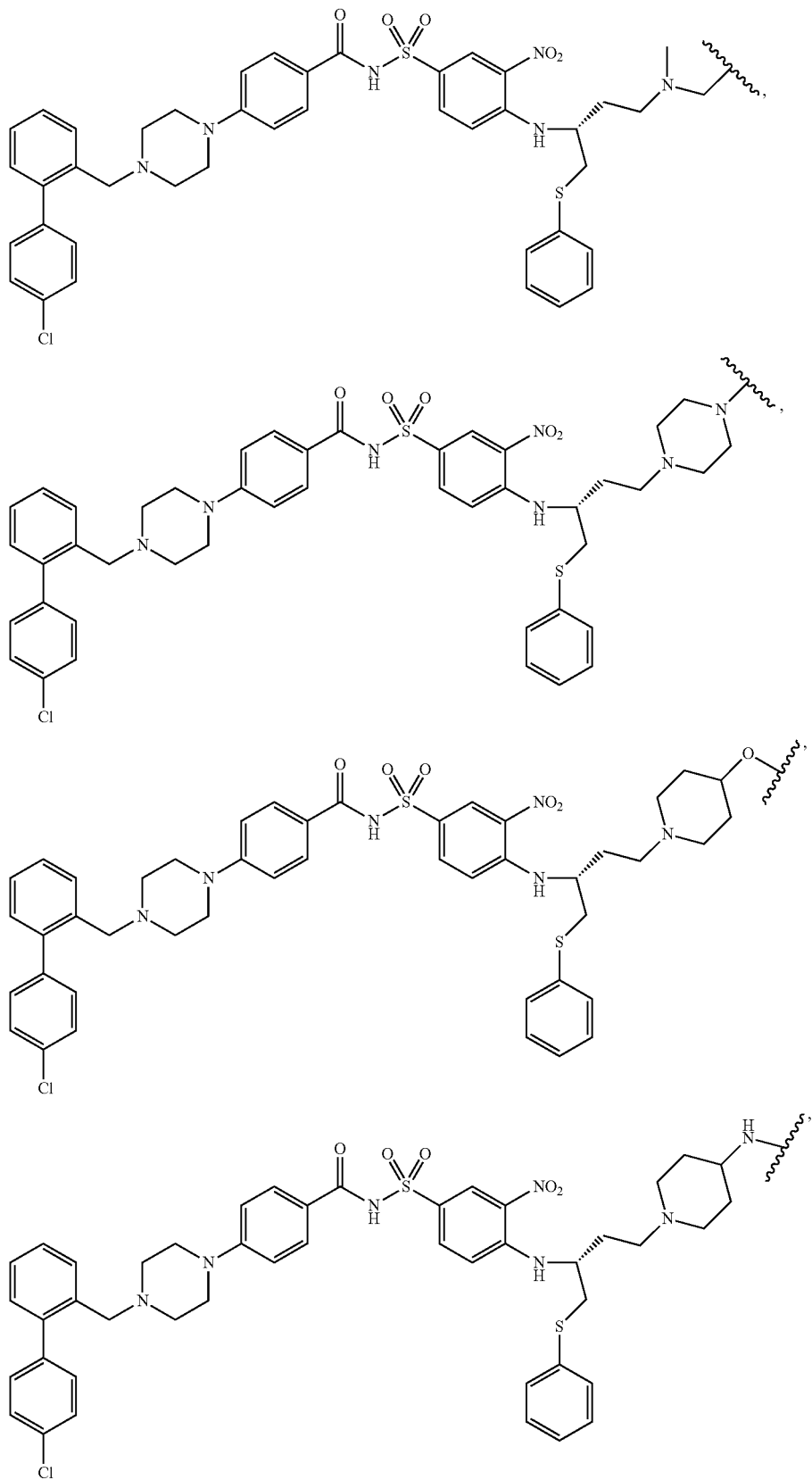

-continued
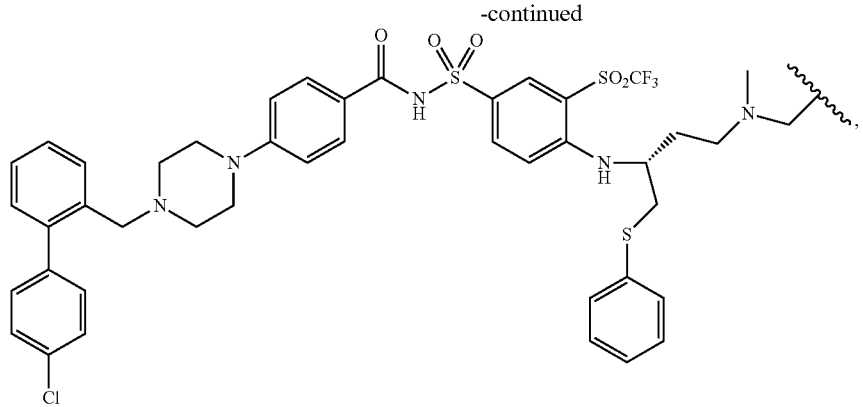
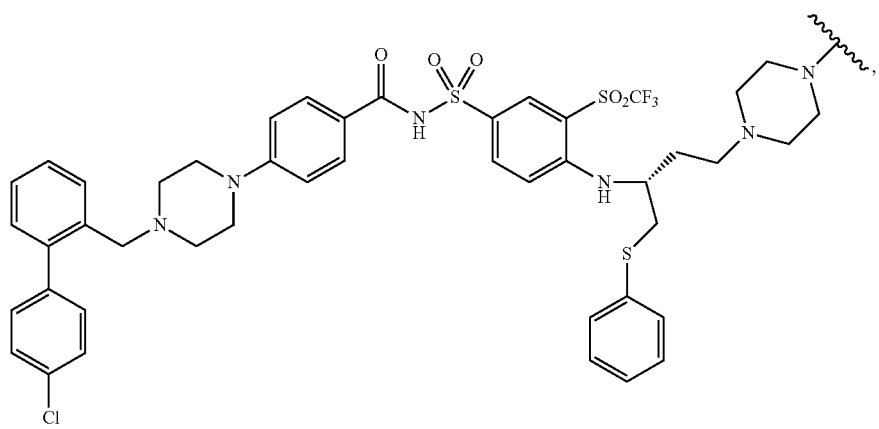
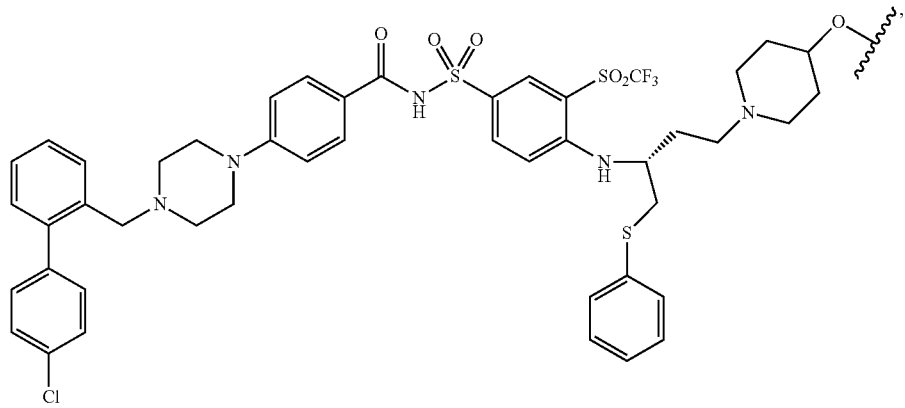
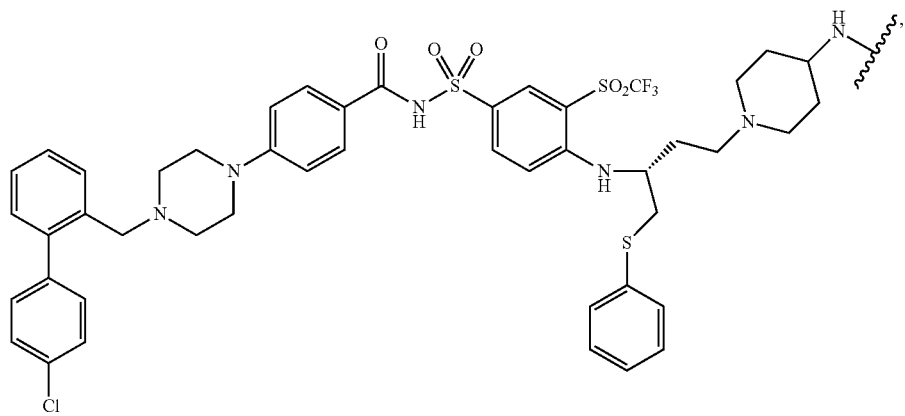

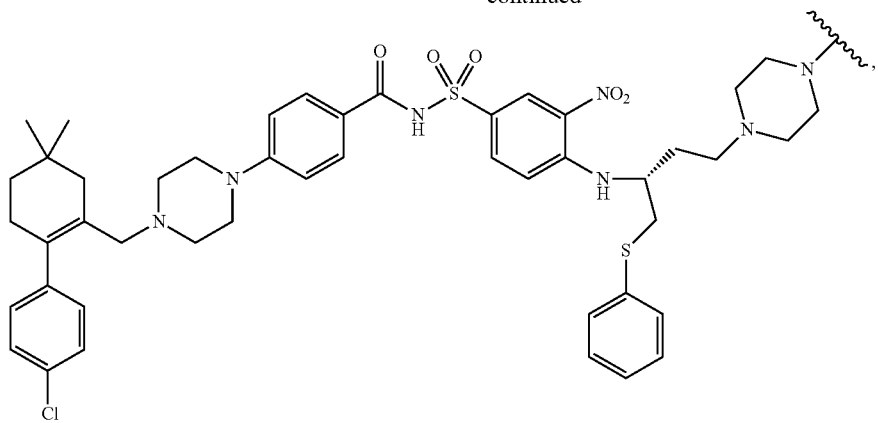
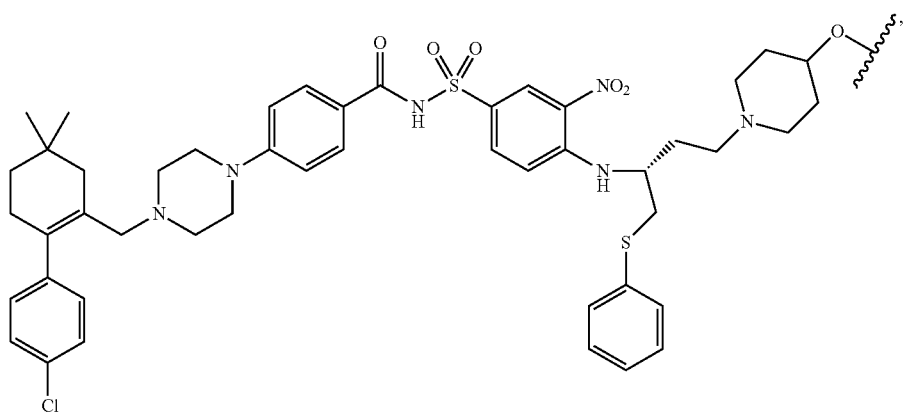
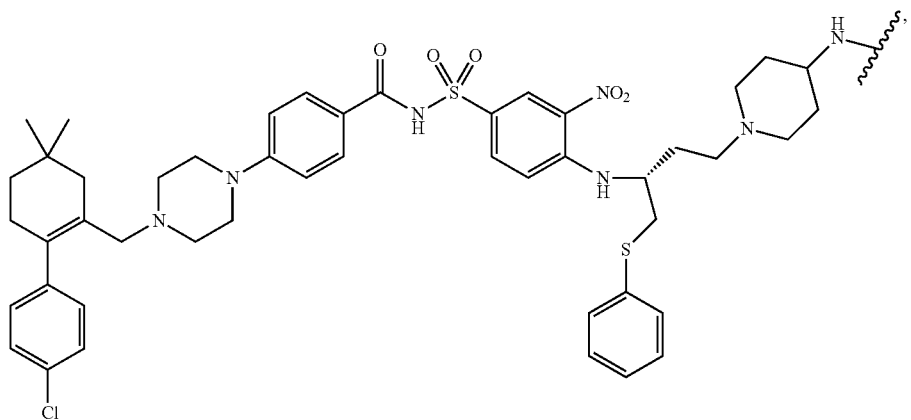
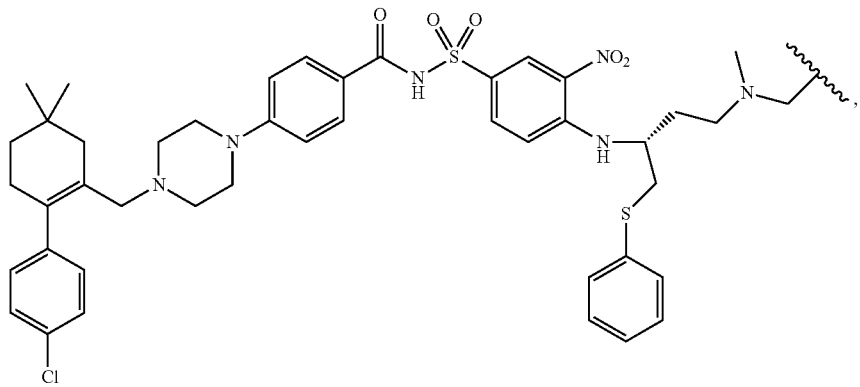

-continued
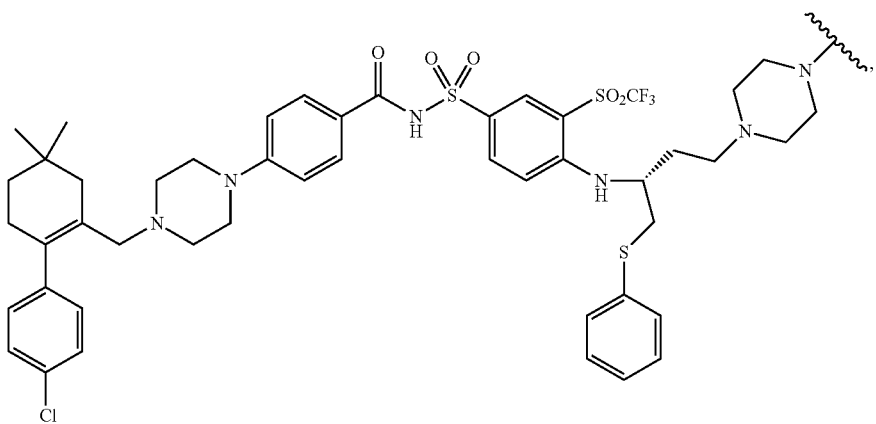
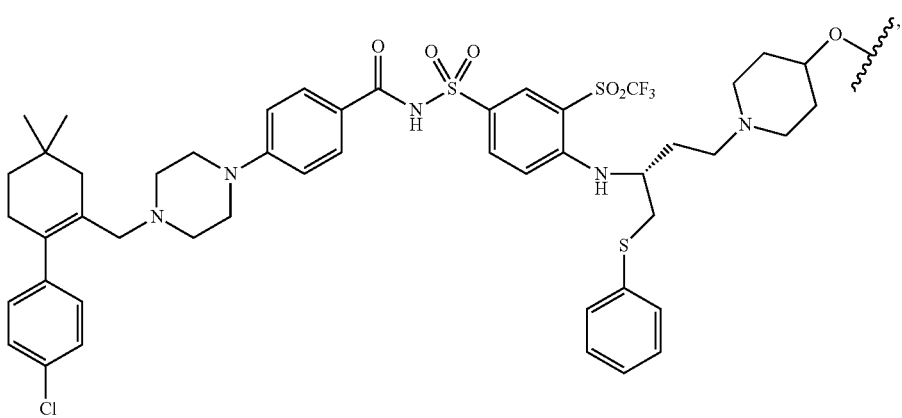
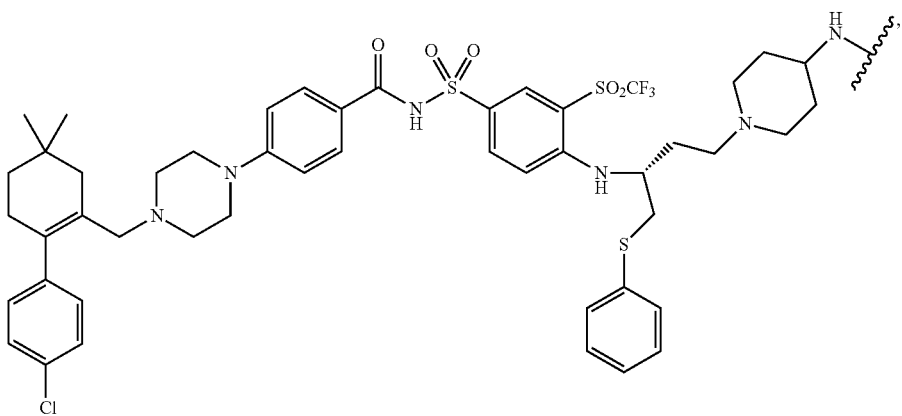
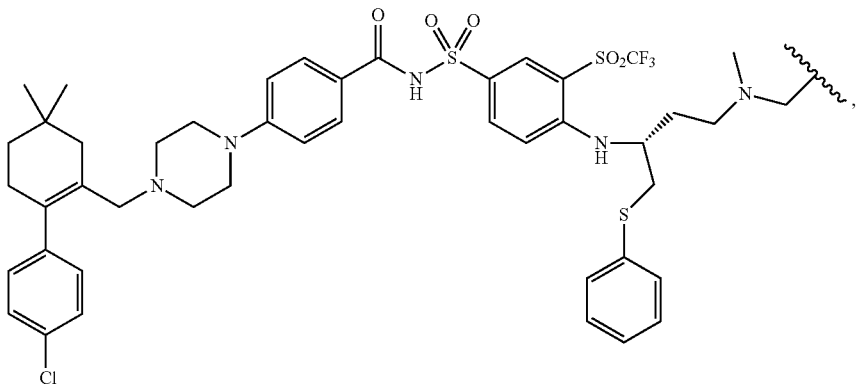

-continued
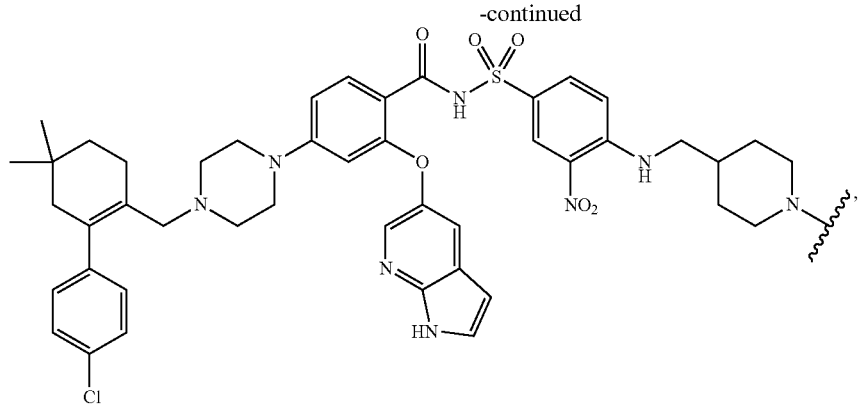
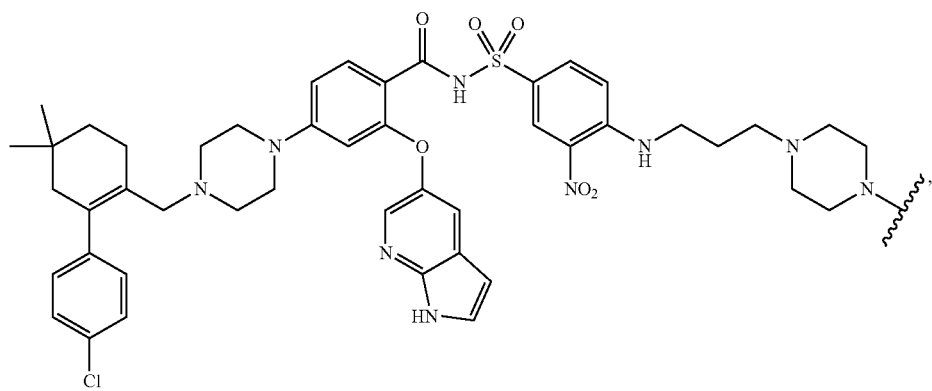
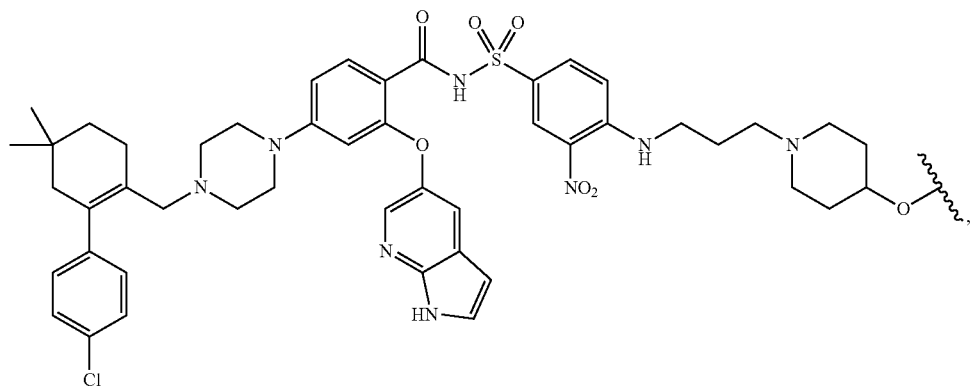
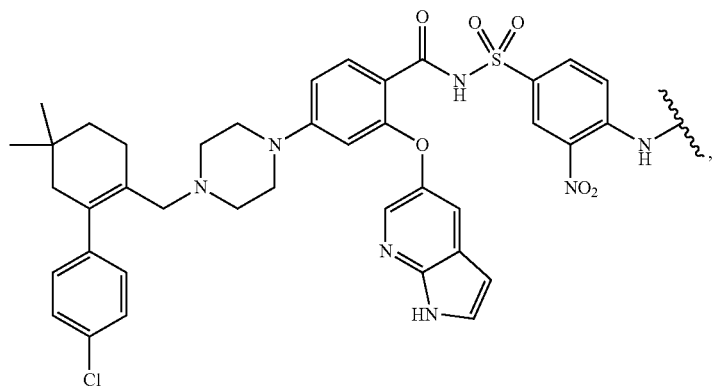

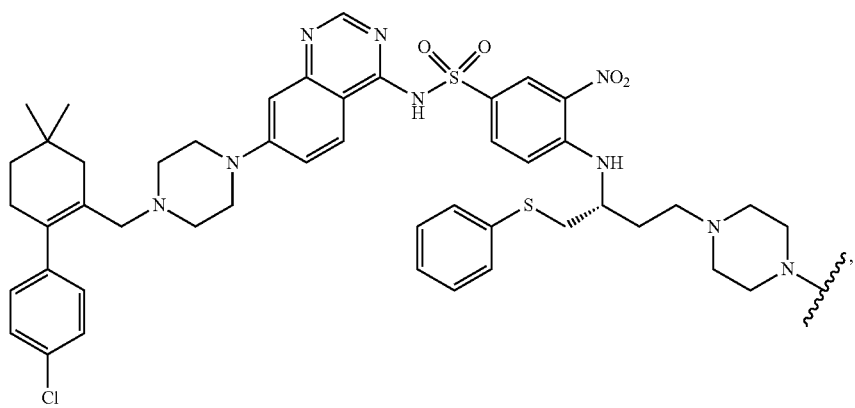
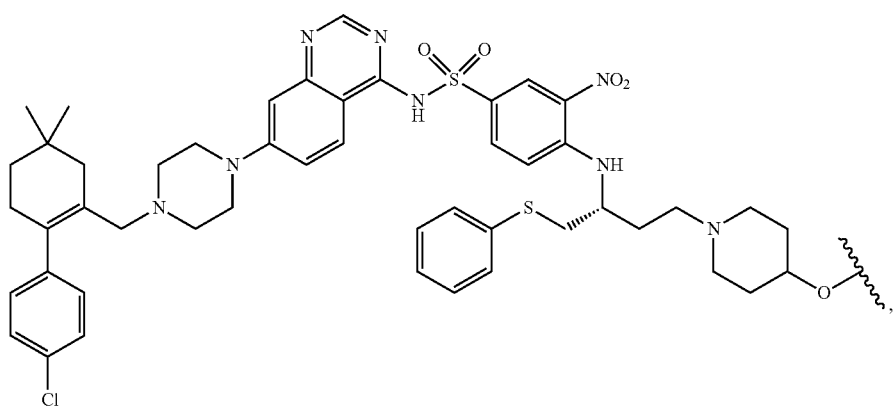
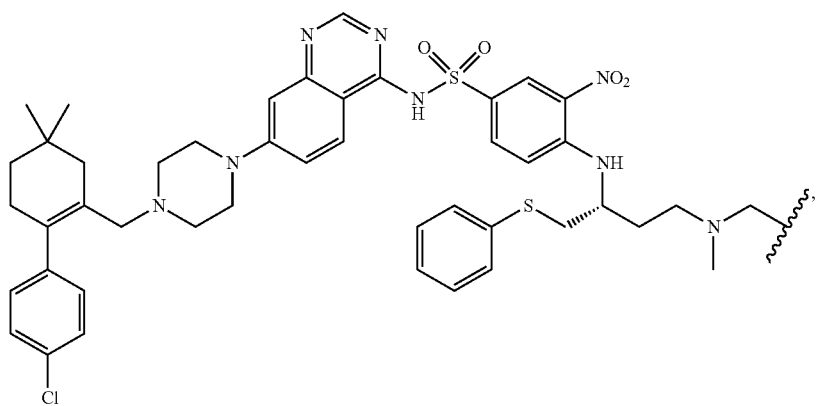
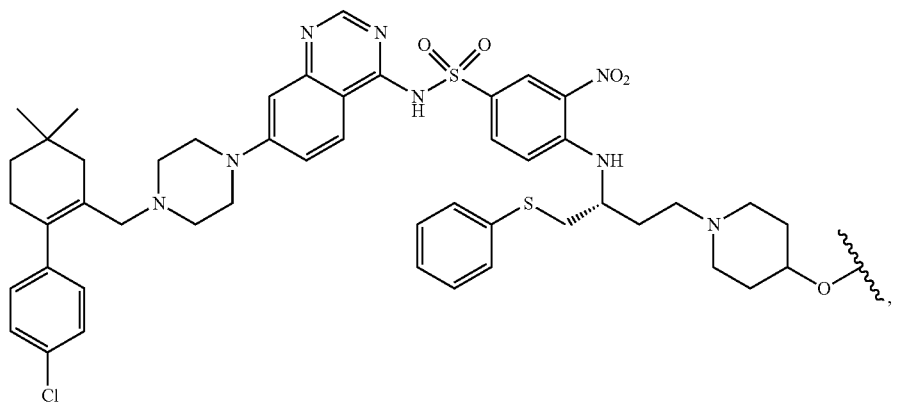

-continued
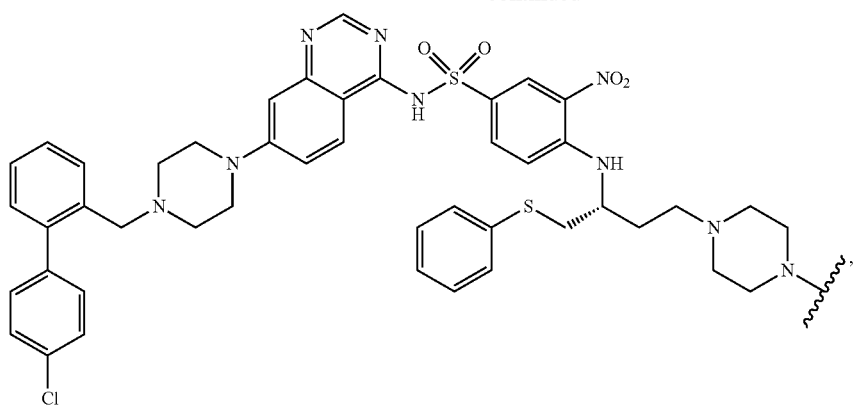
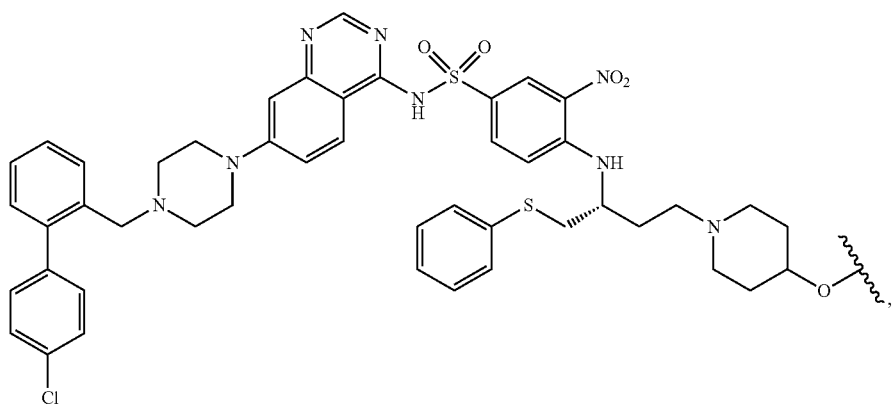
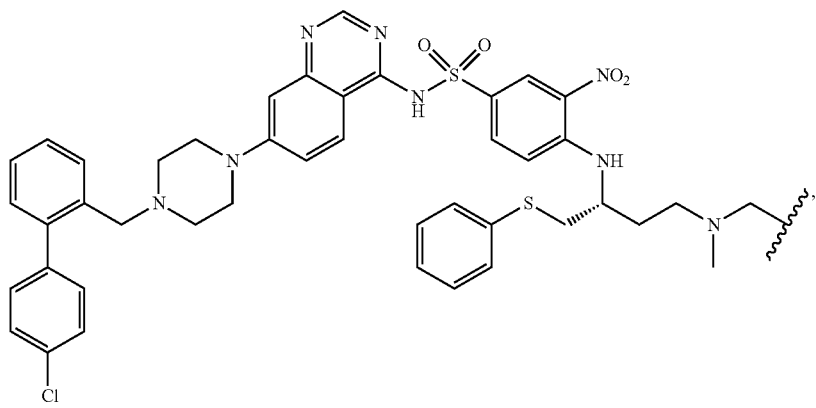
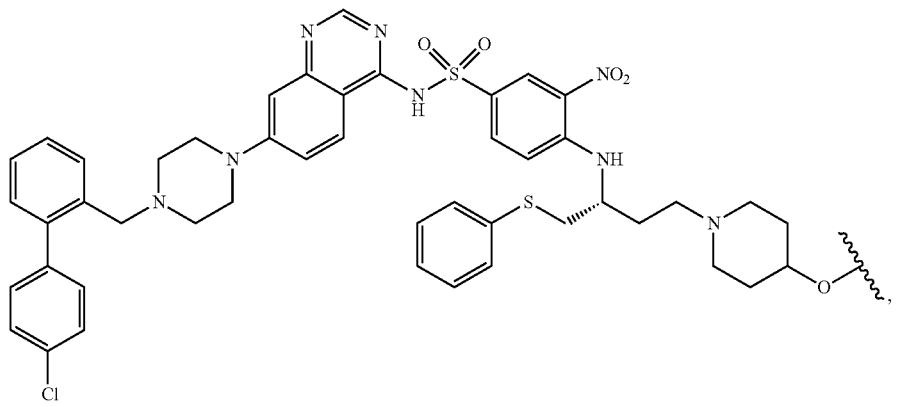

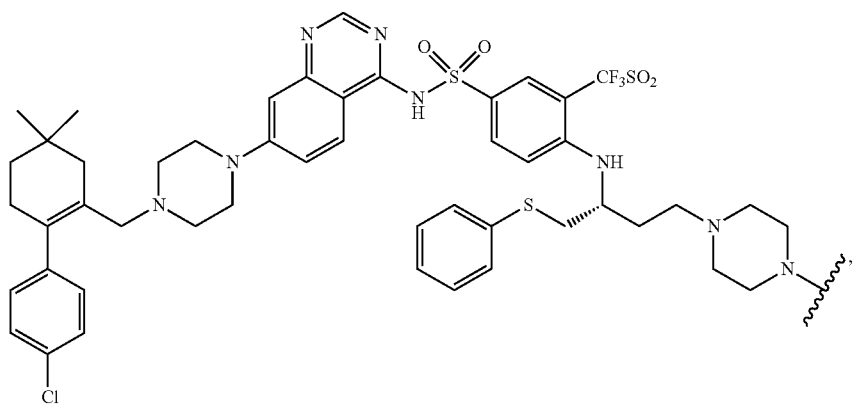
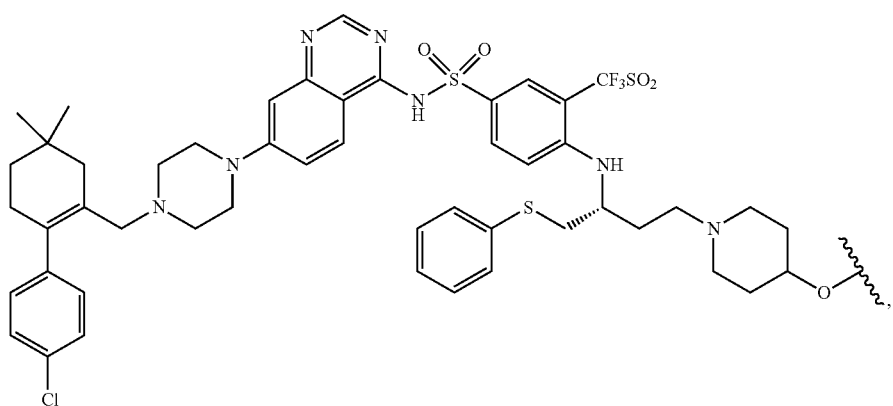
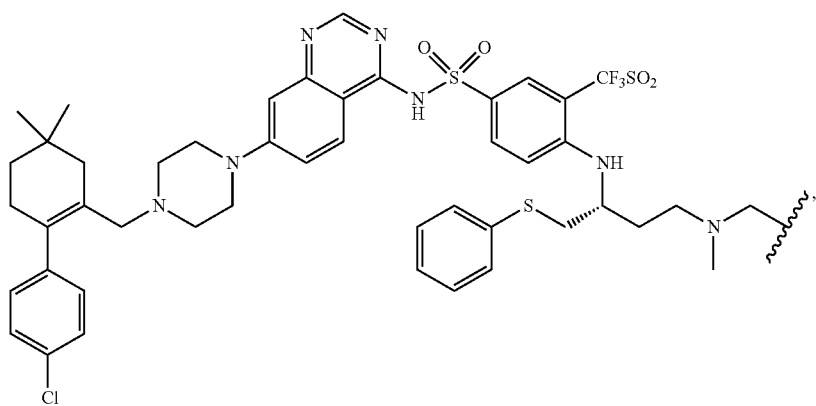
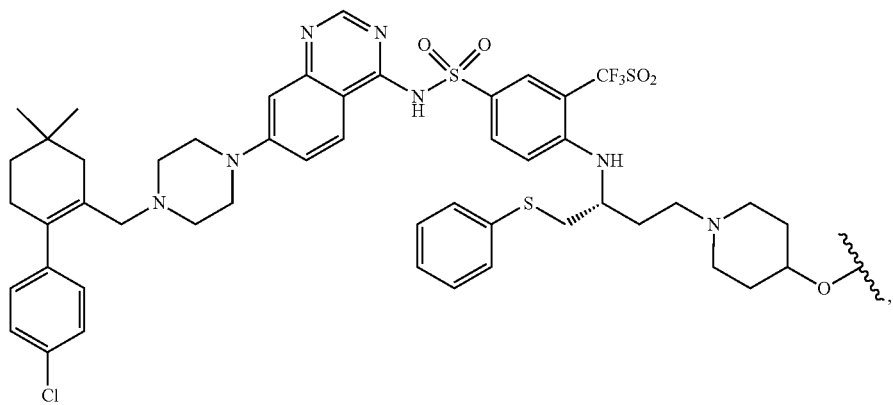

-continued
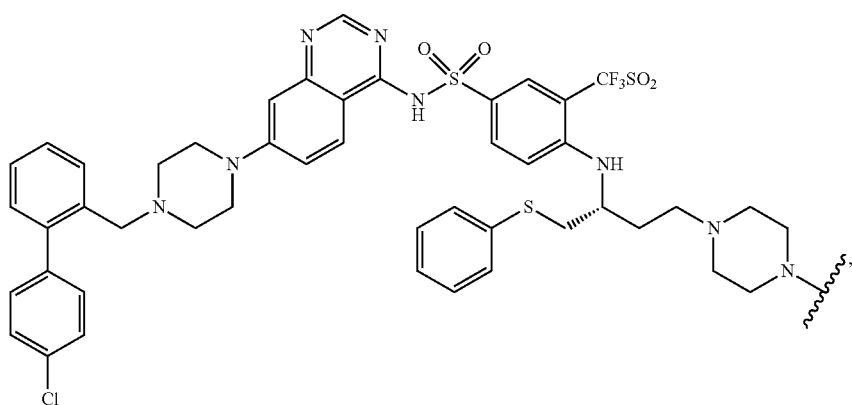
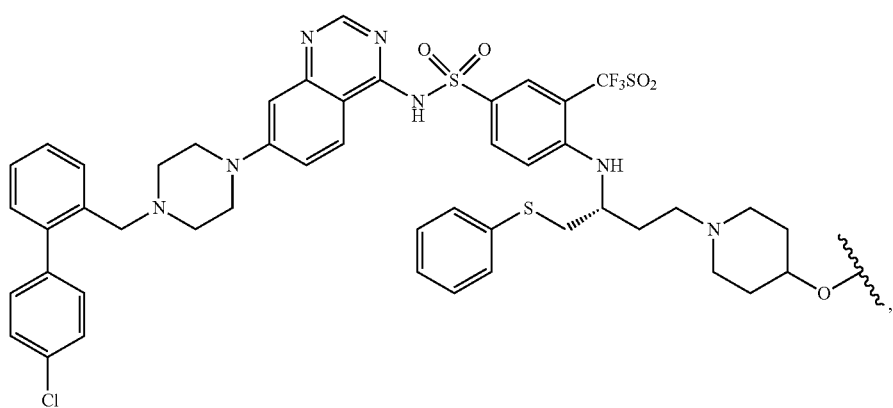
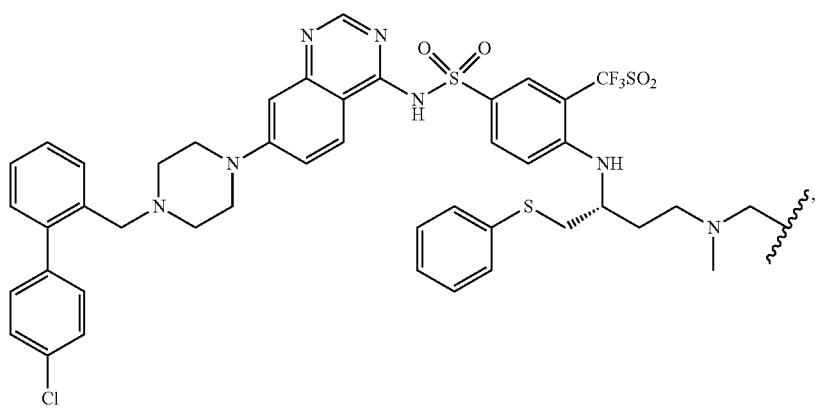
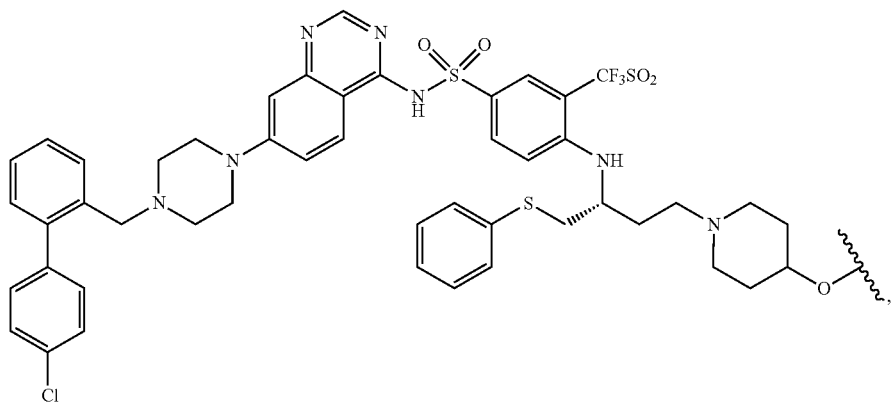

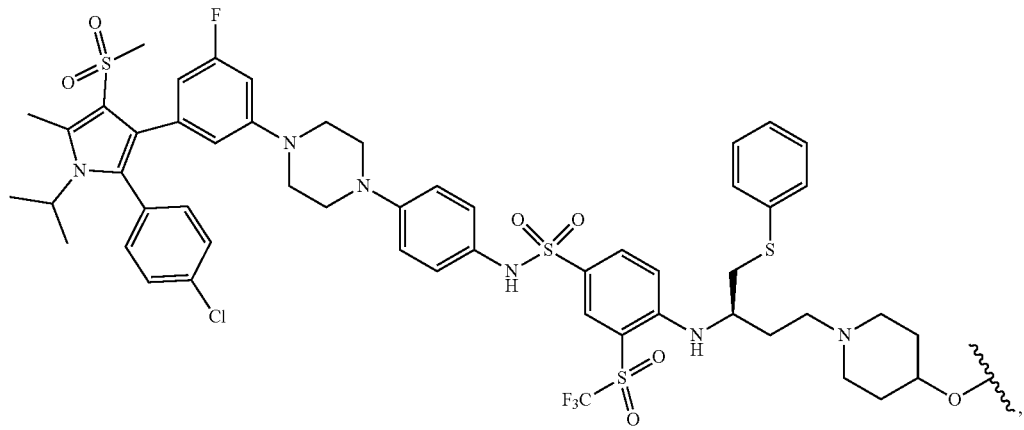
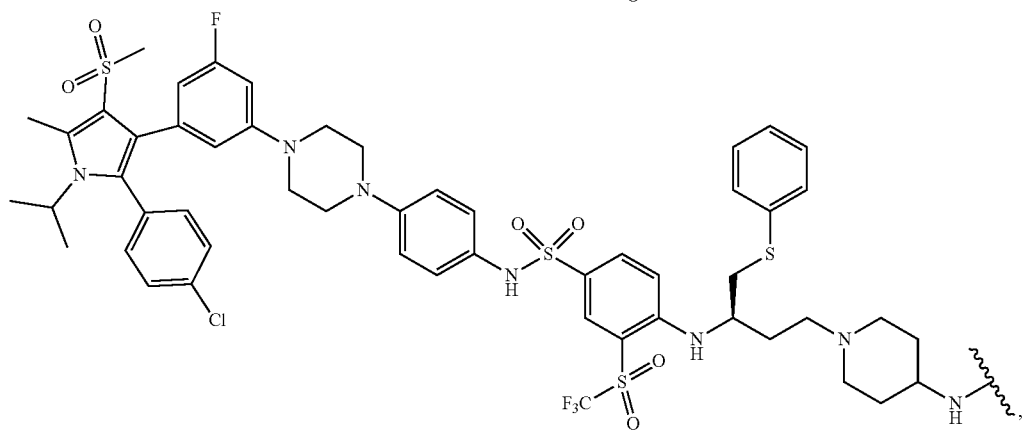
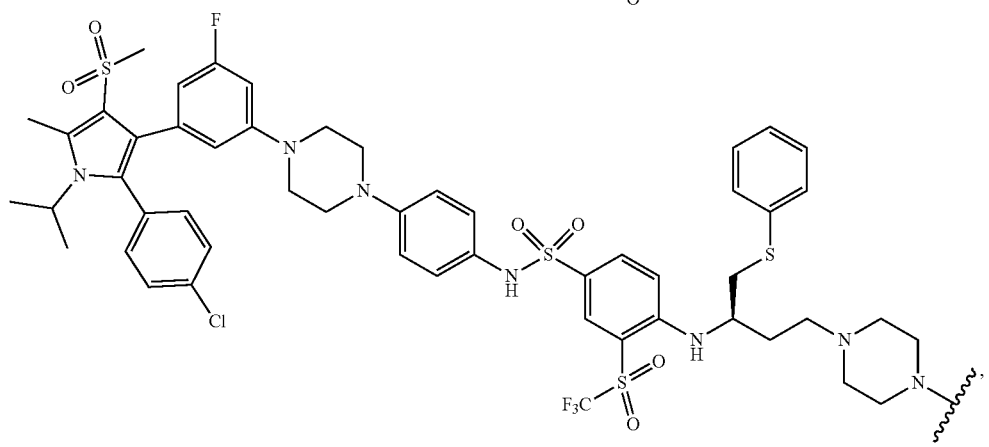
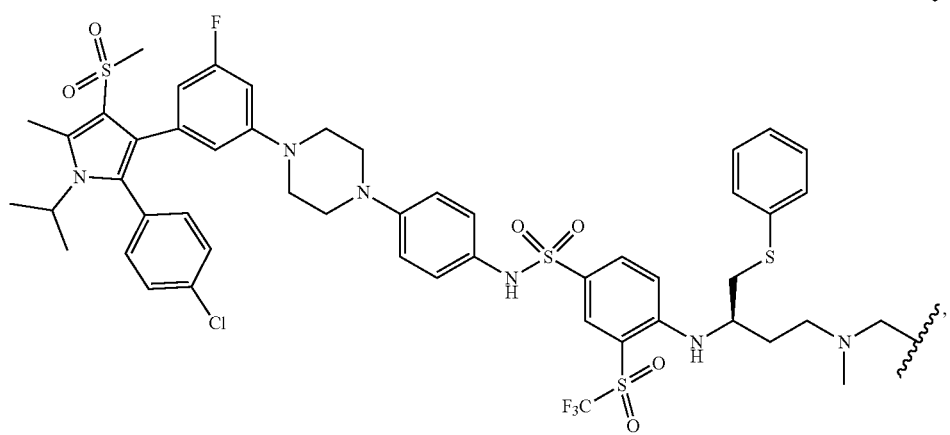

-continued
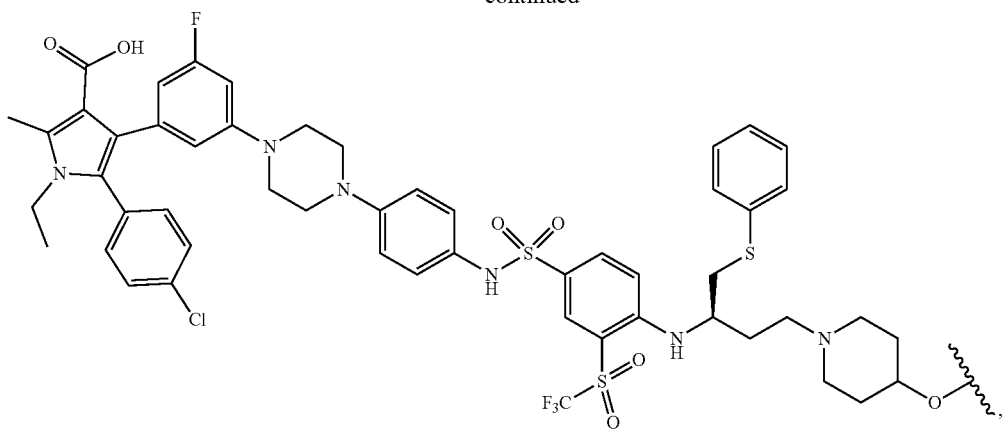
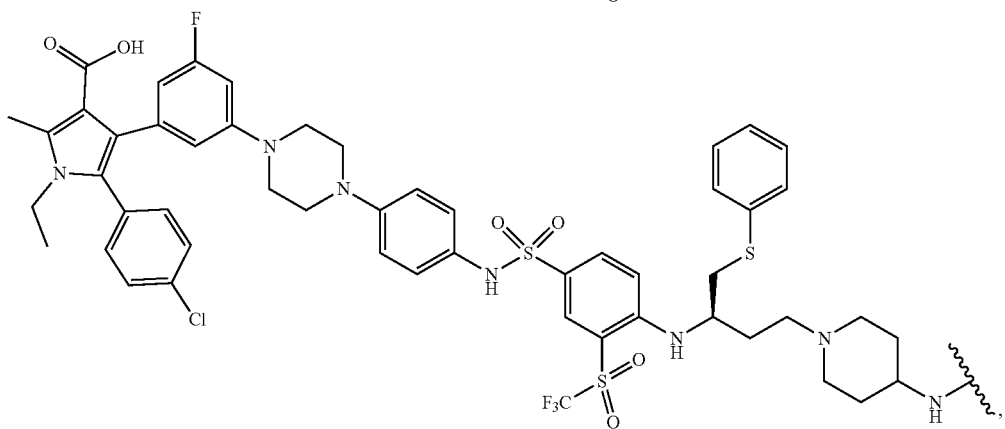
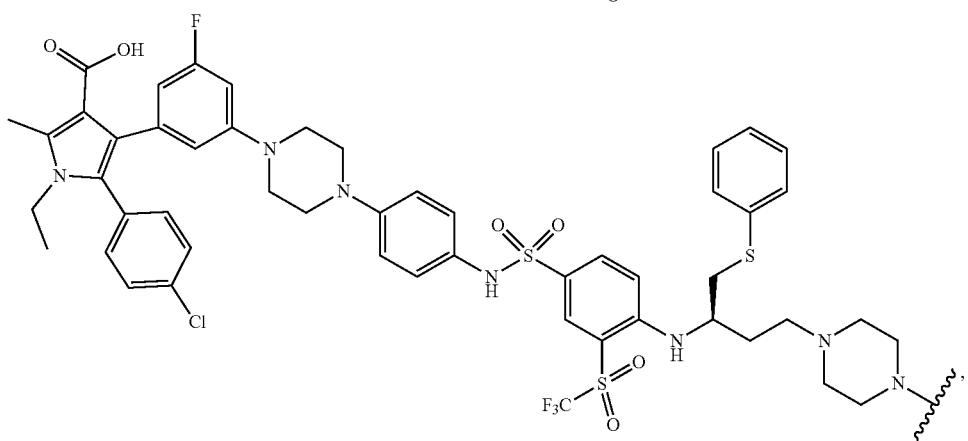
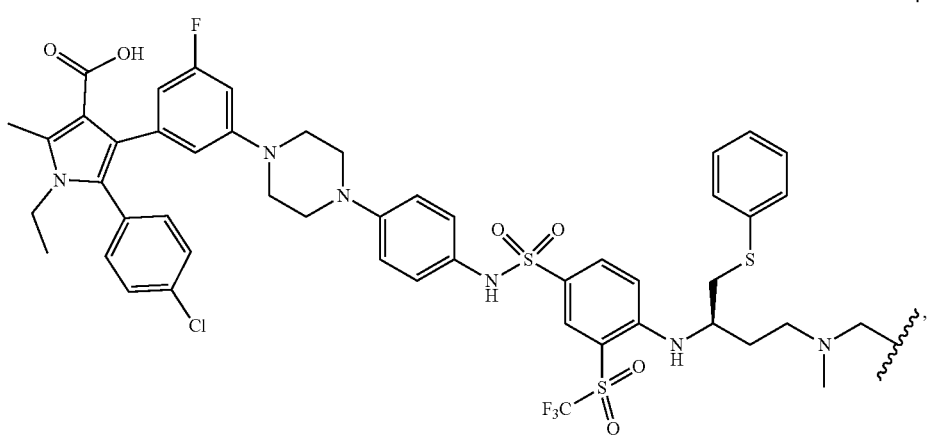

239                                          240
                    -continued
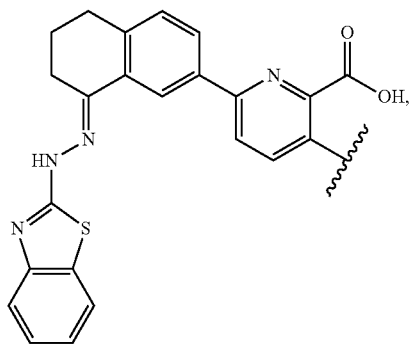
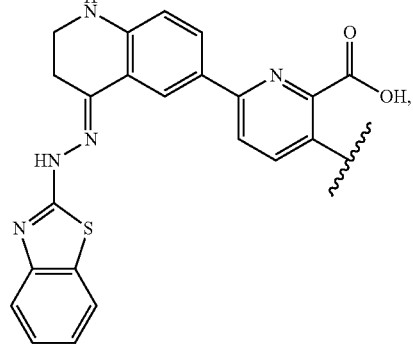
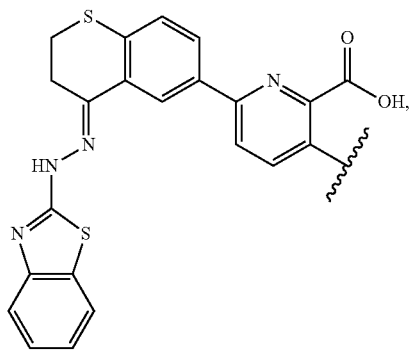
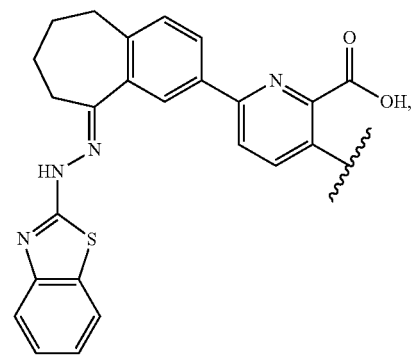
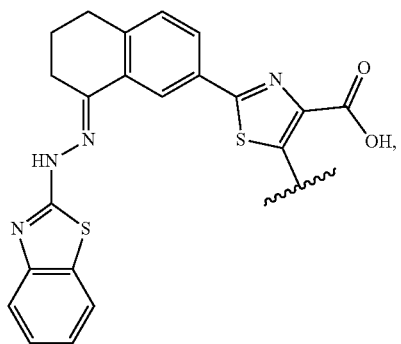
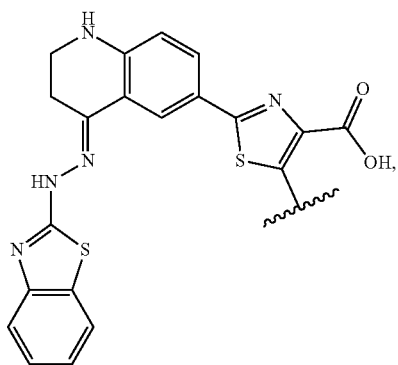
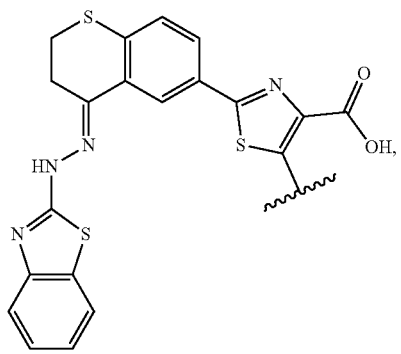
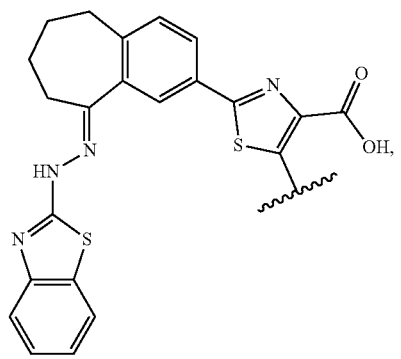

-continued
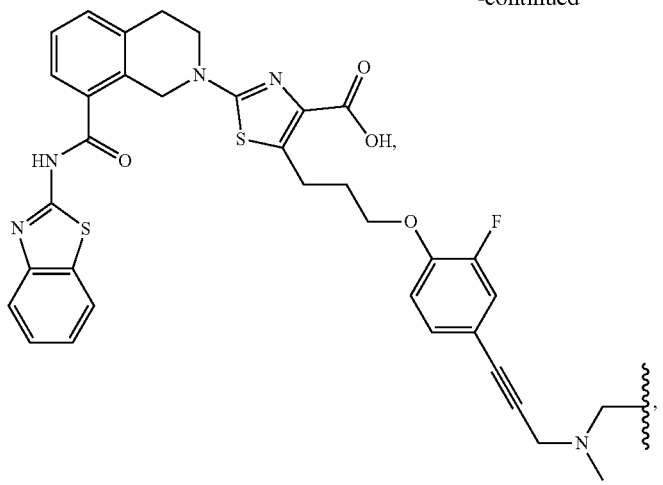
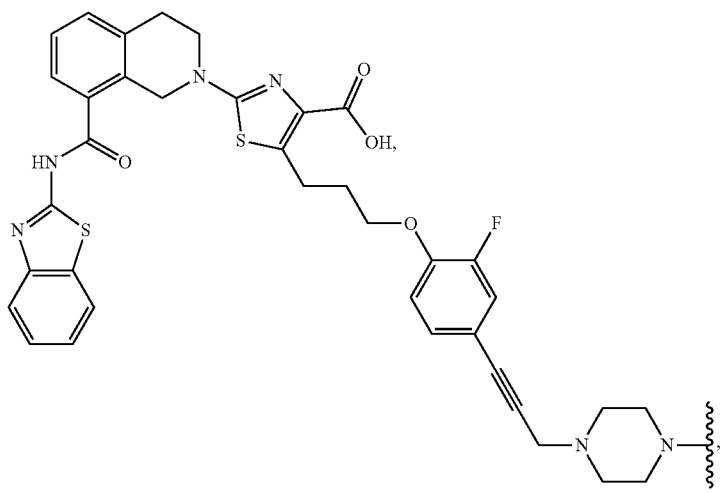
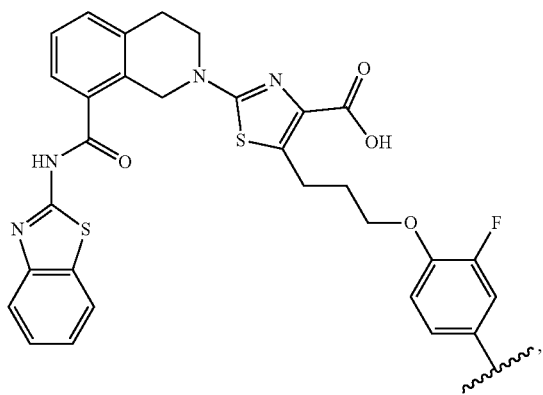

-continued
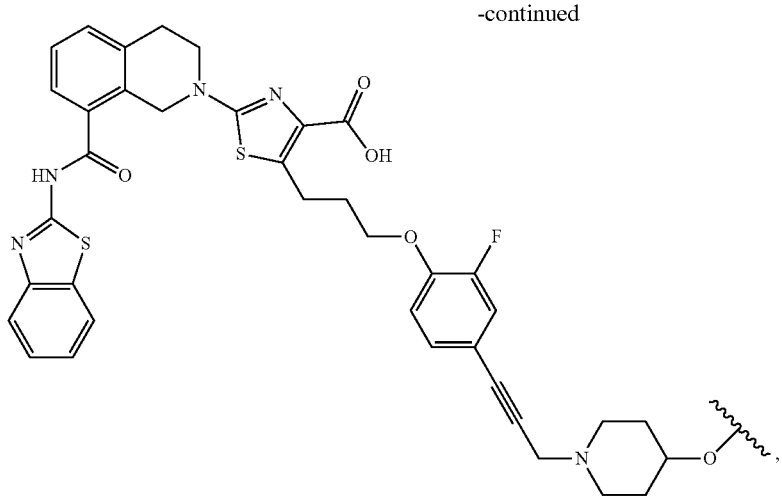
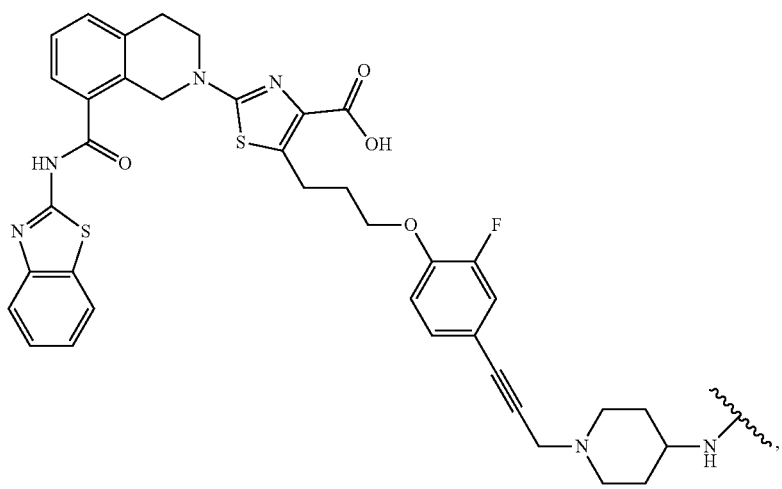
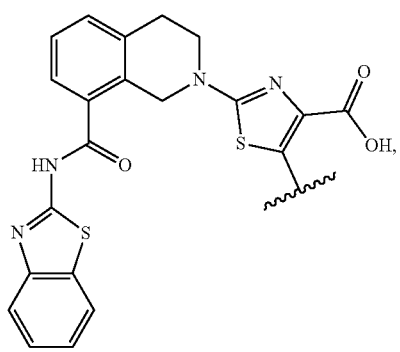
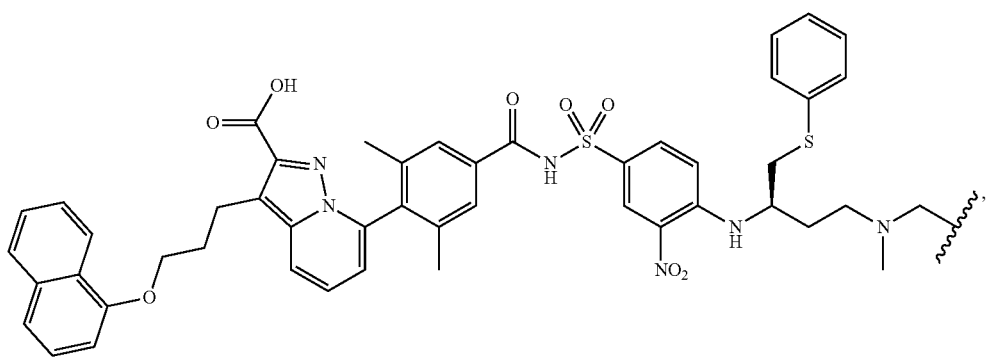

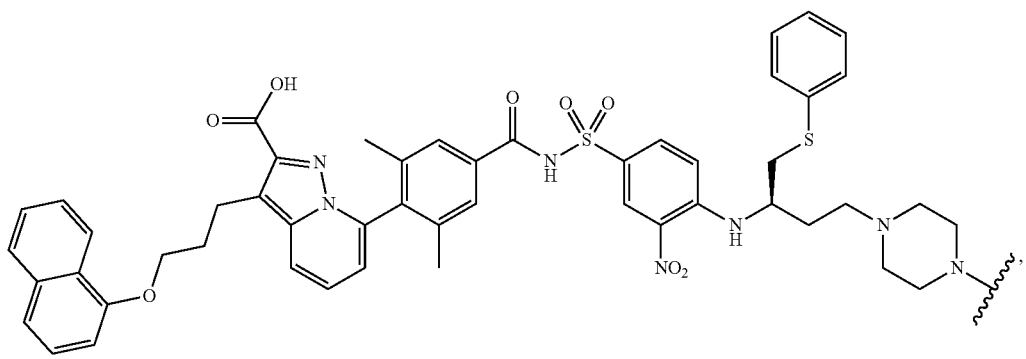
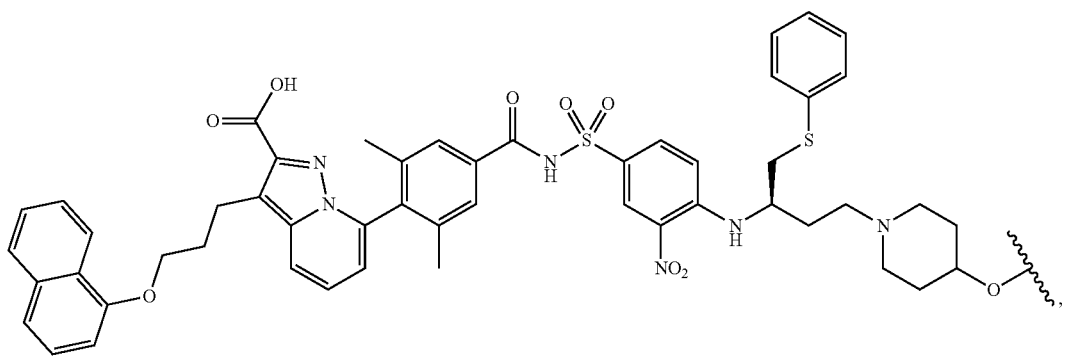
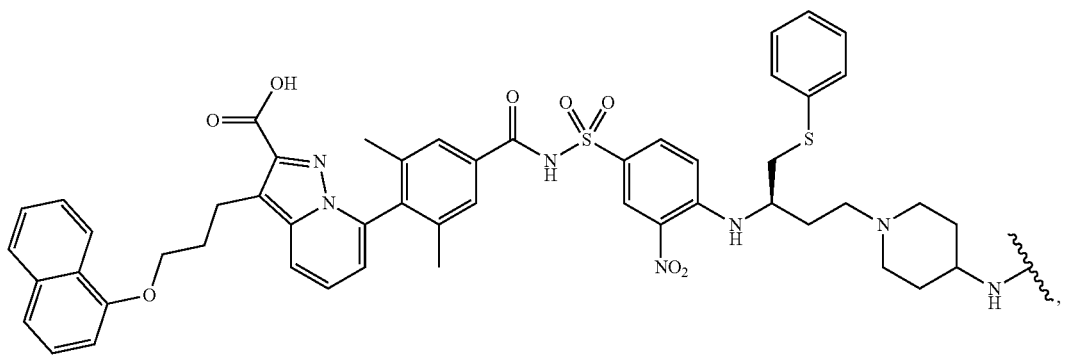
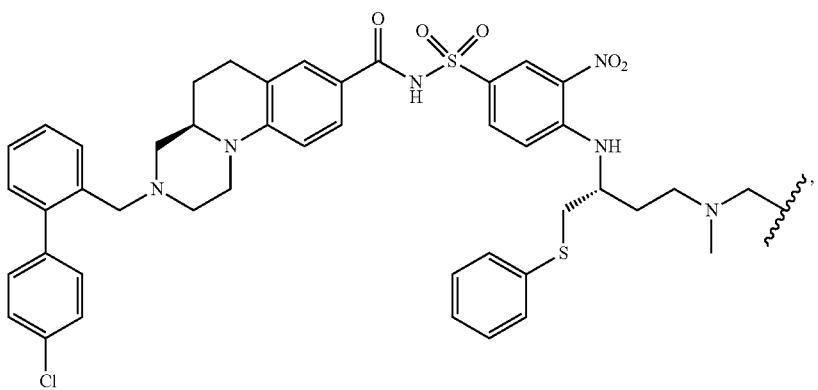

-continued
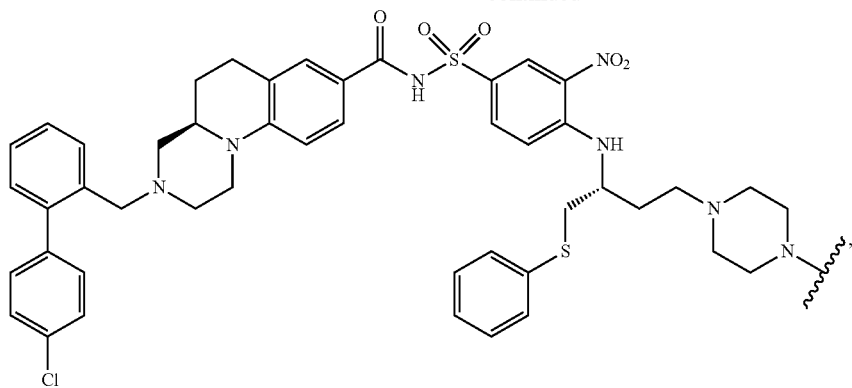
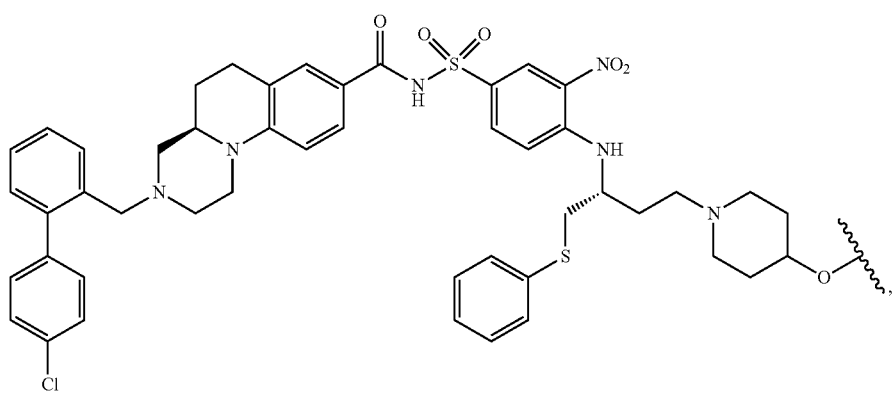
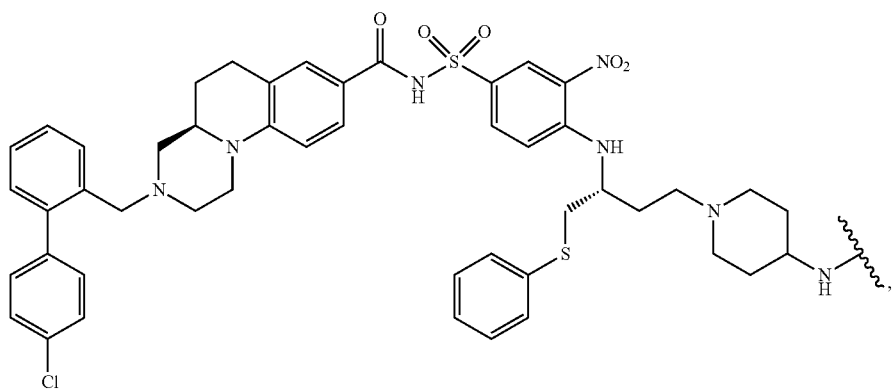
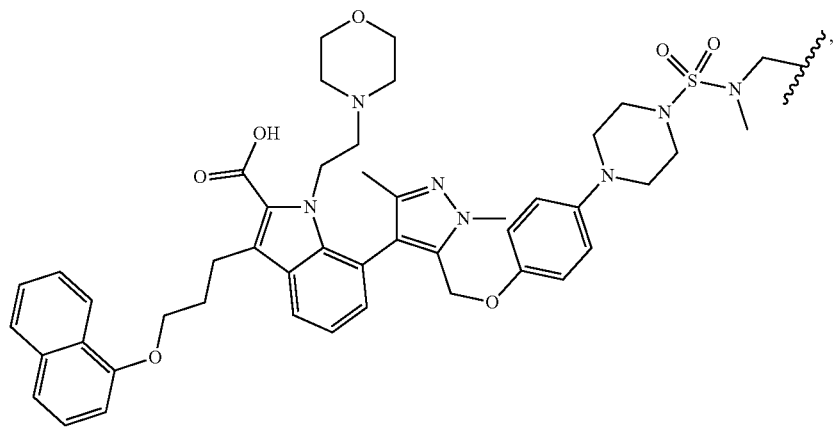

-continued
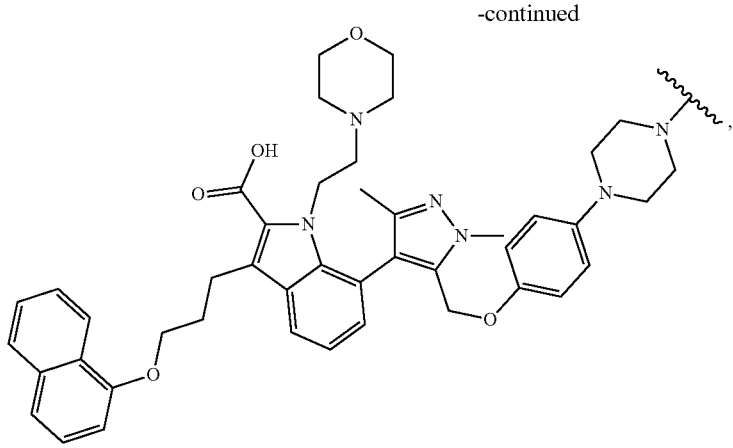
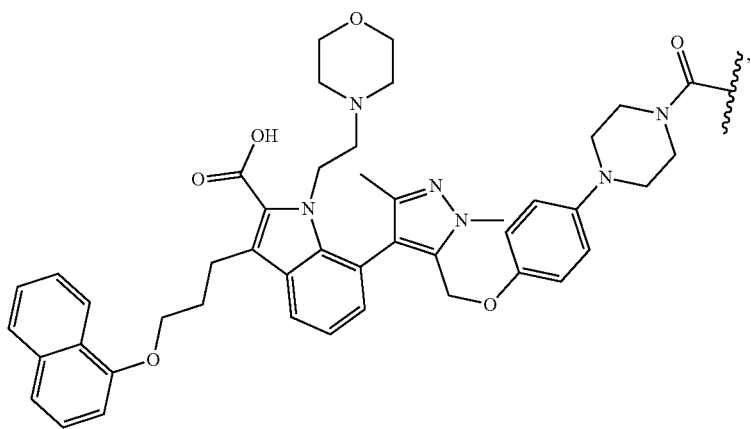
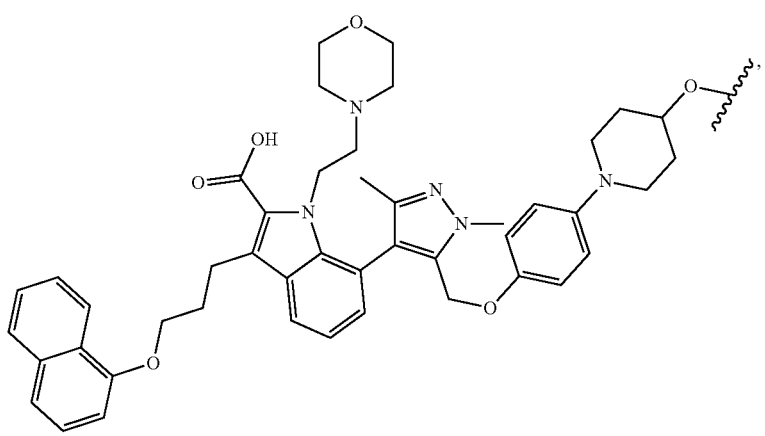

-continued
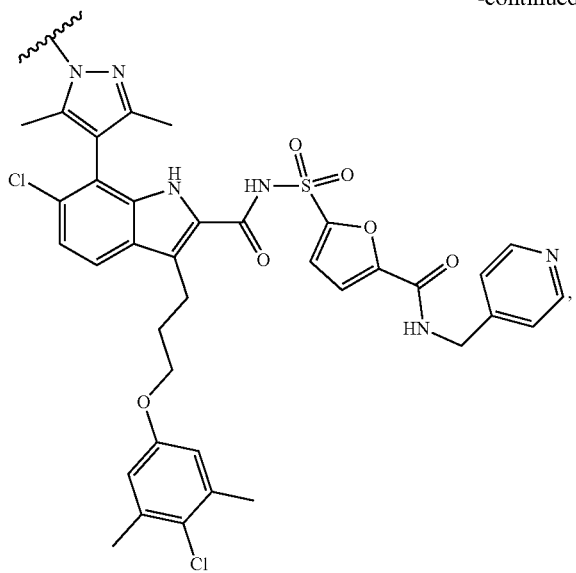
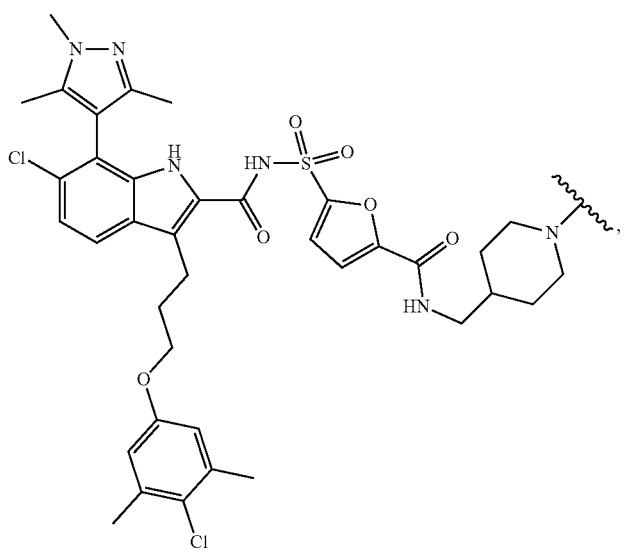
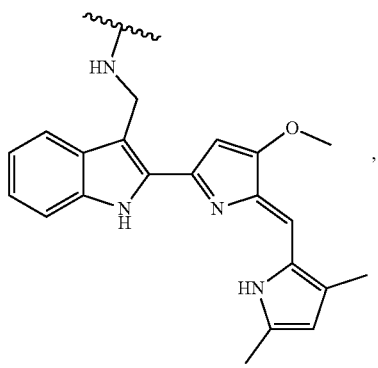
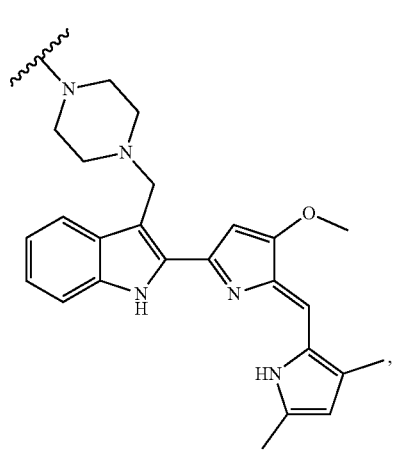
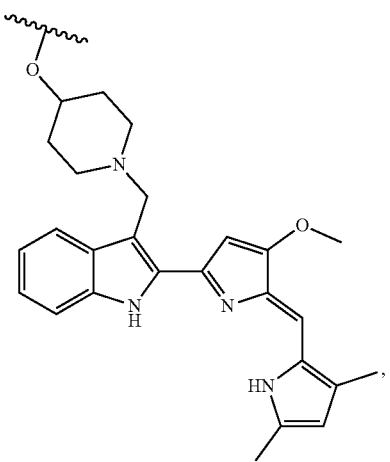

-continued
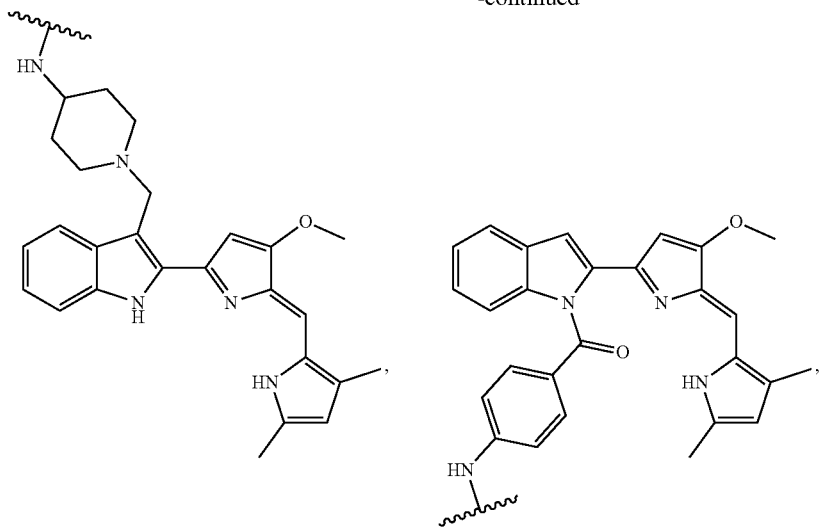
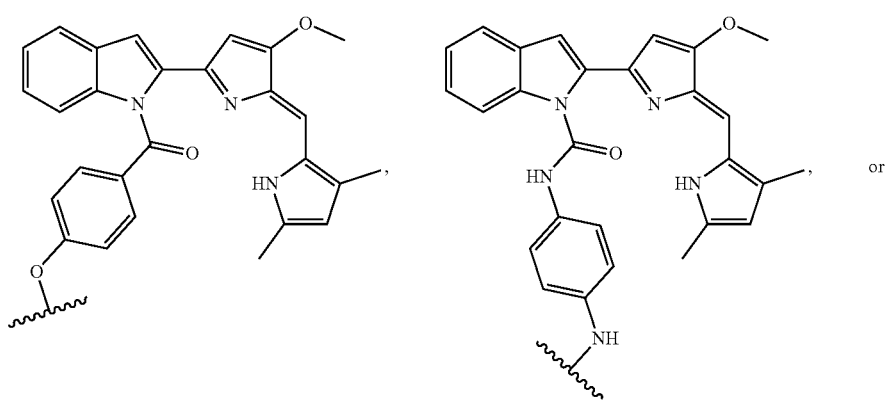
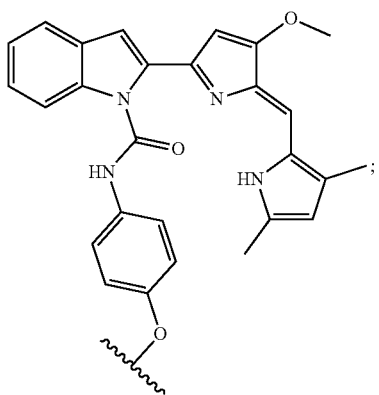 [SMILES: *Oc1ccc(NC(=O)n2c(C3=N/C(=C\c4[nH]c(C)cc4C)C(OC)=C3)cc3ccccc32)cc1]
R³ may be absent, an unsubstituted $C_1$-$C_6$ alkyl, or a substituted or unsubstituted $C_3$-$C_6$ ketone; A may be absent, a bond, or a substituted or unsubstituted $C_1$-$C_6$ heterocyclic group; n may be 1 to 2; R⁴ may be a bond or a substituted or unsubstituted $C_1$-$C_{10}$ alkyl; and wherein R² may be
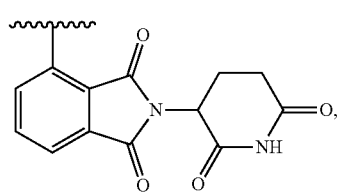

255
-continued
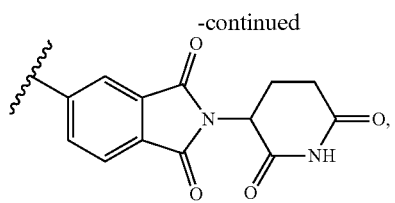
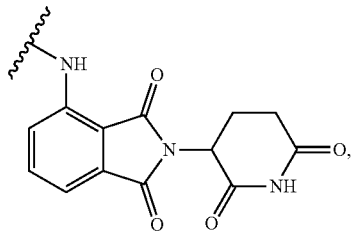
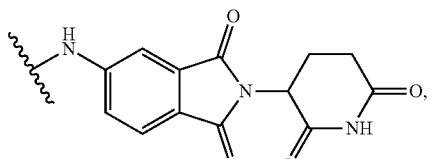
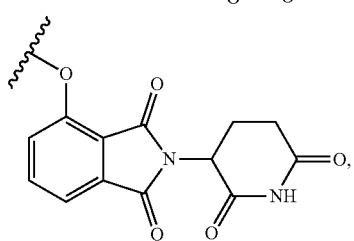
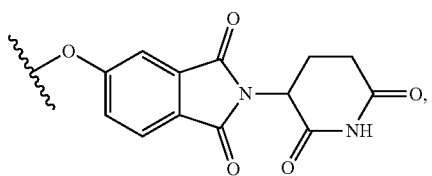
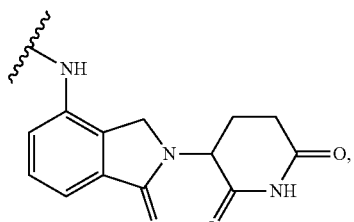
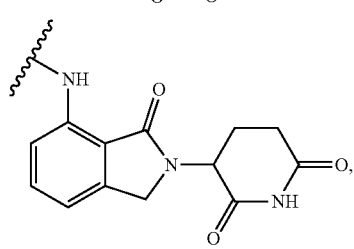
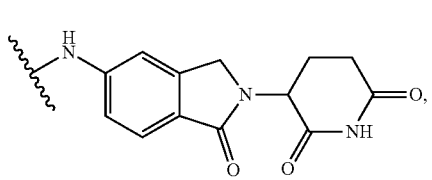
256
-continued
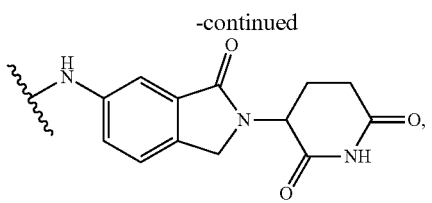
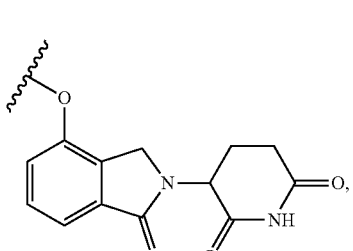
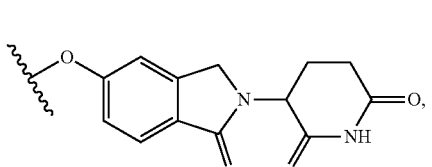
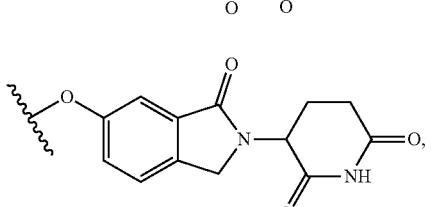
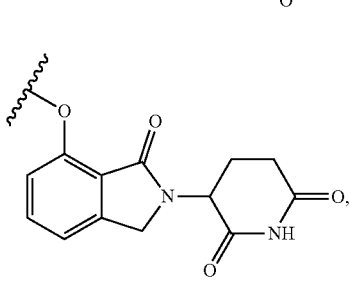
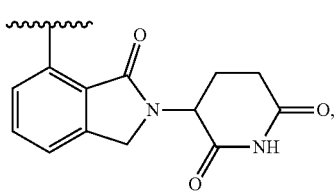
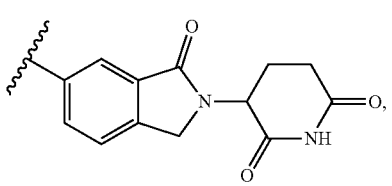
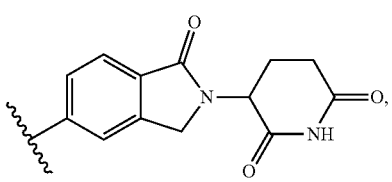

257 -continued
258 -continued
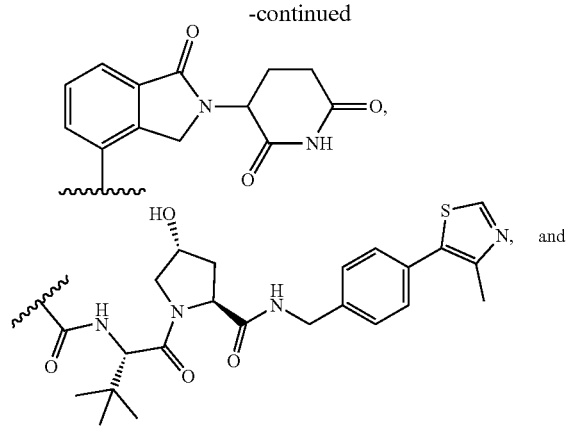
and
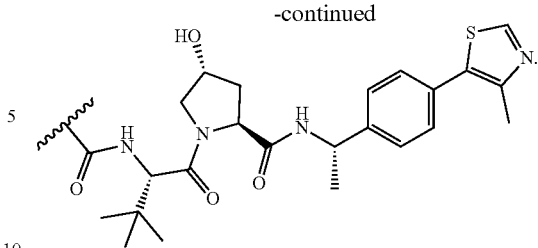
In still another embodiment, a compound of the disclosure comprises Formula (II), wherein $R^1$ may be
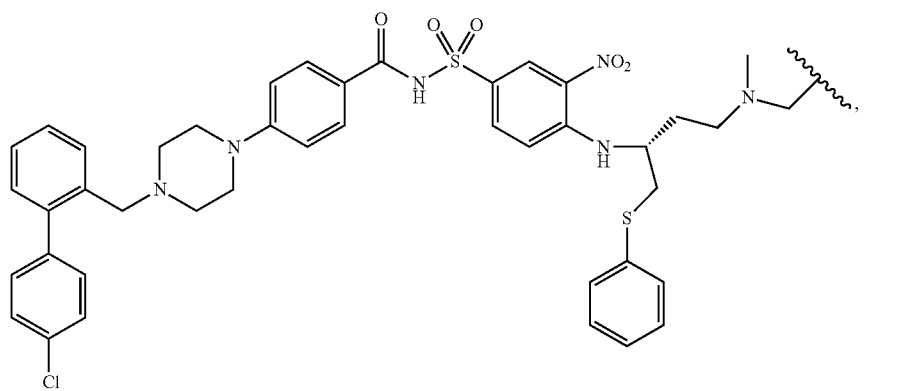
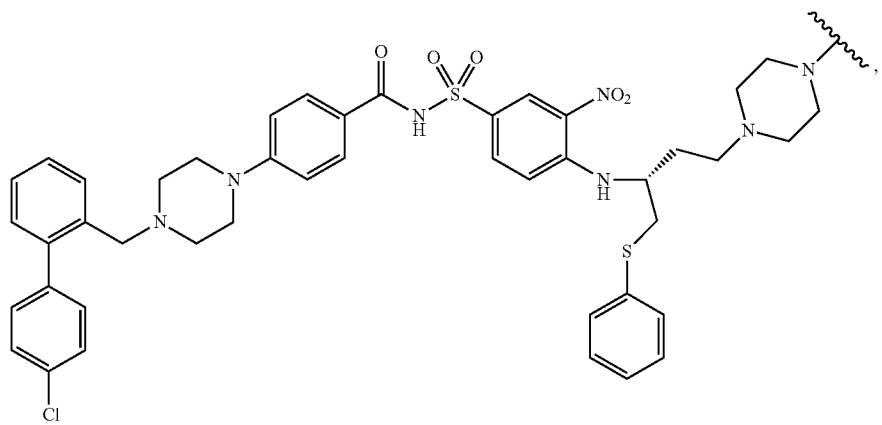
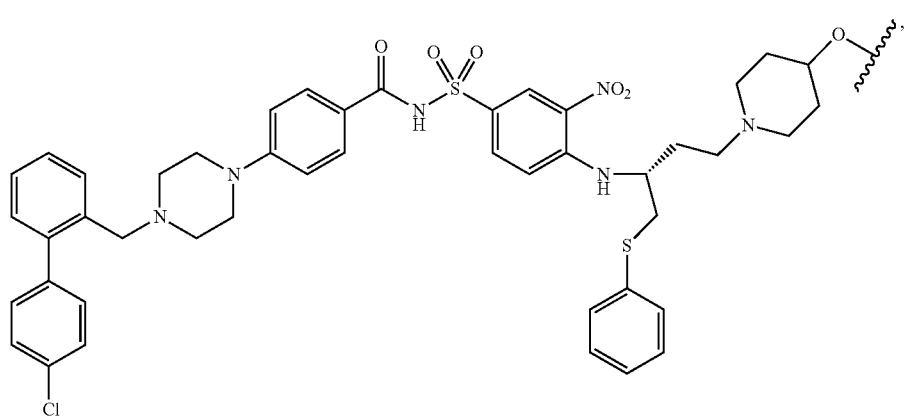

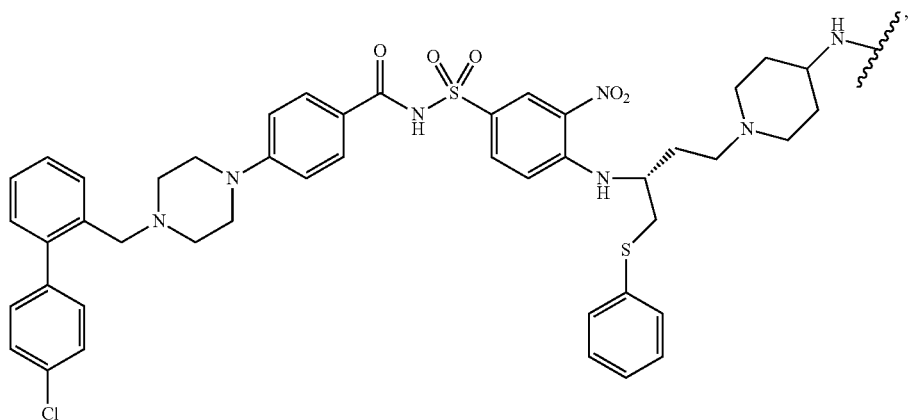
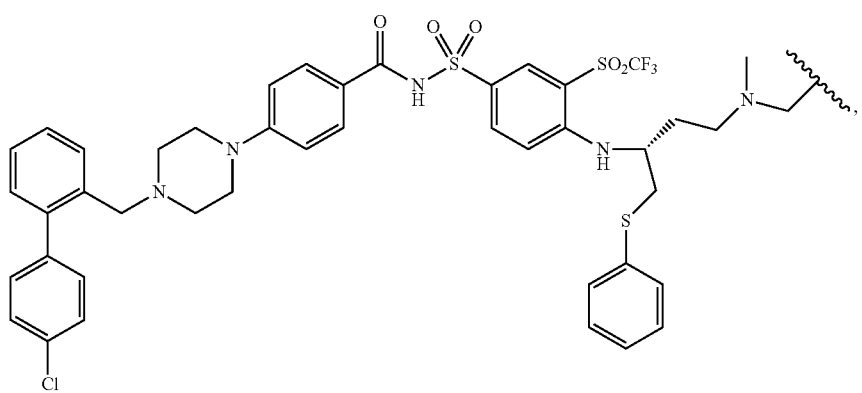
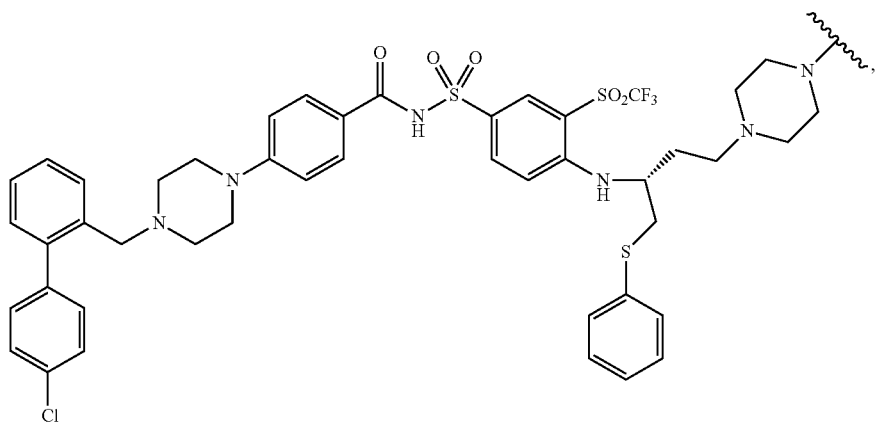
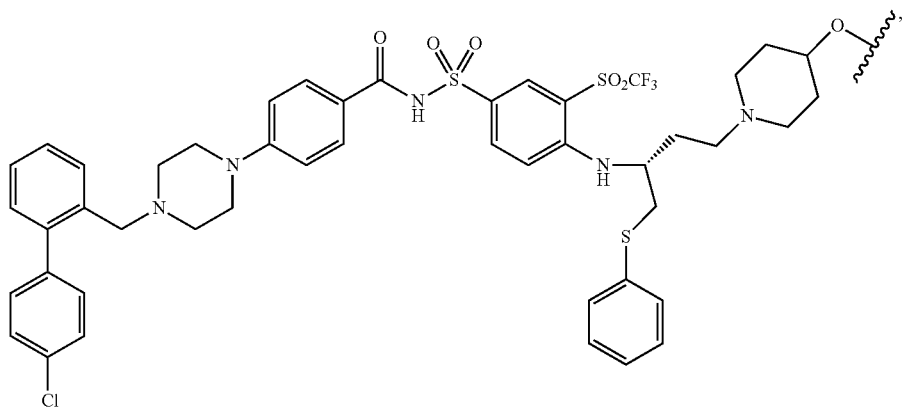

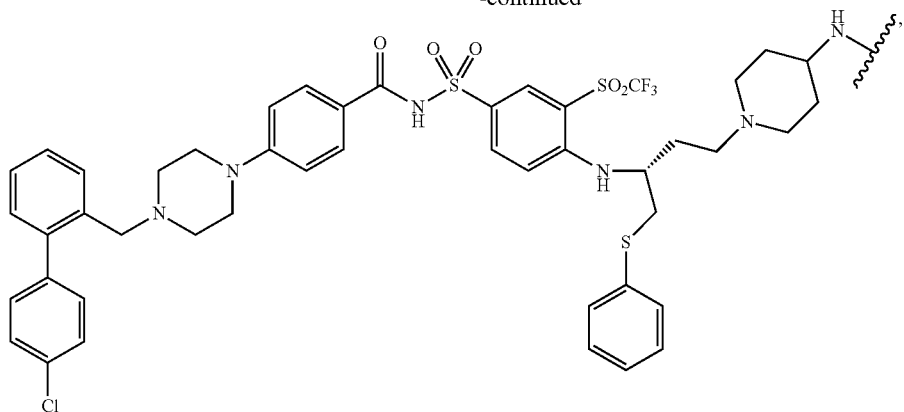
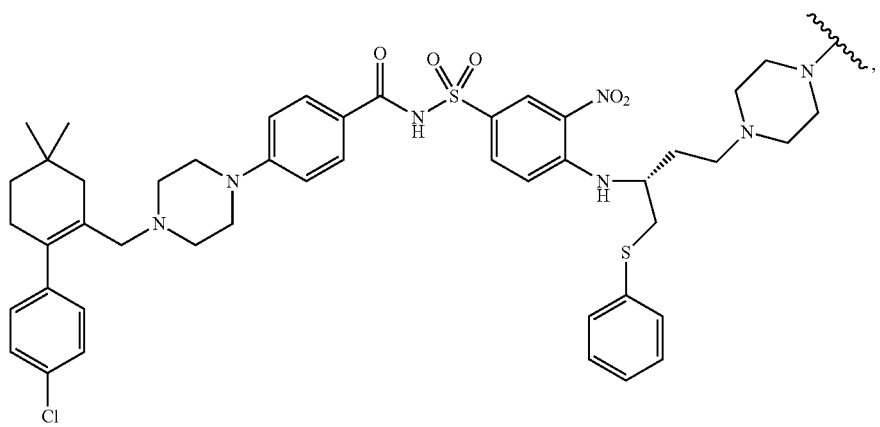
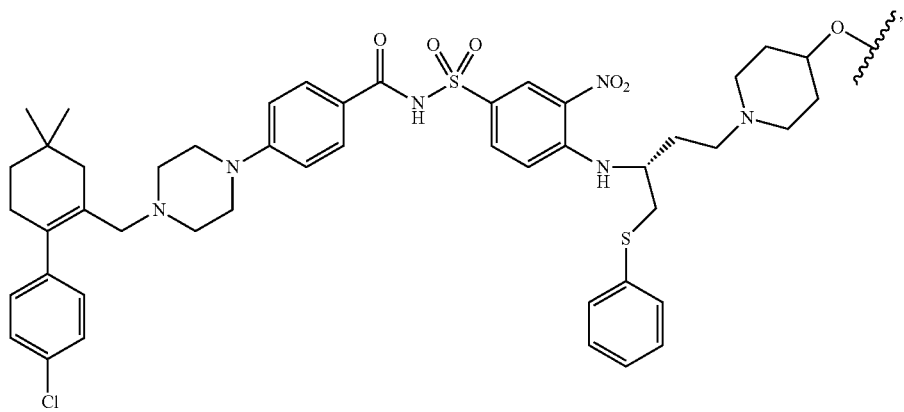
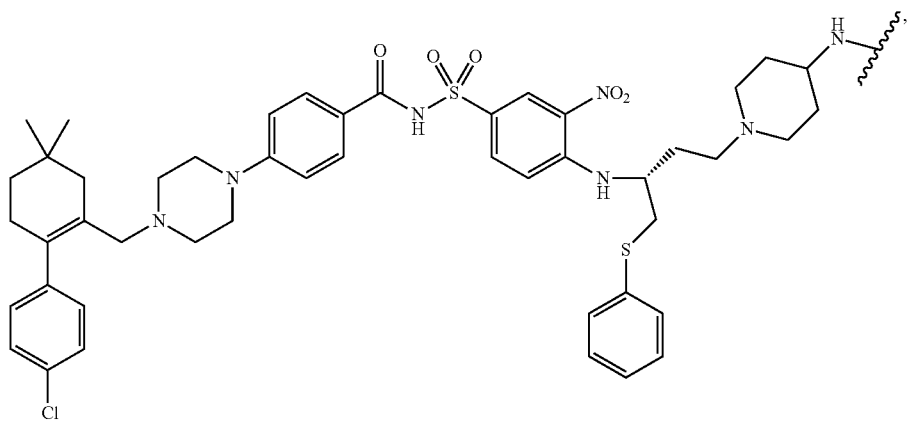

-continued
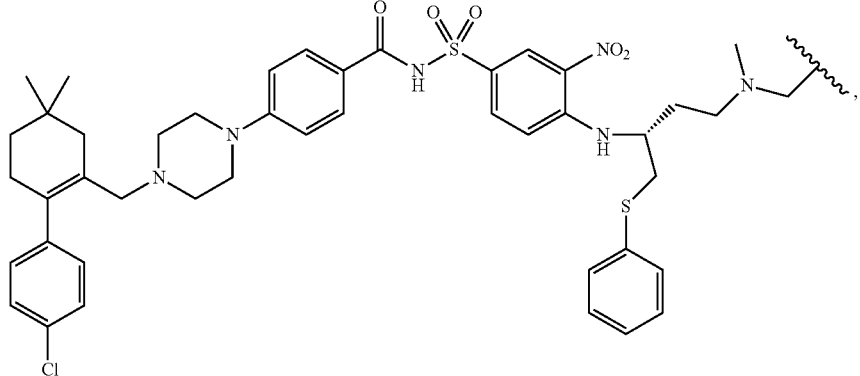
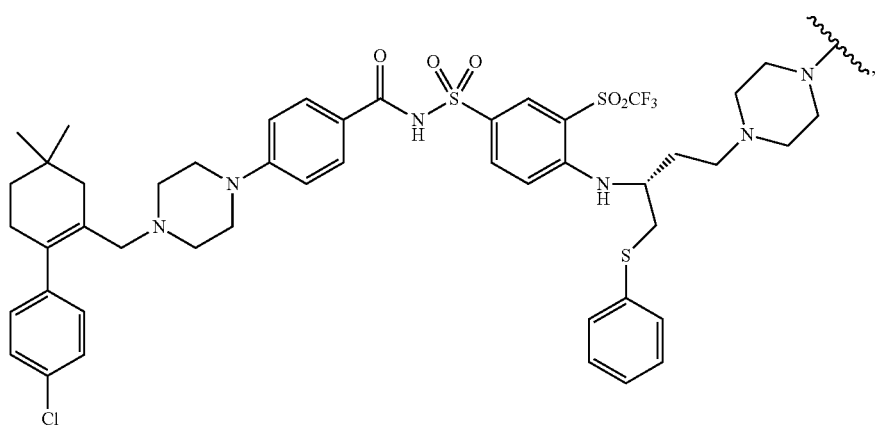
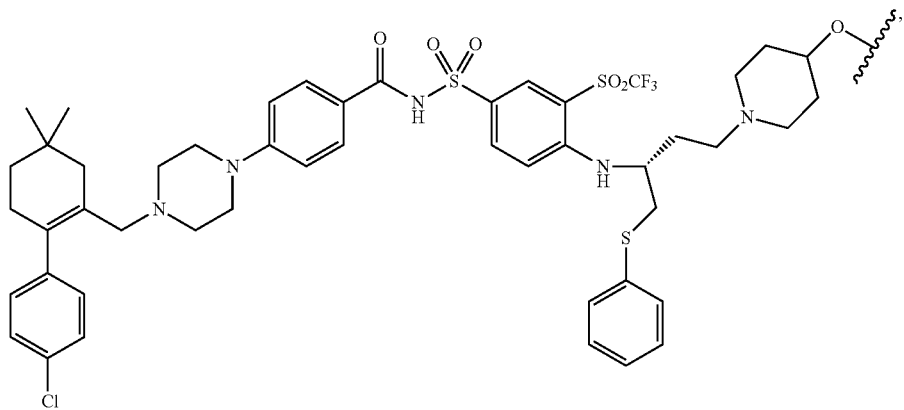
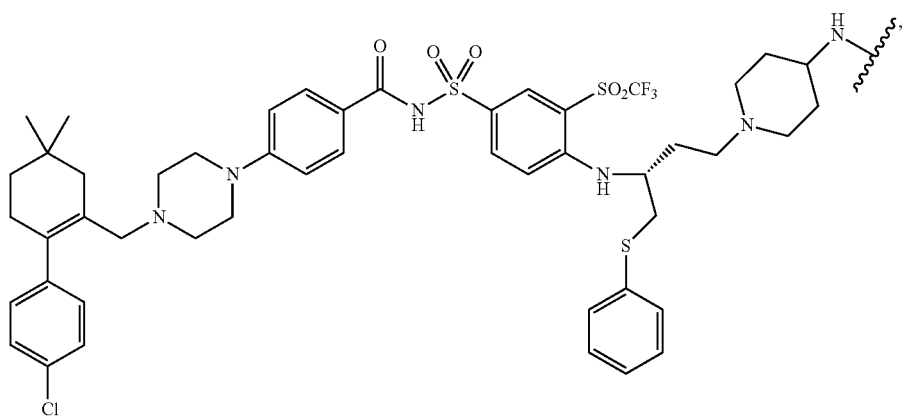

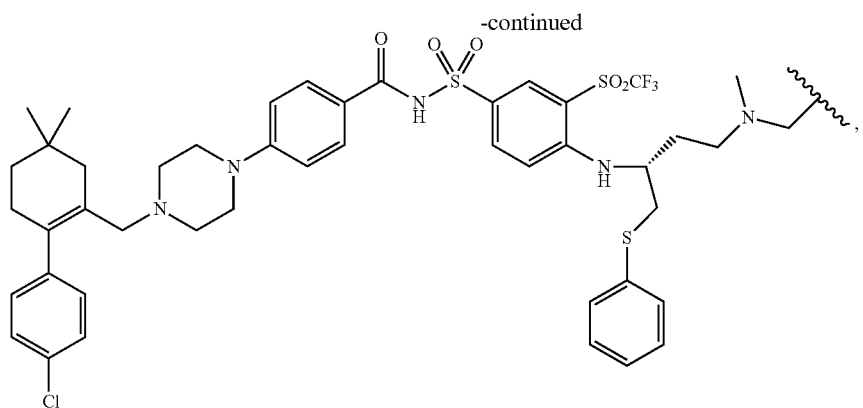
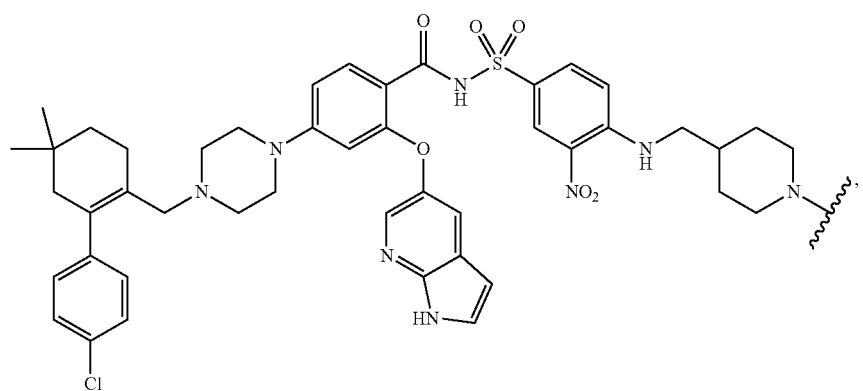
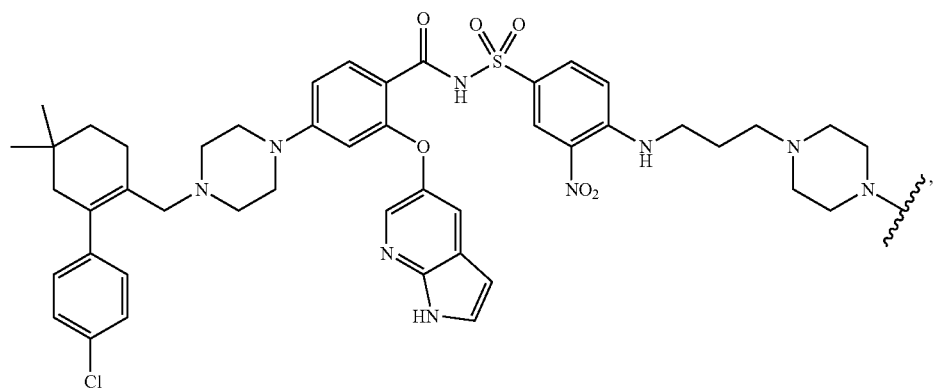
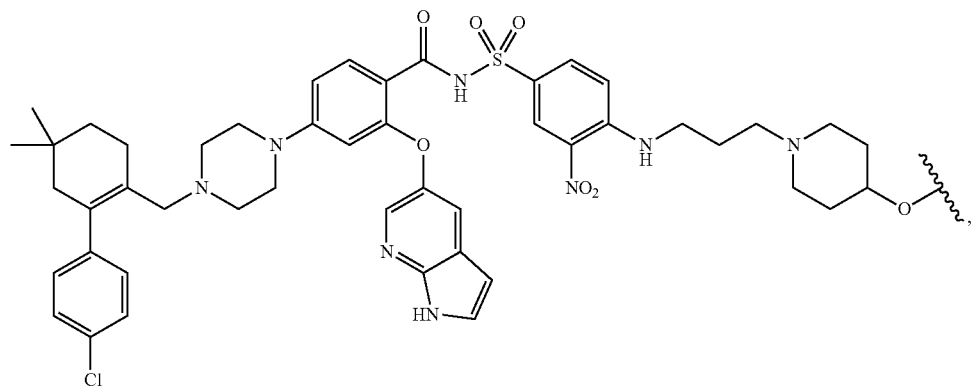

-continued
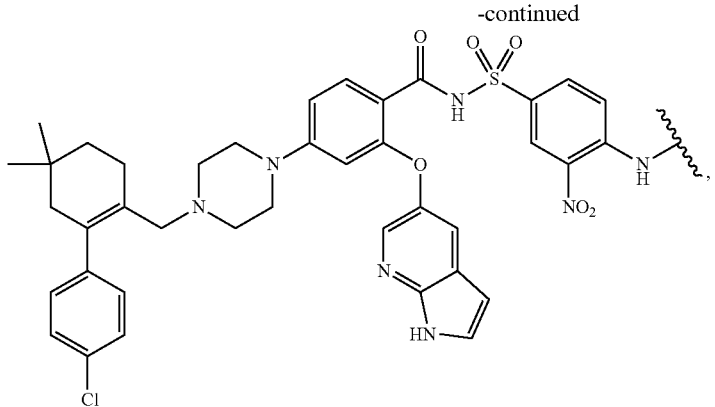
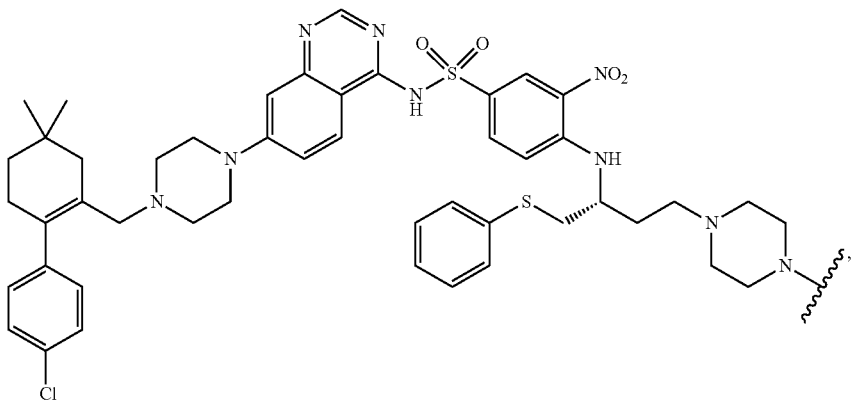
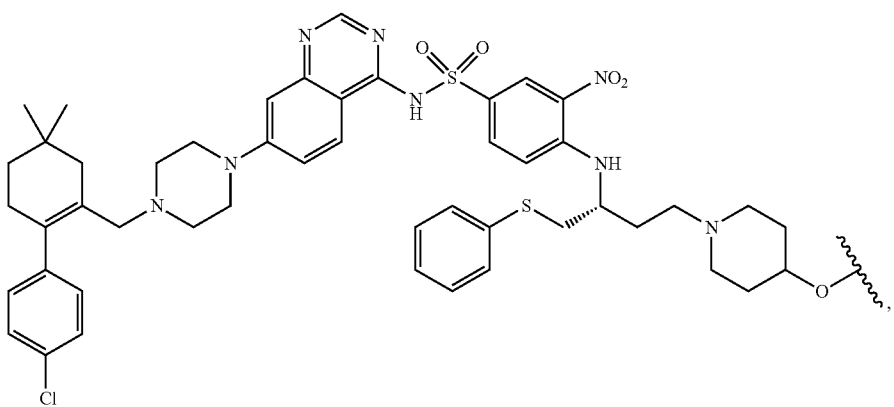
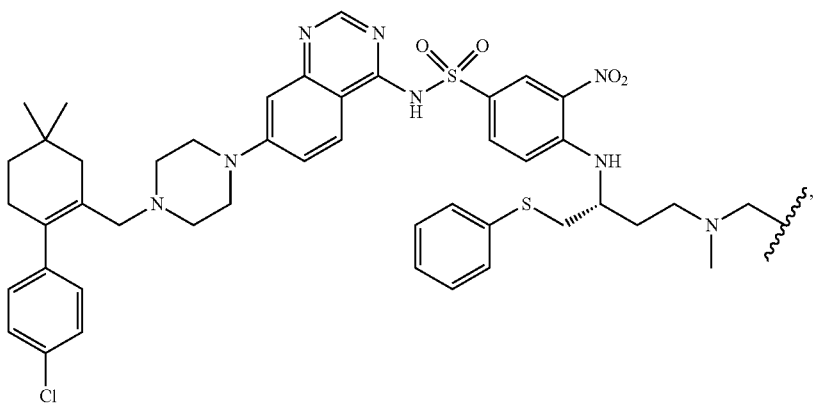

-continued
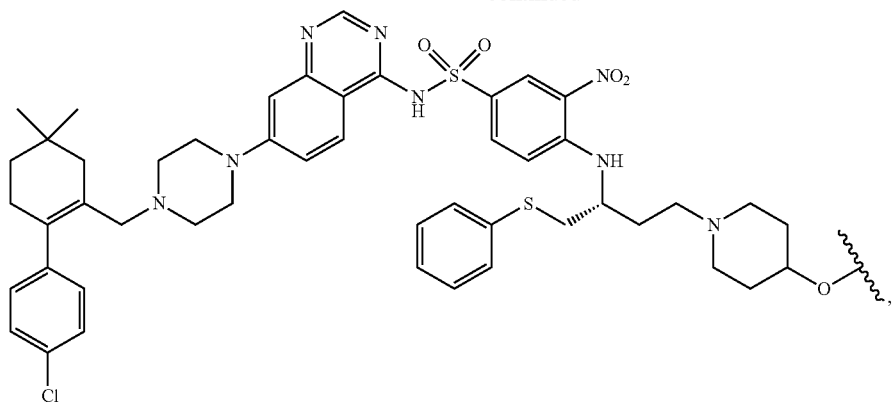
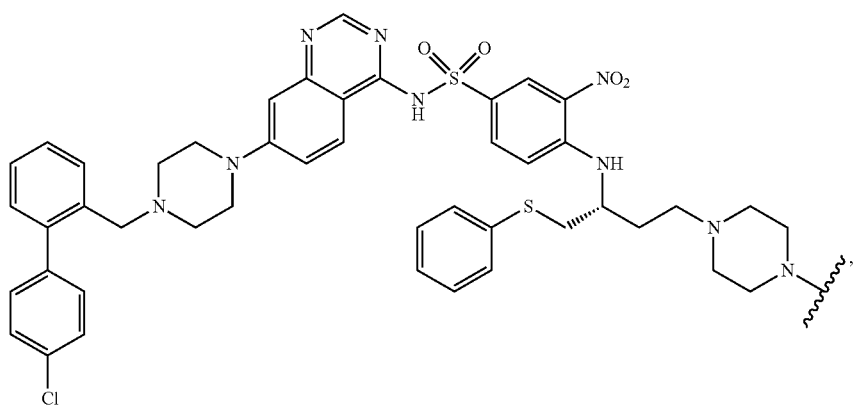
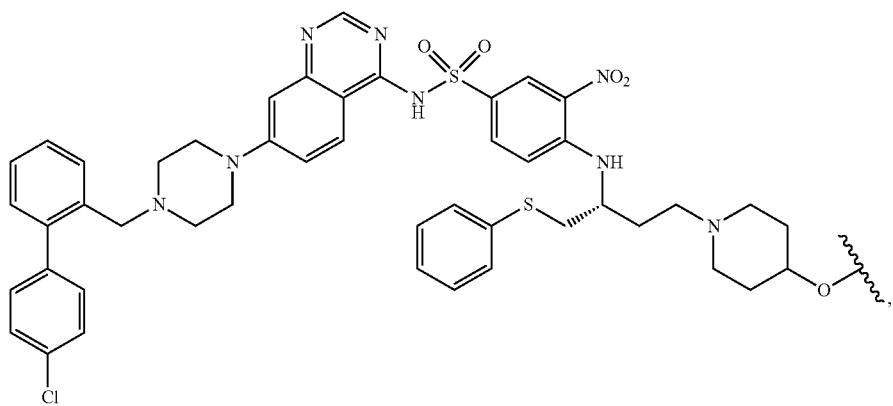
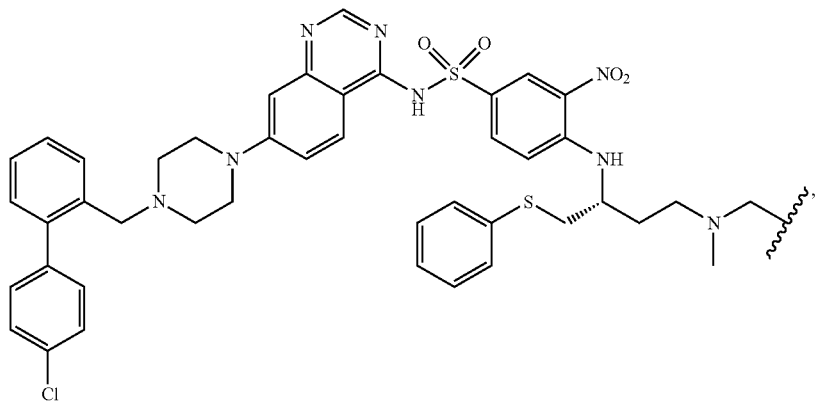

-continued
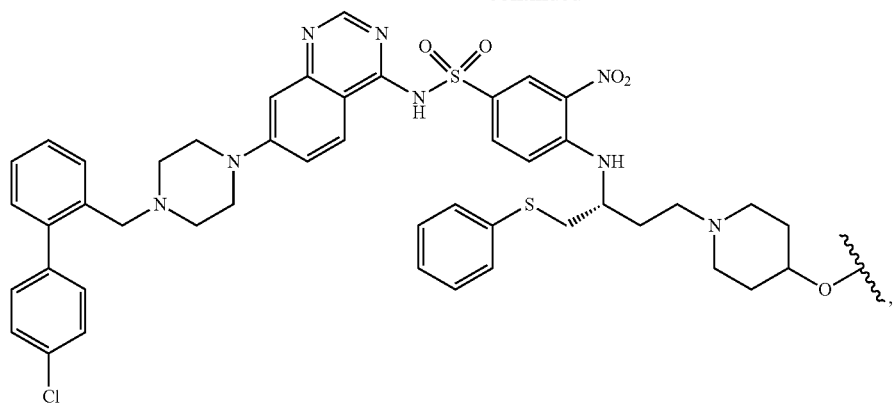
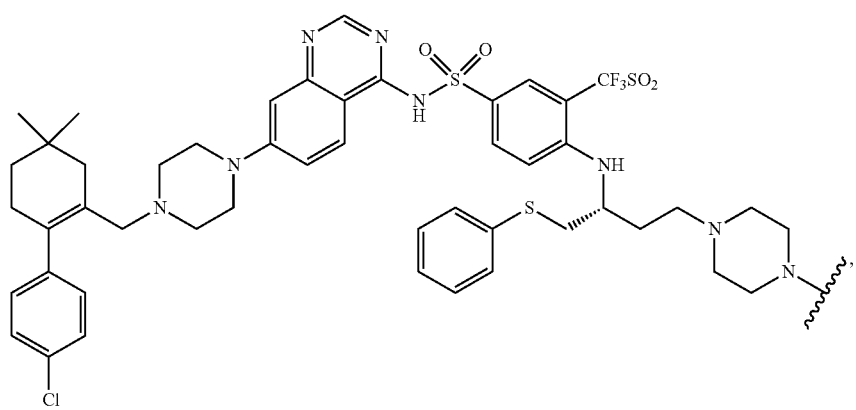
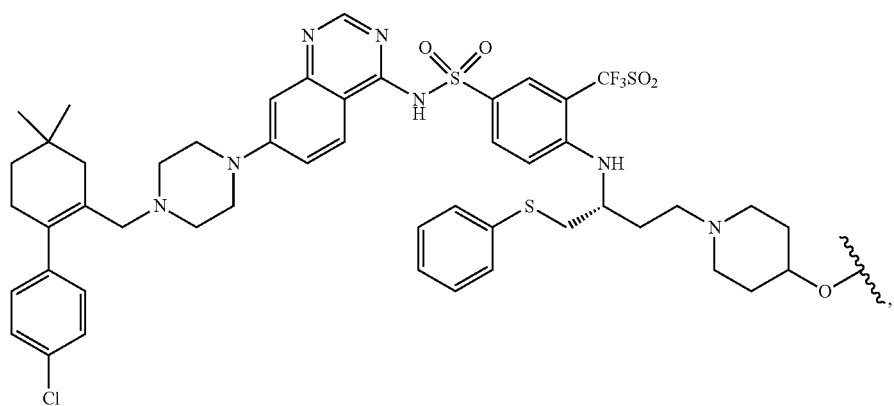
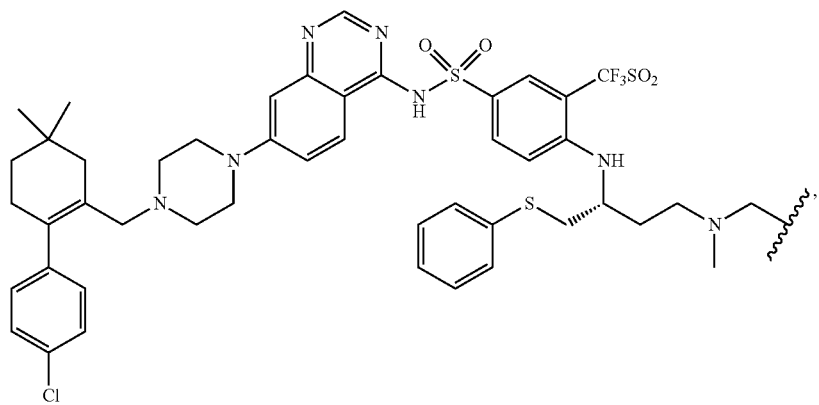

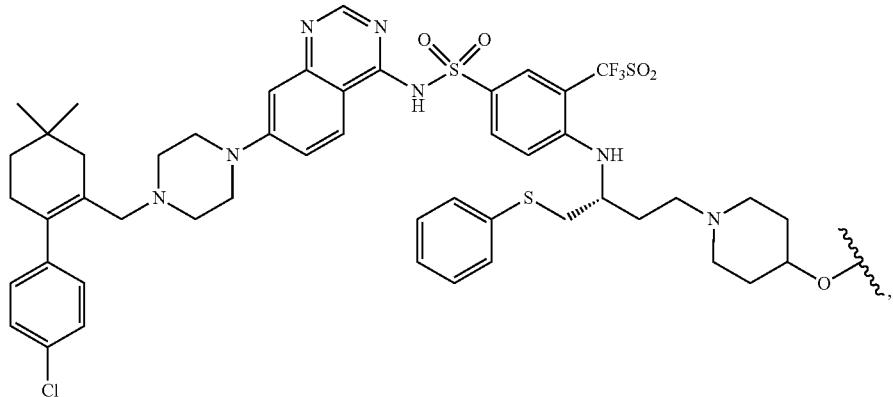
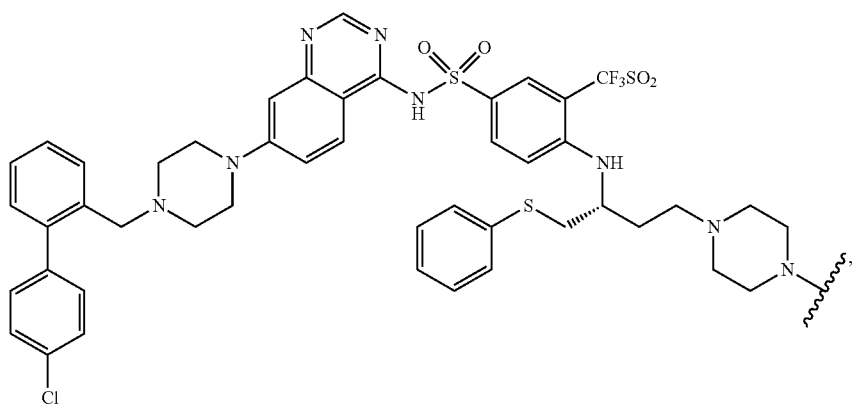
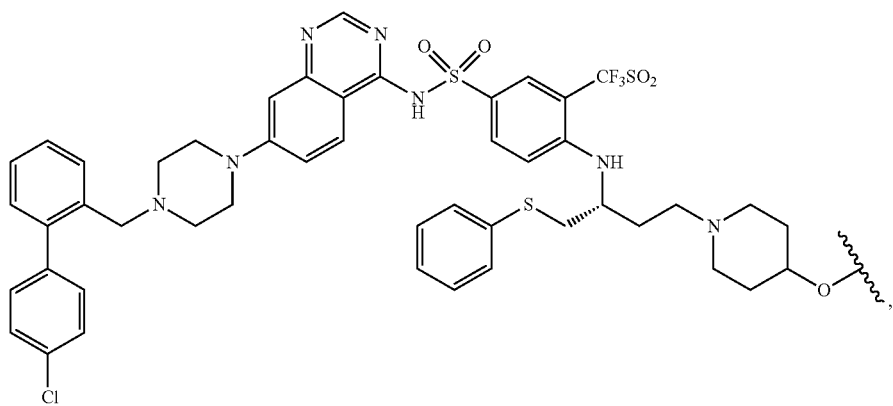
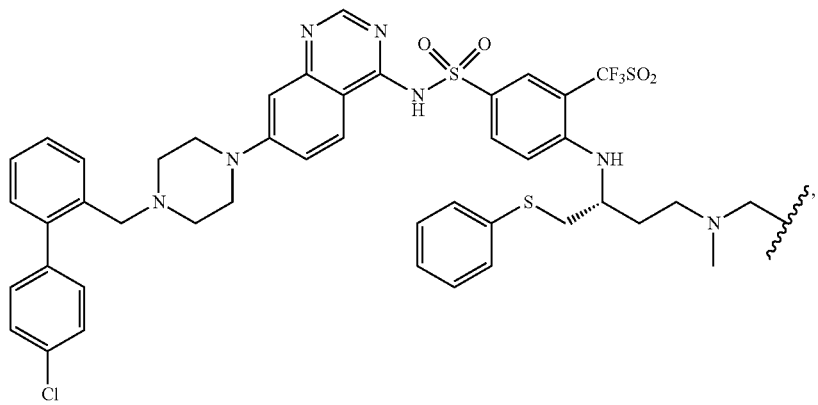

-continued
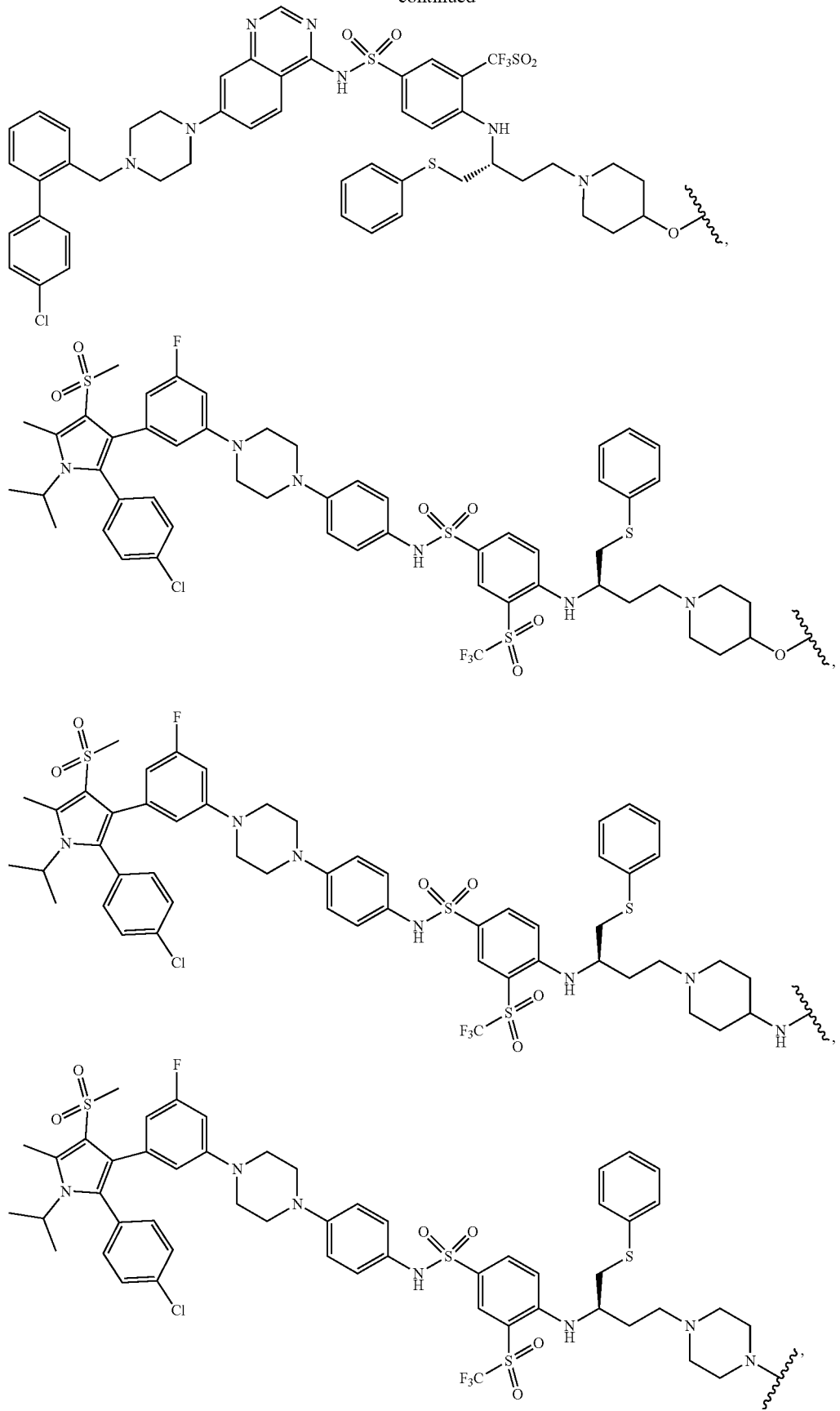

-continued
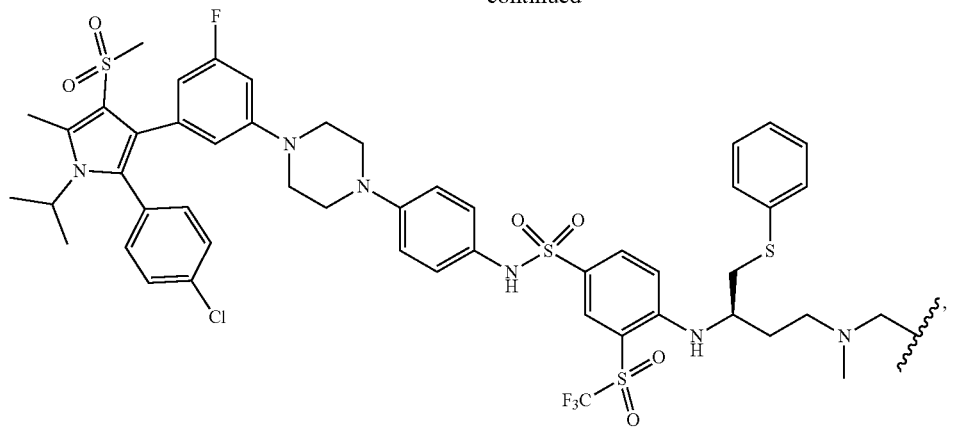
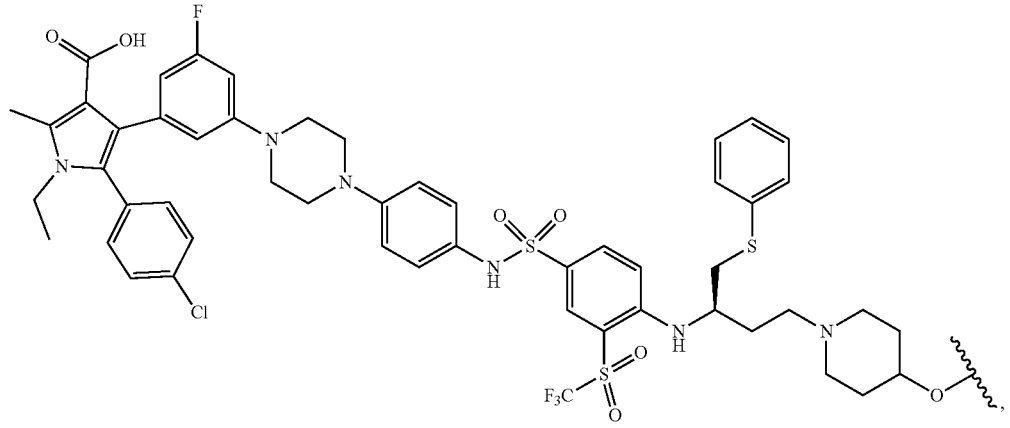
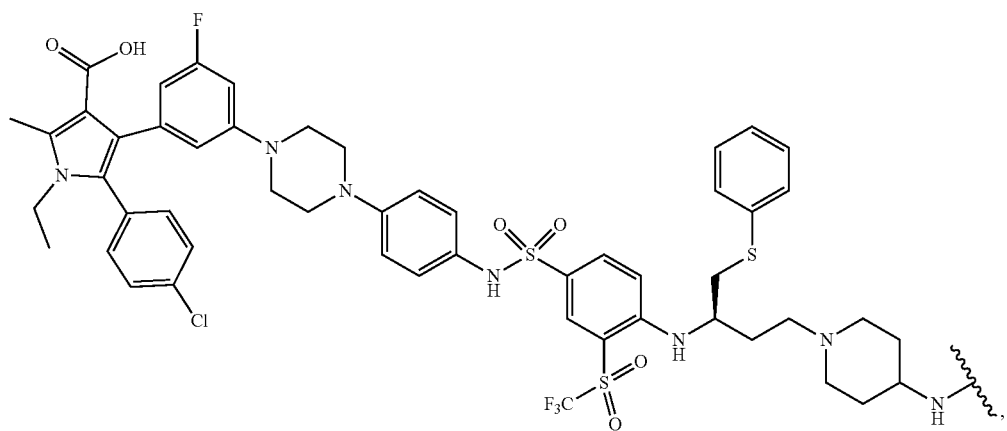
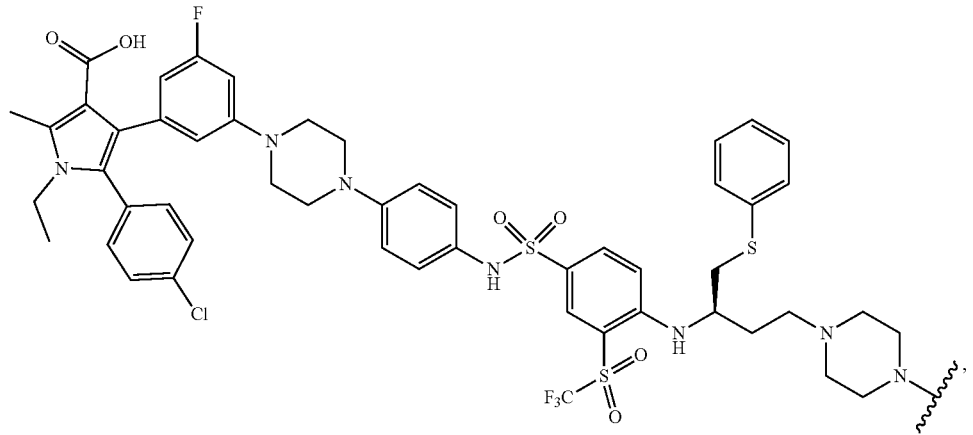

-continued
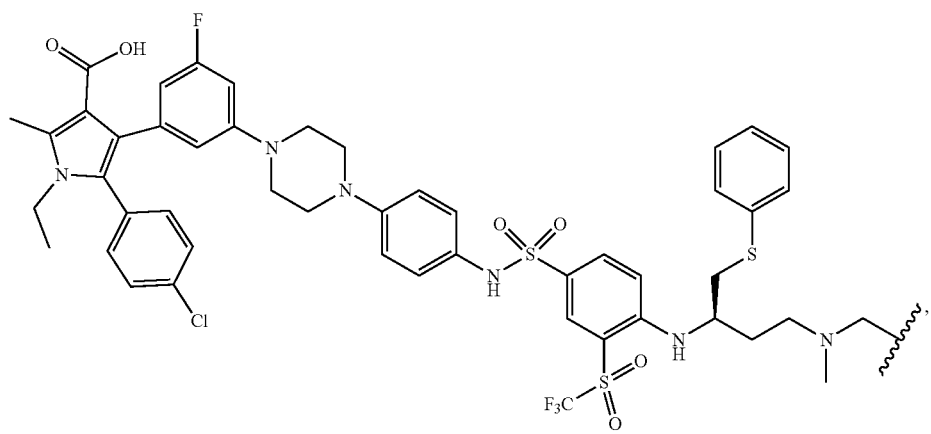
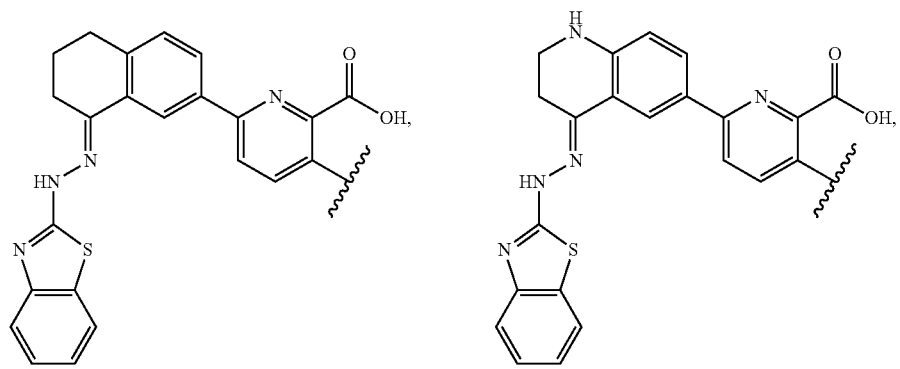
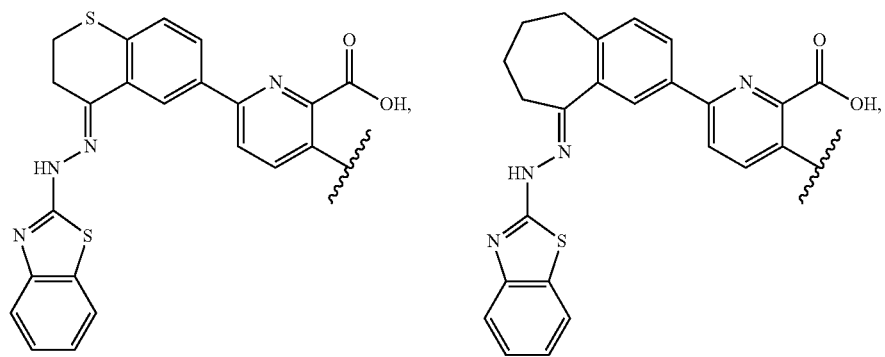
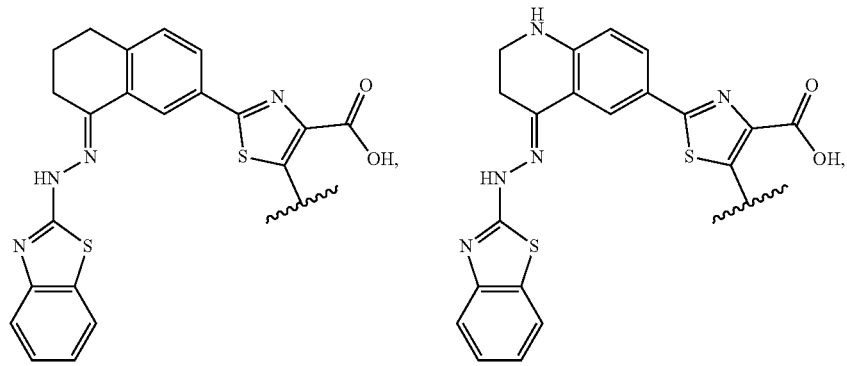

281
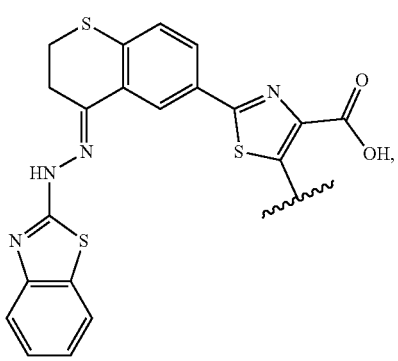
282
-continued

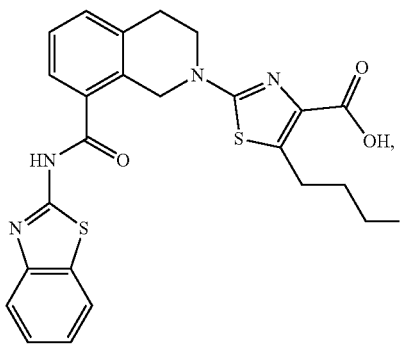
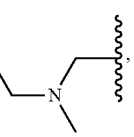
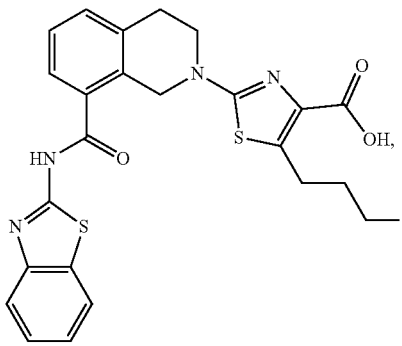
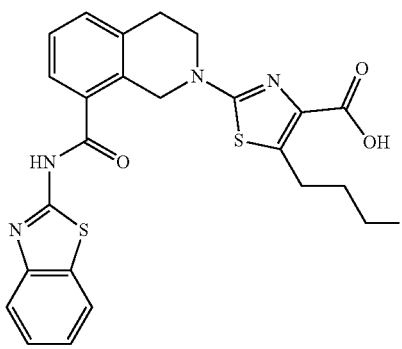

-continued
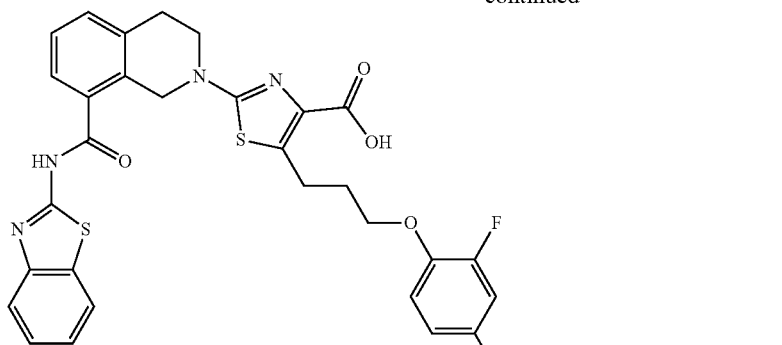
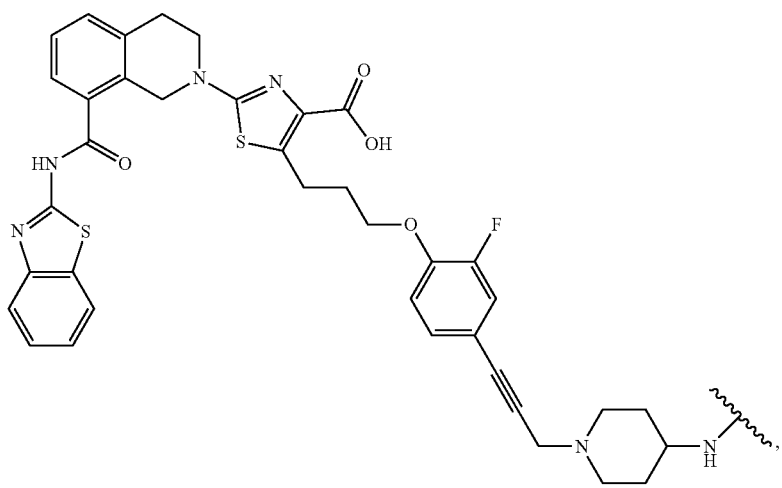
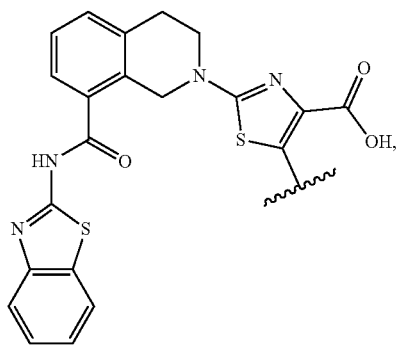 [SMILES: *c1sc(N2CCc3cccc(C(=O)Nc4nc5ccccc5s4)c3C2)nc1C(=O)O]
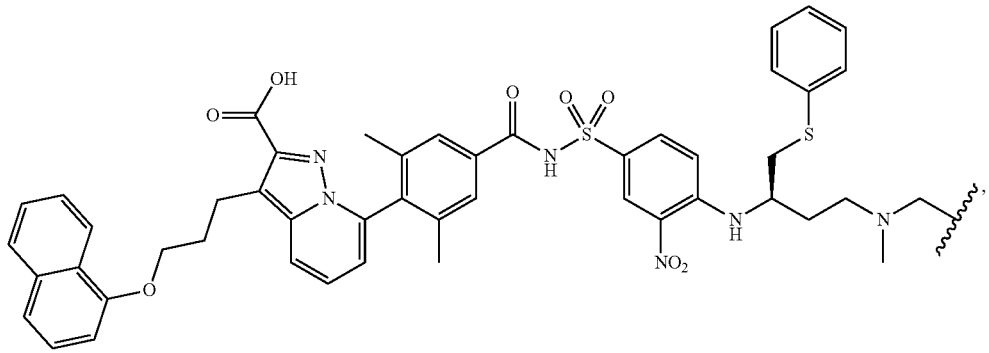

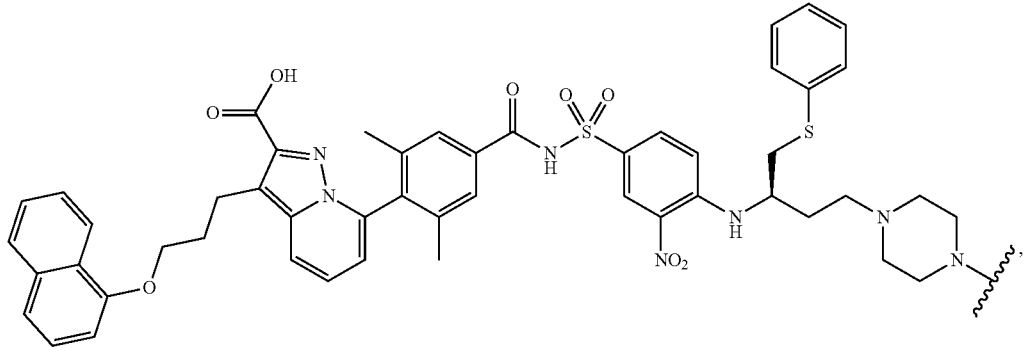
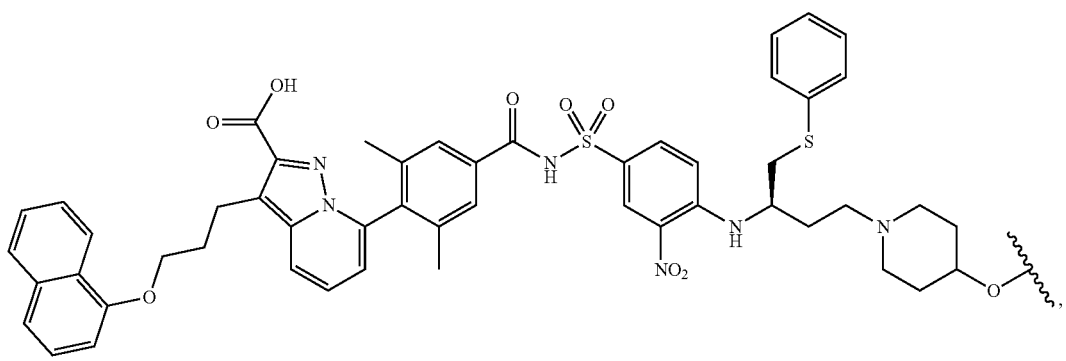
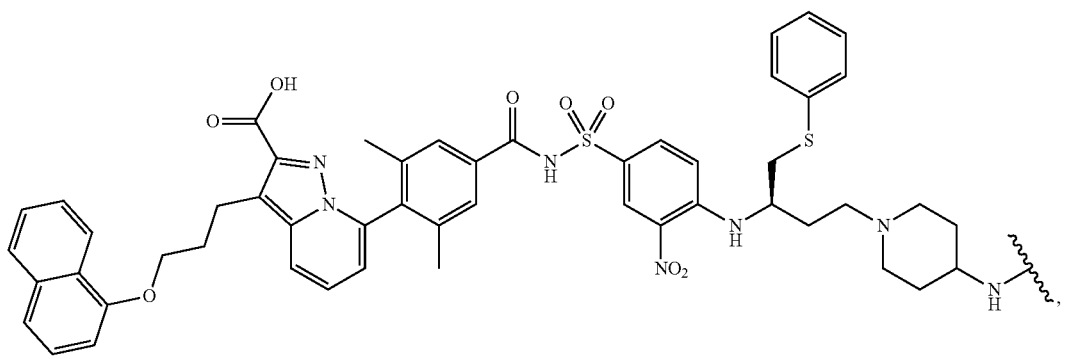
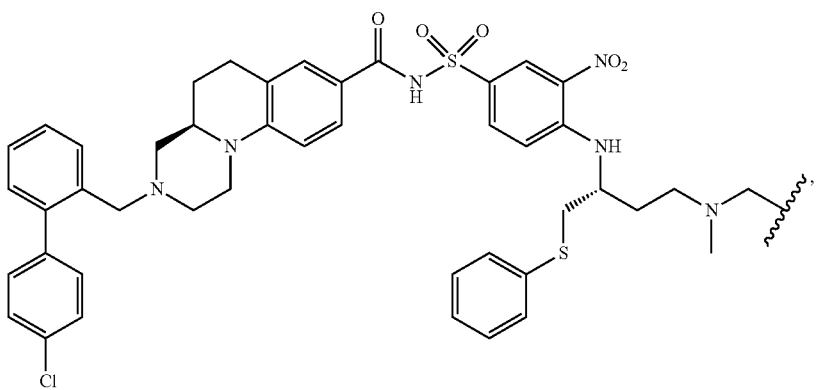

-continued
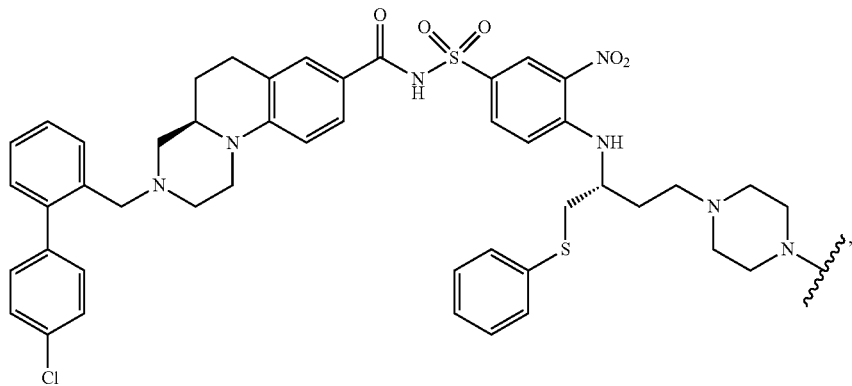
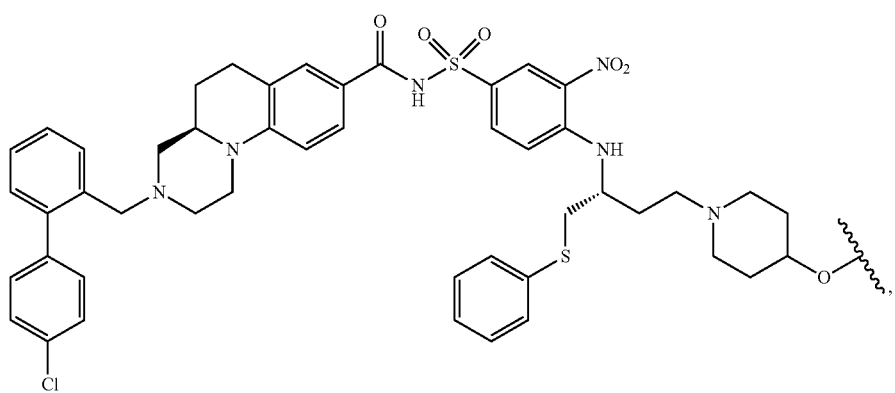
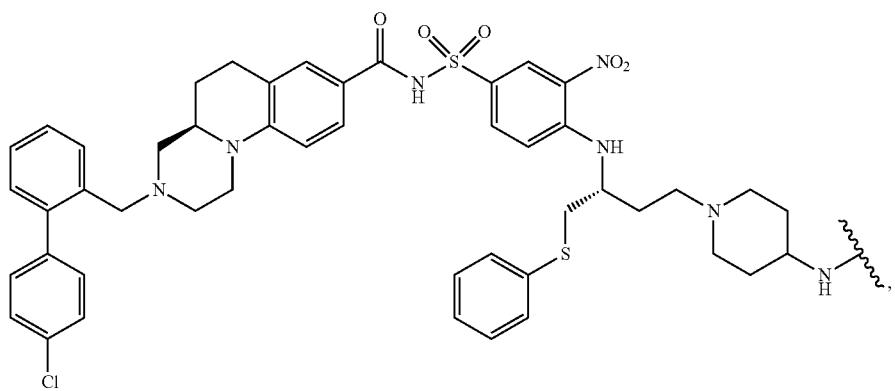
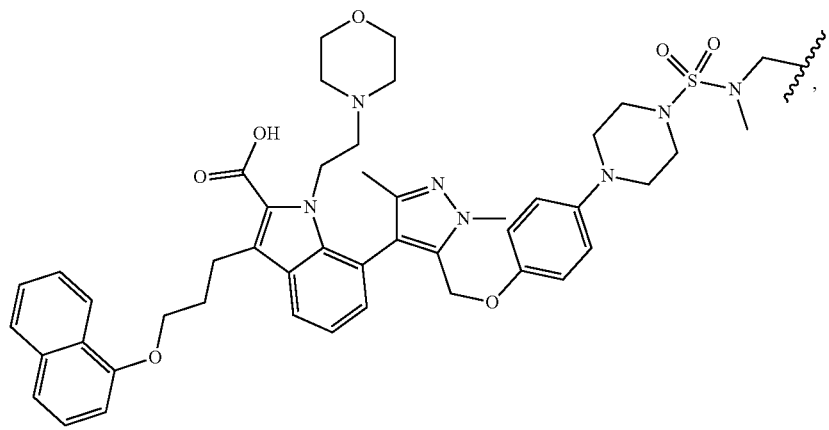

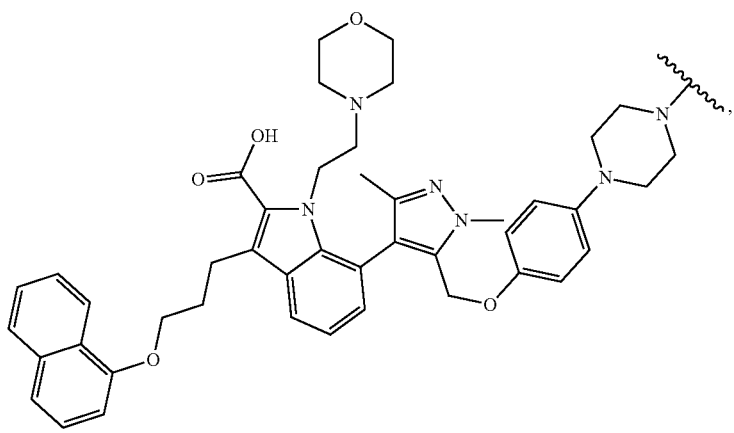
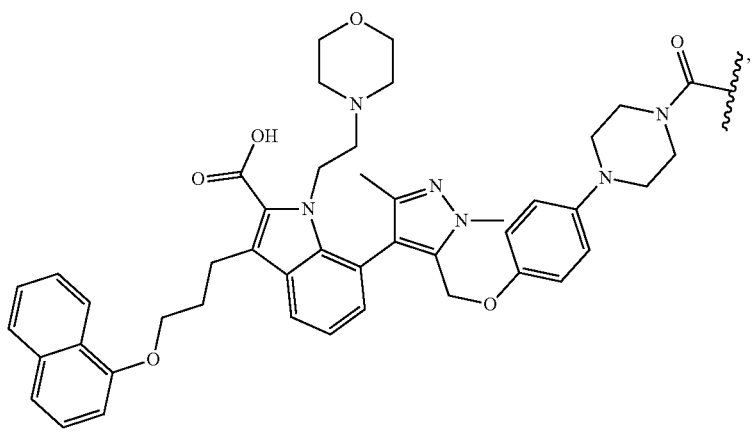
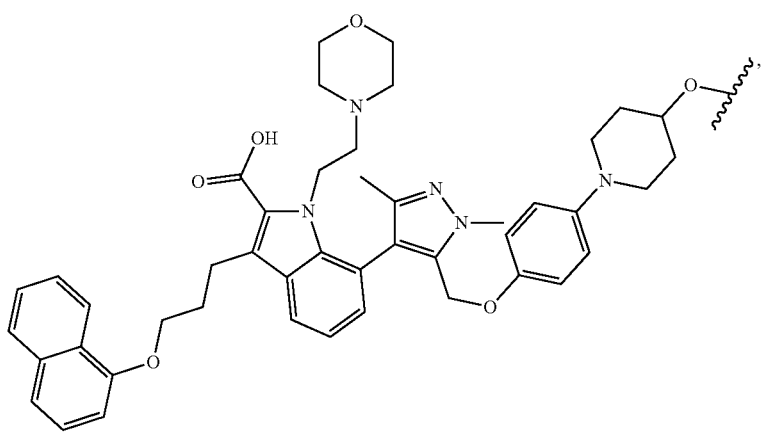

291
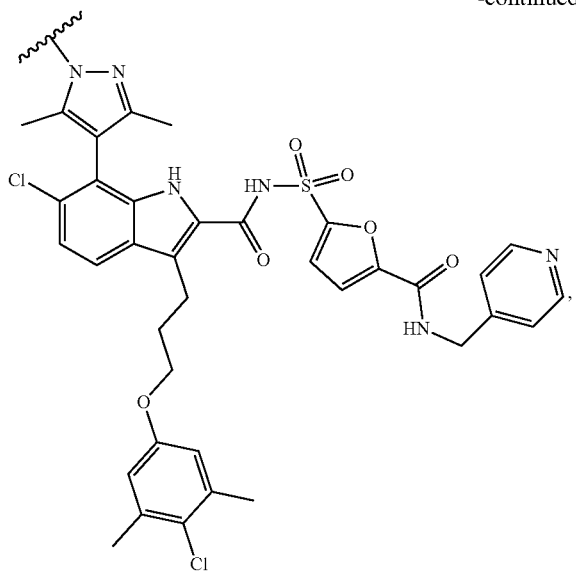
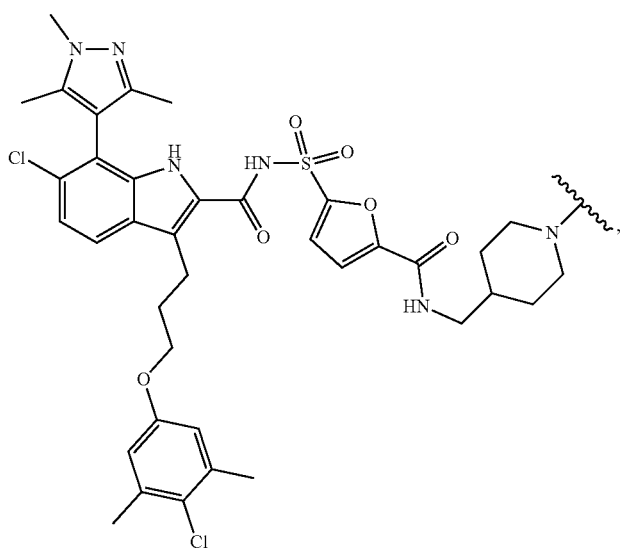
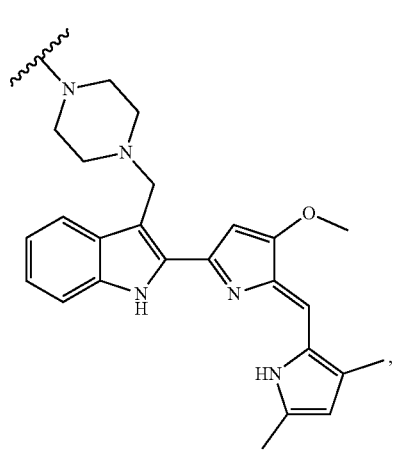
292
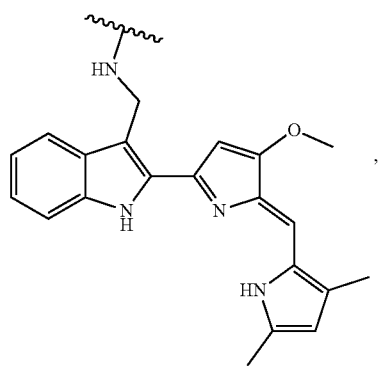
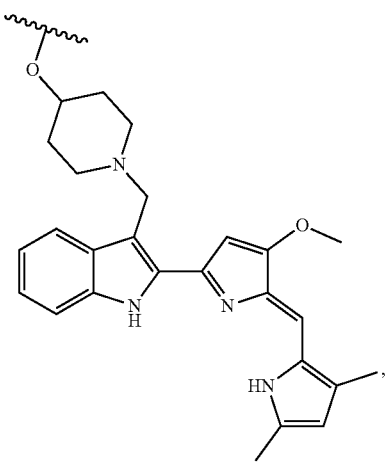

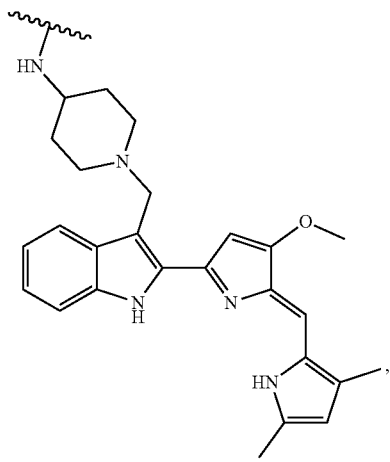
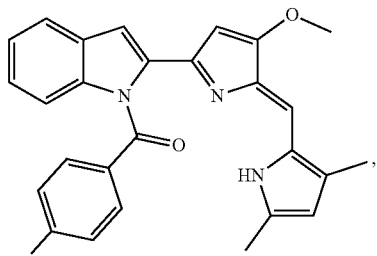
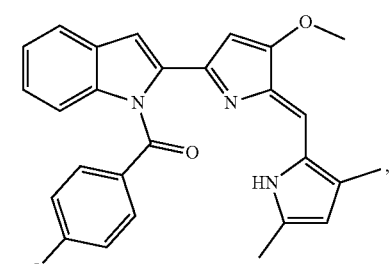
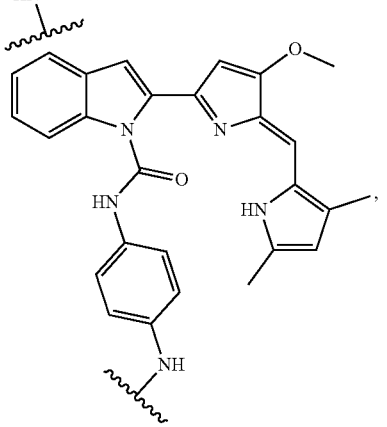 or
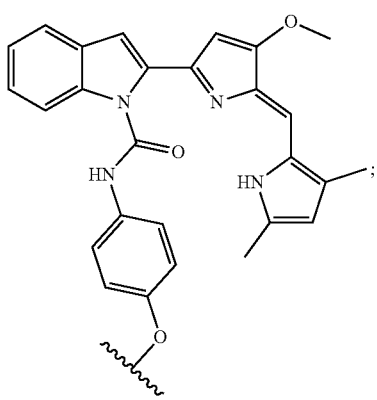
$R^3$ may be absent, an unsubstituted $C_1$-$C_6$ alkyl, or a substituted or unsubstituted $C_3$-$C_6$ ketone; A may be absent, a bond, or a substituted or unsubstituted $C_1$-$C_6$ heterocyclic group; n may be 0 to 3; $R^4$ may be a bond or a substituted $C_1$-$C_{10}$ alkyl, and $R^2$ may be
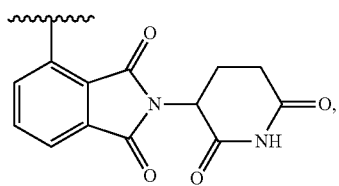
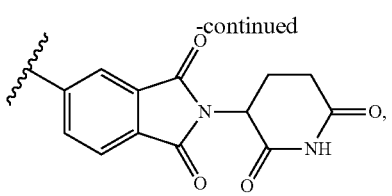
-continued
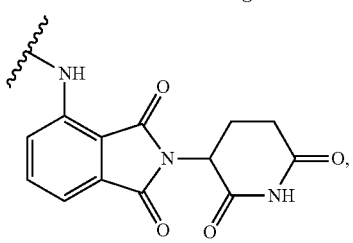

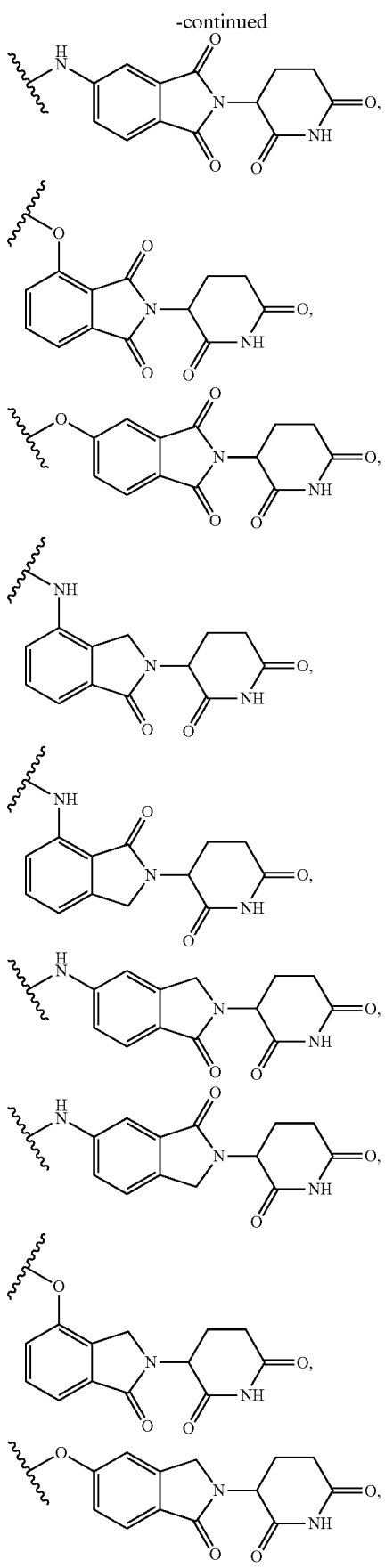
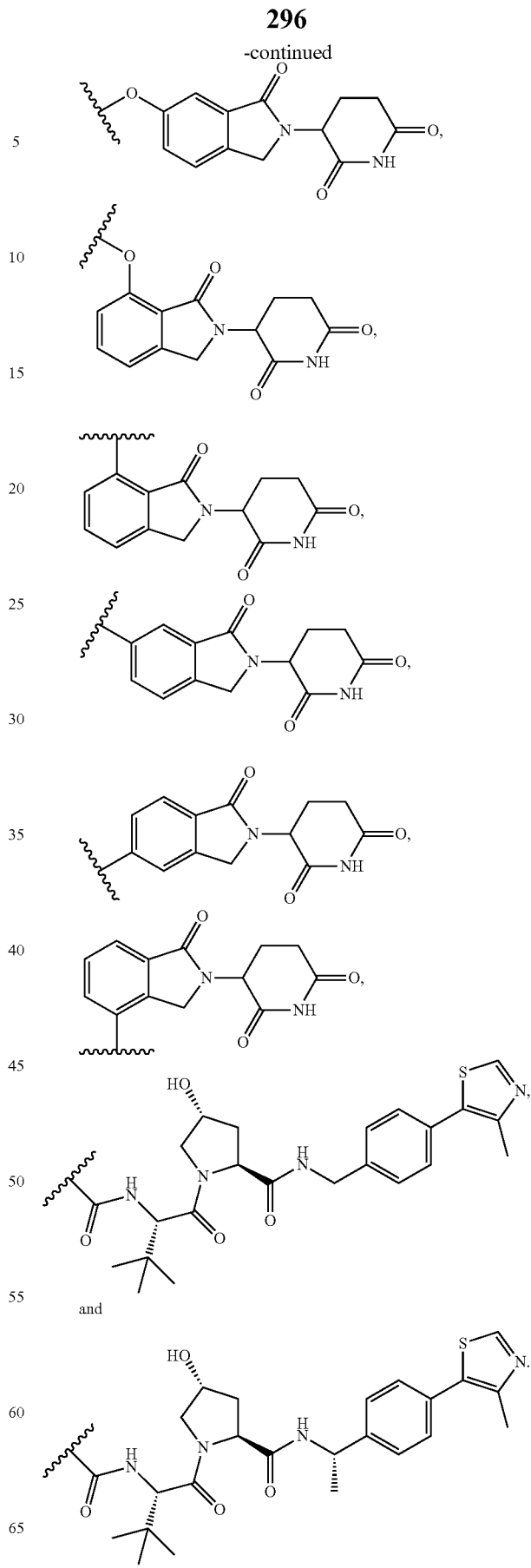

In a different embodiment, a compound of the disclosure comprises Formula (II), wherein R¹ may be
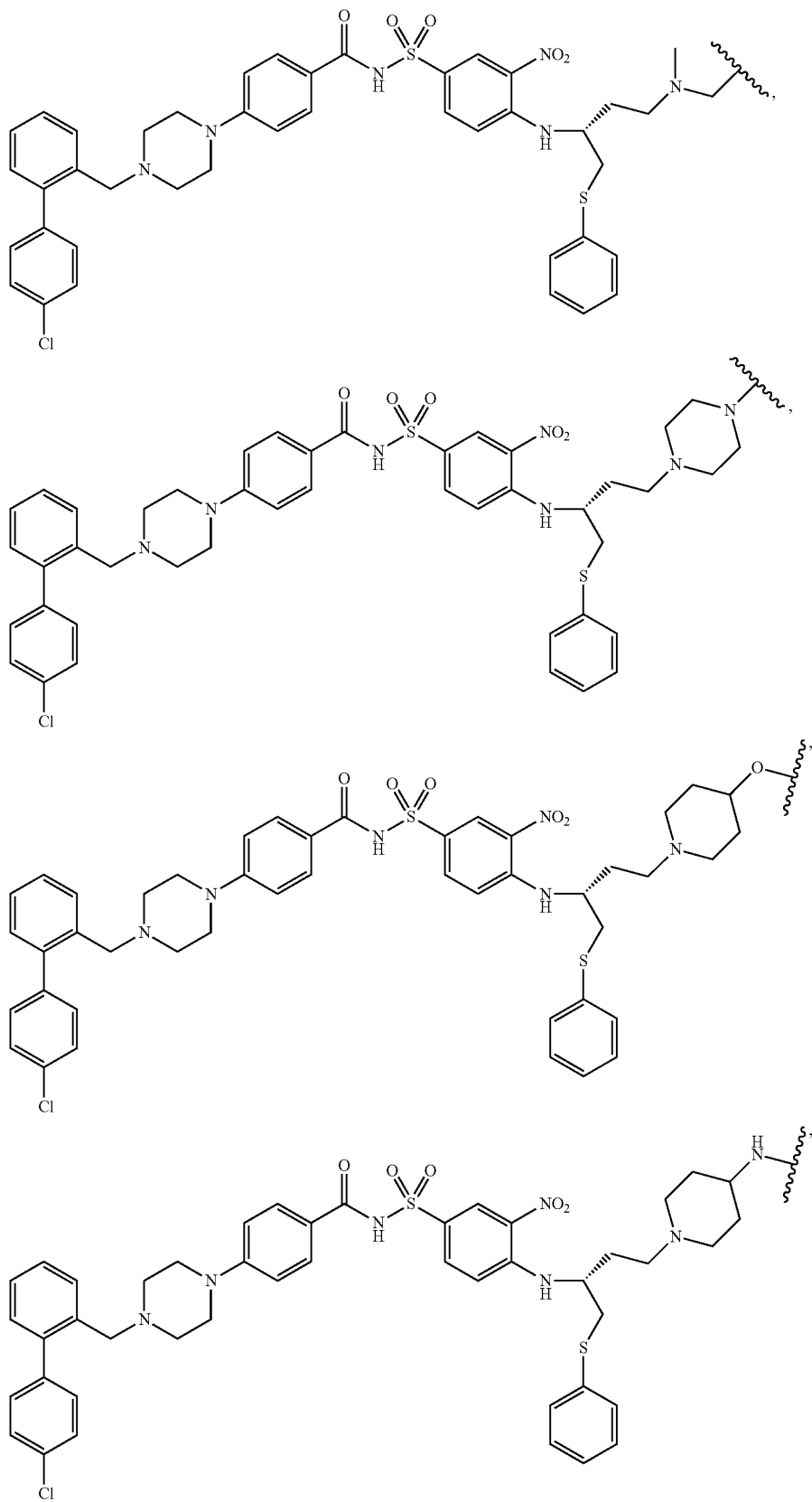

-continued
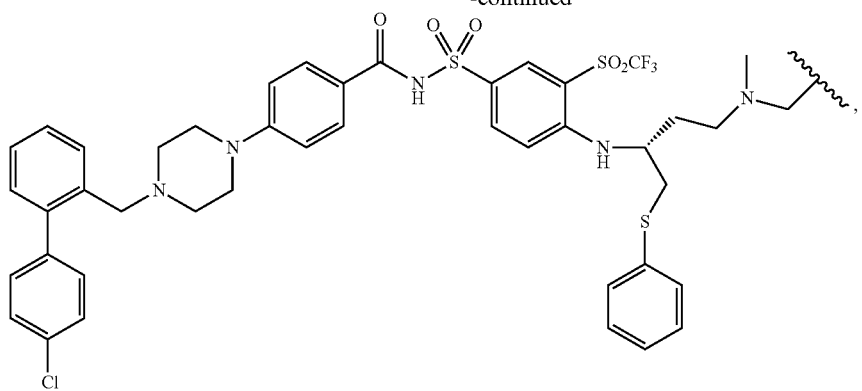
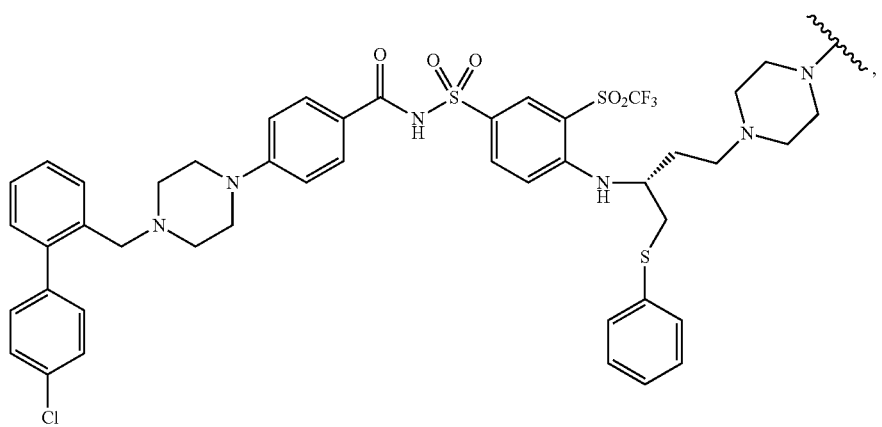
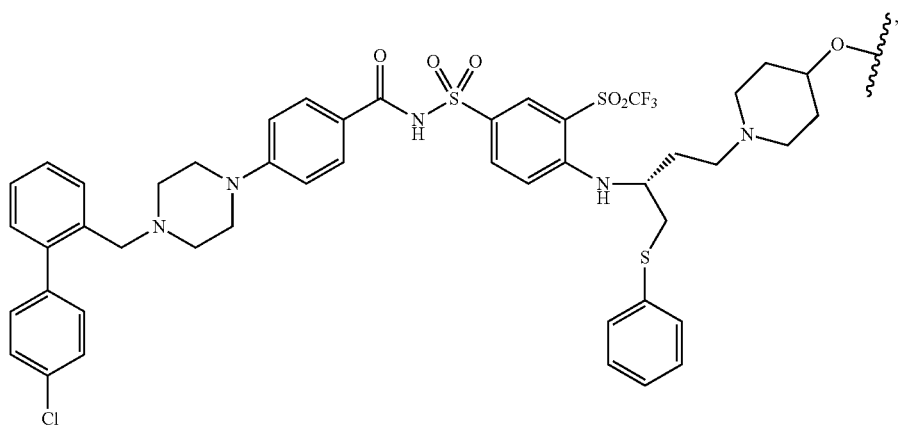
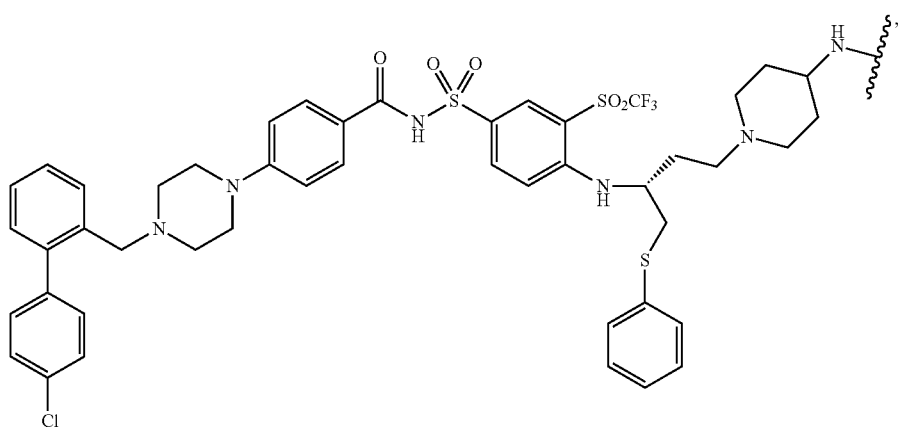

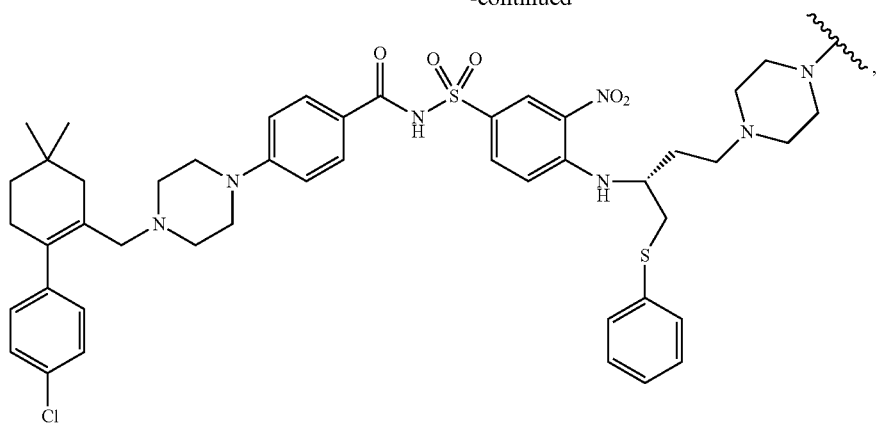
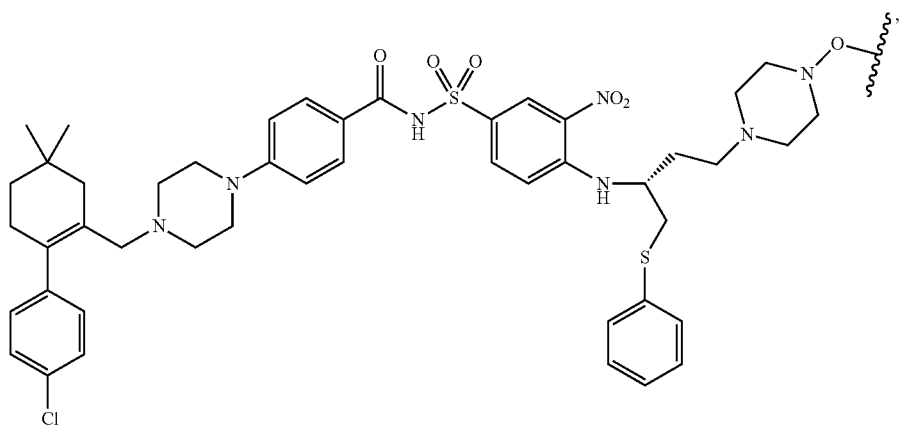
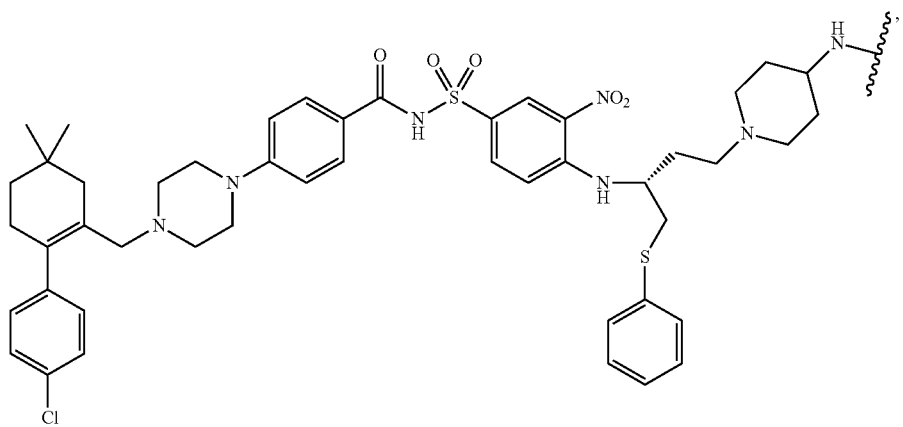
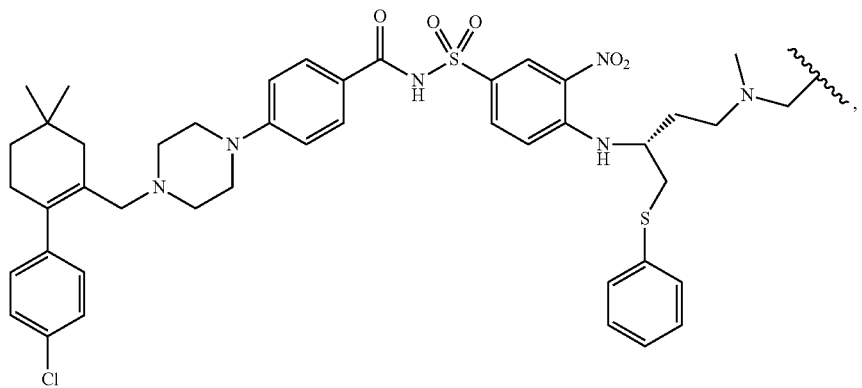

-continued
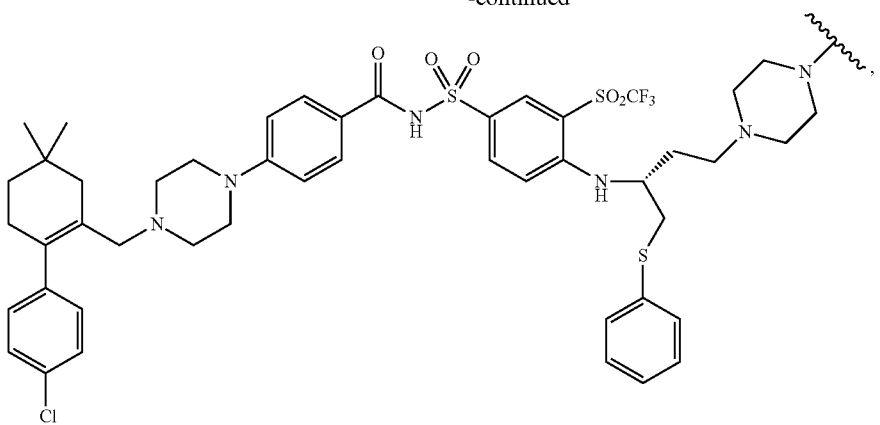
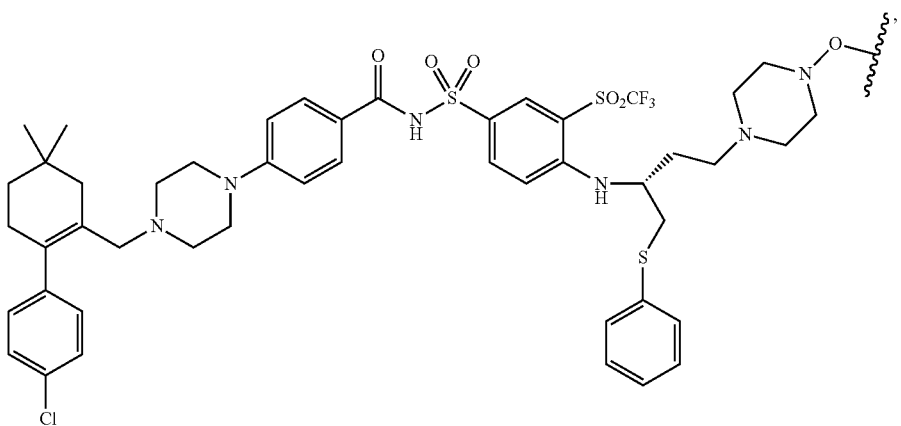
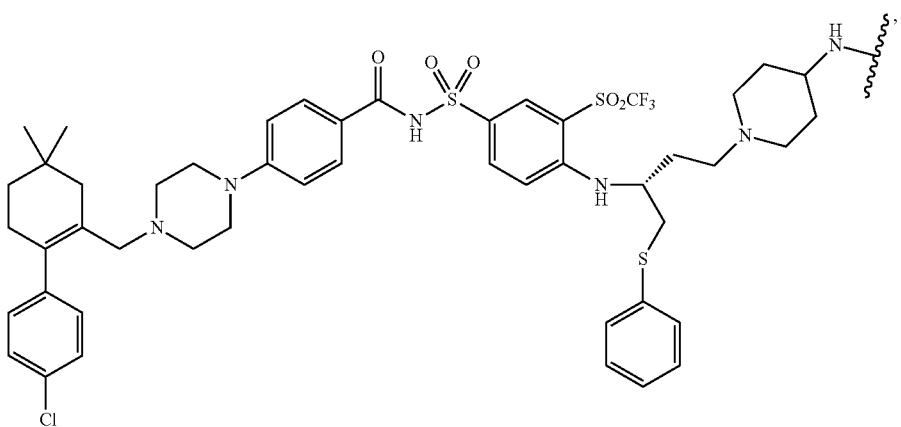
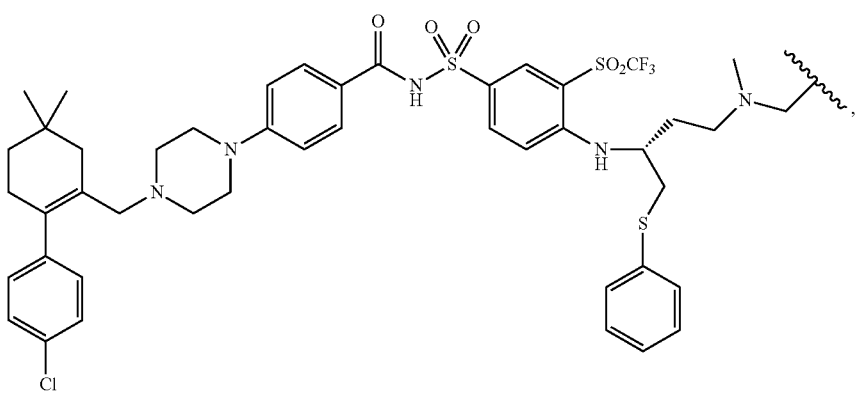

-continued
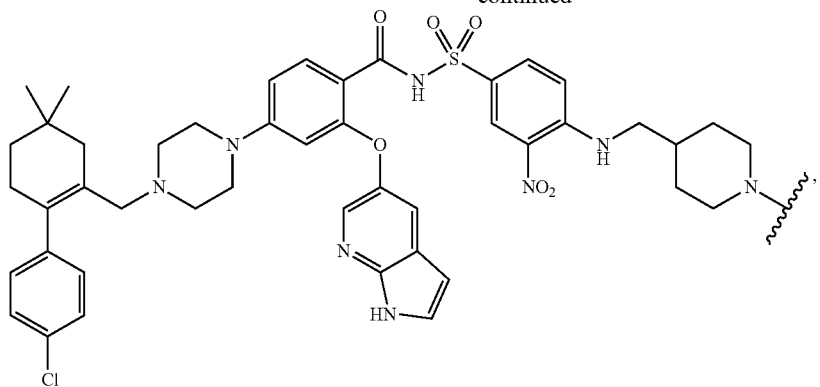
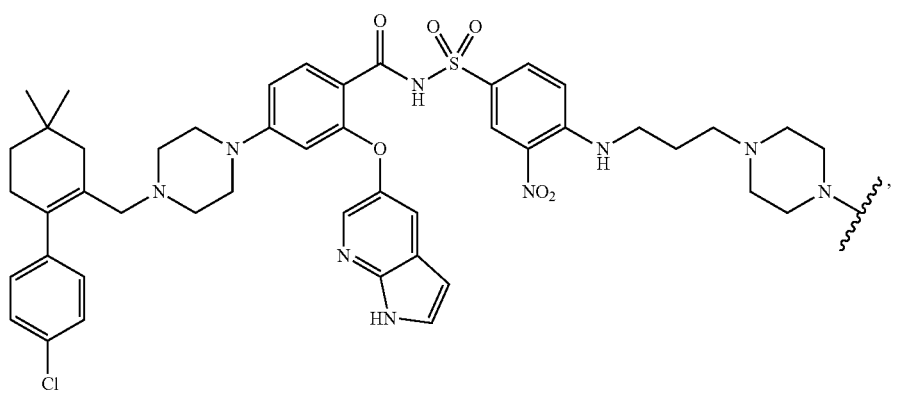
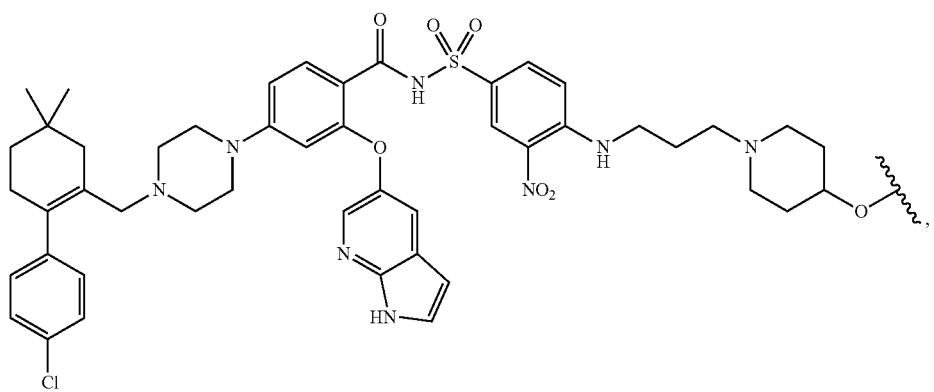
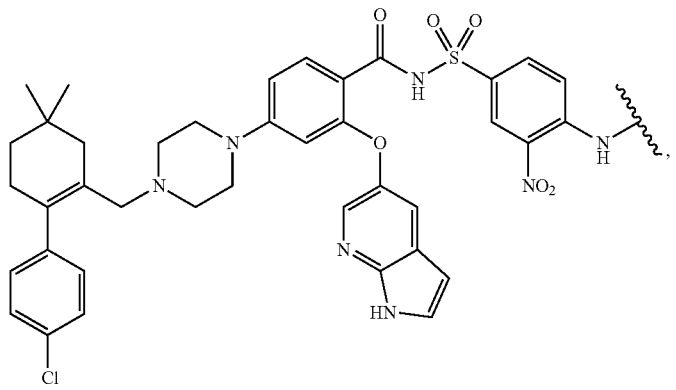

-continued
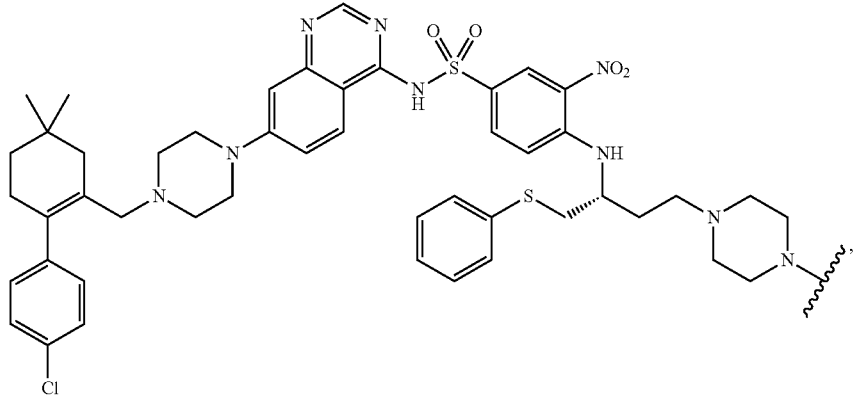
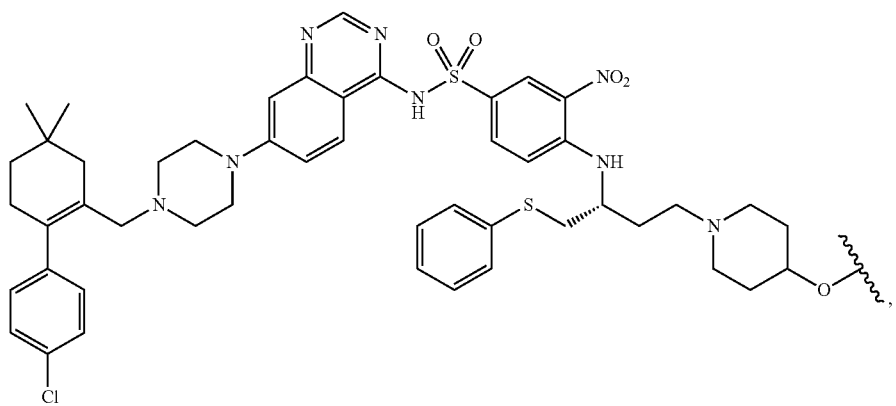
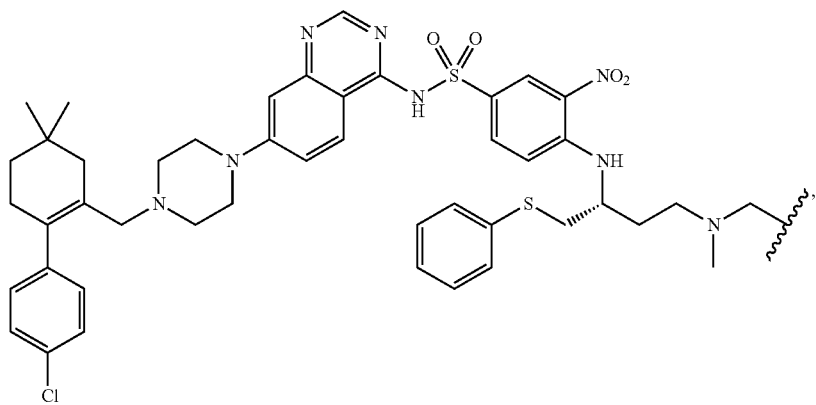
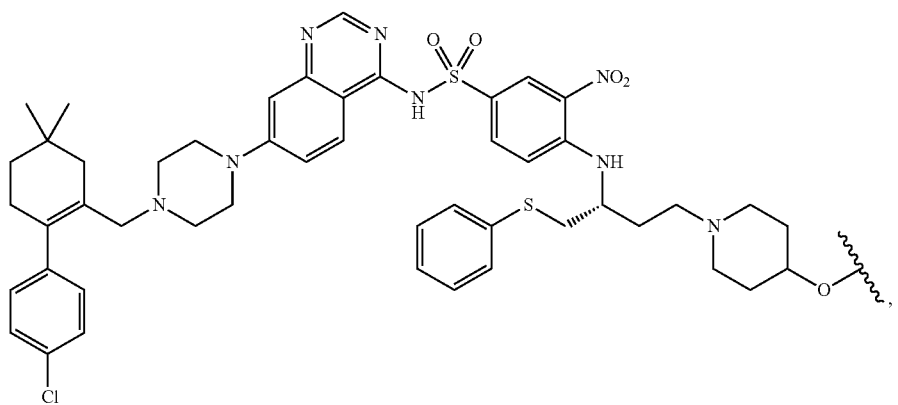

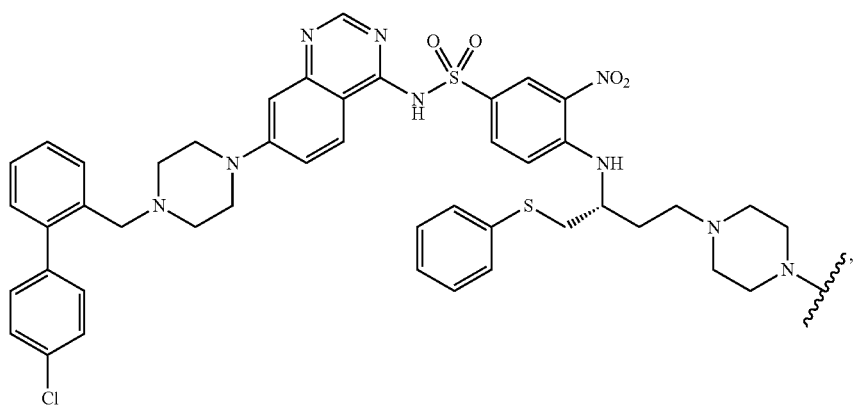
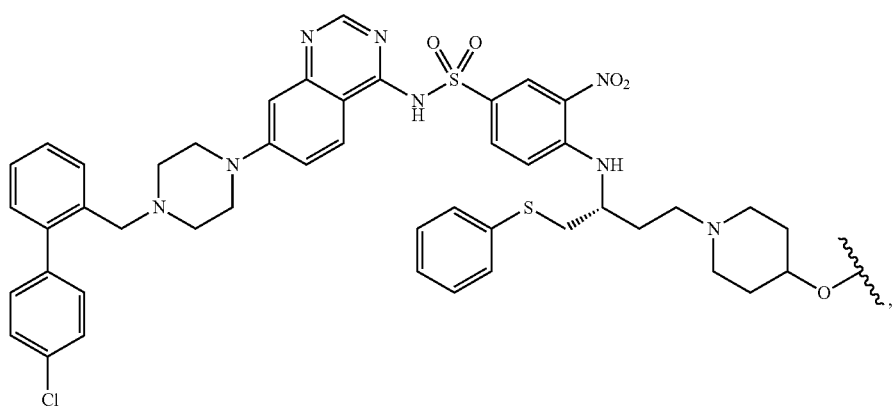
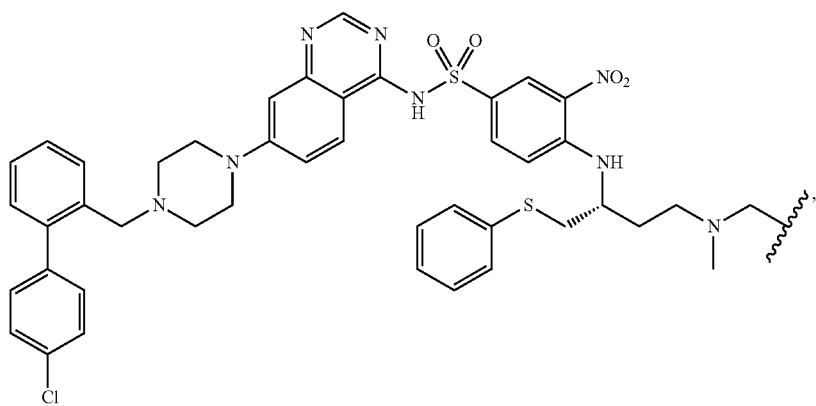
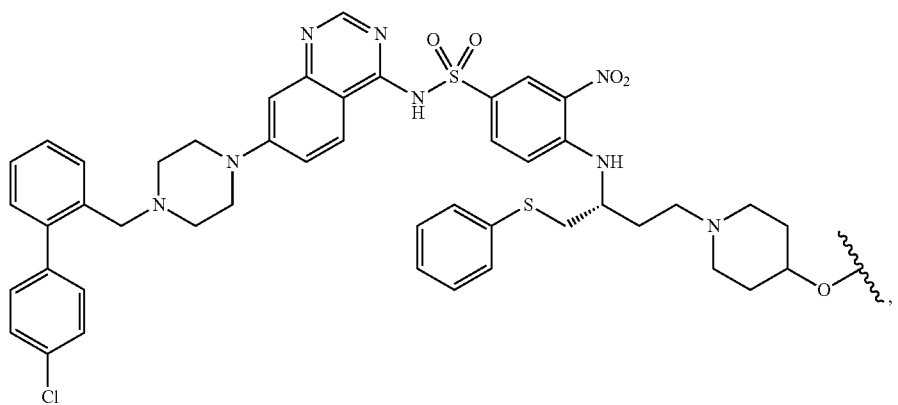

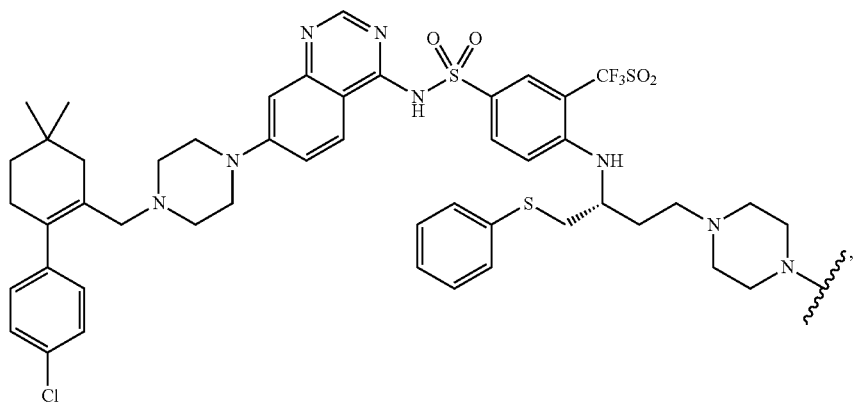
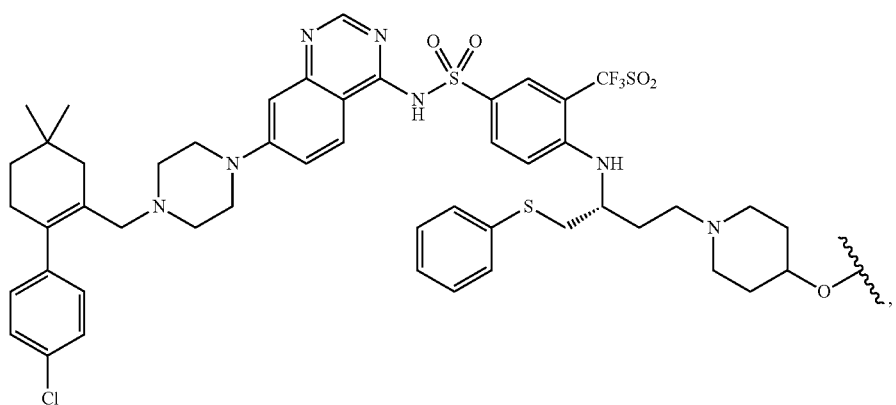
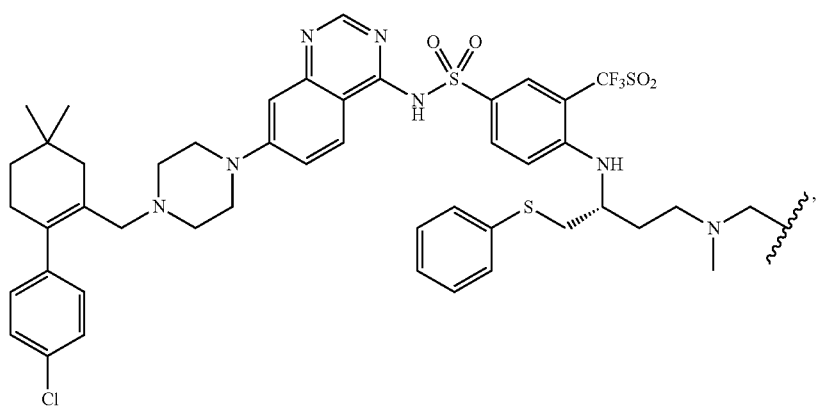
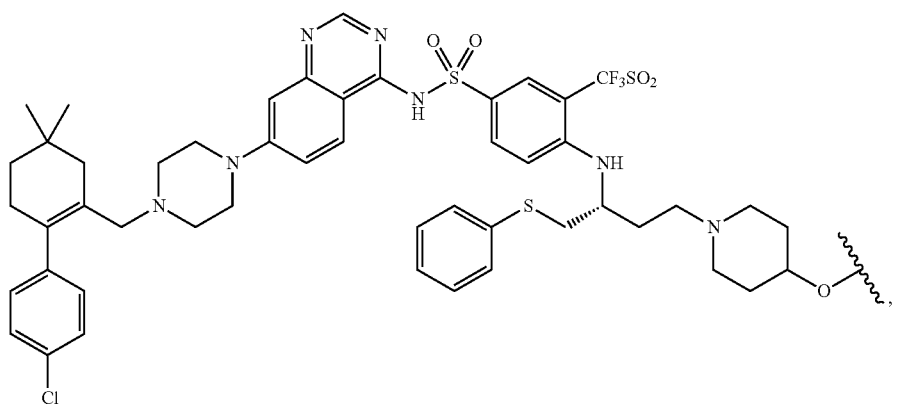

-continued
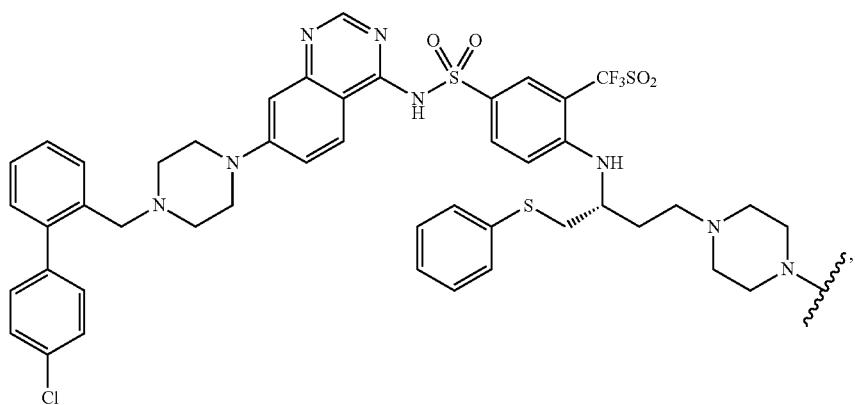
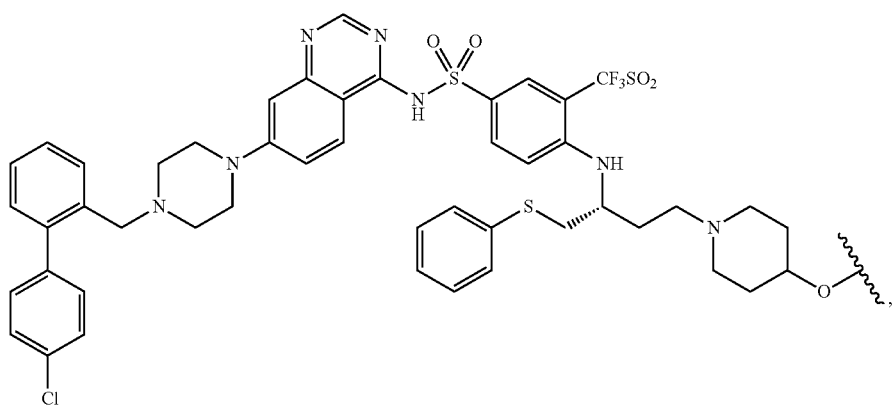
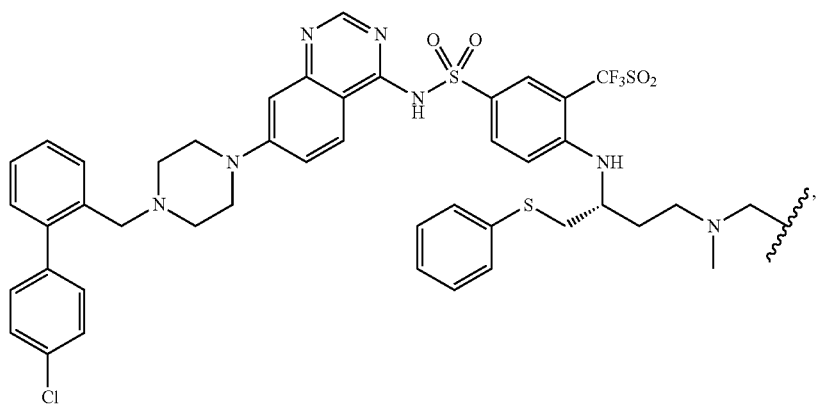
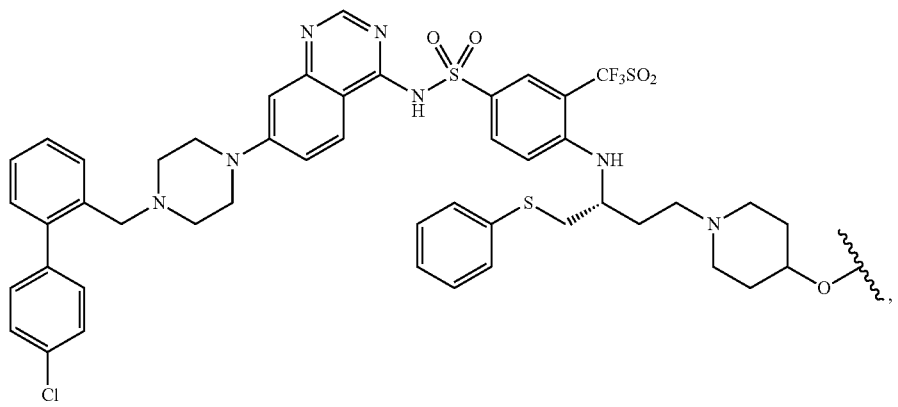

-continued
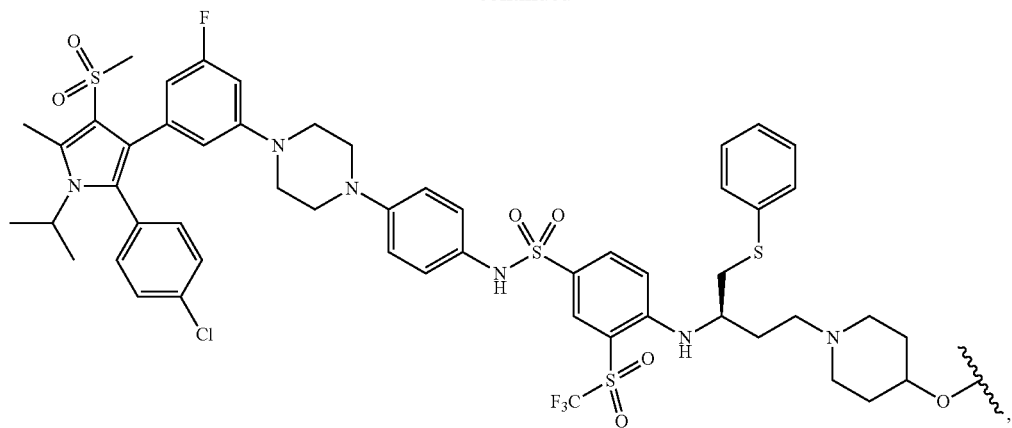
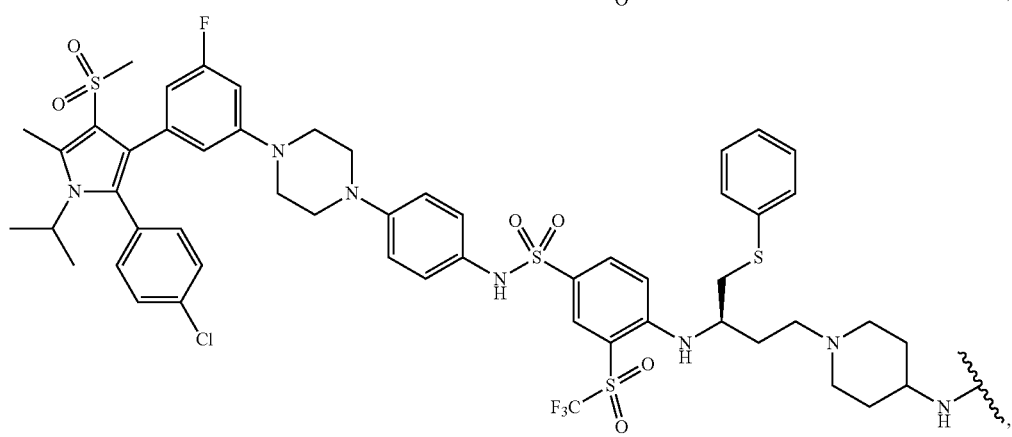
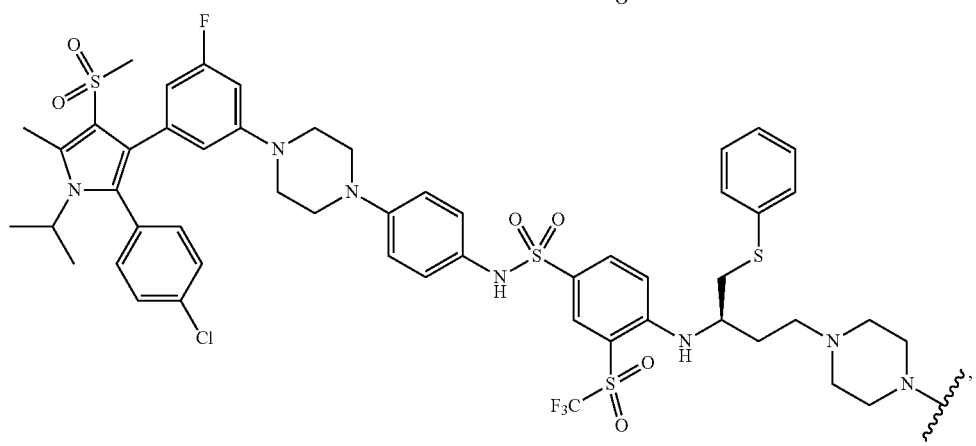
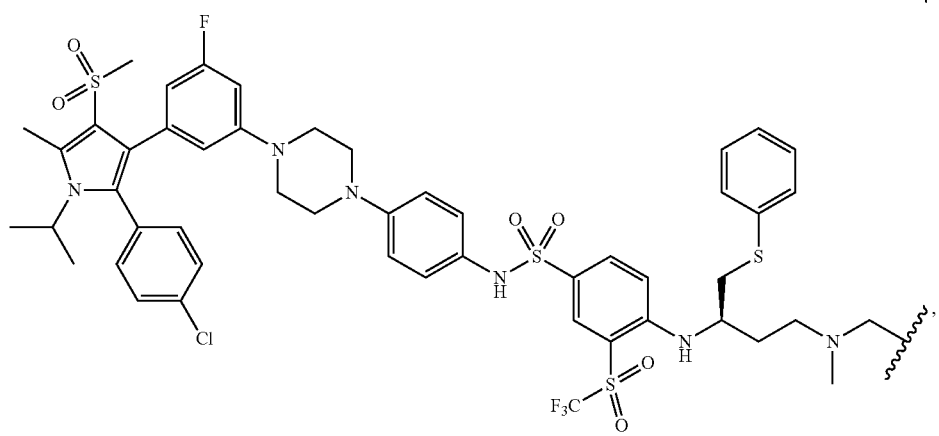

-continued
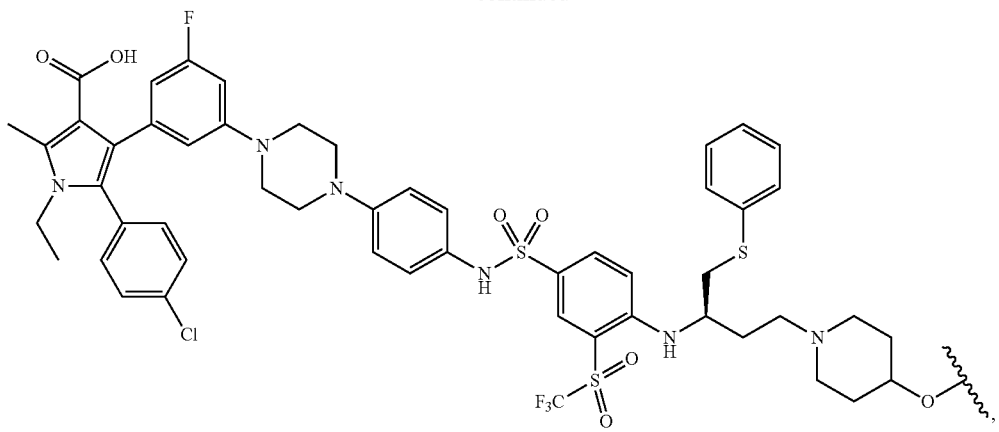
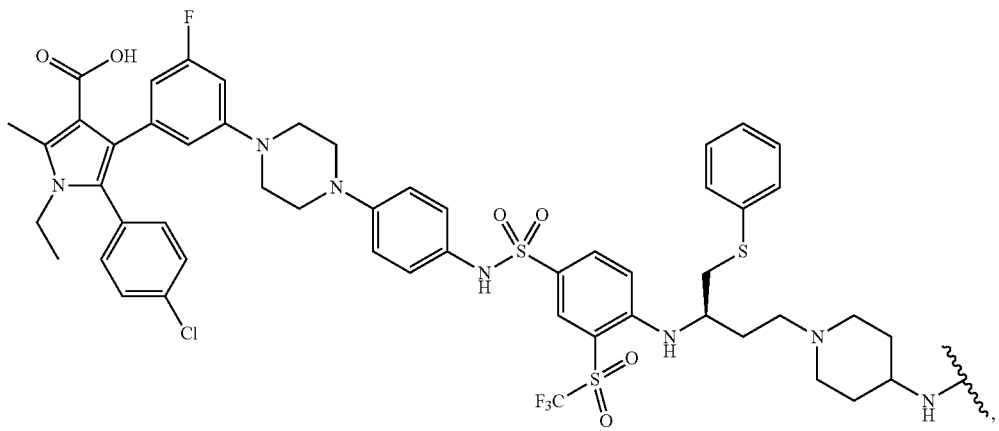
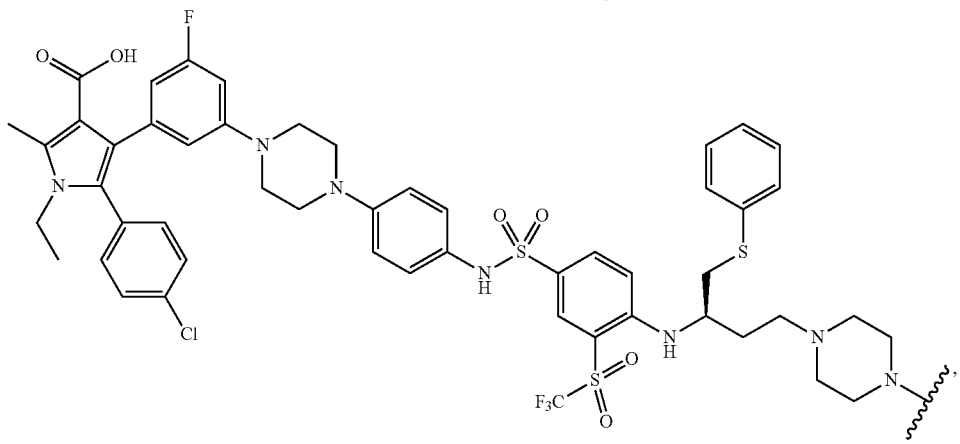
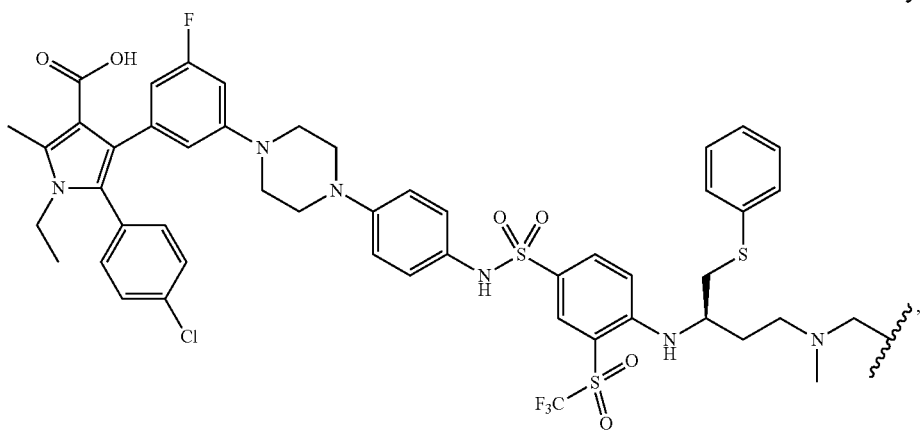

-continued
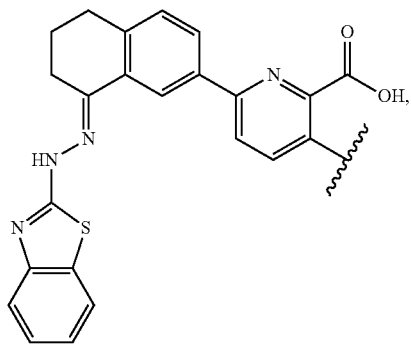
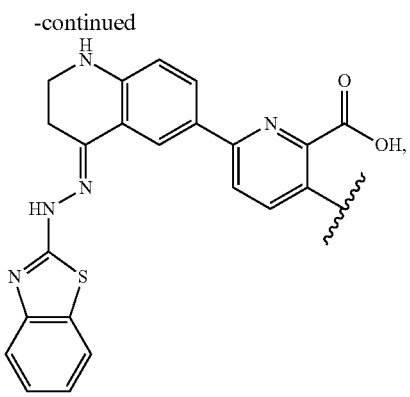
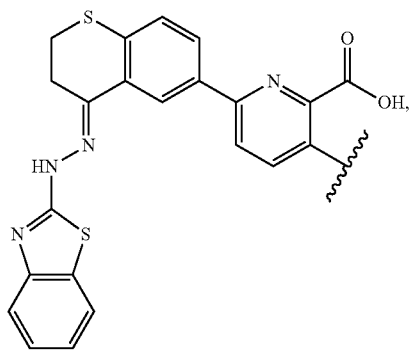
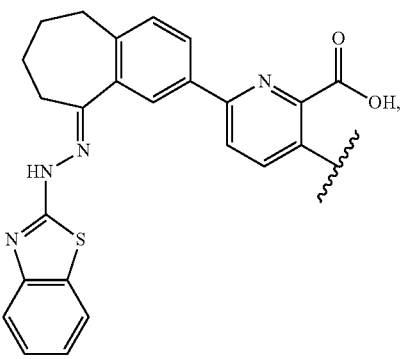
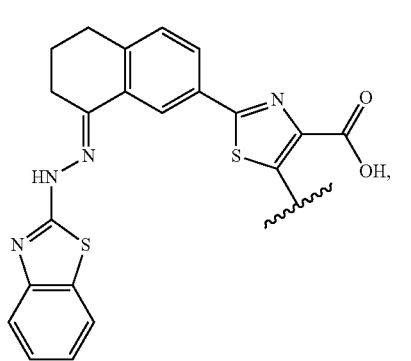
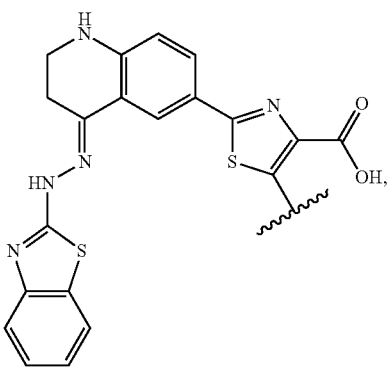
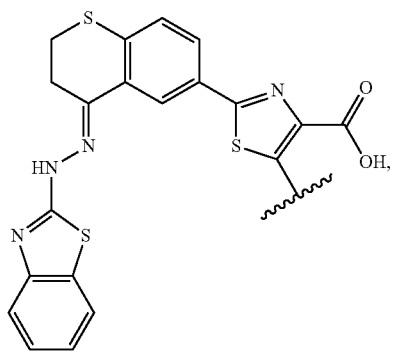
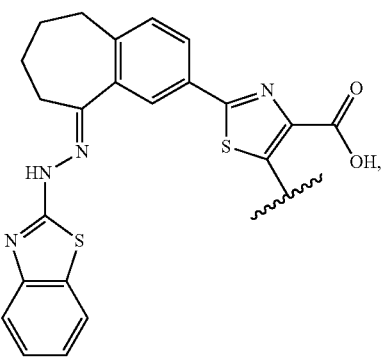

-continued
321
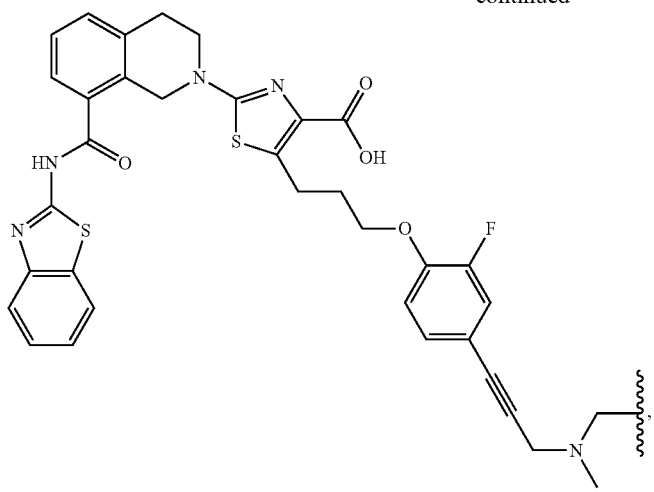
322
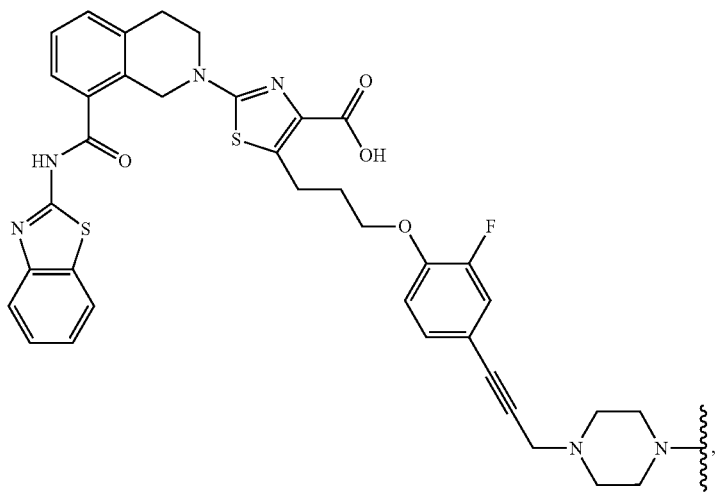
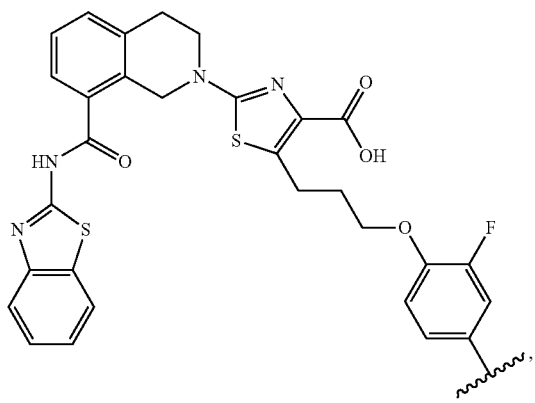

-continued
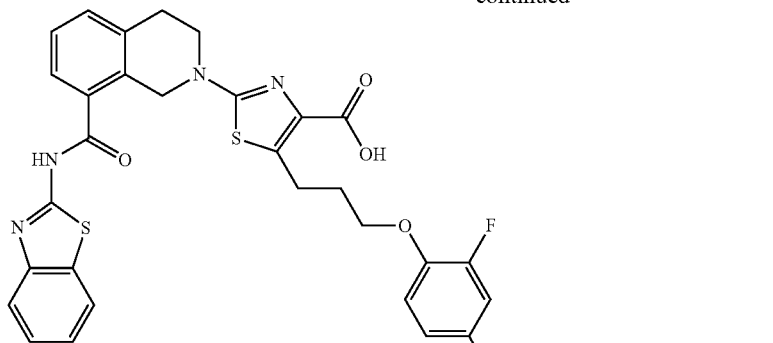
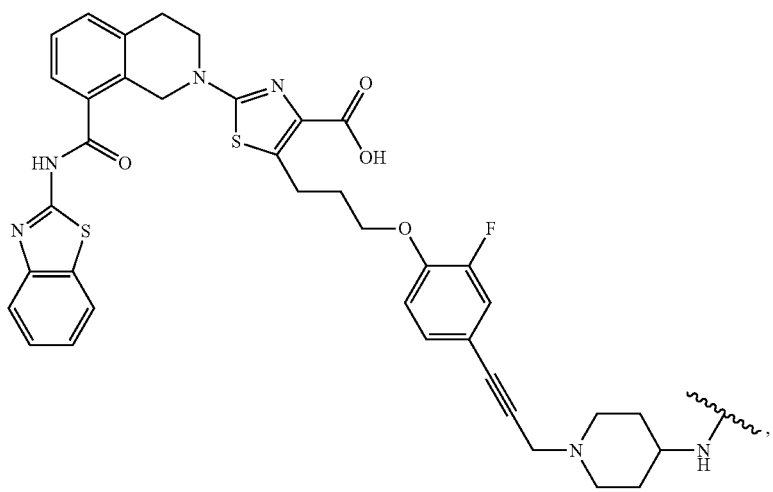
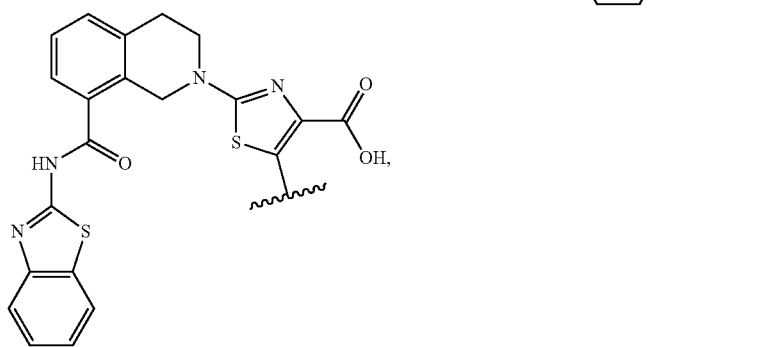
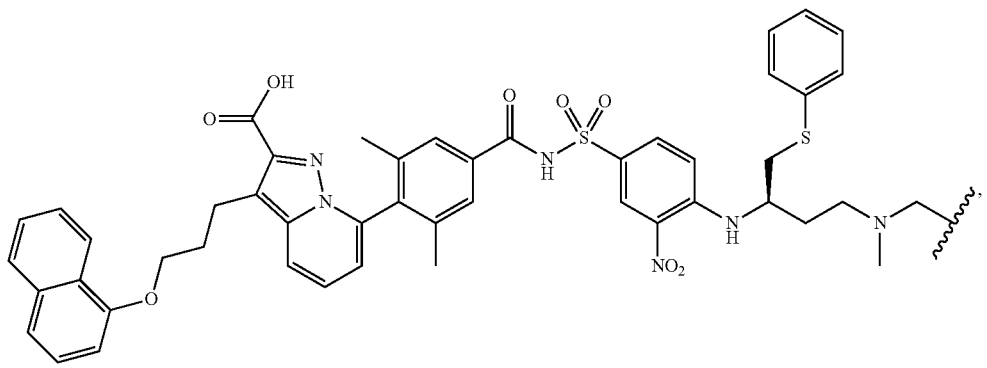

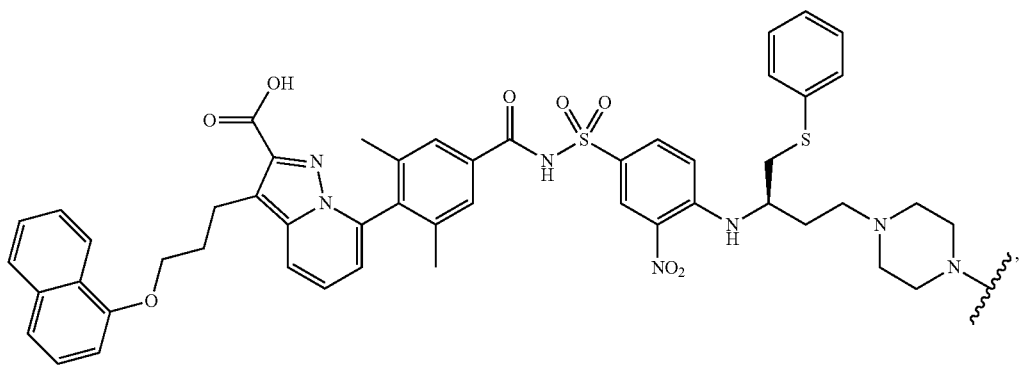
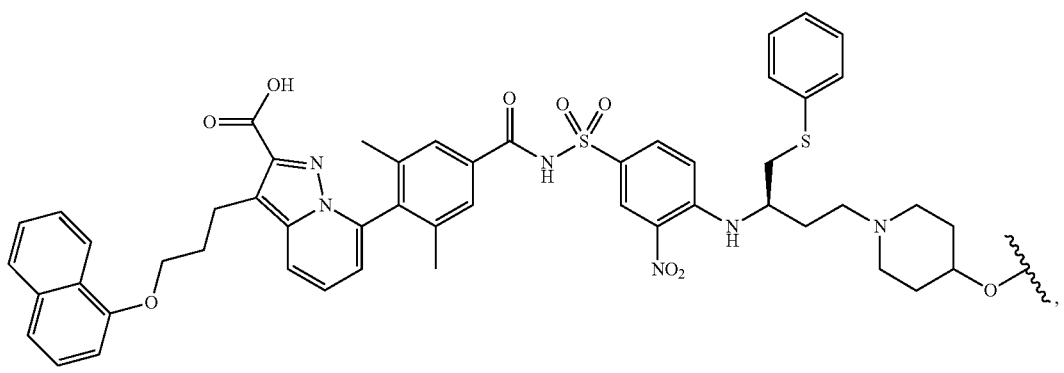
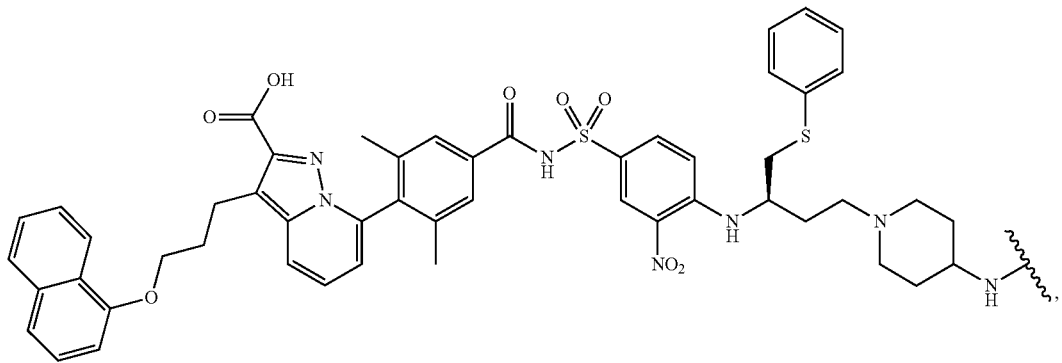
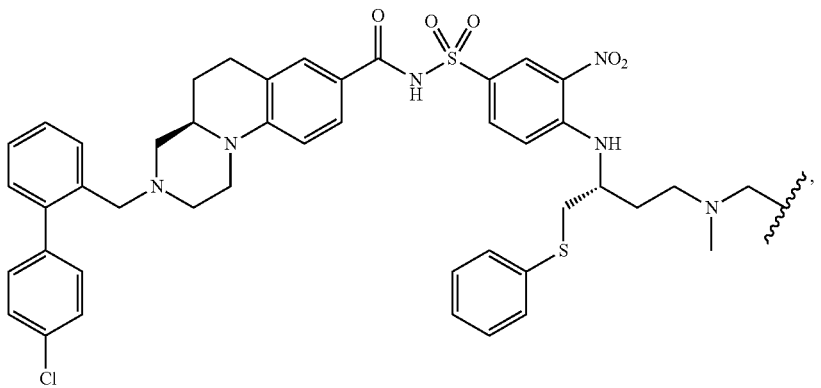

-continued
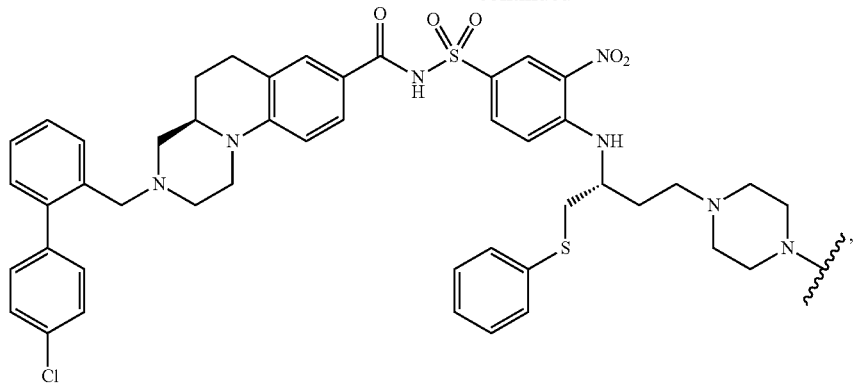
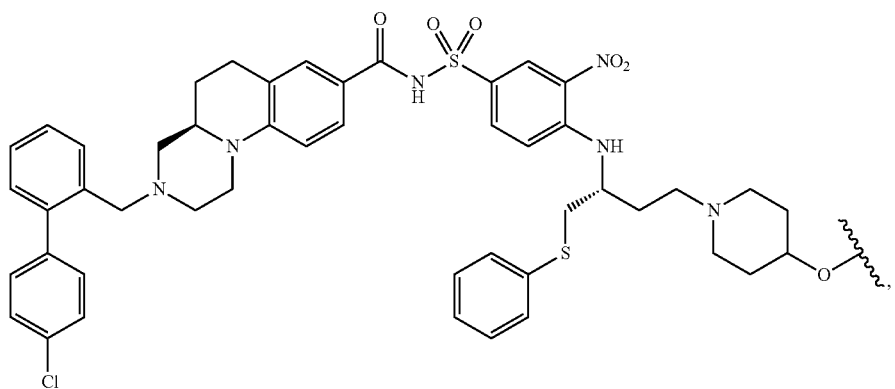
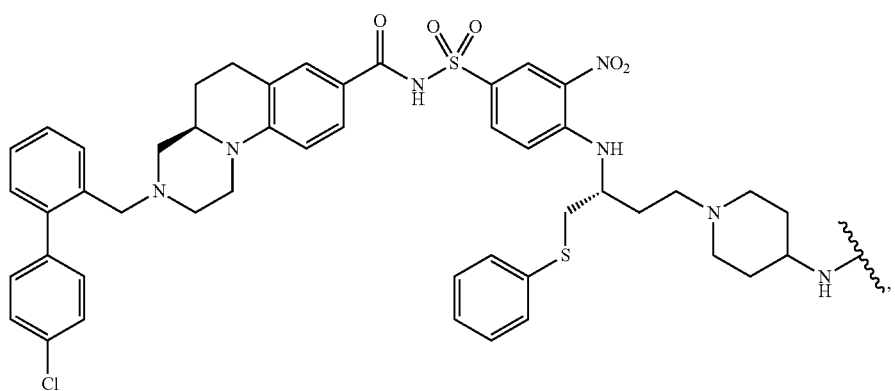
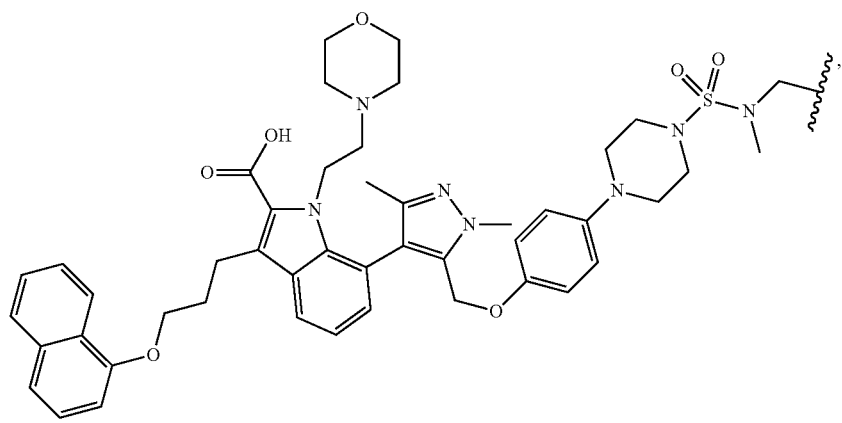

-continued
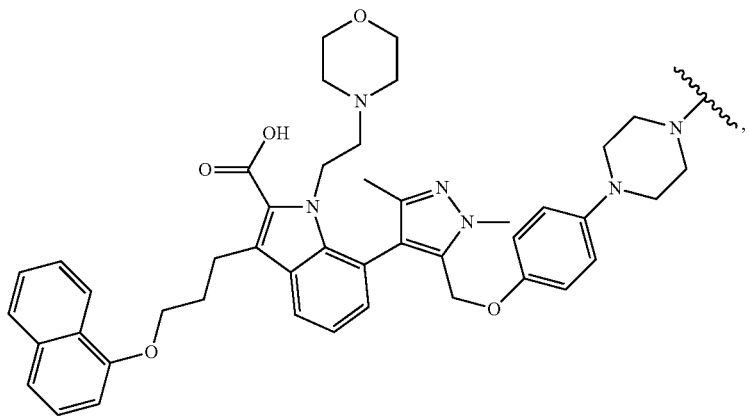
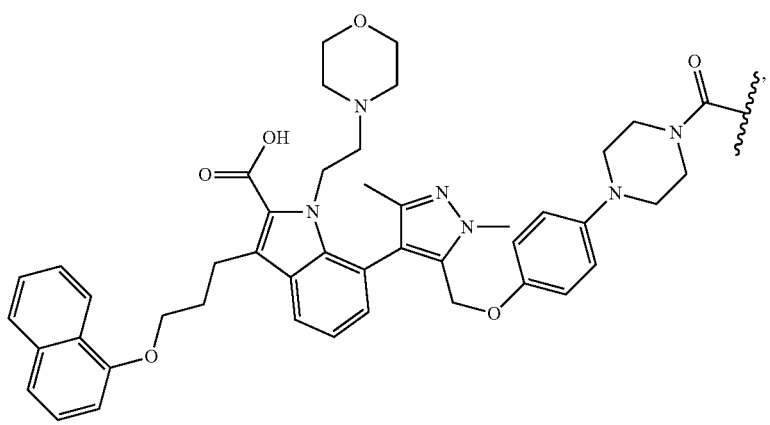
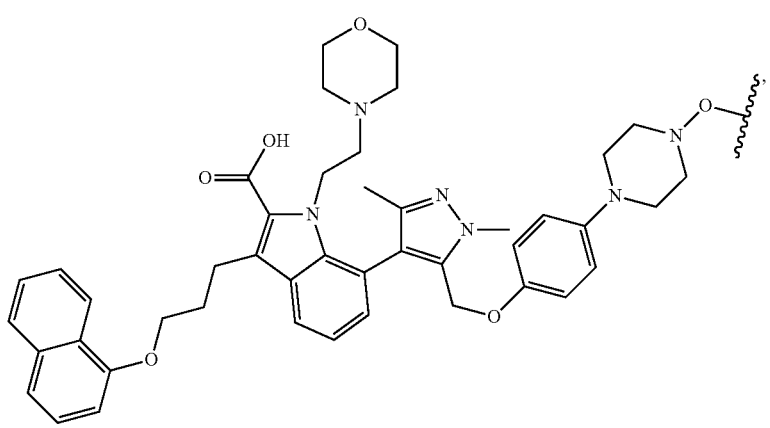

331
332
-continued
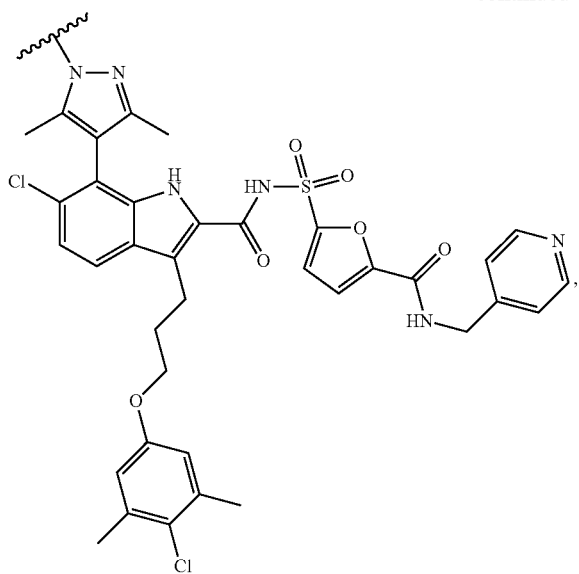
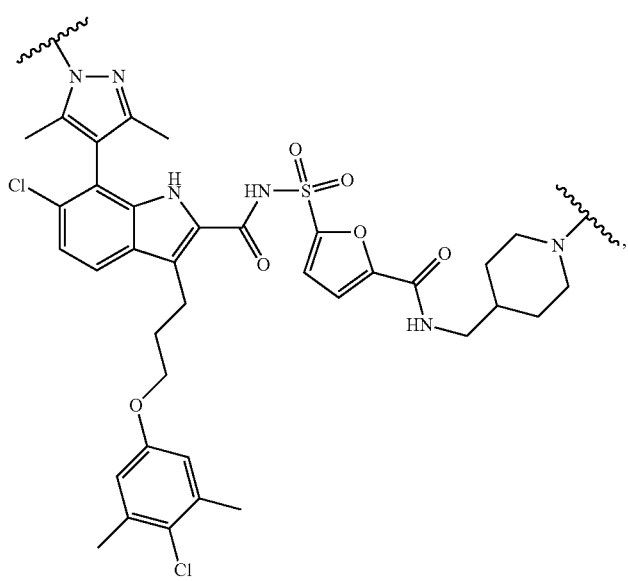
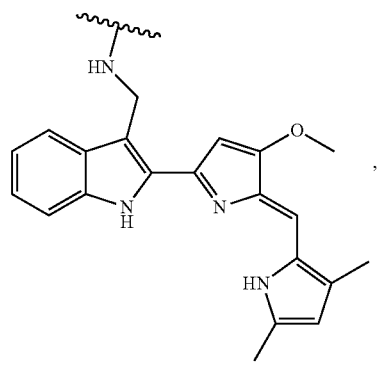
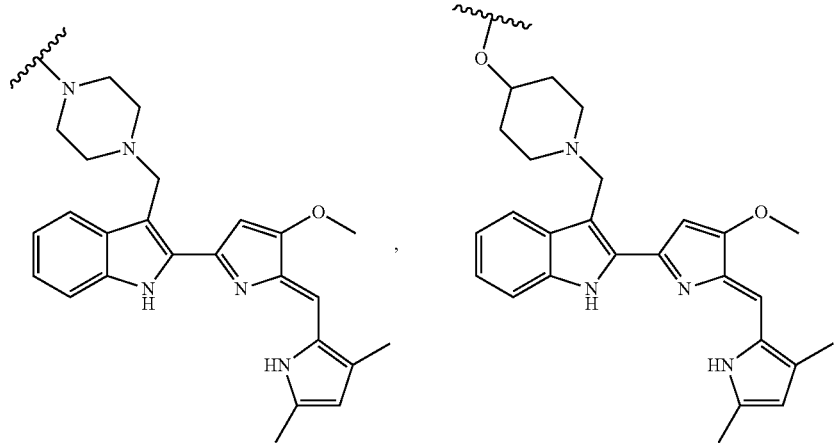

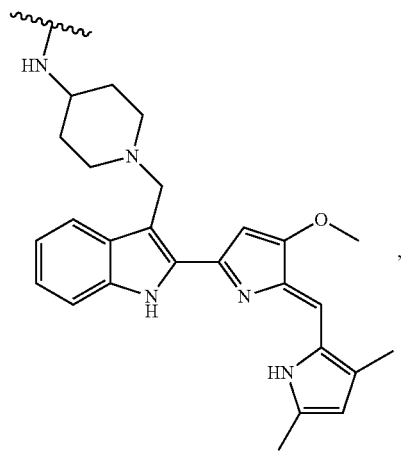,
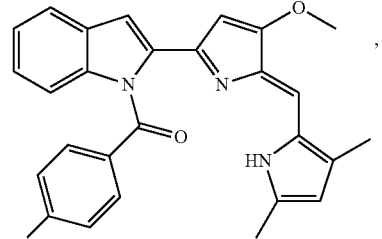,
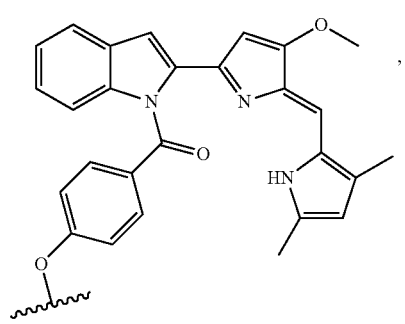,
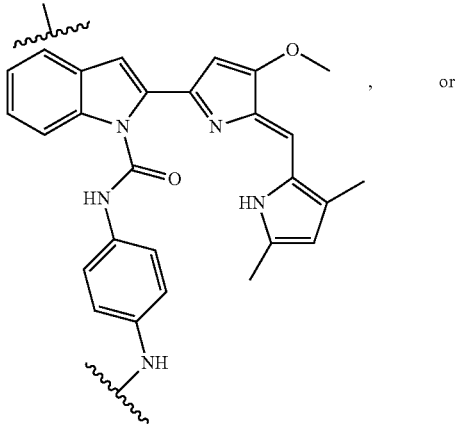, or
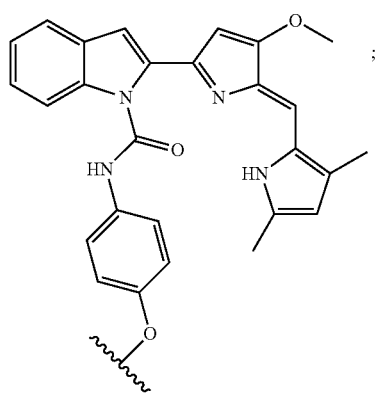;
R³ may be absent, an unsubstituted C₁-C₆ alkyl, or a substituted or unsubstituted C₃-C₆ ketone; A may be absent, a bond, or a substituted or unsubstituted C₁-C₆ heterocyclic group; n may be 0 to 3; R⁴ may be a bond or a substituted or unsubstituted C₁-C₁₀ alkyl; and R² may be
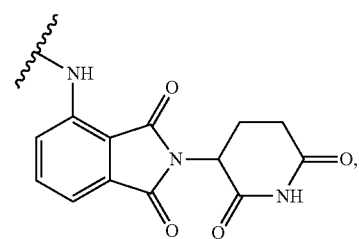 [SMILES: *Nc1cccc2c1C(=O)N(C1CCC(=O)NC1=O)C2=O]
-continued
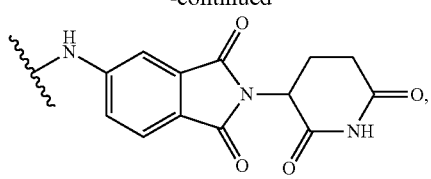,
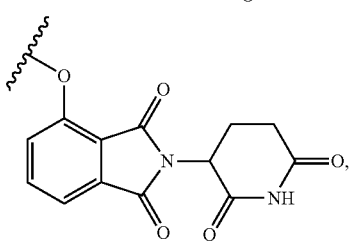,

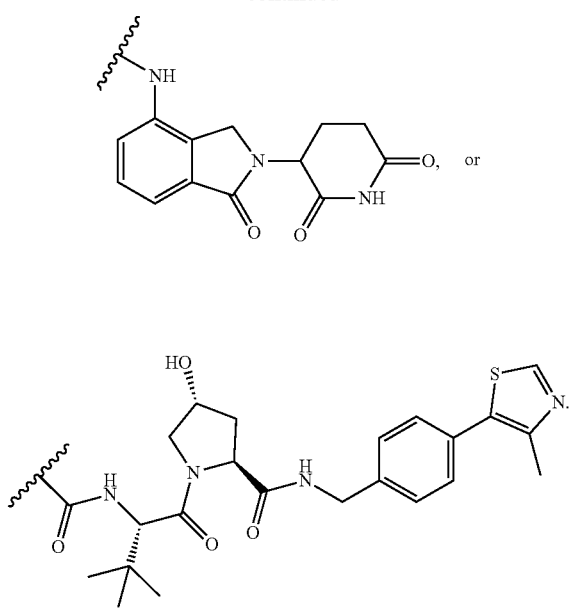

In a preferred embodiment, a compound of the disclosure comprises Formula (II), wherein $R^1$ may be

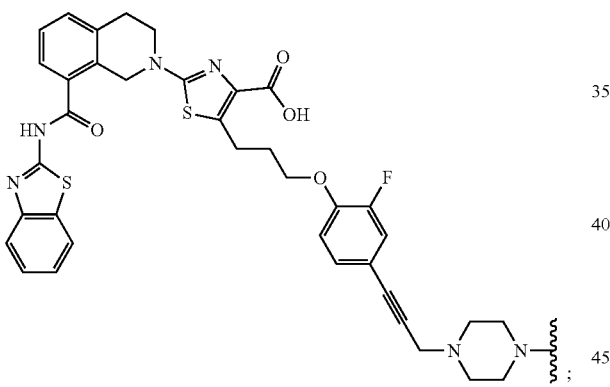

$R^3$ may be 2-pentanone; n may be 2, A may be a triazole; $R^4$ may be a bond; and $R^2$ may be

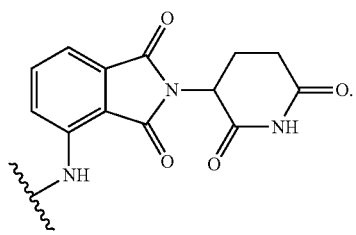

In a preferred embodiment, a compound of the disclosure comprises Formula (II), wherein $R^1$ may be

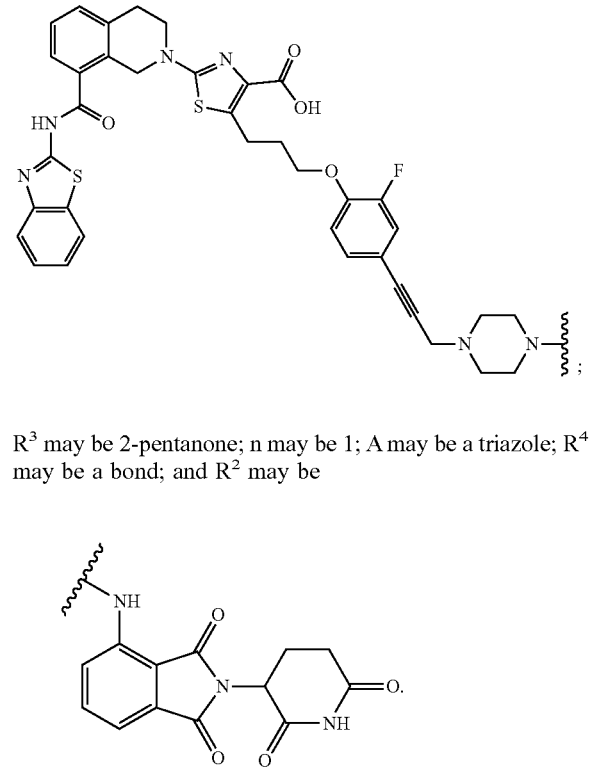

$R^3$ may be 2-pentanone; n may be 1; A may be a triazole; $R^4$ may be a bond; and $R^2$ may be In a preferred embodiment, a compound of the disclosure comprises Formula (II), wherein $R^1$ may be $R^3$ may be propyl; n may be 2; A may be a triazole; $R^4$ may be a bond; and $R^2$ may be In a preferred embodiment, a compound of the disclosure comprises Formula (II), wherein $R^1$ may be

337

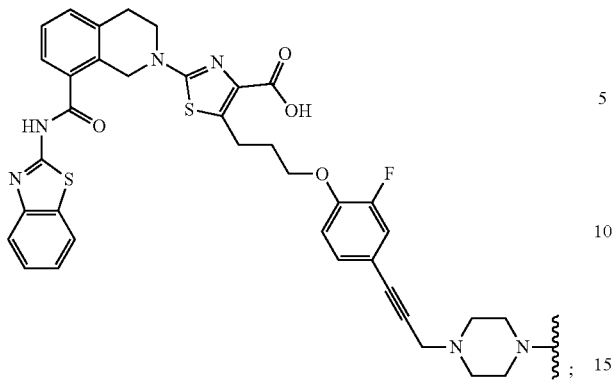

$R^3$ may be 2-pentanone; n may be 3; A may be a triazole; $R^4$ may be a bond; and $R^2$ may be

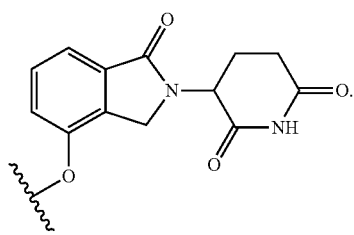 [SMILES: *Oc1cccc2c1CN(C1CCC(=O)NC1=O)C2=O]

In a preferred embodiment, a compound of the disclosure comprises Formula (II), wherein $R^1$ may be

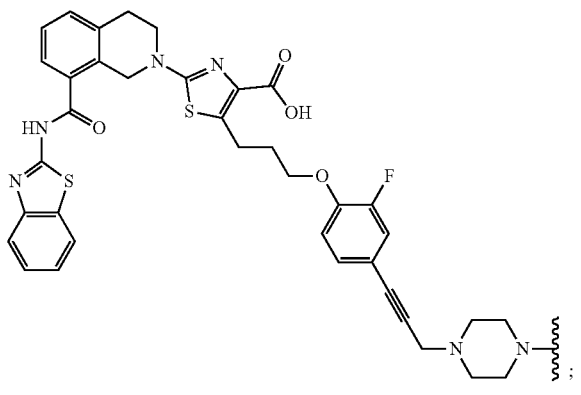 [SMILES: *N1CCN(CC#Cc2ccc(OCCCc3sc(N4CCc5cccc(C(=O)Nc6nc7ccccc7s6)c5C4)nc3C(=O)O)c(F)c2)CC1]

$R^3$ may be 2-pentanone; n may be 1; A may be a triazole; $R^4$ may be a bond; and $R^2$ may be

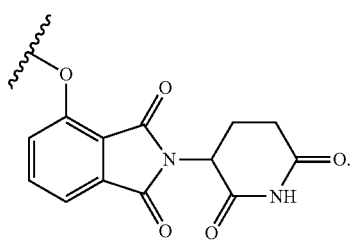 [SMILES: *Oc1cccc2c1C(=O)N(C1CCC(=O)NC1=O)C2=O]

In a preferred embodiment, a compound of the disclosure comprises Formula (II), wherein $R^1$ may be

338

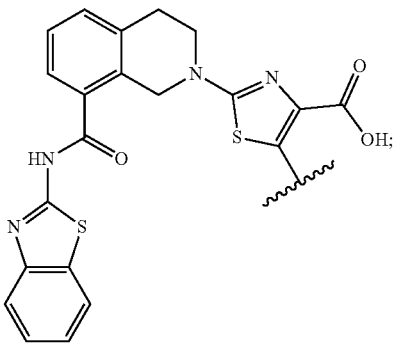 [SMILES: *c1sc(N2CCc3cccc(C(=O)Nc4nc5ccccc5s4)c3C2)nc1C(=O)O]

$R^3$ may be $C_3$-alkyl; n may be 3; A may be a triazole; $R^4$ may be a bond; and $R^2$ may be

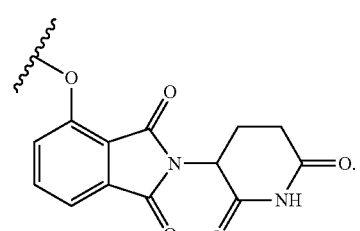

In a preferred embodiment, a compound of the disclosure comprises Formula (II), wherein $R^1$ may be

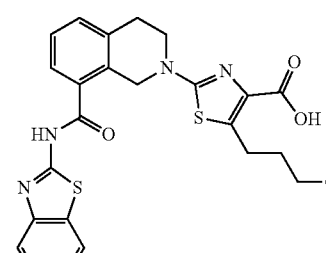

$R^3$ may be 2-pentanone; n may be 2; A may be a triazole; $R^4$ may be a bond; and $R^2$ may be

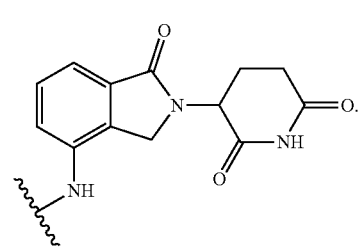 [SMILES: *Nc1cccc2c1CN(C1CCC(=O)NC1=O)C2=O]

In a preferred embodiment, a compound of the disclosure comprises Formula (II), wherein $R^1$ may be

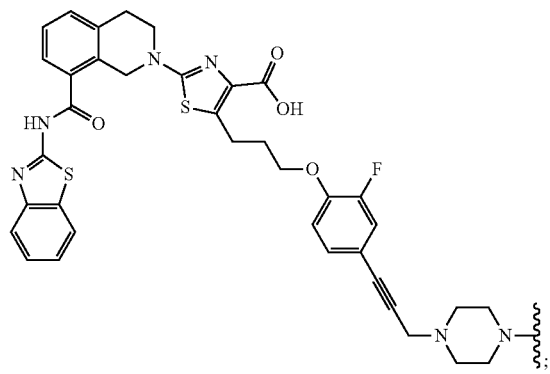 [SMILES: *N1CCN(CC#Cc2ccc(OCCCc3sc(N4CCc5cccc(C(=O)Nc6nc7ccccc7s6)c5C4)nc3C(=O)O)c(F)c2)CC1]

$R^3$ may be 2-pentanone; n may be 1; A may be a triazole; $R^4$ may be a bond; and $R^2$ may be

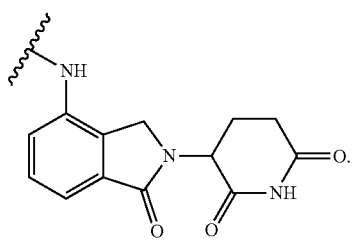 [SMILES: *Nc1cccc2c1CN(C1CCC(=O)NC1=O)C2=O]

In a preferred embodiment, a compound of the disclosure comprises Formula (II), wherein $R^1$ may be

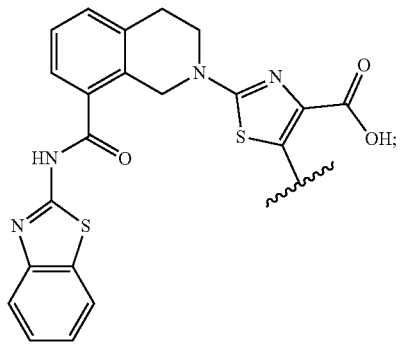 [SMILES: *c1sc(N2CCc3cccc(C(=O)Nc4nc5ccccc5s4)c3C2)nc1C(=O)O]

$R^3$ may be propyl; n may be 2; A may be a triazole; $R^4$ may be a bond; and $R^2$ may be

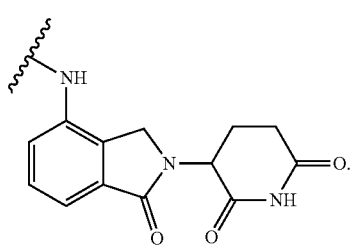 [SMILES: *Nc1cccc2c1CN(C1CCC(=O)NC1=O)C2=O]

In a preferred embodiment, a compound of the disclosure comprises Formula (II), wherein $R^1$ may be $R^3$ may be butan-1-amine; A may be absent; n may be 2; $R^4$ may be N-(4-ethylamino)butyl)acetamide; and $R^2$ may be

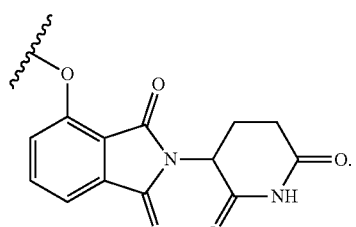

In a preferred embodiment, a compound of the disclosure comprises Formula (II), wherein $R^1$ may be

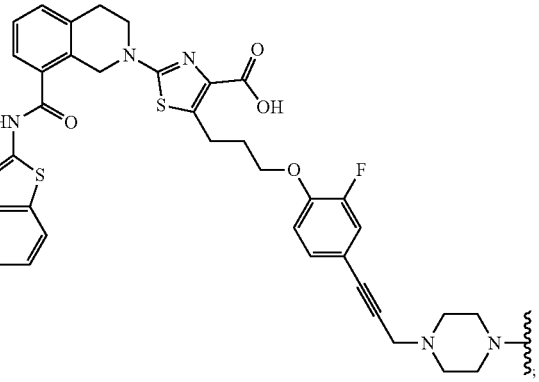

$R^3$ may be 2-pentanone; n may be 2; A may be a triazole; $R^4$ may be C(O); and $R^2$ may be

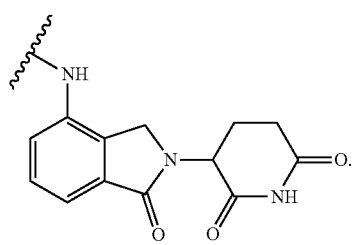 [SMILES: *Nc1cccc2c1CN(C1CCC(=O)NC1=O)C2=O]

In a preferred embodiment, a compound of the disclosure comprises Formula (II), wherein $R^1$ may be

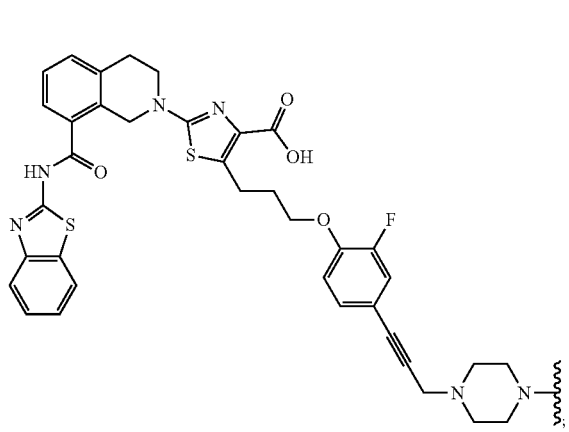 [SMILES: *N1CCN(CC#Cc2ccc(OCCCc3sc(N4CCc5cccc(C(=O)Nc6nc7ccccc7s6)c5C4)nc3C(=O)O)c(F)c2)CC1]

$R^3$ may be 2-pentanone; n may be 2; A may be a triazole; $R^4$ may be a bond; and $R^2$ may be

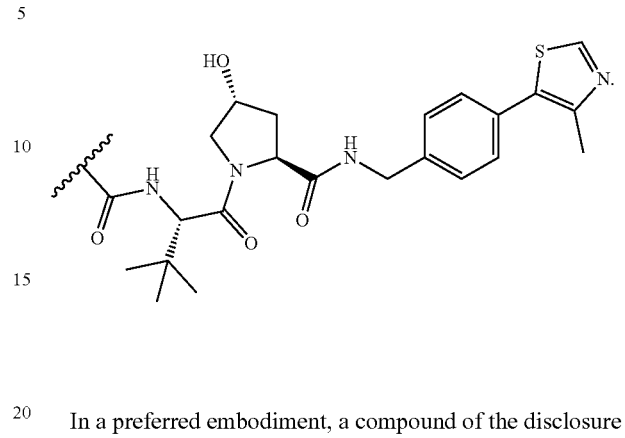

In a preferred embodiment, a compound of the disclosure comprises Formula (II), wherein $R^1$ may be

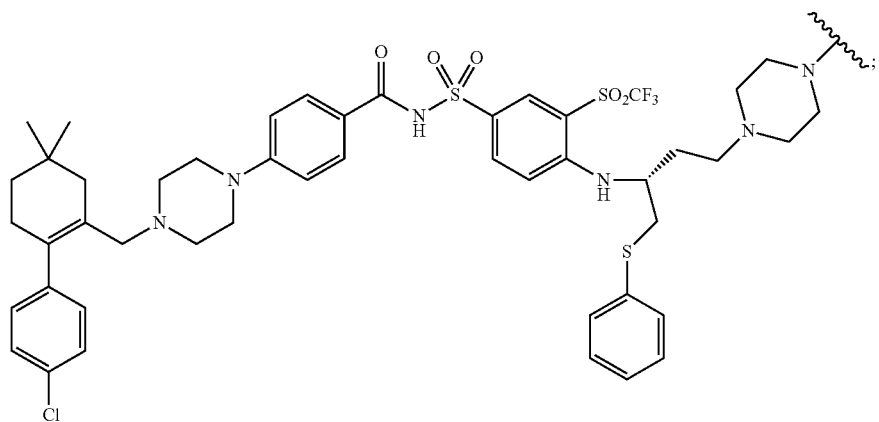

$R^3$ may be 2-pentanone; n may be 2; A may be a triazole; $R^4$ may be a bond; and $R^2$ may be

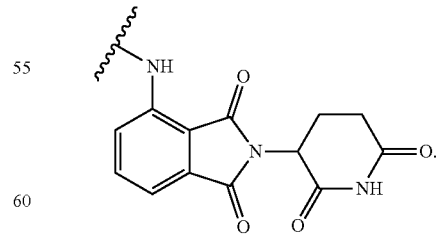

In a preferred embodiment, a compound of the disclosure comprises Formula (II), wherein $R^1$ may be

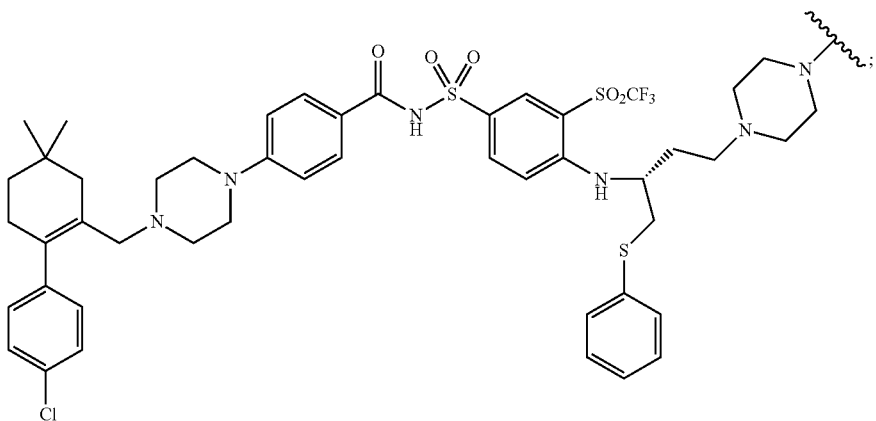
R³ may be 2-pentanone; n may be 1; A may be a triazole; R⁴ may be a bond; and R² may be
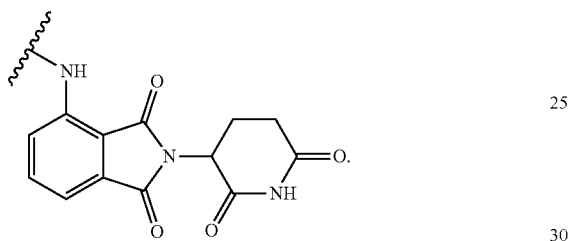
In a preferred embodiment, a compound of the disclosure comprises Formula (II), wherein R¹ may be
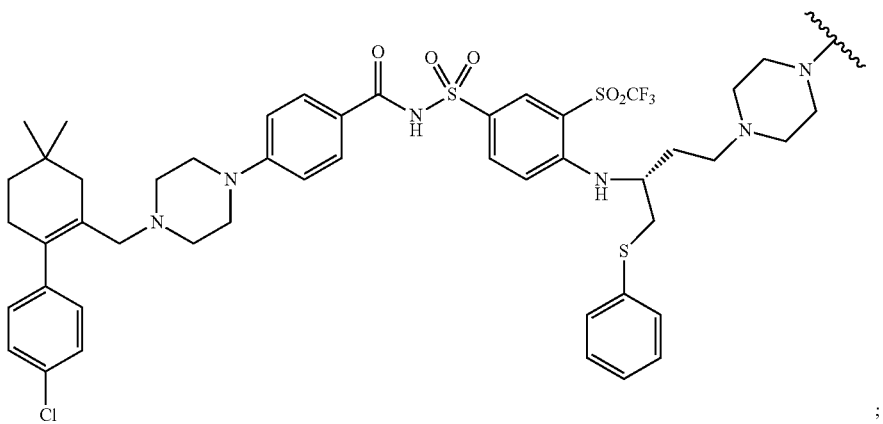
R³ may be C(O)NH; n may be 1; A may be absent; R⁴ may be a bond; and R² may be
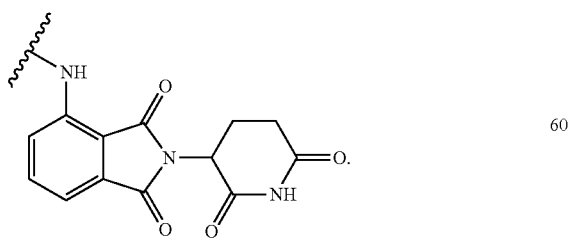
In a preferred embodiment, a compound of the disclosure comprises Formula (II), wherein R¹ may be

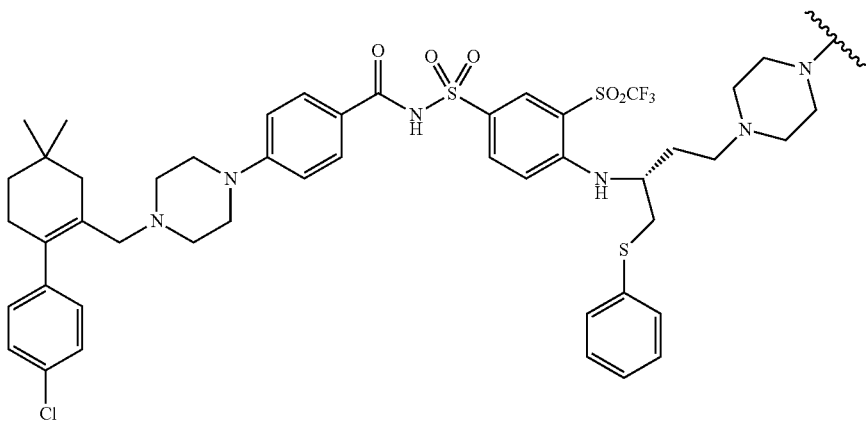
;
R³ may be C(S)NH; n may be 1; A may be absent; R⁴ may be a bond; and R² may be
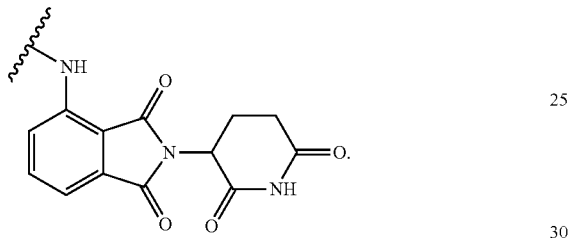
In a preferred embodiment, a compound of the disclosure comprises Formula (II), wherein R¹ may be
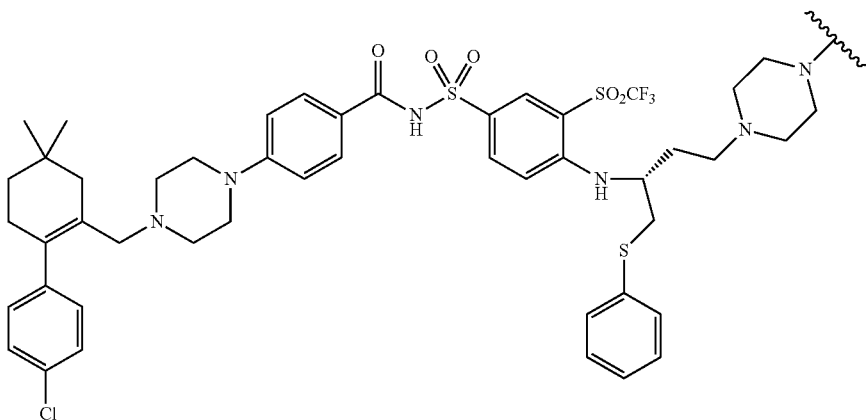
;
R³ may be C(O); n may be 1; A may be absent; R⁴ may be a bond; and R² may be
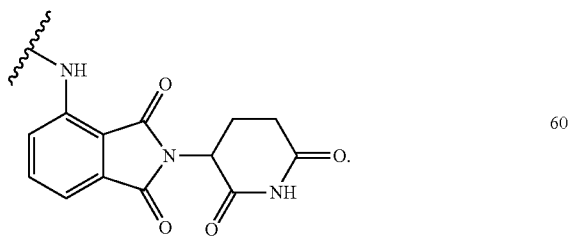
In a preferred embodiment, a compound of the disclosure comprises Formula (II), wherein R¹ may be

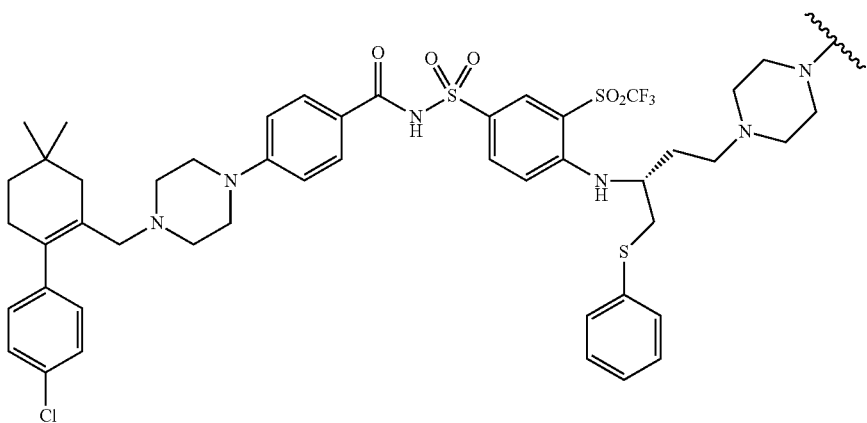
R³ may be C(O); n may be 2; A may be absent; R⁴ may be a bond; and R² may be
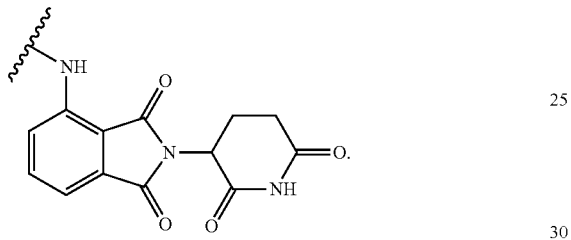
In a preferred embodiment, a compound of the disclosure comprises Formula (II), wherein R¹ may be
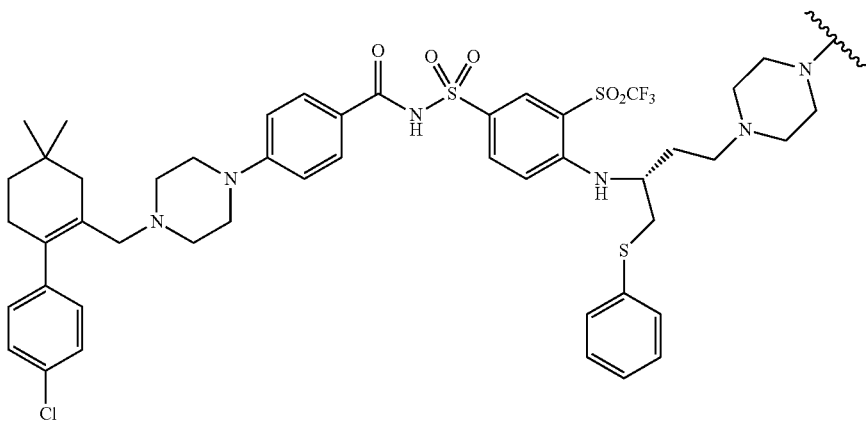
R³ may be C(O); n may be 3; A may be absent; R⁴ may be a bond; and R² may be
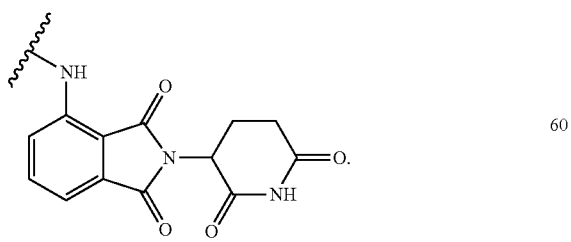
In a preferred embodiment, a compound of the disclosure comprises Formula (II), wherein R¹ may be

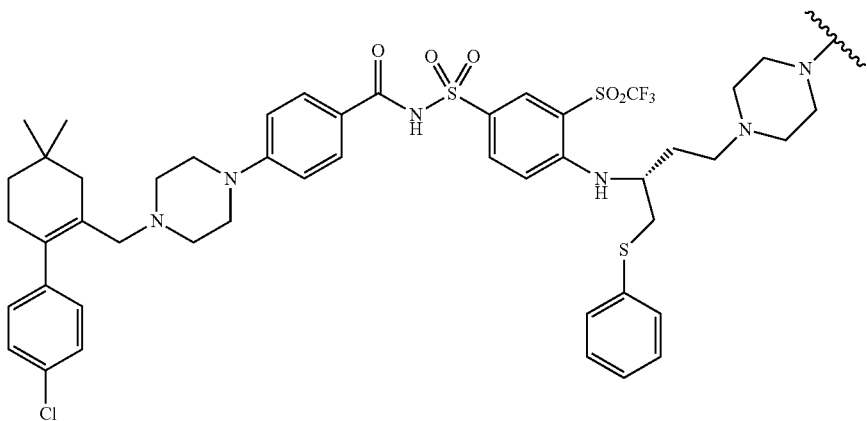
;
R³ may be C(O); n may be 0; A may be absent; R⁴ may be a bond; and R² may be
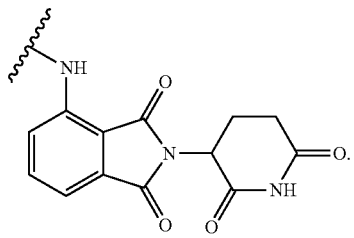 [SMILES: *Nc1cccc2c1C(=O)N(C1CCC(=O)NC1=O)C2=O]
In a preferred embodiment, a compound of the disclosure comprises Formula (II), wherein R¹ may be
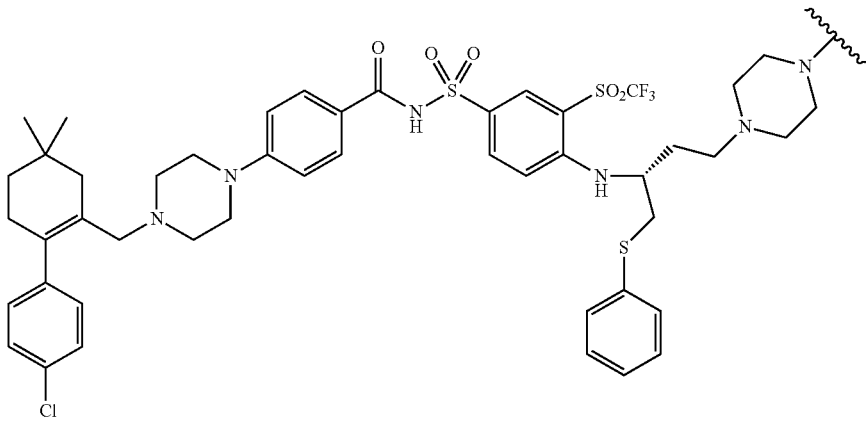
;
R³ may be a bond; n may be 1; A may be absent; R⁴ may be a bond; and R² may be
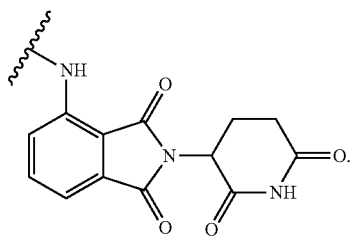 [SMILES: *Nc1cccc2c1C(=O)N(C1CCC(=O)NC1=O)C2=O]
In a preferred embodiment, a compound of the disclosure comprises Formula (II), wherein R¹ may be

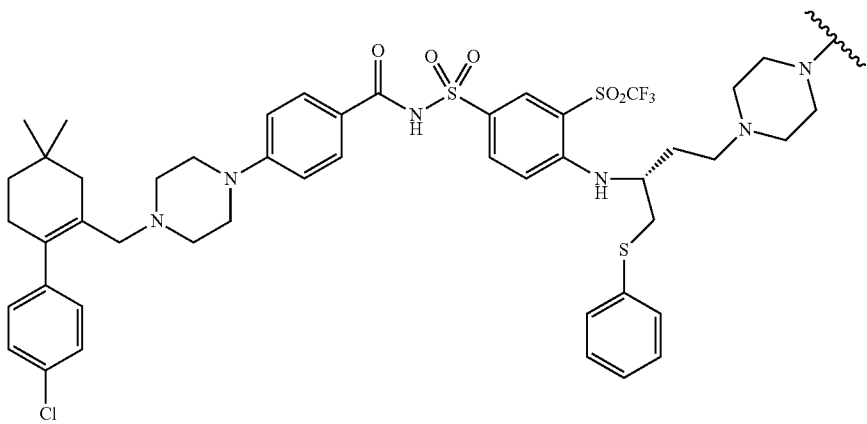
R³ may be C(O)CH₂; n may be 1; A may be a triazole; R⁴ may be a bond; and R² may be
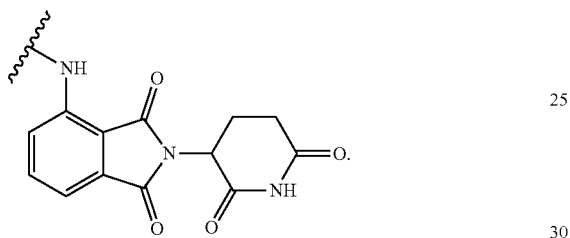
In a preferred embodiment, a compound of the disclosure comprises Formula (II), wherein R¹ may be
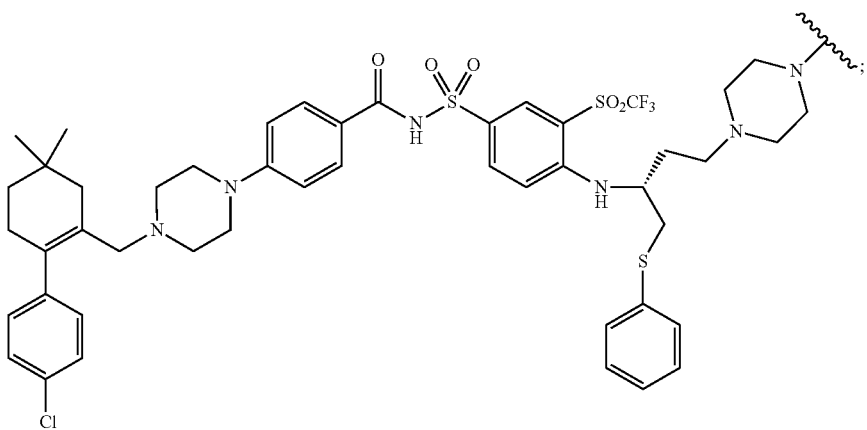
R³ may be C(O)NH; n may be 1; A may be a bond; R⁴ may be (CH₂)₂C(O)NH; and R² may be
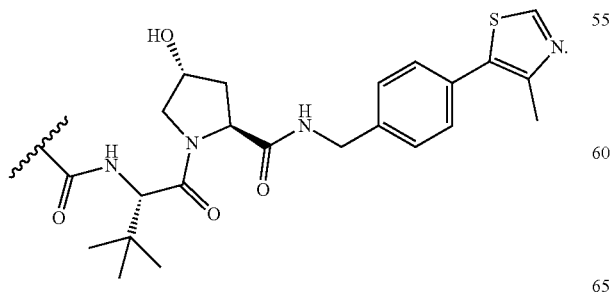
In a preferred embodiment, a compound of the disclosure comprises Formula (II), wherein R¹ may be

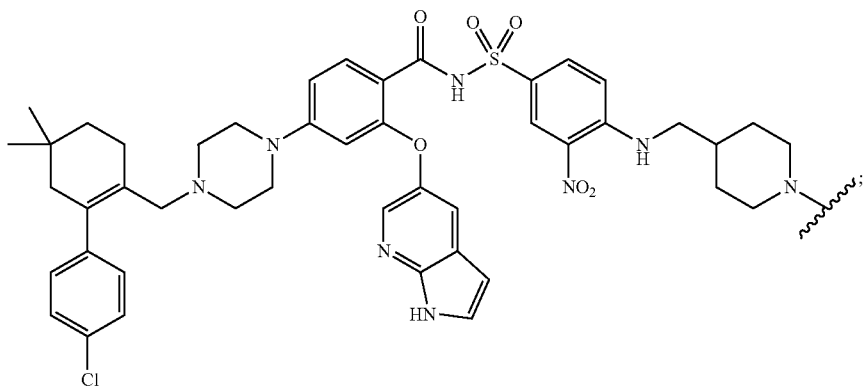 [SMILES: *N1CCC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1]
R³ may be C(O); n may be 2; A may be absent; R⁴ may be a bond; and R² may be
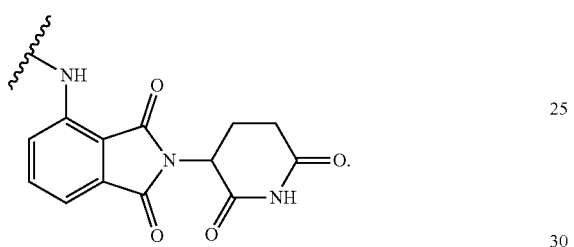
In a preferred embodiment, a compound of the disclosure comprises Formula (II), wherein R¹ may be
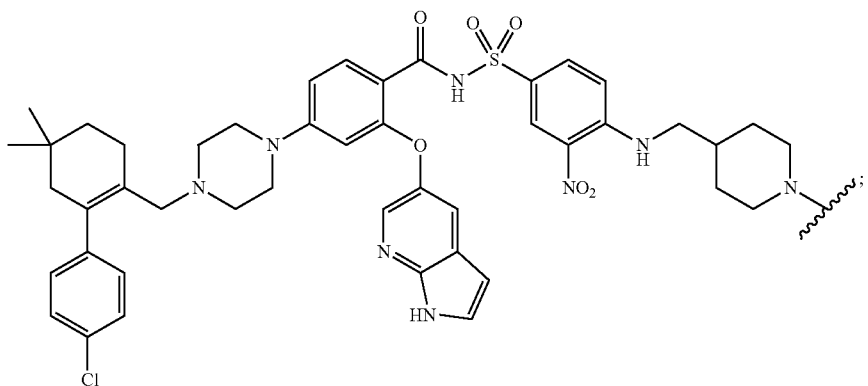 [SMILES: *N1CCC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1]
R³ may be C(O)NH; n may be 1; A may be a bond; R⁴ may be (CH₂)₂C(O)NH; and R² may be
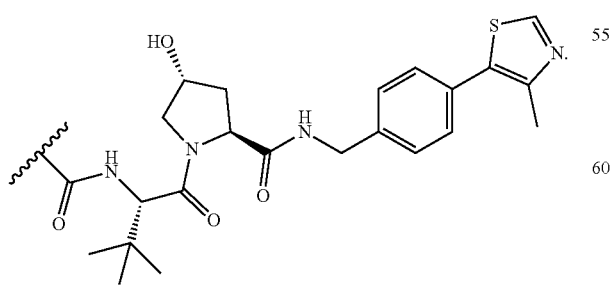
In a preferred embodiment, a compound of the disclosure comprises Formula (II), wherein R¹ may be

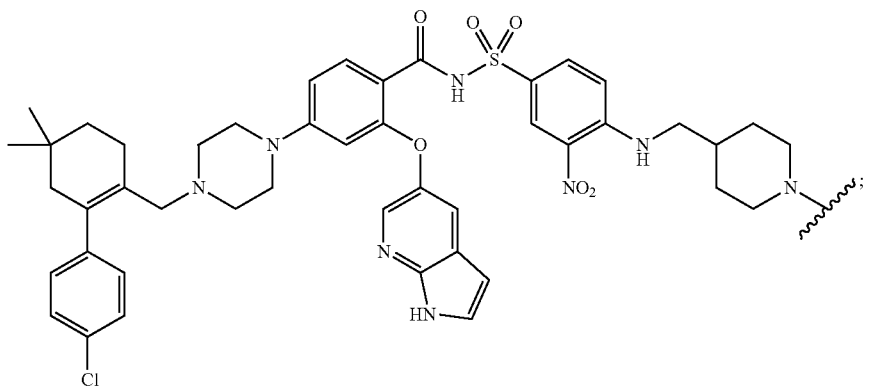 [SMILES: *N1CCC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1]
$R^3$ may be a bond; n may be 0; A may be absent; $R^4$ may be a bond; and $R^2$ may be
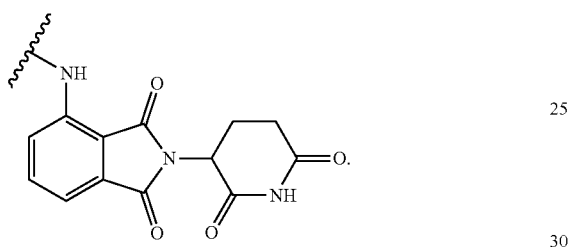
In a preferred embodiment, a compound of the disclosure comprises Formula (II), wherein $R^1$ may be
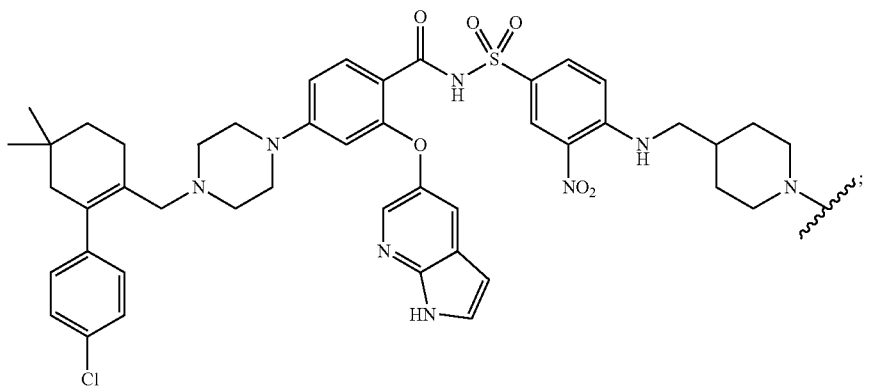 [SMILES: *N1CCC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1]
$R^3$ may be a bond; n may be 1; A may be absent; $R^4$ may be a bond; and $R^2$ may be
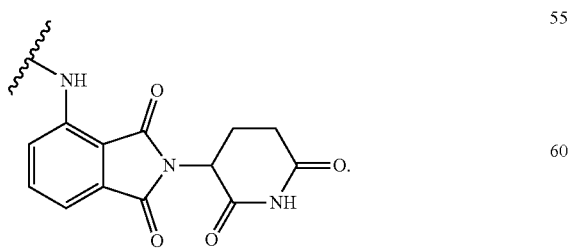
In a preferred embodiment, a compound of the disclosure comprises Formula (II), wherein $R^1$ may be

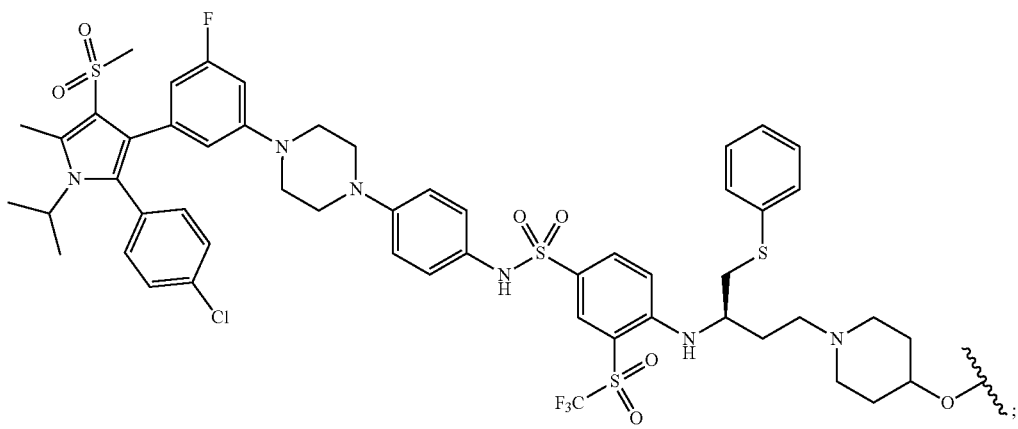 [SMILES: *OC1CCN(CC[C@H](CSc2ccccc2)Nc2ccc(S(=O)(=O)Nc3ccc(N4CCN(c5cc(F)cc(-c6c(S(C)(=O)=O)c(C)n(C(C)C)c6-c6ccc(Cl)cc6)c5)CC4)cc3)cc2S(=O)(=O)C(F)(F)F)CC1]
$R^3$ may be C(O)NH; n may be 1; A may be absent; $R^4$ may be a bond; and $R^2$ may be
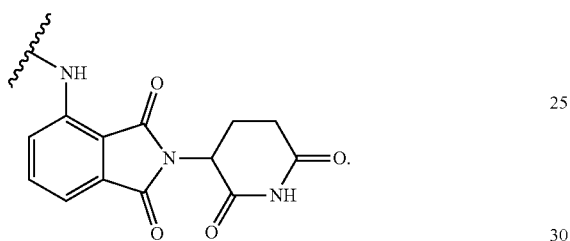
In a preferred embodiment, a compound of the disclosure comprises Formula (II), wherein $R^1$ may be
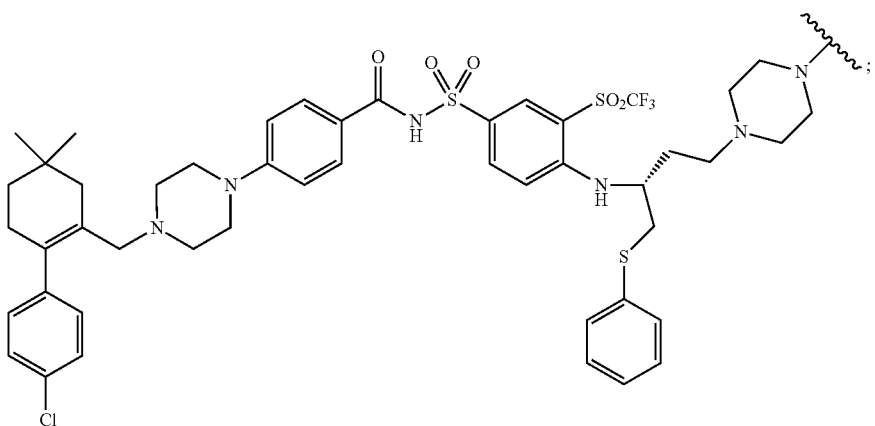
$R^1$ may be a bond; A may be absent; n may be 2; $R^4$ may be N-(4-ethylamino)butyl)acetamide; and $R^2$ may be
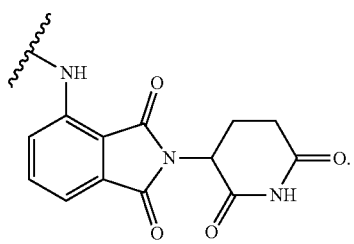 [SMILES: *Nc1cccc2c1C(=O)N(C1CCC(=O)NC1=O)C2=O]
In a preferred embodiment, a compound of the disclosure comprises Formula (II), wherein $R^1$ may be

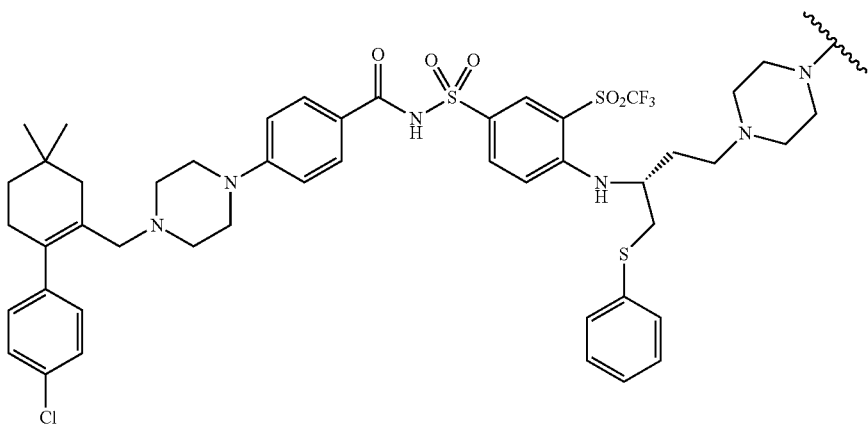

;

$R^3$ may be a bond; A may be absent; n may be 2; $R^4$ may be N-(4-ethylamino)butyl)acetamide; and $R^2$ may be

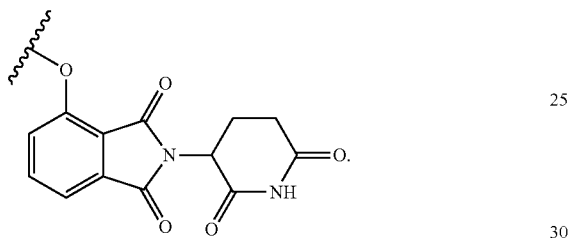

.

In a preferred embodiment, a compound of the disclosure comprises Formula (II), wherein $R^1$ may be

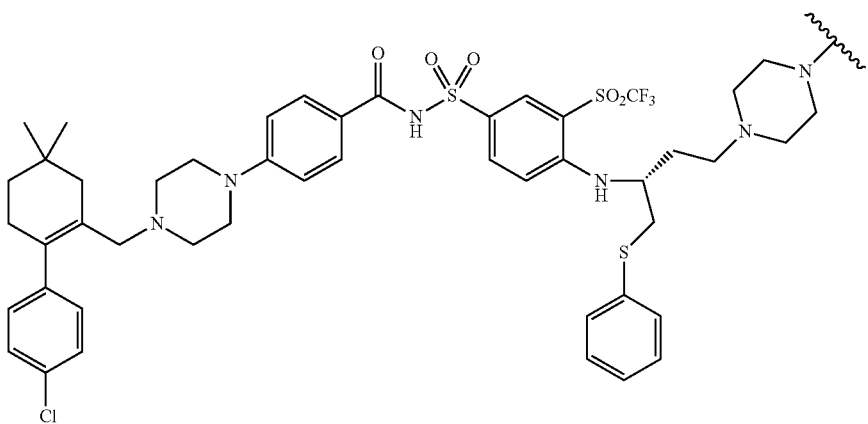

;

$R^3$ may be a bond; A may be absent; n may be 2; $R^4$ may be N-(4-ethylamino)butyl)acetamide; and $R^2$ may be

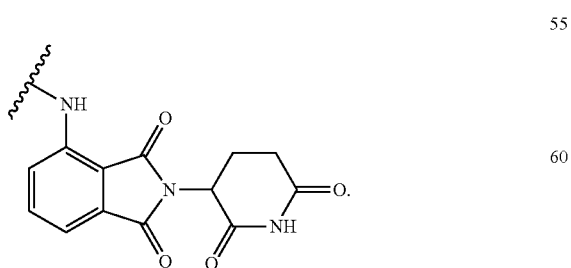

.

In a preferred embodiment, a compound of the disclosure comprises Formula (II), wherein $R^1$ may be

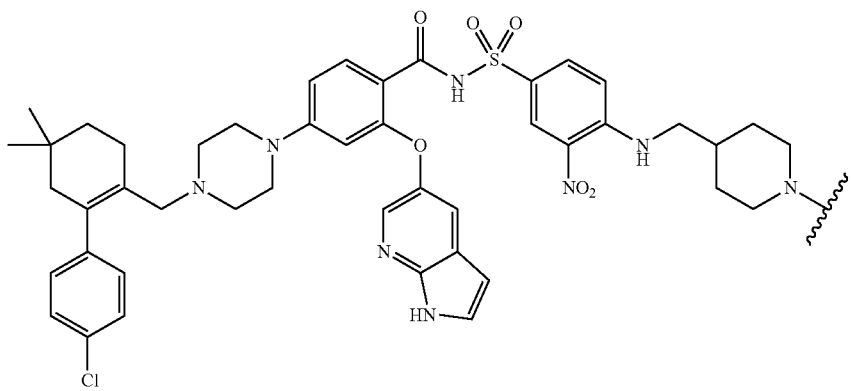
$R^3$ may be a bond; A may be absent; n may be 2; $R^4$ may be a bond; and $R^2$ may be
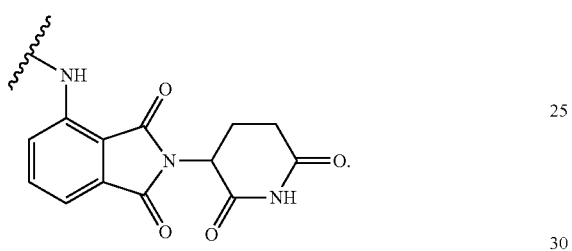
In a preferred embodiment, a compound of the disclosure comprises Formula (II), wherein $R^1$ may be
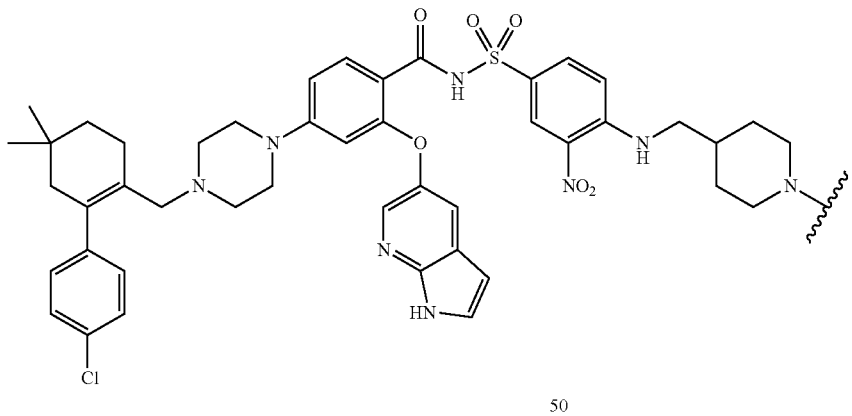
$R^3$ may be 2-pentanone; A may be a triazole; n may be 2; $R^4$ may be a bond; and $R^2$ may be
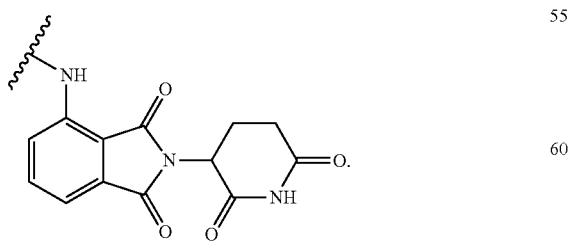
In a preferred embodiment, a compound of the disclosure comprises Formula (II), wherein $R^1$ may be

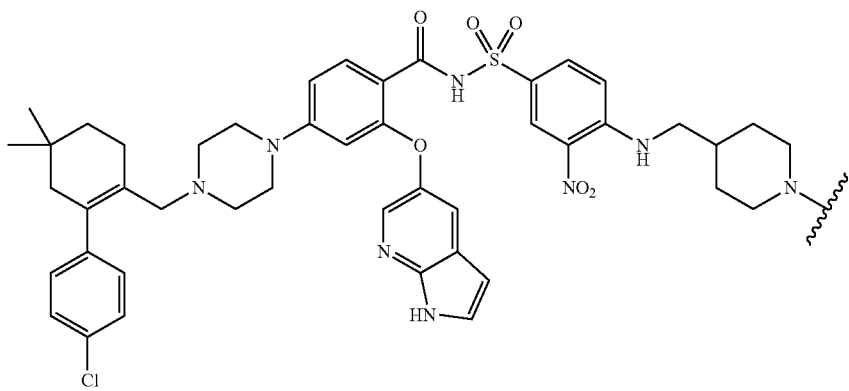

$R^3$ may be 2-pentanone; A may be a triazole; n may be 2; $R^4$ may be a bond; and $R^2$ may be

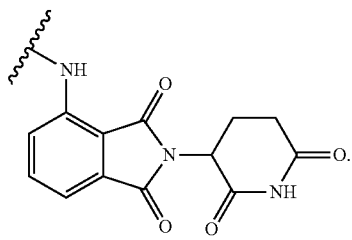 [SMILES: *Nc1cccc2c1C(=O)N(C1CCC(=O)NC1=O)C2=O]

In a preferred embodiment, a compound of the disclosure comprises Formula (II), wherein $R^1$ may be

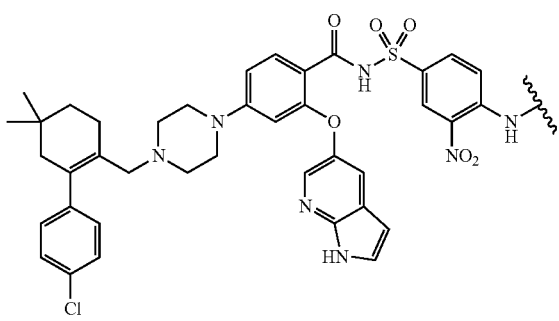

$R^3$ may be N-ethylpropionamide; A may be a triazole; n may be 2; $R^4$ may be a bond; and $R^2$ may be

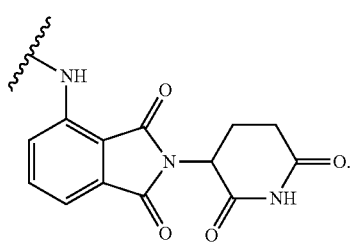 [SMILES: *Nc1cccc2c1C(=O)N(C1CCC(=O)NC1=O)C2=O]

In a preferred embodiment, a compound of the disclosure comprises Formula (II), wherein $R^1$ may be

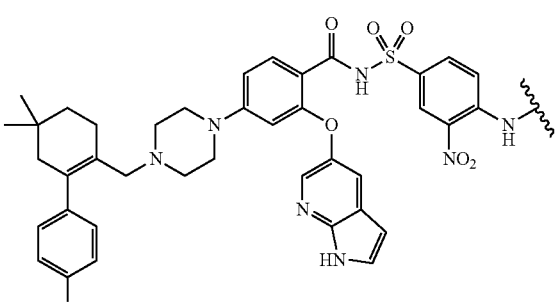

$R^3$ may be propyl; A may be triazole; n may be 3; $R^4$ may be a bond; and $R^2$ may be

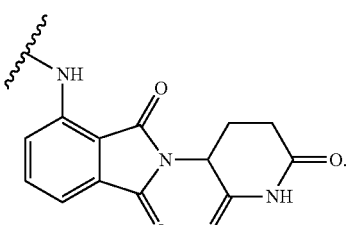

In a preferred embodiment, a compound of the disclosure comprises Formula (II), wherein $R^1$ may be

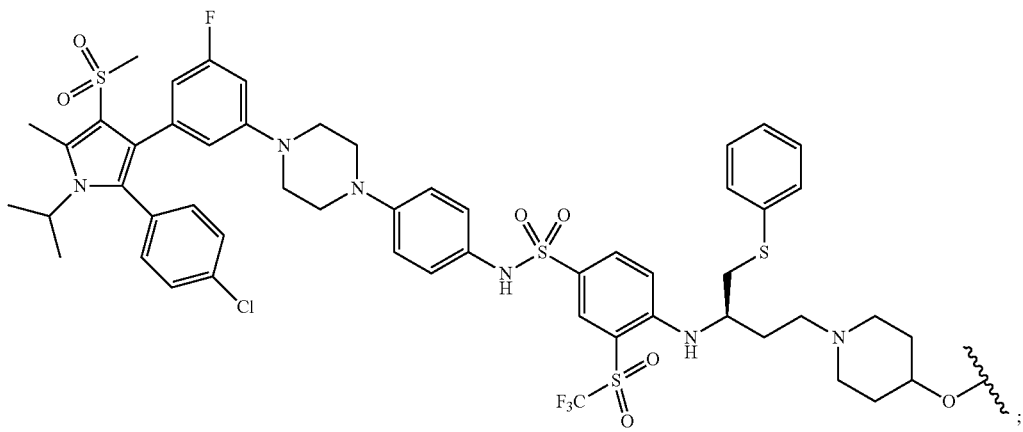 [SMILES: *OC1CCN(CC[C@H](CSc2ccccc2)Nc2ccc(S(=O)(=O)Nc3ccc(N4CCN(c5cc(F)cc(-c6c(S(C)(=O)=O)c(C)n(C(C)C)c6-c6ccc(Cl)cc6)c5)CC4)cc3)cc2S(=O)(=O)C(F)(F)F)CC1]
R³ may be a bond; A is absent; n may be 3; R⁴ may be N-(4-(ethylamino)butyl)acetamide; and R² may be
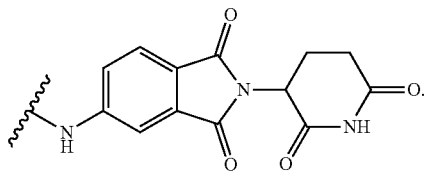 [SMILES: *Nc1ccc2c(c1)C(=O)N(C1CCC(=O)NC1=O)C2=O]
In a preferred embodiment, a compound of the disclosure comprises Formula (II), wherein R¹ may be
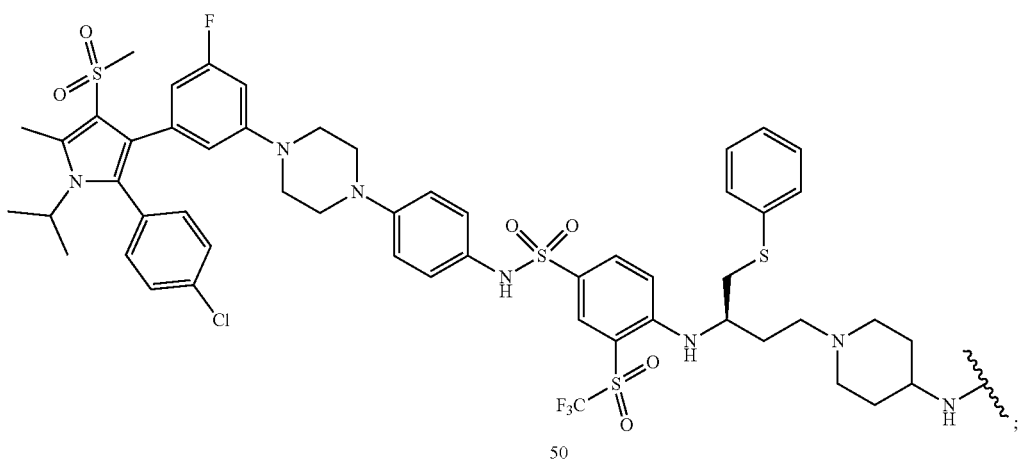
R³ may be propyl; A is a triazole; n may be 2; R⁴ may be a bond; and R² may be
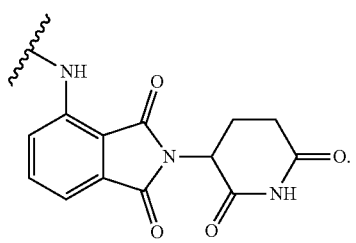 [SMILES: *Nc1cccc2c1C(=O)N(C1CCC(=O)NC1=O)C2=O]
In a preferred embodiment, a compound of the disclosure comprises Formula (II), wherein R¹ may be

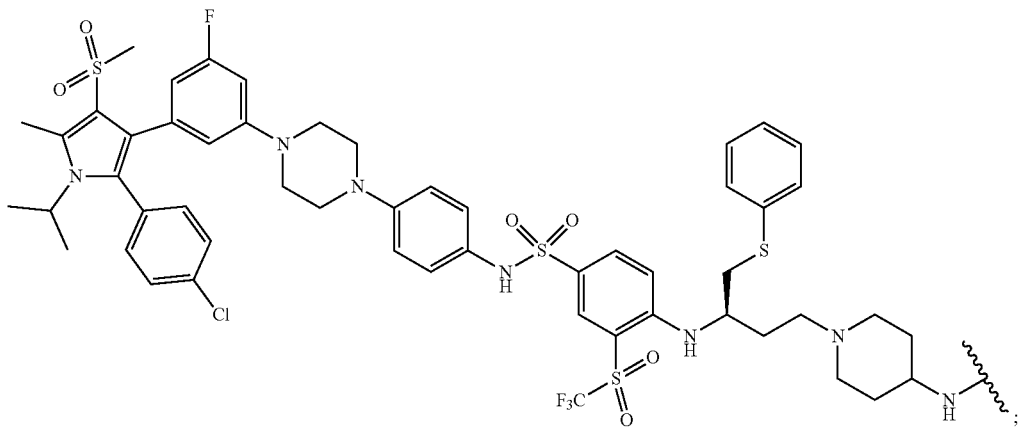 [SMILES: *NC1CCN(CC[C@H](CSc2ccccc2)Nc2ccc(S(=O)(=O)Nc3ccc(N4CCN(c5cc(F)cc(-c6c(S(C)(=O)=O)c(C)n(C(C)C)c6-c6ccc(Cl)cc6)c5)CC4)cc3)cc2S(=O)(=O)C(F)(F)F)CC1 ; ";"]
R³ may be a bond; A is absent; n may be 2; R⁴ may be N-(4-(ethylamino)butyl)acetamide; and R² may be
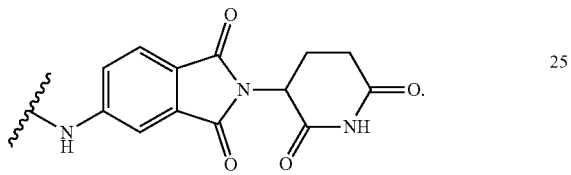
In a preferred embodiment, a compound of the disclosure comprises Formula (II), wherein R¹ may be
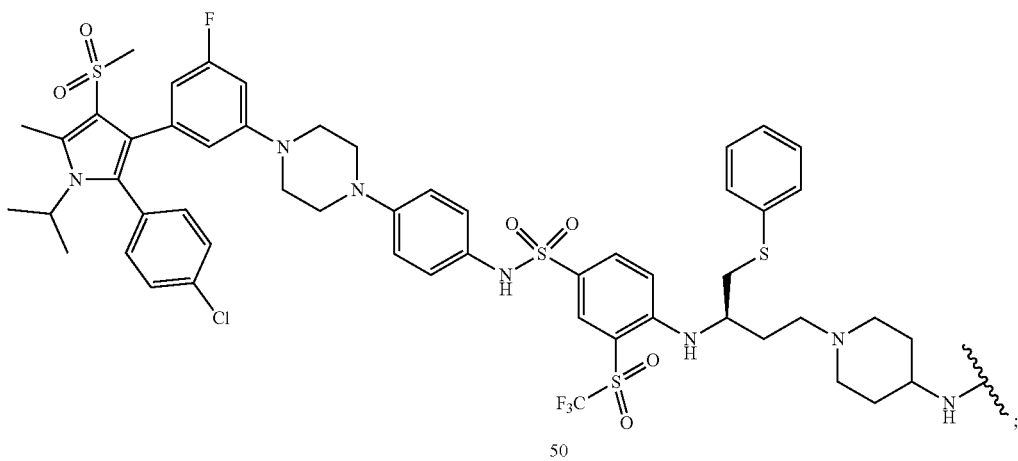
R³ may be a propyl; A is a triazole; n may be 2; R⁴ may be a bond; and R² may be
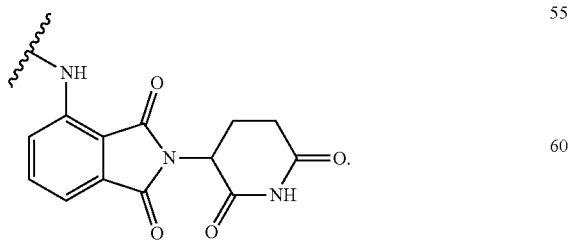
In a preferred embodiment, a compound of the disclosure comprises Formula (II), wherein R¹ may be

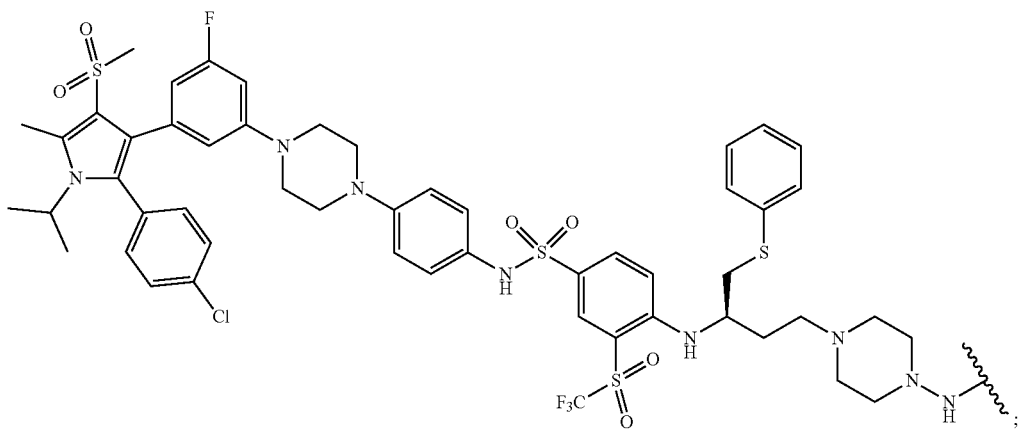 [SMILES: *NN1CCN(CC[C@H](CSc2ccccc2)Nc2ccc(S(=O)(=O)Nc3ccc(N4CCN(c5cc(F)cc(-c6c(S(C)(=O)=O)c(C)n(C(C)C)c6-c6ccc(Cl)cc6)c5)CC4)cc3)cc2S(=O)(=O)C(F)(F)F)CC1 ; ";"]

$R^3$ may by 2-pentanone; A may be triazole; n may be 2; $R^4$ may be a bond; and $R^2$ may be

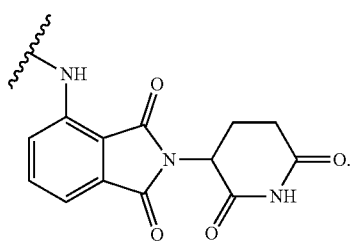 [SMILES: *Nc1cccc2c1C(=O)N(C1CCC(=O)NC1=O)C2=O]

In a preferred embodiment, a compound of the disclosure comprises Formula (II), wherein $R^1$ may be

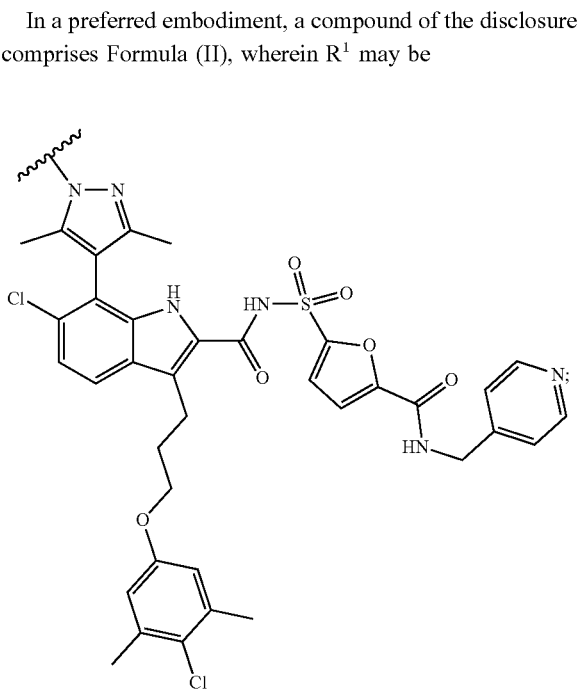

$R^3$ may by N-methylacetamide; A may be a triazole; n may be 2; $R^4$ may be a bond; and $R^2$ may be

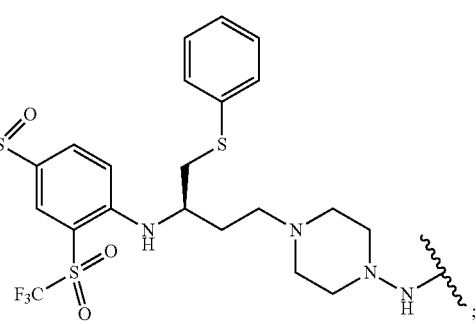

In a preferred embodiment, a compound of the disclosure comprises Formula (II), wherein $R^1$ may be

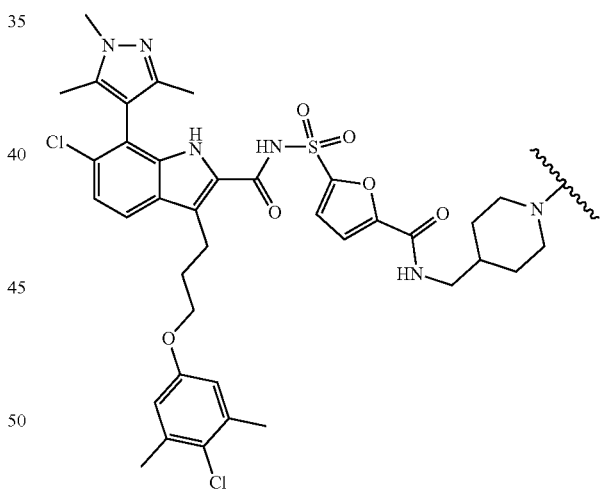

$R^3$ may by 2-pentanone; A may be a triazole; n may be 1; $R^4$ may be a bond; and $R^2$ may be

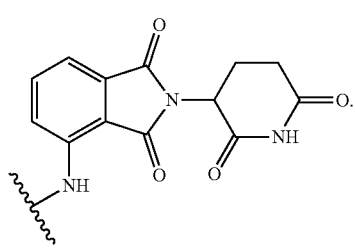 [SMILES: *Nc1cccc2c1C(=O)N(C1CCC(=O)NC1=O)C2=O]

In an exemplary embodiment, a compound of Formula (II) comprises any of the preceding compounds of Formula (II), may be selected from the group consisting of:
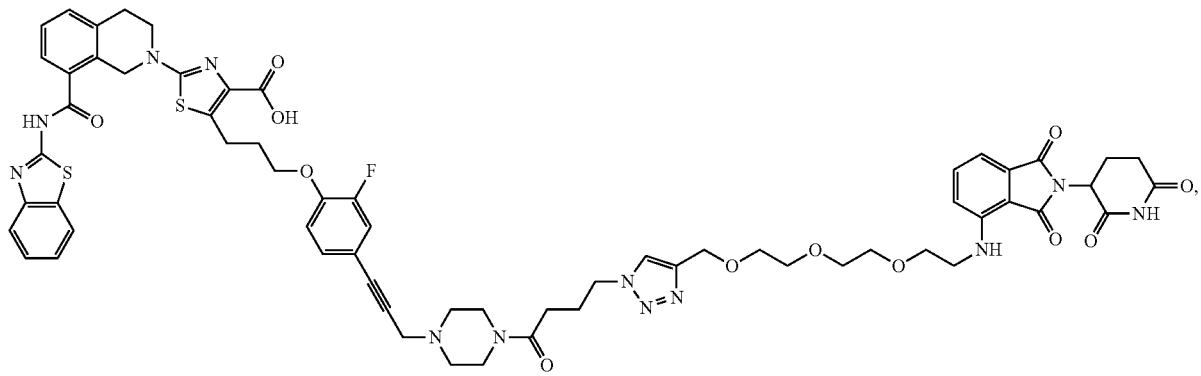
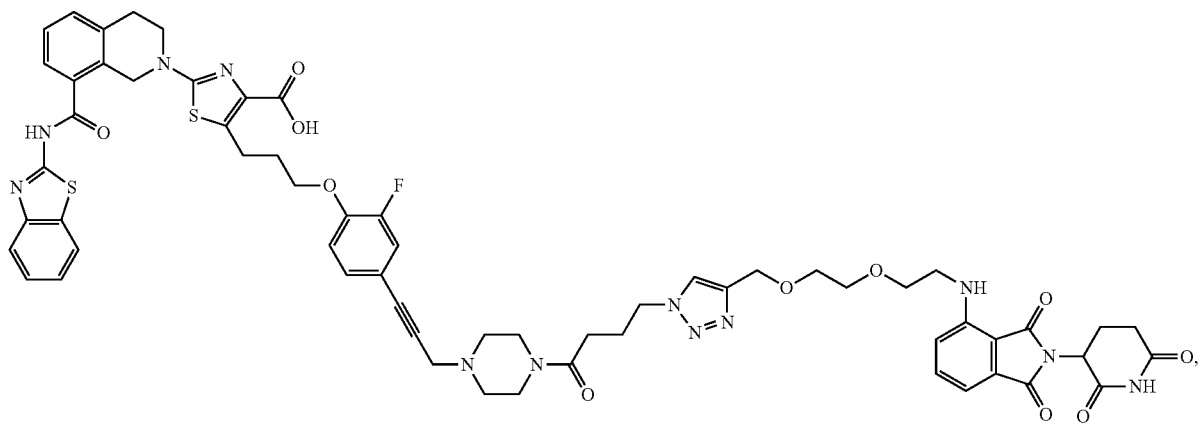
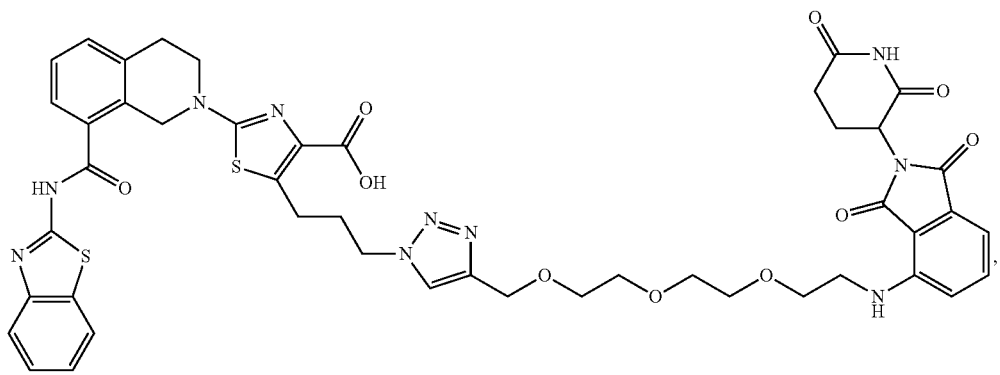
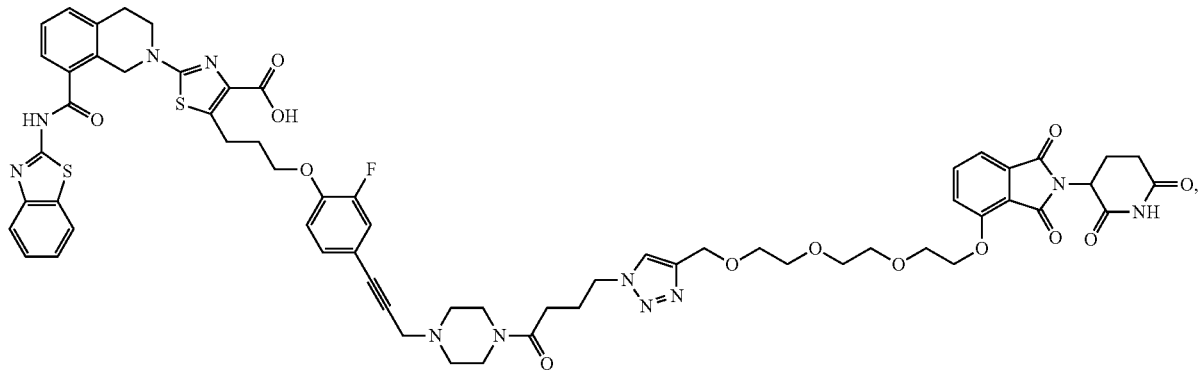

373
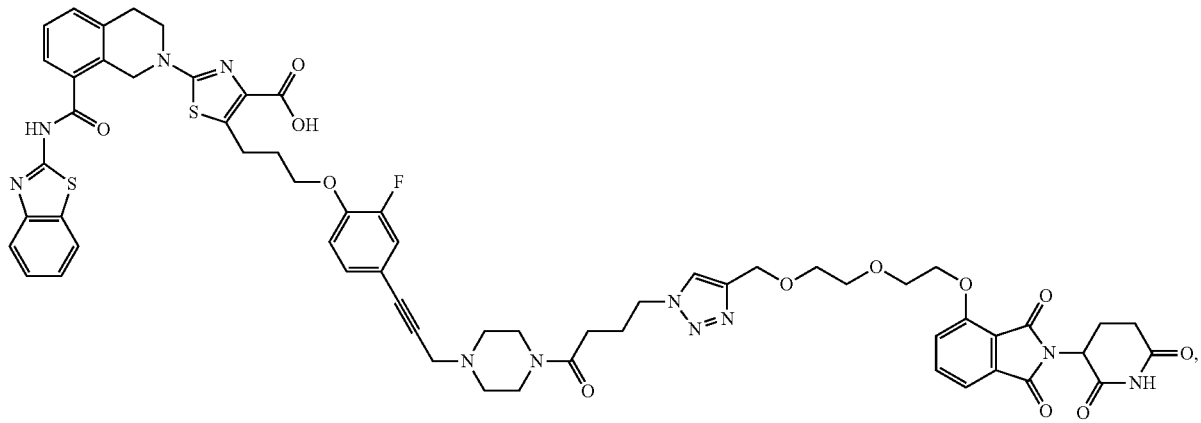
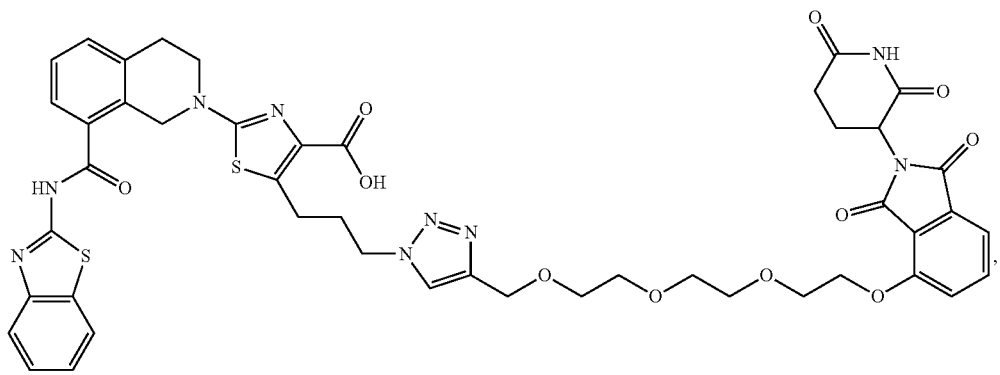
374
-continued
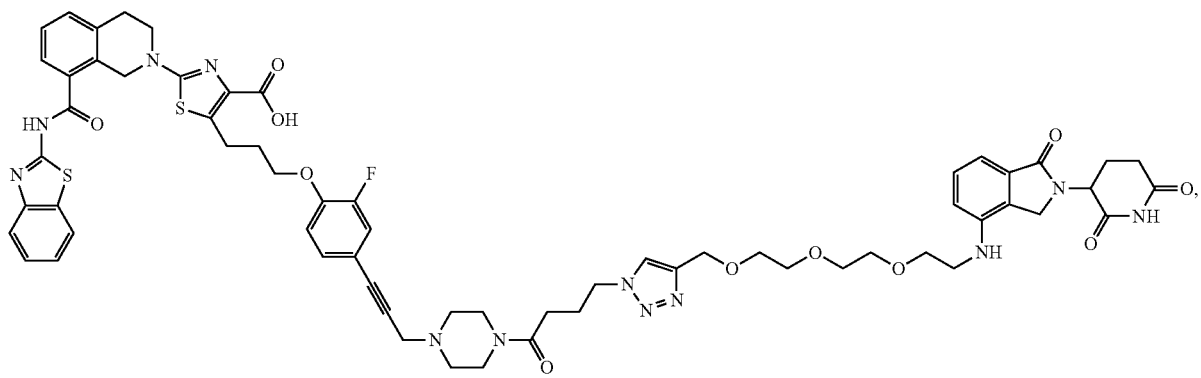
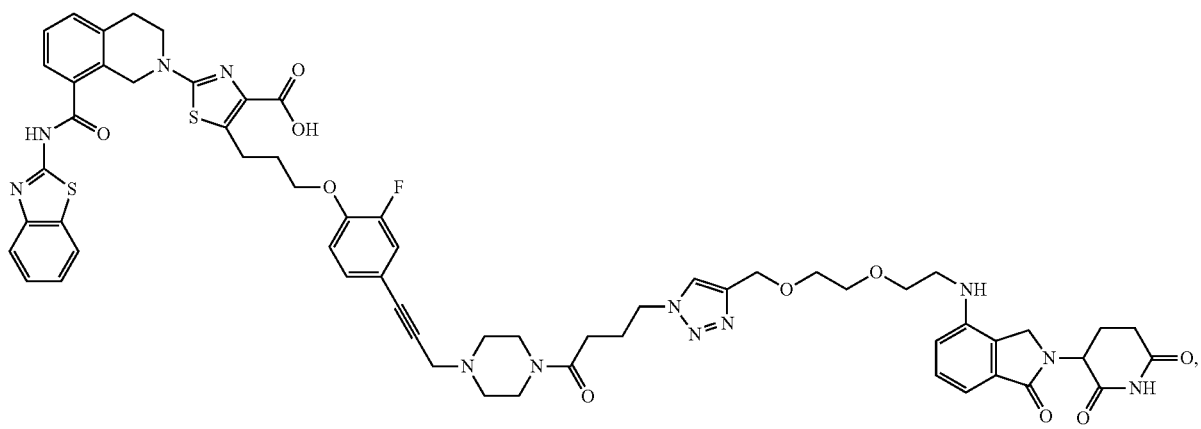

375 376
-continued
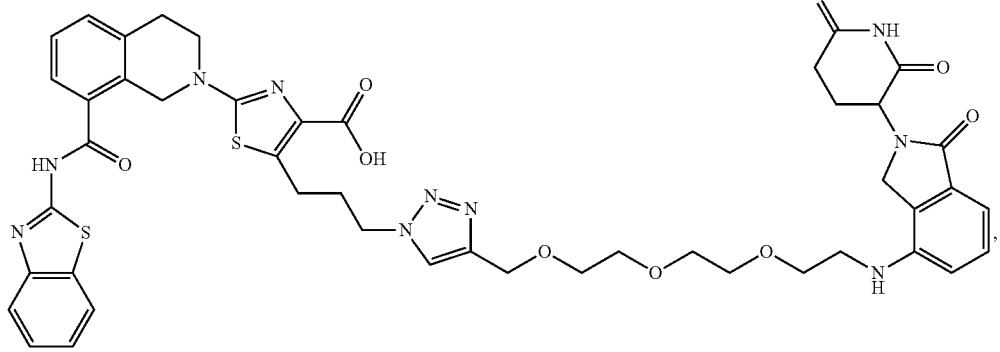
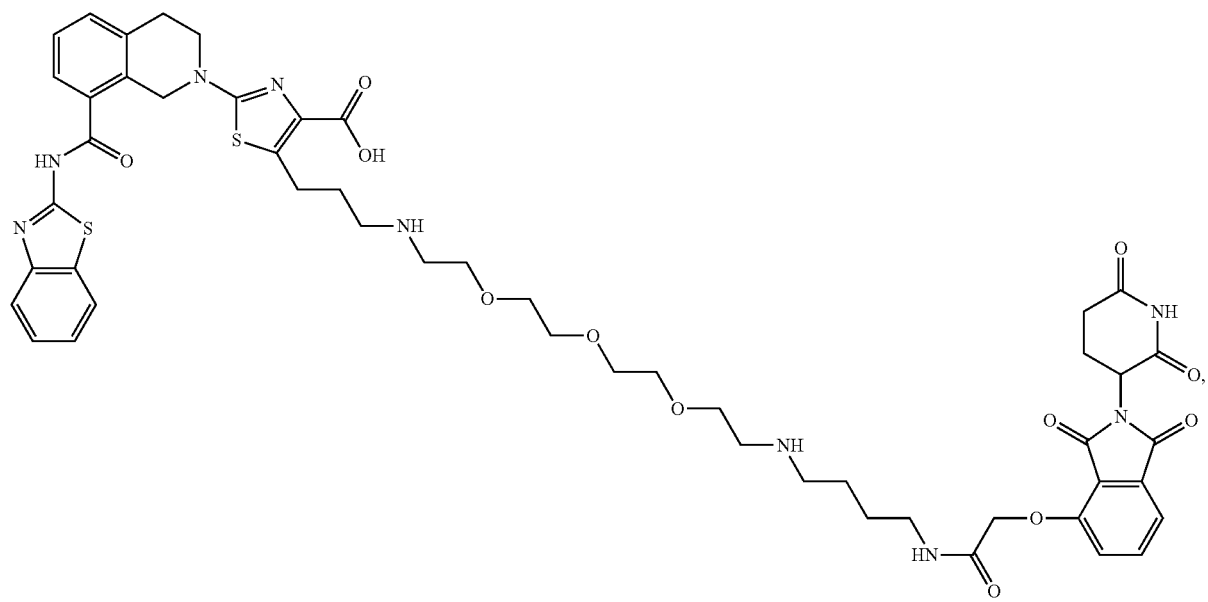
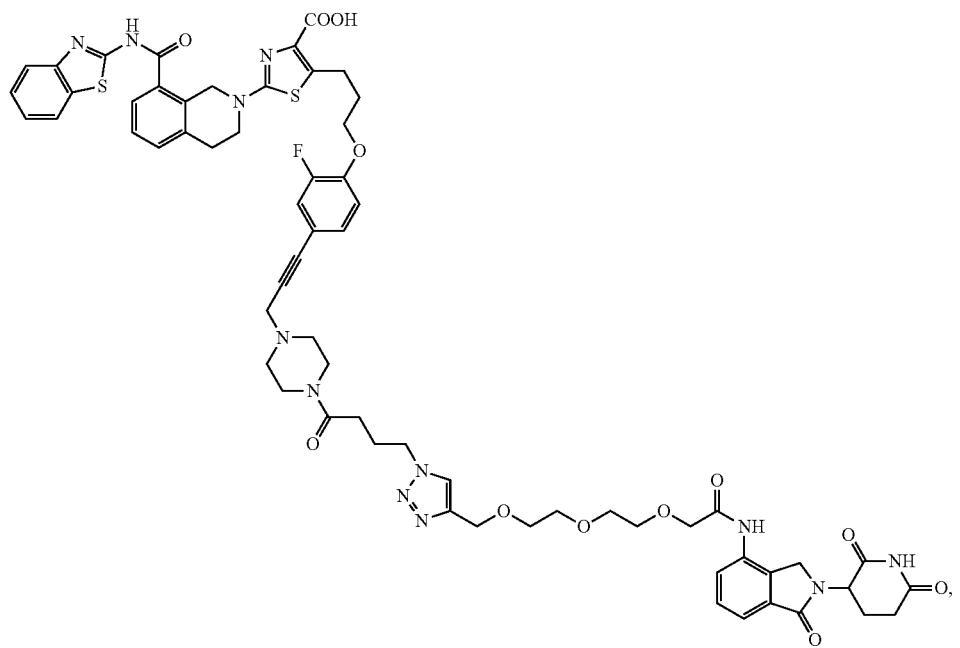

-continued
377
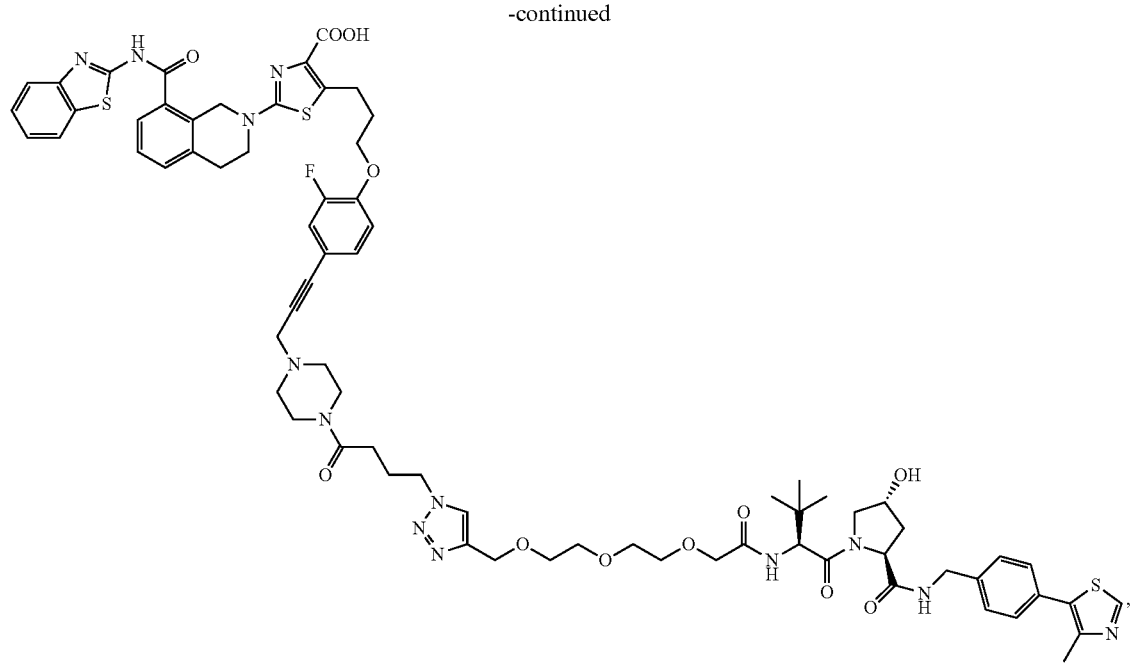
378
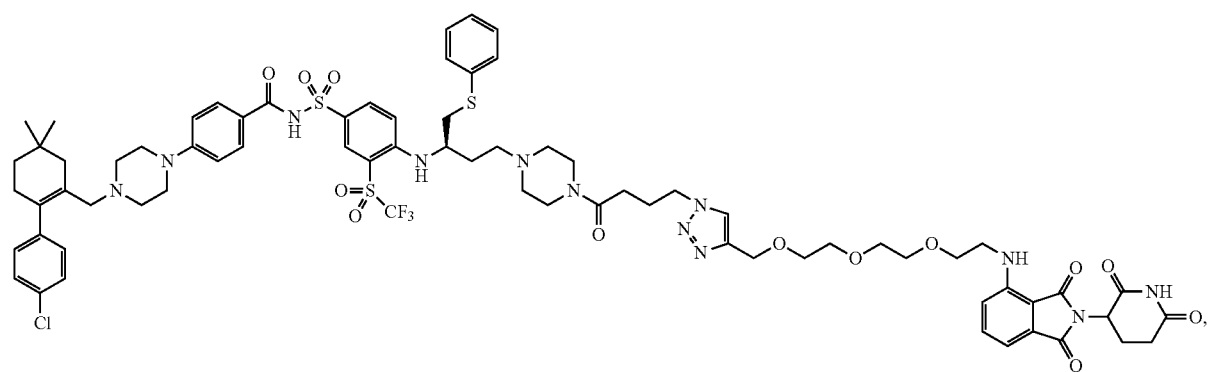
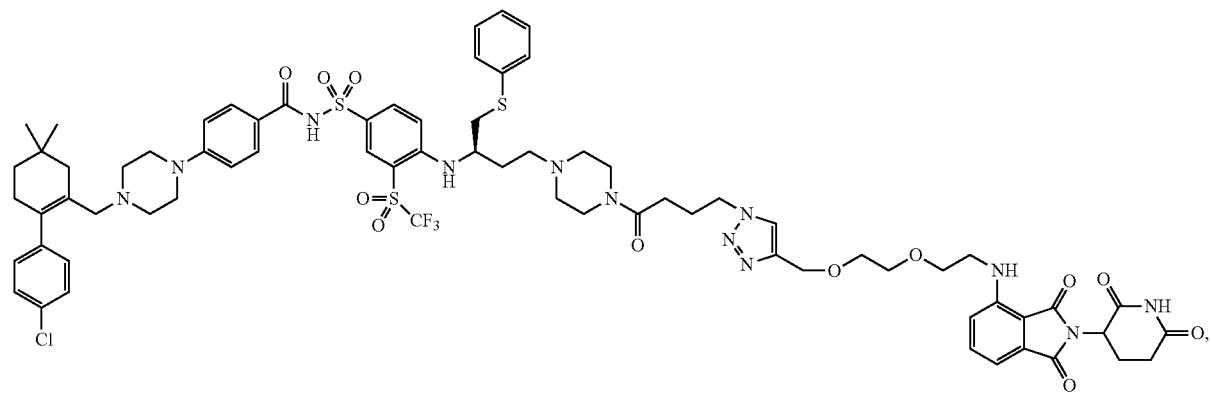

-continued
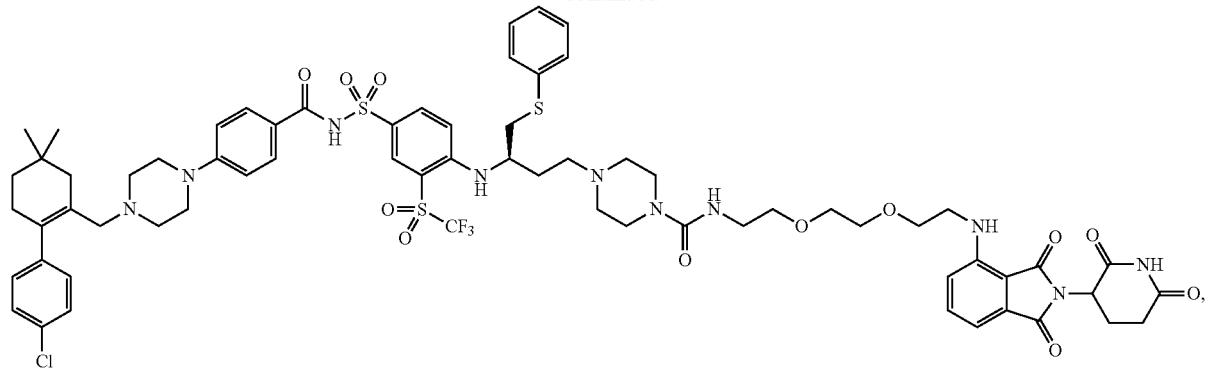
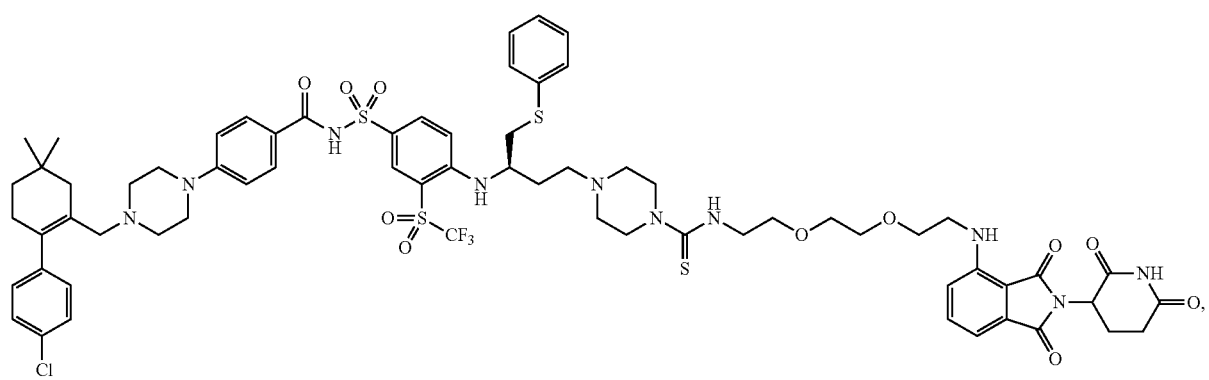
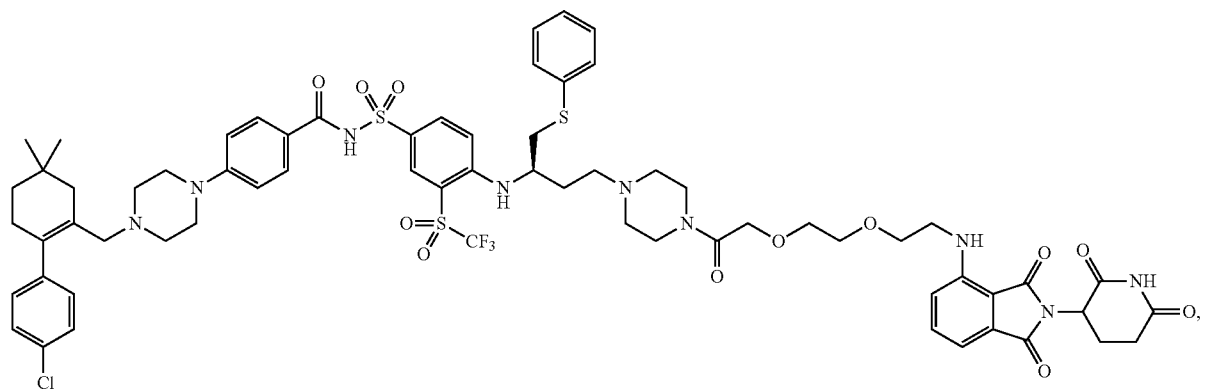
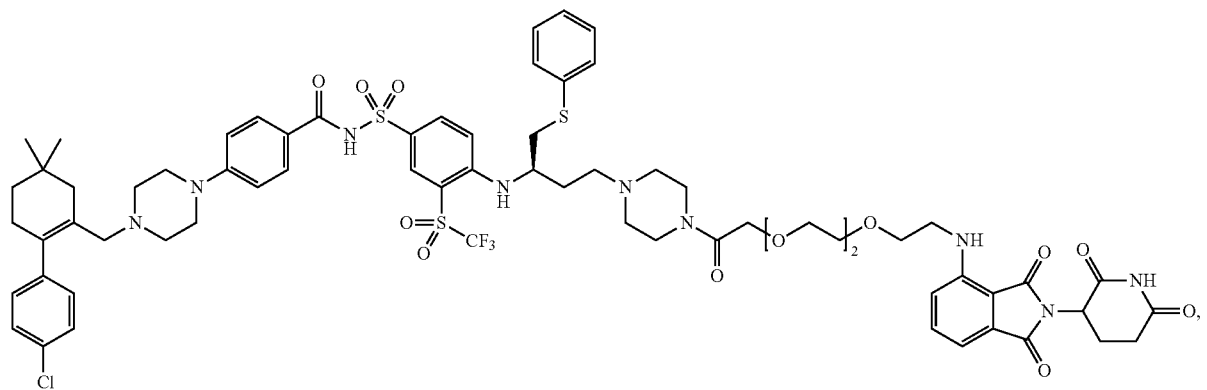

-continued
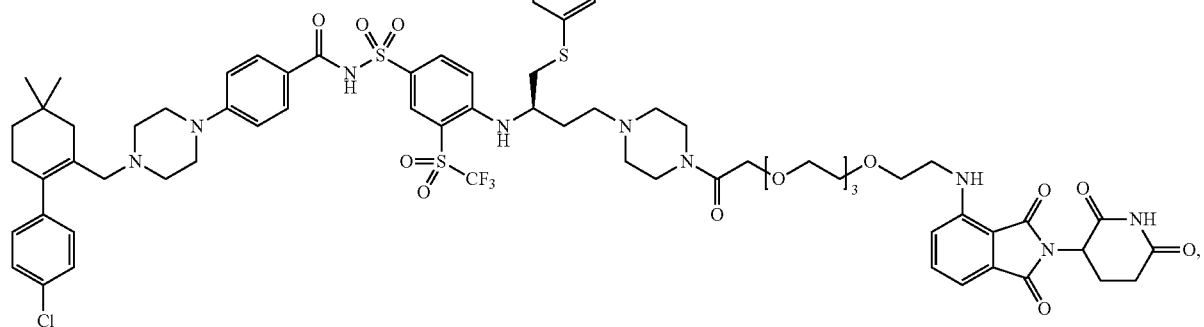
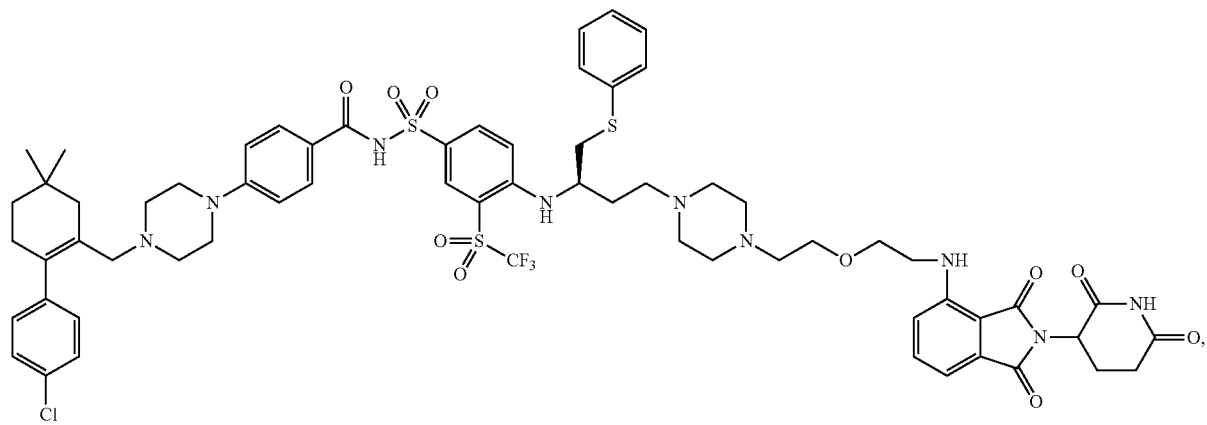
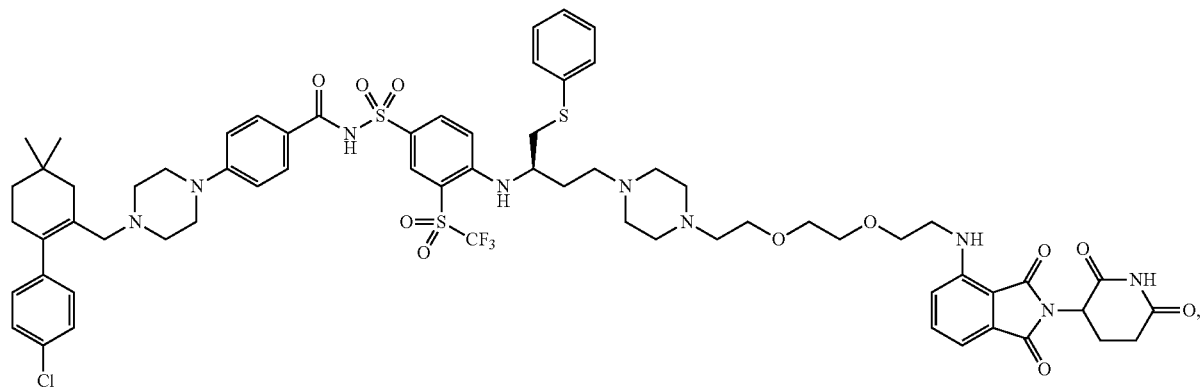
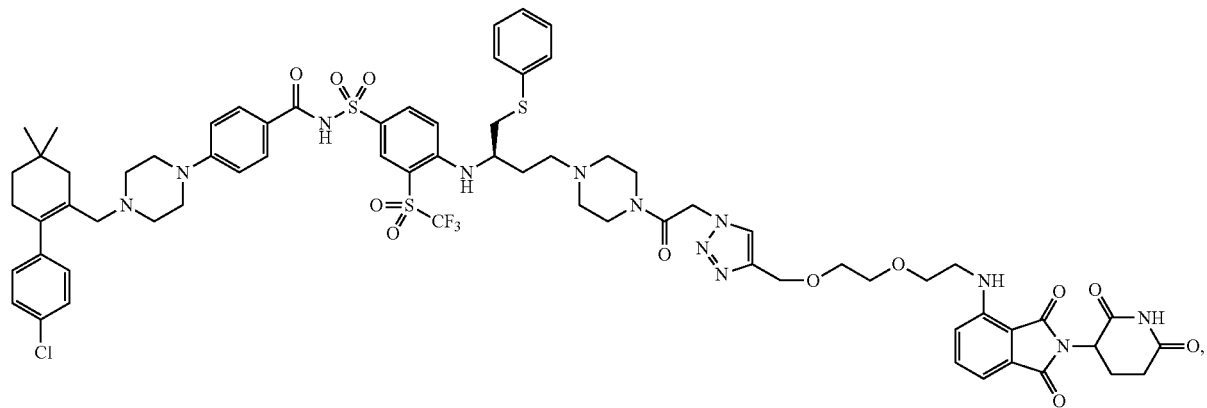

383
384
-continued
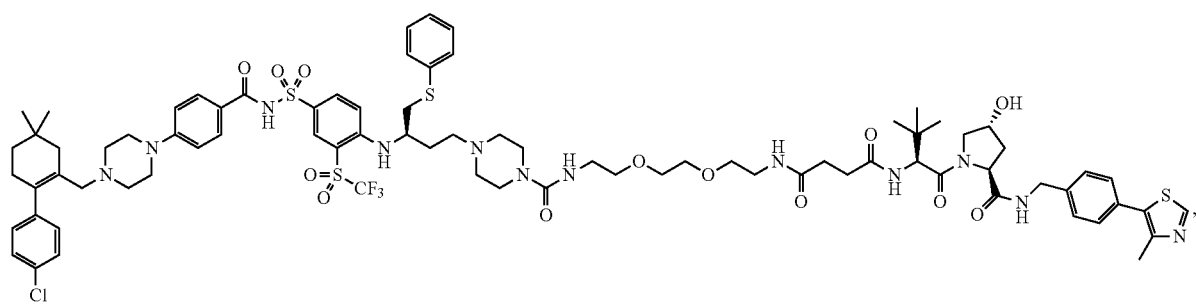
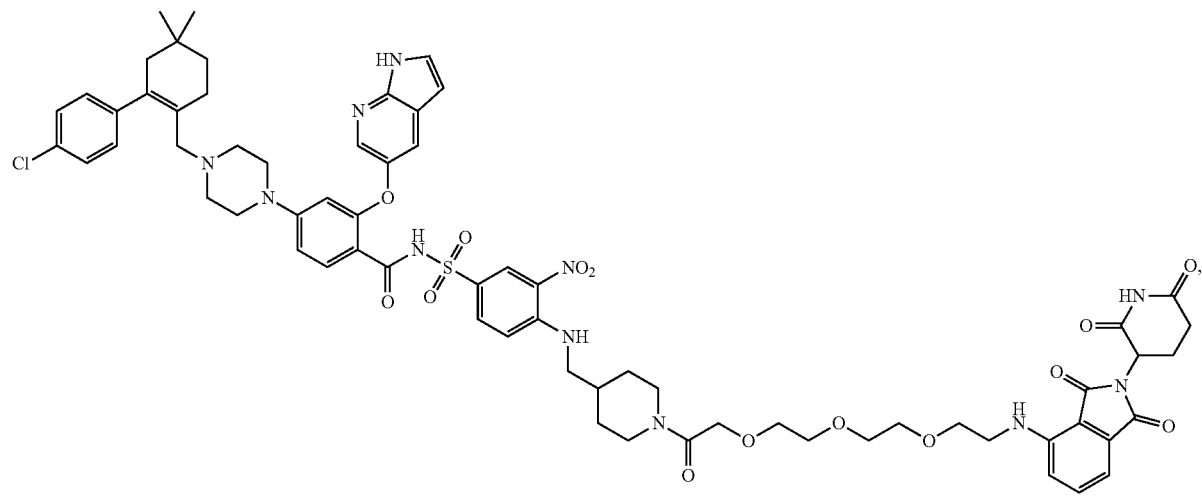
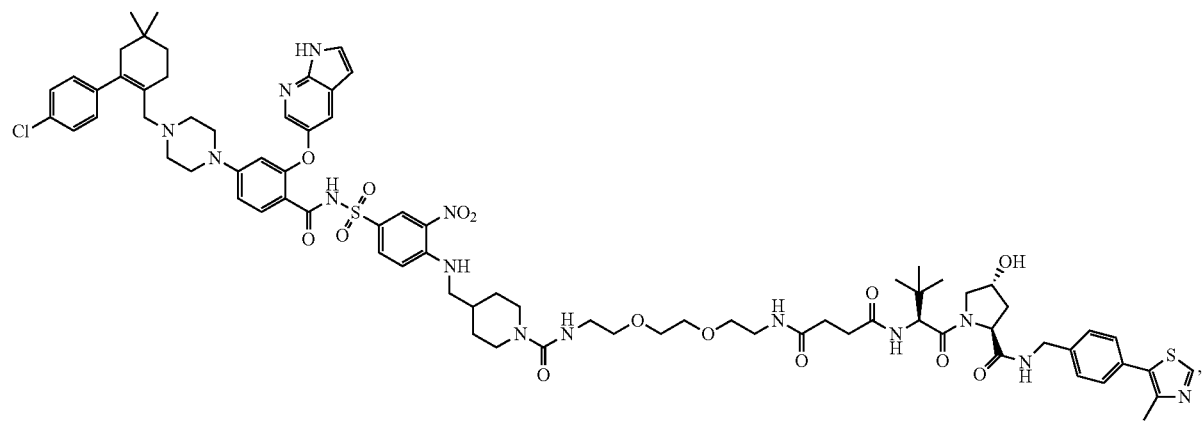

385
-continued
386
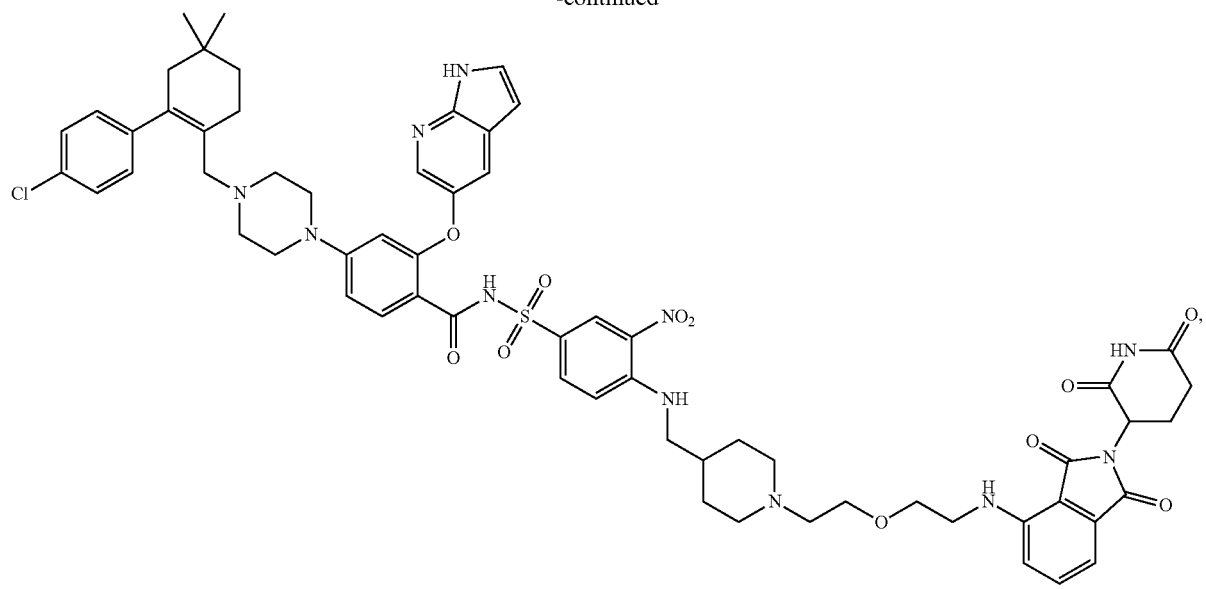
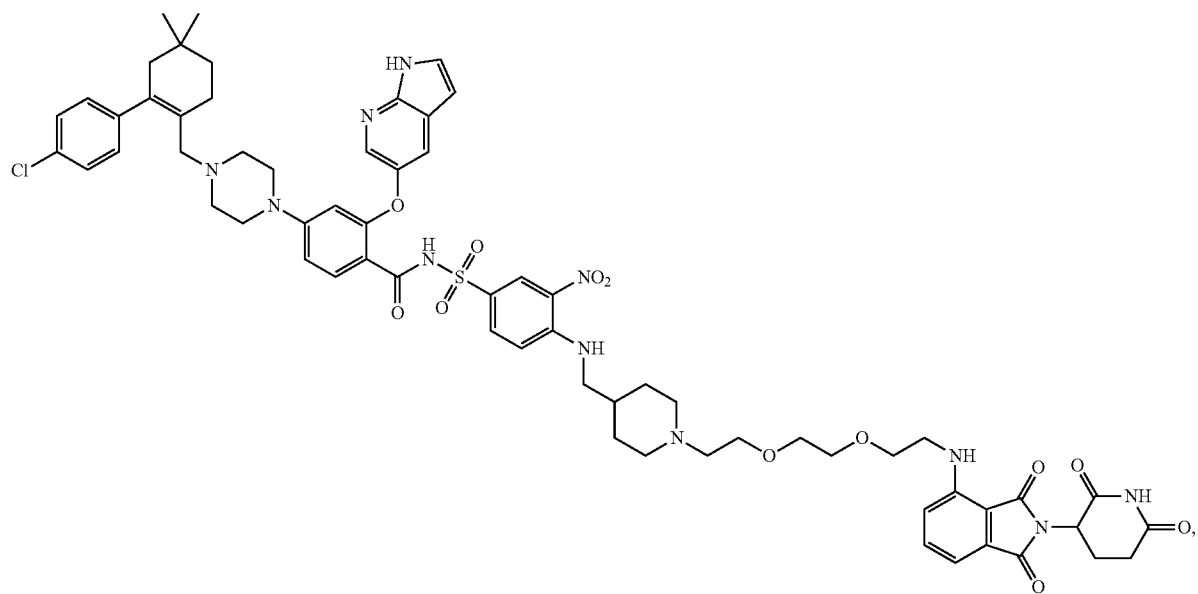
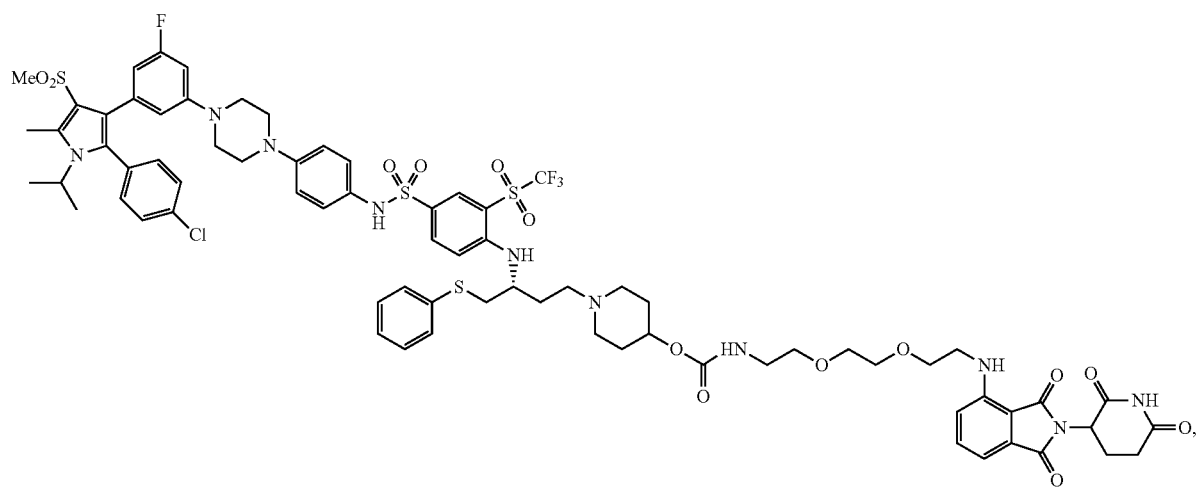

387
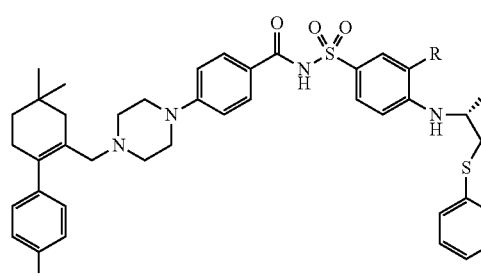 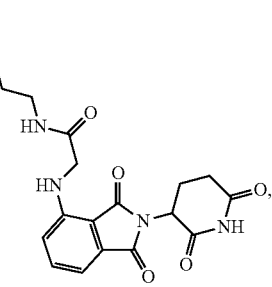
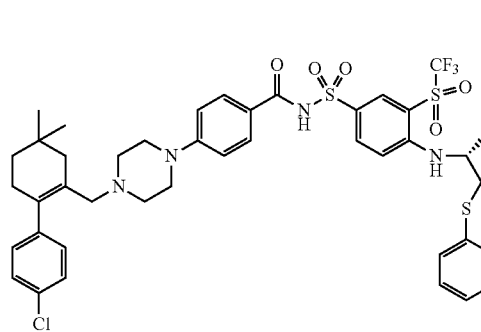 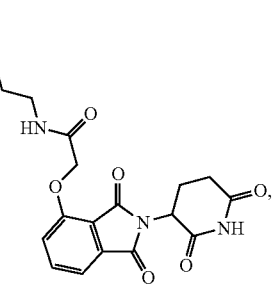
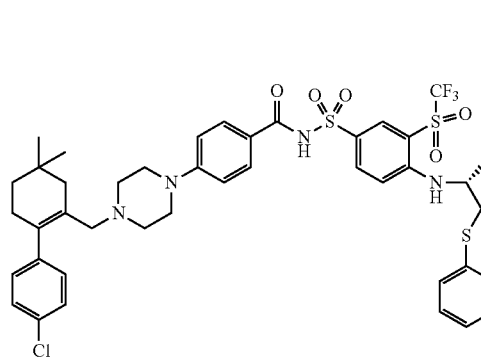 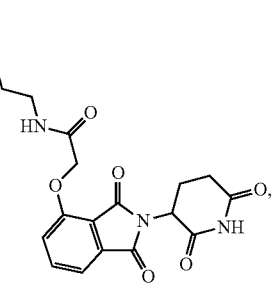
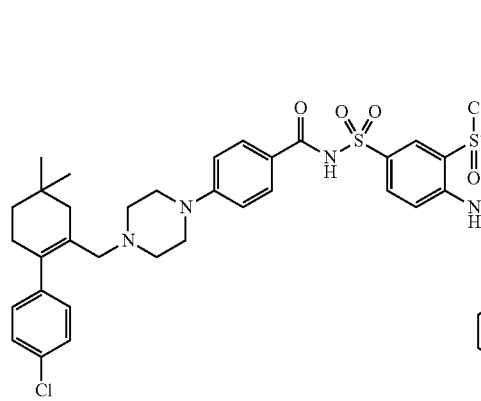 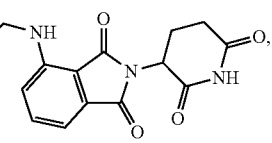
388
-continued

389
-continued
390
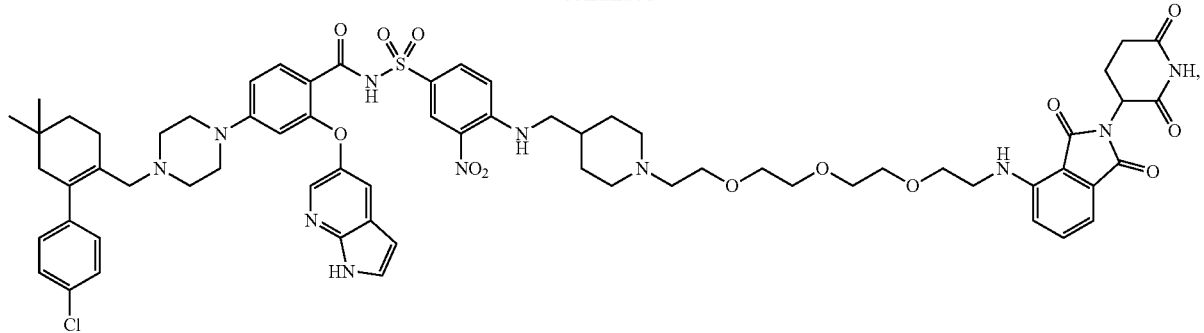
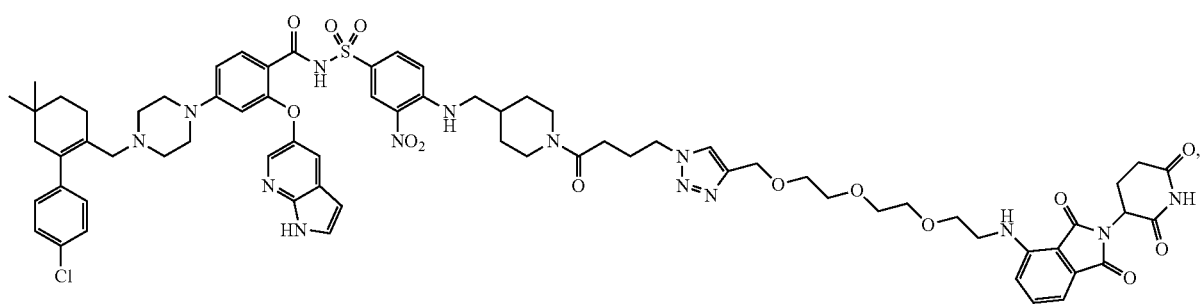
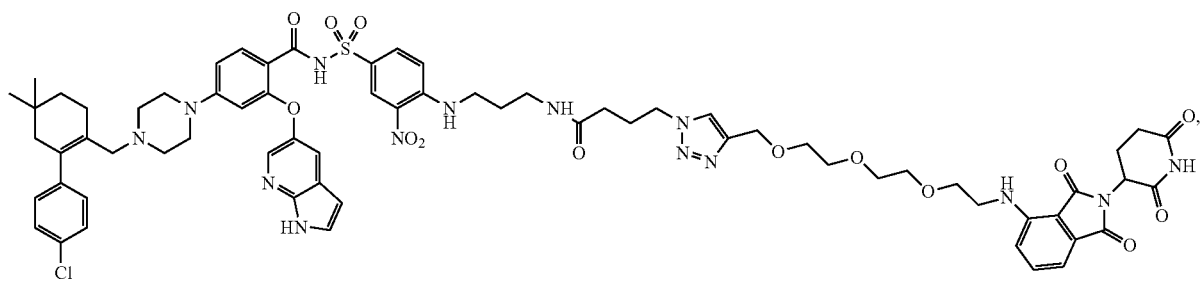
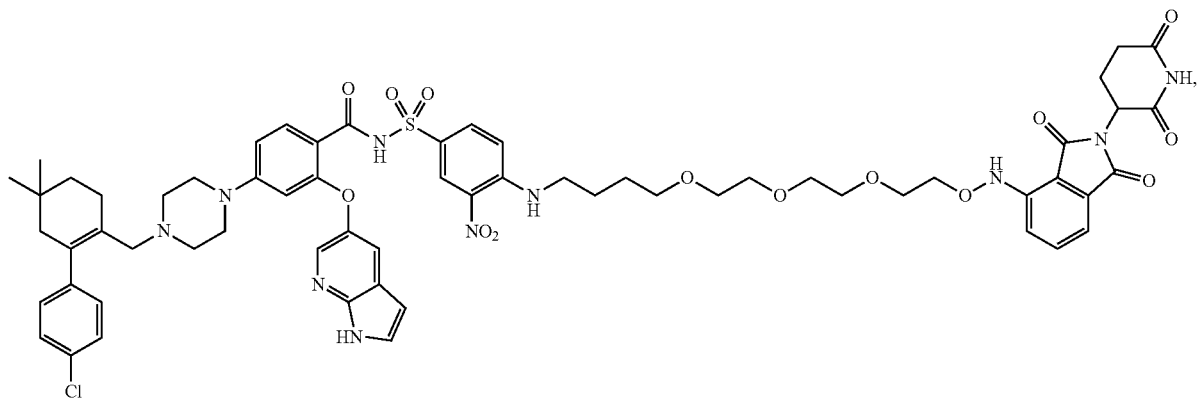
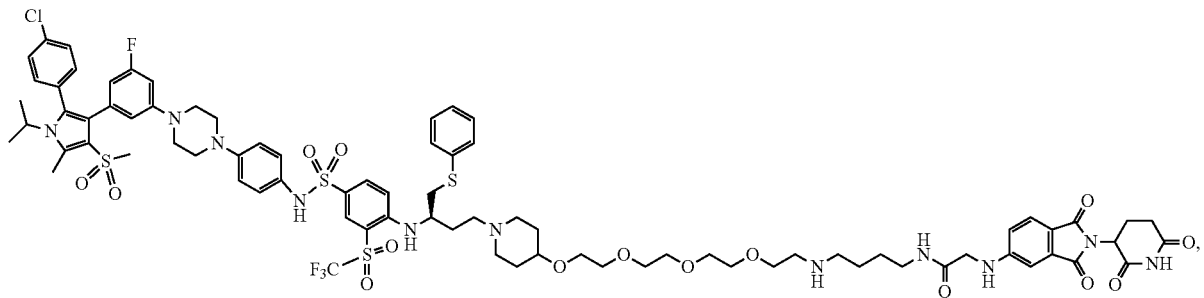

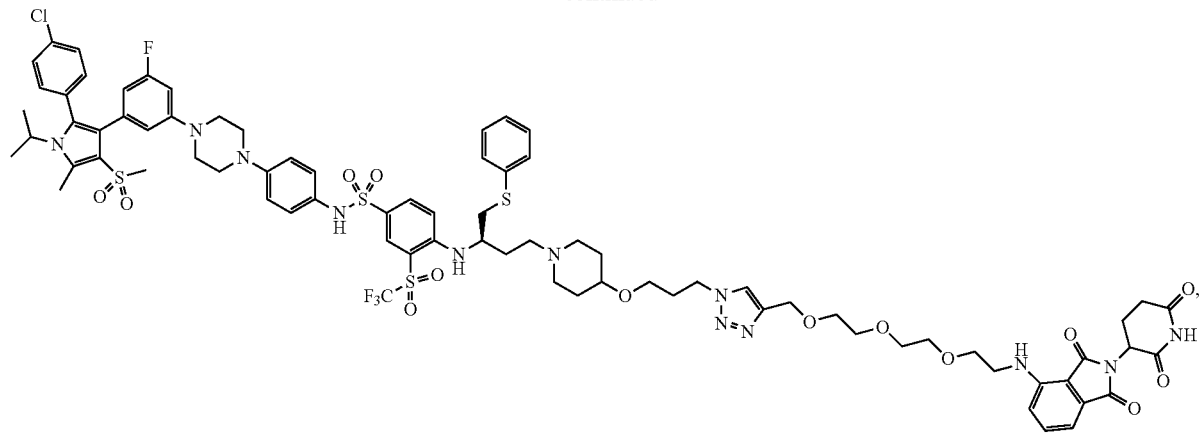
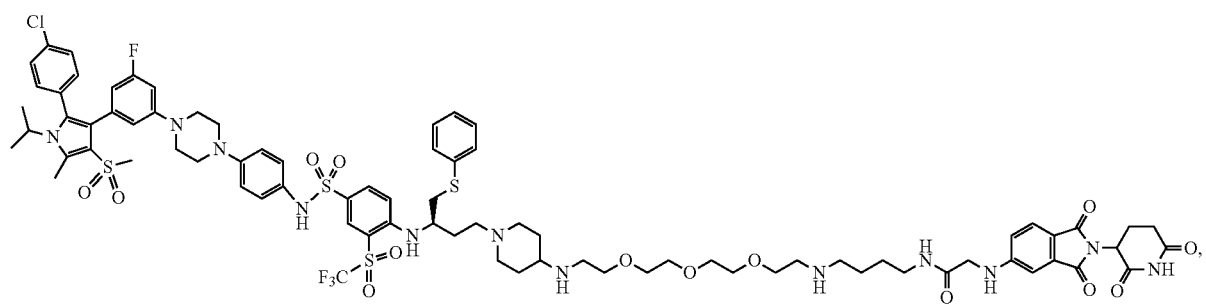
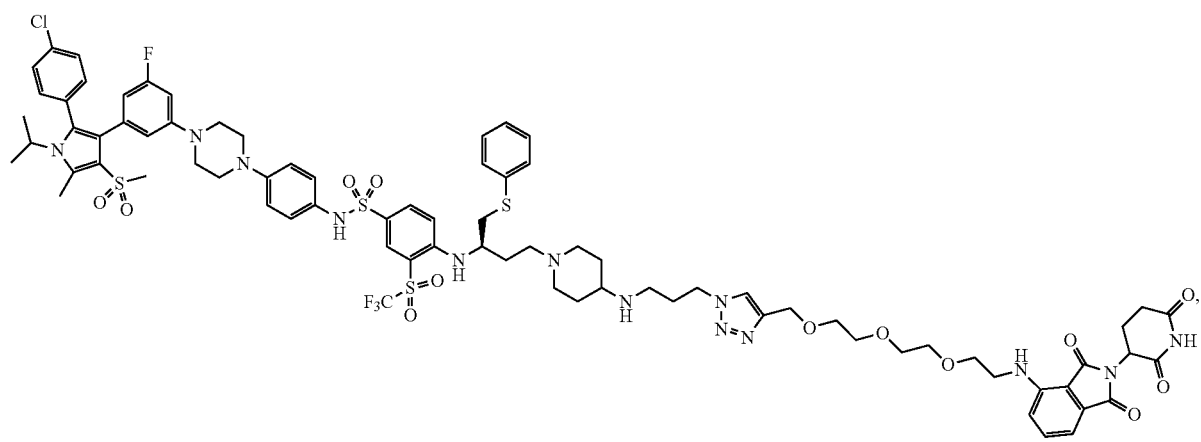
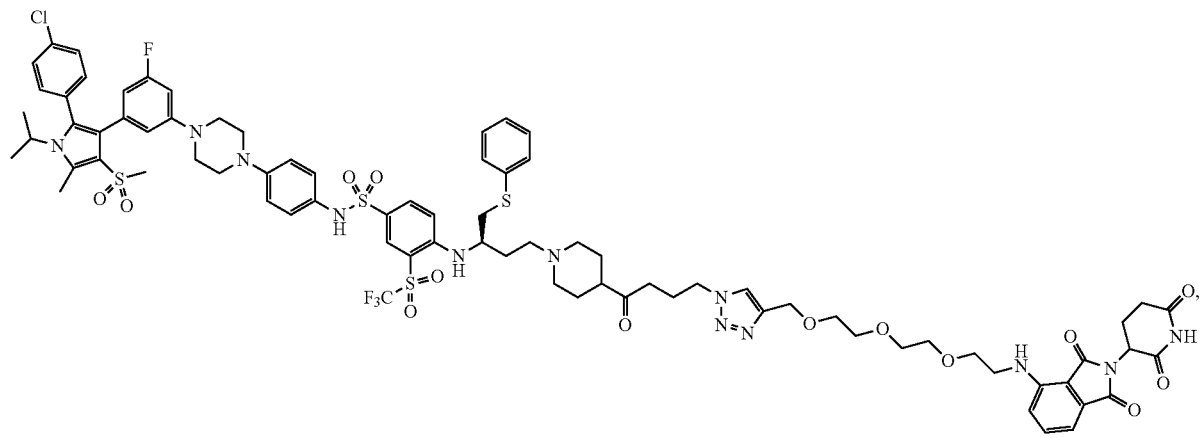

-continued

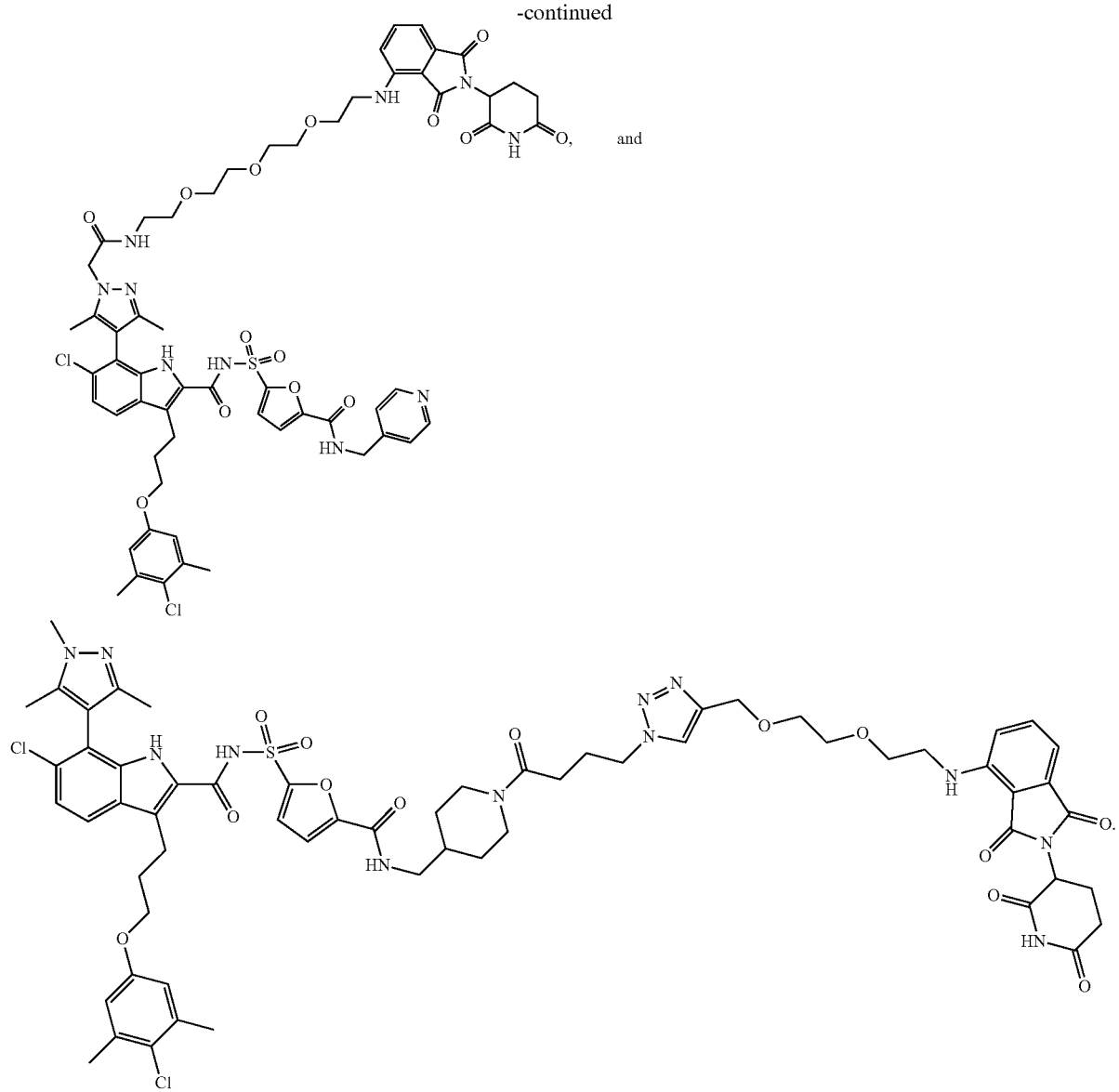

and (c) Components of the Composition

The present disclosure also provides pharmaceutical compositions. The pharmaceutical compositions comprise a compound of Formula (I) or a compound of Formula (II), as an active ingredient and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition a compound of Formula (I) or a compound of Formula (II) is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery a compound of Formula (I) or a compound of Formula (II) in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a compound comprising Formula (I) or a compound comprising Formula (II) may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a compound of Formula (I) or a compound of Formula (II) (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The compound comprising Formula (I) or Formula (II) may be encapsulated in a microemulsion by any method generally known in the art.

(d) Additional Compounds

In an aspect, the composition further comprises at least one or more anticancer therapeutics.

A chemotherapeutic agent refers to a chemical compound that is useful in the treatment of cancer. The compound may be a cytotoxic agent that affects rapidly dividing cells in general, or it may be a targeted therapeutic agent that affects the deregulated proteins of cancer cells. The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Suitable anti-metabolites include, but are not limited to aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcetabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate.

Non-limiting examples of suitable anti-tumor antibiotics include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors include, but are not limited to, amsacrine, etoposide (VP-16), irinotecan, mitoxantrone, RFS 2000, teniposide, and topotecan.

Non-limiting examples of suitable anti-hormonal agents such as aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib;

angiogeneisis inhibitors such as angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide; and growth inhibitory polypeptides such as bortazomib, erythropoietin, interleukins (e.g., IL-1, IL-2, IL-3, IL-6), leukemia inhibitory factor, interferons, romidepsin, thrombopoietin, TNF-α, CD30 ligand, 4-1BB ligand, and Apo-1 ligand.

Non-limiting examples of photodynamic therapeutic agents include am inolevulinic acid, methyl am inolevulinate, retinoids (alitretinon, tam ibarotene, tretinoin), and temoporfin.

Other antineoplastic agents include anagrelide, arsenic trioxide, asparaginase, bexarotene, bropirimine, celecoxib, chemically linked Fab, efaproxiral, etoglucid, ferruginol, lonidamide, masoprocol, miltefosine, mitoguazone, talapanel, trabectedin, and vorinostat.

Also included are pharmaceutically acceptable salts, acids, or derivatives of any of the above listed agents. The mode of administration of the chemotherapeutic agent can and will vary depending upon the agent and the type of tumor or neoplasm. Suitable modes of administration were detailed in Section II(d), below. A skilled practitioner will be able to determine the appropriate dose of the chemotherapeutic agent.

II. Methods

The present disclosure encompasses a method of selectively killing one or more senescent cells in a sample, the method comprising contacting a composition comprising an effective amount of a compound of Formula (I) or a compound of Formula (II) with the sample. In another aspect, the present disclosure encompasses a method of selectively killing one or more senescent cells in a subject in need thereof, the method comprising administering to the subject a composition comprising a therapeutically effective amount of a compound of Formula (I) or a compound of Formula (II).

The present disclosure encompasses a method of selectively killing one or more cancer cells in a sample, the method comprising contacting a composition comprising an effective amount of a compound of Formula (I) or a compound of Formula (II) with the sample. In another aspect, the present disclosure encompasses a method of selectively killing one or more cancer cells in a subject in need thereof, the method comprising administering to the subject a composition comprising a therapeutically effective amount of a compound of Formula (I) or a compound of Formula (II).

By selectively killing one or more senescent cells is meant a composition of the invention does not appreciably kill non-senescent cells at the same concentration. Accordingly, the median lethal dose or LD50 of the inhibitor in non-senescent cells may be about 5 to about 50 times higher than the LD50 of the inhibitor in senescent cells. As used herein, the LD50 is the concentration of inhibitor required to kill half the cells in the cell sample. For example, the LD50 of the inhibitor in non-senescent cells may be greater than about 5, about 6, about 7, about 8, about 9 or about 10 times higher than the LD50 of the inhibitor in senescent cells. Alternatively, the LD50 of the inhibitor in non-senescent cells may be greater than about 10, about 15, about 20, about 25, about 30, about 35, about 40, about 45, or about 50 times higher than the LD50 of the inhibitor in senescent cells. Additionally, the LD50 of the inhibitor in non-senescent cells may be greater than 50 times higher than the LD50 of the inhibitor in senescent cells. In a specific embodiment, the LD50 of the inhibitor in non-senescent cells is greater than 10 times higher than the LD500 of the inhibitor in senescent cells. In another specific embodiment, the LD50 of the inhibitor in non-senescent cells is greater than 20 times higher than the LD50 of the inhibitor in senescent cells.

The progression from an actively dividing cell to a metabolically active, non-dividing cell is termed "senescence" or "cellular senescence." As used herein, the terms "senescence" and "cellular senescence" may be used interchangeably. The term "senescence" also refers to the state into which cells enter after multiple rounds of division and, as a result of cellular pathways, future cell division is prevented from occurring even though the cell remains metabolically active. Senescent cells may differ from their pre-senescent counterparts in one or more of the following ways: 1) they arrest growth and cannot be stimulated to reenter the cell cycle by physiological mitogens; 2) they become resistant to apoptotic cell death; and/or 3) they acquire altered differentiated functions.

In contrast to cancer cells which grow and divide uncontrollably, the ability of most differentiated eukaryotic cells to proliferate is finite. Stated another way, normal cells have an intrinsically determined limit to the number of cell divisions through which they can proceed. This phenomenon has been termed "replicative cellular senescence" and is an intrinsic anticancer mechanism that limits a cell's proliferative ability, thereby preventing neoplastic transformation. Another form of senescence is "premature cellular senescence." Premature cellular senescence, like replicative cellular senescence, is a terminal fate of mitotic cells, characterized by permanent cell cycle arrest. Unlike replicative cellular senescence, however, premature cellular senescence does not require telomere deterioration and can be induced by a variety of stressors including, but not limited to, ultraviolet light, reactive oxygen species, chemotherapeutics, environmental toxin, cigarette smoking, ionizing radiation, distortion of chromatin structure, excessive mitogenic signaling, and oncogenic mutations. Still another form of senescence is therapy-induced senescence (TIS) which refers to the phenomenon of a subset of tumor cells being forced into a senescent state by therapeutic agents. TIS is known to develop because of certain treatments, including radiotherapy and chemotherapy.

The number of senescent cells in various organs and tissues of a subject increases with age. The accumulation of senescent cells may drive the deterioration that underlies aging and age-related diseases. For example, the accumulation of senescent cells in aged tissue may contribute to age-associated tissue dysfunction, reduced regenerative capacity, and disease. In this context, senescence is considered deleterious because it contributes to decrements in tissue renewal and function. As a non-limiting example, an aged tissue may lack the ability to respond to stress when proliferation is required thereby resulting in the reduced fitness seen with aging. A key component of this model is that substantial numbers of senescent cells should be present in tissues with aging, without, or prior to, pathology.

(a) Senescent Cells

A senescent cell may be a cell that ceases to divide but remains metabolically active. The non-dividing cells may remain viable for many weeks, but fail to grow/replicate DNA despite the presence of ample space, nutrients and growth factors in the medium. Thus, the senescence growth arrest is essentially permanent because senescent cells cannot be stimulated to proliferate by known physiological stimuli. Further, a senescent cell of the invention may be resistant to certain apoptotic signals and may acquire widespread changes in gene expression. The resistance to apoptosis may explain the increase in senescent cells with age. Manipulation of pro- and anti-apoptotic proteins may cause cells that are destined to die by apoptosis to senesce and, conversely, cause cells that are destined to senesce to undergo apoptosis.

A senescent cell of the invention may be senescent due to replicative cellular senescence, premature cellular senescence or therapy-induced senescence. Senescent cells that are senescent due to replication may have undergone greater than 60 population doublings. Alternatively, senescent cells that are senescent due to replication may have undergone greater than 40, greater than 50, greater than 60, greater than 70 or greater than 80 population doublings. A senescent cell that is prematurely cellular senescent may be induced by, but not limited to, ultraviolet light, reactive oxygen species, chemotherapeutics, environmental toxin, cigarette smoking, ionizing radiation, distortion of chromatin structure, excessive mitogenic signaling, and oncogenic mutations. In a specific embodiment, premature cellular senescence may be induced by ionizing radiation (IR). In another specific embodiment, premature cellular senescence may also be induced by ectopic transfection with Ras oncogene. A senescent cell that is therapy-induced senescent may have been exposed to DNA-damaging therapy.

A senescent cell of the invention may generally be a eurkaryotic cell. Non-limiting examples of senescent cells may include, but are not limited to, mammary epithelial cells, keratinocytes, cardiac myocytes, chondrocytes, endothelial cells (large vessels), endothelial cells (microvascular), epithelial cells, fibroblasts, follicle dermal papilla cells, hepatocytes, melanocytes, osteoblasts, preadipocytes, primary cells of the immune system, skeletal muscle cells, smooth muscle cells, adipocytes, neurons, glial cells, contractile cells, exocrine secretory epithelial cells, extracellular matrix cells, hormone secreting cells, keratinizing epithelial cells, islet cells, lens cells, mesenchymal stem cells, pancreatic acinar cells, paneth cells of the small intestine, primary cells of hemopoietic linage, primary cells of the nervous system, sense organ and peripheral neuron supporting cells, wet stratified barrier epithelial cells and stem cells. In a specific embodiment, the stem cells are adult stem cells. Adult stem cells are stem cells which maintain and repair the tissue in which they are found and are generally referred to by their tissue of origin. Non-limiting examples of adult stem cells include muscle stem cells, hematopoietic stem cells, heart stem cells, neural stem cells, mesenchymal stem cells, intestinal stem cells, skin stem cells, adipose-derived stem cells, endothelial stem cells, and dental pulp stem cells. In a specific embodiment, a senescent cell of the invention is a fibroblast. In another specific embodiment, a senescent cell may be a hematopoietic stem cell.

Further, a senescent cell of the invention may be found in renewable tissues, including the vasculature, hematopoietic system, epithelial organs and the stroma. A senescent cell of the invention may also be found at sites of aging or chronic age-related pathology, such as osteoarthritis and atherosclerosis. Further, a senescent cell of the invention may be associated with benign dysplastic or preneoplastic lesions and benign prostatic hyperplasia. In an embodiment, a senescent cell of the invention may be found in normal and tumor tissues following DNA-damaging therapy. In a specific embodiment, a senescent cell may be found at a site of aging or age-related pathology.

An age-related pathology may include any disease or condition which is fully or partially mediated by the induction or maintenance of a non-proliferating or senescent state in a cell or a population of cells in a subject. Non-limiting examples include age-related tissue or organ decline which may lack visible indication of pathology, or overt pathology such as a degenerative disease or a function-decreasing disorder. For example, Alzheimer's disease, Parkinson's disease, cataracts, macular degeneration, glaucoma, atherosclerosis, acute coronary syndrome, myocardial infarction, stroke, hypertension, idiopathic pulmonary fibrosis (IPF), chronic obstructive pulmonary disease (COPD), osteoarthritis, type 2 diabetes, obesity, fat dysfunction, coronary artery disease, cerebrovascular disease, periodontal disease, and cancer treatment-related disability such as atrophy and fibrosis in various tissues, brain and heart injury, and therapy-related myelodysplastic syndromes. Additionally, an age-related pathology may include an accelerated aging disease such as progeroid syndromes (i.e., Hutchinson-Gilford progeria syndrome, Werner syndrome, Bloom syndrome, Rothmund-Thomson Syndrome, Cockayne syndrome, xeroderma pigmentosum, trichothiodystrophy, combined xeroderma pigmentosum-Cockayne syndrome, and restrictive dermopathy), ataxia telangiectasia, Fanconi anemia, Friedreich's ataxia, dyskeratosis congenital, aplastic anemia, IPF, and others. A method of identifying an age-related disease or condition as described herein may include detecting the presence of senescent cells.

(b) Detecting Senescent Cells

In an aspect, a method of the invention may comprise detecting senescent cells. Senescent cells may be detected in vivo or in vitro. Suitable markers for detecting senescent cells in vitro and in vivo are known in the art. For example, methods to detect senescent cells may include, but are not limited to, detecting lack of DNA replication by incorporation of a DNA-staining reagent (e.g., 5-bromodeoxyuridine (BrdU), 3H-thymidine), immunostaining for proteins such as proliferating cell nuclear antigen (PCNA) and Ki-67, histochemical staining for senescence-associated β-galactosidase (SA-β-gal), detecting expression of p16, p19, Pai1, Igfbp2, IL-6, Mmp13, Nrg1, differentiated embryo-chondrocyte expressed-1 (DEC1), p15 (a CDK1) and decoy death receptor-2 (DCR2), detecting cytological markers such as senescence-associated heterochromatin foci (SAHFs) and senescence-associated DNA-damage foci (SDFs). SAHFs may be detected by the preferential binding of DNA dyes, such as 4',6-diamidino-2-phenylindole (DAPI), and the presence of certain heterochromatin-associated histone modifications (e.g., H3 Lys9 methylation) and proteins (e.g., heterochromatin protein-1 (HP1)). Additionally, senescent cells may be detected as described in U.S. Pat. No. 5,491,069 and US Patent Application No. 2010/0086941. In certain embodiments, senescent cells are detected by histochemical staining for SA-β-gal.

In certain embodiments, one or more senescent cells are detected in a sample. A sample may be a cell sample, a tissue sample, or a biopsy from a subject. Generally speaking, a sample may be dependent on the age-related pathology. For instance, a sample may be tissue biopsy material. As such, a tissue sample may be from esophagus, stomach, liver, gallbladder, pancreas, adrenal glands, bladder, gallbladder, large intestine, small intestine, kidneys, liver, pancreas, colon, stomach, thymus, spleen, brain, spinal cord, nerves, adipose tissue, heart, lungs, eyes, corneal, skin or islet tissue or organs. In a specific embodiment, a tissue sample may be from lung, skeletal muscle, and brain. In another specific embodiment, a tissue sample may be from liver and heart. Alternatively, a sample may be a cell sample. As such, a cell sample may be oocytes and/or spermatozoa, mesenchymal stem cells, adipocytes, central nervous system neurons and glial cells, contractile cells, exocrine secretory epithelial cells, extracellular matrix cells, hormone secreting cells, keratinizing epithelial cells, islet cells, kidney cells, lens cells, pancreatic acinar cells, paneth cells of small intestine, primary cells of hemopoietic lineage, primary cells of the nervous system, sense organ and peripheral neuron supporting cells or wet stratified barrier epithelial cells. Detection of senescent cells may be used to assess the replicative history of tissues, thereby providing a method for evaluation of the physiological, in contrast to the chronological age of the tissue.

The number of senescent cells may increase with age. The number of senescent cells in a tissue or sample may be from less than 1% to greater than 15%. In an embodiment, the number of senescent cells in a tissue or sample may be less than 1%, less than 2%, less than 3%, less than 4%, or less than 5%. In another embodiment, the number of senescent cells in a tissue or sample may be about 5%, about 6%, about 7%, about 8%, about 9%, or about 10%. In still another embodiment, the number of senescent cells in a tissue or sample may be greater than 10%, greater than 11%, greater than 12%, greater than 13%, greater than 14%, or greater than 15%.

(c) Measuring Cell Death

In an aspect, a method of the invention may comprise measuring cell death of senescent cells. Methods of measuring cell death are known in the art. For example, cell death may be measured by Giemsa staining, trypan blue exclusion, acridine orange/ethidium bromide (AO/EB) double staining for fluorescence microscopy and flow cytometry, propidium iodide (PI) staining, annexin V assay, TUNEL assay, DNA ladder, LDH activity, and MTT assay. In a preferred embodiment, cell death is due to induction of apoptosis. Cell death due to induction of apoptosis may be measured by observation of morphological characteristics including cell shrinkage, cytoplasmic condensation, chromatin segregation and condensation, membrane blebbing, and the formation of membrane-bound apoptotic bodies. Cell death due to induction of apoptosis may be measured by observation of biochemical hallmarks including internucleosomal DNA cleavage into oligonucleosome-length fragments. Traditional cell-based methods of measuring cell death due to induction of apoptosis include light and electron microscopy, vital dyes, and nuclear stains. Biochemical methods include DNA laddering, lactate dehydrogenase enzyme release, and MTT/XTT enzyme activity. Additionally, terminal deoxynucleotidyl transferase-mediated dUTP-biotin nick end labeling of DNA fragments (TUNEL) and in situ end labeling (ISEL) techniques are used, which when used in conjunction with standard flow cytometric staining methods yield informative data relating cell death to various cellular parameters, including cell cycle and cell phenotype. See Loo and Rillema, Methods Cell Biol. 1998; 57:251-64, which is incorporated herein by reference, for a review of these methods. In an exemplary embodiment, cell death due to apoptosis may be measured by the reduction of procaspase-3. Caspase-3 has been implicated as an "effector" caspase associated with the initiation of the "death cascade" and is therefore an important marker of the cell's entry point into the apoptotic signaling pathway. Caspase-3 is activated by the upstream caspase-8 and caspase-9, and since it serves as a convergence point for different signaling pathways, it is well suited as a read-out in an apoptosis assay.

The results of these methods may be used to determine the percentage of viable cells. In a preferred embodiment, cell death may be measured as a reduction in viable cells. Since a composition of the invention selectively kills senescent cells, a reduction in viable cells is indicative of a reduction in senescent cells. As described in Section III(b), the number of senescent cells in a sample may be from less than 1% to greater than 15%. As such, a reduction in viable cells following administration of an inhibitor of the invention may be greater than 15% to less than 1%. For example, the reduction in viable cells may be less than 1%, less than 2%, less than 3%, less than 4%, or less than 5%. Alternatively, the reduction in viable cells may be about 5%, about 6%, about 7%, about 8%, about 9%, or about 10%. Additionally, the reduction in viable cells may be greater than 10%, greater than 11%, greater than 12%, greater than 13%, greater than 14%, or greater than 15%.

(d) Administration

In certain aspects, a therapeutically effective amount of a composition of the invention may be administered to a subject. Administration is performed using standard effective techniques, including peripherally (i.e., not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. For example, if the disease or condition is COPD or IPF, the composition may be administered via inhalation. Alternatively, if the disease or condition is osteoarthritis, then the composition may be administered via intra-articular invention. It is within the skill of one in the art, to determine the route of administration based on the disease or condition to be treated. In a specific embodiment, a composition of the invention is administered orally.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response (e.g., cell death of senescent cells, an anti-aging response, an improvement in symptoms associated with a degenerative disease, or an improvement in symptoms associated with a function-decreasing disorder). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the age-related disease or condition, the degenerative disease, the function-decreasing disorder, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

(e) Subject

A subject may be a rodent, a human, a livestock animal, a companion animal, or a zoological animal. In one embodiment, the subject may be a rodent (e.g., a mouse, a rat, a guinea pig, etc.). In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

The human subject may be of any age. However, since senescent cells are normally associated with aging, a human subject may be an older human subject. In some embodiments, the human subject may be about 30, 35, 40, 45, 50, 55, 60, 65, 70, 75, 80, 85, 90, 95 years of age or older. In some preferred embodiments, the human subject is 30 years of age or older. In other preferred embodiments, the human subject is 40 years of age or older. In other preferred embodiments, the human subject is 45 years of age or older.

In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

Additionally, a subject in need thereof may be a subject suffering from an age-related disease or condition as described below.

(f) Aging and Age-Related Diseases

It has been demonstrated that senescent cells drive age-related pathologies and that selective elimination of these cells can prevent or delay age-related deterioration. Thus, senescent cells may be therapeutic targets in the treatment of aging and age-related disease. As such, removal of senescent cells may delay tissue dysfunction and extend health span. Clearance of senescent cells is expected to improve tissue milieu, thereby improving the function of the remaining non-senescent cells.

The present disclosure provides a method for delaying at least one feature of aging in a subject, the method comprising administering a composition comprising a therapeutically effective amount of a compound of Formula (I) or a compound of Formula (II) to a subject. As used herein, "a feature of aging" may include, but is not limited to, systemic decline of the immune system, muscle atrophy and decreased muscle strength, decreased skin elasticity, delayed wound healing, retinal atrophy, reduced lens transparency, reduced hearing, osteoporosis, sarcopenia, hair graying, skin wrinkling, poor vision, frailty, and cognitive impairment.

In an aspect, a composition of in the invention selectively kills senescent cells. In this way, targeting senescent cells during the course of aging may be a preventative strategy. Accordingly, administration of a composition comprising a therapeutically effective amount of a compound of Formula (I) or a compound of Formula (II) to a subject may prevent comorbidity and delay mortality in an older subject. Further, selective killing of senescent cells may boost the immune system, extend the health span, and improve the quality of life in a subject. Additionally, selective killing of senescent cells may delay sarcopenia. Sarcopenia is the degenerative loss of skeletal muscle mass, quality, and strength associated with aging. As such, a delay in sarcopenia may reduce frailty, reduce risk of falling, reduce fractures, and reduce functional disability in a subject. Furthermore, selective killing of senescent cells may delay aging of the skin. Aged skin has increased wrinkles, decreased immune barrier function and increased susceptibility to skin cancer and trauma. As such, selective killing of senescent cells may delay skin wrinkling, delay the onset of decreased immune barrier function and decrease susceptibility to skin cancer and trauma in a subject. Selective killing of senescent cells may also delay the onset of retinal atrophy and reduced lens transparency as measured by vision tests.

Methods of measuring aging are known in the art. For example, aging may be measured in the bone by incident non-vertebral fractures, incident hip fractures, incident total fractures, incident vertebral fractures, incident repeat fractures, functional recovery after fracture, bone mineral density decrease at the lumbar spine and hip, rate of knee buckling, NSAID use, number of joints with pain, and osteoarthritis. Aging may also be measured in the muscle by functional decline, rate of falls, reaction time and grip strength, muscle mass decrease at upper and lower extremities, and dual tasking 10-meter gait speed. Further, aging may be measured in the cardiovascular system by systolic and diastolic blood pressure change, incident hypertension, major cardiovascular events such as myocardial infarction, stroke, congestive heart disease, and cardiovascular mortality. Additionally, aging may be measured in the brain by cognitive decline, incident depression, and incident dementia. Also, aging may be measured in the immune system by rate of infection, rate of upper respiratory infections, rate of flu-like illness, incident severe infections that lead to hospital admission, incident cancer, rate of implant infections, and rate of gastrointestinal infections. Other indications of aging may include, but not limited to, decline in oral health, tooth loss, rate of GI symptoms, change in fasting glucose and/or insulin levels, body composition, decline in kidney function, quality of life, incident disability regarding activities of daily living, and incident nursing home admission. Methods of measuring skin aging are known in the art and may include trans-epidermal water loss (TEWL), skin hydration, skin elasticity, area ratio analysis of crow's feet, sensitivity, radiance, roughness, spots, laxity, skin tone homogeneity, softness, and relief (variations in depth).

The present disclosure also provides a method of treating an age-related disease or condition, the method comprising administering a composition comprising a therapeutically effective amount of a compound of Formula (I) or a compound of Formula (II) to a subject in need thereof, provided the age-related disease or condition is not cancer. As used herein, "age-related disease or condition" may include, but is not limited to, a degenerative disease or a function-decreasing disorder such as Alzheimer's disease, Parkinson's disease, cataracts, macular degeneration, glaucoma, atherosclerosis, acute coronary syndrome, myocardial infarction, stroke, hypertension, idiopathic pulmonary fibrosis (IPF), chronic obstructive pulmonary disease (COPD), osteoarthritis, type 2 diabetes, obesity, fat dysfunction, coronary artery disease, cerebrovascular disease, periodontal disease, cancer treatment-related disability such as atrophy and fibrosis in various tissues, brain and heart injury, and therapy-related myelodysplastic syndromes, and diseases associated with accelerated aging and/or defects in DNA damage repair and telomere maintenance such as progeroid syndromes (i.e., Hutchinson-Gilford progeria syndrome, Werner syndrome, Bloom syndrome, Rothmund-Thomson Syndrome, Cockayne syndrome, xeroderma pigmentosum, trichothiodystrophy, combined xeroderma pigmentosum-Cockayne syndrome, restrictive dermopathy), ataxia telangiectasia, Fanconi anemia, Friedreich's ataxia, dyskeratosis congenital, aplastic anemia, IPF, and others. Methods of diagnosing and identifying an age-related disease or condition are known in the art.

DEFINITIONS

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

"Bcl-2" as used herein alone or as part of a group references to a member of the Bcl-2 family of proteins comprise the following Bcl-$x_L$, MCL-1, Bcl-W, BFL-1/A1, Bcl-B, BAX, BAK, and BOK.

"Alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms ($C_1$-$C_{20}$ alkyl), suitably 1 to 10 carbon atoms ($C_1$-$C_{10}$ alkyl), preferably 1 to 8 carbon atoms ($C_1$-$C_8$ alkyl), more preferably 1 to 6 carbon atoms ($C_1$-$C_4$ alkyl), and even more preferably 1 to 4 carbon atoms ($C_1$-$C_4$ alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl and the like.

"Aryl" as used herein, alone or as part of a group, includes an organic radical derived from an aromatic hydrocarbon by removal of one hydrogen, and includes monocyclic and polycyclic radicals, such as phenyl, biphenyl, naphthyl.

"Cycloalkyl" as used herein, alone or in combination, means a saturated or partially saturated monocyclic, bicyclic or tricyclic alkyl radical wherein each cyclic moiety contains from about 3 to about 8 carbon atoms, more preferably from about 3 to about 6 carbon atoms. Examples of such cycloalkyl radicals include cyclopropyl, cyclobutyl, cyclopentyl, cyclohexyl and the like.

"Heteroatom" means an atom other than carbon e.g., in the ring of a heterocyclic group or the chain of a heterogeneous group. Preferably, heteroatoms are selected from the group consisting of sulfur, phosphorous, nitrogen, and oxygen atoms. Groups containing more than one heteroatom may contain different heteroatoms.

"Heteroaryl" as used herein, along or in combination, includes an organic radical derived from an aromatic hydrocarbon by removal of one hydrogen and includes at least one heteroatom. Examples of heteroaryl includes pyrrole, thiophene, furan, indole, pyrazine, pyridine, triazole, imidazole, thiazole, oxazole and the like.

"Substituted" means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups. "Unsubstituted" means that the carbon chain or ring contains no other substituents other than carbon and hydrogen.

"Branched" means that the carbon chain is not simply a linear chain. "Unbranched" means that the carbon chain is a linear carbon chain.

"Heteroatom" means an atom other than carbon e.g., in the ring of a heterocyclic group or the chain of a heterogeneous group. Preferably, heteroatoms are selected from the group consisting of sulfur, phosphorous, nitrogen and oxygen atoms. Groups containing more than one heteroatom may contain different heteroatoms.

"Heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), suitably 4 to 7, and more suitably 5 to 6 in the ring. Bicyclic heterocyclic groups contain 8 to 18 member atoms, suitably 9 or 10 in the rings.

"Isomer", "isomeric form", "stereochemically isomeric forms" or "stereoIsomeric forms", as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, epimers, enantiomers and/or conformers of the basic molecular structure of said compound. More in particular, stereogenic centers may have the R- or S-configuration, diastereoisomers may have a syn- or anti-configuration, substituents on bivalent cyclic saturated radicals may have either the cis- or trans-configuration and alkenyl radicals may have the E- or Z-configuration. All stereochemically isomeric forms of said compound both in pure form or in admixture with each other are intended to be embraced within the scope of the present invention.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The compounds of the present invention may be prepared in a number of ways well known to one skilled in the art of organic synthesis. More specifically, the novel compounds of this invention may be prepared using the reactions and techniques described herein. In the description of the synthetic methods described below, it is to be understood that all proposed reaction conditions, including choice of solvent, reaction atmosphere, reaction temperature, duration of the experiment and workup procedures, are chosen to be the conditions standard for that reaction. It is understood by one skilled in the art of organic synthesis that the functionality present on various portions of the molecule must be compatible with the reagents and reactions proposed. Such restrictions to the substituents, which are not compatible with the reaction conditions, will be apparent to one skilled in the art and alternate methods must then be used. Unless otherwise stated, the starting materials for the examples contained herein are either commercially available or are readily prepared by standard methods from known materials. The compounds of Formula (I) or Formula (II) may be synthesized through standard organic chemistry methodology and purification known to those trained in the art of organic synthesis by using commercially available starting materials and reagents.

The following abbreviations are used: s: singlet; d: doublet; t: triplet; q: quartet; m: multiplet; dd: doublet of doublet; dt: doublet of triplet: dq: doublet of quartet; br: broad; AcOH=acetic acid; DCM=dichloromethane; DIPEA=N,N-diisopropylethylamine; DMAP=4-dimethylaminopyridine; DMF=N,N-dimethylformamide; DMSO=dimethylsulfoxide; EDCI=1-ethyl-3-(3-dimethylaminopropyl)carbodiimide; EDTA=ethylenediaminetetraacetic acid; EtOAc=ethyl acetate; FBS=fetal bovine serum; HATU=1-[Bis(dimethylamino)methylene]-1H-1,2,3-triazolo[4,5-b]pyridinium 3-oxid hexafluorophosphate; HCl=hydrochloric acid; MOMCl=chloromethyl methyl ether; PBS=phosphate buffered saline; TBAF=tetra-n-butylammonium fluoride; TBSCl=tert-butyldimethylchlorosilane; TBS-T=tris-buffered saline; TEA=triethylamine; THF=tetrahydrofuran; and TFA=trifluoroacetic acid.

Example 1: Synthesis of XZ-13906

Preparation of (4-bromo-2-fluorophenoxy)(tert-butyl)dimethylsilane (2)

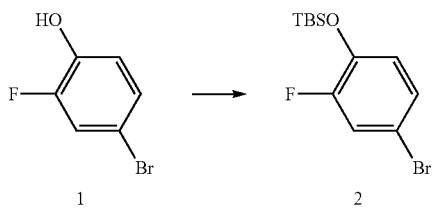 [SMILES: Oc1ccc(Br)cc1F ; CC(C)(C)[Si](C)(C)Oc1ccc(Br)cc1F]

4-Bromo-2-fluorophenol (1.0 g, 5.24 mmol), TBSCl (1.03 g, 6.83 mmol) and imidazole (713 mg, 10.48 mmol) were dissolved in 20 mL DMF and the mixture was stirred at room temperature for 16 hours. Water was added to the reaction mixture and extracted with EtOAc. The combined organic phases were washed with water x1, brine x1, dried over $Na_2SO_4$, filtered and evaporated to dryness. The resulting oil was further purified by column chromatography to afford 1.60 g compound 2 as colorless oil. Yield 100%. $^1$H NMR (400 MHz, $CDCl_3$) δ 7.22 (dd, J=10.1, 2.4 Hz, 1H), 7.15-7.07 (m, 1H), 6.79 (t, J=8.7 Hz, 1H), 1.00 (s, 9H), 0.19 (d, J=0.9 Hz, 6H) ppm.

Preparation of tert-butyl 4-(prop-2-ynyl)piperazine-1-carboxylate (4)

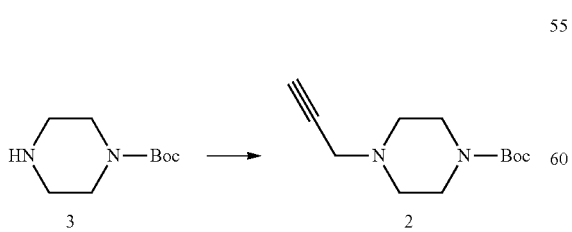

1-Boc-Piperazine 3 (1.0 g, 5.38 mmol), 80% 3-bromoprop-1-yne toluene solution (900 µL, 8.07 mmol), and DIPEA (1.78 mL, 10.76 mmol) were dissolved in 25 mL DCM and the mixture was stirred at room temperature for 16 hours. Water was added to the reaction mixture and the aqueous phase was extracted with DCM. The combined organic phases were washed with brine, dried over $Na_2SO_4$, filtered and evaporated to dryness. The resulting oil was further purified by column chromatography to afford 1.13 g compound 4. Yield 94%. $^1$H NMR (400 MHz, $CDCl_3$) δ 3.54-3.42 (m, 4H), 3.33 (d, J=2.4 Hz, 2H), 2.57-2.46 (m, 4H), 2.26 (t, J=2.4 Hz, 1H), 1.46 (s, 9H) ppm.

Preparation of tert-butyl 4-(3-(4-(tert-butyldimethylsilyloxy)-3-fluorophenyl)prop-2-ynyl)piperazine-1-carboxylate (5)

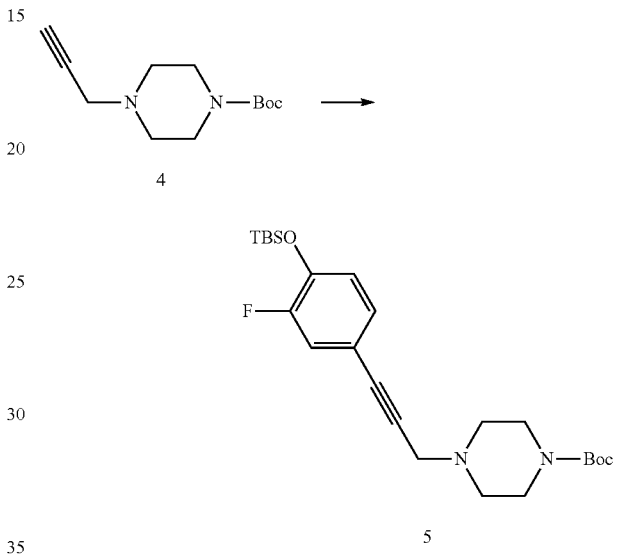

A mixture of compound 2 (612 mg, 2 mmol), compound 4 (448 mg, 2 mmol), $Pd(PPh_3)_4$ (68 mg, 0.06 mmol), CuI (12 mg, 0.06 mmol), and TEA (700 µL, 4.2 mmol) were stirred in 15 mL DMF at 100° C. under Argon for 20 hours. Water was added to the reaction mixture and extracted with EtOAc. The combined organic phases were washed with water x1, brine x1, dried over $Na_2SO_4$, filtered and evaporated to dryness. The resulting oil was further purified by column chromatography to afford 220 mg compound 5. Yield 25%. $^1$H NMR (400 MHz, $CDCl_3$) δ 7.13 (dd, J=11.1, 2.0 Hz, 1H), 7.10-7.04 (m, 1H), 6.83 (t, J=8.5 Hz, 1H), 3.58-3.41 (m, 6H), 2.68-2.50 (m, 4H), 1.47 (s, 9H), 1.00 (s, 9H), 0.19 (d, J=0.9 Hz, 6H) ppm.

Preparation of tert-butyl 4-(3-(3-fluoro-4-hydroxyphenyl)prop-2-ynyl)piperazine-1-carboxylate (6)

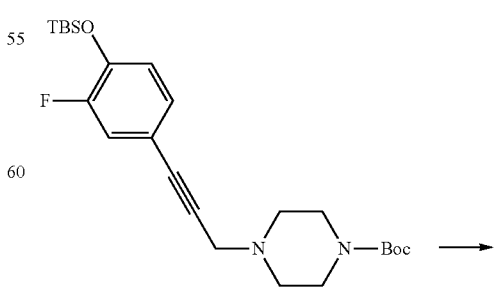

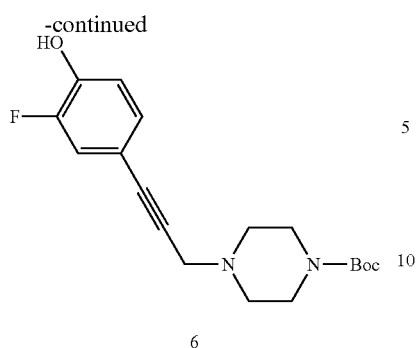

6

To a solution of compound 5 (180 mg, 0.4 mmol) in 5 mL THF was added 0.8 mL TBAF solution (1.0 M in THF) dropwise. After 30 minutes, water was added to the reaction mixture and extracted with EtOAc. The organic phase was washed with saturated NH$_4$Cl (aq) x1, brine x1, dried over Na$_2$SO$_4$, filtered and evaporated to dryness. The resulting mixture was further purified by column chromatography to afford 126 mg compound 6 as brown solid. Yield 94%. $^1$H NMR (400 MHz, CDCl$_3$) δ 7.09-7.00 (m, 2H), 6.89 (t, J=8.8 Hz, 1H), 3.59-3.45 (m, 6H), 2.70-2.54 (m, 4H), 2.08 (s, 1H), 1.47 (s, 9H) ppm.

Preparation of 2-(2,6-dioxopiperidin-3-yl)-4-(2-(2-(2-(prop-2-ynyloxy)ethoxy)ethoxy) ethylamino) isoindoline-1,3-dione (9)

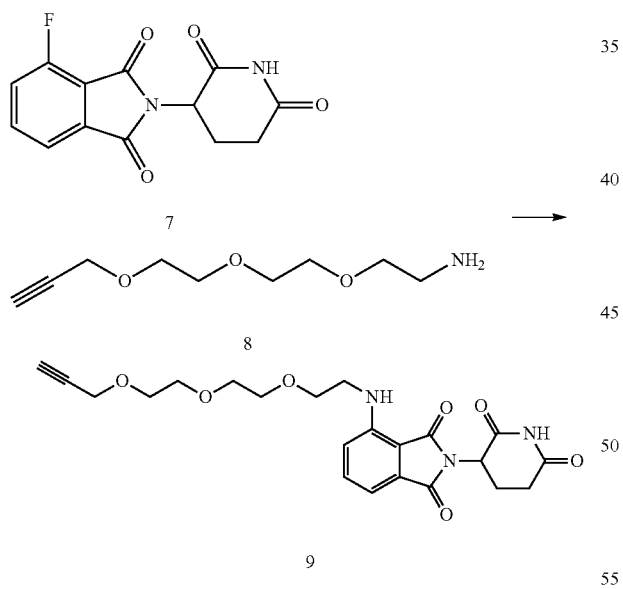

2-(2,6-Dioxopiperidin-3-yl)-4-fluoroisoindoline-1,3-dione (7) was synthesized according to reported method with minor modifications (*Chem. Biol.* 22:755-763, 2015). Compound 7 (100 mg, 0.36 mmol), amine 8 (68 mg, 0.36 mmol), and DIPEA (120 μL, 0.72 mmol) in 4 mL DMF were stirred at 90° C. for 16 hours. Water was added to the reaction mixture and extracted with EtOAc. The organic phase was washed with water x1, brine x1, dried over Na$_2$SO$_4$, filtered and evaporated to dryness. The resulting mixture was further purified by column chromatography to afford 95 mg compound 9 as a green solid. Yield 59%. $^1$H NMR (400 MHz, CDCl$_3$) δ 8.02 (s, 1H), 7.64-7.34 (m, 1H), 7.10 (d, J=7.1 Hz, 1H), 6.93 (d, J=8.6 Hz, 1H), 6.67-6.11 (m, 1H), 4.91 (dd, J=12.1, 5.3 Hz, 1H), 4.20 (d, J=2.2 Hz, 2H), 3.83-3.60 (m, 10H), 3.55-3.40 (m, 2H), 2.99-2.60 (m, 3H), 2.43 (t, J=2.1 Hz, 1H), 2.21-2.03 (m, 1H) ppm.

Preparation of 2-(8-(benzo[d]thiazol-2-ylcarbamoyl)-3,4-dihydroisoquinolin-2(1H)-yl)-5-(3-(4-(3-(4-(tert-butoxycarbonyl)piperazin-1-yl)prop-1-ynyl)-2-fluorophenoxy)propyl)thiazole-4-carboxylic Acid (11)

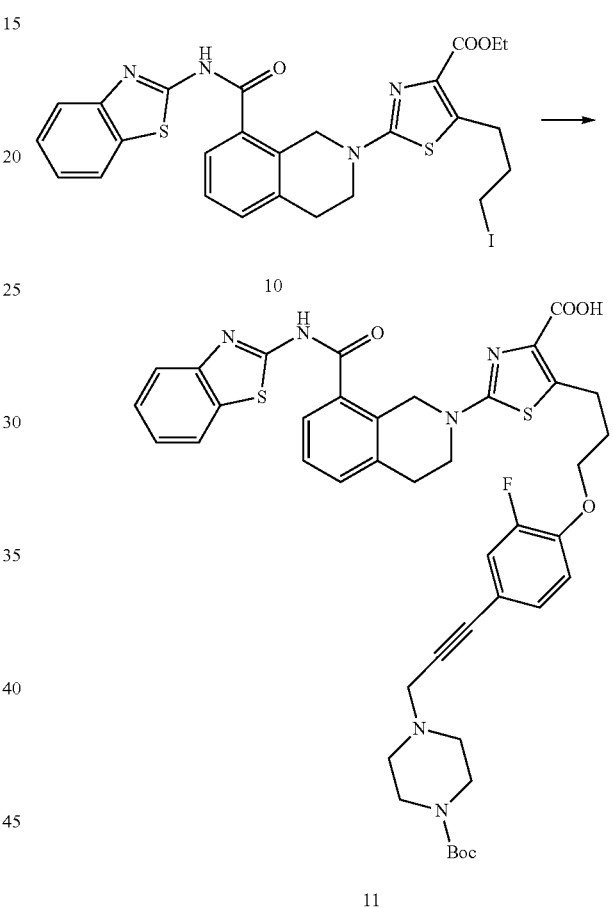

Compound 10 was synthesized according to reported method with minor modifications (*ACS Med Chem Lett.* 5:1088-1093, 2014). Compound 6 (200 mg, 0.60 mmol) in 5 mL DMF was cooled to 0° C. and 40 mg 95% NaH was added to the solution. The resulting reaction mixture was stirred for 10 min before the addition of compound 10 (250 mg, 0.40 mmol) in 5 mL THF. The mixture was stirred at room temperature for 3 hours and quenched by adding 1 mL water. The pH was adjusted to 5 using 1N HCl (aq) and the resulted solution was extracted with EtOAc. The organic phase was washed with water x1, brine x1, dried over Na$_2$SO$_4$, filtered and evaporated to dryness. The resulting mixture was further purified by column chromatography to afford 130 mg compound 11. Yield 41%. $^1$H NMR (400 MHz, CDCl$_3$) δ 7.90-7.76 (m, 1H), 7.69-7.59 (m, 1H), 7.54-7.41 (m, 1H), 7.36-7.29 (m, 4H), 7.14-7.05 (m, 2H), 6.80 (t, J=8.5 Hz, 1H), 4.93 (s, 2H), 4.00 (t, J=6.2 Hz, 2H), 3.79-3.65 (m, 2H), 3.57-3.49 (m, 6H), 3.28 (t, J=7.3 Hz, 2H), 3.09-2.88 (m, 2H), 2.74-2.46 (m, 4H), 2.30-2.06 (m, 2H), 1.46 (s, 9H) ppm.

Preparation of 2-(8-(benzo[d]thiazol-2-ylcarbamoyl)-3,4-dihydroisoquinolin-2(1H)-yl)-5-(3-(2-fluoro-4-(3-(piperazin-1-yl)prop-1-ynyl)phenoxy)propyl)thiazole-4-carboxylic Acid (12)

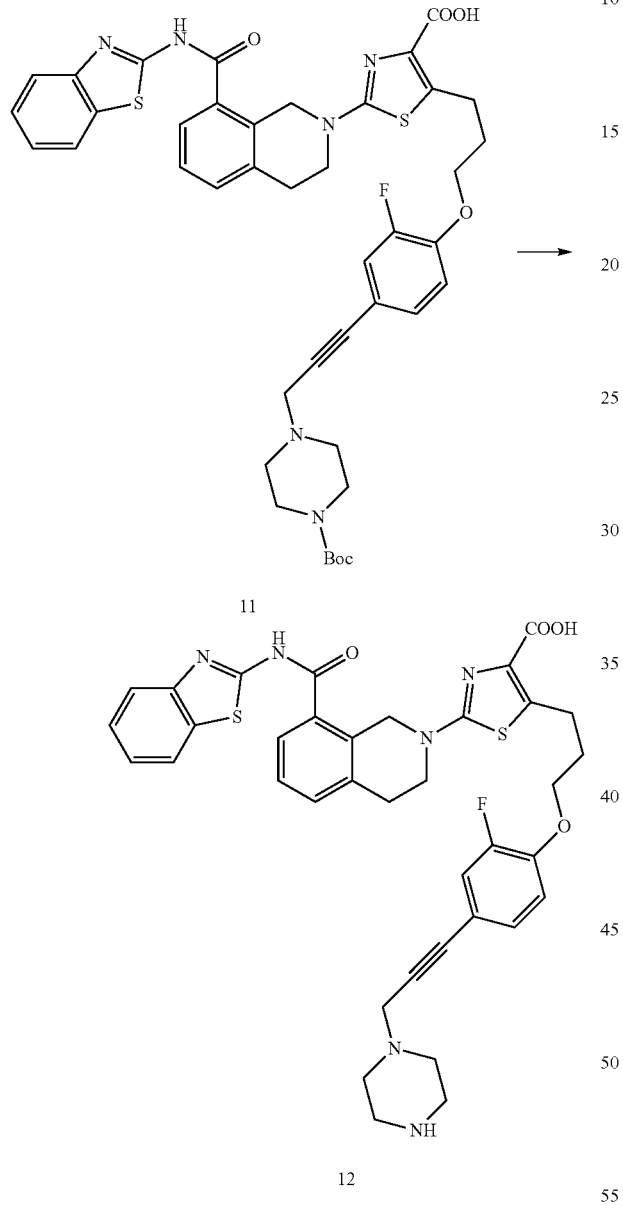

A mixture of compound 11 (130 mg) and TFA (1 mL) in 3 mL DCM was stirred at room temperature for 1 hour. The solvent was removed under reduced pressure and the crude product was crystallized in Et₂O and MeOH to give 110 mg compound 12 as a pale yellow solid. ¹H NMR (400 MHz, CD₃OD) δ 7.93 (d, J=7.7 Hz, 1H), 7.78 (d, J=7.7 Hz, 1H), 7.63 (d, J=7.2 Hz, 1H), 7.52-7.28 (m, 5H), 7.18-7.07 (m, 2H), 6.99 (t, J=8.7 Hz, 1H), 4.91 (s, 2H), 4.07 (t, J=6.1 Hz, 2H), 3.89-3.77 (m, 2H), 3.62 (s, 2H), 3.28-3.20 (m, 6H), 3.09-3.05 (m, 2H), 2.93-2.80 (m, 4H), 2.20-2.07 (m, 2H) ppm.

Preparation of 5-(3-(4-(3-(4-(4-azidobutanoyl)piperazin-1-yl)prop-1-ynyl)-2-fluorophenoxy)propyl)-2-(8-(benzo[d]thiazol-2-ylcarbamoyl)-3,4-dihydroisoquinolin-2(1H)-yl)thiazole-4-carboxylic Acid (13)

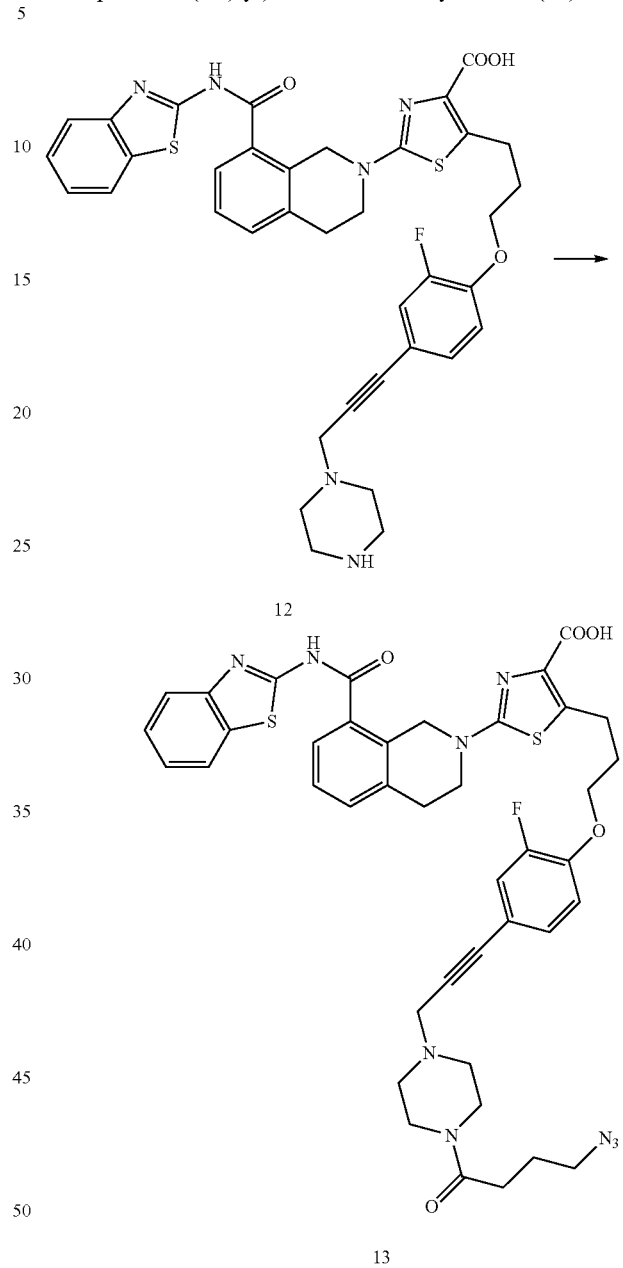

Compound 12 (100 mg) and TEA (157 µL) in 4 mL DCM was stirred at room temperature. 4-Azidobutanoyl chloride (16.4 mg) in 660 µL DCM was then added dropwise to the mixture. The reaction was quenched after stirred for 10 minutes by adding 1 mL MeOH. DCM was added and the mixture was washed water x1, brine x1, dried over Na₂SO₄, filtered and evaporated to dryness. The crude product was crystallized in MeOH to give 85 mg pale yellow solid. ¹H NMR (400 MHz, CDCl₃) δ 7.86 (d, J=7.8 Hz, 1H), 7.69-7.59 (m, 2H), 7.44-7.29 (m, 4H), 7.15-7.05 (m, 2H), 6.82 (t, J=8.7 Hz, 1H), 4.95 (s, 2H), 4.04 (t, J=6.3 Hz, 2H), 3.81-3.64 (m, 6H), 3.44-3.24 (m, 6H), 3.06 (t, J=5.9 Hz, 2H), 2.89-2.58 (m, 4H), 2.42 (t, J=7.2 Hz, 2H), 2.22-2.11 (m, 2H), 1.99-1.87 (m, 2H) ppm.

Preparation of 2-(8-(benzo[d]thiazol-2-ylcarbamoyl)-3,4-dihydroisoquinolin-2(1H)-yl)-5-(3-(4-(3-(4-(4-(4-((2-(2-(2-(2-(2,6-dioxopiperidin-3-yl)-1,3-dioxoisoindolin-4-ylamino)ethoxy)ethoxy)ethoxy)methyl)-1H-1,2,3-triazol-1-yl)butanoyl)piperazin-1-yl)prop-1-ynyl)-2-fluorophenoxy)propyl)thiazole-4-carboxylic Acid (XZ-13906)

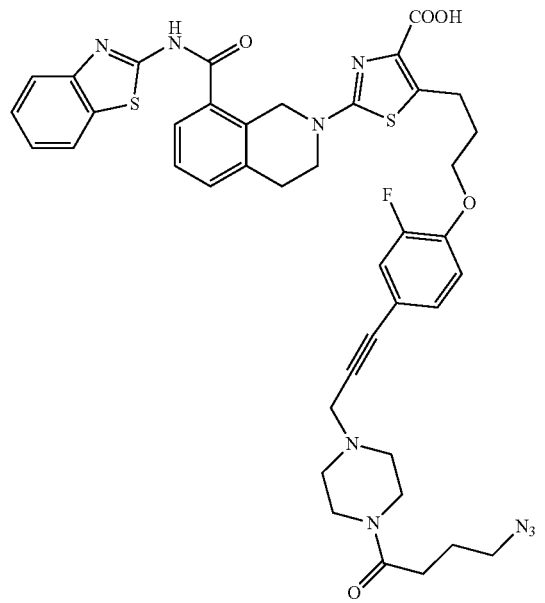

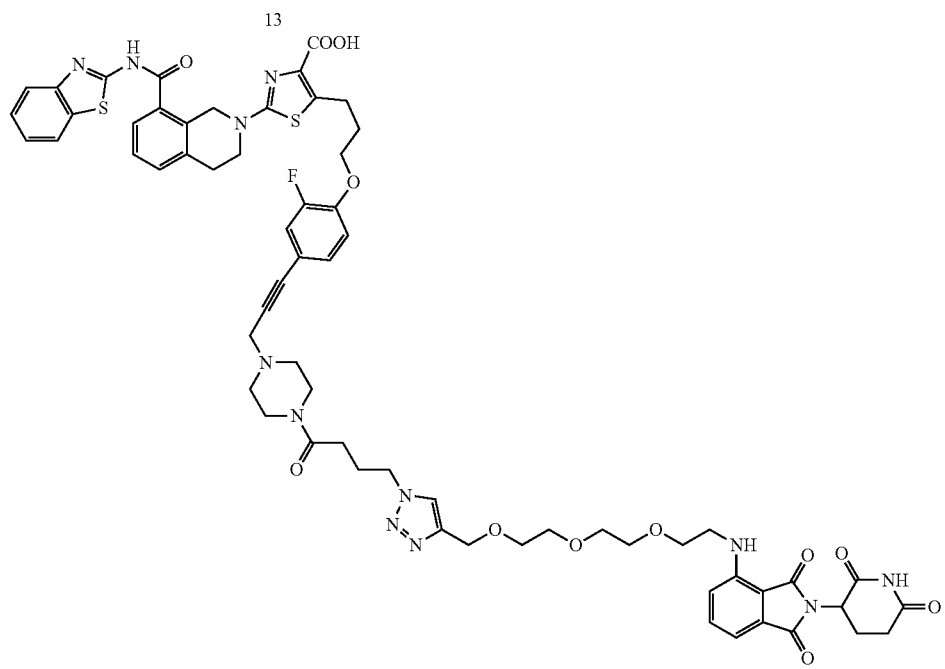

XZ-13906

To a mixture of compound 13 (18 mg), compound 9 (10 mg) in 1 mL t-BuOH under Argon was added CuSO$_4$.5H$_2$O (1.0 mg) and sodium ascorbate (0.8 mg) in 0.2 mL water. The mixture was stirred at 65° C. for 16 hours and extracted with DCM. The organic phase was washed brine x1, dried over Na$_2$SO$_4$, filtered and evaporated to dryness. The crude product was purified using reverse phase preparative HPLC to give 4.0 mg pure product as yellow solid. $^1$H NMR (400 MHz, CDCl$_3$) δ 10.17 (s, 1H), 7.92-7.82 (m, 2H), 7.71 (d, J=6.9 Hz, 1H), 7.53 (s, 1H), 7.50-7.43 (m, 2H), 7.37 (t, J=7.5 Hz, 1H), 7.33-7.27 (m, 2H), 7.15-7.02 (m, 3H), 6.87 (d, J=8.6 Hz, 1H), 6.79 (t, J=8.4 Hz, 1H), 6.48 (br s, 1H), 4.99-4.83 (m, 3H), 4.70-4.53 (m, 2H), 4.37 (t, J=5.9 Hz, 2H), 4.11-3.94 (m, 4H), 3.82-3.56 (m, 16H), 3.42 (t, J=4.8 Hz, 2H), 3.35-3.06 (m, 6H), 3.02 (t, J=5.7 Hz, 2H), 2.89-2.67 (m, 3H), 2.33-2.05 (m, 7H) ppm.

Example 2: Synthesis of XZ-13942
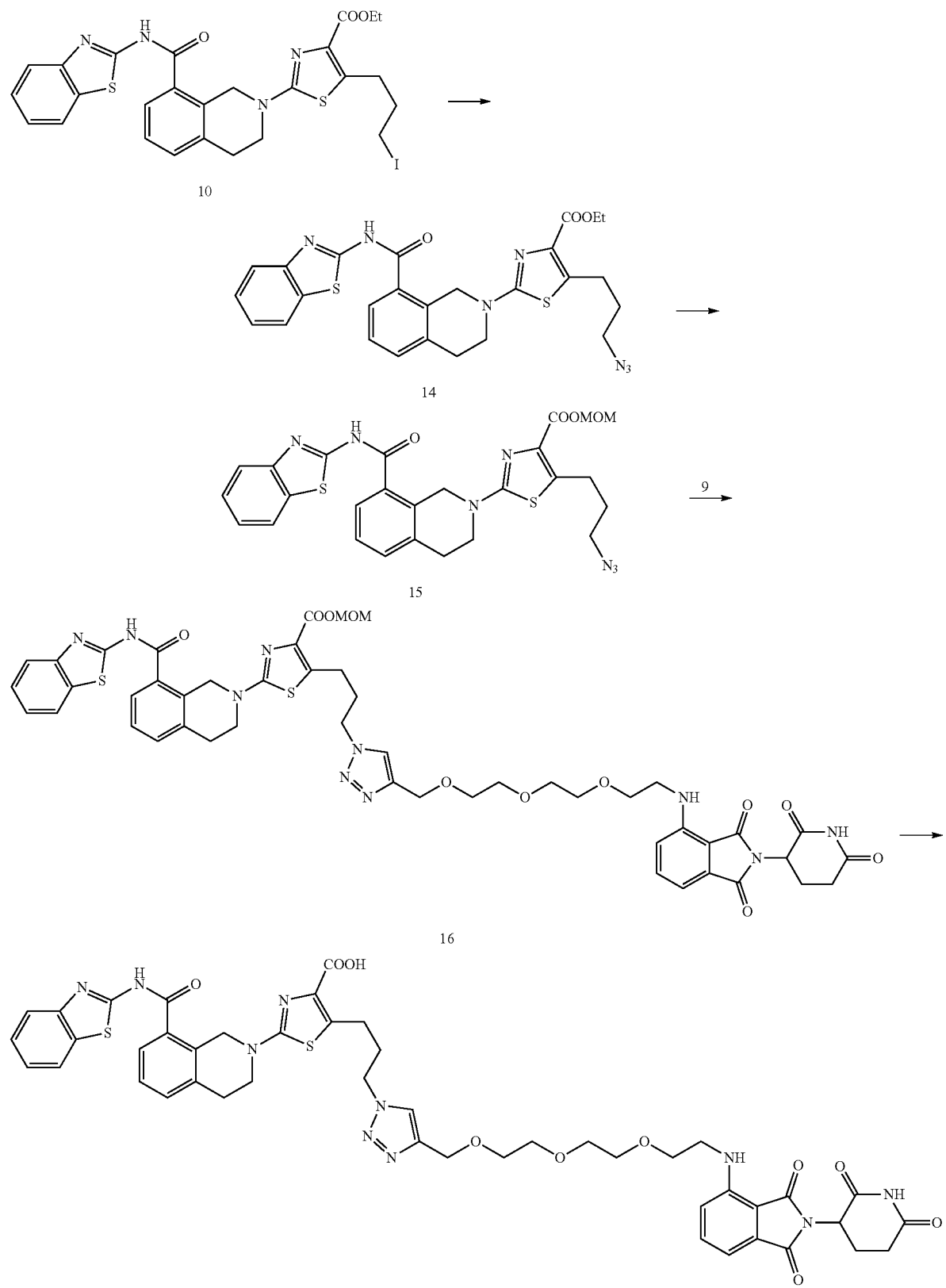

421
Preparation of ethyl 5-(3-azidopropyl)-2-(8-(benzo[d]thiazol-2-ylcarbamoyl)-3,4-dihydroisoquinolin-2(1H)-yl)thiazole-4-carboxylate (14)

422
Preparation of methoxymethyl 5-(3-azidopropyl)-2-(8-(benzo[d]thiazol-2-ylcarbamoyl)-3,4-dihydroisoquinolin-2(1H)-yl)thiazole-4-carboxylate (15)

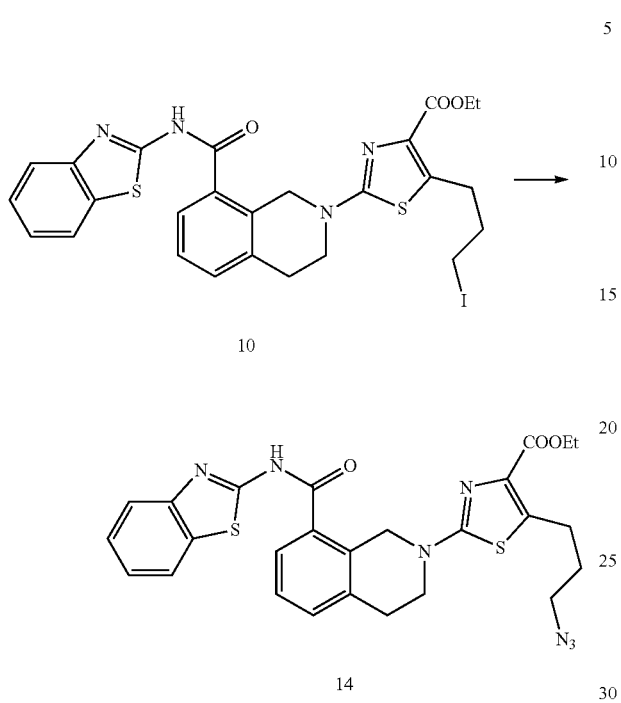

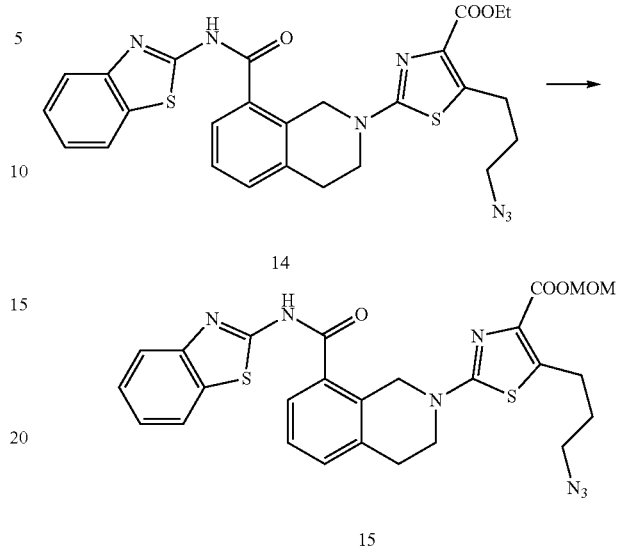

Compound 10 (100 mg) and NaN₃ (13 mg) were stirred in 5 mL DMSO at 45° C. overnight. The mixture was poured into water and extracted with EtOAc. The organic phase was washed with water x1, brine x1, dried over Na₂SO₄, filtered and evaporated to dryness to give 85 mg pure product as white solid. Yield 98%. $^1$H NMR (400 MHz, CDCl₃) δ 7.82 (d, J=6.7 Hz, 1H), 7.54 (d, J=7.6 Hz, 1H), 7.35-7.26 (m, 4H), 7.18 (t, J=7.6 Hz, 1H), 4.87 (s, 2H), 4.28 (q, J=7.1 Hz, 2H), 3.90-3.79 (m, 2H), 3.31 (t, J=6.6 Hz, 2H), 3.11 (t, J=7.4 Hz, 2H), 3.03-2.92 (m, 2H), 1.98-1.82 (m, 2H), 1.31 (t, J=7.1 Hz, 3H) ppm.

Compound 14 (85 mg) and NaOH (26.5 mg) were stirred in a mixture of ethanol and water at 50° C. for 5 hours. The mixture was cooled to room temperature and neutralized with 1N HCl (aq.). The precipitated solid was collected and dissolved in 4 mL DMF. Then Na₂CO₃ (17 mg) and MOMCl (12 mg) was added into the mixture. After 16 hours, the mixture was poured into water and extracted with EtOAc. The organic phase was washed with water x1, brine x1, dried over Na₂SO₄, filtered and evaporated to dryness. The resulting mixture was purified via column chromatography using EtOAc and hexanes as eluents to afford 53 mg compound 15. Yield 61%. $^1$H NMR (400 MHz, CDCl₃) δ 7.88 (d, J=7.7 Hz, 1H), 7.75 (d, J=7.1 Hz, 1H), 7.68 (d, J=7.9 Hz, 1H), 7.51-7.29 (m, 5H), 5.40 (s, 2H), 4.94 (s, 2H), 3.90 (t, J=6.1 Hz, 2H), 3.50 (s, 3H), 3.35 (t, J=6.8 Hz, 2H), 3.17 (t, J=7.5 Hz, 2H), 3.08 (t, J=6.1 Hz, 2H), 1.99-1.88 (m, 2H) ppm.

Preparation of 2-(8-(benzo[d]thiazol-2-ylcarbamoyl)-3,4-dihydroisoquinolin-2(1H)-yl)-5-(3-(4-((2-(2-(2-((2-(2,6-dioxopiperidin-3-yl)-1,3-dioxoisoindolin-4-yl)amino)ethoxy)ethoxy)ethoxy)methyl)-1H-1,2,3-triazol-1-yl)propyl)thiazole-4-carboxylic acid (XZ13942)

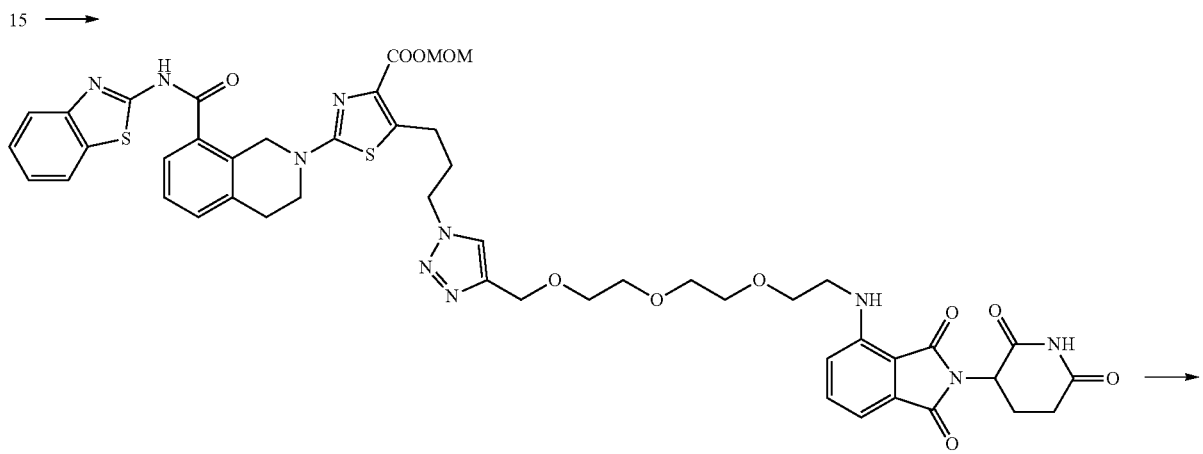

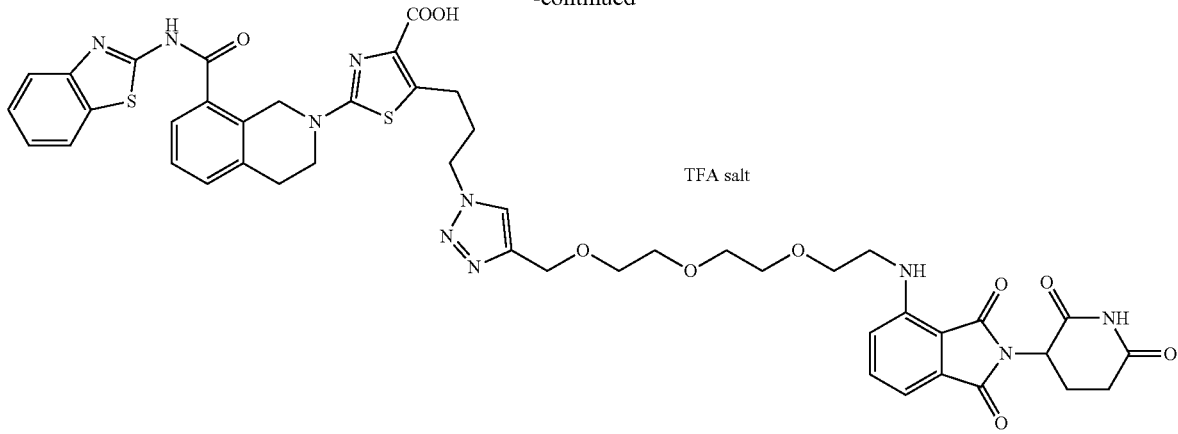

XZ13942

To a mixture of compound 15 (10 mg), compound 9 (8.7 mg) in 2 mL t-BuOH-THF (1:1, v/v) under argon was added $CuSO_4 \cdot 5H_2O$ (0.9 mg) and sodium ascorbate (0.7 mg) in 0.4 mL water. The mixture was stirred at 60° C. for 16 hours and extracted with DCM. The organic phase was washed with brine x1, dried over $Na_2SO_4$, filtered and evaporated to dryness. The crude product was purified via column chromatography using DCM and methanol as eluents to afford 14 mg compound 16. Yield 78%. Compound 16 (9.0 mg) and 0.1 mL TFA was stirred in 3 mL DCM for 1 hour. The solvent was removed under reduced pressure. Then $Et_2O$ was added into the residue and the precipitated solid was collected to afford 8.4 mg pure XZ13942. Yield 79%. $^1$H NMR (400 MHz, $CDCl_3$) δ 10.03 (s, 1H), 7.94 (d, J=6.4 Hz, 1H), 7.87 (d, J=7.7 Hz, 1H), 7.77 (d, J=6.7 Hz, 1H), 7.64-7.29 (m, 6H), 7.07 (d, J=7.0 Hz, 1H), 6.88 (d, J=8.5 Hz, 1H), 5.03-4.86 (m, 3H), 4.75-4.55 (m, 2H), 4.46-4.30 (m, 2H), 3.86-3.58 (m, 12H), 3.46-3.33 (m, 2H), 3.25-2.98 (m, 4H), 2.92-2.68 (m, 3H), 2.28-2.05 (m, 3H) ppm.

Example 3: Synthesis of XZ-14424

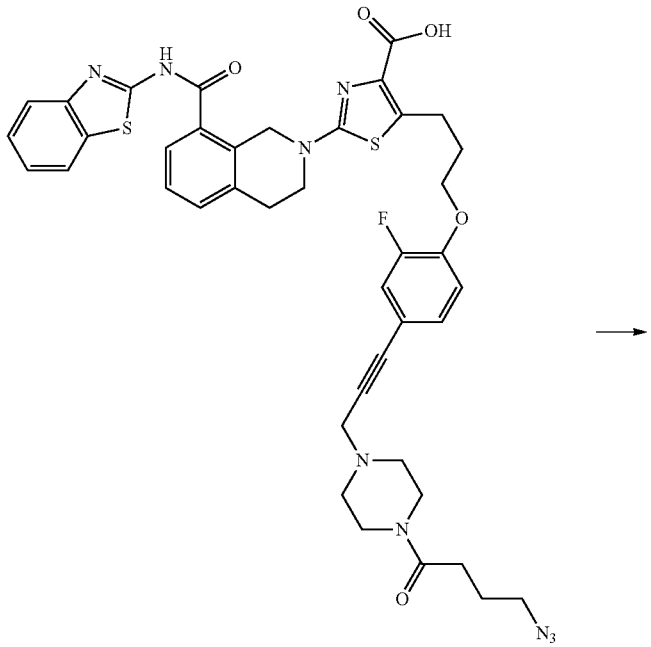

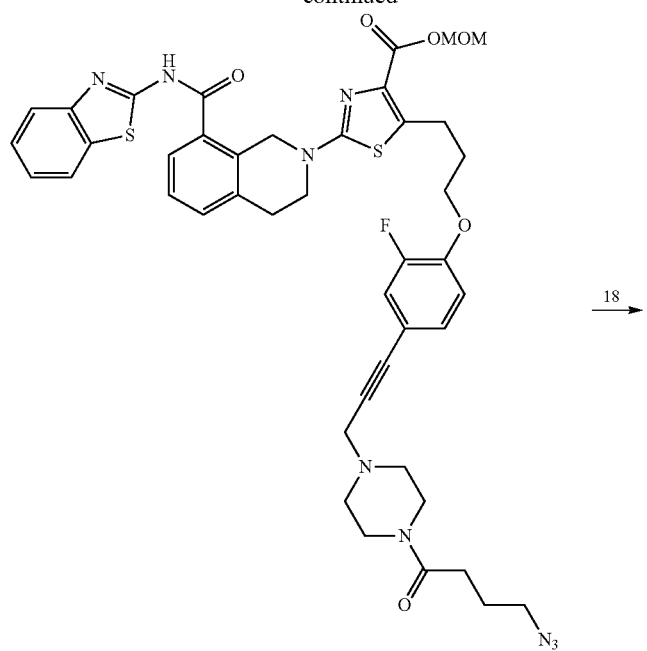
19
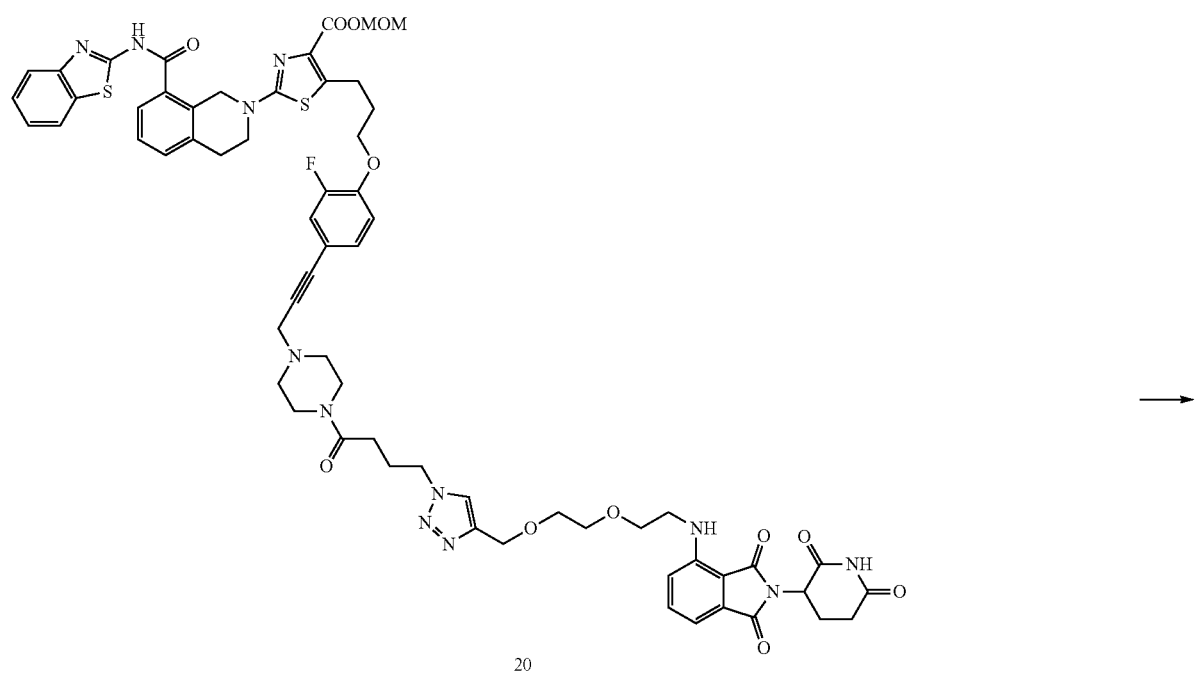
20

-continued

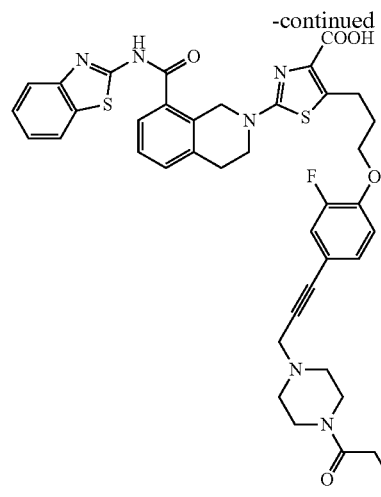

XZ14424

Preparation of 2-(2,6-dioxopiperidin-3-yl)-4-((2-(2-(prop-2-yn-1-yloxy)ethoxy)ethyl)amino) isoindoline-1,3-dione (18)

Preparation of methoxymethyl 5-(3-(4-(3-(4-(4-azidobutanoyl)piperazin-1-yl)prop-1-yn-1-yl)-2-fluorophenoxy)propyl)-2-(8-(benzo[d]thiazol-2-yl-carbamoyl)-3,4-dihydroisoquinolin-2(1H)-yl) thiazole-4-carboxylate (19)

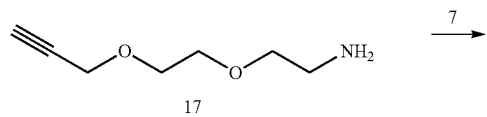

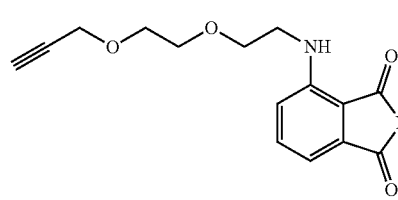

Compound 7 (107 mg), amine 17 (84 mg), and DIPEA (193 μL) in 5 mL DMF were stirred at 85° C. for 16 hours. Water was added to the reaction mixture and extracted with EtOAc. The organic phase was washed with water x1, brine x1, dried over $Na_2SO_4$, filtered and evaporated to dryness. The resulting mixture was purified by column chromatography using EtOAc and hexanes as eluents to afford 50 mg compound 18 as a green solid. Yield 32%. $^1$H NMR (400 MHz, $CDCl_3$) δ 7.98 (s, 1H), 7.62-7.35 (m, 1H), 7.11 (d, J=7.1 Hz, 1H), 6.93 (d, J=8.5 Hz, 1H), 4.92 (dd, J=11.9, 5.3 Hz, 1H), 4.21 (d, J=2.3 Hz, 2H), 3.78-3.66 (m, 6H), 3.49 (t, J=5.4 Hz, 2H), 2.93-2.68 (m, 3H), 2.48-2.41 (m, 1H), 2.18-2.09 (m, 1H) ppm.

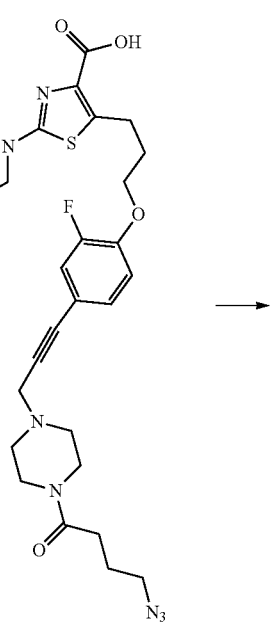

-continued

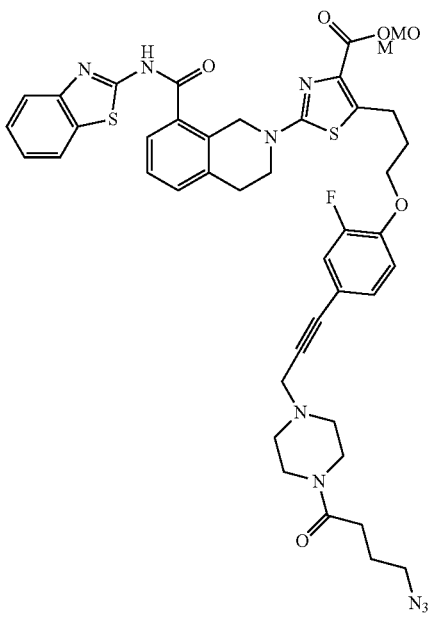

19

Compound 13 (26 mg), Na$_2$CO$_3$ (4.1 mg) and MOMCl (2.8 mg) were stirred in 2 mL DMF for 24 hours. Then it was poured into water and extracted with EtOAc. The organic phase was washed with water x1, brine x1, dried over Na$_2$SO$_4$, filtered and evaporated to dryness. The resulting mixture was purified via column chromatography using DCM and methanol as eluents to afford 15 mg compound 19. Yield 58%. $^1$H NMR (400 MHz, CDCl$_3$) δ 7.90-7.77 (m, 1H), 7.54 (d, J=7.6 Hz, 1H), 7.37-7.25 (m, 4H), 7.18 (t, J=7.6 Hz, 1H), 7.12-7.04 (m, 2H), 6.81 (t, J=8.4 Hz, 1H), 5.34 (s, 2H), 4.88 (s, 2H), 4.03 (t, J=6.2 Hz, 2H), 3.81 (t, J=6.0 Hz, 2H), 3.76-3.64 (m, 2H), 3.63-3.49 (m, 4H), 3.44 (s, 3H), 3.36 (t, J=6.3 Hz, 2H), 3.25 (t, J=7.4 Hz, 2H), 3.00 (t, J=5.9 Hz, 2H), 2.71-2.53 (m, 4H), 2.40 (t, J=7.2 Hz, 2H), 2.23-2.06 (m, 2H), 1.98-1.84 (m, 2H) ppm.

Preparation of 2-(8-(benzo[d]thiazol-2-ylcarbamoyl)-3,4-dihydroisoquinolin-2(1H)-yl)-5-(3-(4-(3-(4-(4-(4-((2-(2-((2-(2,6-dioxopiperidin-3-yl)-1,3-dioxoisoindolin-4-yl)amino)ethoxy)ethoxy)methyl)-1H-1,2,3-triazol-1-yl)butanoyl)piperazin-1-yl)prop-1-yn-1-yl)-2-fluorophenoxy)propyl)thiazole-4-carboxylic Acid (XZ14424)

19 —18→

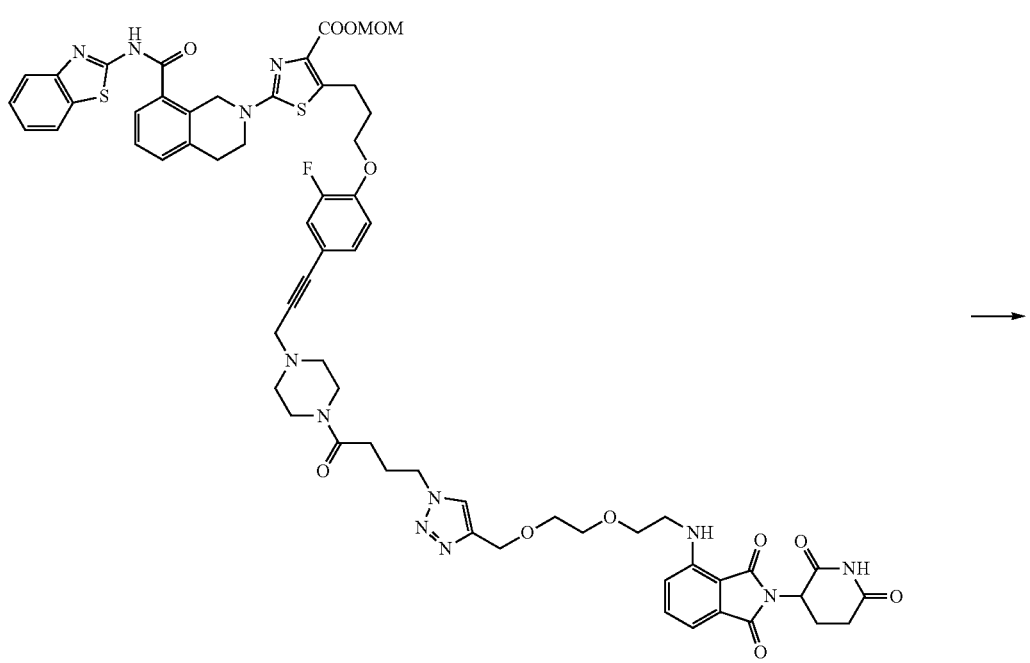

20

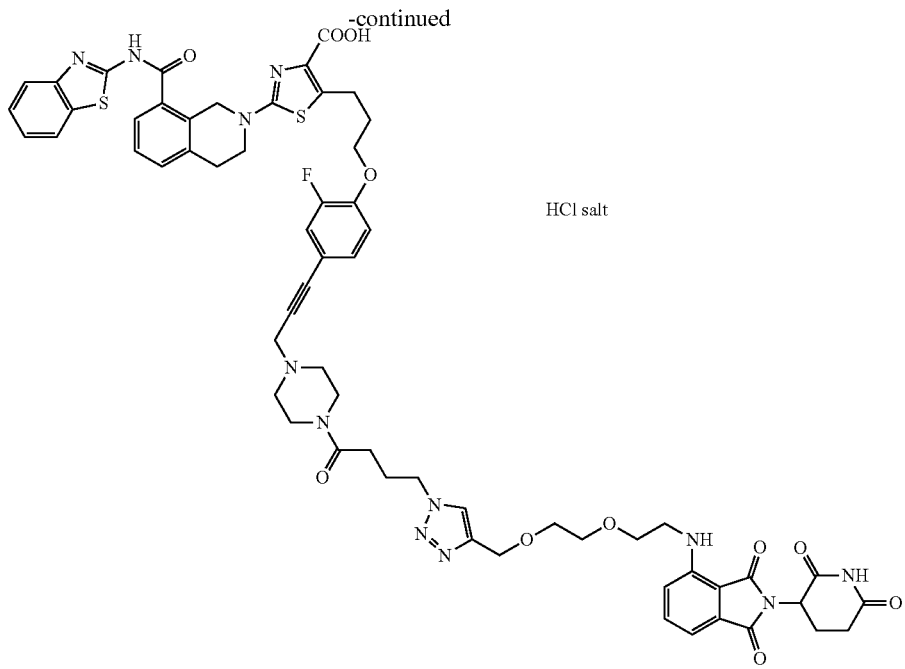

XZ14424

To a mixture of compound 19 (13.0 mg), compound 18 (8.0 mg) in 2 mL t-BuOH-THF (1:1, v/v) under argon was added CuSO$_4$.5H$_2$O (0.82 mg) and sodium ascorbate (0.65 mg) in 0.4 mL water. The mixture was stirred at 55° C. for 16 hours and extracted with DCM. The organic phase was washed with brine x1, dried over Na$_2$SO$_4$, filtered and evaporated to dryness. The crude product was purified via column chromatography using DCM and methanol as eluents to afford 20 mg compound 20. Yield 91%. Compound 20 (20.0 mg) and 0.1 mL HCl solution (4.0 M in 1,4-dioxane) was stirred in 4 mL DCM-methanol (3:1, v/v) for 3 hours. The solvents were removed under reduced pressure. Et$_2$O was then added to the residue and the precipitated solid was collected to afford 15.4 mg pure XZ14424. Yield 73%. $^1$H NMR (400 MHz, CD$_3$OD) δ 8.02 (s, 1H), 7.92 (d, J=7.9 Hz, 1H), 7.79 (d, J=7.9 Hz, 2H), 7.61-7.44 (m, 4H), 7.36 (t, J=7.5 Hz, 1H), 7.31-7.18 (m, 2H), 7.12-6.95 (m, 3H), 5.14 (s, 2H), 5.01 (dd, J=12.7, 5.4 Hz, 1H), 4.64 (s, 2H), 4.47 (t, J=6.5 Hz, 2H), 4.34 (s, 2H), 4.16 (t, J=5.5 Hz, 2H), 3.99-3.88 (m, 2H), 3.77-3.44 (m, 14H), 3.38-3.33 (m, 4H), 3.26-3.19 (m, 2H), 2.89-2.62 (m, 3H), 2.52-2.38 (m, 2H), 2.25-2.04 (m, 5H) ppm.

Example 4: Synthesis of XZ-14418

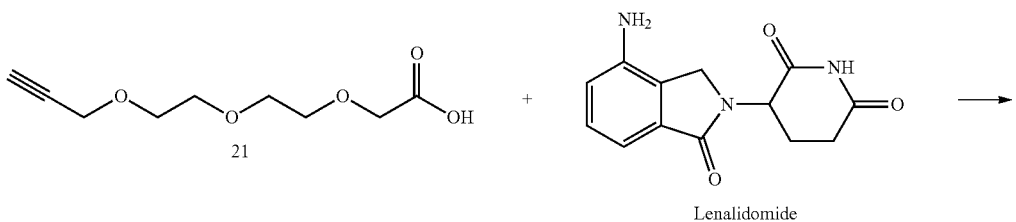

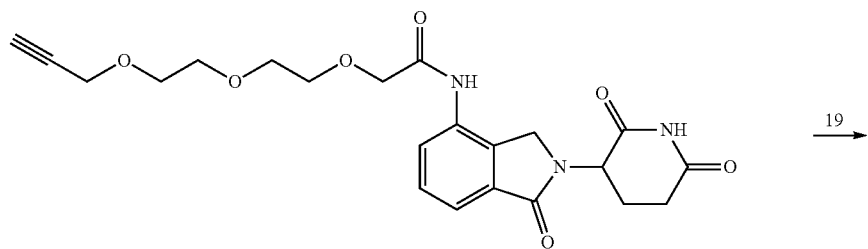

433
434
-continued
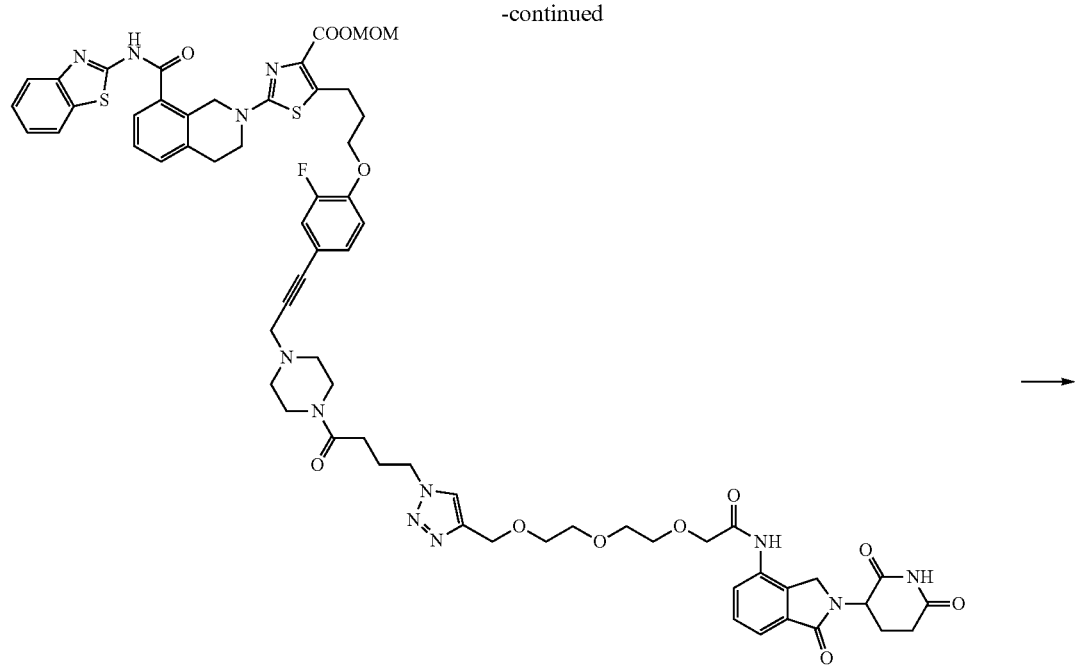
23
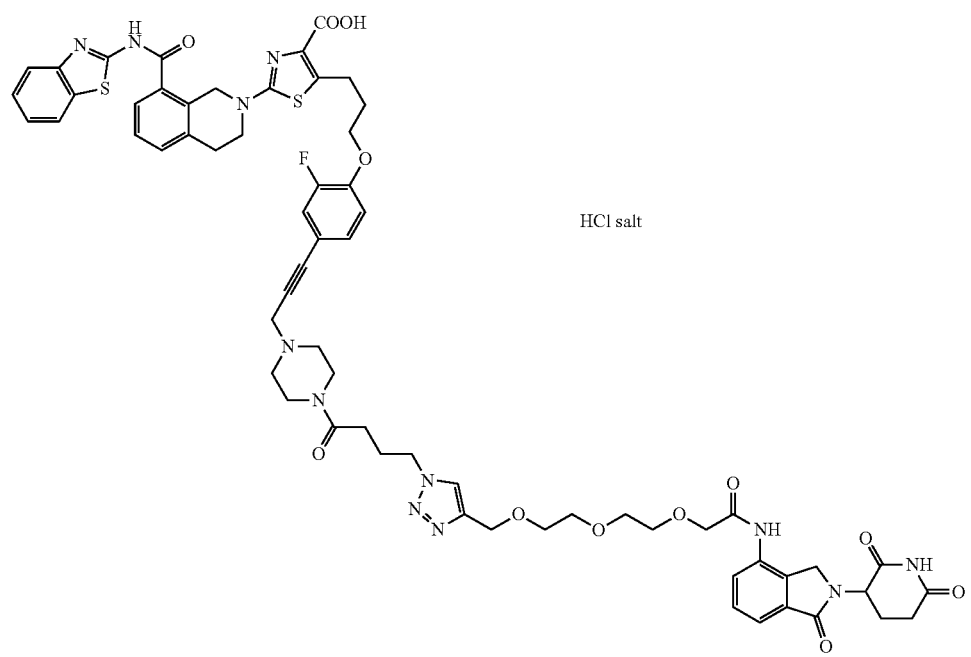
HCl salt
XZ14418

435

Preparation of N-(2-(2,6-dioxopiperidin-3-yl)-1-oxoisoindolin-4-yl)-2-(2-(2-(prop-2-ynyloxy)ethoxy)ethoxy)acetamide (22)

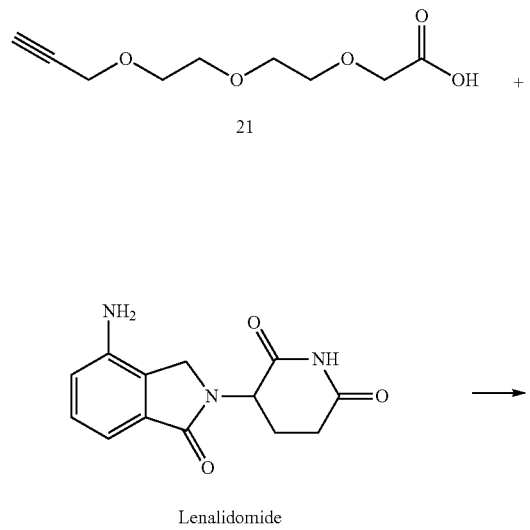

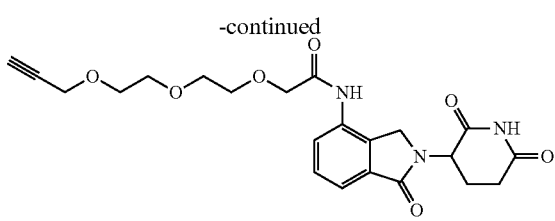

Lenalidomide (61 mg), compound 21 (57 mg), HATU (94 mg) and DIPEA (59 µL) were stirred in 5 mL DCM overnight. The mixture was concentrated under reduced pressure and purified via column chromatography using DCM and methanol as eluents to afford 58 mg compound 22. Yield 56%. $^1$H NMR (400 MHz, CDCl$_3$) δ 8.92 (s, 1H), 7.97 (s, 1H), 7.74 (d, J=7.5 Hz, 1H), 7.68 (d, J=7.9 Hz, 1H), 7.49 (t, J=7.7 Hz, 1H), 5.20 (dd, J=13.3, 5.1 Hz, 1H), 4.45 (s, 2H), 4.14 (d, J=3.4 Hz, 2H), 3.96 (s, 2H), 3.83-3.57 (m, 8H), 2.98-2.70 (m, 2H), 2.49-2.28 (m, 2H), 2.27-2.13 (m, 1H) ppm.

Preparation of 2-(8-(benzo[d]thiazol-2-ylcarbamoyl)-3,4-dihydroisoquinolin-2(1H)-yl)-5-(3-(4-(3-(4-(4-(4-((2-(2-(2-(2-(2,6-dioxopiperidin-3-yl)-1-oxoisoindolin-4-ylamino)-2-oxoethoxy)ethoxy)ethoxy)methyl)-1H-1,2,3-triazol-1-yl)butanoyl)piperazin-1-yl)prop-1-ynyl)-2-fluorophenoxy)propyl)thiazole-4-carboxylic Acid (XZ14418)

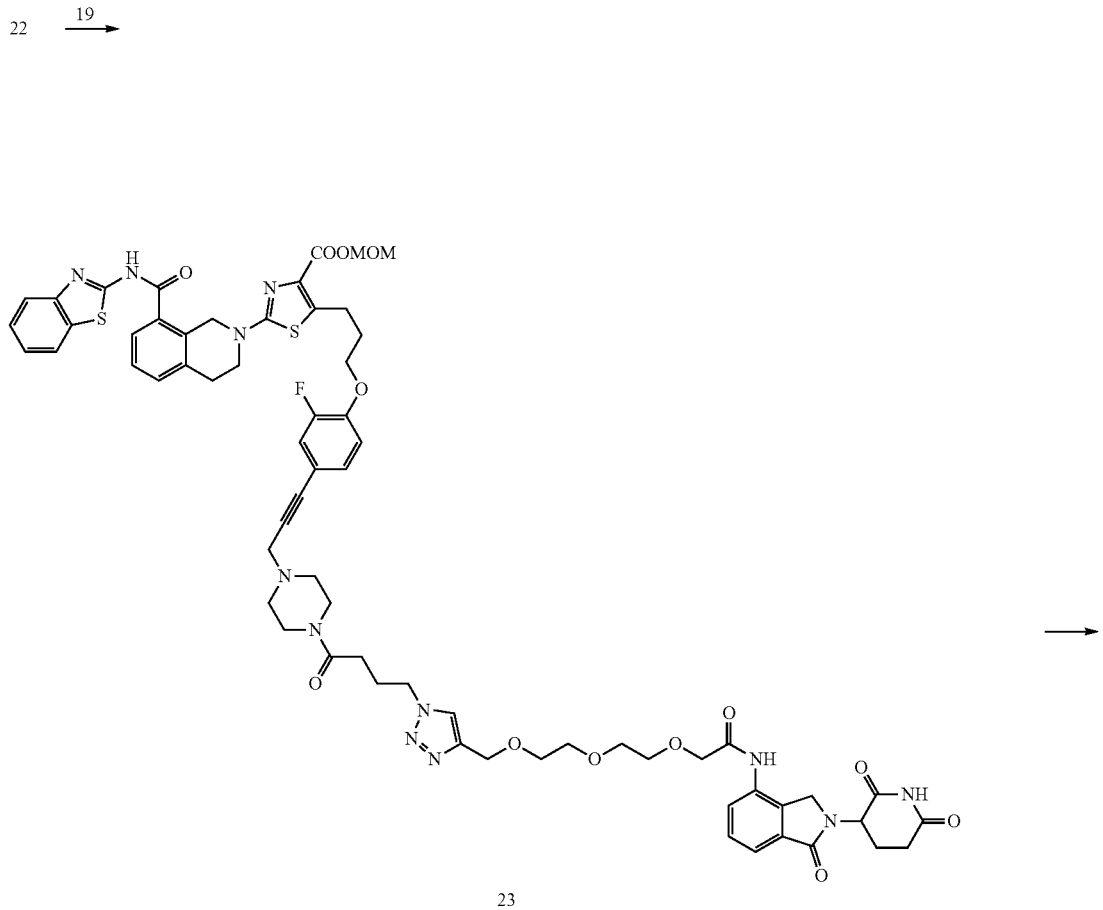

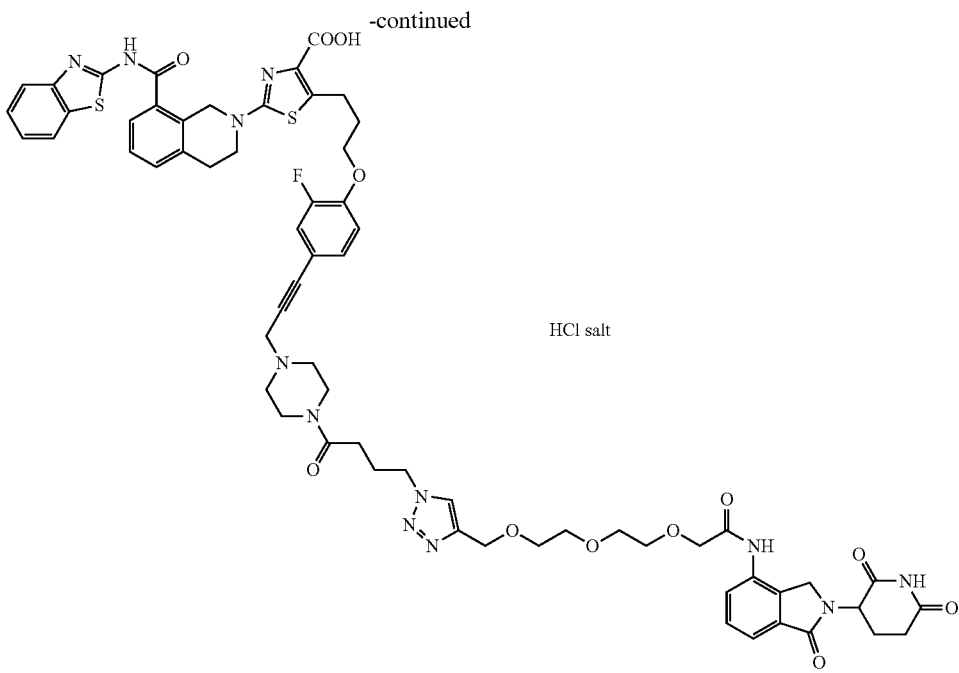

XZ14418

To a mixture of compound 19 (12.0 mg), compound 22 (7.4 mg) in 4 mL t-BuOH-THF (1:3, v/v) under Argon was added $CuSO_4 \cdot 5H_2O$ (0.70 mg) and sodium ascorbate (0.56 mg) in 0.4 mL water. The mixture was stirred at 55° C. for 16 hours and extracted with DCM. The organic phase was washed with brine x1, dried over $Na_2SO_4$, filtered and evaporated to dryness. The crude product was purified via column chromatography using DCM and methanol as eluents to afford 15.0 mg compound 23. Yield 85%. Compound 23 (15.0 mg) and 0.1 mL HCl solution (4.0 M in 1,4-dioxane) was stirred in 4 mL 5 mL DCM for 10 minutes. The solvent was removed under reduced pressure. Then $Et_2O$ was added into the residue and the precipitated solid was collected to afford 11.8 mg pure XZ14418. Yield 75%. $^1$H NMR (400 MHz, $CD_3OD$) δ 8.00-7.89 (m, 2H), 7.84-7.76 (m, 2H), 7.69 (d, J=7.8 Hz, 1H), 7.64 (d, J=7.1 Hz, 1H), 7.59-7.43 (m, 4H), 7.37 (t, J=7.6 Hz, 1H), 7.31-7.19 (m, 2H), 7.06 (t, J=8.5 Hz, 1H), 5.23-5.04 (m, 3H), 4.57-4.45 (m, 4H), 4.41 (t, J=6.8 Hz, 2H), 4.33 (s, 2H), 4.23-4.12 (m, 4H), 3.93 (t, J=5.7 Hz, 2H), 3.82-3.63 (m, 10H), 3.37-3.33 (m, 8H), 3.21 (t, J=5.5 Hz, 2H), 2.96-2.67 (m, 2H), 2.57-2.36 (m, 3H), 2.28-2.11 (m, 5H) ppm.

Example 5: Synthesis of XZ-14455

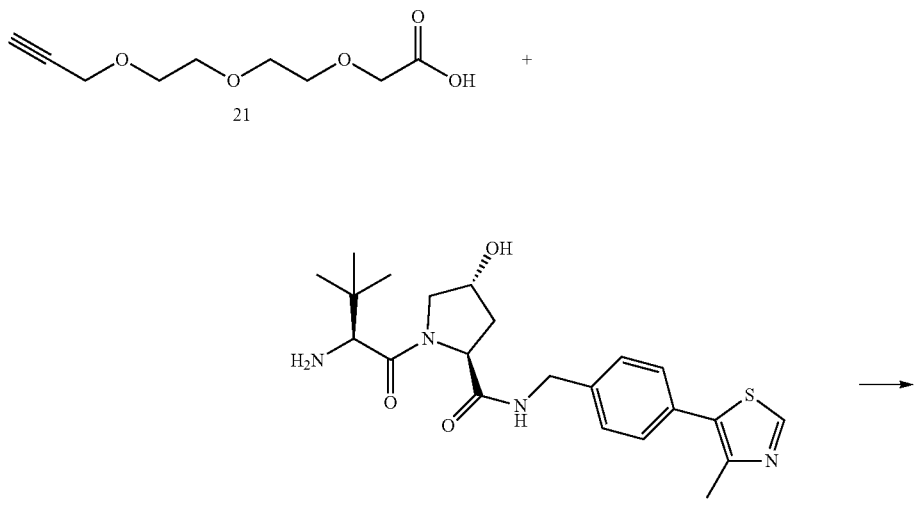

-continued
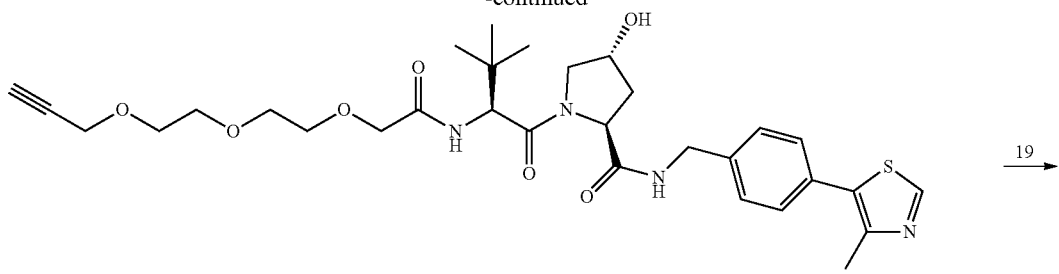
25
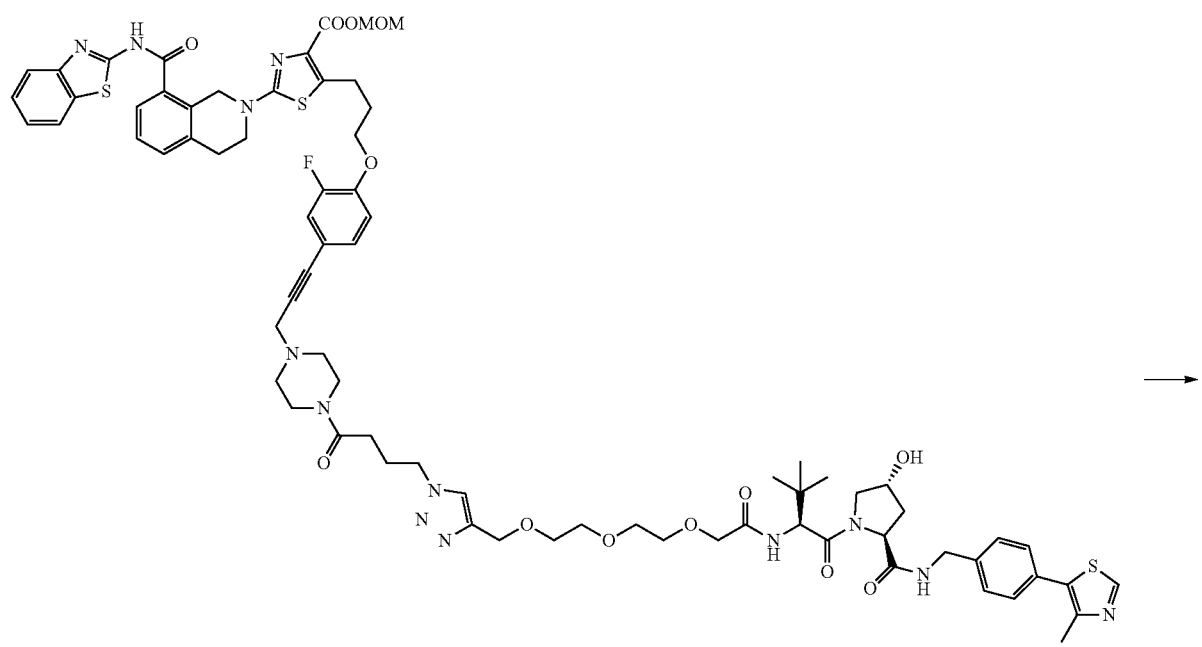
26
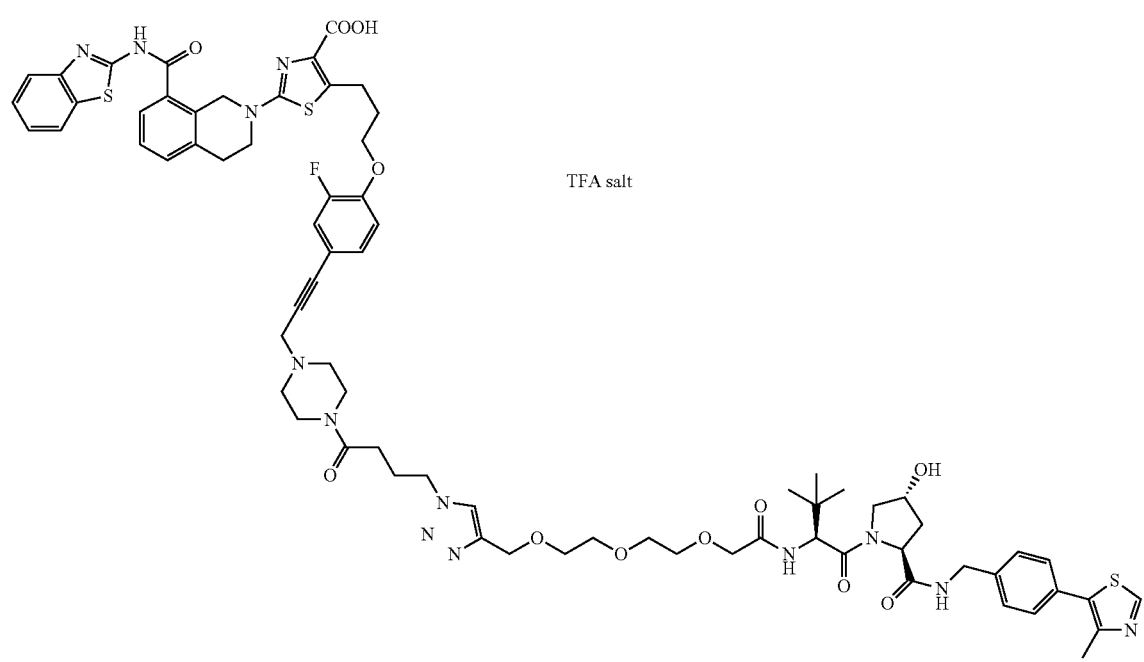
TFA salt
XZ14455

Preparation of (2S,4R)-1-((S)-2-tert-butyl-4-oxo-6, 9,12-trioxa-3-azapentadec-14-yne)-4-hydroxy-N-(4-(4-methylthiazol-5-yl)benzyl)pyrrolidine-2-carboxamide (25)

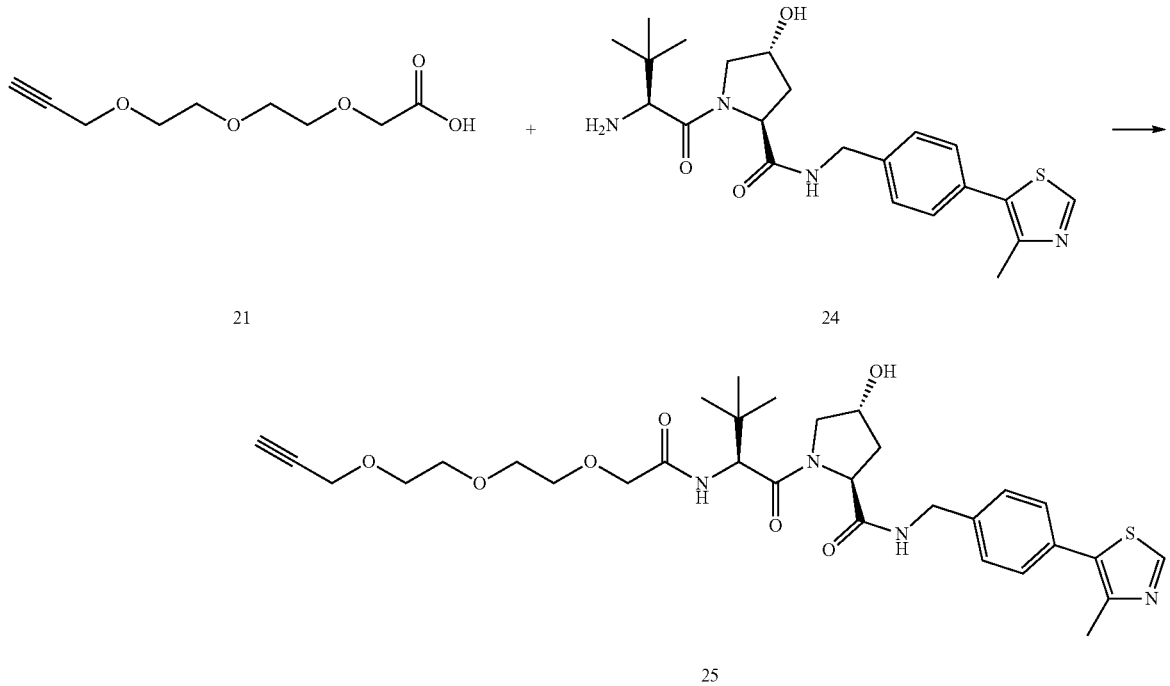

A mixture of compound 21, compound 24, HATU, and DIPEA in DCM was stirred at room temperature overnight. The mixture was concentrated under reduced pressure and purified via column chromatography using DCM and methanol as eluents to afford the title compound. $^1$H NMR (400 MHz, CDCl$_3$) δ 8.68 (s, 1H), 7.60-7.25 (m, 6H), 4.70 (t, J=8.0 Hz, 1H), 4.62-4.37 (m, 3H), 4.33 (dd, J=15.0, 5.3 Hz, 1H), 4.22-4.10 (m, 2H), 4.02-3.91 (m, 3H), 3.65-3.46 (m, 9H), 2.55-2.37 (m, 5H), 2.21-2.09 (m, 1H), 0.91 (s, 9H) ppm.

Preparation of 2-(8-(benzo[d]thiazol-2-ylcarbamoyl)-3,4-dihydroisoquinolin-2(1H)-yl)-5-(3-(2-fluoro-4-(3-(4-(4-(4-((S)-12-((2S,4R)-4-hydroxy-2-((4-(4-methylthiazol-5-yl)benzyl)carbamoyl)pyrrolidine-1-carbonyl)-13,13-dimethyl-10-oxo-2,5, 8-trioxa-11-azatetradecyl)-1H-1,2,3-triazol-1-yl)butanoyl)piperazin-1-yl)prop-1-yn-1-yl)phenoxy)propyl)thiazole-4-carboxylic Acid (XZ14455)

To a mixture of compound 19 (17.0 mg), compound 25 (17.0 mg) in 4 mL t-BuOH-THF (1:1, v/v) under argon was added CuSO$_4$.5H$_2$O (1.0 mg) and sodium ascorbate (0.8 mg) in 0.4 mL water. The mixture was stirred at 50° C. for 5 hours and extracted with DCM. The organic phase was washed with brine x1, dried over Na$_2$SO$_4$, filtered and evaporated to dryness. The crude product was purified via column chromatography using DCM and methanol as eluents to afford 14.9 mg compound 26. Yield 51%. Compound 26 (3.5 mg) and 0.1 mL TFA was stirred in 2 mL DCM for 6 hours. The solvent was removed under reduced pressure. Then Et$_2$O was added into the residue. The precipitated solid was filtered and washed with EtOAc followed by DCM-hexanes (1:1 v/v) to afford 3.5 mg pure XZ14455. Yield 83%. $^1$H NMR (400 MHz, CD$_3$OD) δ 8.86 (s, 1H), 8.00-7.89 (m, 2H), 7.78 (d, J=7.9 Hz, 1H), 7.71-7.59 (m, 1H), 7.53-7.30 (m, 8H), 7.29-7.17 (m, 2H), 7.02 (t, J=8.5 Hz, 1H), 4.89 (s, 2H), 4.73-4.20 (m, 12H), 4.17-3.96 (m, 4H), 3.92-3.59 (m, 15H), 3.40-3.33 (m, 2H), 3.28-3.23 (m, 2H), 3.07 (t, J=5.8 Hz, 2H), 2.49-2.36 (m, 5H), 2.31-1.94 (m, 6H), 1.02 (s, 9H) ppm.

Example 6: Synthesis of XZ-14439

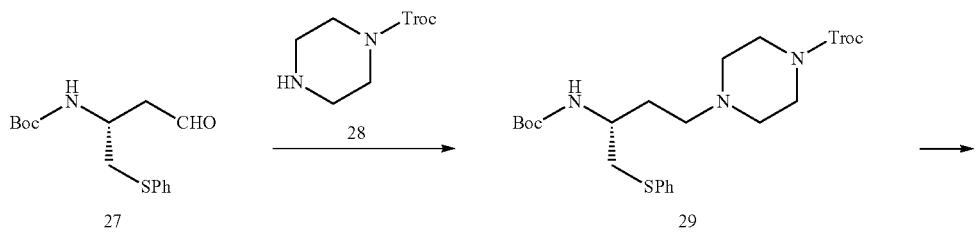

-continued
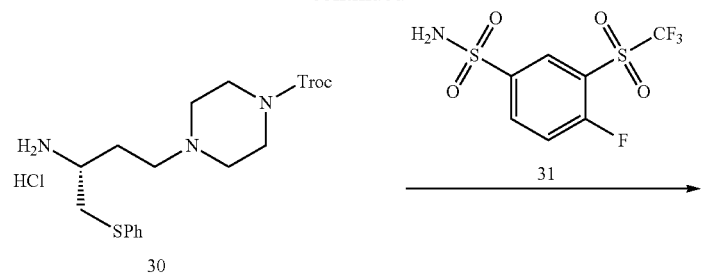
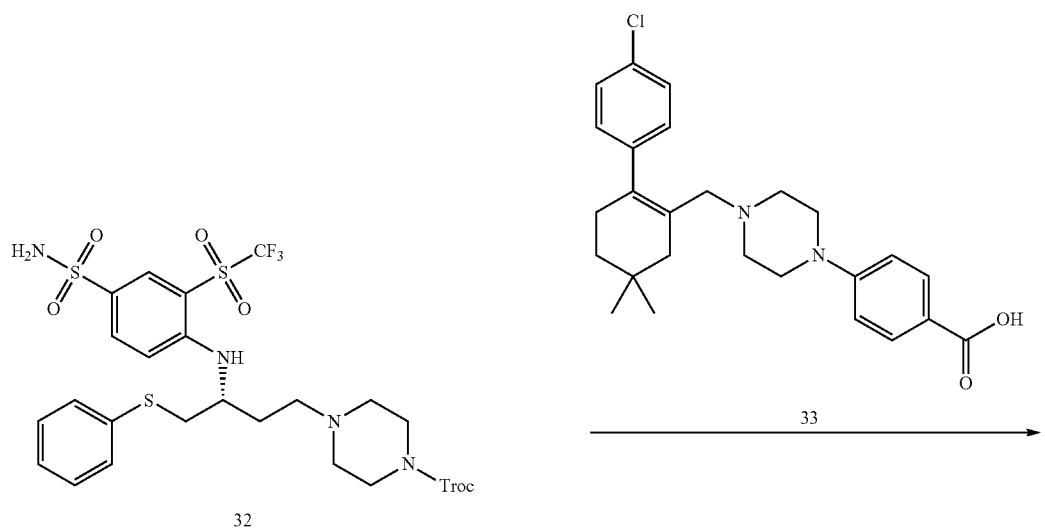
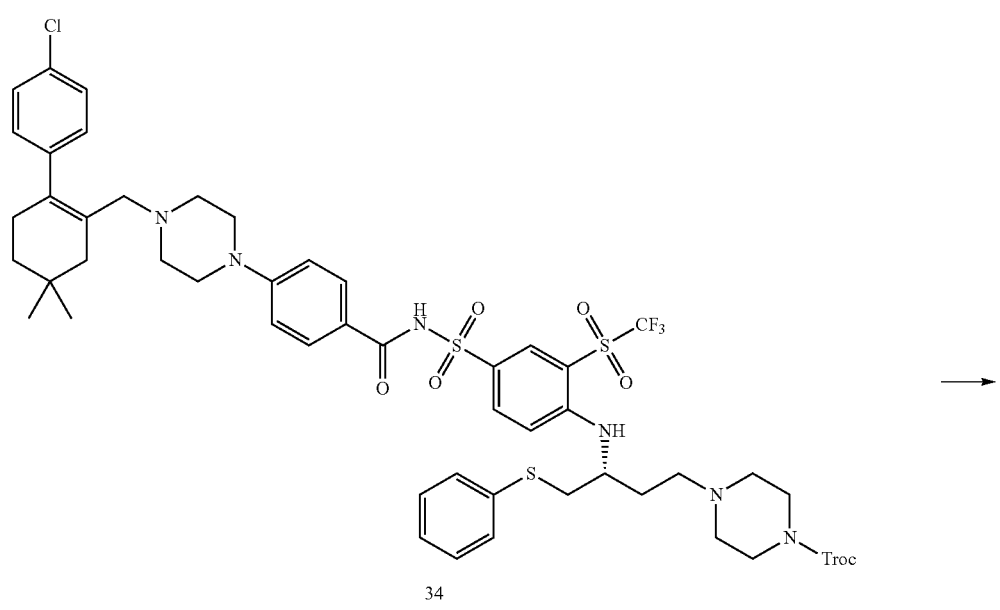

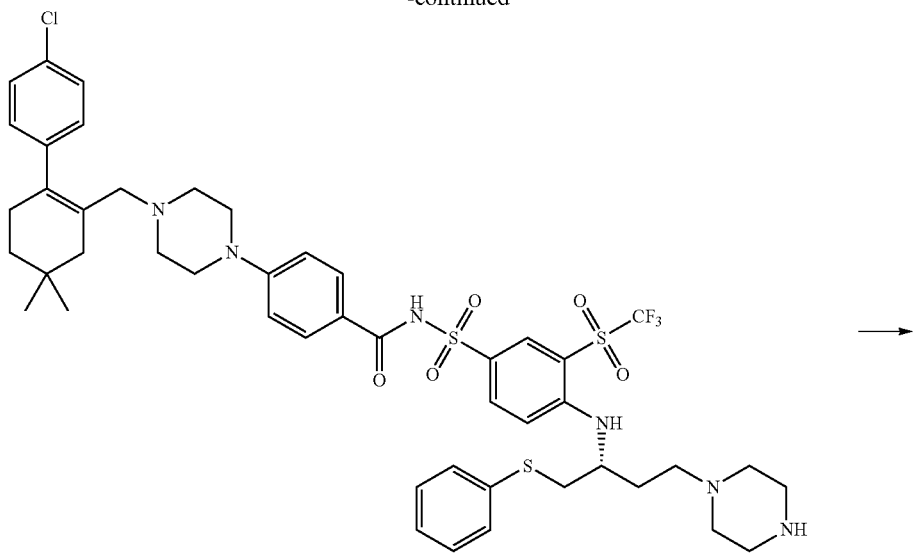
35
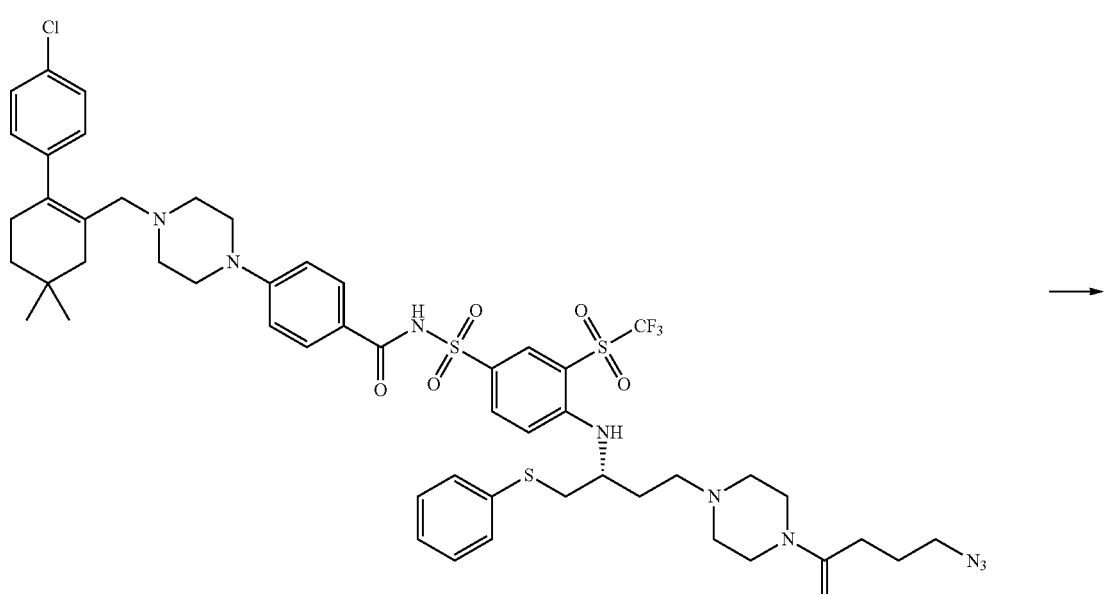
36
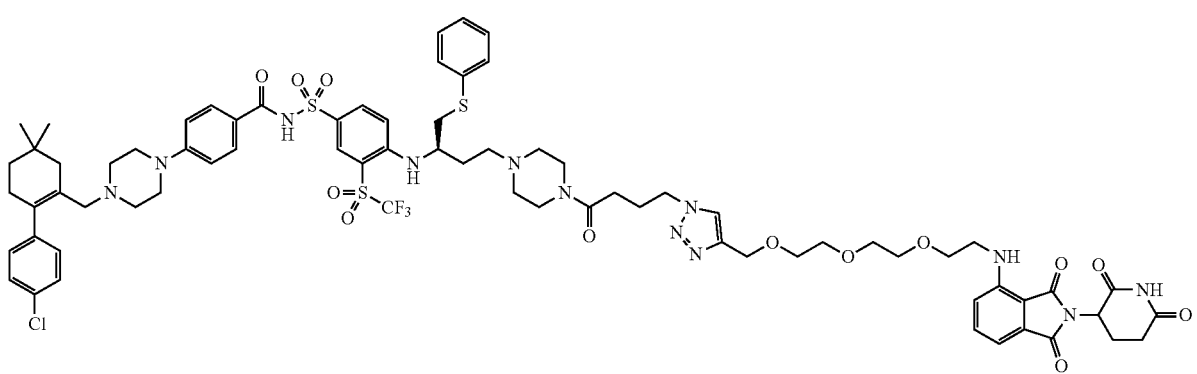
XZ14439

Preparation of 2,2,2-trichloroethyl (R)-4-(3-((tert-butoxycarbonyl)amino)-4-(phenylthio)butyl)piperazine-1-carboxylate (29)

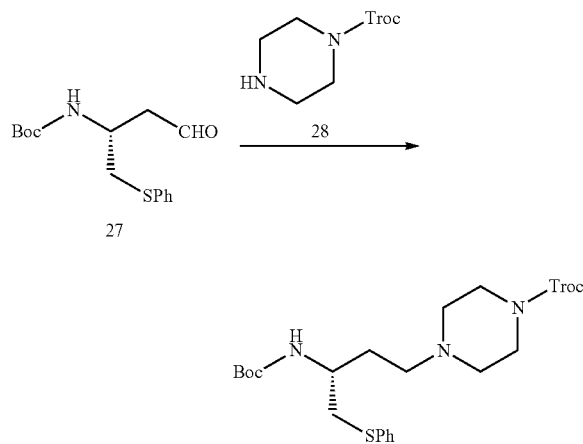

To a mixture of compound 27 (592 mg), compound 28 (753 mg), and TEA (1.12 mL) in 15 mL DCM was added 638 mg NaBH(OAc)$_3$. The solution was stirred at room temperature for 1 hour. Then it was poured into water and extracted with DCM. The organic phase was washed with brine x1, dried over Na$_2$SO$_4$, filtered and evaporated to dryness. The crude product was purified via column chromatography using EtOAc and hexanes as eluents to afford 733 mg compound 29. Yield 68%. $^1$H NMR (400 MHz, CDCl$_3$) δ 7.43-7.36 (m, 2H), 7.32-7.27 (m, 2H), 7.19 (t, J=7.3 Hz, 1H), 5.44 (br s, 1H), 4.76 (s, 2H), 3.99-3.84 (m, 1H), 3.72-3.49 (m, 4H), 3.23 (dd, J=13.3, 4.6 Hz, 1H), 3.10-2.95 (m, 1H), 2.61-2.31 (m, 6H), 1.96-1.61 (m, 2H), 1.43 (s, 9H) ppm.

Preparation of 2,2,2-trichloroethyl (R)-4-(3-amino-4-(phenylthio)butyl)piperazine-1-carboxylate (30)

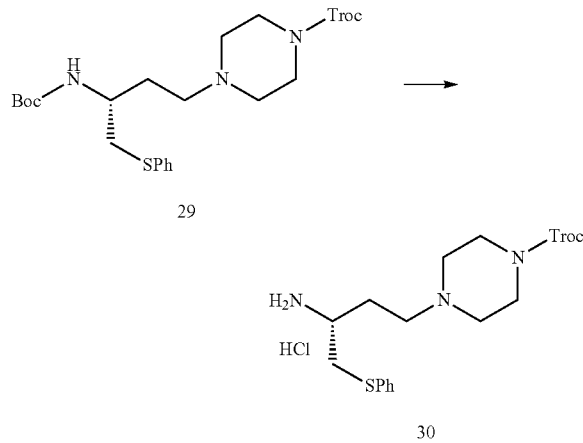

To a mixture of compound 29 (733 mg) in 5 mL DCM was added 5 mL HCl solution (4.0 M in 1,4-dioxane). The mixture was stirred at room temperature for 1 hour and the solvents were removed under reduced pressure. The solid was washed with Et$_2$O to afford 647 mg compound 30 as white solid. Yield 99%. $^1$H NMR (400 MHz, CDCl$_3$) δ 7.41-7.33 (m, 2H), 7.31-7.26 (m, 2H), 7.23-7.15 (m, 1H), 4.74 (s, 2H), 3.73-3.41 (m, 4H), 3.20-2.66 (m, 5H), 2.58-2.28 (m, 6H), 1.84-1.57 (m, 2H) ppm.

Preparation of 2,2,2-trichloroethyl (R)-4-(4-(phenylthio)-3-((4-sulfamoyl-2-((trifluoromethyl)sulfonyl)phenyl)amino)butyl)piperazine-1-carboxylate (32)

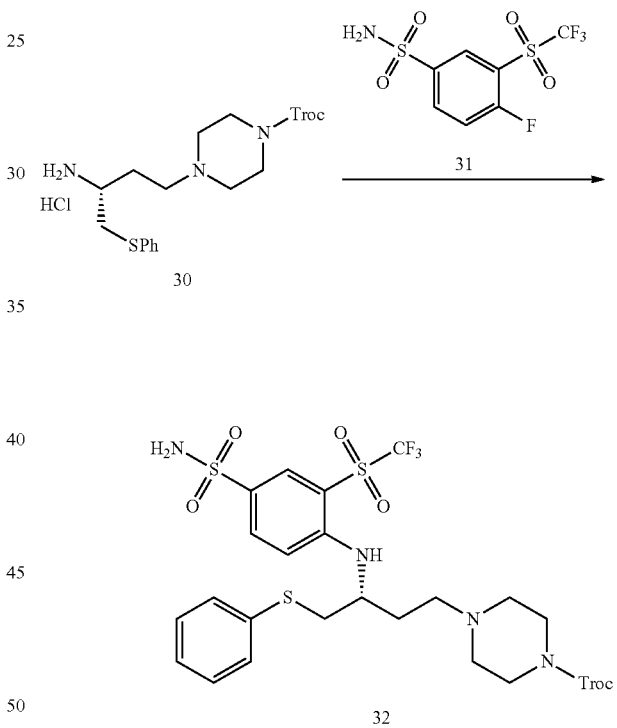

A mixture of compound 30 (647 mg), 4-fluoro-3-((trifluoromethyl)sulfonyl)benzenesulfonamide 31 (417 mg) and TEA (945 µL) in 20 mL acetonitrile was refluxed for 4 hours. The solvent was evaporated under reduced pressure and the crude product was purified via column chromatography using EtOAc and hexanes as eluents to afford 780 mg compound 32 as white solid. Yield 79%. $^1$H NMR (400 MHz, CDCl$_3$) δ 8.24 (d, J=2.2 Hz, 1H), 7.84 (d, J=9.1 Hz, 1H), 7.42-7.37 (m, 2H), 7.36-7.27 (m, 3H), 7.05 (d, J=8.6 Hz, 1H), 6.65 (br s, 1H), 5.13 (br s, J=10.8 Hz, 2H), 4.76 (s, 2H), 3.94 (s, 1H), 3.58 (s, 4H), 3.16-2.97 (m, 2H), 2.82-2.26 (m, 6H), 2.17 (s, 1H), 1.77 (s, 1H) ppm.

Preparation of 2,2,2-trichloroethyl (R)-4-(3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazine-1-carboxylate (34)

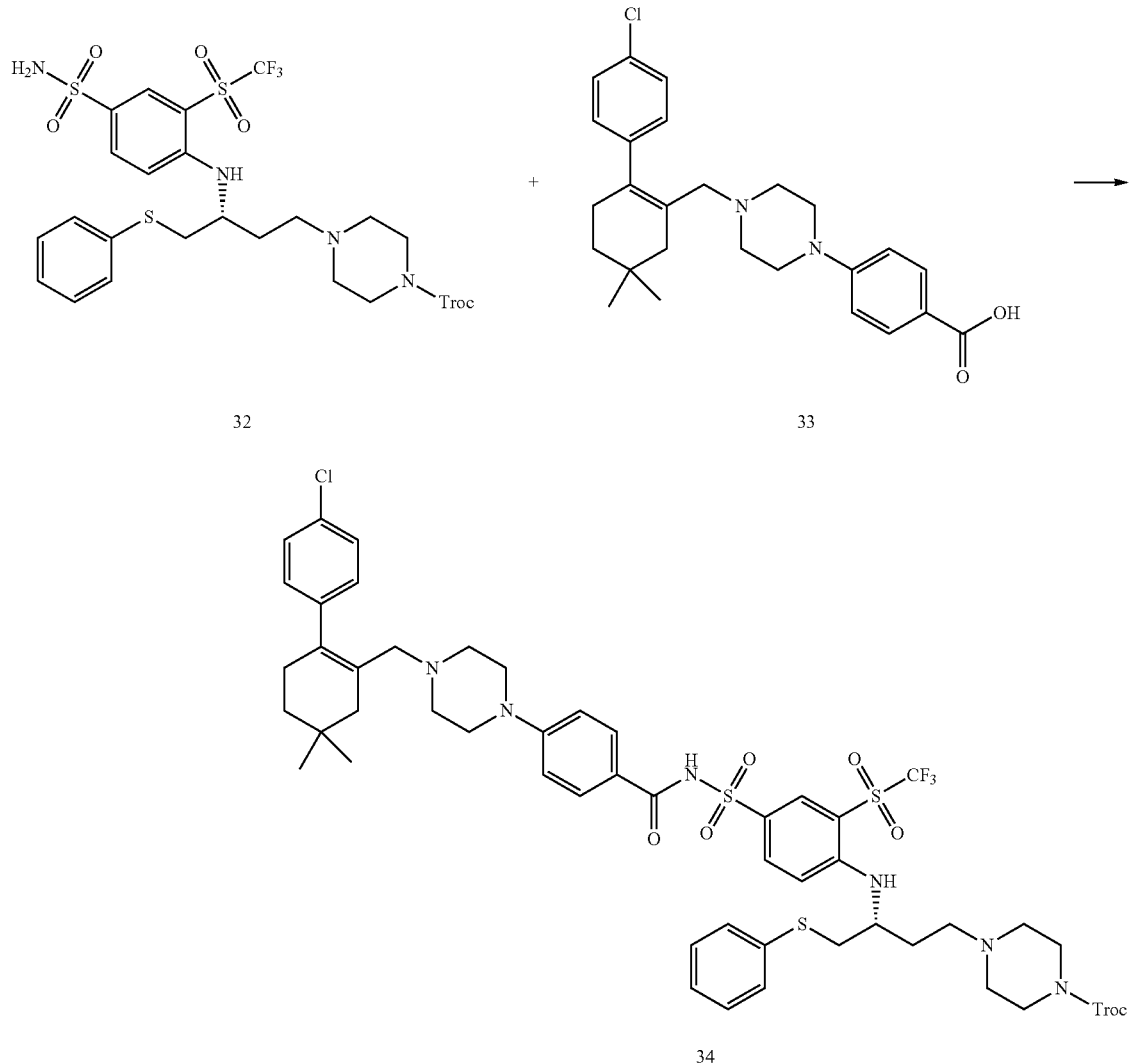

A mixture of compound 32 (780 mg), 4-(4-((4'-chloro-4,4-dimethyl-3,4,5,6-tetrahydro-[1,1'-biphenyl]-2-yl)methyl)piperazin-1-yl)benzoic acid 33 (470 mg), EDCI (411 mg) and DMAP (262 mg) in DCM was stirred at room temperature overnight. The solvent was evaporated under reduced pressure and the crude product was purified via column chromatography using DCM and methanol as eluents to afford 859 mg compound 34 as white solid. Yield 70%. $^1$H NMR (400 MHz, CDCl$_3$) δ 8.35 (s, 1H), 8.10 (d, J=8.7 Hz, 1H), 7.66 (d, J=8.0 Hz, 2H), 7.43-7.18 (m, 7H), 7.12-6.96 (m, 3H), 6.74 (s, 1H), 6.56 (d, J=7.9 Hz, 1H), 4.74 (s, 2H), 3.93-3.83 (m, 1H), 3.61-3.42 (m, 4H), 3.39-3.25 (m, 4H), 3.16-2.83 (m, 4H), 2.44-2.02 (m, 15H), 1.77-1.60 (m, 1H), 1.56-1.42 (m, 2H), 0.98 (s, 6H) ppm.

Preparation of (R)-4-(4-((4'-chloro-4,4-dimethyl-3,4,5,6-tetrahydro-[1,1'-biphenyl]-2-yl)methyl)piperazin-1-yl)-N-((4-((1-(phenylthio)-4-(piperazin-1-yl)butan-2-yl)amino)-3-((trifluoromethyl)sulfonyl)phenyl)sulfonyl)benzamide (35)

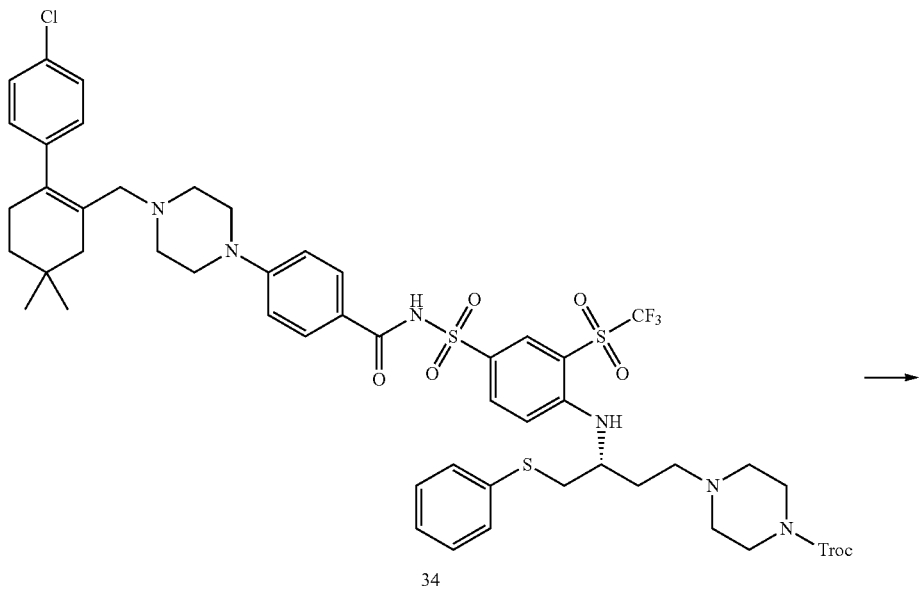

Zinc powder (960 mg) was added to a mixture of compound 34 (316 mg) and AcOH (600 μL) in 20 mL THF. The reaction was stirred at room temperature for 5 hours. The solid was removed by filtration and the filtrate was poured into water and extracted with EtOAc. The organic phase was washed with brine x1, dried over $Na_2SO_4$, filtered and evaporated to dryness. The crude product was purified via column chromatography using DCM, methanol, and TEA as eluents to afford 210 mg compound 35. Yield 78%. $^1$H NMR (400 MHz, $CDCl_3$) δ 8.21 (s, 1H), 7.93 (d, J=9.2 Hz, 1H), 7.85 (d, J=8.6 Hz, 2H), 7.33-7.24 (m, 2H), 7.22-7.15 (m, 6H), 7.15-7.08 (m, 1H), 6.92 (d, J=8.3 Hz, 2H), 6.77 (d, J=8.4 Hz, 1H), 6.66 (d, J=8.7 Hz, 2H), 6.46 (d, J=9.3 Hz, 1H), 3.83-3.67 (m, 1H), 3.17-3.08 (m, 4H), 3.02-2.92 (m, 5H), 2.89-2.78 (m, 1H), 2.72 (s, 2H), 2.64-2.13 (m, 12H), 2.04-1.91 (m, 3H), 1.62-1.49 (m, 1H), 1.39 (t, J=6.3 Hz, 2H), 0.91 (s, 6H) ppm.

Preparation of (R)—N-((4-((4-(4-(4-azidobutanoyl)piperazin-1-yl)-1-(phenylthio)butan-2-yl)amino)-3-((trifluoromethyl)sulfonyl)phenyl)sulfonyl)-4-(4-((4'-chloro-4,4-dimethyl-3,4,5,6-tetrahydro-[1,1'-biphenyl]-2-yl)methyl)piperazin-1-yl)benzamide (36)

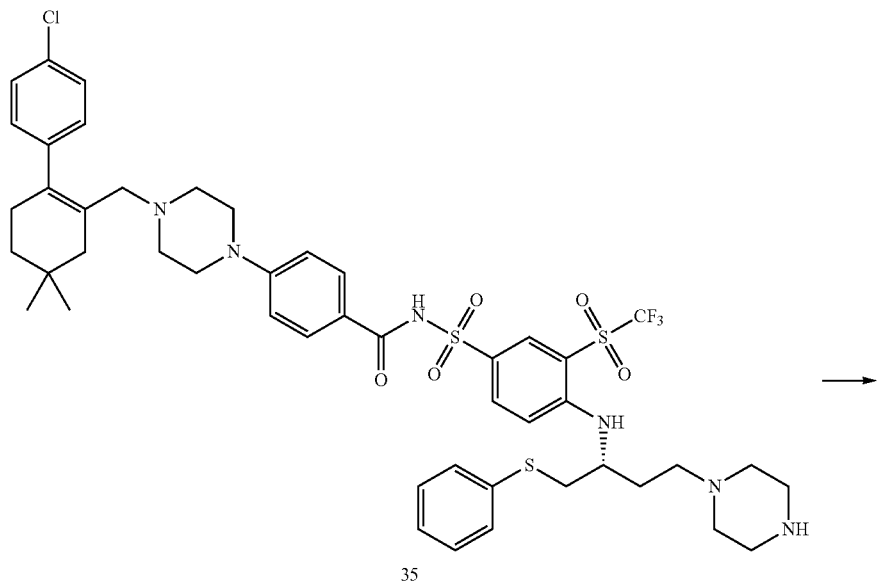

35

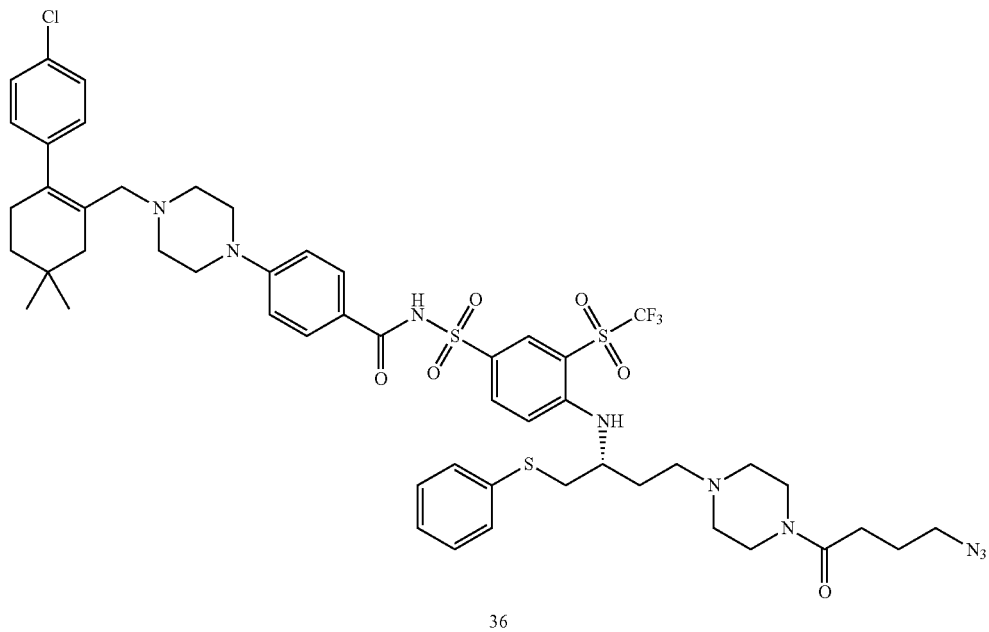

36

HATU (30 mg) was added to a mixture of compound 35 (50 mg), 4-azidobutanoic acid (6.7 mg), DIPEA (13.5 μL) in 2 mL DCM. The mixture was stirred at room temperature for 1 hour. The solvent was removed under reduced pressure and the crude product was purified via column chromatography using DCM and methanol as eluents to afford 40 mg compound 36. Yield 72%. $^1$H NMR (400 MHz, CDCl$_3$) δ 8.35 (d, J=2.2 Hz, 1H), 8.11 (dd, J=9.2, 2.2 Hz, 1H), 7.67 (d, J=8.9 Hz, 2H), 7.40-7.35 (m, 2H), 7.34-7.27 (m, 3H), 7.26-7.24 (m, 2H), 7.09 (d, J=8.5 Hz, 1H), 7.02-6.96 (m, 2H), 6.76 (d, J=9.0 Hz, 2H), 6.58 (d, J=9.4 Hz, 1H), 3.99-3.81 (m, 1H), 3.72-3.60 (m, 1H), 3.53-3.33 (m, 5H), 3.32-3.22 (m, 4H), 3.11 (dd, J=13.8, 4.9 Hz, 1H), 3.00 (dd, J=13.8, 7.5 Hz, 1H), 2.87 (s, 2H), 2.51-2.20 (m, 14H), 2.19-2.08 (m, 1H), 2.06-1.99 (m, 2H), 1.97-1.85 (m, 2H), 1.71-1.64 (m, 1H), 1.46 (t, J=6.4 Hz, 2H), 0.97 (s, 6H) ppm.

Preparation of 4-(4-((4'-chloro-4,4-dimethyl-3,4,5,6-tetrahydro-[1,1'-biphenyl]-2-yl)methyl)piperazin-1-yl)-N-((4-(((2R)-4-(4-(4-(4-((2-(2-(2-((2-(2,6-dioxopiperidin-3-yl)-1,3-dioxoisoindolin-4-yl)amino)ethoxy)ethoxy)ethoxy)methyl)-1H-1,2,3-triazol-1-yl)butanoyl)piperazin-1-yl)-1-(phenylthio)butan-2-yl)amino)-3-((trifluoromethyl)sulfonyl)phenyl)sulfonyl)benzamide (XZ-14439)

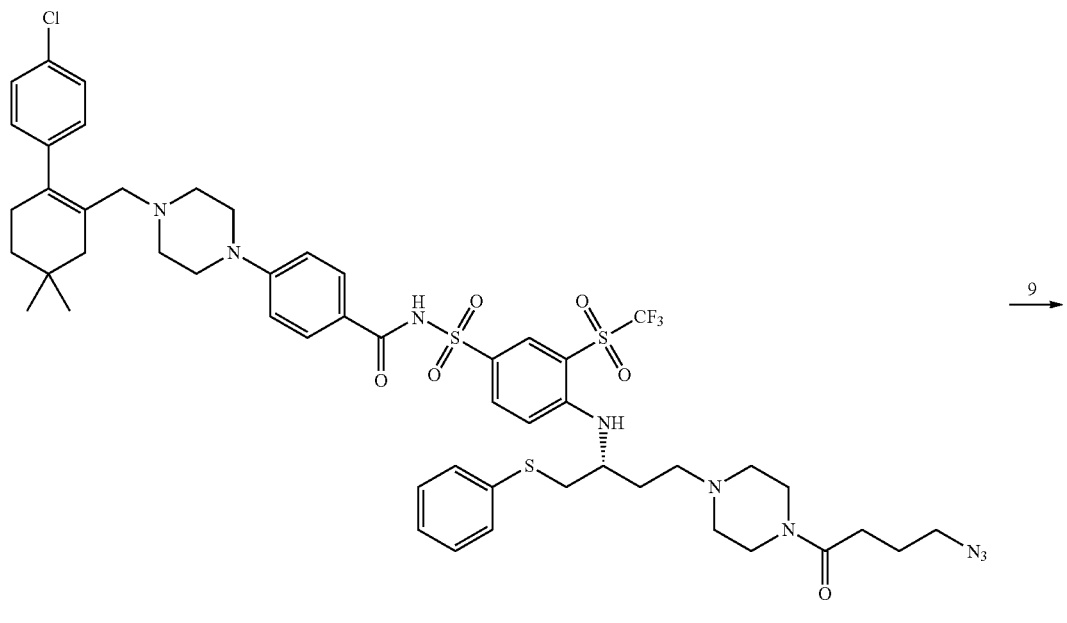

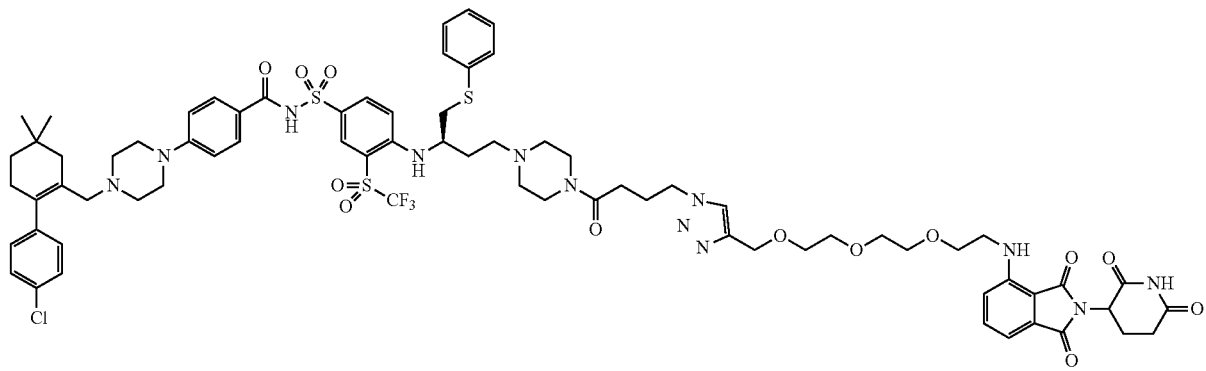

To a mixture of compound 36 (7.5 mg), compound 9 (3.7 mg) in 2 mL t-BuOH-THF (1:1, v/v) under argon was added CuSO$_4$.5H$_2$O (0.35 mg) and sodium ascorbate (0.28 mg) in 0.4 mL water. The mixture was stirred at 50° C. for 3 hours and extracted with DCM. The organic phase was washed with brine x1, dried over Na$_2$SO$_4$, filtered and evaporated to dryness. The crude product was purified via column chromatography using DCM and methanol as eluents to afford 5.9 mg XZ14439. Yield 56%. $^1$H NMR (400 MHz, CDCl$_3$ and CD$_3$OD) δ 8.33 (s, 1H), 8.10 (d, J=7.8 Hz, 1H), 7.79-7.65 (m, 3H), 7.54-7.44 (m, 1H), 7.43-7.35 (m, 2H), 7.33-7.32 (m, 1H), 7.30-7.22 (m, 4H), 7.12-7.02 (m, 2H), 6.99 (d, J=8.3 Hz, 2H), 6.92 (d, J=8.6 Hz, 1H), 6.77 (d, J=8.9 Hz, 2H), 6.61 (d, J=9.3 Hz, 1H), 5.02-4.85 (m, 1H), 4.66 (s, 2H), 4.41 (t, J=6.6 Hz, 2H), 4.00-3.79 (m, 1H), 3.80-3.58 (m, 12H), 3.52-3.38 (m, 4H), 3.31-3.23 (m, 4H), 3.12 (dd, J=13.8, 5.0 Hz, 1H), 3.02 (dd, J=13.9, 7.3 Hz, 1H), 2.84-2.77 (m, 5H), 2.50-2.06 (m, 18H), 2.01 (s, 2H), 1.74-1.63 (m, 1H), 1.46 (t, J=6.4 Hz, 2H), 0.98 (s, 6H) ppm.

Example 7: Synthesis of PZ-15227

Preparation of 4-(4-((4'-chloro-4,4-dimethyl-3,4,5,6-tetrahydro-[1,1'-biphenyl]-2-yl)methyl)piperazin-1-yl)-N-((4-(((2R)-4-(4-(4-(4-((2-(2-((2-(2,6-dioxopiperidin-3-yl)-1,3-dioxoisoindolin-4-yl)amino)ethoxy)ethoxy)methyl)-1H-1,2,3-triazol-1-yl)butanoyl)piperazin-1-yl)-1-(phenylthio)butan-2-yl)amino)-3-((trifluoromethyl)sulfonyl)phenyl)sulfonyl)benzamide (PZ-15227)

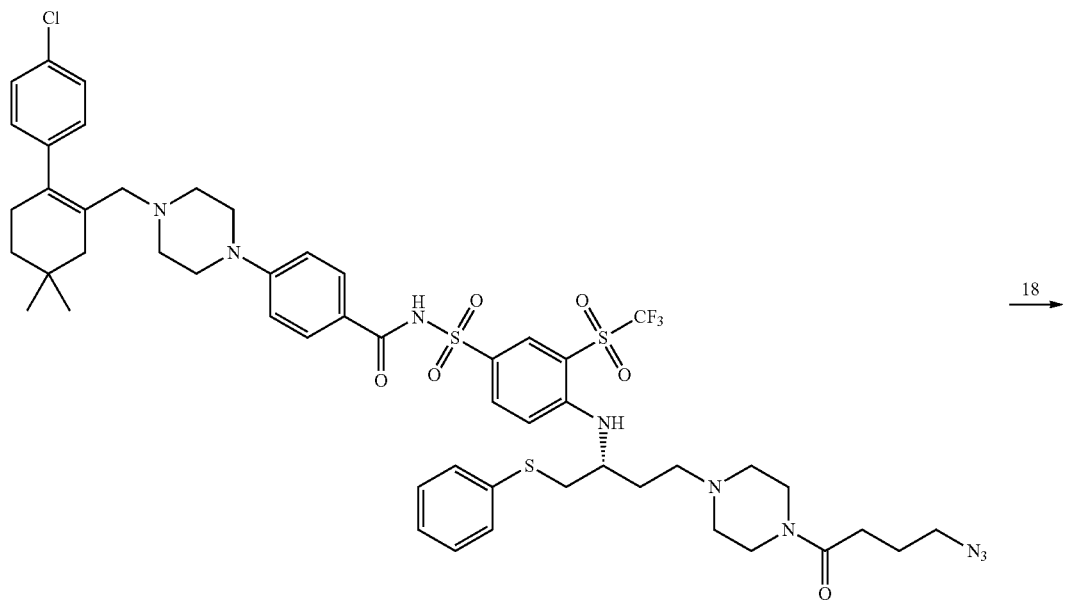

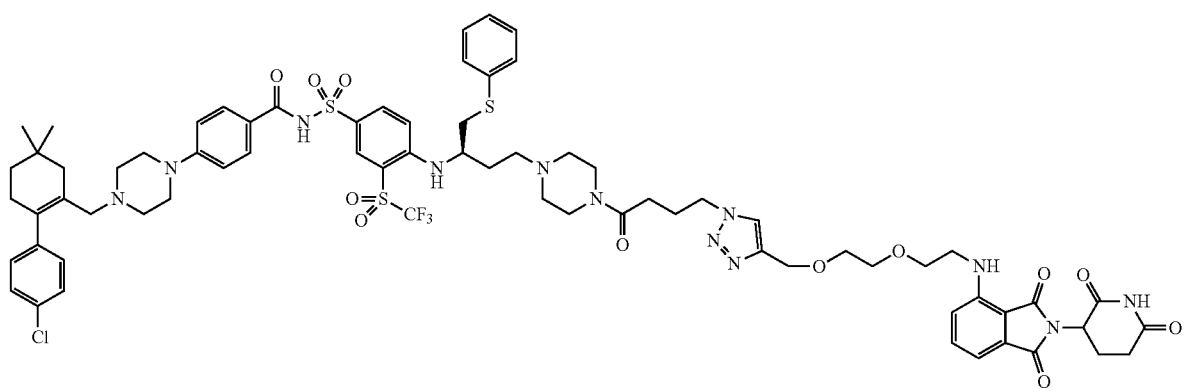

PZ15227

To a mixture of compound 36 (25.0 mg), compound 18 (11.0 mg) in 3 mL t-BuOH-THF (1:2, v/v) under Argon was added CuSO$_4$.5H$_2$O (1.15 mg) and sodium ascorbate (0.91 mg) in 0.3 mL water. The mixture was stirred at 50° C. overnight and extracted with DCM. The organic phase was washed with brine x1, dried over Na$_2$SO$_4$, filtered and evaporated to dryness. The crude product was purified via column chromatography using DCM and methanol as eluents to afford 23 mg PZ15227. Yield 67%. $^1$H NMR (400 MHz, CDCl$_3$ and CD$_3$OD) δ 9.05 (br s, 1H), 8.36 (s, 1H), 8.10 (d, J=7.8 Hz, 1H), 7.79-7.64 (m, 3H), 7.54-7.42 (m, 1H), 7.43-7.22 (m, 7H), 7.10-7.02 (m, 2H), 6.99 (d, J=7.2 Hz, 2H), 6.92 (d, J=8.8 Hz, 1H), 6.77 (d, J=8.8 Hz, 2H), 6.61 (d, J=9.3 Hz, 1H), 6.50 (br s, 1H), 4.99-4.85 (m, 1H), 4.69 (s, 2H), 4.42-4.37 (m, 2H), 4.00-3.77 (m, 1H), 3.80-3.58 (m, 8H), 3.52-3.20 (m, 8H), 3.12-3.00 (m, 2H), 2.84-2.75 (m, 5H), 2.45-1.98 (m, 20H), 1.74-1.60 (m, 1H), 1.46 (t, J=6.4 Hz, 2H), 0.97 (s, 6H) ppm.

Example 8: Synthesis of XZ-14509
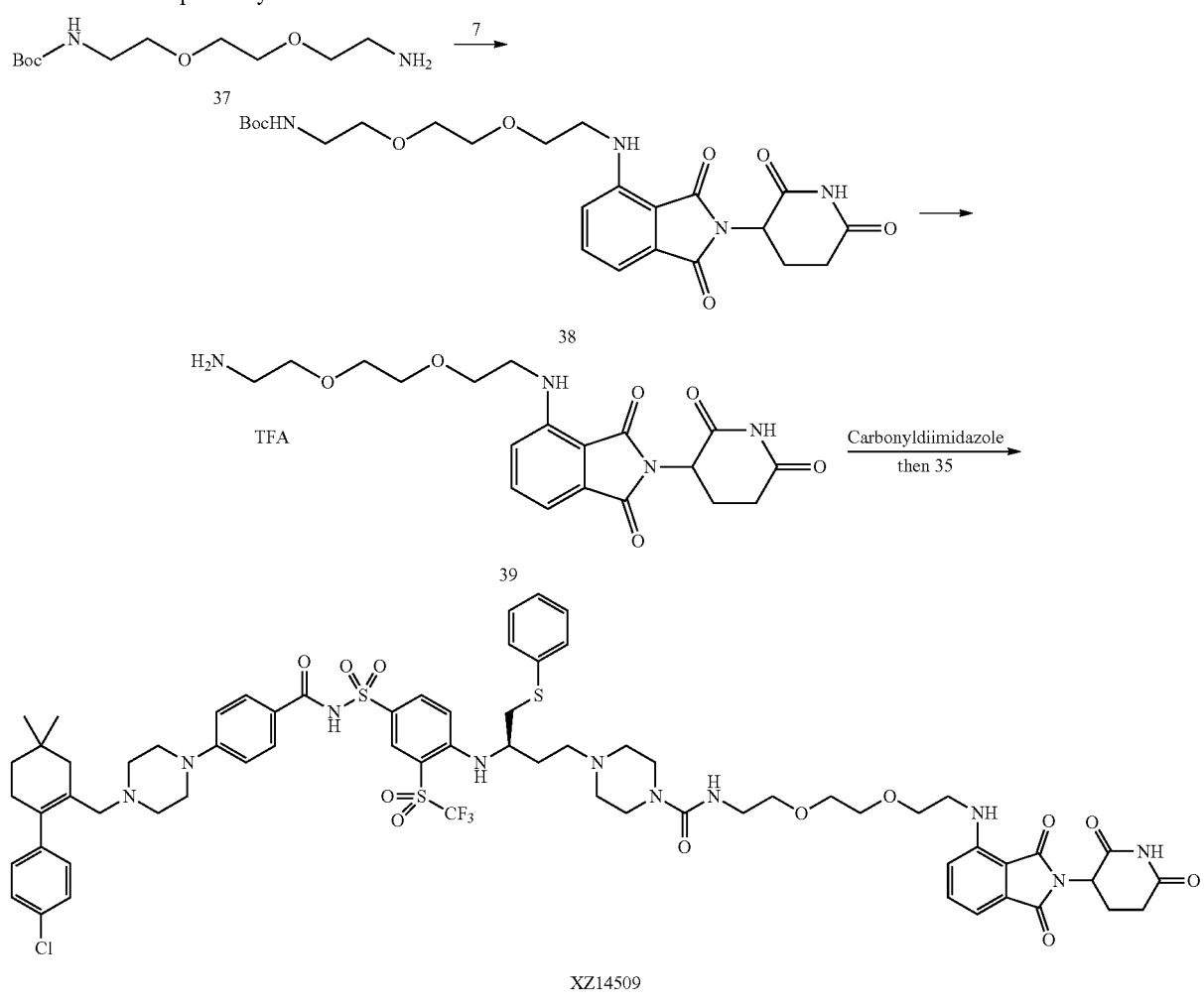
Preparation of 4-((2-(2-(2-aminoethoxy)ethoxy)ethyl)amino)-2-(2-oxopiperidin-3-yl)isoindoline-1,3-dione (39)
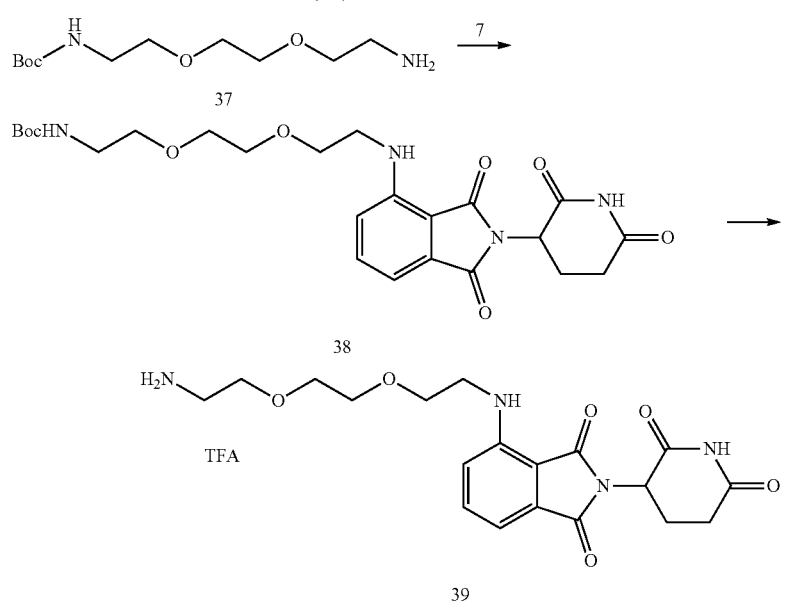

Compound 7 (200 mg), amine 37 (178 mg), and DIPEA (240 μL) in 5 mL DMF were stirred at 90° C. for 16 hours. Water was added to the reaction mixture and extracted with EtOAc. The organic phase was washed with water x1, brine x1, dried over $Na_2SO_4$, filtered and evaporated to dryness. The resulting mixture was purified by column chromatography to afford 183 mg compound 38. Yield 50%. To a mixture of compound 38 (160 mg) in 5 mL DCM was added 0.5 mL TFA. The mixture was stirred at room temperature for 2 h and the solvent was evaporated under reduced pressure. The salt was washed with $Et_2O$ to afford pure compound 39. $^1$H NMR (400 MHz, $CDCl_3$) δ 9.63 (br s, 1H), 7.82 (br s, 2H), 7.48 (dd, J=8.4, 7.2 Hz, 1H), 7.04 (d, J=7.0 Hz, 1H), 6.87 (d, J=8.5 Hz, 1H), 5.13-4.82 (m, 1H), 3.85-3.60 (m, 8H), 3.55-3.37 (m, 2H), 3.28-3.12 (m, 2H), 2.81-2.58 (m, 3H), 2.09-1.88 (m, 1H) ppm.

Preparation of 4-((R)-3-(4-(N-(4-(4-((2-(4-chlorophenyl)-5,5-dimethylcyclohex-1-enyl)methyl)piperazin-1-yl)benzoyl)sulfamoyl)-2-(trifluoromethylsulfonyl)phenylamino)-4-(phenylthio)butyl)-N-(2-(2-(2-(2-(2,6-dioxopiperidin-3-yl)-1,3-dioxoisoindolin-4-ylamino)ethoxy)ethoxy)ethyl)piperazine-1-carboxamide (XZ-14509)

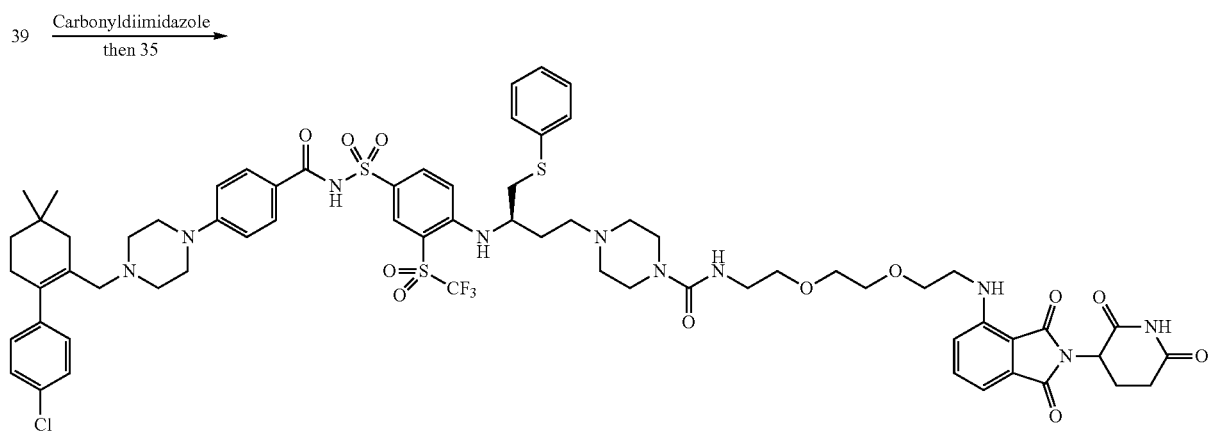

XZ14509

A mixture of compound 39 (20 mg), carbonyldiimidazole (CDI) (10 mg) and TEA (7.0 μL) in 3 mL DCM was stirred at room temperature for 2 hours. Compound 35 (15 mg) and DIPEA (0.05 mL) were then added into the above solution. The mixture was stirred overnight and quenched by the addition of $NH_4Cl$ (aq.), extracted with DCM and the organic phase was washed with water x1, brine x1, dried over $Na_2SO_4$, filtered and evaporated to dryness. The crude product was purified by column chromatography using DCM and methanol as eluents to afford 6.7 mg compound XZ14509. Yield 31%. $^1$H NMR (400 MHz, $CDCl_3$) δ 9.24 (br s, 1H), 8.35 (s, 1H), 8.14-7.98 (m, 1H), 7.81-7.62 (m, 2H), 7.52-7.40 (m, 1H), 7.39-7.27 (m, 4H), 7.24-7.15 (m, 1H), 7.12-6.94 (m, 4H), 6.87 (d, J=8.6 Hz, 1H), 6.73 (d, J=7.2 Hz, 2H), 6.66-6.57 (m, 1H), 6.56-6.46 (m, 1H), 5.20-5.02 (br s, 1H), 5.00-4.83 (m, 1H), 3.95-3.81 (m, 1H), 3.75-3.69 (m, 2H), 3.67-3.61 (m, 4H), 3.61-3.53 (m, 2H), 3.49-3.38 (m, 4H), 3.38-3.18 (m, 8H), 3.12-2.95 (m, 2H), 2.88-2.66 (m, 5H), 2.47-2.18 (m, 12H), 2.17-1.98 (m, 4H), 1.69-1.57 (m, 1H), 1.46 (t, J=6.3 Hz, 2H), 0.97 (s, 6H) ppm.

Example 9: Synthesis of XZ-14516

Preparation of 4-(4-((2-(4-chlorophenyl)-5,5-dimethylcyclohex-1-enyl)methyl)piperazin-1-yl)-N-(4-((2R)-4-(4-(2-(2-(2-(2-(2,6-dioxopiperidin-3-yl)-1,3-dioxoisoindolin-4-ylamino)ethoxy)ethoxy)ethylcarbamothioyl)piperazin-1-yl)-1-(phenylthio)butan-2-ylamino)-3-(trifluoromethylsulfonyl)phenylsulfonyl)benzamide (XZ-14516)

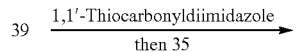

-continued

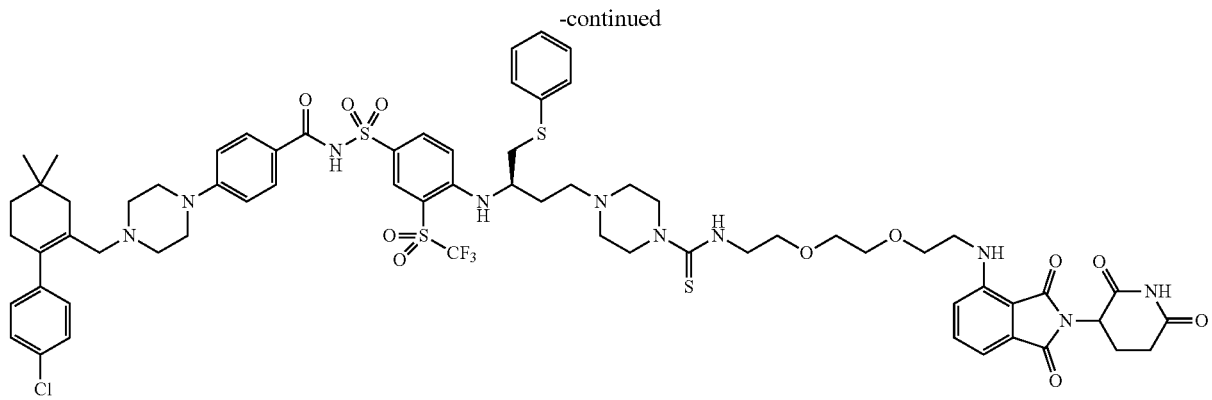

XZ14516

A mixture of compound 39 (12 mg), 1,1'-thiocarbonyldiimidazole (6 mg) and TEA (4.2 µL) in 2 mL DCM was stirred at room temperature for 1 hour. Then compound 35 (6.5 mg) and DIPEA (0.05 mL) were added into the above solution. The mixture was stirred overnight and quenched by the addition of NH$_4$Cl (aq). Subsequently, it was with DCM and the organic phase was washed with water x1, brine x1, dried over Na$_2$SO$_4$, filtered and evaporated to dryness. The crude product was purified by column chromatography using DCM and methanol as eluents to afford 6.4 mg compound XZ14516. Yield 68%. $^1$H NMR (400 MHz, CDCl$_3$) δ 8.90 (br s, 1H), 8.37 (d, J=2.1 Hz, 1H), 8.15-8.00 (m, 1H), 7.65 (d, J=7.6 Hz, 2H), 7.51-7.42 (m, 1H), 7.38-7.27 (m, 5H), 7.12-7.05 (m, 2H), 6.99 (d, J=8.4 Hz, 2H), 6.87 (d, J=8.5 Hz, 1H), 6.75 (dd, J=9.0, 3.8 Hz, 2H), 6.62 (dd, J=12.9, 9.5 Hz, 1H), 6.51 (t, J=5.2 Hz, 1H), 6.22 (br s, 1H), 4.95-4.80 (m, 1H), 3.90-3.61 (m, 15H), 3.48-3.41 (m, 2H), 3.30-3.20 (m, 4H), 3.13-2.96 (m, 2H), 2.88-2.71 (m, 5H), 2.47-2.22 (m, 12H), 2.13-2.00 (m, 4H), 1.75-1.70 (m, 1H), 1.46 (t, J=6.4 Hz, 2H), 0.99 (s, 6H) ppm.

Example 10: Synthesis of XZ-14515, XZ-14510, and XZ-14540

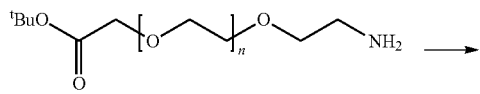

40a, n = 1
40b, n = 2
40c, n = 3

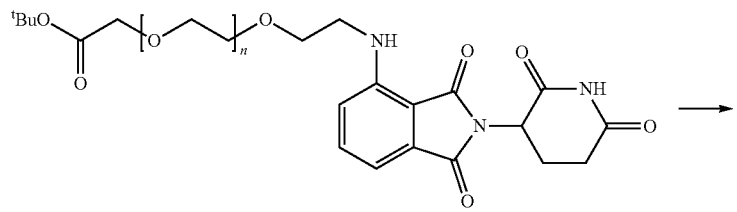

41a, n = 1
41b, n = 2
41c, n = 3

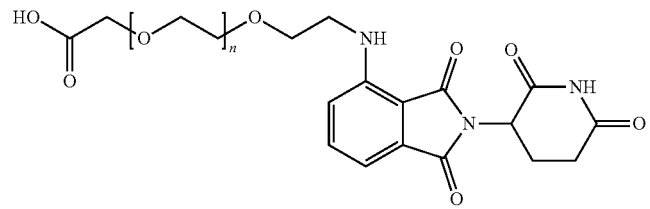

42a, n = 1
42b, n = 2
42c, n = 3

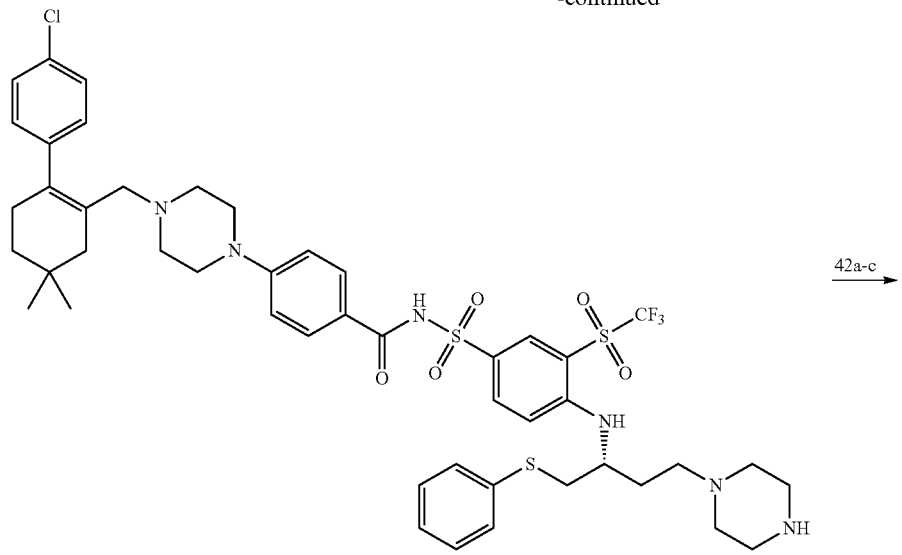

35

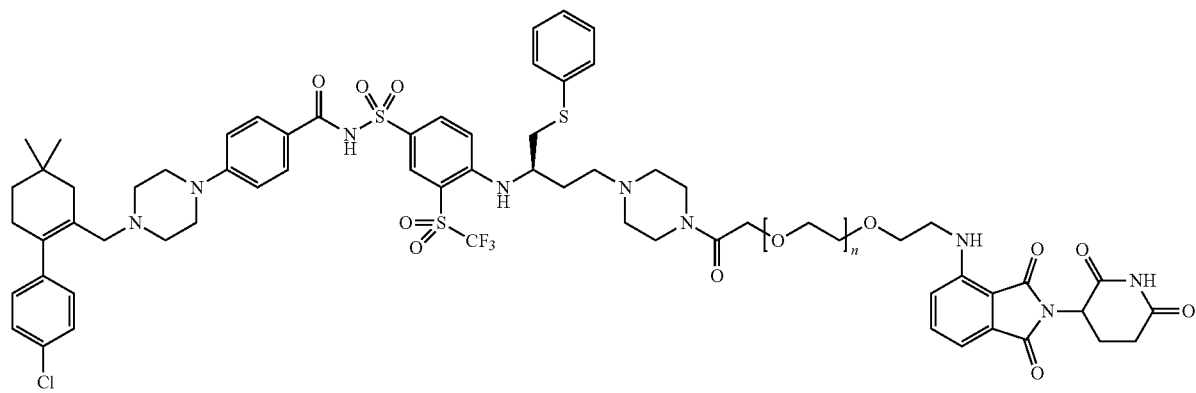

XZ14515, n = 1
XZ14510, n = 2
XZ14540, n = 3

General Procedure for the Preparation of 41a-c

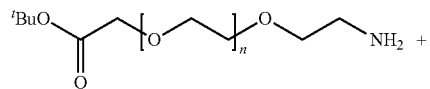

40a, n = 1
40b, n = 2
40c, n = 3

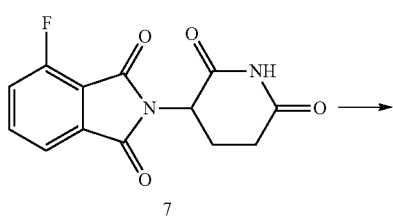

7

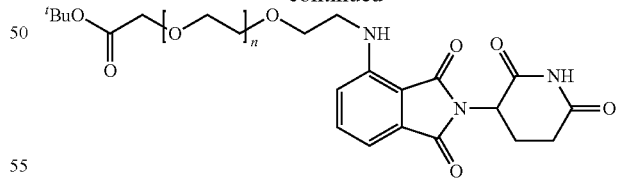

41a, n = 1
41b, n = 2
41c, n = 3

A mixture of compound 7 (1.0 equiv.), corresponding amine 40a-c (1.0 equiv.), and DIPEA (2.0 equiv.) in DMF were stirred at 90° C. overnight. The mixture was poured into water and extracted with EtOAc. The organic phase was washed with water x1, brine x1, dried over $Na_2SO_4$, filtered and evaporated to dryness. The crude product was purified by column chromatography using EtOAc and hexanes as eluents.

General Procedure for the Preparation of 42a-c

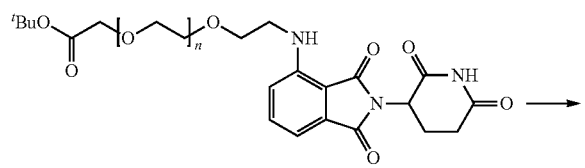

41a, n = 1
41b, n = 2
41c, n = 3

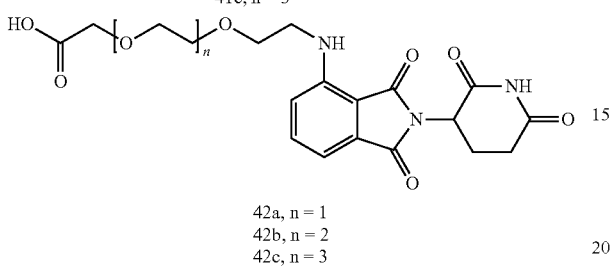

42a, n = 1
42b, n = 2
42c, n = 3

To a mixture of compound 41a, 41b, or 41c in DCM was added TFA. The mixture was stirred at room temperature overnight and the solvent was removed under reduced pressure. The crude product was washed with Et$_2$O to give the corresponding acid 42a, 42b, and 42c, respectively.

Preparation of 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(2-(2-((2-(2,6-dioxopiperidin-3-yl)-1,3-dioxoisoindolin-4-yl)amino)ethoxy)ethoxy)acetyl)piperazin-1-yl)-1-(phenylthio)butan-2-yl)amino)-3-((trifluoromethyl)sulfonyl)phenyl)sulfonyl)benzamide (XZ-14515)

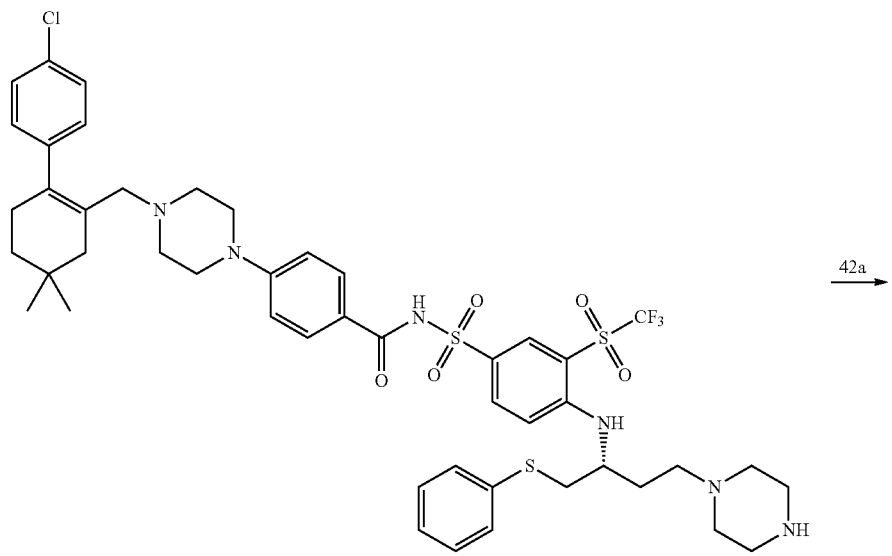

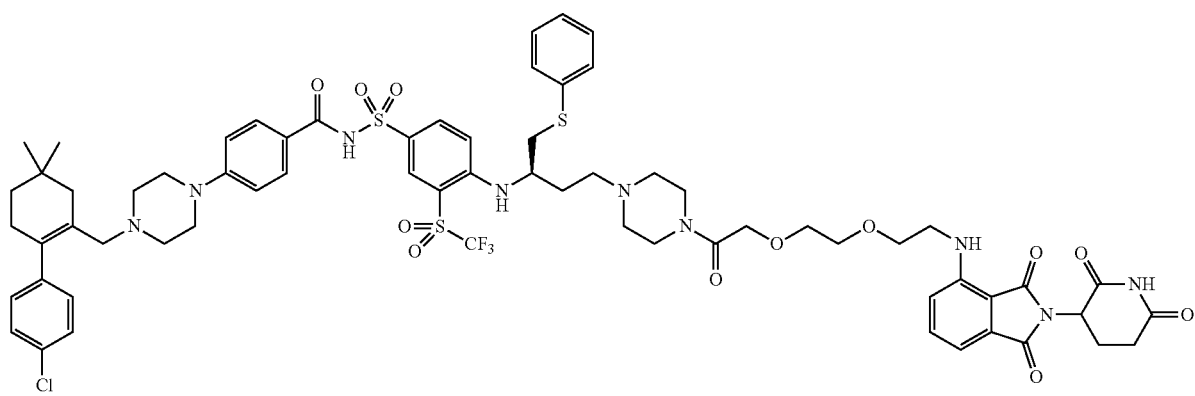

XZ-14515

A mixture of compound 35 (10 mg), 42a (5.5 mg), HATU (4 mg) and DIPEA (20 mg) in 3 mL DCM was stirred at room temperature for 1 hour. NH$_4$Cl (aq.) was then added to the mixture and the resulted mixture was extracted with DCM. The organic phase was washed with water x1, brine x1, dried over Na$_2$SO$_4$, filtered and evaporated to dryness. The crude product was purified by column chromatography using DCM and methanol as eluents to afford 6.6 mg pure XZ-14515. Yield 47%. $^1$H NMR (400 MHz, CDCl$_3$ and CD$_3$OD) δ 9.11 (br s, 1H), 8.36 (s, 1H), 8.08 (d, J=9.1 Hz, 1H), 7.66 (d, J=8.2 Hz, 2H), 7.46 (t, J=7.8 Hz, 1H), 7.39-7.27 (m, 6H), 7.14-7.02 (m, 2H), 6.98 (d, J=8.3 Hz, 2H), 6.88 (d, J=8.5 Hz, 1H), 6.75 (d, J=8.6 Hz, 2H), 6.58 (d, J=5.8 Hz, 1H), 6.52-6.43 (br s, 1H), 4.91-4.81 (m, 1H), 4.26-4.15 (m, 2H), 3.94-3.81 (m, 1H), 3.70-3.33 (m, 12H), 3.31-3.22 (m, 4H), 3.12-2.93 (m, 2H), 2.89-2.55 (m, 5H), 2.49-2.00 (m, 16H), 1.74-1.70 (m, 1H), 1.51-1.45 (m, 2H), 0.98 (s, 6H) ppm.

Preparation of 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(2-(2-(2-((2-(2,6-dioxopiperidin-3-yl)-1,3-dioxoisoindolin-4-yl)amino)ethoxy)ethoxy)ethoxy)acetyl)piperazin-1-yl)-1-(phenylthio)butan-2-yl)amino)-3-((trifluoromethyl)sulfonyl)phenyl)sulfonyl)benzamide (XZ-14510)

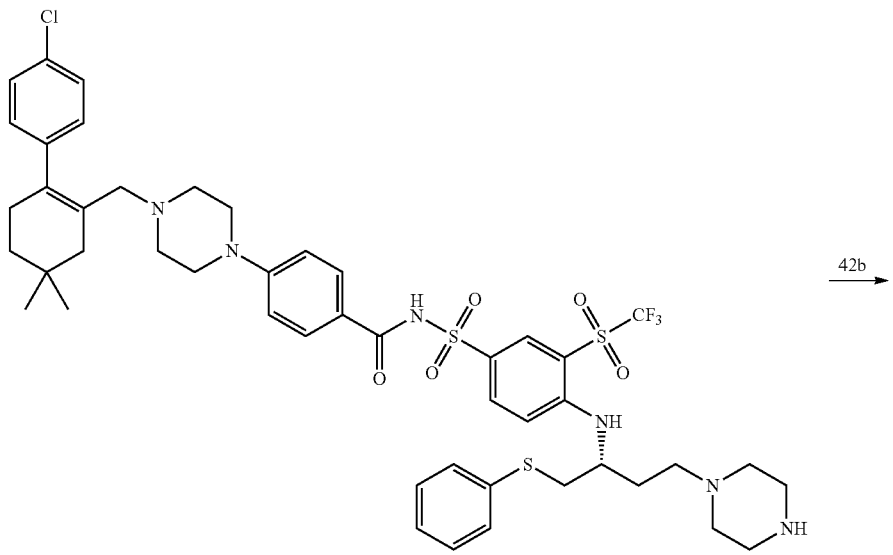

35

42b →

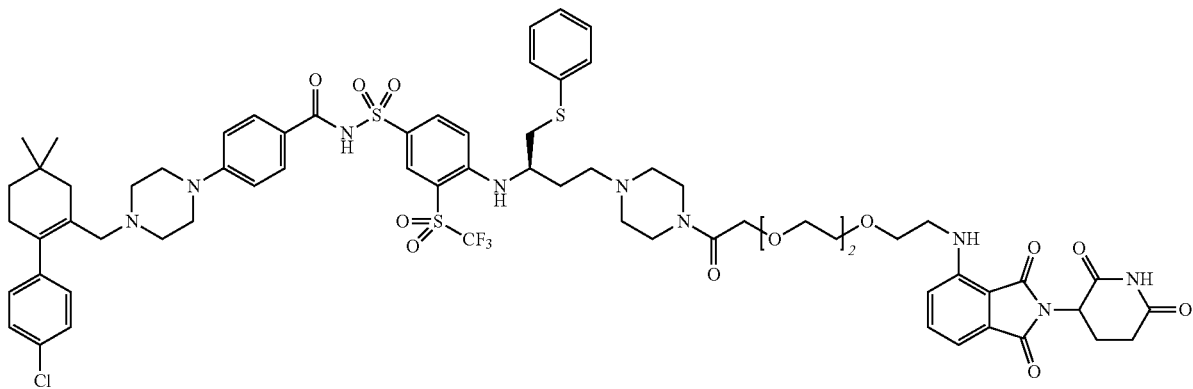

XZ-14510

A mixture of compound 35 (10 mg), 42b (5 mg), HATU (4 mg) and DIPEA (20 mg) in 3 mL DCM was stirred at room temperature for 1 hour. NH$_4$Cl (aq) was then added to the mixture and the resulted mixture was extracted with DCM. The organic phase was washed with water x1, brine x1, dried over Na$_2$SO$_4$, filtered and evaporated to dryness. The crude product was purified by column chromatography using DCM and methanol as eluents to afford 6.2 mg pure XZ-14510. Yield 44%. $^1$H NMR (400 MHz, CDCl$_3$ and CD$_3$OD) δ 8.33-8.28 (m, 1H), 8.07 (d, J=9.0 Hz, 1H), 7.78 (d, J=8.8 Hz, 2H), 7.54-7.45 (m, 1H), 7.41-7.37 (m, 1H), 7.33-7.20 (m, 5H), 7.09 (d, J=7.1 Hz, 1H), 7.06-6.98 (m, 3H), 6.94 (d, J=8.6 Hz, 1H), 6.79 (d, J=8.9 Hz, 2H), 6.61 (d, J=9.4 Hz, 1H), 5.00-4.86 (m, 1H), 4.21 (s, 2H), 3.93-3.84 (m, 1H), 3.70-3.39 (m, 16H), 3.32-3.25 (m, 4H), 3.12-3.00 (m, 2H), 2.93-2.71 (m, 5H), 2.46-2.24 (m, 12H), 2.09-2.00 (m, 4H), 1.75-1.63 (m, 1H), 1.47 (t, J=6.3 Hz, 2H), 0.99 (s, 6H) ppm.

Preparation of 4-(4-((4'-chloro-4,4-dimethyl-3,4,5,6-tetrahydro-[1,1'-biphenyl]-2-yl)methyl)piperazin-1-yl)-N-((4-(((2R)-4-(4-(14-((2-(2,6-dioxopiperidin-3-yl)-1,3-dioxoisoindolin-4-yl)amino)-3,6,9,12-tetraoxatetradecanoyl)piperazin-1-yl)-1-(phenylthio)butan-2-yl)amino)-3-((trifluoromethyl)sulfonyl)phenyl)sulfonyl)benzamide (XZ-14540)

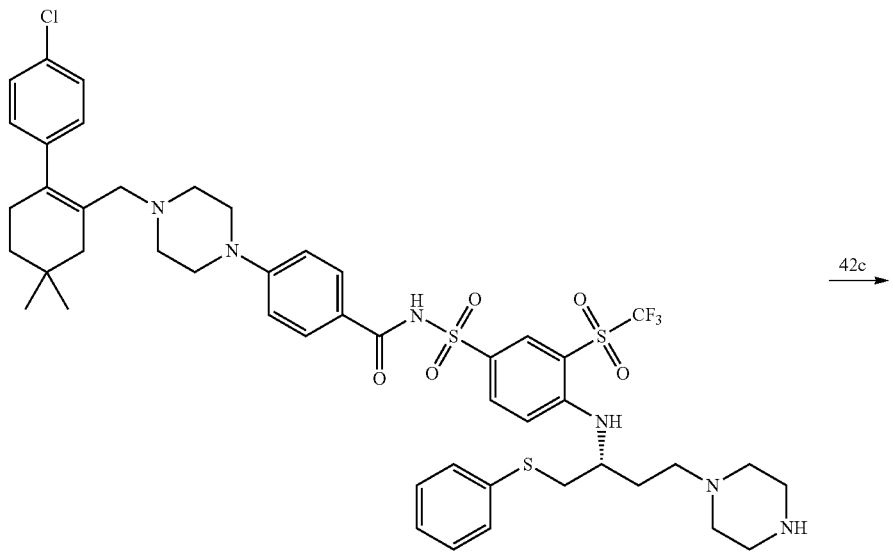

35

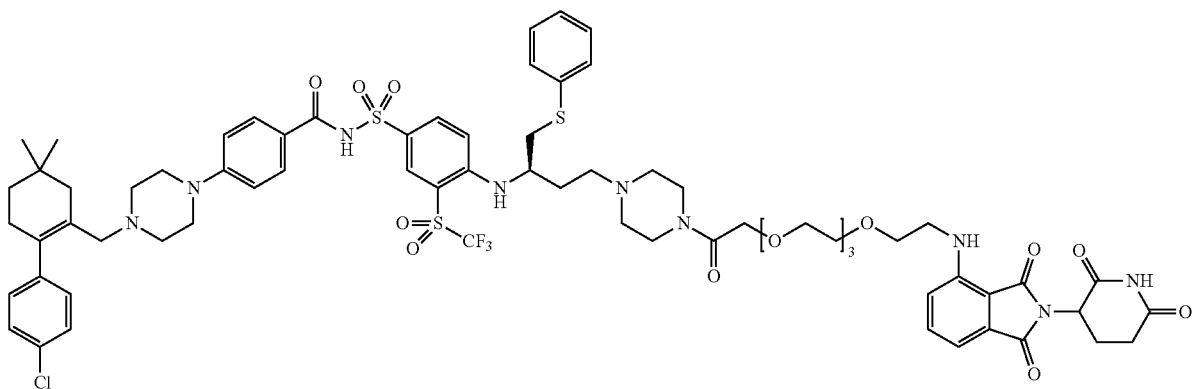

XZ-14540

A mixture of compound 35 (12 mg), 42c (8.2 mg), HATU (5 mg) and DIPEA (30 mg) in 3 mL DCM was stirred at room temperature for 2 hours. NH₄Cl (aq.) was then added to the mixture and the resulted mixture was extracted with DCM. The organic phase was washed with water x1, brine x1, dried over Na₂SO₄, filtered and evaporated to dryness. The crude product was purified by column chromatography using DCM and methanol as eluents to afford 13.6 mg pure XZ14540. Yield 76%. ¹H NMR (400 MHz, CDCl₃ and CD₃OD) δ 8.81 (br s, 1H), 8.33 (s, 1H), 8.13-7.99 (m, 1H), 7.79-7.60 (m, 2H), 7.45 (t, J=7.8 Hz, 1H), 7.38-7.26 (m, 5H), 7.24-7.17 (m, 1H), 7.12-6.94 (m, 4H), 6.88 (d, J=8.6 Hz, 1H), 6.73 (d, J=8.8 Hz, 2H), 6.61-6.50 (m, 1H), 6.46 (br s, 1H), 4.95-4.84 (m, 1H), 4.16 (s, 2H), 3.88-3.80 (m, 1H), 3.72-3.39 (m, 20H), 3.32-3.25 (m, 4H), 3.12-3.01 (m, 2H), 2.93-2.71 (m, 5H), 2.46-2.24 (m, 12H), 2.09-2.00 (m, 4H), 1.75-1.63 (m, 1H), 1.47 (t, J=6.3 Hz, 2H), 0.96 (s, 6H) ppm.

Example 11: Synthesis of XZ-15416, XZ-15405, and XZ-15418

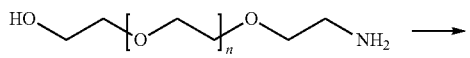

43a, n = 0
43b, n = 1
43c, n = 2

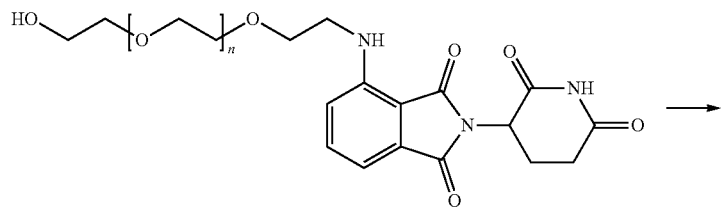

44a, n = 0
44b, n = 1
44c, n = 2

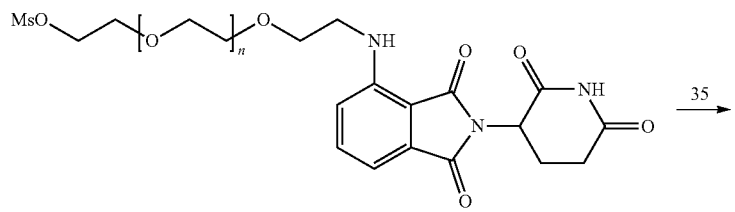

45a, n = 0
45b, n = 1
45c, n = 2

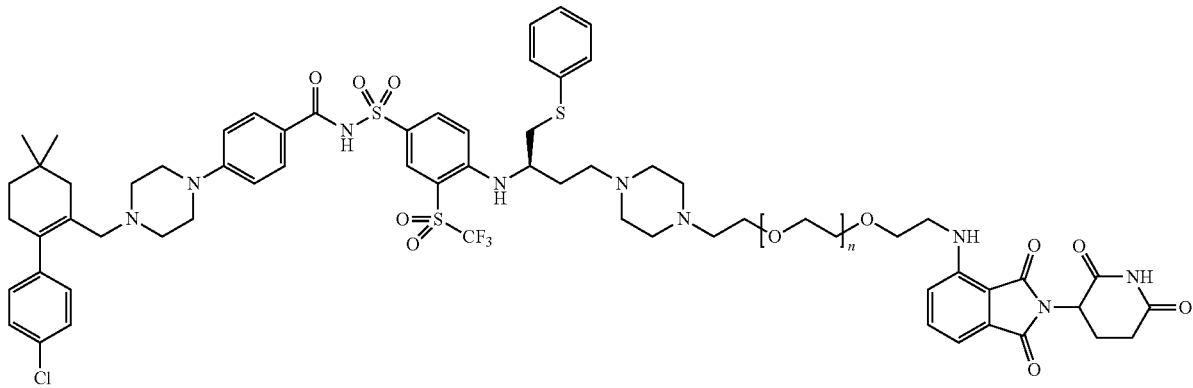

XZ15416, n = 0
XZ15405, n = 1
XZ15418, n = 2

General Procedure for the Preparation of 44a-c

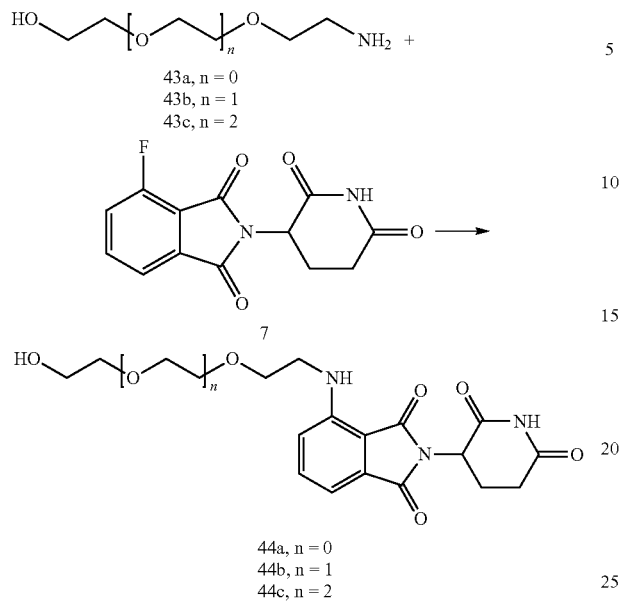

43a, n = 0
43b, n = 1
43c, n = 2

7

44a, n = 0
44b, n = 1
44c, n = 2

A mixture of compound 7 (1.0 equiv.), corresponding amine 43a-c (1.0 equiv.) and DIPEA (2.0 equiv.) in DMF were stirred at 90° C. overnight. The mixture was poured into water and extracted with EtOAc. The organic phase was washed with water x1, brine x1, dried over $Na_2SO_4$, filtered and evaporated to dryness. The crude product was purified by column chromatography using DCM and methanol as eluents.

Preparation of 2-(2,6-Dioxopiperidin-3-yl)-4-((2-(2-hydroxyethoxy)ethyl)amino) isoindoline-1,3-dione (44a)

$^1$H NMR (400 MHz, $CDCl_3$) δ 8.25 (br s, 1H), 7.58-7.46 (m, 1H), 7.11 (d, J=7.1 Hz, 1H), 6.91 (d, J=8.5 Hz, 1H), 6.57 (t, J=5.4 Hz, 1H), 4.92 (dd, J=12.2, 5.3 Hz, 1H), 3.81-3.71 (m, 4H), 3.66-3.61 (m, 2H), 3.48 (dd, J=10.7, 5.3 Hz, 2H), 2.92-2.67 (m, 3H), 2.32 (br s, 1H), 2.18-2.07 (m, 1H) ppm.

Preparation of 2-(2,6-Dioxopiperidin-3-yl)-4-((2-(2-(2-hydroxyethoxy)ethoxy)ethyl)amino) isoindoline-1,3-dione (44b)

$^1$H NMR (400 MHz, $CDCl_3$) δ 8.19 (br s, 1H), 7.55-7.44 (m, 1H), 7.10 (d, J=7.1 Hz, 1H), 6.91 (d, J=8.5 Hz, 1H), 6.57 (t, J=5.2 Hz, 1H), 4.91 (dd, J=12.0, 5.4 Hz, 1H), 3.85-3.65 (m, 8H), 3.64-3.59 (m, 2H), 3.51-3.43 (m, 2H), 2.92-2.68 (m, 3H), 2.57 (br s, 1H), 2.18-2.07 (m, 1H) ppm.

Preparation of 2-(2,6-Dioxopiperidin-3-yl)-4-((2-(2-(2-(2-hydroxyethoxy)ethoxy)ethoxy) ethyl)amino) isoindoline-1,3-dione (44c)

$^1$H NMR (400 MHz, $CDCl_3$) δ 8.23 (br s, 1H), 7.58-7.40 (m, 1H), 7.10 (d, J=7.1 Hz, 1H), 6.92 (d, J=8.6 Hz, 1H), 6.52 (t, J=5.5 Hz, 1H), 4.92 (dd, J=12.0, 5.4 Hz, 1H), 3.77-3.65 (m, 12H), 3.63-3.58 (m, 2H), 3.52-3.44 (m, 2H), 3.00-2.59 (m, 4H), 2.24-2.04 (m, 1H) ppm.

General Procedure for the Preparation of 45a-c

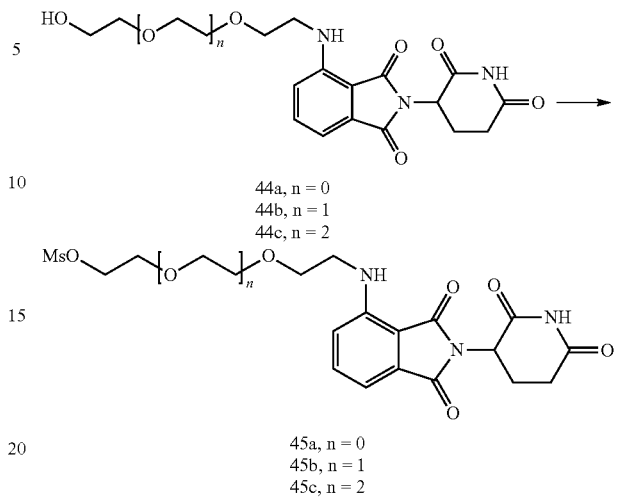

44a, n = 0
44b, n = 1
44c, n = 2

45a, n = 0
45b, n = 1
45c, n = 2

To a mixture of 44a, 44b, or 44c (1.0 equiv.), TEA (4.0 equiv.) in DCM was added MsCl (1.2 equiv.). The mixture was stirred at room temperature for 3 hours. Then the mixture was poured into water and extracted with EtOAc. The organic phase was washed with water x1, brine x1, dried over $Na_2SO_4$, filtered and evaporated to dryness. The crude product was purified by column chromatography using DCM and methanol as eluents.

Preparation of 2-(2-((2-(2,6-Dioxopiperidin-3-yl)-1,3-dioxoisoindolin-4-yl)amino)ethoxy)ethyl methanesulfonate (45a)

$^1$H NMR (400 MHz, $CDCl_3$) δ 8.10 (br s, 1H), 7.63-7.44 (m, 1H), 7.12 (d, J=7.1 Hz, 1H), 6.93 (d, J=8.5 Hz, 1H), 6.49 (t, J=5.5 Hz, 1H), 4.91 (dd, J=12.1, 5.3 Hz, 1H), 4.48-4.35 (m, 2H), 3.86-3.66 (m, 4H), 3.58-3.41 (m, 2H), 3.13-2.69 (m, 6H), 2.23-2.05 (m, 1H) ppm.

Preparation of 2-(2-(2-((2-(2,6-Dioxopiperidin-3-yl)-1,3-dioxoisoindolin-4-yl)amino)ethoxy)ethoxy) ethyl methanesulfonate (45b)

$^1$H NMR (400 MHz, $CDCl_3$) δ 8.14 (br s, 1H), 7.65-7.45 (m, 1H), 7.12 (d, J=7.1 Hz, 1H), 6.91 (d, J=8.5 Hz, 1H), 6.51 (t, J=5.1 Hz, 1H), 4.94 (dd, J=12.0, 5.3 Hz, 1H), 4.39 (dd, J=5.3, 3.7 Hz, 2H), 4.00-3.66 (m, 8H), 3.52-3.44 (m, 2H), 3.05 (s, 3H), 2.93-2.62 (m, 3H), 2.28-2.06 (m, 1H) ppm.

Preparation of 2-(2-(2-(2-((2-(2,6-Dioxopiperidin-3-yl)-1,3-dioxoisoindolin-4-yl)amino)ethoxy)ethoxy) ethoxy)ethyl methanesulfonate (45c)

$^1$H NMR (400 MHz, $CDCl_3$) δ 8.20 (br s, 1H), 7.60-7.41 (m, 1H), 7.10 (d, J=7.1 Hz, 1H), 6.92 (d, J=8.5 Hz, 1H), 6.48 (t, J=5.6 Hz, 1H), 4.92 (dd, J=11.8, 5.4 Hz, 1H), 4.36 (dd, J=5.3, 3.7 Hz, 2H), 3.82-3.60 (m, 12H), 3.54-3.40 (m, 2H), 3.07 (s, 3H), 2.98-2.65 (m, 3H), 2.24-2.06 (m, 1H) ppm.

Preparation of 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(2-((2-(2,6-dioxopiperidin-3-yl)-1,3-dioxoisoindolin-4-yl)amino)ethoxy)ethyl)piperazin-1-yl)-1-(phenylthio)butan-2-yl)amino)-3-((trifluoromethyl)sulfonyl)phenyl)sulfonyl)benzamide (XZ-15416)

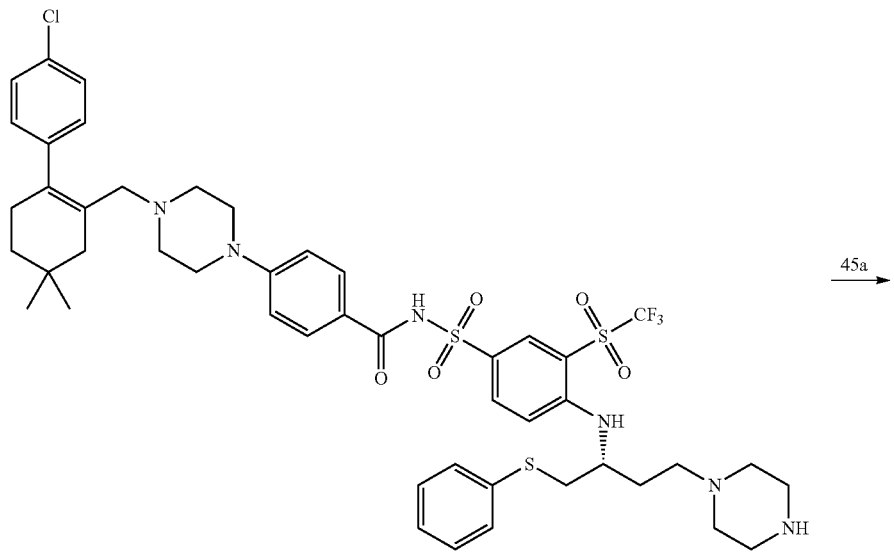

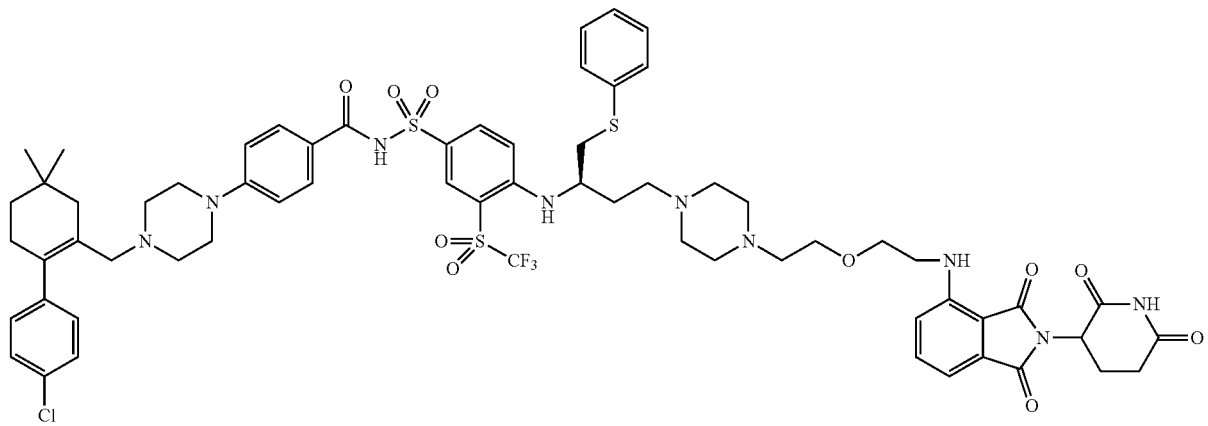

XZ-15416

A mixture of compound 35 (25 mg), 45a (12 mg), DIPEA (60 µL) and NaI (1.6 mg) in 2 mL 1,4-dioxane was heated at 90° C. overnight. Then the mixture was poured into water and extracted with EtOAc. The organic phase was washed with water x1, NH$_4$Cl (aq) x1, brine x1, dried over Na$_2$SO$_4$, filtered and evaporated to dryness. The crude product was purified by column chromatography using DCM and methanol as eluents to afford 8.8 mg pure XZ-15416. Yield 26%.

$^1$H NMR (400 MHz, CDCl$_3$) δ 8.35 (s, 1H), 8.09-7.98 (m, 1H), 7.72 (d, J=8.7 Hz, 2H), 7.48 (t, J=7.9 Hz, 1H), 7.40-7.29 (m, 5H), 7.25-7.20 (m, 1H), 7.10 (d, J=7.1 Hz, 1H), 7.06-6.95 (m, 3H), 6.89 (d, J=8.4 Hz, 1H), 6.73 (d, J=9.1 Hz, 2H), 6.66-6.55 (m, 1H), 6.53-6.42 (m, 1H), 4.98-4.82 (m, 1H), 3.93-3.80 (m, 1H), 3.76-3.40 (m, 6H), 3.32-2.64 (m, 17H), 2.43-1.97 (m, 16H), 1.70-1.66 (m, 1H), 1.52-1.41 (m, 2H), 1.01-0.95 (m, 6H) ppm.

Preparation of 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(2-(2-((2-(2,6-dioxopiperidin-3-yl)-1,3-dioxoisoindolin-4-yl)amino)ethoxy)ethoxy)ethyl)piperazin-1-yl)-1-(phenylthio)butan-2-yl)amino)-3-((trifluoromethyl)sulfonyl)phenyl)sulfonyl)benzamide (XZ-15405)

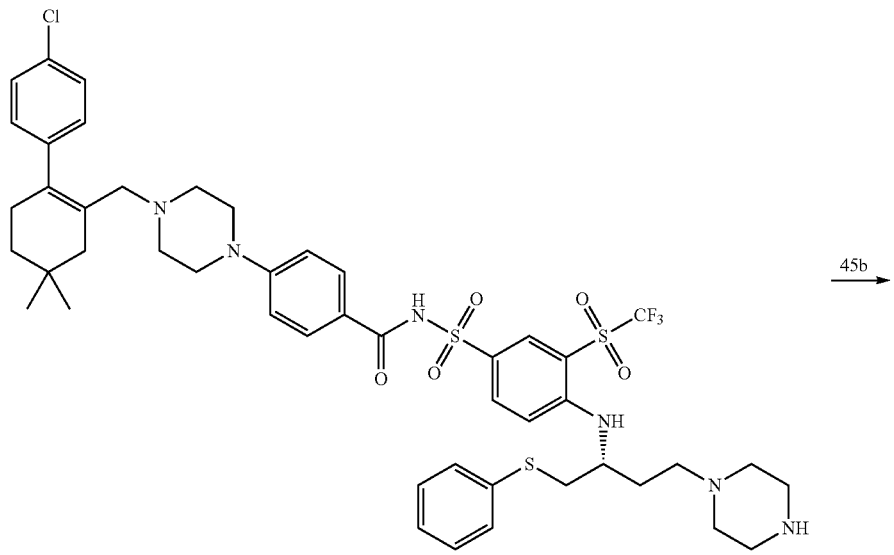

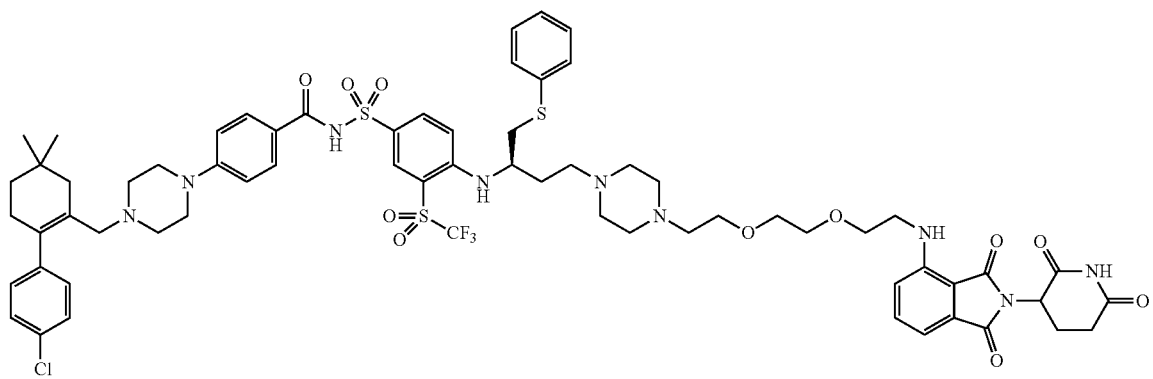

XZ-15405

A mixture of compound 35 (10 mg), 45b (6 mg), TEA (20 μL) and NaI (1.0 mg) in 2 mL 1,4-dioxane was heated at 80° C. overnight. The reaction mixture was then poured into water and extracted with EtOAc. The organic phase was washed with water x1, NH$_4$Cl (aq) x1, brine x1, dried over Na$_2$SO$_4$, filtered and evaporated to dryness. The crude product was purified by column chromatography using DCM and methanol as eluents to afford 5.8 mg pure XZ-15405. Yield 42%. $^1$H NMR (400 MHz, CDCl$_3$) δ 8.33 (s, 1H), 8.02 (t, J=8.9 Hz, 1H), 7.76 (d, J=7.0 Hz, 2H), 7.52-7.46 (m, 1H), 7.41-7.33 (m, 2H), 7.32-7.27 (m, 3H), 7.25-7.21 (m, 1H), 7.10 (dd, J=7.1, 2.3 Hz, 1H), 7.04-6.92 (m, 3H), 6.88 (d, J=8.6 Hz, 1H), 6.75 (d, J=8.4 Hz, 2H), 6.56-6.40 (m, 2H), 4.96-4.73 (m, 1H), 3.86-3.40 (m, 11H), 3.33-2.51 (m, 17H), 2.50-1.79 (m, 16H), 1.74-1.60 (m, 1H), 1.48-1.37 (m, 2H), 0.95 (d, J=5.4 Hz, 6H) ppm.

Preparation of 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(2-(2-(2-((2-(2,6-dioxopiperidin-3-yl)-1,3-dioxoisoindolin-4-yl)amino)ethoxy)ethoxy)ethoxy)ethyl)piperazin-1-yl)-1-(phenylthio)butan-2-yl)amino)-3-((trifluoromethyl)sulfonyl)phenyl)sulfonyl)benzamide (XZ-15418)

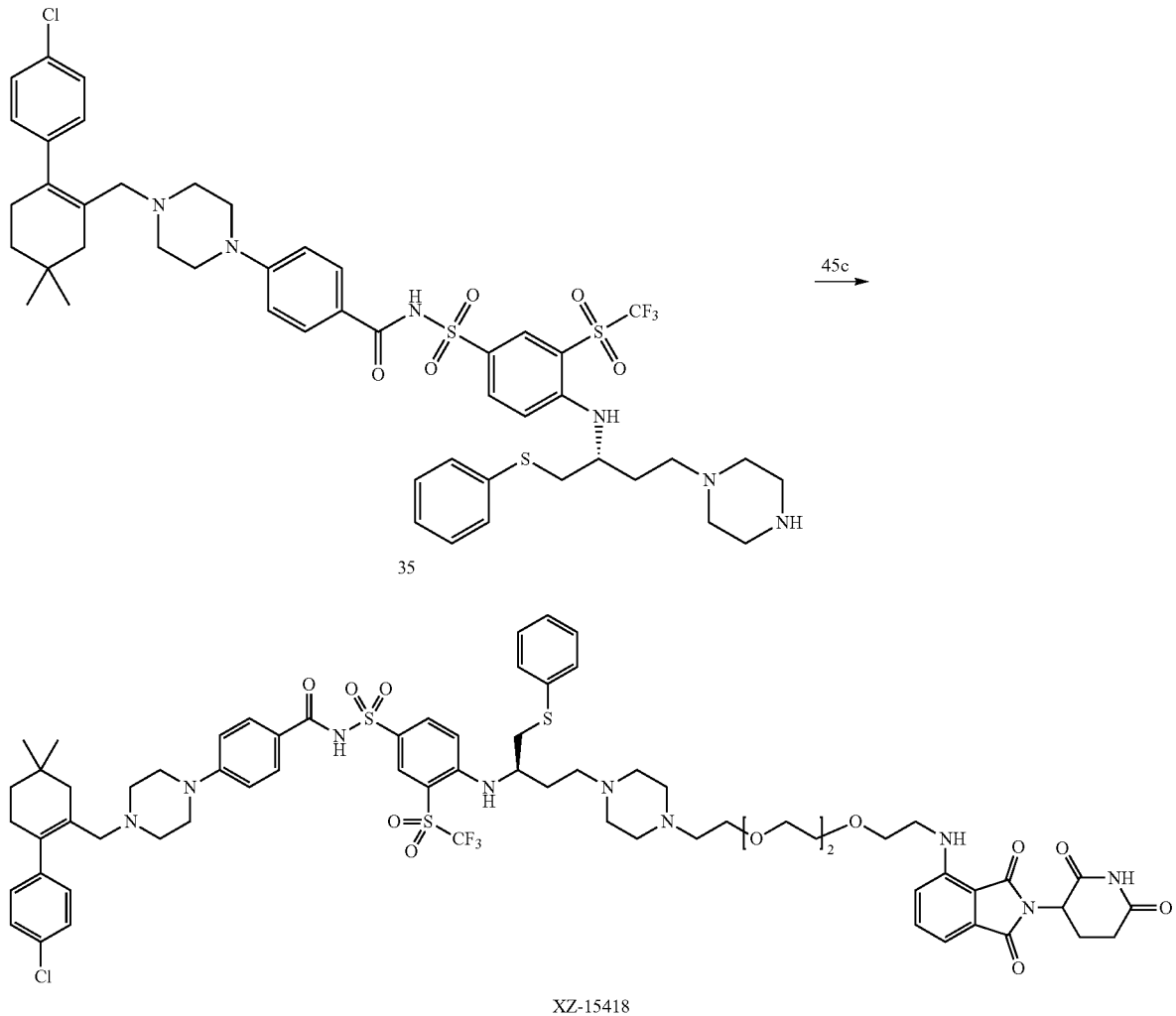

A mixture of compound 35 (42 mg), 45c (24 mg), DIPEA (100 µL) and NaI (3 mg) in 3 mL 1,4-dioxane was heated at 90° C. overnight. The reaction mixture was then poured into water and extracted with EtOAc. The organic phase was washed with water x1, NH₄Cl (aq) x1, brine x1, dried over Na₂SO₄, filtered and evaporated to dryness. The crude product was purified by column chromatography using DCM and methanol as eluents to afford 16.4 mg pure XZ-15418. Yield 25%. $^1$H NMR (400 MHz, CDCl$_3$) δ 8.31 (s, 1H), 8.01 (d, J=8.9 Hz, 1H), 7.81 (d, J=8.5 Hz, 2H), 7.47 (t, J=7.8 Hz, 1H), 7.38-7.28 (m, 5H), 7.25-7.21 (m, 1H), 7.08 (d, J=7.1 Hz, 1H), 6.99 (d, J=8.3 Hz, 2H), 6.96-6.85 (m, 2H), 6.75 (d, J=8.7 Hz, 2H), 6.54-6.43 (m, 2H), 4.96-4.83 (m, 1H), 3.90-3.39 (m, 15H), 3.28-2.68 (m, 17H), 2.51-1.95 (m, 16H), 1.61-1.57 (m, 1H), 1.47-1.41 (m, 2H), 0.97-0.93 (m, 6H) ppm.

483 484
Example 12: Synthesis of XZ-15421
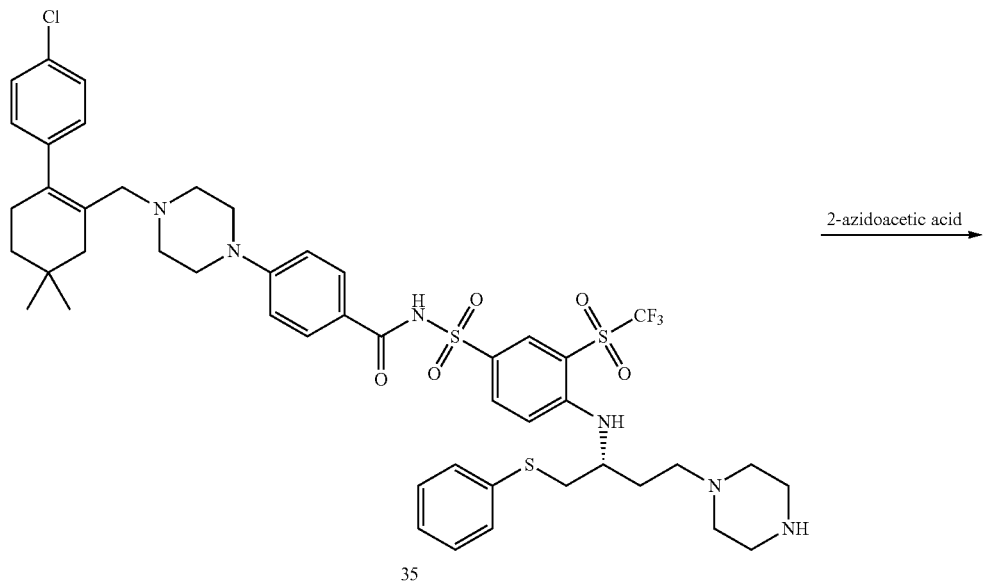
35
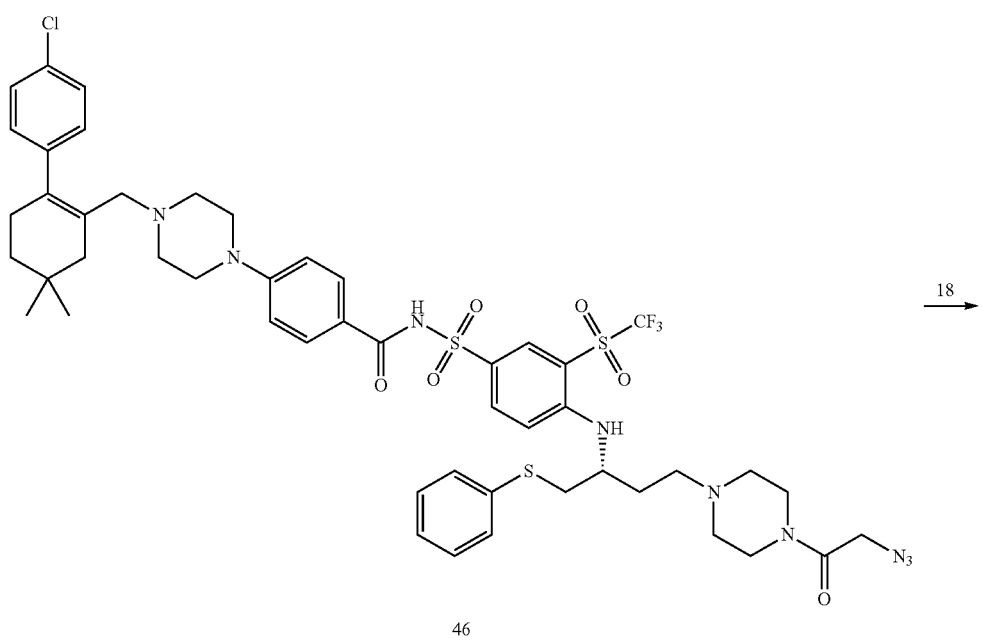
46
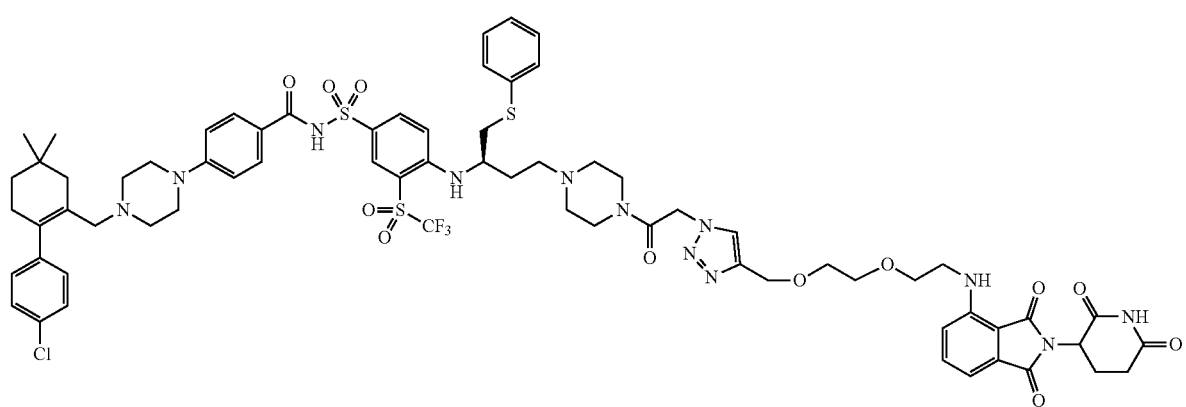
XZ-15421

Preparation of (R)—N-(4-(4-(4-(2-azidoacetyl)piperazin-1-yl)-1-(phenylthio)butan-2-ylamino)-3-(trifluoromethylsulfonyl)phenylsulfonyl)-4-(4-(2-(4-chlorophenyl)-5,5-dimethylcyclohex-1-enyl)methyl)piperazin-1-yl)benzamide (46)

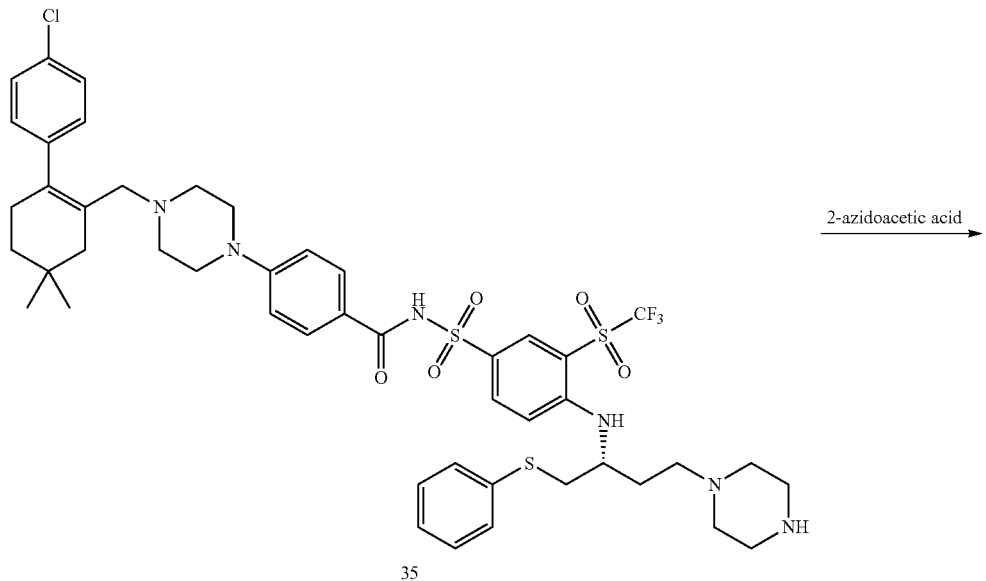

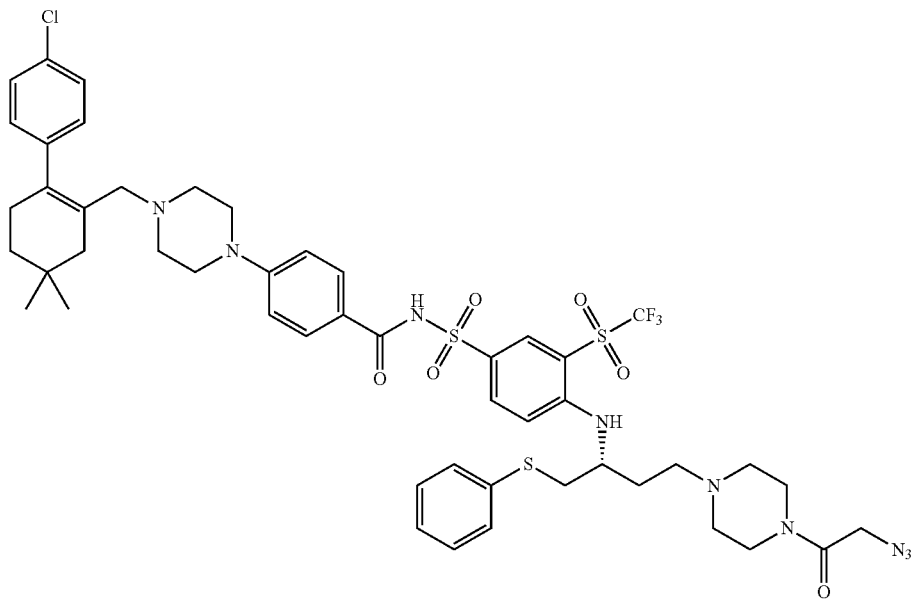

To a mixture of compound 35 (48 mg), 2-azidoacetic acid (8 mg), and DIPEA (13 μL) in 5 mL DCM was added HATU (21 mg). The mixture was stirred at room temperature for 3 hours. The solvent was removed under reduced pressure and the crude product was purified via column chromatography using DCM and methanol as eluents to afford 48 mg compound 46. Yield 87%. $^1$H NMR (400 MHz, CDCl$_3$) δ 8.35 (d, J=1.9 Hz, 1H), 8.11 (dd, J=9.1, 1.8 Hz, 1H), 7.66 (d, J=8.8 Hz, 2H), 7.40-7.26 (m, 6H), 7.08 (d, J=8.4 Hz, 1H), 6.98 (d, J=8.3 Hz, 2H), 6.76 (d, J=8.8 Hz, 2H), 6.57 (d, J=9.4 Hz, 1H), 3.93-3.81 (m, 3H), 3.74-3.64 (m, 1H), 3.55-3.42 (m, 1H), 3.36-3.22 (m, 6H), 3.11 (dd, J=13.8, 4.8 Hz, 1H), 2.99 (dd, J=13.8, 7.5 Hz, 1H), 2.85 (s, 2H), 2.50-2.21 (m, 12H), 2.20-2.08 (m, 1H), 2.03-1.96 (m, 2H), 1.75-1.61 (m, 1H), 1.46 (t, J=6.4 Hz, 2H), 0.97 (s, 6H) ppm.

Preparation of 4-(4-((2-(4-chlorophenyl)-5,5-dimethylcyclohex-1-enyl)methyl)piperazin-1-yl)-N-(4-((2R)-4-(4-(2-(4-((2-(2-(2-(2,6-dioxopiperidin-3-yl)-1,3-dioxoisoindolin-4-ylamino)ethoxy)ethoxy)methyl)-1H-1,2,3-triazol-1-yl)acetyl)piperazin-1-yl)-1-(phenylthio)butan-2-ylamino)-3-(trifluoromethylsulfonyl)phenyl)sulfonyl)benzamide (XZ-15421)

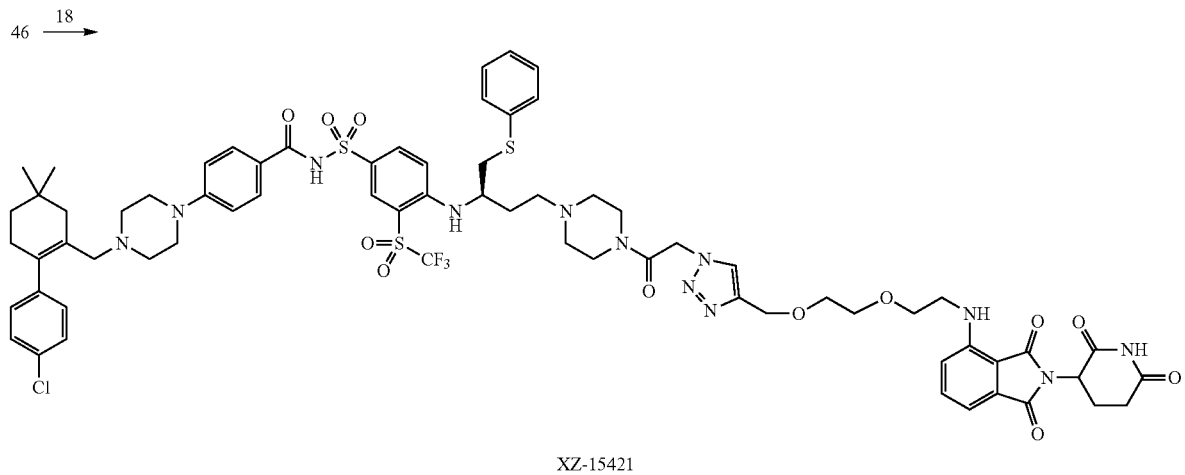

XZ-15421

To a mixture of compound 46 (24.0 mg) and compound 18 (11.0 mg) in 2 mL t-BuOH-THF (1:1, v/v) under argon was added CuSO$_4$·5H$_2$O (1.15 mg) and sodium ascorbate (0.91 mg) in 0.3 mL water. The mixture was stirred at 50° C. for 2 hours and extracted with DCM. The organic phase was washed with brine x1, dried over Na$_2$SO$_4$, filtered and evaporated to dryness. The crude product was purified via column chromatography using DCM and methanol as eluents to afford 16.4 mg XZ-15421. Yield 50%. $^1$H NMR (400 MHz, d$_6$-acetone) δ 9.91 (s, 1H), 8.34 (s, 1H), 8.10 (d, J=9.2 Hz, 1H), 7.92-7.78 (m, 3H), 7.66-7.55 (m, 1H), 7.48-7.20 (m, 7H), 7.17-7.00 (m, 6H), 6.90 (d, J=8.6 Hz, 2H), 6.70-6.54 (m, 1H), 5.31 (s, 2H), 5.14-5.05 (m, 1H), 4.63 (s, 2H), 4.33-4.25 (m, 1H), 3.79-3.20 (m, 20H), 3.02-2.83 (m, 5H), 2.58-2.11 (m, 14H), 1.87-1.82 (m, 1H), 1.48 (t, J=6.4 Hz, 2H), 1.00 (s, 6H) ppm.

Example 13: Synthesis of XZ-14529

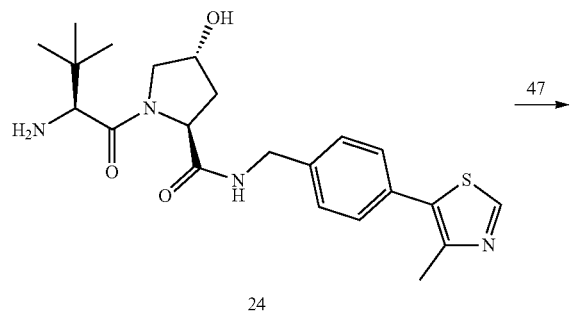

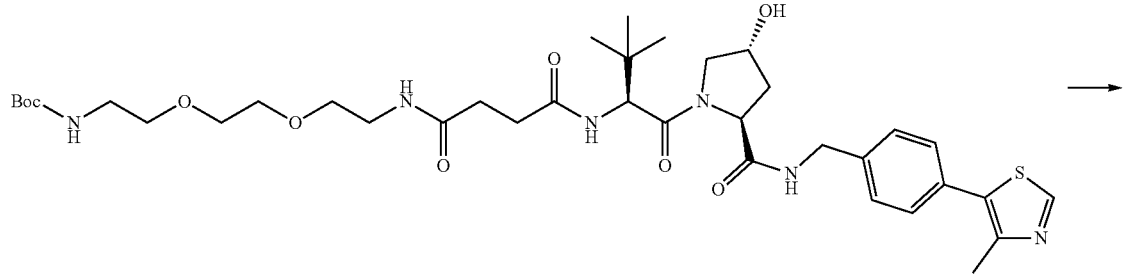

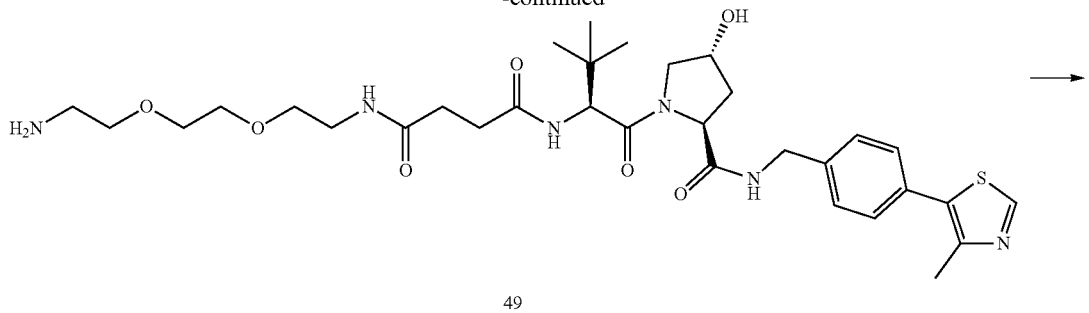

49

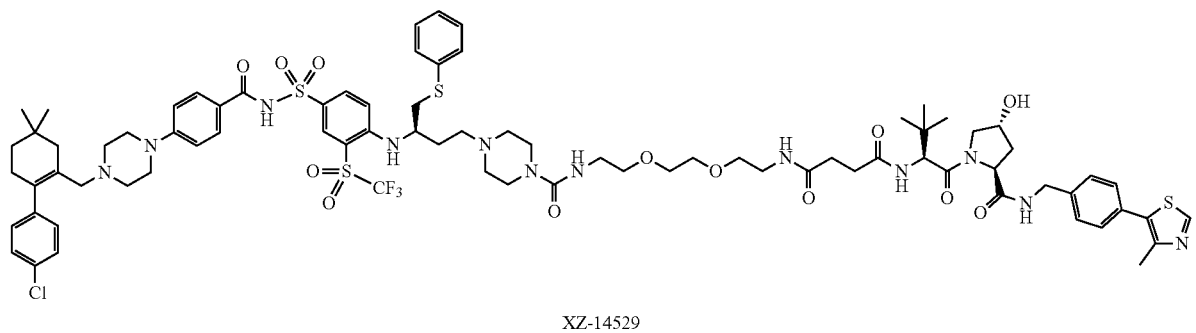

XZ-14529

Preparation of 2,2-dimethyl-4,15-dioxo-3,8,11-trioxa-5,14-diazaoctadecan-18-oic Acid (47)

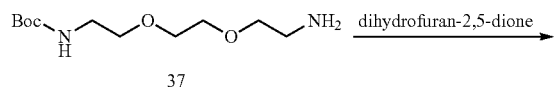

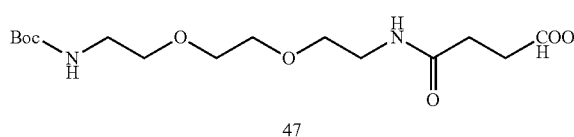

A mixture of compound 37 (250 mg), dihydrofuran-2,5-dione (120 mg), and TEA (210 µL) in 10 mL DCM was stirred at room temperature overnight. The reaction mixture was then poured into water and extracted with DCM. The organic phase was washed with 1N HCl (aq.) x1, brine x1, dried over Na$_2$SO$_4$, filtered and evaporated to dryness to give 320 mg compound 47. Yield 92%. $^1$H NMR (400 MHz, CDCl$_3$) δ 3.72-3.51 (m, 8H), 3.49-3.42 (m, 2H), 3.39-3.26 (m, 2H), 2.74-2.62 (m, 2H), 2.58-2.44 (m, 2H), 1.46 (s, 9H) ppm.

Preparation of tert-butyl ((S)-15-((2S,4R)-4-hydroxy-2-((4-(4-methylthiazol-5-yl)benzyl)carbamoyl)pyrrolidine-1-carbonyl)-16,16-dimethyl-10,13-dioxo-3,6-dioxa-9,14-diazaheptadecyl)carbamate (48)

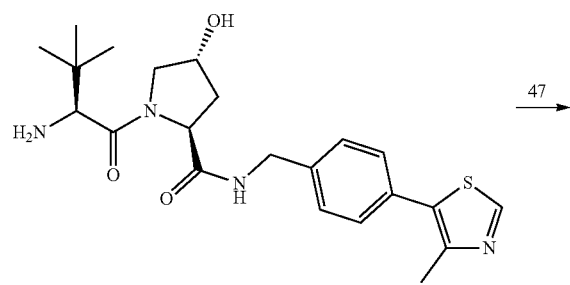

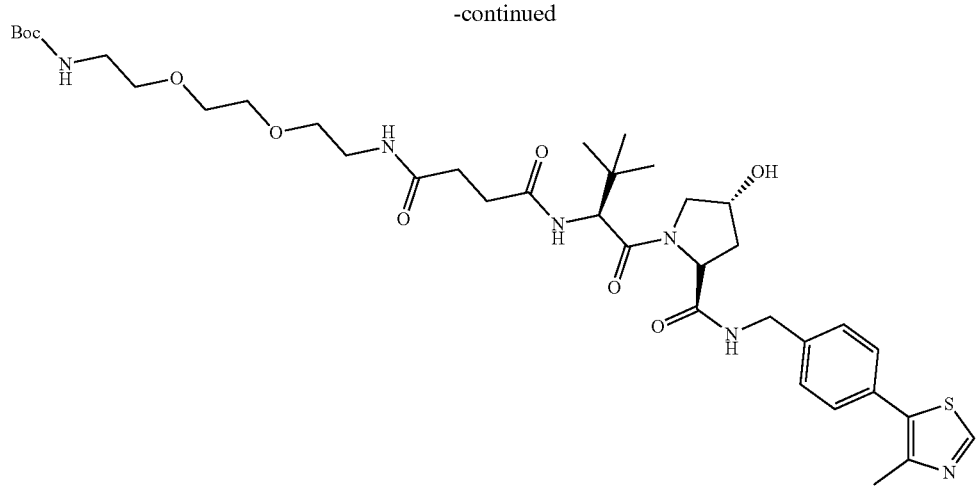

48

To a mixture of compound 47 (100 mg), compound 24 (190 mg), and DIPEA (167 μL) in 10 mL DCM was added 116 mg HATU. The resulted mixture was stirred at room temperature for 2 hours before poured into water and extracted with DCM. The organic phase was washed with brine x1, dried over $Na_2SO_4$, filtered and evaporated to dryness to give 136 mg compound 48. Yield 62%. $^1$H NMR (400 MHz, $CDCl_3$) δ 8.67 (s, 1H), 7.53 (br s, 1H), 7.40-7.29 (m, 4H), 6.97 (br s, 1H), 6.53 (br s, 1H), 5.12 (br s, 1H), 4.72 (t, J=8.0 Hz, 1H), 4.62-4.44 (m, 3H), 4.33 (dd, J=15.0, 5.3 Hz, 1H), 4.12-3.91 (m, 1H), 3.65-3.46 (m, 9H), 3.45-3.22 (m, 4H), 2.55-2.37 (m, 8H), 2.21-2.09 (m, 1H), 1.43 (s, 9H), 0.91 (s, 9H) ppm.

Preparation of N1-(2-(2-(2-aminoethoxy)ethoxy)ethyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide (49)

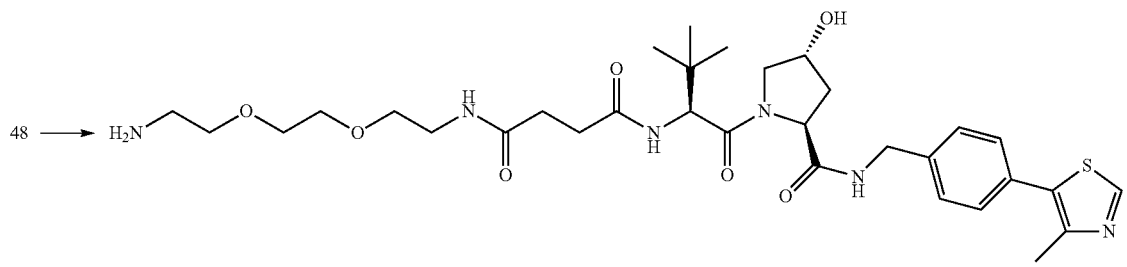

49

To a mixture of compound 48 (100 mg) in 10 mL DCM was added TFA (440 μL). The reaction was stirred at room temperature for 2 days. Then it was neutralized with $NaHCO_3$ (aq) and extracted with DCM. The organic phase was washed with brine x1, dried over $Na_2SO_4$, filtered and evaporated to dryness to give the crude product which can be used in the next step without further purification. $^1$H NMR (400 MHz, $CDCl_3$) δ 8.67 (s, 1H), 7.67-7.58 (m, 1H), 7.39-7.28 (m, 5H), 6.94 (d, J=8.2 Hz, 1H), 4.70 (t, J=8.3 Hz, 1H), 4.56-4.30 (m, 4H), 4.03 (d, J=10.9 Hz, 1H), 3.64-3.49 (m, 9H), 3.43-3.34 (m, 2H), 2.89 (t, J=4.9 Hz, 2H), 2.57-2.36 (m, 8H), 2.20-2.13 (m, 1H), 0.95 (s, 9H) ppm.

Preparation of N1-(2-(2-(2-(4-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazine-1-carboxamido)ethoxy)ethoxy)ethyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide (XZ-14529)

35 —49→

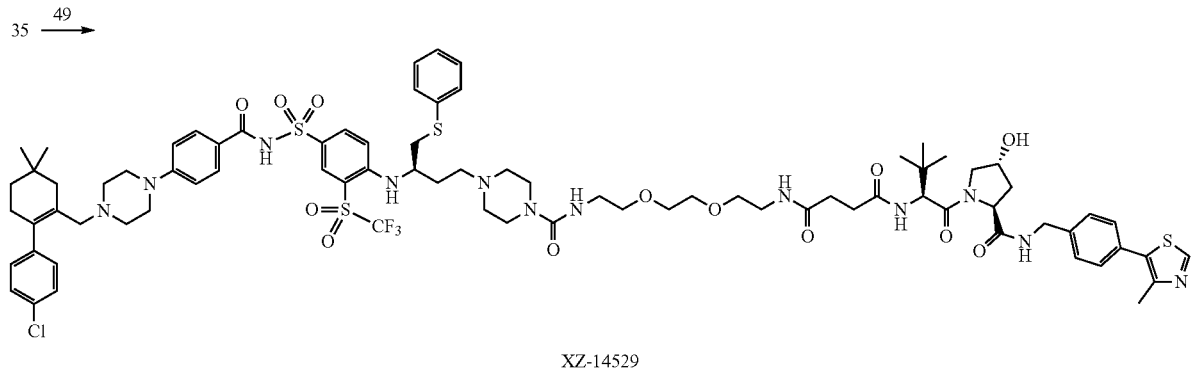

XZ-14529

A mixture of compound 49 (26 mg) and CDI (7.7 mg) in 2 mL THF was stirred at room temperature for 1 hour. Compound 35 (14.6 mg) and DIPEA (0.05 mL) were then added. The mixture was stirred overnight and quenched by the addition of NH₄Cl (aq.), extracted with DCM and the organic phase was washed with water x1, brine x1, dried over Na₂SO₄, filtered and evaporated to dryness. The crude product was purified by column chromatography using DCM and methanol as eluents to afford 21.1 mg compound XZ-14529. Yield 85%. ¹H NMR (400 MHz, CDCl₃ and CD₃OD) δ 8.70 (s, 1H), 8.32 (s, 1H), 8.03 (d, J=8.8 Hz, 1H), 7.95-7.76 (m, 3H), 7.50-7.38 (m, 2H), 7.37-7.34 (m, 4H), 7.32-7.17 (m, 5H), 7.06-6.95 (m, 3H), 6.78 (d, J=8.9 Hz, 2H), 6.65 (d, J=9.4 Hz, 1H), 5.87-5.72 (m, 1H), 4.66-4.47 (m, 4H), 4.45-4.33 (m, 1H), 4.01-3.22 (m, 23H), 3.16-3.03 (m, 2H), 2.84 (s, 2H), 2.52-1.98 (m, 24H), 1.75-1.63 (m, 1H), 1.48 (t, J=6.3 Hz, 2H), 0.99 (m, 15H) ppm.

Example 14: Synthesis of XZ-14523

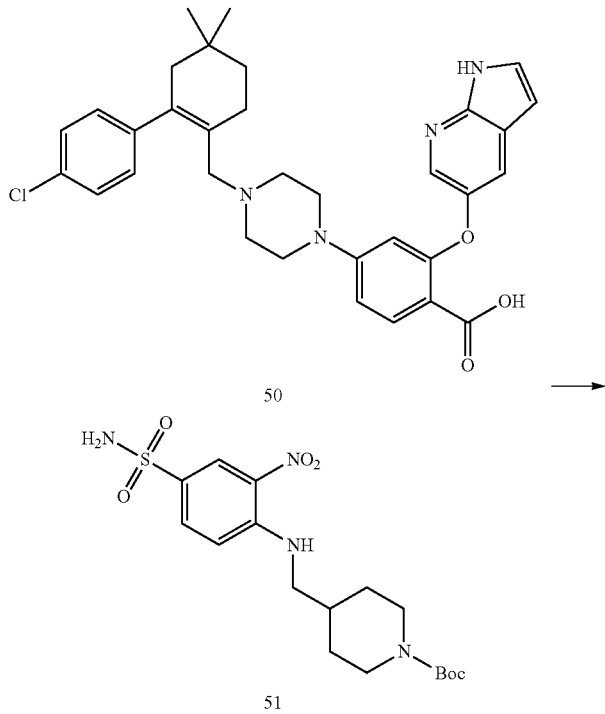

495
-continued
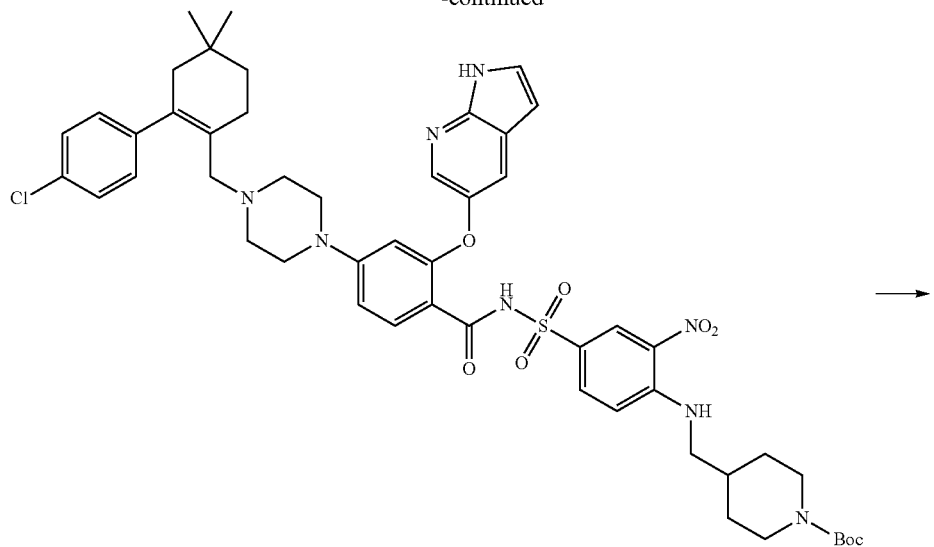
52
496
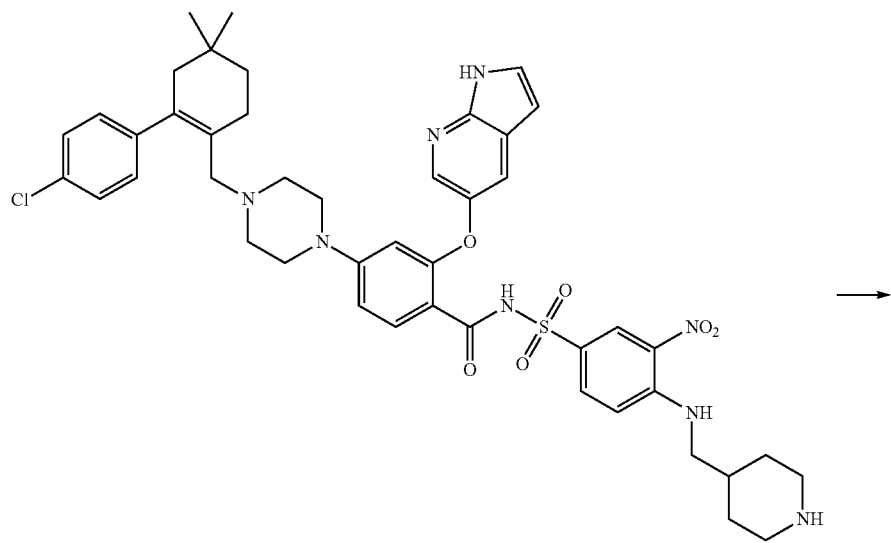
53

497
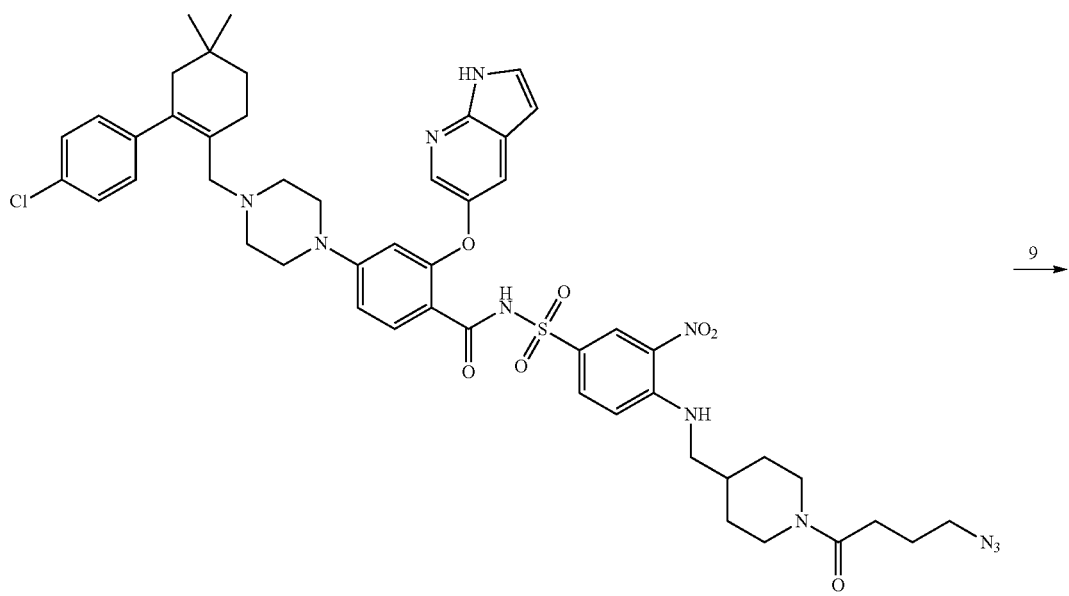
54
498
-continued
9 →
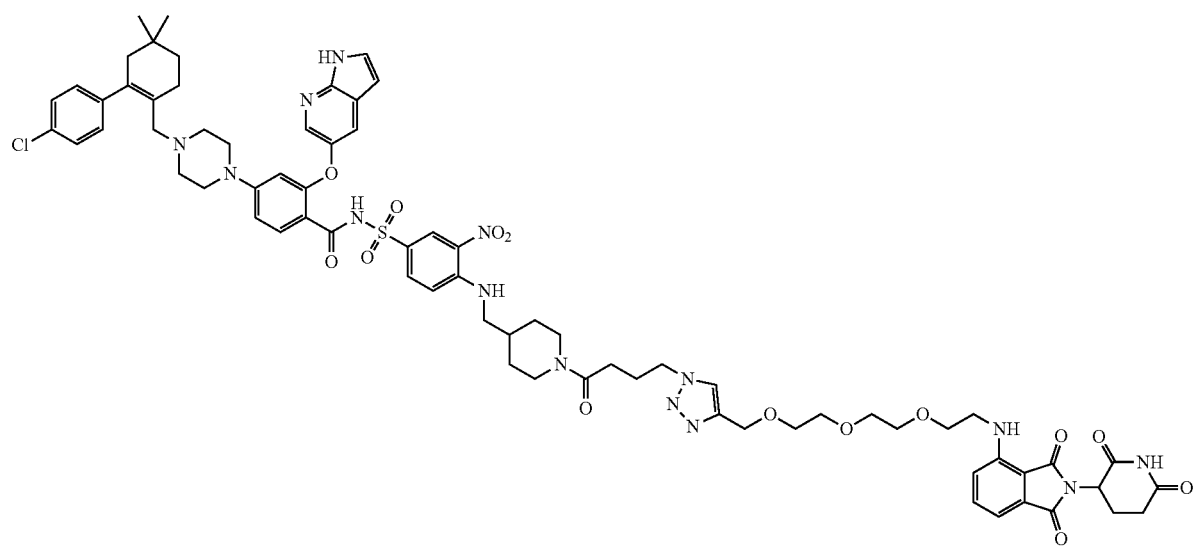
XZ-14523

Preparation of tert-butyl 4-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)piperidine-1-carboxylate (52)

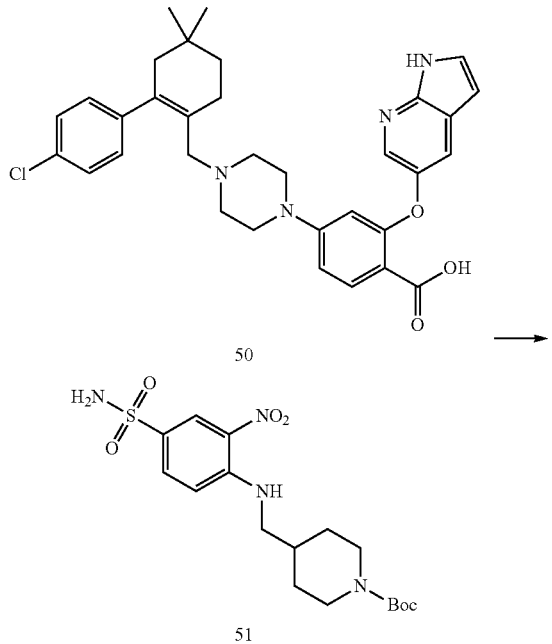

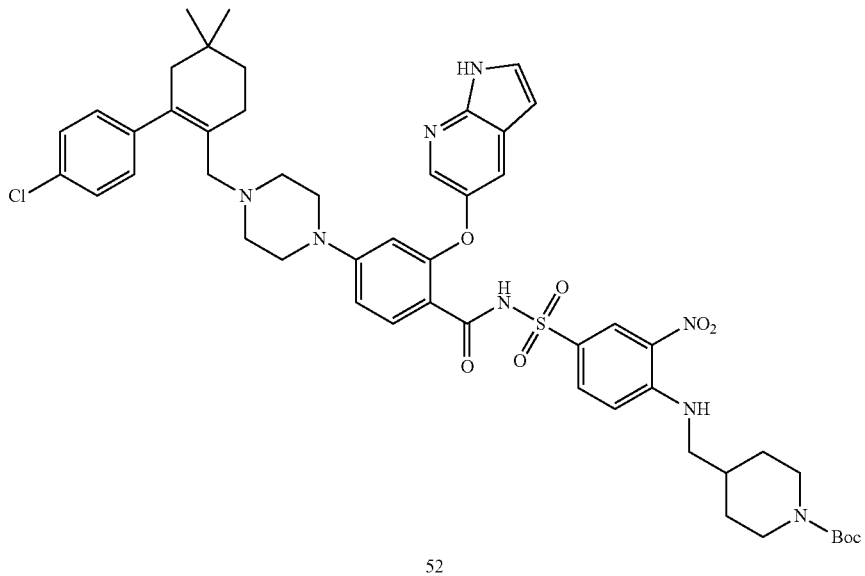

A mixture of compound 50 (571 mg), 51 (415 mg), DMAP (244 mg), EDCI (250 mg), and TEA (280 μL) in 20 mL DCM was stirred at room temperature overnight. The solvent was removed under reduced pressure and the residue was purified via column chromatography using DCM and methanol as eluents to give 758 mg pure product as yellow solid. Yield 79%. $^1$H NMR (400 MHz, CDCl$_3$) δ 10.14 (br s, 1H), 9.72 (br s, 1H), 8.89 (d, J=2.2 Hz, 1H), 8.52 (t, J=5.4 Hz, 1H), 8.21 (d, J=2.5 Hz, 1H), 8.16 (dd, J=9.2, 2.1 Hz, 1H), 7.95 (d, J=9.1 Hz, 1H), 7.71 (d, J=2.5 Hz, 1H), 7.53-7.43 (m, 1H), 7.22 (d, J=8.4 Hz, 2H), 6.94-6.83 (m, 3H), 6.60-6.47 (m, 2H), 5.98 (d, J=2.1 Hz, 1H), 4.27-4.13 (m, 2H), 3.32-3.20 (m, 2H), 3.13-3.01 (m, 4H), 2.83-2.65 (m, 4H), 2.26-2.10 (m, 6H), 1.96 (s, 2H), 1.92-1.74 (m, 3H), 1.47 (s, 9H), 1.40 (t, J=6.4 Hz, 2H), 1.25-1.18 (m, 2H), 0.93 (s, 6H) ppm.

501

Preparation of 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(piperidin-4-ylmethylamino)phenylsulfonyl)benzamide (53)

52 ⟶

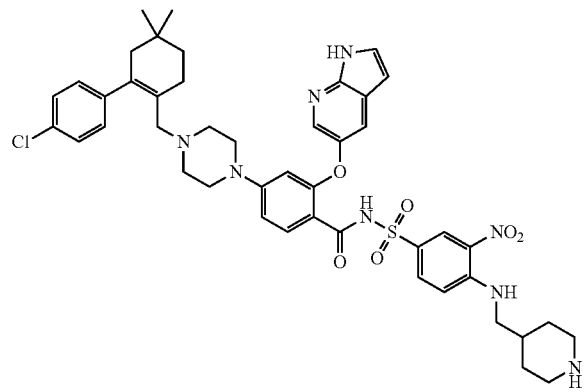

53

To a solution of compound 52 (578 mg) in 20 mL DCM was added TFA (440 μL). The reaction mixture was stirred at room temperature overnight. Solvent was removed under reduced pressure and Et$_2$O was added to the residue. The precipitated solid was collected by filtration and can be used directly in the next step without further purification. $^1$H NMR (400 MHz, d$_6$-DMSO) δ 11.88-11.54 (m, 2H), 9.34 (br s, 1H), 8.66 (t, J=6.1 Hz, 1H), 8.59-8.45 (m, 2H), 8.29-8.08 (m, 1H), 8.01 (d, J=2.6 Hz, 1H), 7.80 (dd, J=9.2, 2.2 Hz, 1H), 7.57-7.45 (m, 3H), 7.36 (d, J=8.4 Hz, 2H), 7.12 (d, J=9.4 Hz, 1H), 7.05 (d, J=8.3 Hz, 2H), 6.69 (dd, J=9.0, 2.0 Hz, 1H), 6.37 (dd, J=3.3, 1.9 Hz, 1H), 6.22 (s, 1H), 3.84-3.44 (m, 4H), 3.39-3.15 (m, 6H), 3.10-2.60 (m, 6H), 2.22-2.10 (m, 2H), 2.04-1.76 (m, 5H), 1.49-1.26 (m, 4H), 0.91 (s, 6H) ppm.

Preparation of 2-((1H-pyrrolo[2,3-b]pyridin-5-yl)oxy)-N-((4-(((1-(4-azidobutanoyl)piperidin-4-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)benzamide (54)

53 ⟶

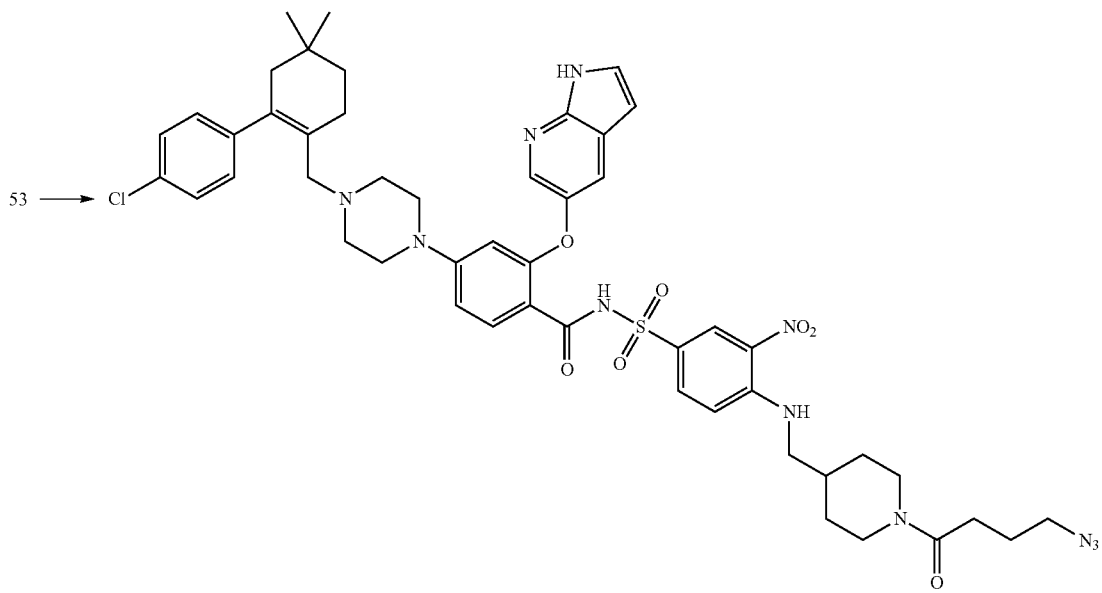

54

To a solution of compound 53 (60 mg), 4-azidobutanoic acid (7 mg), and DIPEA (42 μL) in 5 mL DCM was added HATU (20 mg). The resulted mixture was stirred at room temperature for 2 hours. Solvent was removed under reduced pressure and the crude product was purified via column chromatography using DCM and methanol as eluents to afford 46 mg compound 54. Yield 94%. $^1$H NMR (400 MHz, CDCl$_3$) δ 10.14 (br s, 1H), 9.46 (s, 1H), 8.90 (d, J=2.2 Hz, 1H), 8.52 (t, J=5.4 Hz, 1H), 8.27-8.10 (m, 2H), 7.95 (d, J=9.1 Hz, 1H), 7.71 (d, J=2.5 Hz, 1H), 7.51-7.44 (m, 1H), 7.22 (d, J=8.4 Hz, 2H), 7.01-6.76 (m, 3H), 6.62-6.43 (m, 2H), 5.98 (d, J=2.1 Hz, 1H), 4.72 (d, J=13.5 Hz, 1H), 3.94 (d, J=13.8 Hz, 1H), 3.40 (t, J=6.4 Hz, 2H), 3.34-3.20 (m, 2H), 3.13-2.98 (m, 5H), 2.74 (s, 2H), 2.58 (t, J=11.7 Hz, 1H), 2.44 (t, J=7.2 Hz, 2H), 2.29-2.09 (m, 6H), 2.04-1.82 (m, 7H), 1.40 (t, J=6.4 Hz, 2H), 1.28-1.18 (m, 2H), 0.93 (s, 6H) ppm.

Preparation of 2-((1H-pyrrolo[2,3-b]pyridin-5-yl) oxy)-4-(4-((4'-chloro-5,5-dimethyl-3,4,5,6-tetrahydro-[1,1'-biphenyl]-2-yl)methyl)piperazin-1-yl)-N-((4-(((1-(4-(4-((2-(2-(2-((2-(2,6-dioxopiperidin-3-yl)-1,3-dioxoisoindolin-4-yl)amino)ethoxy)ethoxy) ethoxy)methyl)-1H-1,2,3-triazol-1-yl)butanoyl) piperidin-4-yl)methyl)amino)-3-nitrophenyl) sulfonyl)benzamide (XZ-14523)

54 + 9 ⟶

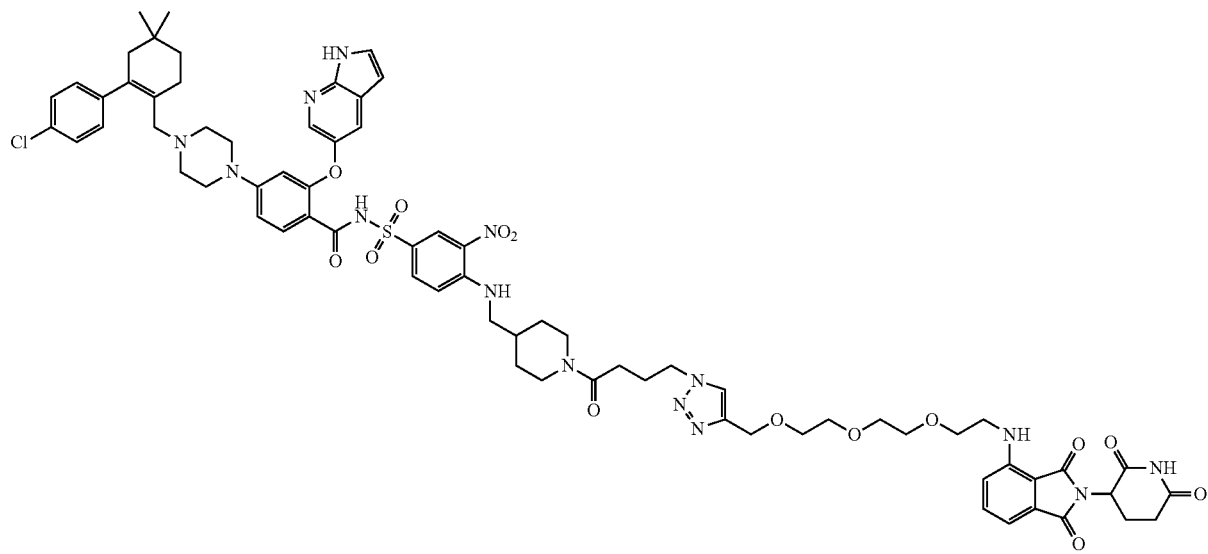

XZ-14523

To a mixture of compound 54 (20.0 mg), compound 9 (10.0 mg) in 2 mL t-BuOH-THF (1:1, v/v) under argon was added CuSO$_4$·5H$_2$O (1.0 mg) and sodium ascorbate (0.8 mg) in 0.3 mL water. The mixture was stirred at 55° C. for 3 hours and extracted with DCM. The organic phase was washed with brine x1, dried over Na$_2$SO$_4$, filtered and evaporated to dryness. The crude product was purified via column chromatography using DCM and methanol as eluents to afford 23.2 mg XZ-15423. Yield 82%. $^1$H NMR (400 MHz, CDCl$_3$) δ 10.07 (br s, 1H), 9.88 (br s, 1H), 9.61 (br s, 1H), 8.89 (d, J=2.2 Hz, 1H), 8.64-8.46 (m, 1H), 8.19 (d, J=2.5 Hz, 1H), 8.07 (d, J=9.2 Hz, 1H), 7.93 (d, J=9.1 Hz, 1H), 7.69 (d, J=2.5 Hz, 1H), 7.62 (s, 1H), 7.52-7.42 (m, 2H), 7.23 (d, J=8.3 Hz, 2H), 7.08 (d, J=7.1 Hz, 1H), 6.96-6.83 (m, 4H), 6.61-6.39 (m, 3H), 5.98 (d, J=2.0 Hz, 1H), 4.98-4.90 (m, 1H), 4.76-4.63 (m, 3H), 4.53-4.37 (m, 2H), 3.88-3.62 (m, 11H), 3.50-3.41 (m, 2H), 3.33-3.22 (m, 2H), 3.10-3.02 (m, 4H), 3.02-2.69 (m, 6H), 2.55 (t, J=11.8 Hz, 1H), 2.38-2.11 (m, 11H), 2.00-1.80 (m, 5H), 1.41 (t, J=7.3 Hz, 2H), 1.27-1.21 (m, 2H), 0.93 (s, 6H) ppm.

Example 15: Synthesis of XZ-14522

Preparation of 2-((1H-pyrrolo-[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(2-(2-(2-(2-((2-(2,6-dioxopiperidin-3-yl)-1,3-dioxoisoindolin-4-yl)amino)ethoxy)ethoxy)ethoxy)acetyl)piperidin-4-yl)methyl)amino)-3-nitrophenyl)sulfonyl)benzamide (XZ-14522)

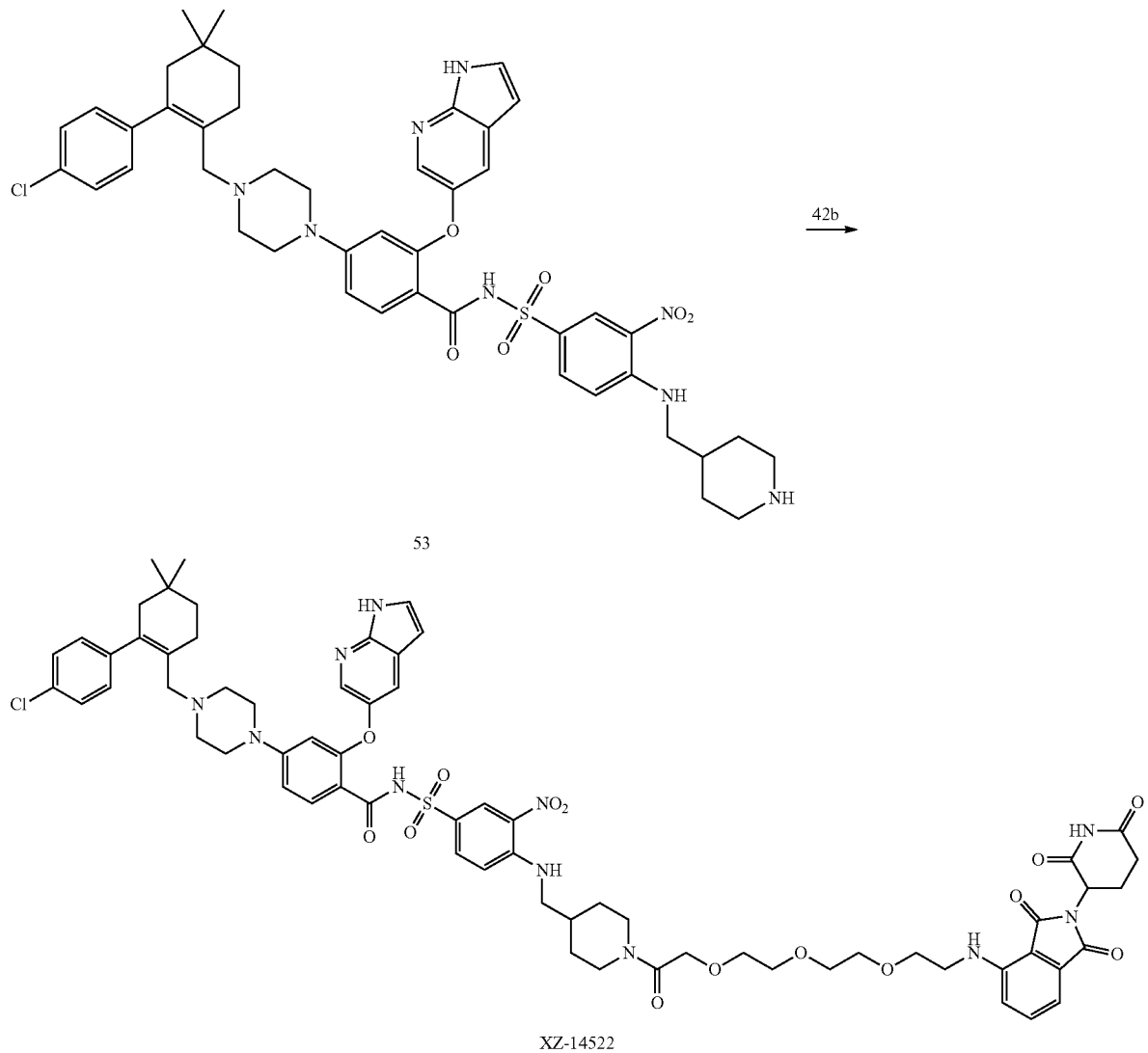 [SMILES: CC1(C)CCC(CN2CCN(c3ccc(C(=O)NS(=O)(=O)c4ccc(NCC5CCNCC5)c([N+](=O)[O-])c4)c(Oc4cnc5[nH]ccc5c4)c3)CC2)=C(c2ccc(Cl)cc2)C1 ; CC1(C)CCC(CN2CCN(c3ccc(C(=O)NS(=O)(=O)c4ccc(NCC5CCN(C(=O)COCCOCCOCCNc6cccc7c6C(=O)N(C6CCC(=O)NC6=O)C7=O)CC5)c([N+](=O)[O-])c4)c(Oc4cnc5[nH]ccc5c4)c3)CC2)=C(c2ccc(Cl)cc2)C1]

A solution of compound 53 (12 mg), compound 42b (5 mg), HATU (4 mg), and DIPEA (20 mg) in 3 mL DCM was stirred at room temperature for 2 hours. NH₄Cl (aq) was then added and extracted with DCM. The organic phase was washed with water x1, brine x1, dried over Na₂SO₄, filtered and evaporated to dryness. The crude product was purified by column chromatography using DCM and methanol as eluents to afford 10.8 mg pure XZ-14522. Yield 82%. $^1$H NMR (400 MHz, CDCl₃) δ 10.24 (d, J=6.9 Hz, 1H), 10.10 (br s, 1H), 9.82 (br s, 1H), 8.87 (s, 1H), 8.49 (t, J=5.3 Hz, 1H), 8.16 (d, J=2.1 Hz, 1H), 8.07 (d, J=9.0 Hz, 1H), 7.92 (d, J=9.1 Hz, 1H), 7.75-7.62 (m, 1H), 7.54-7.41 (m, 2H), 7.23 (d, J=8.3 Hz, 2H), 7.08 (d, J=7.1 Hz, 1H), 6.99-6.78 (m, 4H), 6.60-6.43 (m, 3H), 6.04-5.81 (m, 1H), 5.01-4.85 (m, 1H), 4.63 (d, J=12.5 Hz, 1H), 4.39-4.00 (m, 3H), 3.75-3.64 (m, 10H), 3.52-3.40 (m, 2H), 3.31-2.67 (m, 12H), 2.59 (t, J=12.4 Hz, 1H), 2.27-1.81 (m, 12H), 1.46-1.38 (m, 2H), 1.26-1.24 (m, 2H), 0.93 (s, 6H) ppm.

Example 16: Synthesis of XZ-14528

Preparation of N1-(2-(2-(2-(4-(((4-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-2-nitrophenyl)amino)methyl)piperidine-1-carboxamido)ethoxy)ethoxy)ethyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide (XZ-14528)

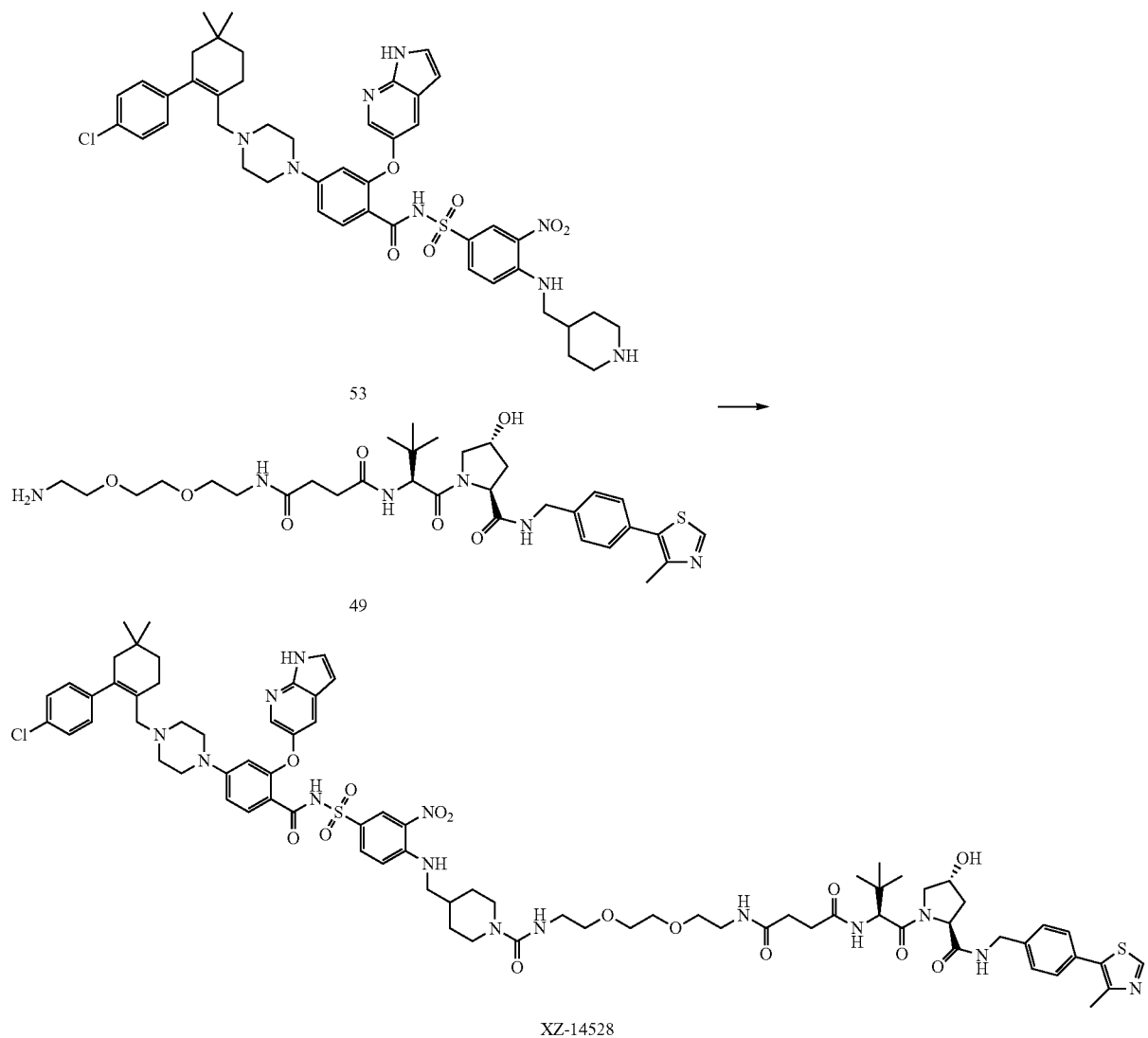

A mixture of compound 49 (26 mg) and CDI (7.7 mg) in 2 mL THF was stirred at room temperature for 1 hour. Compound 53 (18.1 mg) and DIPEA (0.05 mL) were then added. The mixture was stirred overnight and quenched by the addition of NH$_4$Cl (aq.), extracted with DCM and the organic phase was washed with water x1, brine x1, dried over Na$_2$SO$_4$, filtered and evaporated to dryness. The crude product was purified by column chromatography using DCM and methanol as eluents to afford 16.8 mg compound XZ-14528. Yield 72%. $^1$H NMR (400 MHz, CDCl$_3$) δ 9.49 (s, 1H), 8.85 (d, J=2.2 Hz, 1H), 8.67 (s, 1H), 8.57-8.43 (m, 1H), 8.15 (d, J=2.5 Hz, 1H), 7.99 (d, J=9.2 Hz, 1H), 7.92 (d, J=9.1 Hz, 1H), 7.62 (d, J=2.4 Hz, 1H), 7.46-7.40 (m, 2H), 7.38-7.32 (m, 4H), 7.23 (d, J=8.3 Hz, 2H), 6.97-6.88 (m, 3H), 6.80 (d, J=9.4 Hz, 1H), 6.62-6.47 (m, 3H), 6.02 (d, J=1.7 Hz, 1H), 5.24-5.17 (m, 1H), 4.73 (t, J=8.0 Hz, 1H), 4.63-4.47 (m, 3H), 4.35 (dd, J=15.0, 5.2 Hz, 1H), 4.10-3.89 (m, 4H), 3.64-3.47 (m, 12H), 3.46-3.37 (m, 4H), 3.24 (t, J=6.1 Hz, 2H), 3.15-3.01 (m, 4H), 2.87-2.71 (m, 4H), 2.60-2.38 (m, 8H), 2.20-1.76 (m, 8H), 1.42-1.34 (m, 2H), 1.28-1.24 (m, 2H), 0.98-0.92 (m, 15H) ppm.

509                                                                 510
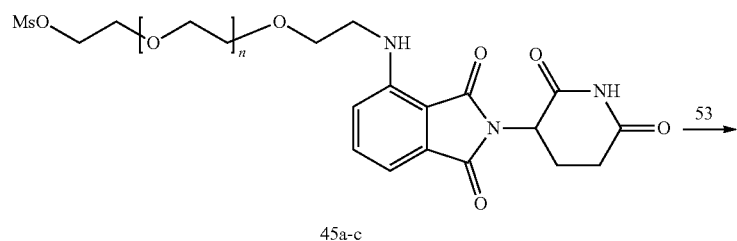
45a-c → 53
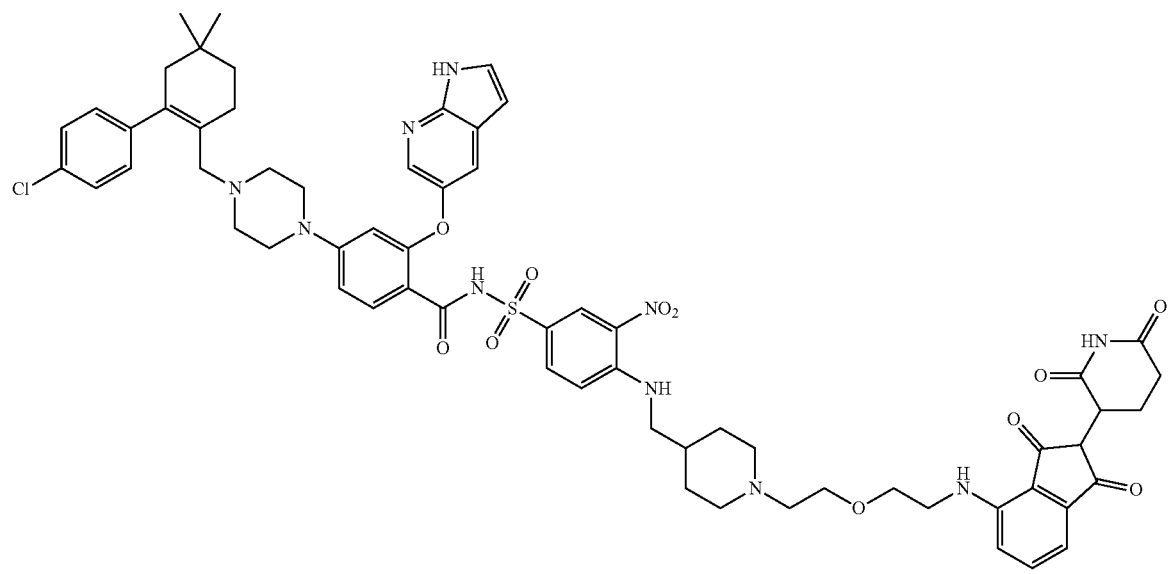
XZ15434
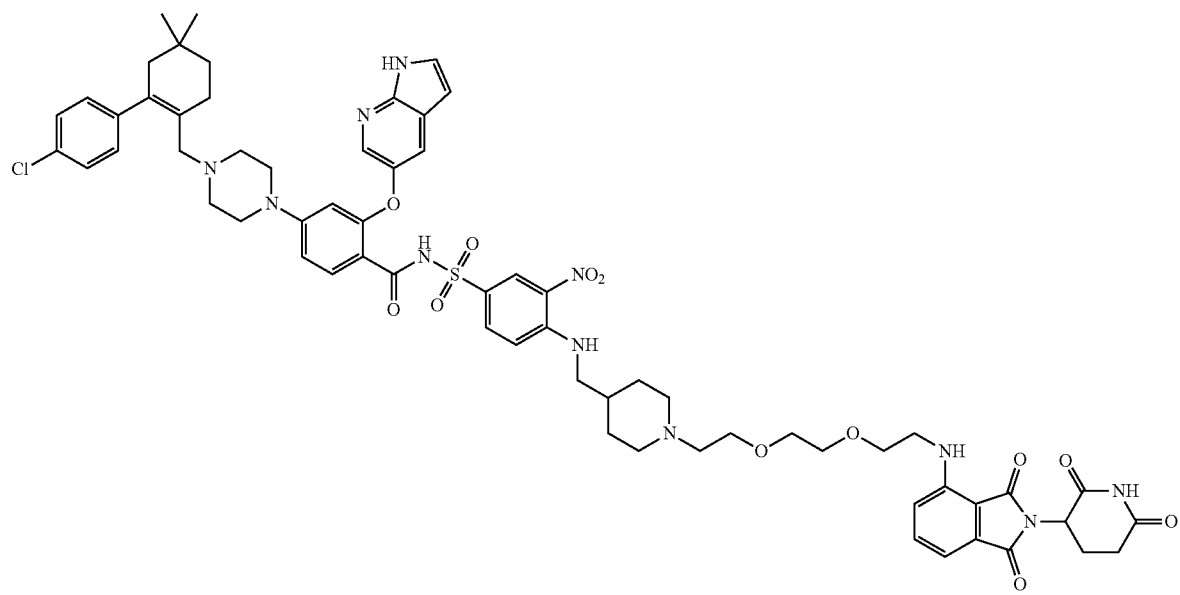
XZ15438

-continued
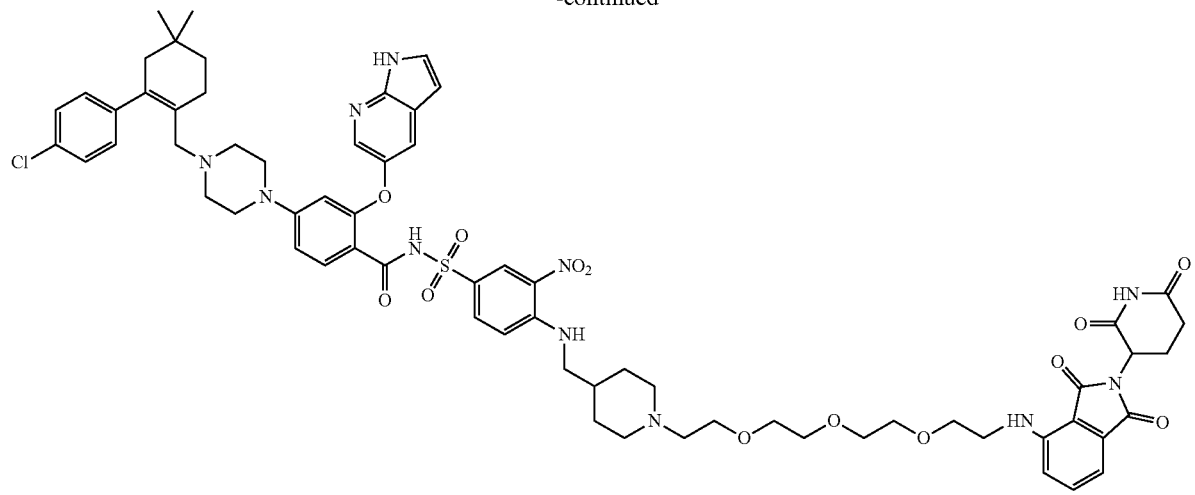
XZ15436
Example 17: Synthesis of XZ-15434
Preparation of 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((1-(2-(2-(2-(2,6-dioxopiperidin-3-yl)-1,3-dioxoisoindolin-4-ylamino)ethoxy)ethyl)piperidin-4-yl)methylamino)-3-nitrophenylsulfonyl)benzamide (XZ-15434)
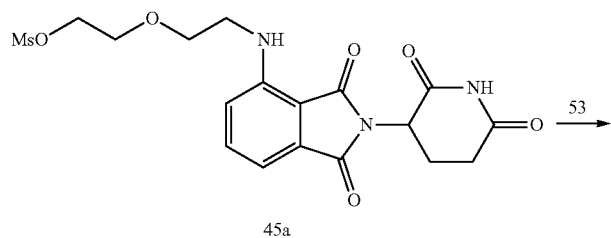
45a
→ 53
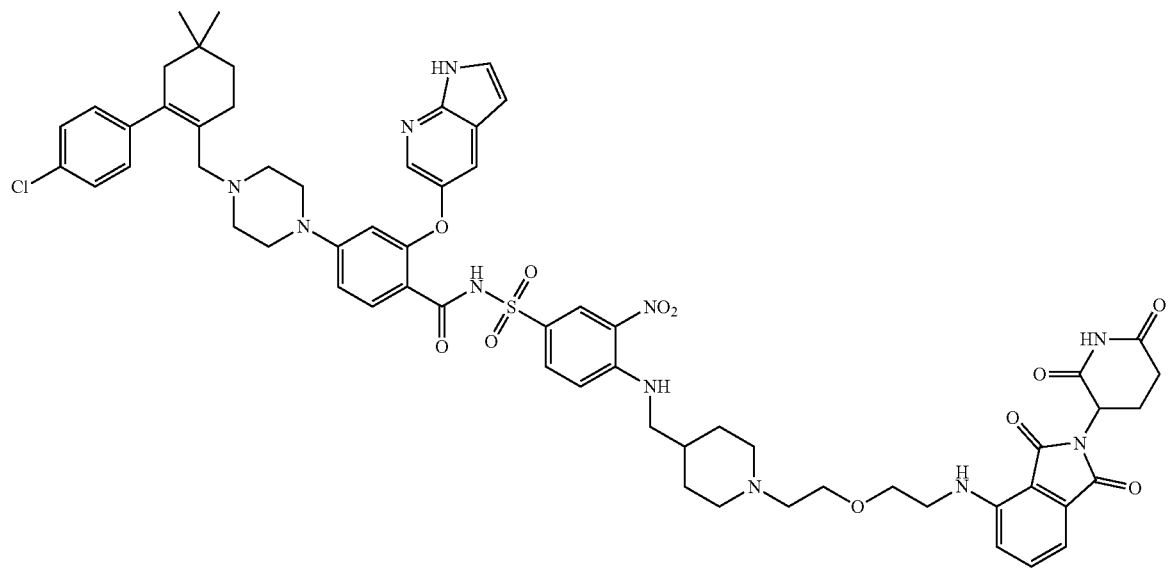
XZ-15434

A mixture of compound 53 (37 mg), compound 45a (14 mg), DIPEA (100 µL), and NaI (3 mg) in 2 mL 1,4-dioxane was heated at 90° C. overnight. The mixture was then poured into water and extracted with EtOAc. The organic phase was washed with water x1, NH₄Cl (aq.) x1, brine x1, dried over Na₂SO₄, filtered and evaporated to dryness. The crude product was purified by column chromatography using DCM and methanol as eluents to afford 10.7 mg compound XZ-15434. Yield 31%. ¹H NMR (400 MHz, CDCl₃ and CD₃OD) δ 8.77 (s, 1H), 8.43 (s, 1H), 8.04 (s, 1H), 7.94-7.83 (m, 2H), 7.59 (s, 1H), 7.50 (dd, J=8.5, 7.2 Hz, 1H), 7.42 (d, J=3.4 Hz, 1H), 7.26-7.17 (m, 2H), 7.09 (d, J=7.0 Hz, 1H), 6.96-6.87 (m, 3H), 6.75 (s, 1H), 6.55 (dd, J=9.1, 2.1 Hz, 1H), 6.45 (d, J=2.8 Hz, 1H), 6.03 (s, 1H), 5.00-4.86 (m, 1H), 3.96-3.88 (m, 2H), 3.75-3.68 (m, 2H), 3.57-3.44 (m, 4H), 3.30-2.58 (m, 15H), 2.24-1.83 (m, 12H), 1.45-1.31 (m, 4H), 0.92 (s, 6H) ppm.

Example 18: Synthesis of XZ-15438

Preparation of 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((1-(2-(2-(2-(2-(2,6-dioxopiperidin-3-yl)-1,3-dioxoisoindolin-4-ylamino)ethoxy)ethoxy)ethyl)piperidin-4-yl)methylamino)-3-nitrophenylsulfonyl)benzamide (XZ-15438)

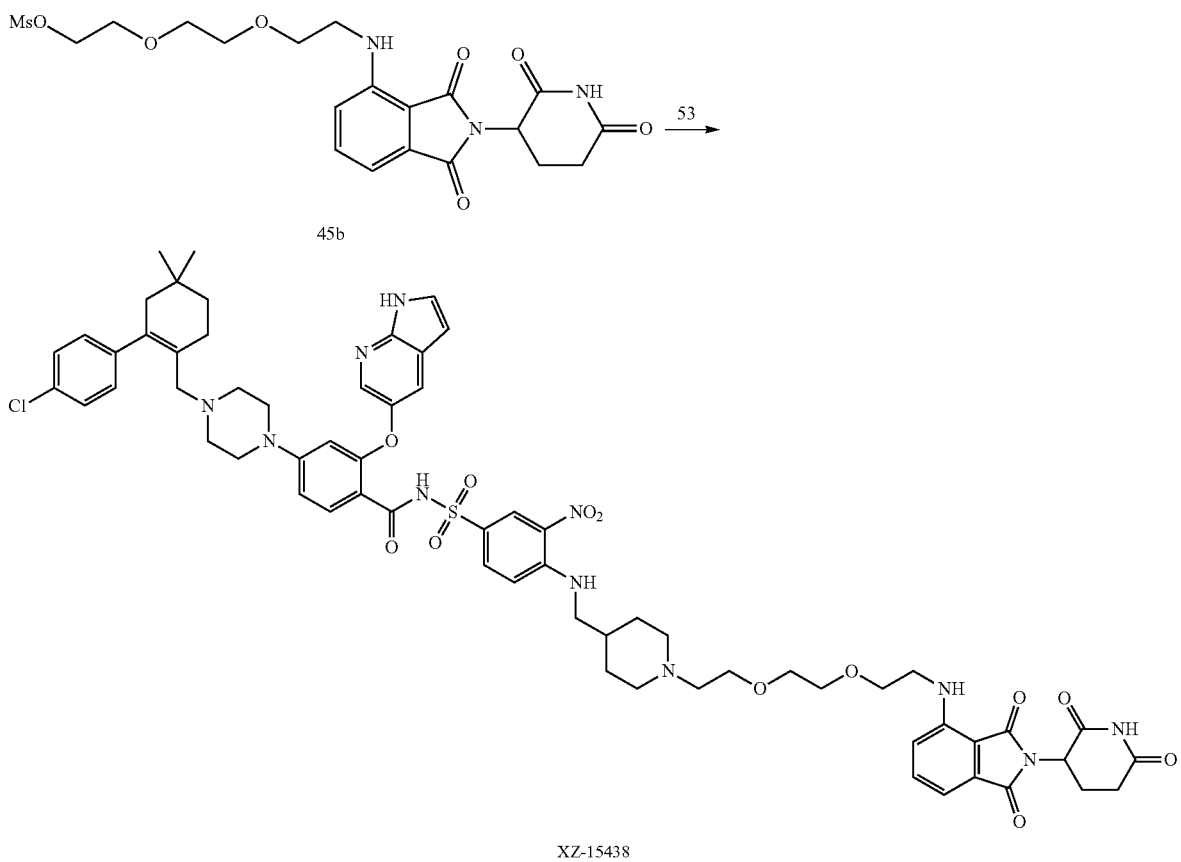

A mixture of compound 53 (37 mg), compound 45b (15 mg), DIPEA (100 µL), and NaI (3 mg) in 2 mL 1,4-dioxane was heated at 90° C. overnight. The mixture was then poured into water and extracted with EtOAc. The organic phase was washed with water x1, NH₄Cl (aq) x1, brine x1, dried over Na₂SO₄, filtered and evaporated to dryness. The crude product was purified by column chromatography using DCM and methanol as eluents to afford 11.7 mg compound XZ-15438. Yield 31%. ¹H NMR (400 MHz, CDCl₃ and CD₃OD) δ 10.61 (br s, 1H), 10.19 (br s, 1H), 8.81 (s, 1H), 8.39 (s, 1H), 8.04 (s, 1H), 7.87 (d, J=8.9 Hz, 1H), 7.74 (s, 1H), 7.62 (s, 1H), 7.48 (d, J=8.0 Hz, 2H), 7.23 (d, J=8.2 Hz, 2H), 7.06 (d, J=7.0 Hz, 1H), 6.97-6.82 (m, 3H), 6.70-6.43 (m, 4H), 6.01 (s, 1H), 5.15-4.90 (m, 1H), 4.17-3.83 (m, 2H), 3.78-3.58 (m, 8H), 3.48-3.40 (m, 2H), 3.21-2.73 (m, 15H), 2.25-1.94 (m, 12H), 1.45-1.33 (m, 4H), 0.93 (s, 6H) ppm.

Example 19: Synthesis of XZ-15436

Preparation of 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((1-(2-(2-(2-(2-(2,6-dioxopiperidin-3-yl)-1,3-dioxoisoindolin-4-ylamino)ethoxy)ethoxy)ethoxy)ethyl)piperidin-4-yl)methylamino)-3-nitrophenylsulfonyl)benzamide (XZ-15436)

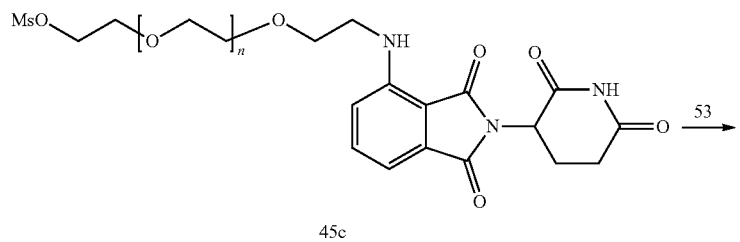

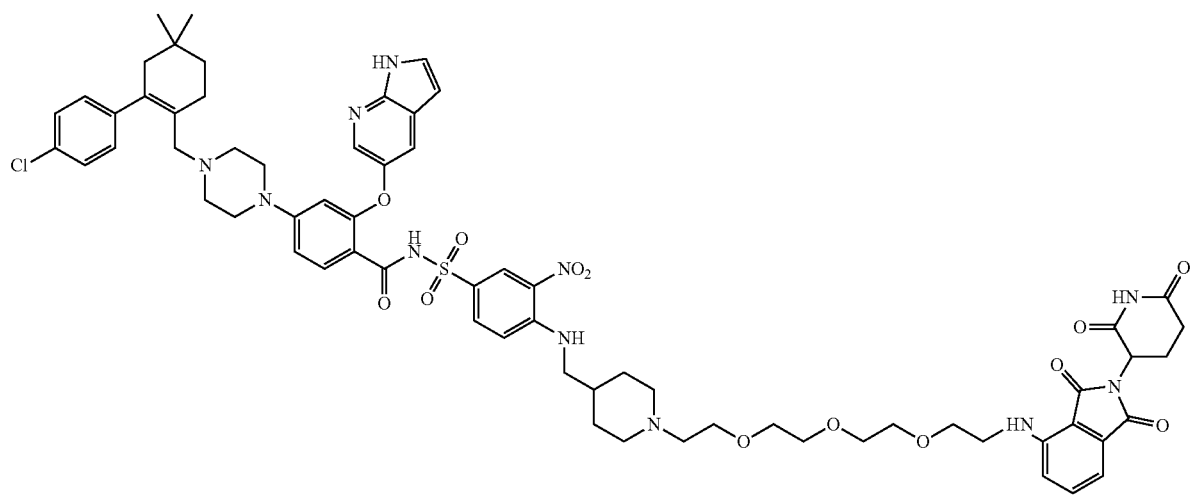

XZ-15436

A mixture of compound 53 (37 mg), compound 45c (16 mg), DIPEA (100 µL), and NaI (3 mg) in 2 mL 1,4-dioxane was heated at 90° C. overnight. The mixture was then poured into water and extracted with EtOAc. The organic phase was washed with water x1, NH$_4$Cl (aq) x1, brine x1, dried over Na$_2$SO$_4$, filtered and evaporated to dryness. The crude product was purified by column chromatography using DCM and methanol as eluents to afford 15.0 mg compound XZ-15436. Yield 39%. $^1$H NMR (400 MHz, CDCl$_3$ and CD$_3$OD) δ 10.59 (br s, 1H), 10.06 (br s, 1H), 8.83 (d, J=2.2 Hz, 1H), 8.43 (t, J=5.4 Hz, 1H), 8.11 (d, J=2.3 Hz, 1H), 7.90 (d, J=9.1 Hz, 2H), 7.63 (d, J=2.4 Hz, 1H), 7.54-7.42 (m, 2H), 7.22 (d, J=8.4 Hz, 2H), 7.07 (d, J=7.1 Hz, 1H), 6.98-6.84 (m, 3H), 6.73 (d, J=9.2 Hz, 1H), 6.61-6.45 (m, 3H), 6.01 (d, J=2.0 Hz, 1H), 5.01-4.93 (m, 1H), 3.94-3.79 (m, 2H), 3.76-3.61 (m, 10H), 3.54-3.40 (m, 4H), 3.27-3.17 (m, 2H), 3.16-2.43 (m, 13H), 2.28-2.09 (m, 7H), 1.98-1.82 (m, 5H), 1.41 (t, J=6.4 Hz, 2H), 1.26-1.23 (m, 2H), 0.93 (s, 6H) ppm.

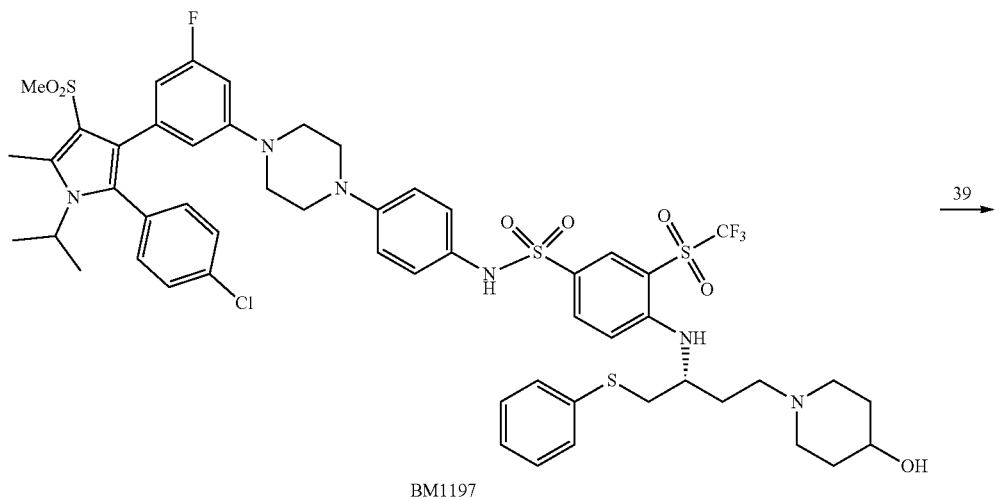

BM1197

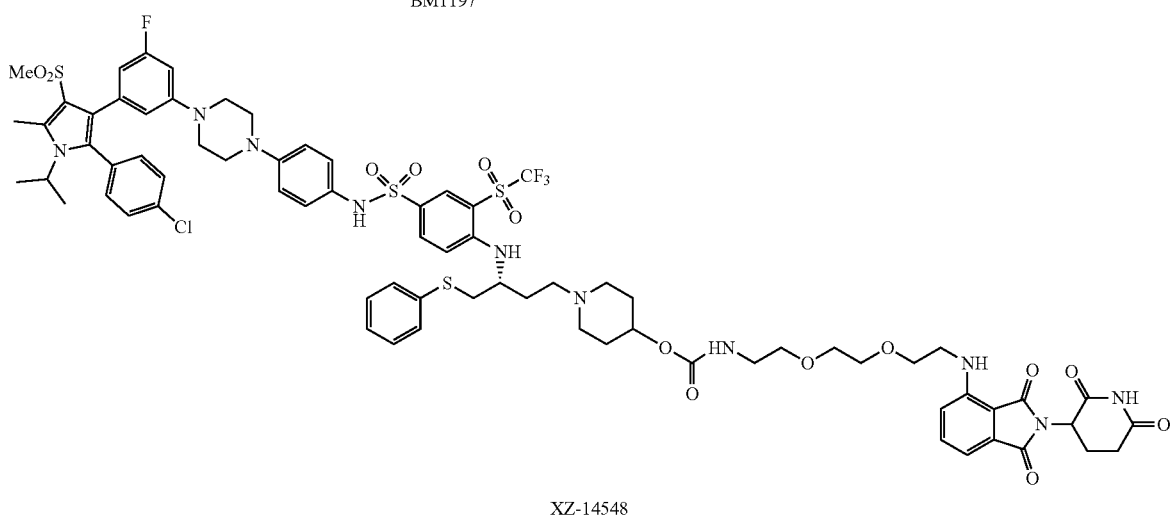

XZ-14548

Example 20: Synthesis of XZ-14548

Preparation of 1-((R)-3-((4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-((trifluoromethyl)sulfonyl)phenyl)amino)-4-(phenylthio)butyl)piperidin-4-yl (2-(2-(2-((2-(2,6-dioxopiperidin-3-yl)-1,3-dioxoisoindolin-4-yl)amino)ethoxy)ethoxy)ethyl)carbamate (XZ-14548)

A mixture of BM1197 (11.5 mg) and CDI (10 mg) in 1.5 mL dichloroethane was heated at 60° C. overnight. A solution of compound 39 (5.5 mg) and TEA (0.3 mL) in 0.5 mL DMSO was then added and the resulted mixture was heated to 70° C. overnight. After cooled to room temperature, the mixture was poured into water and extracted with EtOAc. The organic phase was washed with water x1, brine x1, dried over $Na_2SO_4$, filtered and evaporated to dryness. The crude product was purified by column chromatography using DCM and methanol as eluents to afford 3.6 mg compound XZ-14548. Yield 22%. $^1$H NMR (400 MHz, $CDCl_3$) δ 8.79 (br s, 1H), 7.99 (s, 1H), 7.65-7.56 (m, 1H), 7.54-7.46 (m, 1H), 7.37-7.27 (m, 4H), 7.26-7.20 (m, 2H), 7.14-7.05 (m, 3H), 7.03-6.94 (m, 3H), 6.91 (d, J=8.4 Hz, 1H), 6.81 (d, J=8.8 Hz, 2H), 6.70 (s, 1H), 6.66-6.50 (m, 2H), 6.43 (d, J=11.9 Hz, 1H), 6.30 (d, J=8.7 Hz, 1H), 5.34-5.26 (m, 1H), 4.98-4.88 (m, 1H), 4.73-4.55 (m, 1H), 4.48-4.34 (m, 1H), 3.96-3.81 (m, 1H), 3.75-3.37 (m, 12H), 3.22-3.03 (m, 10H), 2.96-2.61 (m, 10H), 2.57-2.43 (m, 1H), 2.40-1.63 (m, 11H), 1.45 (d, J=7.1 Hz, 6H) ppm.

Example 21: Evaluation of Compounds of Formula (I) and Formula (II) for their Ability to Selectively Kill Senescent Cells Normal WI38 (NSC) and IR-induced senescent WI38 cells (IR-SC) were incubated with vehicle or increasing concentrations of compounds of Formula (I) or Formula (II) for 72 hours. The cells were digested with 0.25% trypsin and 1 mM EDTA, and harvested in PBS containing 2% FBS. After incubation with propidium iodide (PI, 100 ng/ml) in PBS at room temperature for 1 minute, cells were centrifuged at 1,200 rpm for 6 minutes to remove PI and then resuspended in PBS containing 2% FBS for analysis using a flow cytometer. Viable cells (PI– cells) were analyzed by flow cytometry at a constant flow rate to count the number of cells and calculated as a percentage of control cells treated with vehicle. Table 1 depicts the EC50 values of the compounds of Formula (I) and compounds of Formula (II) against normal WI38 and IR-induced senescent WI38.

Figure 2A:
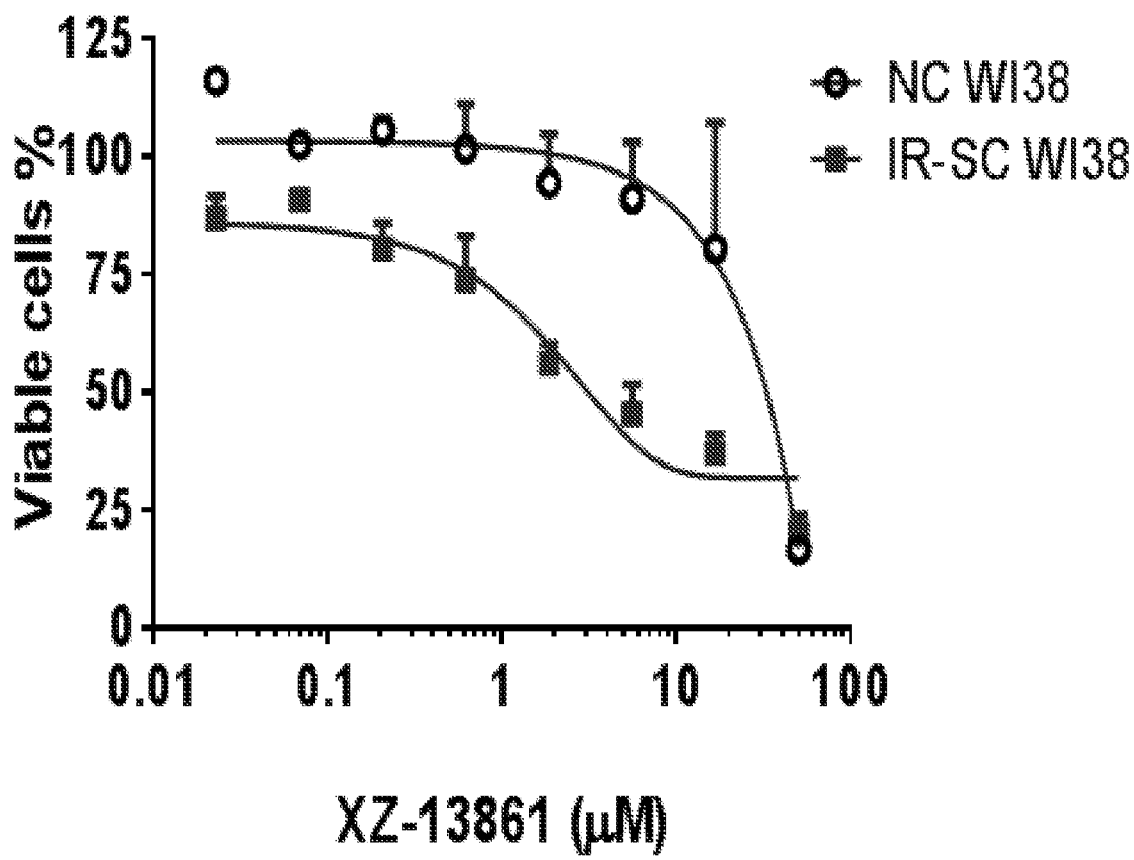
FIG. 2A and FIG. 2B depicts graphs show that compound 11 (XZ-13861) (FIG. 2A) and XZ-13906 (FIG. 2B) selectively inhibits IR-SC WI38 cells but not normal WI38 cells in a dose-dependent manner.
Figure 2B:
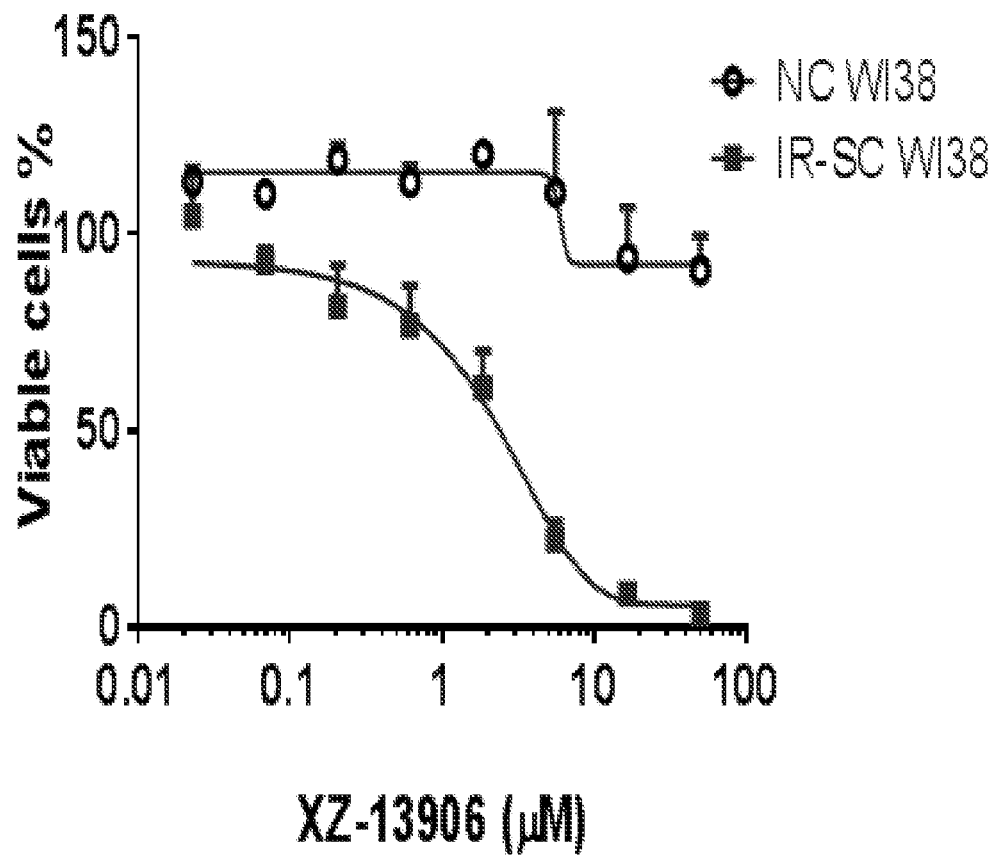

Both compound 11 (XZ-13861) (FIG. 2A) and XZ-12906 (FIG. 2B) selectively inhibit IR-SC WI38 cells but not normal WI 38 cells in a dose dependent manner.

Example 22: Evaluation of Compounds of Formula (I) and Formula (II) for their Ability to Kill Cancer Cells RS4; 11 and NCI-H146 cancer cells were incubated with vehicle or increasing concentrations of compounds of Formula (I) and Formula (II). At 72 hours post-treatment cell viability was measured by MTS and EC50 was calculated as a percentage of control cells treated with vehicle. Table 1 depicts the EC50 values of compounds of Formula (I) and Formula (II) against RS4; 11 and NCI-H146.

TABLE 1

EC50 values of compounds of Formula (I) and Formula (II) against RS4; 11 and NCI-H146.

| Compound | WI38 EC50 (µM) | | Ratio | EC50 (nM) | |
|---|---|---|---|---|---|
| | NSC | IR-SC | NSC/SC | RS4 | NCI-H146 |
| ABT-263 | 12.6 | 0.61 | 20.6 | 16.00 | 27.47 |
| XZ-14439 | >20 | 0.87 | >20.88 | 84.43 | 69.55 |
| PZ-15227 | >10 | 0.108 | >92 | 113.62 | 68.86 |
| XZ-15421 | >10 | <0.1562 | >64.02 | 72.92 | |
| XZ-14510 | >10 | 0.177 | >56 | 219.89 | 111.98 |
| XZ-14509 | >10 | 0.226 | >44.22 | 90.00 | 64.95 |
| XZ-14515 | >10 | 0.158 | >63.27 | 173.16 | 79.17 |
| XZ-14516 | >10 | 0.092 | >109 | 1088.63 | 517.16 |
| XZ-14540 | >10 | 1.13 | 8.86 | 82.43 | 76.25 |
| XZ-14437 | >20 | 4.55 | >4.4 | 460 | >250 |
| XZ-14529 | >10 | >10 | — | 822.56 | >2000 |
| XZ-15416 | >10 | <0.1562 | >64.02 | 30.71 | >10 |
| XZ-15405 | >10 | 0.152 | >65.97 | 24.78 | |
| XZ-15418 | >10 | 0.172 | >58.06 | 12.33 | |
| ABT-199 | >10 | >10 | — | | |
| XZ-14522 | >10 | >10 | — | 46.98 | 1103.7 |
| XZ-14523 | >10 | >10 | — | 160.86 | 1255.91 |
| XZ-14528 | >10 | >10 | — | 396.62 | >2000 |
| XZ-13906 | 100 | 2.4 | 41.67 | >2000 | >2000 |
| XZ-14455 | 5.0 | 1.47 | 3.40 | >2000 | >2000 |
| XZ-14424 | 1.6 | 1.4 | 1.2 | | |
| XZ-13861 | 32.8 | 3.12 | 10.51 | | |

Example 23: Protein Degradation Assays in Senescent Cells

Figure 3A:
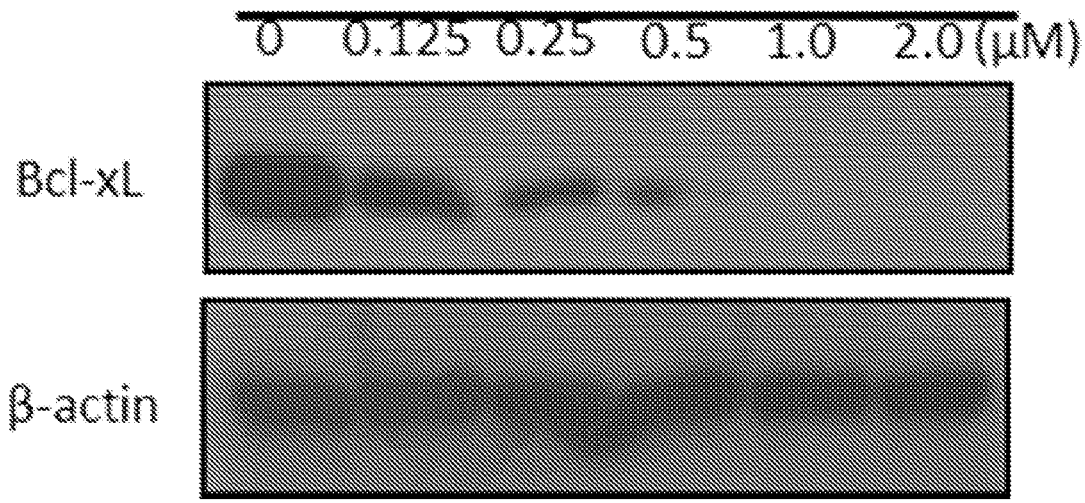
FIG. 3A and FIG. 3B depicts graphs that show that XZ-14439 dose dependent (FIG. 3A) and time dependently (FIG. 3B) depletes Bcl-xL in IR-SC WI38 cells.
Figure 3B:
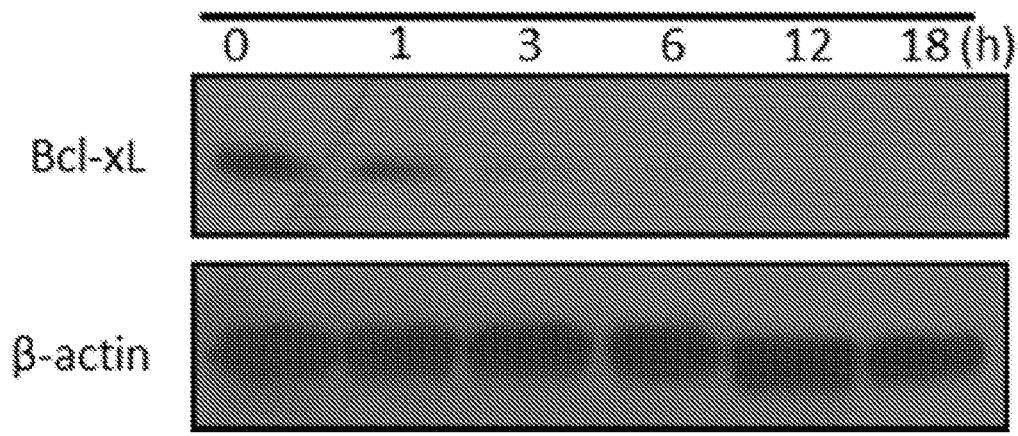

IR-SC WI38 cells were incubated with vehicle or increasing concentrations of XZ-14439 for 18 hours at increasing contractions (FIG. 3A) and at a fixed concentration of XZ-14439 for increasing times (FIG. 3B). The cells were digested with 0.25% trypsin and 1 mM EDTA, and harvested in RIPA lysis buffer with 1 Phosphatase Inhibitor Cocktail 3 and 1% Protease Inhibitor Cocktail. An equal amount of protein (15-30 µg/lane) from each cell extract was resolved on a 12% SDS-PAGE gel. Proteins were blotted onto a NOVEX PVDF membrane by electrophoresis. The membranes were blocked with TBS-T blocking buffer (5% nonfat milk in 25 mM Tris-HCL, pH 7.4; 3 mM KCl; 1n40 mM NaCl; and 0.05% Tween) and probed with primary antibodies (at a predetermined optimal concentration) overnight at 4° C. or for 1 hour at room temperature. After extensive washing with TBS-T, the membranes were incubated with an appropriate peroxidase-conjugated secondary antibody (Jackson ImmunoResearch Europe, Suffolk, UK) for 1 hour at room temperature. After three washes with TBS-T, the proteins of interest were detected with ECL Western Blotting Detection Reagents and recorded with autoradiography (Pierce Biotech, Rockford, Ill., USA). The primary antibody Bcl-xl (#2762), Bcl-2 antibody (#2872S) and β-actin (13E5, #4970) were purchased from Cell Signaling.

XZ-14439 depletes Bcl-xL in IR-SC WI38 cells in both a dose dependent (FIG. 3A) and time dependent (FIG. 3B) manner.

Example 24: Protein Degradation Assays in Cancer Cells

Figure 4A:
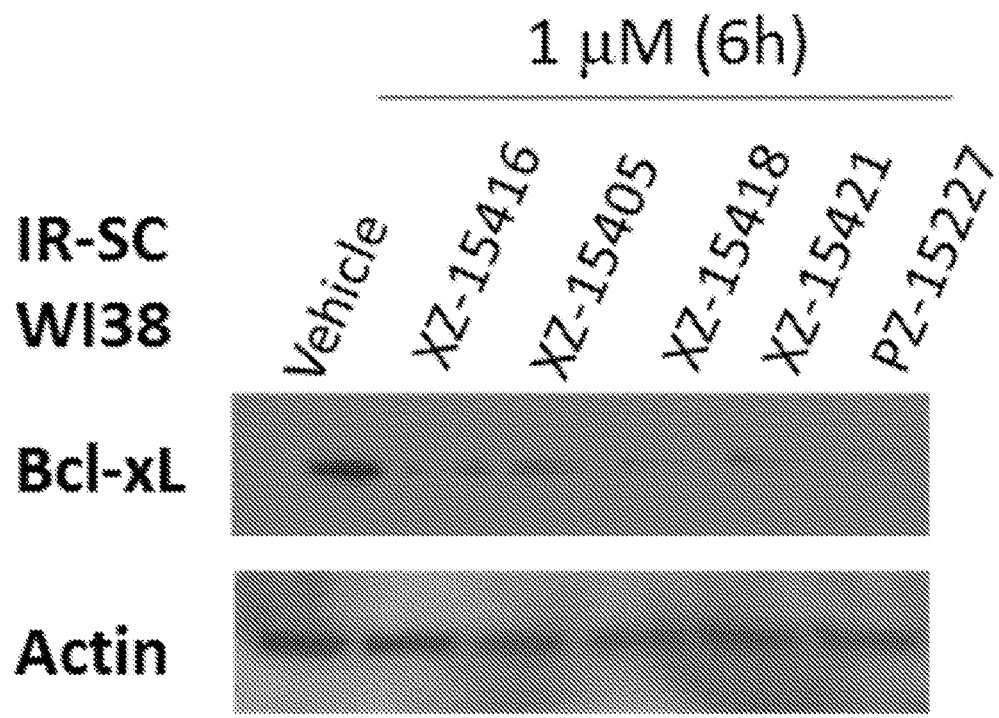
FIG. 4A and FIG. 4B depicts graphs that show that XZ-15416, XZ-15405, XZ-15418, XZ-15421, and PZ-15227 deplete Bcl-xL in IR-SC WI38 (FIG. 4A) and RS4; 11 (FIG. 4B) cells.

IR-SC WI38 (FIG. 4A) and RS4; 11 (FIG. 4B) cells were incubated with vehicle or increasing concentrations of compounds of Formula (I) or Formula (II) for 6 or 16 hours, at 1 µM (FIG. 4A) and 100 nm (FIG. 4B), respectively. The cells were harvested in RIPA lysis buffer with 1% Phosphatase Inhibitor Cocktail 3 and 1 Protease Inhibitor Cocktail. An equal amount of protein (15-30 µg/lane) from each cell extract was resolved on a 12% SDS-PAGE gel. Proteins were blotted onto a NOVEX PVDF membrane by electrophoresis. The membranes were blocked with TBS-T blocking buffer (5% nonfat milk in 25 mM Tris-HCL, pH 7.4; 3 mM KCl; 140 mM NaCl; and 0.05% Tween) and probed with primary antibodies (at a predetermined optimal concentration) overnight at 4° C. or for 1 hour at room temperature. After extensive washing with TBS-T, the membranes were incubated with an appropriate peroxidase-conjugated secondary antibody (Jackson ImmunoResearch Europe, Suffolk, UK) for 1 hour at room temperature. After three washes with TBS-T, the proteins of interest were detected with ECL Western Blotting Detection Reagents and recorded with autoradiography. The primary antibody Bcl-xl (#2762), Bcl-2 antibody (#2872S), Bcl-w (#2724S), Mcl-1 (#5453s) and β-actin (13E5, #4970) were purchased from Cell Signaling.

Figure 4B:
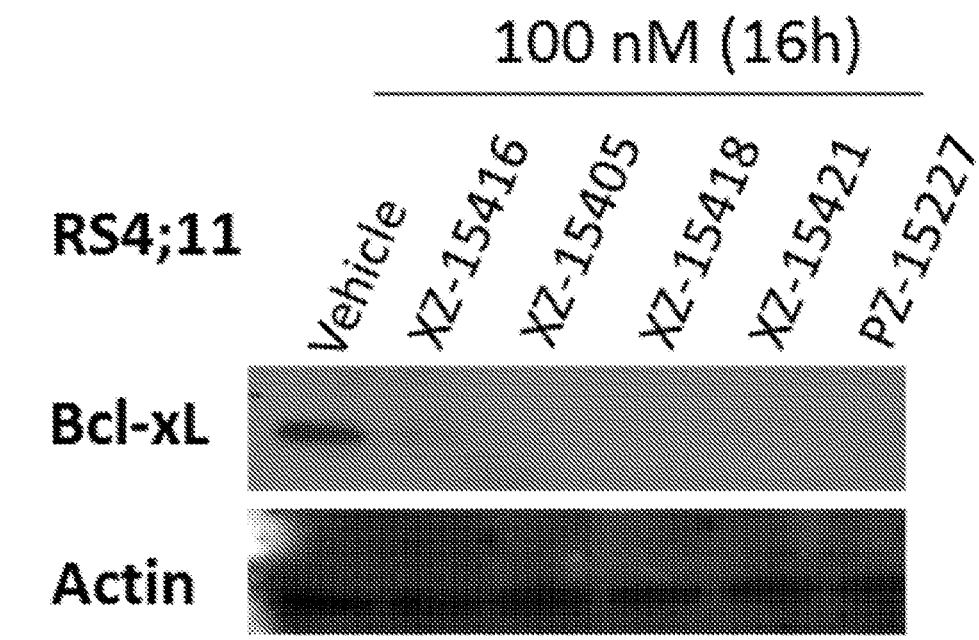

XZ-15416, XZ-15405, XZ-15418, XZ-15421, and PZ-15227 deplete Bcl-xL in IR-SC WI38 and RS4; 11 cells at 1 µM (FIG. 4A) and 200 nM (FIG. 4B).

REFERENCES

Aguilar, A., et al., (2013) A potent and highly efficacious Bcl-2/Bcl-xL inhibitor, *J Med Chem* 56: 3048-3067.

Bai. L., et al. (2014) BM-1197: a novel and specific Bcl-2/Bcl-xL inhibitor inducing complete and long-lasting tumor regression in vivo, *PLOS One* 9:e99404.

Baker, D. J., et al., (2011) Clearance of p16Ink4a-positive senescent cells delays ageing-associated disorders, *Nature* 479:232-236.

Baker, D. J., et al., (2016) Naturally occurring p16(Ink4a)-positive cells shorten healthy lifespan, *Nature* 530:184-189.

Bajwa, N., et al., (2012) Inhibitors of the anti-apoptotic Bcl-2 proteins: a patent review, *Expert Opin. Ther. Patents* 22:37-55.

Bruncko, M., et al., (2007) Studies leading to potent, dual inhibitors of Bcl-2 and Bcl-xL, *J Med Chem* 50:641-662.

Bruncko, M., et al., (2015) Structure-guided design of a series of MCL-1 inhibitors with high affinity and selectivity, *J Med Chem* 58:2180-2194.

Campisi, J., (2005) Senescent cells, tumor suppression, and organismal aging: good citizens, bad neighbors, *Cell* 120:513-522.

Campisi, J., (2011) Cellular senescence: putting the paradoxes in perspective, *Curr. Opin. Genet. Dev.* 21:107-112.

Chang, J., et al., (2016) Clearance of senescent cells by ABT263 rejuvenates aged hematopoietic stem cells in mice, *Nat. Med.* 22:78-83.

Chen, J., et al., (2012) Structure-based discovery of BM-957 as a potent small-molecule inhibitor of Bcl-2 and Bcl-xL capable of achieving complete tumor regression, *J Med Chem* 55:8502-8514.

Delbridge, A. R., et al., (2016) Thirty years of BCL-2: translating cell death discoveries into novel cancer therapies, *Nat. Rev. Cancer* 16:99-109.

Jing, L., et al., (2015) Hijacking the E3 Ubiquitin Ligase Cereblon to Efficiently Target BRD4, *Chem. Biol.* 22:755-763, 2015

Rodier, F. and Campisi, J., (2011) Four faces of cellular senescence, *J. Cell Biol.* 192:547-556.

Park. C. M., et al., (2008) Discovery of an Orally Bioavailable Small Molecule Inhibitor of Prosurvival B-Cell Lymphoma 2 Proteins, *J Med Chem* 51:6902-6915.

Pelz, N. F., et al., (2016) Discovery of 2-Indole-acylsulfonamide Myeloid Cell Leukemia 1 (Mcl-1) Inhibitors Using Fragment-Based Methods, *J Med Chem* 59:2054-2066.

Sleebs, B. E., et al., Quinazoline Sulfonamides as Dual Binders of the Proteins B-Cell Lymphoma 2 and B-Cell Lymphoma Extra Long with Potent Proapoptotic Cell-Based Activity (2011) *J Med Chem* 54:1914-1916.

Sleebs, B. E., et al., (2013) Discovery of Potent and Selective Benzothiazole Hydrazone Inhibitors of Bcl-$X_L$, *J Med Chem* 56:5514-5540.

Tanaka, Y., et al., (2013) Discovery of potent Mcl-1/Bcl-xL dual inhibitors by using a hybridization strategy based on structural analysis of target proteins, *J Med Chem* 56:9635-9645.

Tao, Z. F., et al., (2014) Discovery of a Potent and Selective BCL-XL Inhibitor with in Vivo Activity, *ACS Med Chem Lett* 5:1088-1093.

Zhou, H., et al., (2012) Structure-based design of potent Bcl-2/Bcl-xL inhibitors with strong in vivo antitumor activity, *J Med Chem* 55:6149-6161.

Lessene, G., et al., (2008) BCL-2 family antagonists for cancer therapy, *Nat. Rev. Drug Discov.* 7:989-1000.

Vogler, M., et al., (2009) Bcl-2 inhibitors: small molecules with a big impact on cancer therapy, *Cell Death Differ.* 16:360-367

Vogler, M., (2014) Targeting BCL2-Proteins for the Treatment of Solid Tumours, *Adv. Med.* 1-14.

Zhu, Y., et al., (2015) The Achilles' heel of senescent cells: from transcriptome to senolytic drugs, *Aging Cell* 14:644-658.

What is claimed is:

1. The compound of the formula:

BCL-L-E3 wherein,

BCL is a protein targeting unit which binds to one or more anti-apoptotic Bcl-2 family proteins;

E3 is an E3 ubiquitin ligase binding unit which binds to the CRBN or VHL E3 ubiquitin ligase; and L is a linker unit with two ends, each of which covalently links to one of BCL and E3 through one or more of the following functional groups: alkyl, branched alkyl, ether, thioether, ester, amine, amide, carbamate, carbamide, sulfone, aryl, heteroaryl, cycloalkyl, or heterocycle;

wherein the linker comprises two ends, wherein each of the two ends are the same or different;

wherein the linker unit comprises a length of 1-30 atoms, and wherein the compound has the following chemical structure:

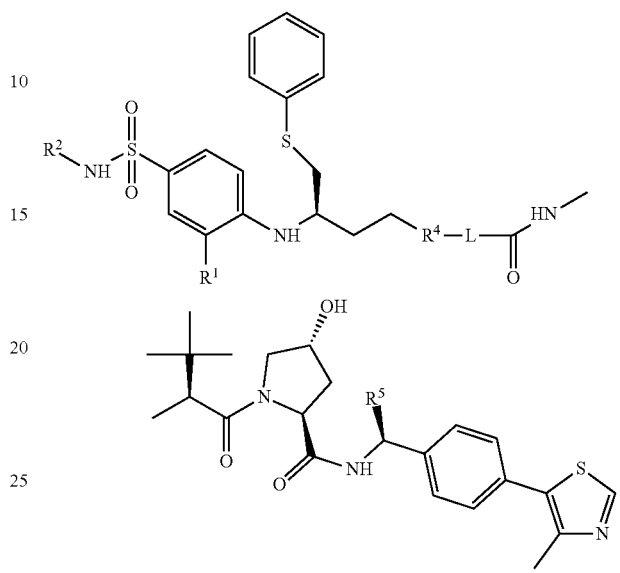

where BCL is the portion of the structure depicted to the left of L and E3 is the portion of the structure depicted to the right of L;

where $R^1$ is $NO_2$ or $SO_2CF_3$;

where $R^2$ is one of the following:

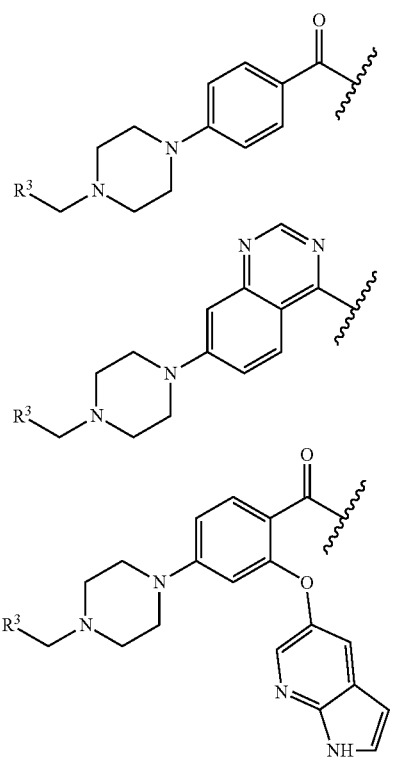

-continued

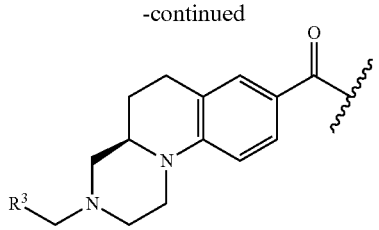

where R³ is one of the following:

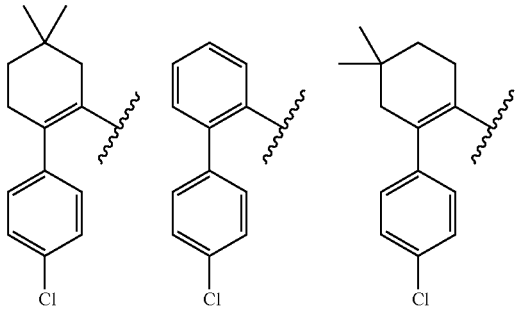

where R⁴ is one of the following, wherein the bond between R⁴ and the remainder of BCL is indicated by α and the bond between R⁴ and L is indicated by ß:

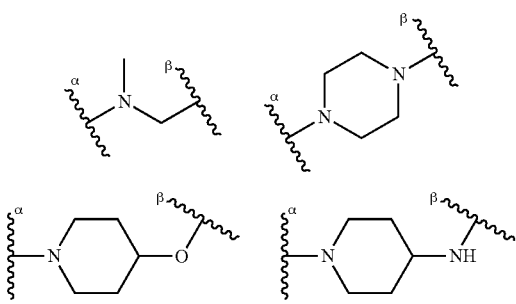

where R⁵ is H or CH₃.

2. The compound of claim 1, where BCL is:

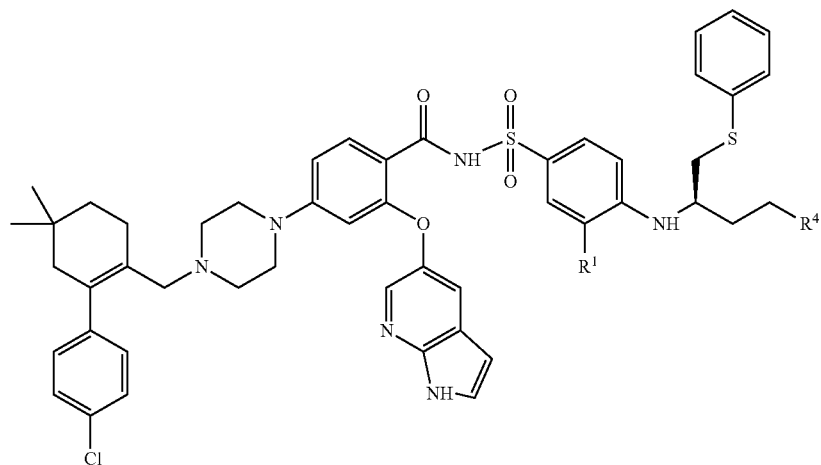

where R⁴ is selected from one of the following, wherein the bond between R⁴ and the remainder of BCL is indicated by α and the bond between R⁴ and L is indicated by ß:

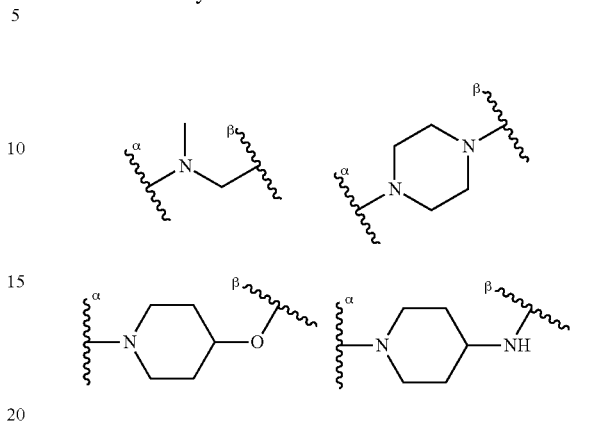

where E3 is selected from one of the following:

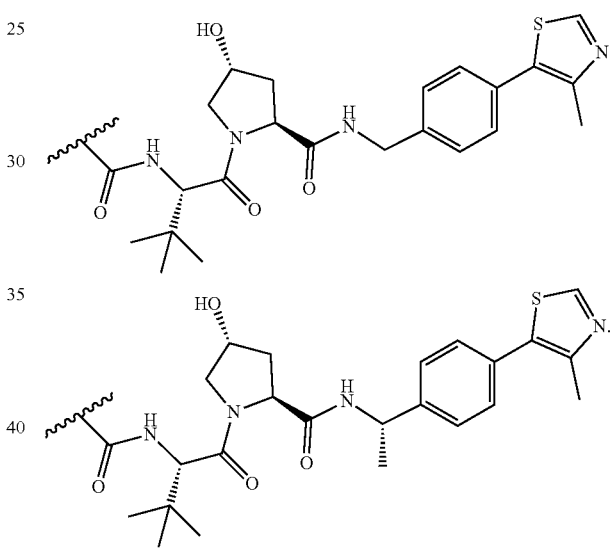

3. The compound of claim 1, where BCL is:

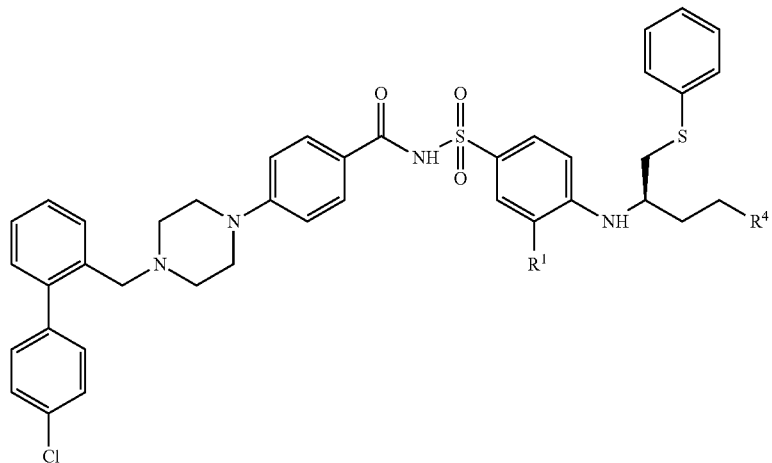

where R¹ is $NO_2$ or $SO_2CF_3$;
where R⁴ is selected from one of the following, wherein the bond between R⁴ and the remainder of BCL is indicated by α and the bond between R⁴ and L is indicated by ß:

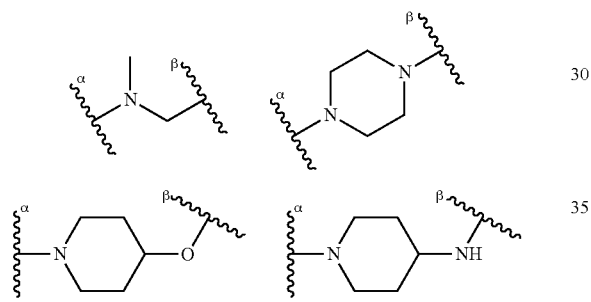

where E3 is selected from one of the following:

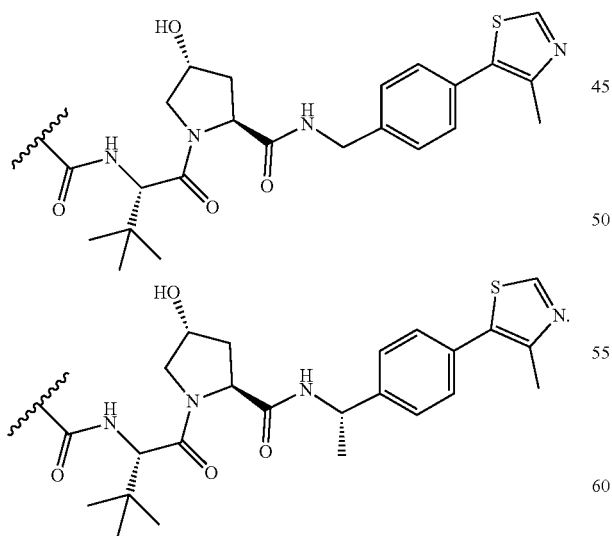

4. The compound of claim 3, where the length of the linker is 5-7 atoms in length and the linker contains only alkyl, branched alkyl, heterocyclic, ether, or amide groups.

5. The compound of claim 4, where the linker contains only unbranched alkyl, heterocyclic, or amide groups.

6. The compound of claim 1 where, BCL is:

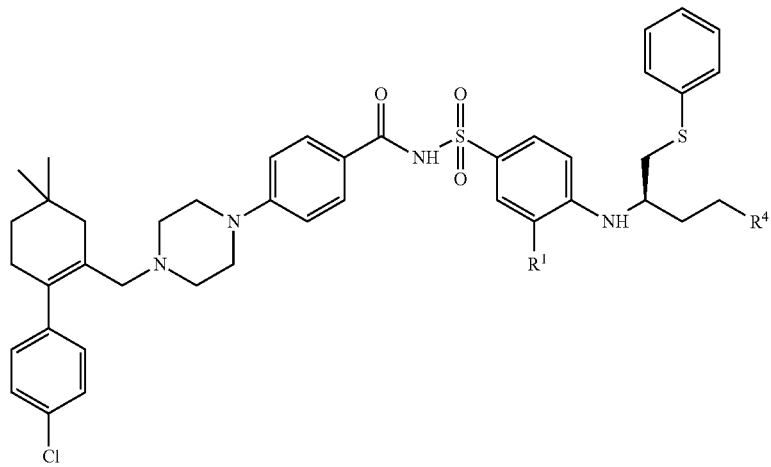

where $R^1$ is $NO_2$ or $SO_2CF_3$;

where $R^4$ is selected from one of the following, wherein the bond between $R^4$ and the remainder of BCL is indicated by α and the bond between $R^4$ and L is indicated by ß:

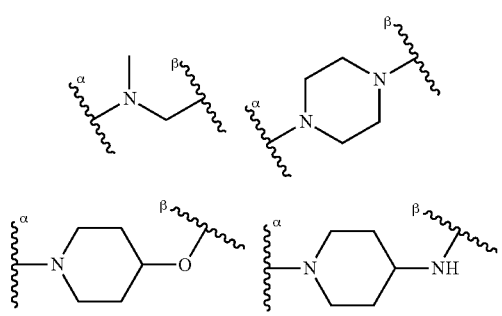

Where E3 is selected from one of the following:

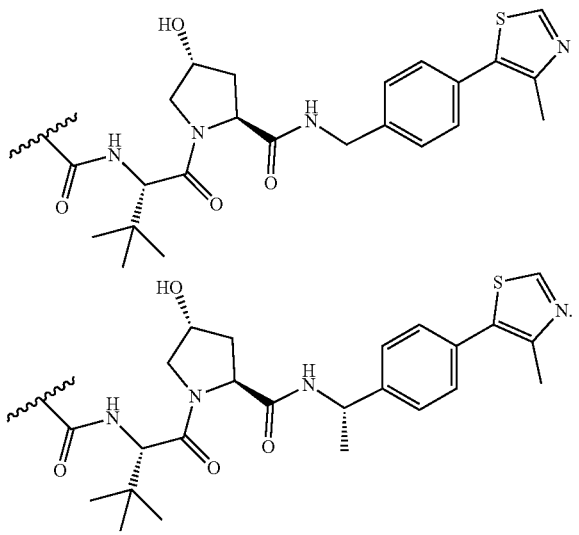

7. The compound of claim 6, where the length of the linker is 5-7 atoms in length and the linker contains only alkyl, branched alkyl, heterocyclic, ether, or amide groups.

8. The compound of claim 7, where the linker contains only unbranched alkyl, heterocyclic, or amide groups.

9. The compound of claim 2, where the length of the linker is 5-7 atoms in length and the linker contains only alkyl, branched alkyl, heterocyclic, ether, or amide groups.

10. The compound of claim 9, where the linker contains only unbranched alkyl, heterocyclic, or amide groups.

11. The compound of claim 1,
where BCL is:

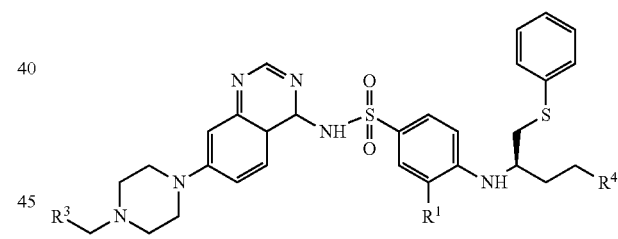

where $R^1$ is $NO_2$ or $SO_2CF_3$;

where $R^4$ is selected from one of the following, wherein the bond between $R^4$ and the remainder of BCL is indicated by α and the bond between $R^4$ and L is indicated by ß:

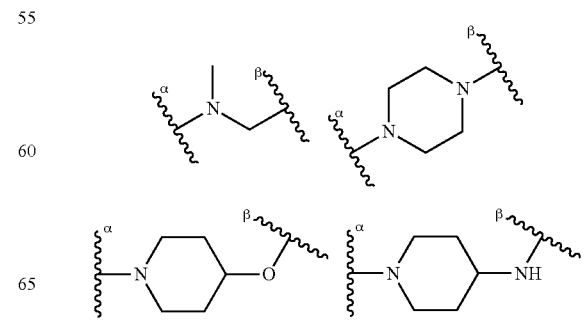

where R³ is selected from one of the following:

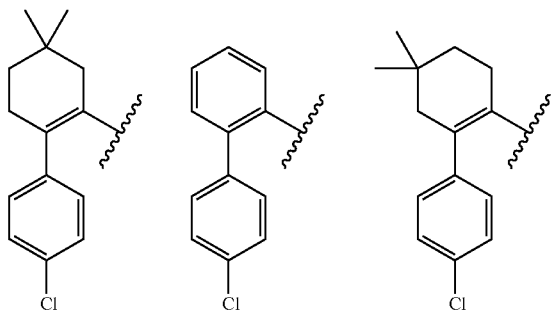

where E3 is selected from one of the following:

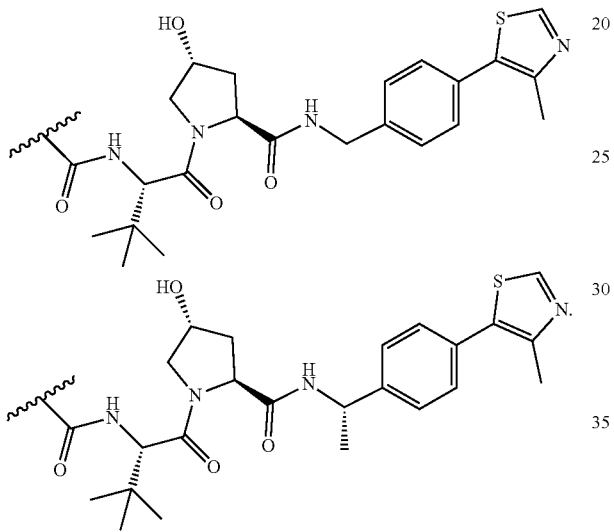

12. The compound of claim 11, where the length of the linker is 5-7 atoms in length and the linker contains only alkyl, branched alkyl, heterocyclic, ether, or amide groups.

13. The compound of claim 12, where the linker contains only unbranched alkyl, heterocyclic, or amide groups.

14. The compound of claim 1 where, BCL is:

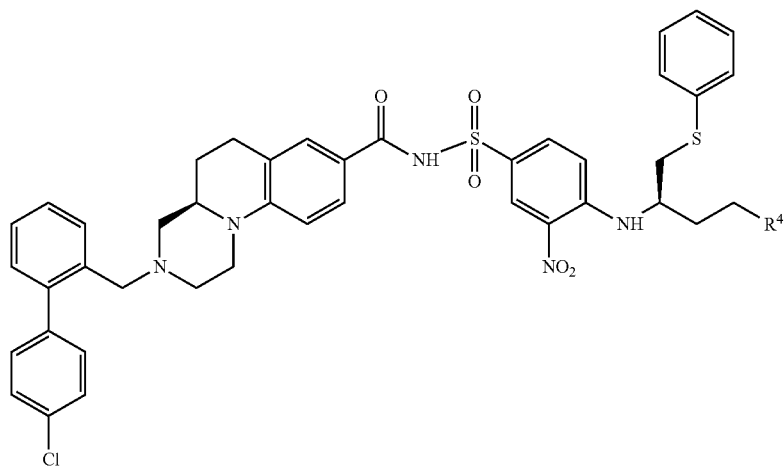

where R⁴ is selected from one of the following, wherein the bond between R⁴ and the remainder of BCL is indicated by α and the bond between R⁴ and L is indicated by ß:

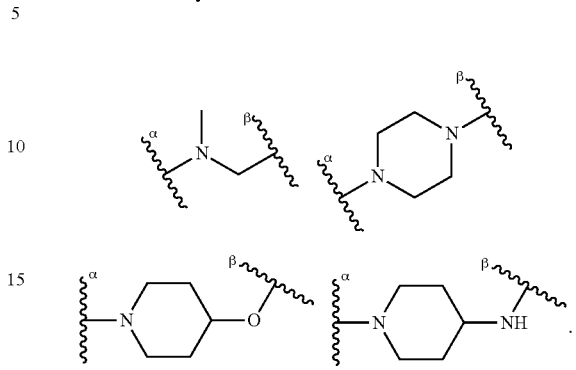

15. The compound of claim 14, where the length of the linker is 5-7 atoms in length and the linker contains only alkyl, branched alkyl, heterocyclic, ether, or amide groups.

16. The compound of claim 15, where the linker contains only unbranched alkyl, heterocyclic, or amide groups.

17. The compound of the formula:

BCL-L-E3 wherein,
BCL is a protein targeting unit which binds to one or more anti-apoptotic Bcl-2 family proteins;
E3 is an E3 ubiquitin ligase binding unit which binds to the CRBN or VHL E3 ubiquitin ligase; and
L is a linker unit with two ends, each of which covalently links to one of BCL and E3 through one or more of the following functional groups: alkyl, branched alkyl, ether, thioether, ester, amine, amide, carbamate, carbamide, sulfone, aryl, heteroaryl, cycloalkyl, or heterocycle;
wherein the linker comprises two ends, wherein each of the two ends are the same or different;
wherein the linker unit comprises a length of 1-30 atoms, and
wherein the compound has the following chemical structure:

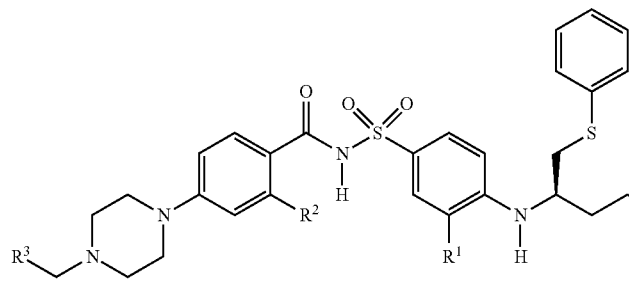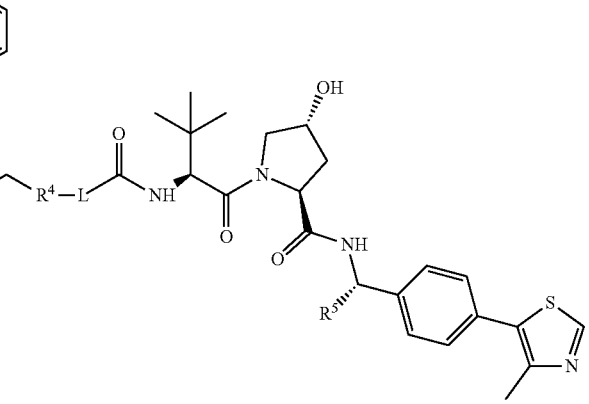

where BCL is the portion of the structure depicted to the left of L and E3 is the portion of the structure depicted to the right of L;

where $R^1$ is $NO_2$ or $SO_2CF_3$, where $R^2$ is H or

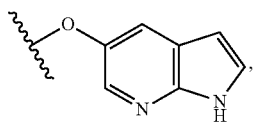

where $R^3$ is selected from one of the following:

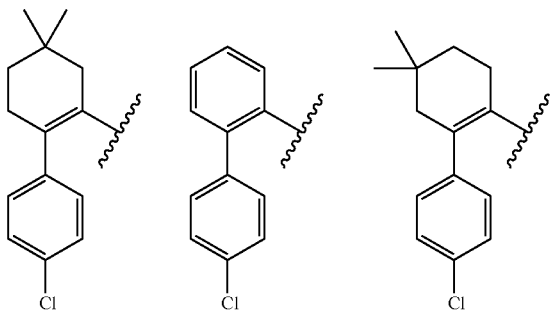

where $R^4$ is selected from one of the following, wherein the bond between $R^4$ and the remainder of BCL is indicated by α and the bond between $R^4$ and L is indicated by ß:

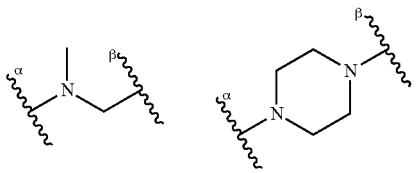

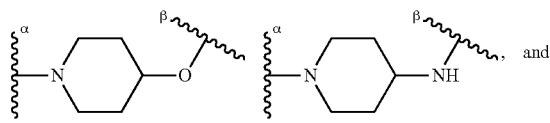

where $R^5$ is H or $CH_3$.

18. The compound of claim 17, where the length of the linker is 5-7 atoms in length and the linker contains only alkyl, branched alkyl, heterocyclic, ether, or amide groups.

19. The compound of claim 18, where the linker contains only unbranched alkyl, heterocyclic, or amide groups.

* * * * *